US012612407B2

(12) United States Patent
Zhang et al.

(10) Patent No.: US 12,612,407 B2
(45) Date of Patent: Apr. 28, 2026

(54) IMIDAZO[2,1-F][1,2,4]TRIAZIN-4-AMINE DERIVATIVES AS TLR7 AGONIST

(71) Applicant: BEIGENE, LTD., Grand Cayman (KY)

(72) Inventors: Guoliang Zhang, Beijing (CN); Jianzhuang Miao, Beijing (CN); Changyou Zhou, Beijing (CN); Gang Chen, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 1298 days.

(21) Appl. No.: 17/428,853

(22) PCT Filed: Feb. 6, 2020

(86) PCT No.: PCT/CN2020/074436

§ 371 (c)(1),
(2) Date: Mar. 10, 2022

(87) PCT Pub. No.: WO2020/160710

PCT Pub. Date: Aug. 13, 2020

(65) Prior Publication Data

US 2023/0167117 A1    Jun. 1, 2023

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01); *C07B 2200/05* (2013.01)

(58) Field of Classification Search
CPC .................................................... C07D 487/04
See application file for complete search history.

(56) References Cited

U.S. PATENT DOCUMENTS

| | | | |
|---|---|---|---|
| 9,556,178 B2 * | 1/2017 | Purandare | .............. A61K 45/06 |
| 9,962,388 B2 | 5/2018 | Ding et al. | |
| 10,138,248 B2 | 11/2018 | Buesking et al. | |
| 11,111,249 B2 | 9/2021 | Zhang et al. | |
| 11,117,898 B2 | 9/2021 | Zhang et al. | |
| 2010/0210598 A1 | 8/2010 | Carson et al. | |
| 2013/0324547 A1 | 12/2013 | Boivin et al. | |
| 2014/0056953 A1 | 2/2014 | Foeger | |
| 2017/0106607 A1 | 4/2017 | Anderson | |
| 2017/0273983 A1 | 9/2017 | Ding et al. | |
| 2018/0095426 A1 | 4/2018 | Albers | |
| 2018/0210298 A1 | 7/2018 | Shi | |
| 2020/0062758 A1 | 2/2020 | Liu et al. | |
| 2020/0131187 A1 | 4/2020 | Zhang | |
| 2021/0380593 A1 | 12/2021 | Zhang | |
| 2022/0119394 A1 | 4/2022 | Zhang et al. | |
| 2022/0289752 A1 | 9/2022 | Zhang et al. | |

FOREIGN PATENT DOCUMENTS

| | | |
|---|---|---|
| CN | 102365280 A | 2/2012 |
| CN | 102439011 A | 5/2012 |
| CN | 102596958 A | 7/2012 |
| CN | 105367576 A | 3/2016 |
| CN | 107344941 A | 11/2017 |
| CN | 108069969 A | 5/2018 |
| JP | 2014-035140 A | 2/2014 |
| JP | 2017-524037 A | 8/2017 |
| JP | 2017-538734 A | 12/2017 |
| WO | 2010084425 | 7/2010 |
| WO | 2011035231 | 3/2011 |
| WO | WO-2014035140 A2 | 3/2014 |
| WO | WO-2014056953 A1 | 4/2014 |
| WO | WO-2016023511 A1 | 2/2016 |
| WO | WO-2016183094 A1 | 11/2016 |
| WO | WO-2017106607 | 6/2017 |
| WO | WO-2017223414 A1 | 12/2017 |
| WO | WO-2018095426 | 5/2018 |
| WO | WO-2018210298 | 11/2018 |
| WO | WO-2020160710 A1 | 8/2020 |
| WO | WO-2020160711 A1 | 8/2020 |
| WO | WO-2021023105 A1 | 2/2021 |

OTHER PUBLICATIONS

Search Report and Written Opinion in SG Application No. 11202108284T, mailed Dec. 5, 2022, 9 pages.
Notice of Allowance issued in U.S. Appl. No. 17/428,856, dated Dec. 18, 2024.
Restriction Requirement for U.S. Appl. No. 17/428,856 dated Jun. 7, 2024.
Office Action for Japan Application No. 2021-546230 dated Mar. 5, 2024.
European Search Report in EP Application No. 20752173.3, mailed Oct. 7, 2022, 7 pages.
International Search Report and Written Opinion for PCT/CN2020/106190, mailed Nov. 3, 2020, 24 pages.
Lochmuller, C. H. et al., "Chromatographic resolution of enantiomers selective review," J. Chromatogr., vol. 113, No. 3, Oct. 1975, pp. 283-302.
Adams, S., "Toll-like receptor agonists in cancer therapy," Immunotherapy 1(6):949-964 (2009).
Aranda, F. et al., "Trial Watch: Toll-like receptor agonists in oncological indications," Oncoimmunology 3: e29179 (Aug. 2014).
Barton, G. M. et al., "Toll-like receptors and their ligands," Curr. Top. Microbiol. Immunol. 270:81-92 (2002).
International Search Report and Written Opinion for PCT/CN2020/074436, mailed Apr. 26, 2020, 10 pages.
International Search Report and Written Opinion for PCT/CN2020/074437, mailed Apr. 26, 2020, 15 pages.
Iwasaki, A. et al., "Toll-like receptor control of the adaptive immune responses," Nat. Immunol. 5(10):987-995 (2004).

(Continued)

*Primary Examiner* — John S Kenyon
*Assistant Examiner* — Rehana Ismail
(74) *Attorney, Agent, or Firm* — Foley & Lardner LLP

(57) ABSTRACT

An imidazo [2,1-f] [1,2,4] triazin-4-amine derivative or a stereoisomer thereof, or a pharmaceutically acceptable salt thereof which are used as a TLR7 agonist in the treatment of cancer are provided. Pharmaceutical compositions comprising the imidazo [2,1-f] [1,2,4] triazin-4-amine derivative or a stereoisomer thereof, or a pharmaceutically acceptable salt thereof are also provided.

14 Claims, No Drawings

(56) References Cited

OTHER PUBLICATIONS

Karroum, N. B. et al., "Novel and selective TLR7 antagonists among the Imidazo[1,2-a]pyrazines, Imidazo[1,5-a]quinoxalines, and Pyrazolo[1,5-a]quinoxalines Series," J. Med. Chem., vol. 62, Jul. 2019, pp. 7015-7031.
Monk, B. J. et al., "A phase 2, randomized, double-bind, placebo-controlled study of chemo-immunotherapy combination using motolimod with pegylated liposomal doxorubicin in recurrent or persistent ovarian cancer: a Gynecologic Oncology Group partners study," Ann Oncol. May 1, 2017;28(5):996-1004.
Salunke, D. B. et al., "Structure-activity relationships in human toll-like receptor 8-active 2, 3-diamino-furo [2,3-c] pyridines," J. Med. Chem., vol. 55, Aug. 2012, pp. 8137-8151.
Shayan, G. et al., "Phase Ib Study of Immune Biomarker Modulation with Neoadjuvant Cetuximab and TLR8 Stimulation in Head and Neck Cancer to Overcome Suppressive Myeloid Signals," Clin. Cancer Res. Jan. 24, 2018(1):62-72.
Stary, G. et al., "Tumoricidal activity of TLR7/8-activated inflammatory dendritic cells," J. Exp. Med. 204(6):1441-1451 (2007).
Van Duin, D. et al., "Triggering TLR signaling in vaccination," Trends Immunol. 27(1):49-55 (2006).

* cited by examiner

IMIDAZO[2,1-F][1,2,4]TRIAZIN-4-AMINE DERIVATIVES AS TLR7 AGONIST

CROSS-REFERENCE TO RELATED APPLICATIONS

This application is a U.S. National Stage Application under 35 U.S.C. § 371 of International Application No. PCT/CN2020/074436, filed Feb. 6, 2020, which claims priority to Patent Application Nos. PCT/CN2019/074732 (CN), filed on Feb. 7, 2019, PCT/CN2019/098757 (CN), filed on Jul. 31, 2019, and PCT/CN2020/073673 (CN), filed on Jan. 22, 2020, the disclosures of each of which is hereby incorporated by reference in its entirety for all purposes.

FIELD OF THE INVENTION

Disclosed herein is an imidazo[2,1-f][1,2,4]triazin-4-amine derivative or a stereoisomer thereof, or a pharmaceutically acceptable salt thereof useful as a TLR7 agonist, and a pharmaceutical composition comprising the same. Also disclosed herein is a method of treating cancer using the imidazo[2,1-f][1,2,4]triazin-4-amine derivative or a stereoisomer thereof, or a pharmaceutically acceptable salt thereof as TLR7 agonist.

BACKGROUND OF THE INVENTION

Toll-like receptors (TLRs) belong to a family of pattern recognition receptors (PRRs) which play a critical role in early innate immune response by sensing highly conserved molecular patterns of diverse pathogens (PAMPs) as well as endogenous danger-associated molecular patterns (DAMPs) (Barton, G. M. and R. Medzhitov (2002). "Toll-like receptors and their ligands." Curr Top Microbiol Immunol 270: 81-92).

Ten different TLRs have been identified in human. Among them, TLR7, TLR8, and TLR9 belong to the same subfamily of TLRs based on their genomic structures, sequence similarities, and endosomal localizations. They have a restricted pattern of expression, limited to certain types of immune cells. TLR7 is expressed in B cells and plasmacytoid dendritic cells (pDC); TLR8 is expressed in monocytes and myeloid dendritic cells (mDC) (Iwasaki, A. and R. Medzhitov (2004). "Toll-like receptor control of the adaptive immune responses." Nat Immunol 5(10): 987-995).

In addition to the natural ligand single-stranded RNA, the imidazoquinolones (or 'imiquimod-like' ligands) and guanosine analogs are shown to activate TLR7 and/or 8 with varying specificity. Activation of TLR7 and/or TLR8 triggers the maturation of dendritic cells (DCs) and the secretion of proinflammatory cytokines (van Duin, D., et al. (2006). "Triggering TLR signaling in vaccination." Trends Immunol 27(1): 49-55). CTLs and NK cells are further activated and proliferated by stimulated DC through cytokines and antigen presentation. The properties of TLR agonists thus constitute an efficient strategy for boosting anticancer immunity (Adams, S. (2009). "Toll-like receptor agonists in cancer therapy." Immunotherapy 1(6): 949-964).

Imiquimod (TLR7 agonist) is being successfully used for the treatment of many primary skin tumors and cutaneous metastasis as the single antitumor agent with immunostimulatory capacity (Stary, G., et al. (2007). "Tumoricidal activity of TLR7/8-activated inflammatory dendritic cells." J Exp Med 204(6): 1441-1451, Aranda, F., et al. (2014). "Trial Watch: Toll-like receptor agonists in oncological indications." *Oncoimmunology* 3: e29179).

WO2016023511 disclosed pyrrolopyrimidine compounds as a TLR7 agonist for treating antiviral drugs.

Currently, intensive effort has been put into preclinical and clinical development of TLR agonists for cancer therapy. Therefore, there is a need to develop more potent TLR agonists for treating cancer.

SUMMARY OF THE INVENTION

Unexpectedly and surprisingly, the inventors found that the imidazo[2,1-f][1,2,4]triazin-4-amine derivatives disclosed herein demonstrate more potent TLR7 agonist activity, when ring A in Formula (II) is directly substituted with a heterocyclyl ring. The inventors also found that the branching of the alkyl moiety in position 2 of the imidazo[2,1-f][1,2,4]triazin-4-amine derivatives unexpectedly improved the TLR7 agonist activity.

In the first aspect, disclosed herein is a compound of Formula (II), (II)

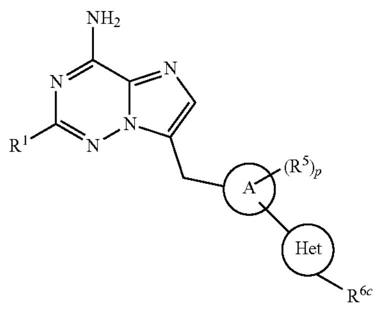

or a pharmaceutically acceptable salt thereof, or a stereoisomer thereof, wherein $R^1$ is —$OR^{1a}$, —$SR^{1a}$, —$NR^{1a}R^{1b}$, —$COR^{1a}$, —$SO_2R^{1a}$, —C(═O)$OR^{1a}$, —C(═O)$NR^{1a}R^{1b}$, —C(═$NR^{1a}$)$NR^{1b}R^{1c}$, —N($R^{1a}$)C(═O)$R^{1b}$, —N($R^{1a}$)C(═O)$OR^{1b}$, —N($R^{1a}$)C(O)$NR^{1b}R^{1c}$, —N($R^{1a}$)S(O)$NR^{1b}R^{1c}$, —N($R^{1a}$)$S(O)_2NR^{1b}R^{1c}$, —$NR^{1a}SO_2R^{1b}$, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is independently and optionally substituted with one or two or three substituents $R^{1d}$;

$R^{1a}$, $R^{1b}$, and $R^{1c}$ are independently hydrogen, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with one or two or three substituents selected from halogen, —$C_{1-8}$alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3$—$(OCH_2CH_2)_n$— (wherein n is a number of 3 to 10) or —$OR^{1f}$;

wherein $R^{1e}$ is halogen, nitro, cyano, hydroxy, amino (—$NH_2$), alkylamino, dialkylamino, or —$C_{1-6}$alkyl optionally substituted with halogen;

wherein $R^{1f}$ is alkyl, cycloalkyl, heterocyclyl, aryl, or heteroaryl, each of which is optionally substituted with —$C_{1-4}$alkyl or halogen;

$R^{1d}$, at each occurrence, is independently hydrogen, oxo, —CN, —$NO_2$, amino (—$NH_2$), alkylamino, dialkylamino, halogen, haloalkyl, alkyl, haloalkoxy, alkoxy, alkenyl, alkynyl, cycloalkyl, cycloalkenyl, cycloalkynyl, heterocyclyl, aryl, or heteroaryl;

Ring A is aryl or heteroaryl;

Het is heterocyclyl;

$R^5$ is halogen, hydroxy, alkyl, haloalkyl, alkoxy, haloalkoxy, -oxo, or —C(═O)$OR^{5a}$, wherein $R^{5a}$ is hydrogen, alkyl, or haloalkyl;

p is a number of 0, 1, 2 or 3;

$R^{6c}$ is independently hydrogen, halogen, cyano, —$NO_2$, —$OR^{6d}$, —$SR^{6d}$, —$NR^{6d}R^{6e}$, —$COR^{6d}$, —$SO_2R^{6d}$, —C(═O)$OR^{6d}$, —C(═O)$NR^{6d}R^{6e}$, —C(═$NR^{6d}$)$NR^{6e}R^{6f}$, —N($R^{6d}$)C(═O)$R^{6e}$, —N($R^{6d}$)C(═O)$OR^{6e}$, —N($R^{6d}$)C(O)$NR^{6e}R^{6f}$, N($R^{6d}$)S(O)$NR^{6e}R^{6f}$, N($R^{6d}$)S(O)$_2NR^{6e}R^{6f}$, $NR^{6d}SO_2R^{6e}$, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is independently and optionally substituted with one or two or three substituents $R^{6g}$;

$R^{6d}$, $R^{6e}$ and $R^{6f}$, are independently hydrogen, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with one or two or three substituents $R^{6g}$;

$R^{6g}$, at each occurrence, is independently hydrogen, halogen, cyano, —$NO_2$, —$OR^{6h}$, —$SR^{6h}$, —$NR^{6h}R^{6i}$, —$COR^{6h}$, —$SO_2R^{6h}$, —C(═O)$OR^{6h}$, —C(═O)$NR^{6h}R^{6i}$, —C(═$NR^{6h}$)$NR^{6i}R^{6j}$, —N($R^{6h}$)C(═O)$R^{6i}$, —N($R^{6h}$)C(═O)$OR^{6i}$, —N($R^{6h}$)C(O)$NR^{6i}R^{6j}$, —N($R^{6h}$)S(O)$NR^{6i}R^{6j}$, —N($R^{6h}$)S(O)$_2NR^{6i}R^{6h}$, —$NR^{6h}SO_2R^{6i}$, alkyl, alkenyl, alkynyl, cycloalkyl, cycloalkenyl, cycloalkynyl, heterocyclyl, aryl, or heteroaryl, $R^{6h}$, $R^{6i}$ and $R^{6j}$, are independently hydrogen, alkyl, alkoxy, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl or heteroaryl is independently and optionally substituted with one or two or three substituents selected from halogen, —$C_{1-4}$alkyl, —$C_{1-4}$alkoxy, hydroxy, nitro, —$NH_2$, alkylamino, dialkylamino, or cyano.

Definition of $R^1$

In some embodiments, $R^1$ is —$OR^{1a}$ or —$NR^{1a}R^{1b}$, wherein $R^{1a}$ and $R^{1b}$ are defined as for Formula (II).

In some embodiments, $R^1$ is —$OR^{1a}$, or —$NR^{1a}R^{1b}$; wherein $R^{1a}$, $R^{1b}$, are independently hydrogen, —$C_{1-8}$alkyl, or —$C_{2-8}$alkenyl, each of said —$C_{1-8}$alkyl is optionally substituted with one or two or three substituents selected from heterocyclyl optionally substituted with $R^{1e}$, aryl optionally substituted with $R^{1e}$, $CH_3$—($OCH_2CH_2$)$_n$— (wherein n is a number of 3 to 10, preferably 4-8, more preferably 5-7) or —$OR^{1f}$;

wherein $R^{1e}$ is halogen, or —$C_{1-6}$alkyl optionally substituted with halogen;

wherein $R^{1f}$ is —$C_{1-8}$alkyl, aryl, or heteroaryl, each of which is optionally substituted with —$C_{1-4}$alkyl or halogen.

In some embodiments, $R^1$ is —$OR^{1a}$, wherein $R^{1a}$ is hydrogen.

In some embodiments, $R^1$ is —$OR^{1a}$, wherein $R^{1a}$ is —$C_{1-8}$alkyl optionally substituted with one or two or three substituents selected from halogen, —$C_{1-8}$alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3$—($OCH_2CH_2$)$_n$— (wherein n is a number of 3 to 10) or —$OR^{1f}$, wherein $R^{1e}$ and $R^{1f}$ are defined as for Formula (II).

In some embodiments, $R^1$ is —$OR^{1a}$, wherein $R^{1a}$ is unsubstituted $C_{1-8}$alkyl. In some embodiments, $R^1$ is —$OR^{1a}$, wherein $R^{1a}$ is straight. In some embodiments, $R^1$ is —$OR^{1a}$, wherein $R^{1a}$ is a branched alkyl. In some embodiments, $R^1$ is —$OR^{1a}$, wherein $R^{1a}$ is a branched alkyl, preferably —$C_{4-8}$alkyl, wherein the branched substituent is at the alpha position with respect to the oxygen atom, including, but not limited to butan-2-yl, pentan-2-yl, pentan-3-yl, heptan-2-yl, heptan-3-yl, heptan-4-yl, octan-2-yl, octan-3-yl, octan-4-yl, or octan-5-yl. In some embodiments, $R^1$ is methoxy, ethoxy, propoxy, butoxy, pentoxy, hexoxy, heptoxy or octoxy. In some embodiments, $R^1$ is preferably propoxy, isopropoxy, n-butoxy, isobutoxy, butan-2-yloxy (sec-butoxy), pentan-2-yloxy, pentan-3-yloxy, 2-methylbutoxy, heptan-2-yloxy, heptan-3-yloxy, heptan-4-yloxy, octan-2-yloxy, octan-3-yloxy, octan-4-yloxy, or octan-5-yloxy. In some embodiments, $R^1$ is n-butoxy, butan-2-yloxy (sec-butoxy), pentan-2-yloxy, pentan-3-yloxy, heptan-2-yloxy, heptan-3-yloxy, heptan-4-yloxy, octan-2-yloxy, octan-3-yloxy, octan-4-yloxy, or octan-5-yloxy.

In some embodiments, $R^1$ is —$OR^{1a}$, wherein $R^{1a}$ is —$C_{1-8}$alkyl, preferably —$C_{4-5}$alkyl, said alkyl is substituted with 1 to 3 halogens, e.g., fluoro.

In some embodiments, $R^1$ is —$OR^{1a}$, wherein $R^{1a}$ is —$C_{1-8}$alkyl, preferably —$C_{1-3}$alkyl, said alkyl is substituted with cycloalkyl optionally substituted with $R^{1e}$, heterocyclyl optionally substituted with $R^{1e}$, aryl optionally substituted with $R^{1e}$, or heteroaryl optionally substituted with $R^{1e}$, wherein $R^{1e}$ is defined as for Formula (II).

In some embodiments, $R^1$ is —$OR^{1a}$, wherein $R^{1a}$ is —$C_{1-8}$alkyl, preferably —$C_{1-3}$alkyl, said alkyl is substituted with heteroaryl, e.g., 5- to 6-membered heteroaryl comprising one or two or three heteroatoms selected from oxygen, nitrogen or optionally oxidized sulfur as ring members, said heteroaryl is optionally substituted with —$C_{1-6}$alkyl, preferably —$C_{1-4}$alkyl, more preferably methyl. In some embodiments, heteroaryl is pyridinyl, or imidazoyl or isoxazolyl. In some embodiments, $R^1$ is pyridin-3-ylmethoxy, 2-(1H-imidazol-1-yl)ethoxy, or (5-methylisoxazol-3-yl)methoxy.

In some embodiments, $R^1$ is —$OR^{1a}$, wherein $R^{1a}$ is —$C_{1-8}$alkyl, preferably —$C_{1-3}$alkyl, said alkyl is substituted with aryl, e.g., phenyl. In some embodiments, $R^1$ is 2-phenethoxy or 3-phenylpropoxy.

In some embodiments, $R^1$ is —$OR^{1a}$, wherein $R^{1a}$ is —$C_{1-8}$alkyl, preferably —$C_{1-3}$alkyl, said alkyl is substituted with —$OR^{1f}$, wherein $R^{1f}$ is —$C_{1-8}$alkyl or aryl (e.g., phenyl). In some embodiments, $R^1$ is 2-methoxyethoxy or 2-phenoxyethoxy.

In some embodiments, $R^1$ is —$OR^{1a}$, wherein $R^{1a}$ is —$C_{1-8}$alkyl, preferably —$C_{1-3}$alkyl, said alkyl is substituted with $CH_3$—($OCH_2CH_2$)$_n$—, wherein n is a number of 3 to 10, preferably 3 or 4 or 5. In some embodiments, $R^1$ is 2,5,8,11-tetraoxatridecan-13-yloxy.

In some embodiments, $R^1$ is —$OR^{1a}$, wherein $R^{1a}$ is —$C_{2-8}$alkenyl; preferably —$C_{2-6}$alkenyl; most preferably —$C_{4-6}$alkenyl. In an example, $R^1$ is but-3-enyloxy.

In some embodiments, $R^1$ is —$NR^{1a}R^{1b}$, wherein $R^{1a}$ and $R^{1b}$ are each hydrogen, or —$C_{1-8}$alkyl, preferably —$C_{1-6}$ alkyl, said alkyl is optionally substituted with one or two or three substituents selected from halogen, —$C_{1-8}$alkyl optionally substituted with $R^{1e}$, cycloalkyl optionally substituted with $R^{1e}$, heterocyclyl optionally substituted with $R^{1e}$, aryl optionally substituted with $R^{1e}$, or heteroaryl optionally substituted with $R^{1e}$, wherein $R^{1e}$ is —$C_{1-6}$alkyl, e.g., methyl.

In some embodiments, $R^1$ is —$NR^{1a}R^{1b}$, wherein $R^{1a}$ is hydrogen, and $R^{1b}$ is straight or branched —$C_{1-8}$alkyl. In some embodiments, $R^1$ is —$NR^{1a}R^{1b}$, wherein $R^{1a}$ is hydrogen, $R^{1b}$ is a branched alkyl, preferably —$C_{4-8}$alkyl, wherein the branched substituent is at the alpha position with respect to the oxygen atom, including, but not limited to butan-2-yl, pentan-2-yl, pentan-3-yl, heptan-2-yl, heptan-3-yl, heptan-4-yl, octan-2-yl, octan-3-yl, octan-4-yl, or octan-5-yl.

In some embodiments, $R^1$ is butylamino, N-butyl-N-methylamino, or isopentylamino.

In some embodiments, $R^1$ is optionally partially or fully deuterated, i.e., one or more carbon-bound hydrogen(s) in the definition of $R^1$ are replaced by one or more deuterium(s).

Definition of $R^5$

In some embodiments, $R^5$ is halogen, hydroxy, $C_{1-8}$alkyl, halo$C_{1-8}$alkyl, $C_{1-8}$alkoxy, halo$C_{1-8}$alkoxy, or —C(═O)$OR^{5a}$, wherein $R^{5a}$ is hydrogen, $C_{1-8}$alkyl, or halo$C_{1-8}$alkyl; and p is a number of 0, 1, or 2.

In some embodiments, $R^5$ is halogen, $C_{1-3}$alkyl, halo$C_{1-3}$alkyl, $C_{1-3}$alkoxy, or halo$C_{1-8}$alkoxy. In some embodiments, $R^5$ is methyl, ethyl, propyl, methoxy, ethoxy, propoxy, isopropoxy, trifluoromethoxy, or trifluoromethyl. In some embodiments, $R^5$ is methyl.

In some embodiments, p is a number of 1.

In some embodiments, $R^5$ and Het-$R^{6c}$ are at ortho positions on ring A.

Definition of Ring A

In some embodiments, Ring A is phenyl.

In some embodiments, ring A is 5- to 8-, preferably 5- to 6-membered heteroaryl comprising one or two or three heteroatoms selected from oxygen, nitrogen or optionally oxidized sulfur as ring members, preferably 5- to 6-membered heteroaryl comprising one or two nitrogen atoms as ring members. In some embodiments, ring A is pyridyl, e.g., pyridin-2-yl, pyridin-3-yl, pyridin-4-yl, pyridin-5-yl or pyridin-6-yl, preferably pyridin-2-yl or pyridin-3-yl. In some embodiments, ring A is pyrazolyl, i.e., 1H-pyrazol-4-yl.

In some embodiments, ring A is 1,2,3,4-tetrahydroisoquinolinyl, e.g., 1,2,3,4-tetrahydroisoquinolin-6-yl or 1,2,3,4-tetrahydroisoquinolin-7-yl.

Definition of Het

In some embodiments, Het is a monocyclic heterocyclyl; in some embodiments, Het is a fused bicyclic heterocyclyl; and in some embodiments, Het is a spiro bicyclic heterocyclyl.

In some embodiments, Het is a saturated heterocyclyl. In some embodiments, Het is a 4-, 5-, 6-, 7- or 8-membered saturated monocyclic heterocyclyl ring comprising one, two or three heteroatoms selected from oxygen, nitrogen or optionally oxidized sulfur as ring members. In some embodiments, Het is a 5-, 6-, 7- or 8-membered saturated monocyclic heterocyclyl ring comprising one or two or three nitrogen heteroatoms as ring members. In some embodiments, Het is a 5- or 6-membered saturated monocyclic heterocyclyl ring comprising one or two nitrogen heteroatoms as ring members. In some embodiments, Het is pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl, piperidin-5-yl), triazolyl (e.g., 1H-1,2,4-triazol-1-yl), azepanyl (e.g., azepan-2-yl, azepan-3-yl, azepan-4-yl, azepan-5-yl), diazepanyl (e.g., 1,4-diazepan-1-yl, 1,4-diazepan-2-yl, 1,4-diazepan-3-yl, 1,4-diazepan-4-yl), piperazinyl (e.g., piperazin-1-yl, piperazin-2-yl, piperazin-3-yl) or morpholino.

In some embodiments, Het is a bicyclic heterocyclyl ring comprising one, two or three heteroatoms selected from oxygen, nitrogen or optionally oxidized sulfur as ring members. In some example, Het is 2,5-diazabicyclo[2.2.1]heptan-2-yl.

In some embodiments, Het is a 6- to 14-membered, and more preferably 7- to 10-membered spiro bicyclic heterocyclyl. In some embodiments, the heterocyclyl is spiroheptanyl, spriodecanyl or spirononanyl comprising one or two nitrogen atoms as ring members. In some embodiments, the heterocyclyl is 8-azaspiro[4.5]decan-8-yl, 2,7-diazaspiro[3.5]nonan-7-yl, 2,8-diazaspiro[4.5]decan-2-yl, 2,7-diazaspiro[3.5]nonan-2-yl, 2,8-diazaspiro[4.5]decan-8-yl.

Definition of $R^{6c}$

In some embodiments, Het is optionally substituted with one or two or three substituents $R^{6c}$. In some embodiments, Het is optionally substituted with one $R^{6c}$.

In some embodiments, $R^{6c}$ is independently hydrogen, halogen, —$OR^{6d}$, —$SR^{6d}$, —$NR^{6d}R^{6e}$, —$COR^{6d}$, —$SO_2R^{6d}$, —C(═O)$NR^{6d}R^{6e}$, or —$C_{1-8}$alkyl, said —$C_{1-8}$ alkyl is independently and optionally substituted with one or two or three substituents $R^{6g}$;

- $R^{6d}$ and $R^{6e}$ are independently hydrogen, —$C_{1-8}$alkyl, —$C_{2-8}$alkenyl, heterocyclyl, or aryl, each of said —$C_{1-8}$alkyl, —$C_{2-8}$alkenyl, heterocyclyl, or aryl is optionally substituted with one or two or three substituents $R^{6g}$;
- $R^{6g}$, at each occurrence, is independently hydrogen, halogen, —$OR^{6h}$, —$SR^{6h}$, —$NR^{6h}R^{6i}$, —N($R^{6h}$)C(═O)$OR^{6i}$, —$C_{1-8}$alkyl, heterocyclyl, aryl, or heteroaryl,
- $R^{6h}$ and $R^{6i}$, are independently hydrogen or —$C_{1-8}$alkyl.

In some embodiments, $R^{6c}$ is —$COR^{6d}$, wherein $R^{6d}$ is —$C_{1-8}$alkyl optionally substituted with one or two substituents $R^{6g}$, wherein $R^{6g}$ is —$NR^{6h}R^{6i}$, —N($R^{6h}$)C(═O)$R^{6i}$, —$C_{1-8}$alkyl, aryl or heteroaryl, wherein $R^{6h}$ and $R^{6i}$ are defined as for formula (II). In some embodiments, $R^{6c}$ is —$COR^{6d}$, wherein $R^{6d}$ is —$C_{1-8}$alkyl (preferably $C_{1-6}$alkyl, more preferably $C_{1-4}$alkyl) optionally substituted with one or two substituents $R^{6g}$, wherein $R^{6g}$ is —$NR^{6h}R^{6i}$, —N($R^{6h}$)C(═O)$R^{6i}$, —$C_{1-8}$alkyl, aryl or heteroaryl, wherein $R^{6h}$ and $R^{6i}$ are each independently hydrogen or —$C_{1-8}$alkyl (preferably $C_{1-6}$alkyl, more preferably $C_{1-4}$alkyl).

In some embodiments, $R^{6c}$ is —$COR^{6d}$, wherein $R^{6d}$ is —$C_{2-8}$alkenyl.

In some embodiments, $R^{6c}$ is —$COR^{6d}$, wherein $R^{6d}$ is heterocyclyl.

In some embodiments, $R^{6c}$ is acetyl, 2-(dimethylamino)acetyl, 2-(dimethylamino)acetyl, aminoacetyl, 2-(methylamino)acetyl, 3-(dimethylamino)propanoyl, 4-(dimethylamino)butanoyl, 5-(dimethylamino)pentanoyl, (2S,3S)-2-amino-3-methylpentanoyl, 2-(methylamino)acetyl, 2-amino-4-methylpentanoyl, 2-amino-3-methylbutanoyl, 2-(dimethylamino)acetyl, phenylpropanoyl, 2-(piperazin-1-yl)acetyl, acryloyl, piperazine-2-carbonyl, piperidine-4-carbonyl, pyrrolidine-2-carbonyl, or 2-(N-methylacetamido)acetyl.

In some embodiments, $R^{6c}$ is —$C_{1-8}$alkoxy, preferably —$C_{1-6}$alkoxy, e.g., methoxy.

In some embodiments, $R^{6c}$ is —$C_{1-8}$alkyl, preferably —$C_{1-6}$alkyl, optionally substituted with one or two substituents $R^{6g}$, wherein $R^{6g}$ is —$OR^{6h}$, —$NR^{6h}R^{6i}$, heterocyclyl, aryl, wherein $R^{6h}$ and $R^{6i}$ are defined as for Formula (II). In some aspects, $R^{6c}$ is —$C_{1-8}$alkyl, preferably —$C_{1-6}$alkyl, optionally substituted with one substituents $R^{6g}$, wherein $R^{6g}$ is —$OR^{6h}$, —$NR^{6h}R^{6i}$, heterocyclyl (e.g., morpholino), aryl (e.g., phenyl), wherein $R^{6h}$ and $R^{6i}$ are —$C_{1-4}$alkyl, preferably methyl. In some embodiments, $R^{6c}$ is methyl, ethyl, isobutyl, methoxymethyl, 2-methoxyethyl, (methylamino)methyl, 2-(dimethylamino)ethyl, (dimethylamino)methyl, 2-aminoethyl, 2-(methylamino)ethyl, 2-(dimethylamino)ethyl, morpholinomethyl, or phenethyl.

In some embodiments, $R^{6c}$ is heterocyclyl, optionally substituted with one substituent $R^{6g}$. In some embodiments, $R^{6c}$ is heterocyclyl, optionally substituted with one substituent $R^{6g}$ which is heterocyclyl. In some embodiments, $R^{6c}$ is 4-morpholinopiperidin-1-yl.

In some embodiments, $R^{6c}$ is —C(═O)$NR^{6d}R^{6e}$, wherein $R^{6d}$ and $R^{6e}$ are independently hydrogen, —$C_{1-8}$alkyl (preferably —$C_{1-3}$alkyl), or aryl, said —$C_{1-8}$alkyl or aryl is independently and optionally substituted with halogen or —$C_{1-4}$alkyl. In some embodiments, $R^{6c}$ is —C(═O)$NR^{6d}R^{6e}$, wherein $R^{6d}$ and $R^{6e}$ are independently hydrogen and —$C_{1-4}$alkyl. In some embodiments, $R^{6c}$ is —C(═O)$NR^{6d}R^{6e}$, wherein $R^{6d}$ and $R^{6e}$ are independently hydrogen and aryl optionally substituted halogen. In some embodiments, $R^{6c}$ is dimethylcarbamoyl, isopropylcarbamoyl, or 2,4,5-trifluorophenylcarbamoyl.

In some embodiments, $R^{6c}$ is —$NR^{6d}R^{6e}$, wherein $R^{6d}$ and $R^{6e}$ are independently hydrogen, or —$C_{1-8}$alkyl (preferably —$C_{1-6}$alkyl, more preferably —$C_{1-3}$alkyl, most preferably methyl). In some embodiments, $R^{6c}$ is dimethylamino, or amino.

In some embodiments, $R^{6c}$ is —$SO_2R^{6d}$, wherein $R^{6d}$ is —$C_{1-8}$alkyl, —$C_{2-8}$alkenyl, —$C_{2-8}$alkynyl, cycloalkyl, cycloalkenyl, cycloalkynyl, heterocyclyl, aryl, or heteroaryl. In some embodiments, $R^{6c}$ is —$SO_2R^{6d}$, wherein $R^{6d}$ is —$C_{1-8}$alkyl (preferably —$C_{1-6}$alkyl). In some embodiments, $R^{6c}$ is propylsulfonyl.

In some embodiments, Het is pyrrolidinyl, optionally substituted with one or two or three substituents selected from methyl, (dimethylamino)methyl, or dimethylamino. In some embodiments, Het is 1-methylpyrrolidin-3-yl, pyrrolidin-1-yl, 3-((dimethylamino)methyl)pyrrolidin-1-yl, or 3-(dimethylamino)pyrrolidin-1-yl.

In some embodiments, Het is piperazinyl, optionally substituted with one or two or three substituents selected from acryloyl, 2-(dimethylamino)acetyl, aminoacetyl, 2-(methylamino)acetyl, 3-(dimethylamino)propanoyl, 2-(piperazin-1-yl)acetyl, piperazine-2-carbonyl, 4-(dimethylamino)butanoyl, 5-(dimethylamino)pentanoyl, methyl, piperidine-4-carbonyl, acetyl, 2-(N-methylacetamido)acetyl, isopropylcarbamoyl, 2,4,5-trifluorophenylcarbamoyl, (2S,3S)-2-amino-3-methylpentanoyl, 2-methoxyethyl, 2-(methylamino)acetyl, ethyl, isobutyl, pyrrolidine-2-carbonyl, 2-amino-4-methylpentanoyl, 2-amino-3-methylbutanoyl, 2-(dimethylamino)acetyl, 2-(methylamino)ethyl, 2-(dimethylamino)ethyl, amino, phenylpropanoyl, propylsulfonyl, or 2-aminoethyl. In some embodiments, Het is piperazin-1-yl, 4-acryloylpiperazin-1-yl, 4-(2-(dimethylamino)acetyl)piperazin-1-yl, (4-aminoacetyl)piperazin-1-yl, piperazin-1-yl, 4-(2-(methylamino)acetyl)piperazin-1-yl), 4-(3-(dimethylamino)propanoyl)piperazin-1-yl, 4-(2-(piperazin-1-yl)acetyl)piperazin-1-yl, 4-(piperazine-2-carbonyl)piperazin-1-yl, 4-acryloylpiperazin-1-yl, 4-(4-(dimethylamino)butanoyl)piperazin-1-yl, 4-(5-(dimethylamino)pentanoyl)piperazin-1-yl, 3,5-dimethylpiperazin-1-yl, 4-(piperidine-4-carbonyl)piperazin-1-yl, 4-acetylpiperazin-1-yl, 4-(2-(N-methylacetamido)acetyl)piperazin-1-yl, 4-(isopropylcarbamoyl)piperazin-1-yl, 4-(2,4,5-trifluorophenylcarbamoyl)piperazin-1-yl, 4-(3,5-dimethylpiperazin-1-yl, 4-((2S,3S)-2-amino-3-methylpentanoyl)piperazin-1-yl, 4-(2-methoxyethyl)piperazin-1-yl, 4-(2-(methylamino)acetyl)piperazin-1-yl, 4-ethylpiperazin-1-yl, 4-isobutylpiperazin-1-yl, 4-(pyrrolidine-2-carbonyl)piperazin-1-yl, 4-(2-amino-4-methylpentanoyl)piperazin-1-yl, 4-(2-amino-3-methylbutanoyl)piperazin-1-yl, 4-(2-(dimethylamino)acetyl)piperazin-1-yl, (S)-2-methylpiperazin-1-yl, (R)-2-methylpiperazin-1-yl, 4-(2-(methylamino)ethyl)piperazin-1-yl, 4-(2-(dimethylamino)ethyl)piperazin-1-yl, 4-(2-amino-3-phenylpropanoyl)piperazin-1-yl, 4-(propylsulfonyl)piperazin-1-yl, 4-(2-aminoethyl)piperazin-1-yl, or 3-methylpiperazin-1-yl.

In some embodiments, Het is piperidinyl, optionally substituted with one or two or three substituents selected from 2-(dimethylamino)acetyl, methoxy, methoxymethyl, (methylamino)methyl, 4-morpholinopiperidin-1-yl, morpholinomethyl, 2-(dimethylamino)ethyl, phenethyl, (dimethylamino)methyl, amino, dimethylamino, or dimethylcarbamoyl. In some embodiments, Het is piperidin-4-yl, 4-(2-(dimethylamino)acetyl)piperidin-1-yl, piperidin-3-yl, piperidin-4-yl, piperidin-1-yl, piperidin-4-yl, 4-methoxypiperidin-1-yl, 4-(methoxymethyl)piperidin-1-yl, 4-((methylamino)methyl)piperidin-1-yl, (4-morpholinopiperidin-1-yl)pyridin-3-yl, 4-(morpholinomethyl)piperidin-1-yl, 4-(2-(dimethylamino)ethyl)piperidin-1-yl, 1-phenethylpiperidin-4-yl, 4-((dimethylamino)methyl)piperidin-1-yl, 4-aminopiperidin-1-yl, 4-(dimethylamino)piperidin-1-yl, or 4-(dimethylcarbamoyl)piperidin-1-yl.

In some embodiments, Het is azepan-1-yl or 1,4-diazepan-1-yl.

In some embodiments, Het is octahydro-2H-isoindol-2-yl.

In some embodiments, Het is morpholino.

In some embodiments, Het is 8-azaspiro[4.5]decan-8-yl, 2,7-diazaspiro[3.5]nonan-7-yl, 2,8-diazaspiro[4.5]decan-2-yl, 2,7-diazaspiro[3.5]nonan-2-yl, 2,8-diazaspiro[4.5]decan-8-yl, (1R,4R)-2,5-diazabicyclo[2.2.1]heptan-2-yl.

In some embodiments, ring A is phenyl, and the methylene group and Het on the phenyl ring are in para positions of the phenyl ring, and said phenyl ring is further optionally substituted with one $R^5$, wherein $R^5$ is defined as in each embodiment above. In other embodiments, ring A is pyridyl, and the methylene group and Het on the pyridyl ring are in para positions of the pyridyl ring, and said pyridyl ring is further optionally substituted with one $R^5$, wherein $R^5$ is defined as in each embodiment above. In some embodiments, ring A is pyridin-2-yl or pyridin-3-yl.

In some embodiments, disclosed herein is a compound, or a pharmaceutically acceptable salt thereof, or a stereoisomer thereof, selected from the specific compounds exemplified herein:

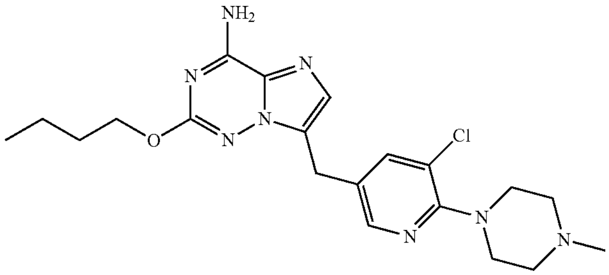
,
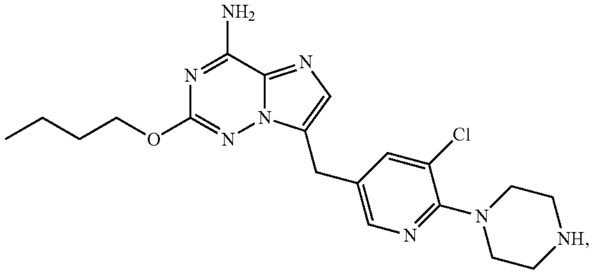
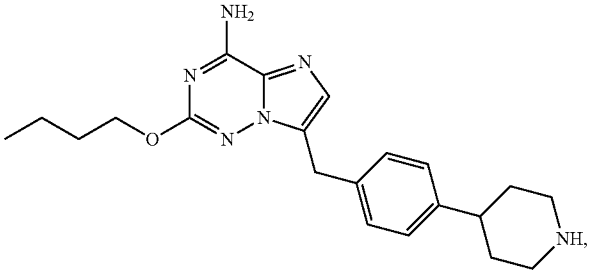
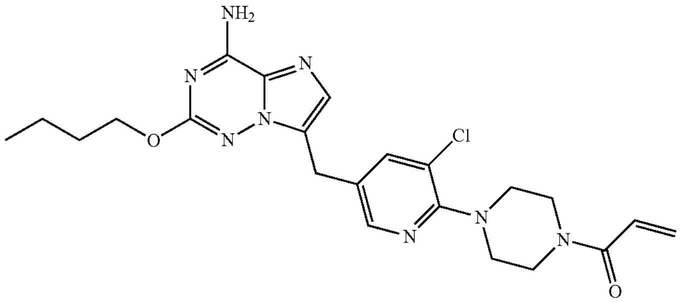
,
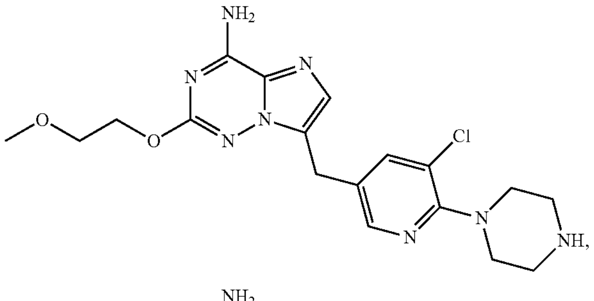
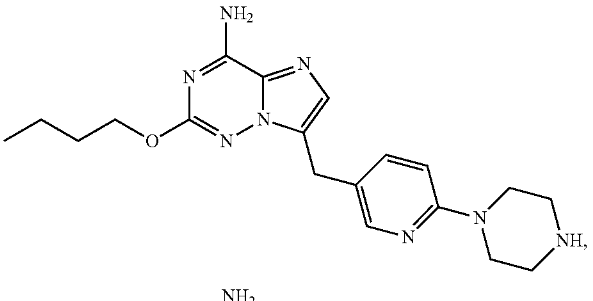
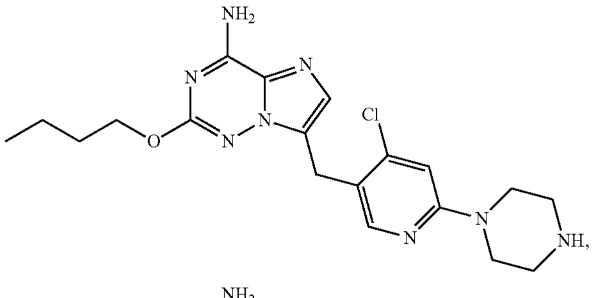
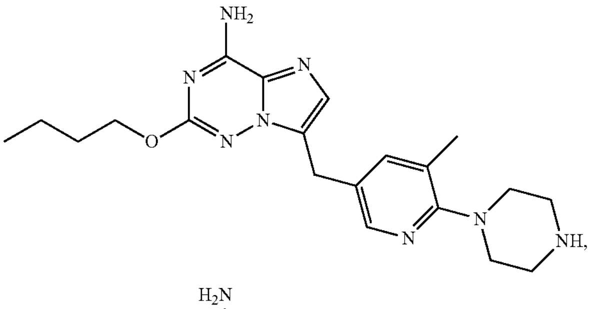
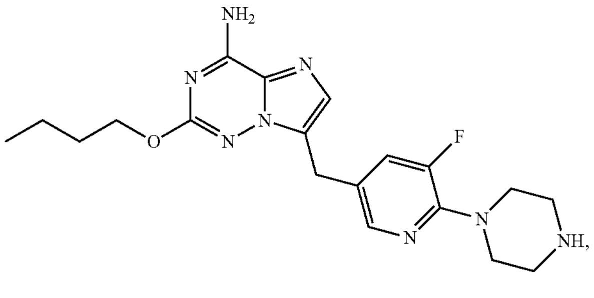
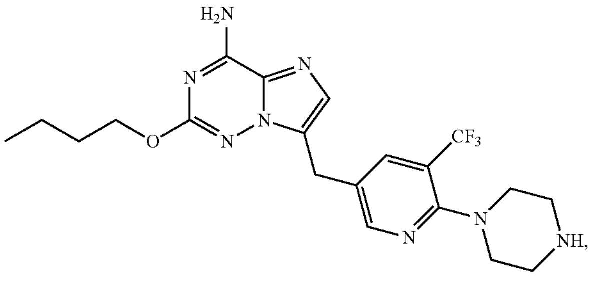

-continued
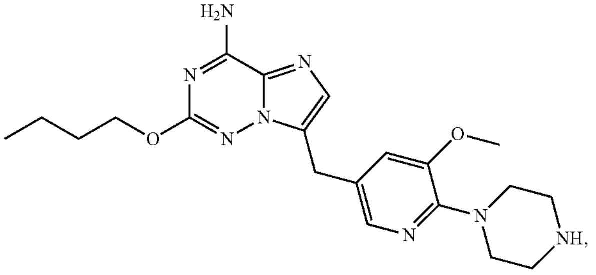
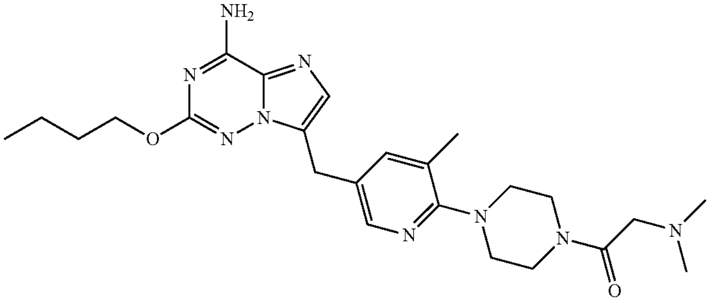
,
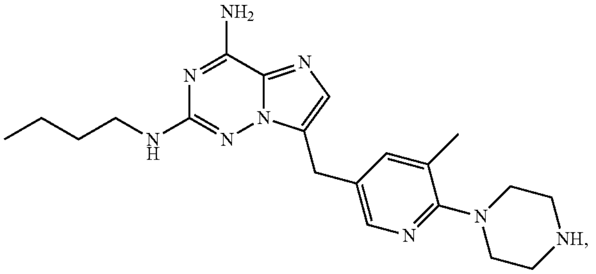
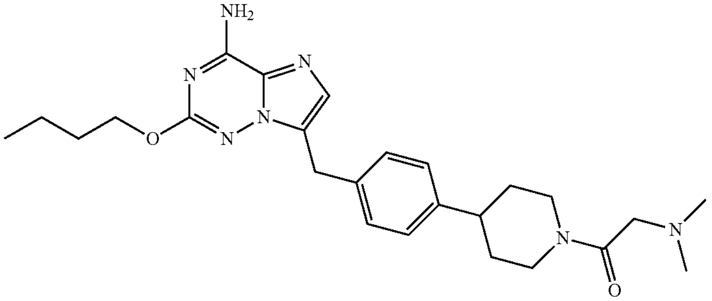
,
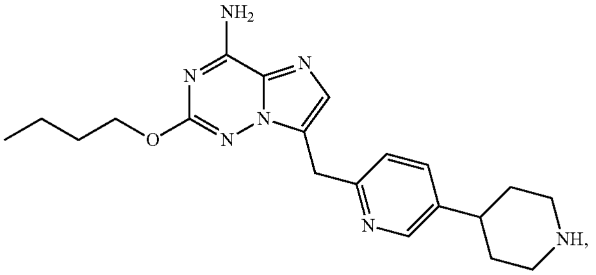
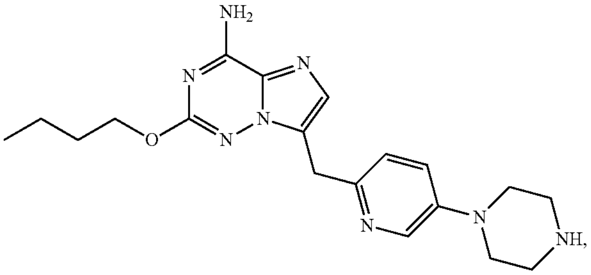
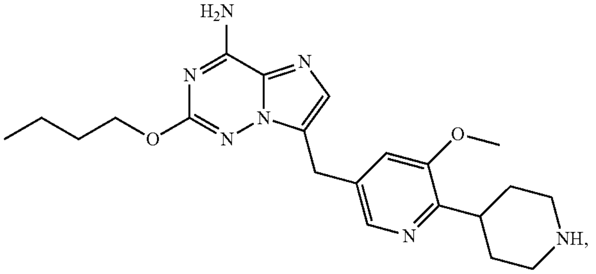
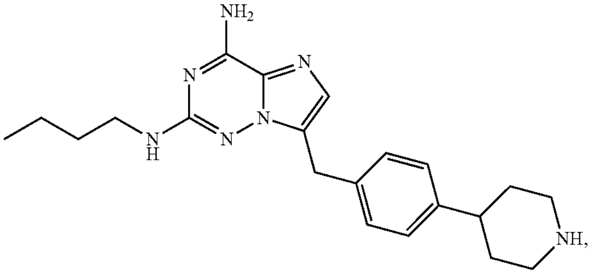

-continued
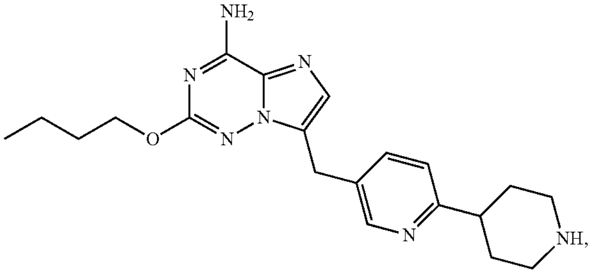
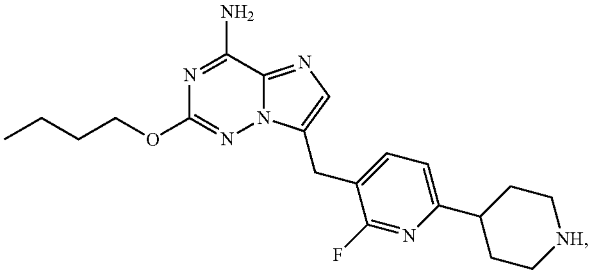
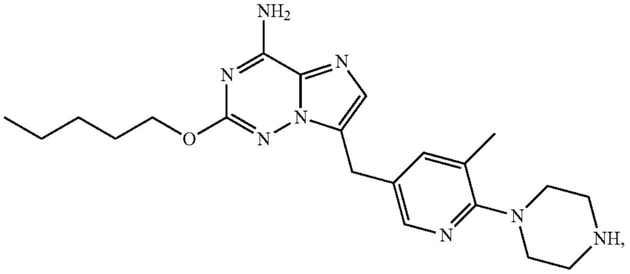
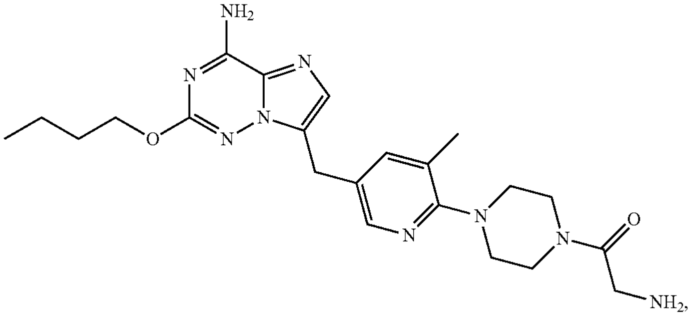
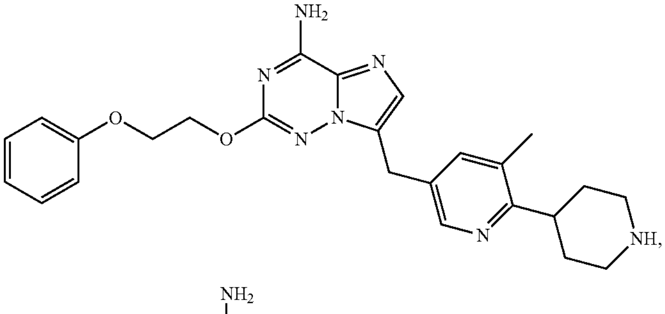
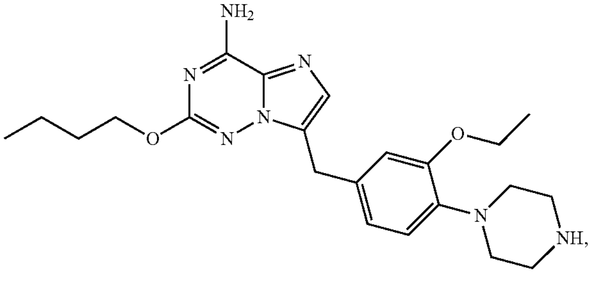
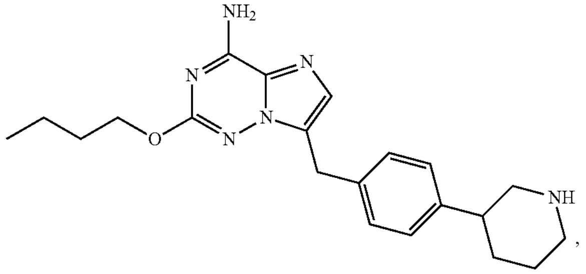
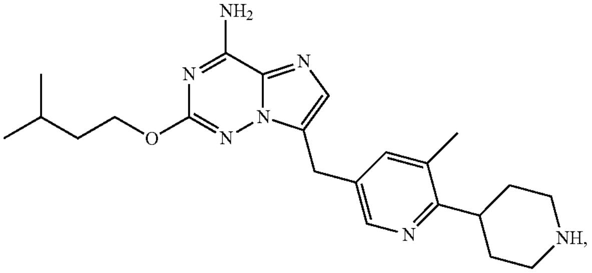
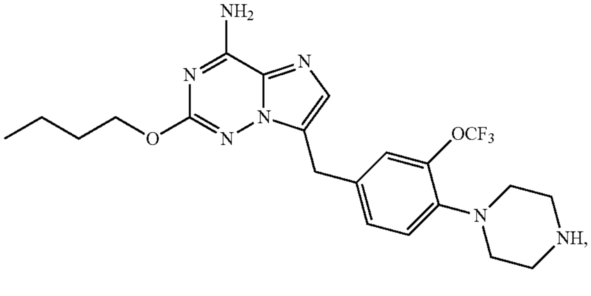

-continued
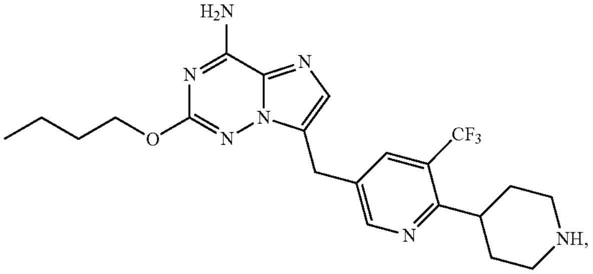
,
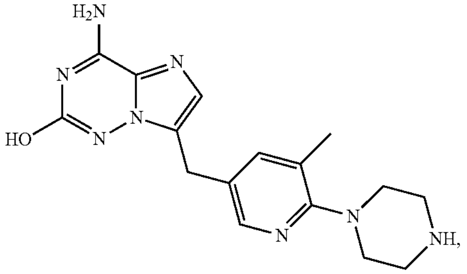
,
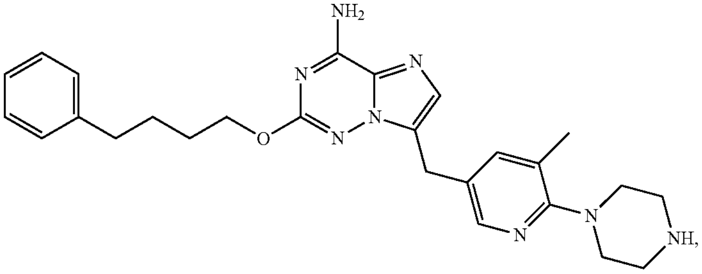
,
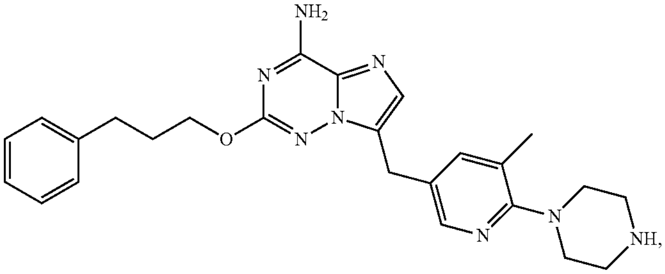
,
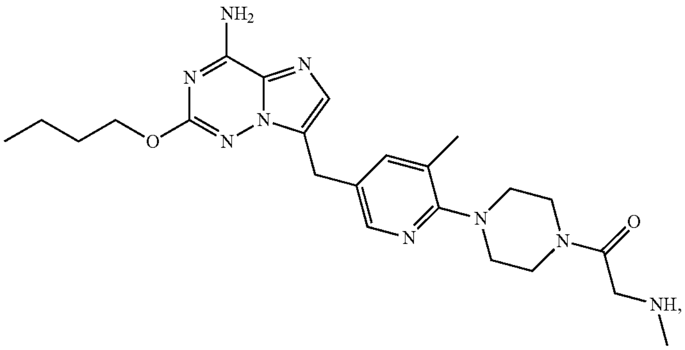
,
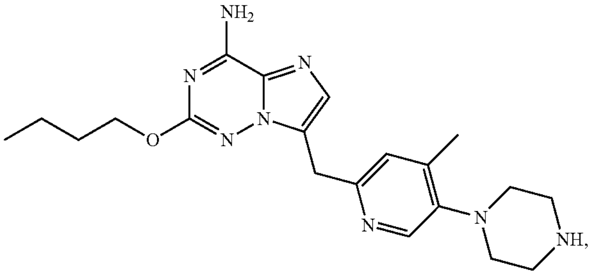
,
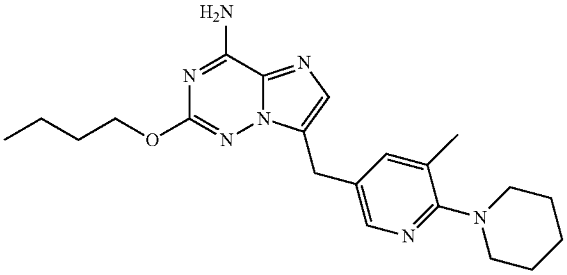
,
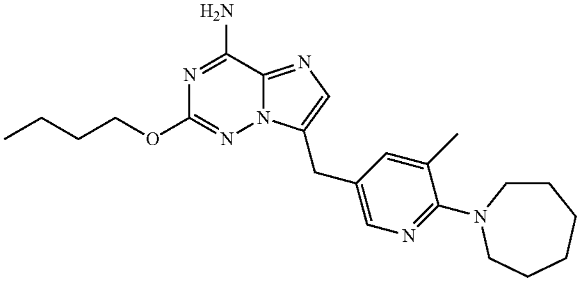
,
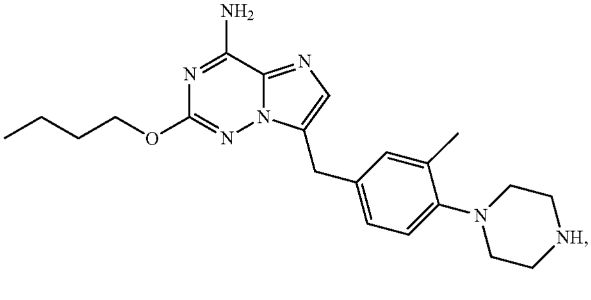
, -continued
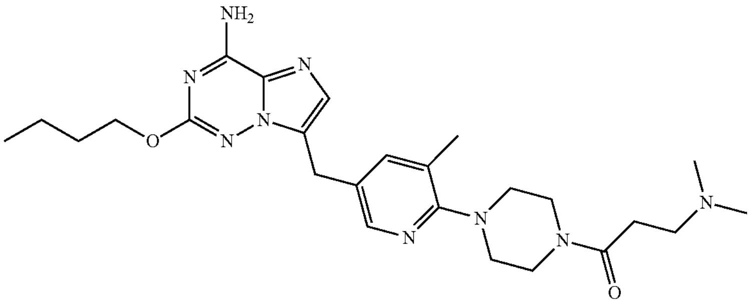
,
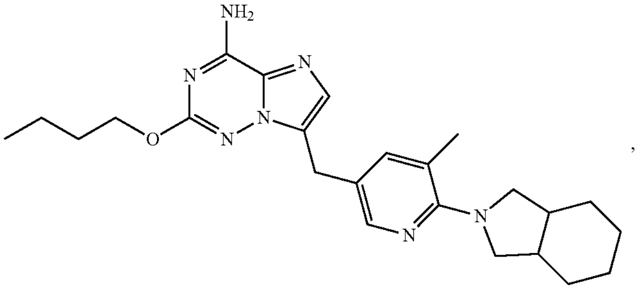
,
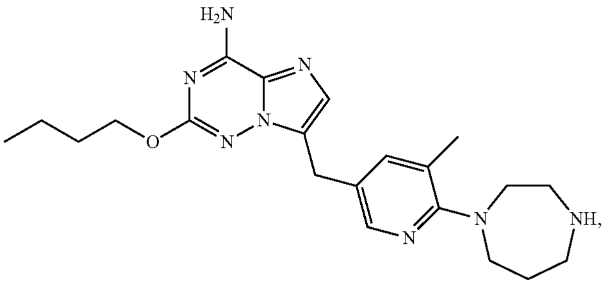
,
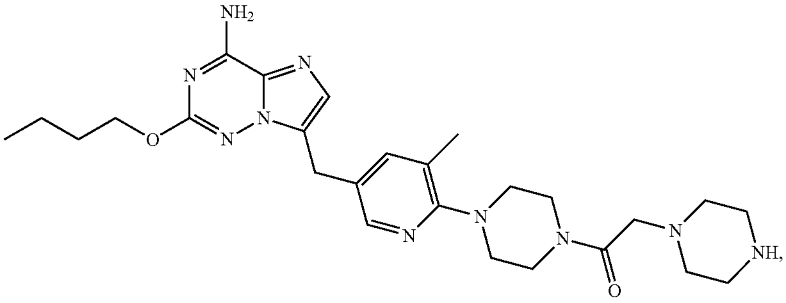
,
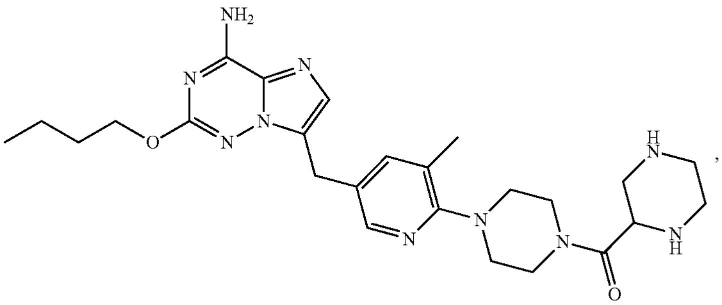
, -continued
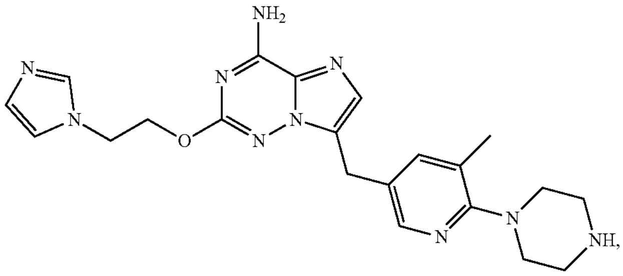
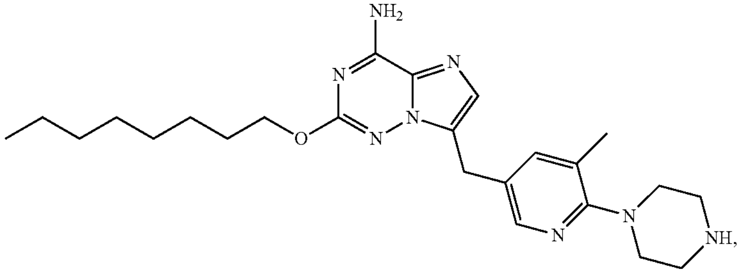
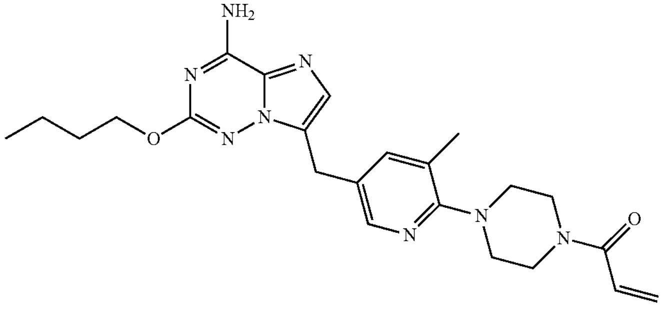
,
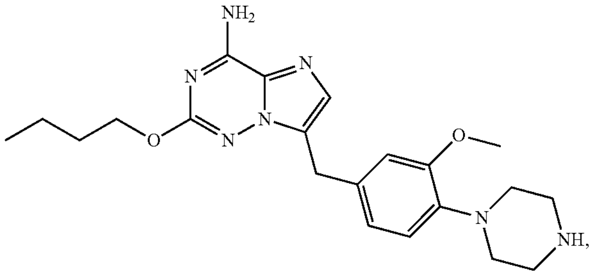
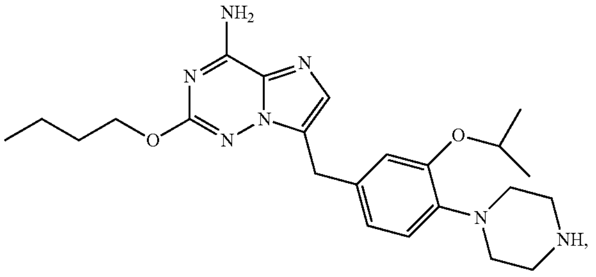
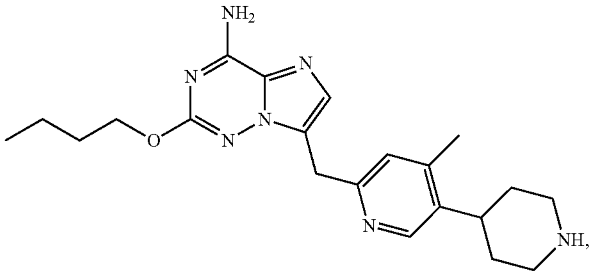
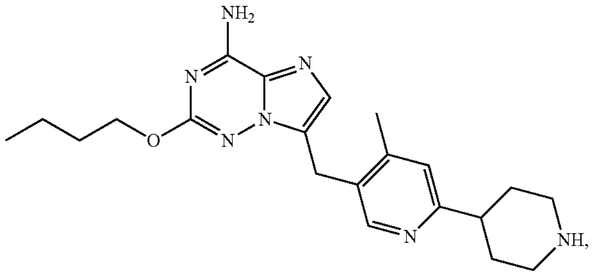
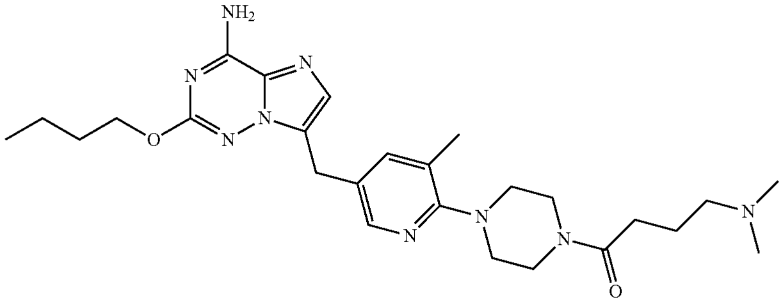
, -continued
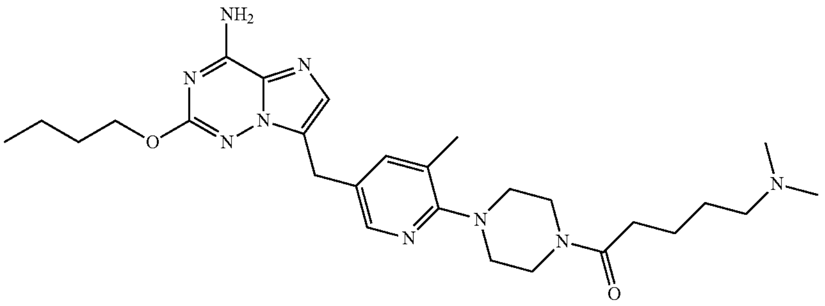
,
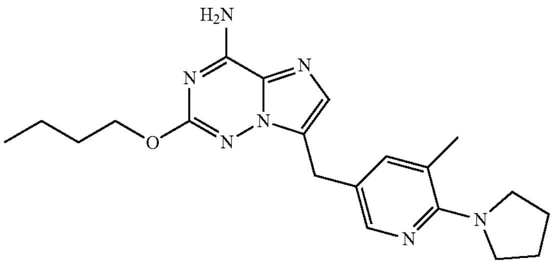
,
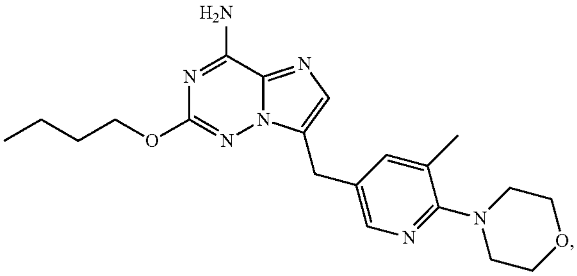
,
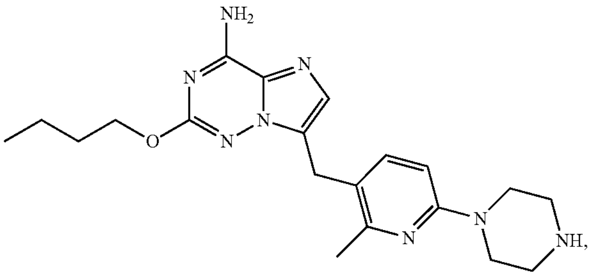
,
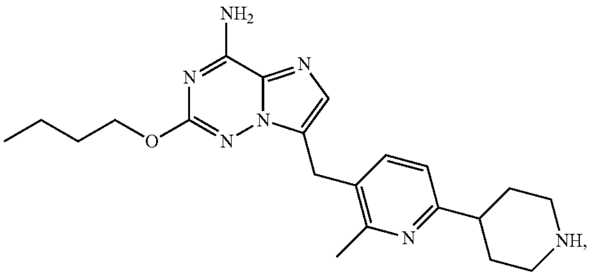
,
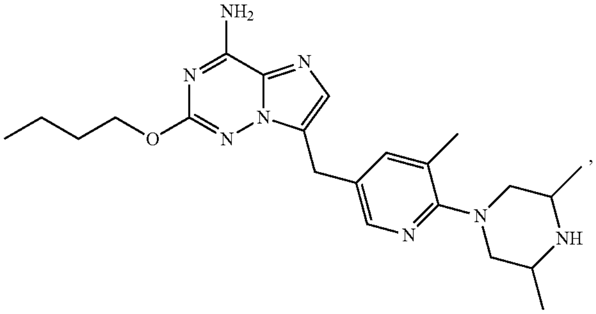
,
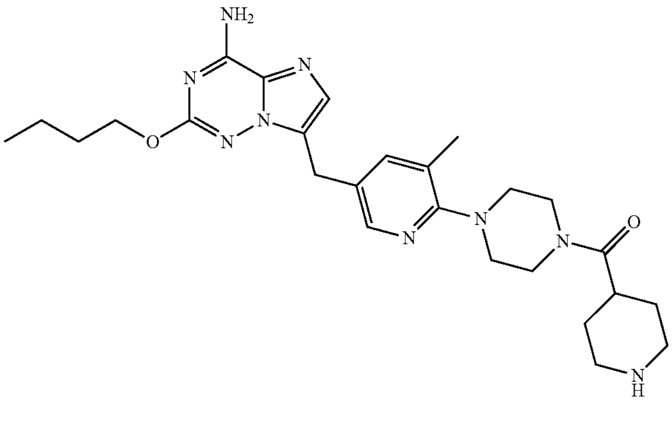
, -continued
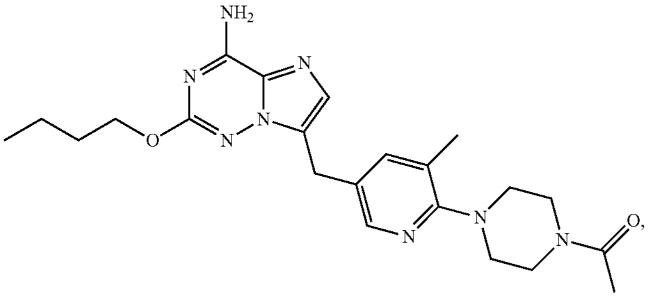
,
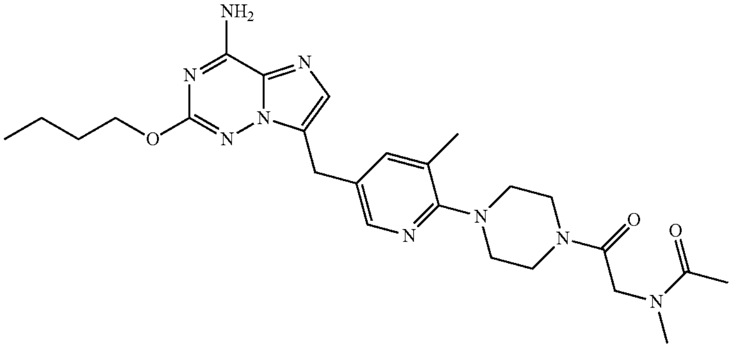
,
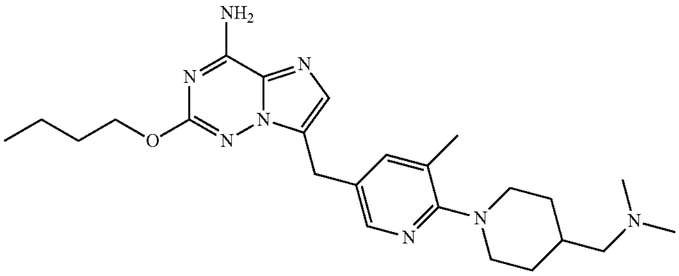
,
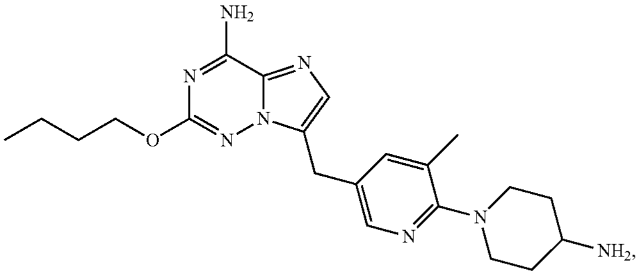
,
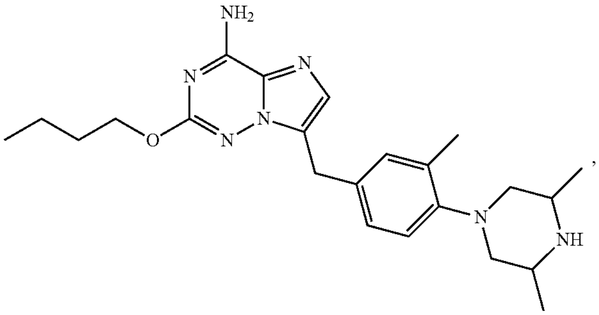
, -continued
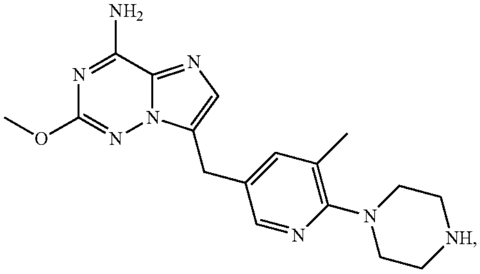
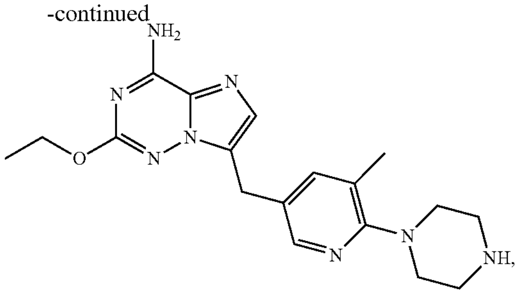
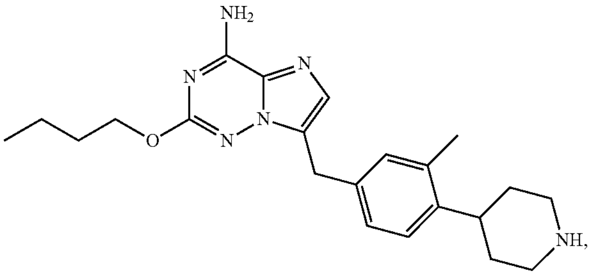
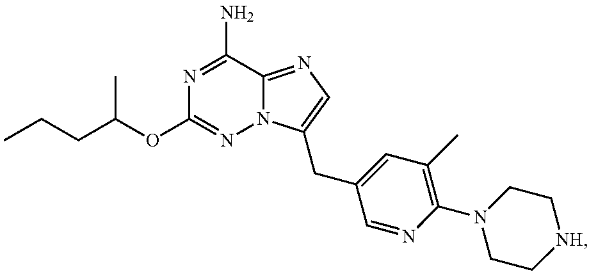
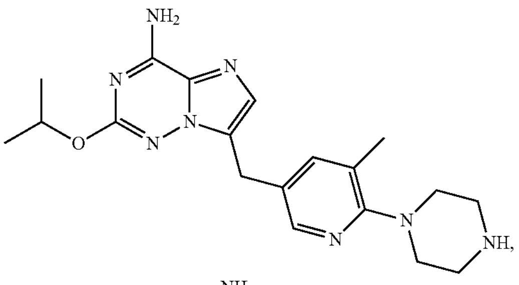
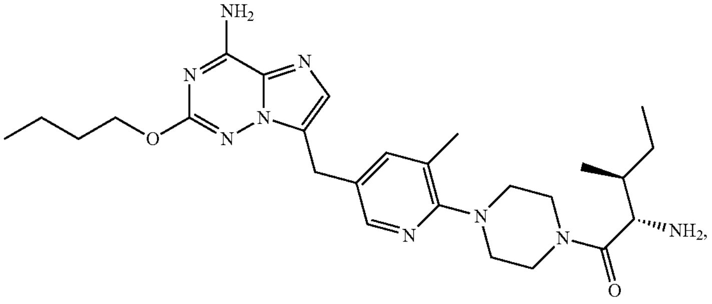
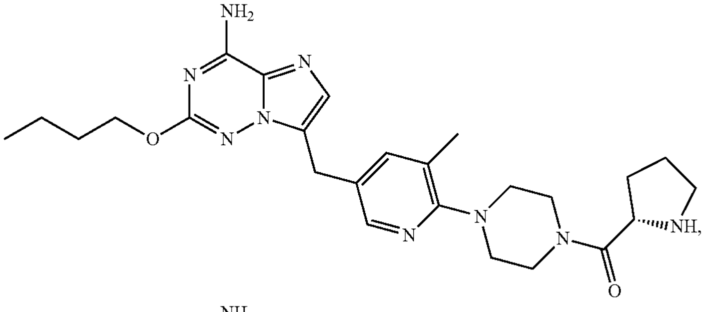
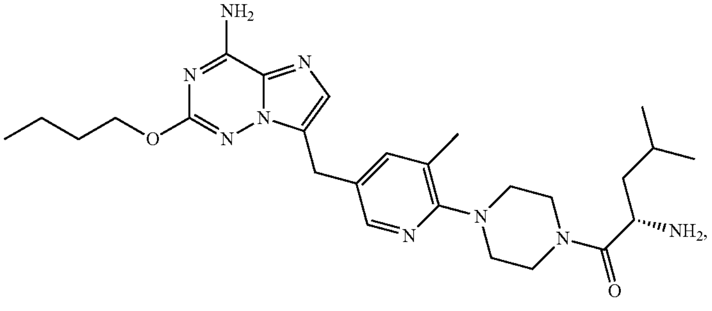

-continued
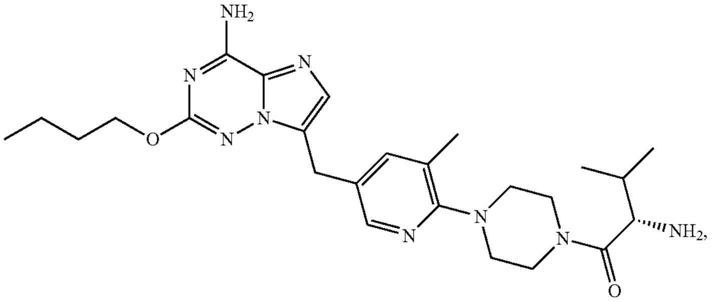
,
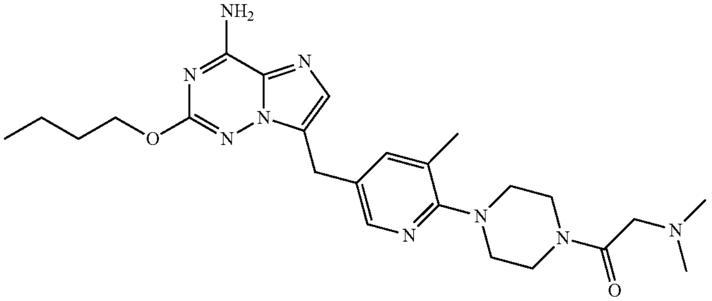
,
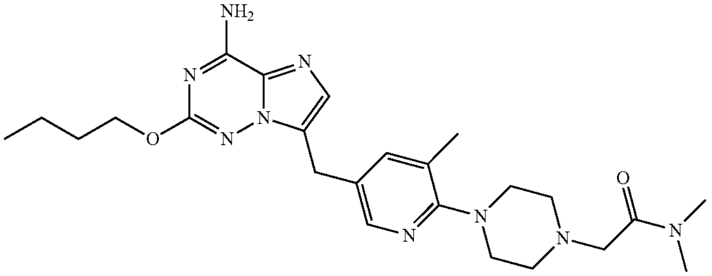
,
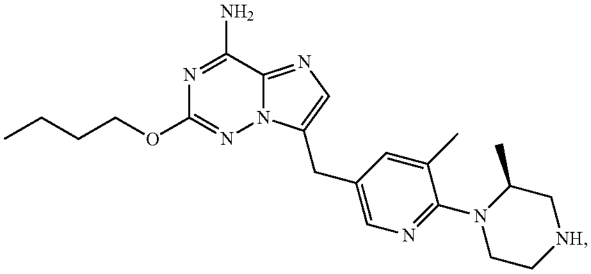
,
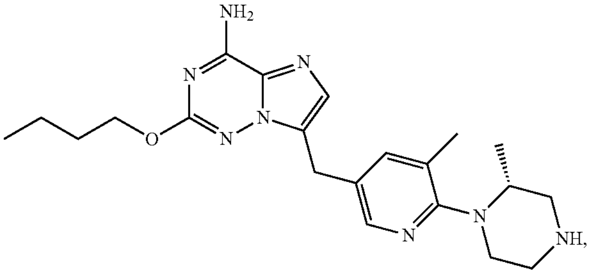
,
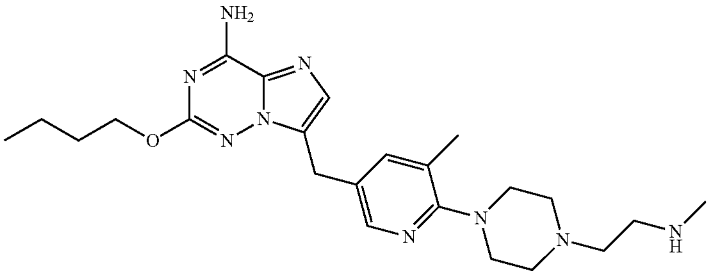
, -continued
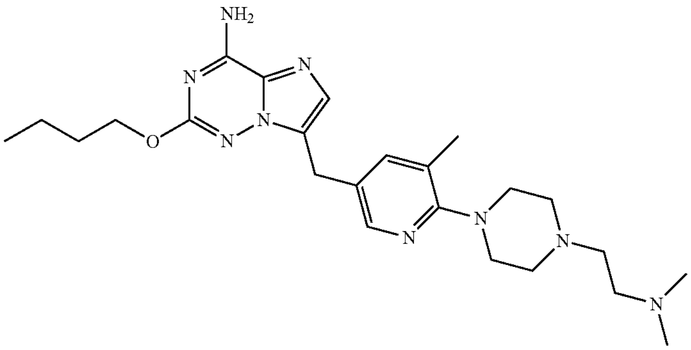
,
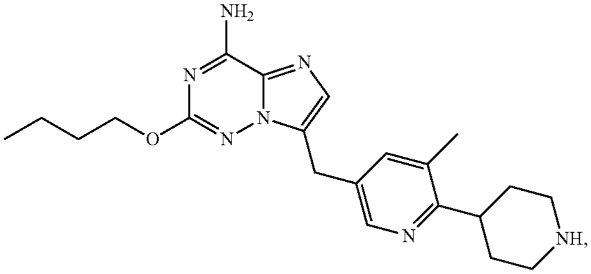
,
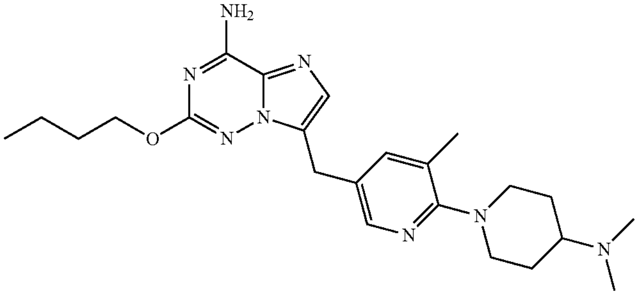
,
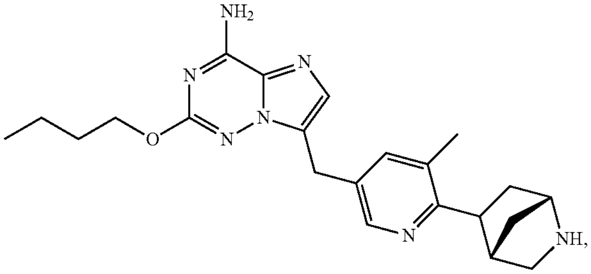
,
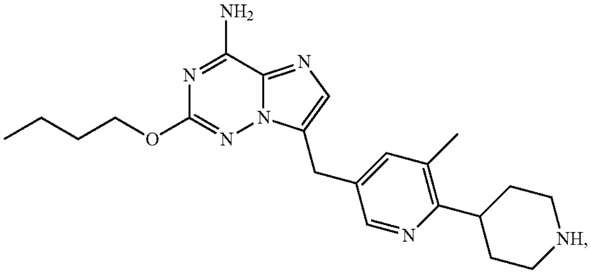
,
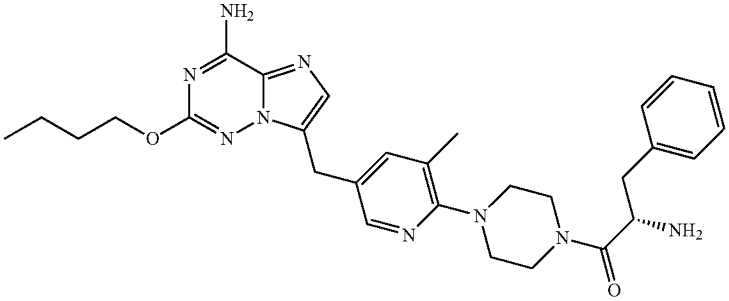
, -continued
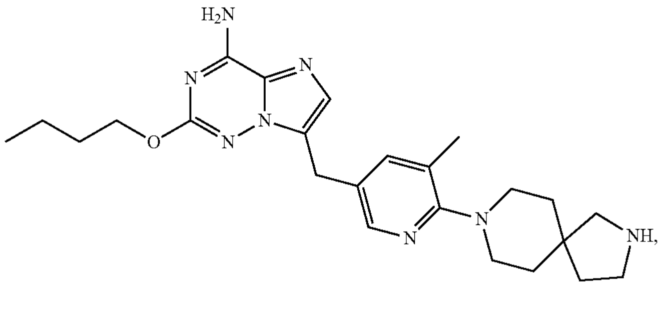
,
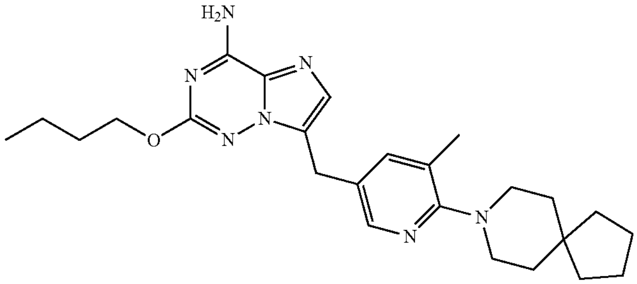
,
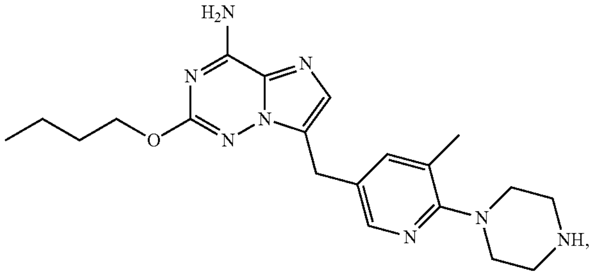
,
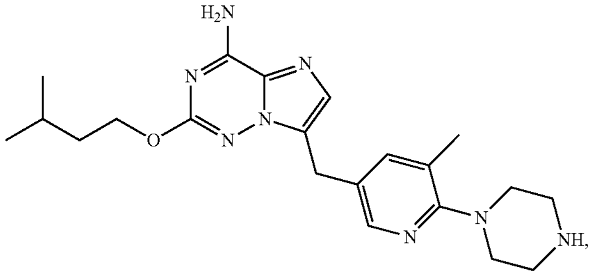
,
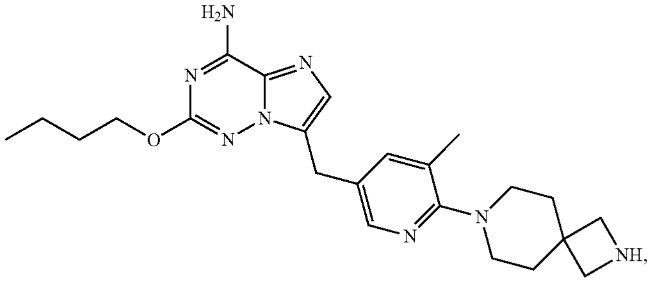
,
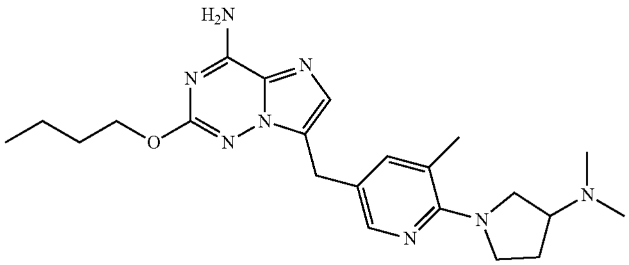
,
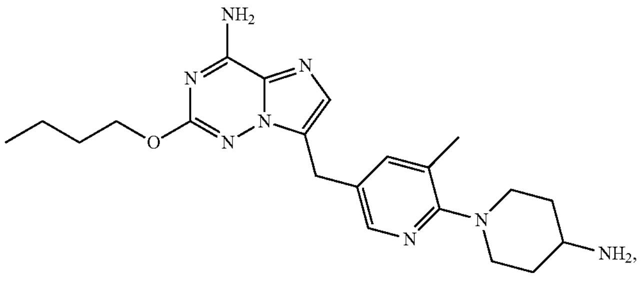
, -continued
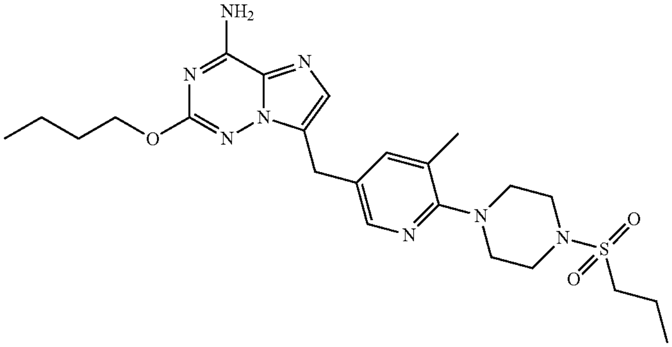
,
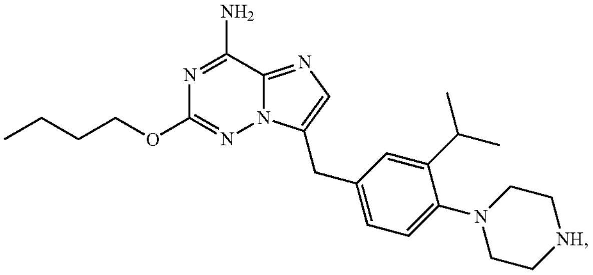
,
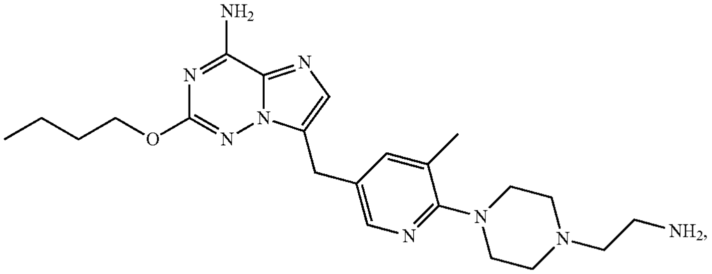
,
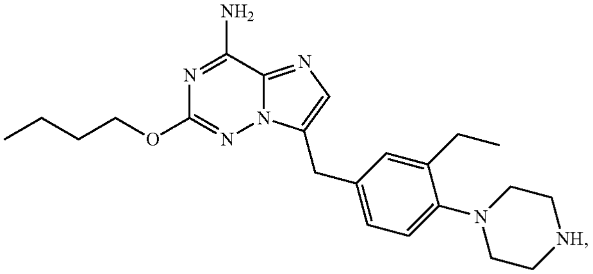
,
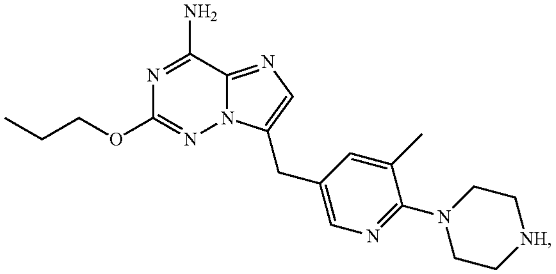
,
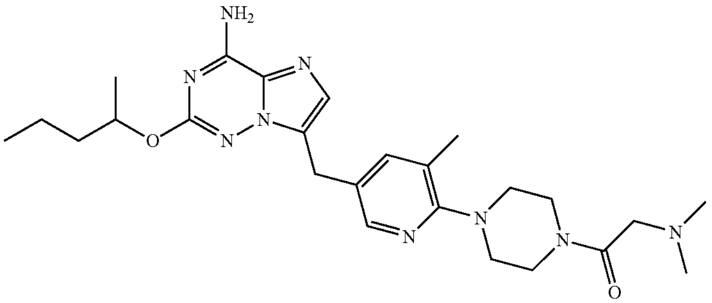
, -continued
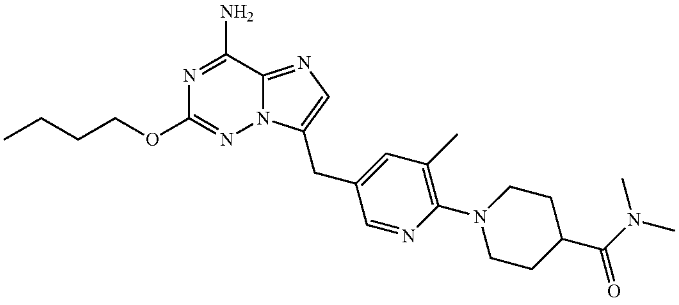
,
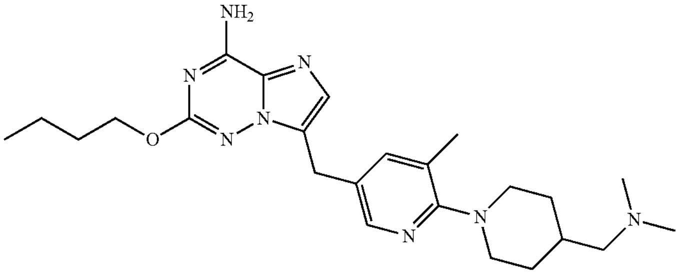
,
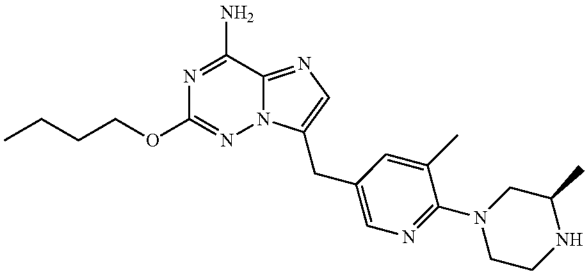
,
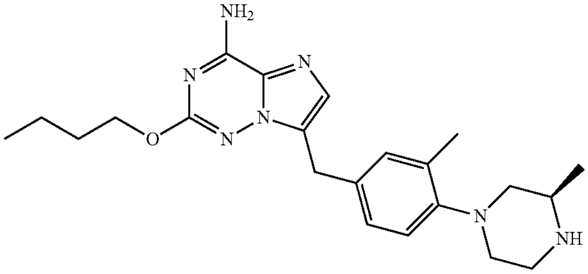
,
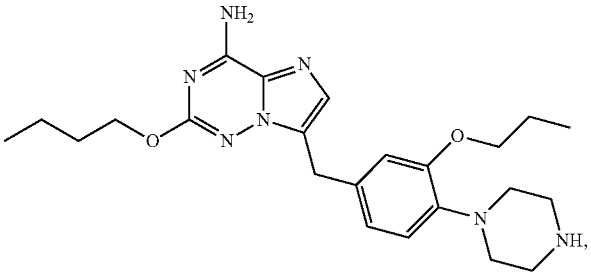
, -continued
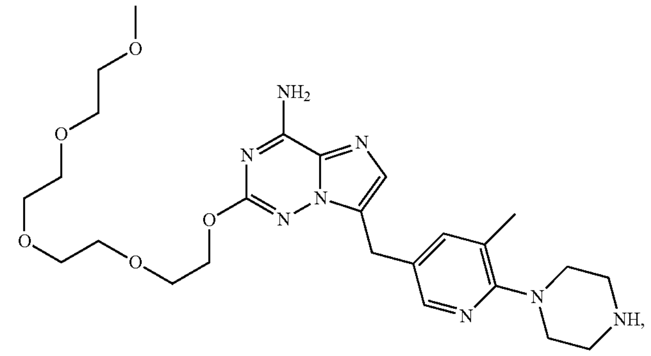
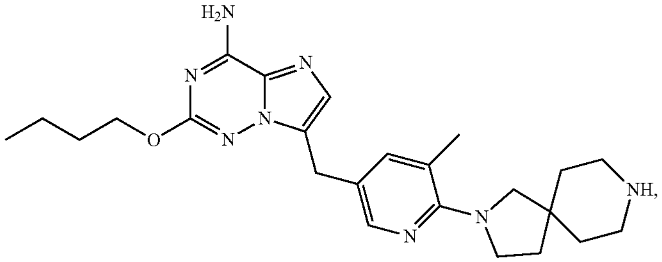
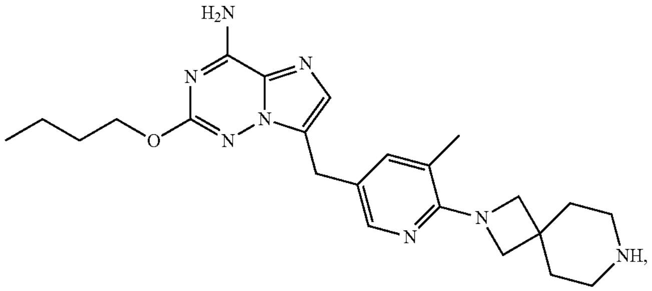
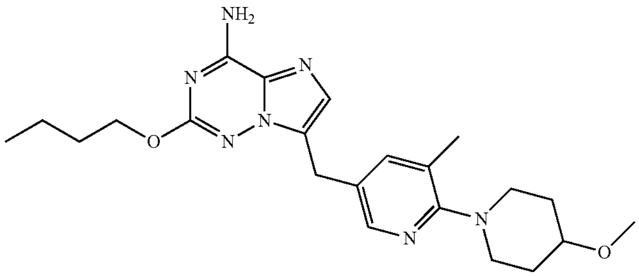
,
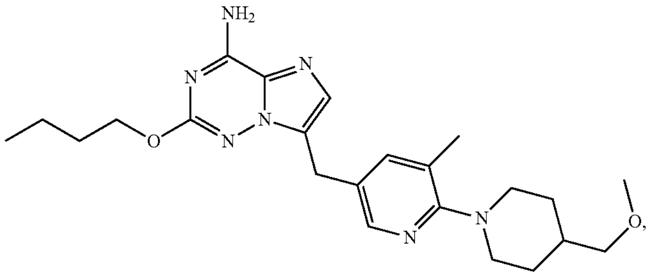
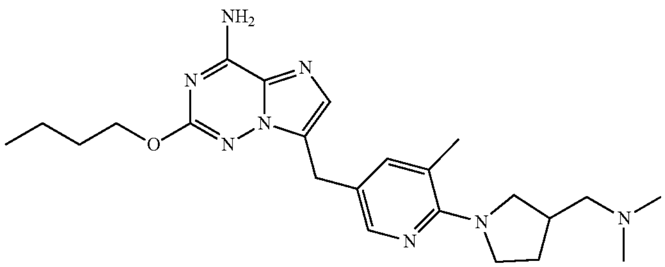
, -continued
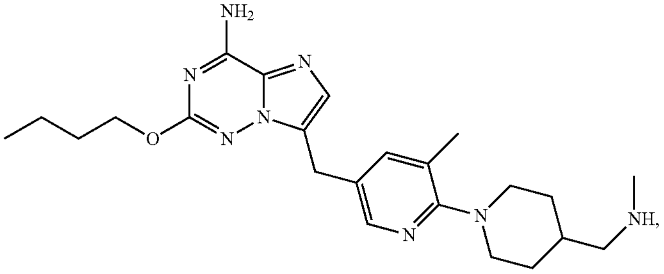
,
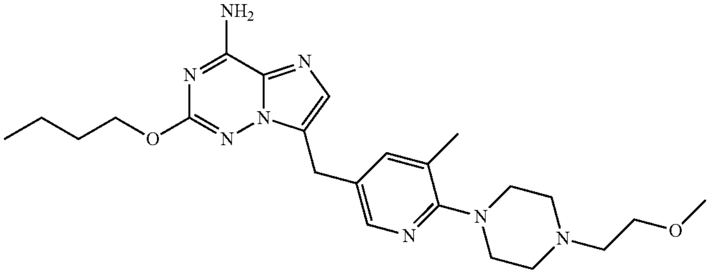
,
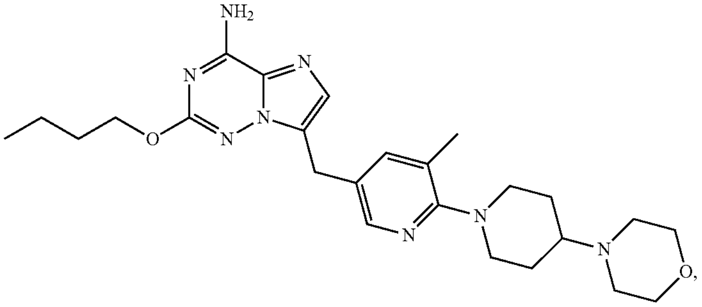
,
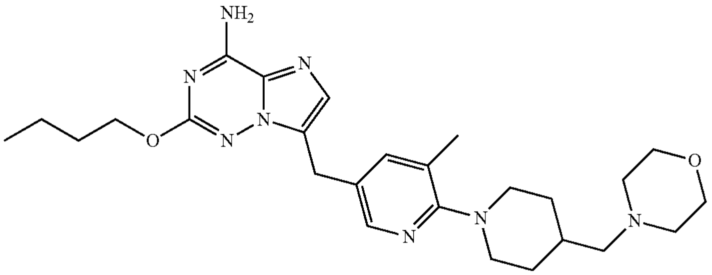
,
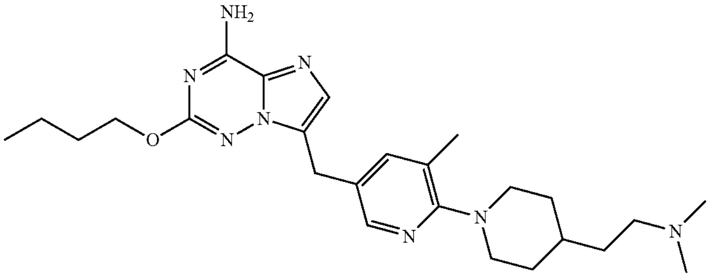
,
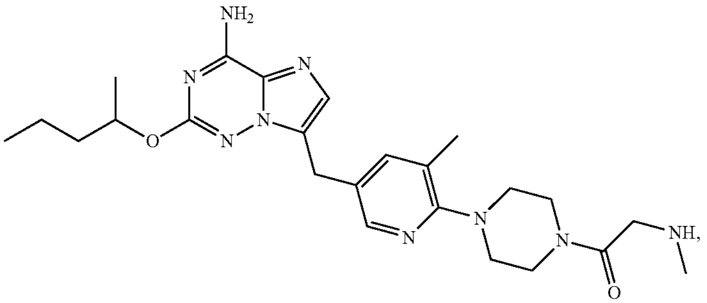
, -continued
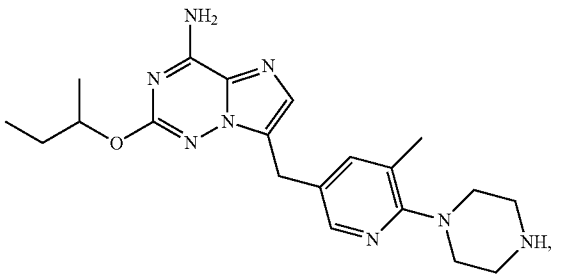
,
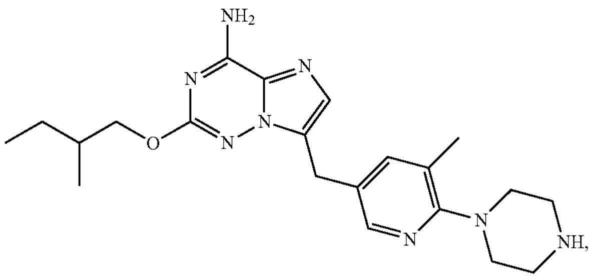
,
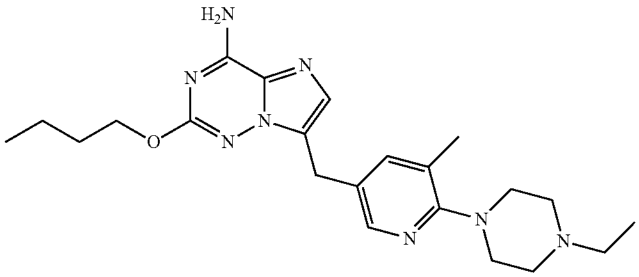
,
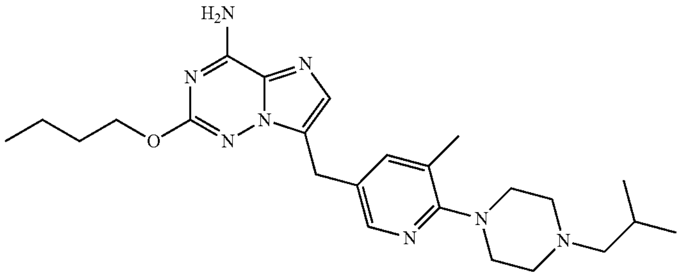
,
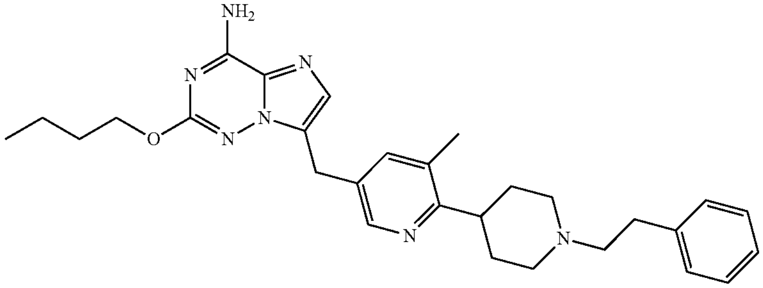
,
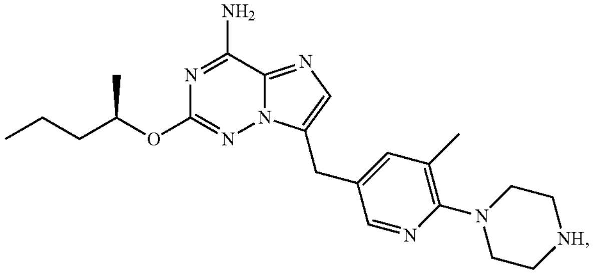
,
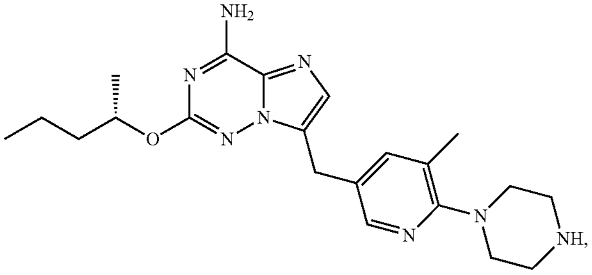
, -continued
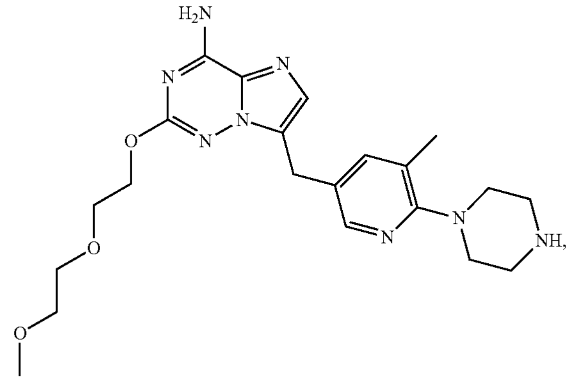
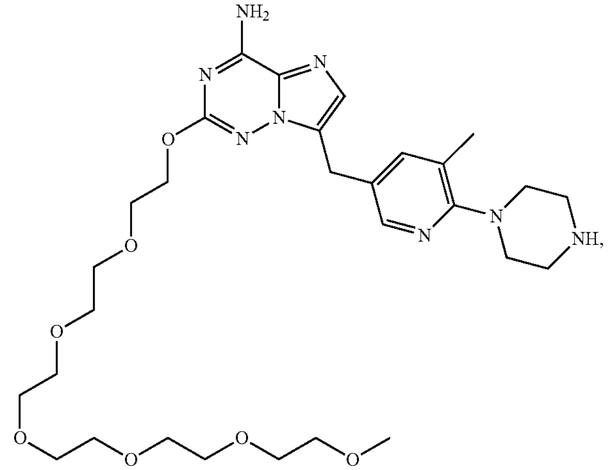
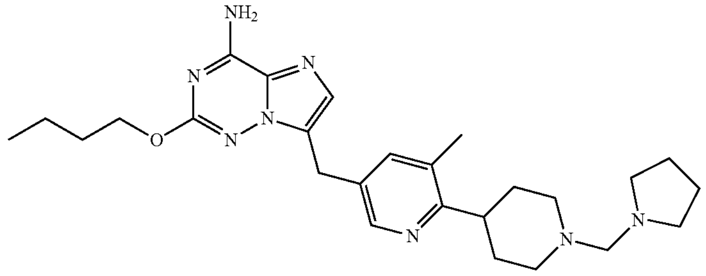
,
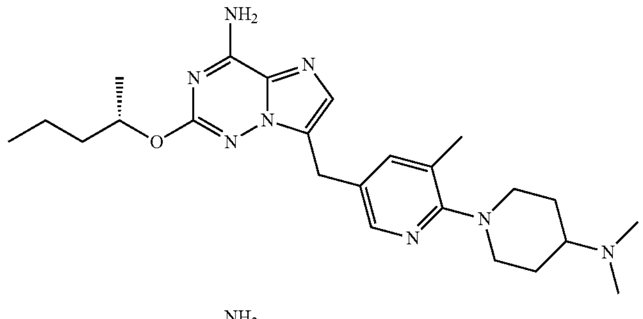
,
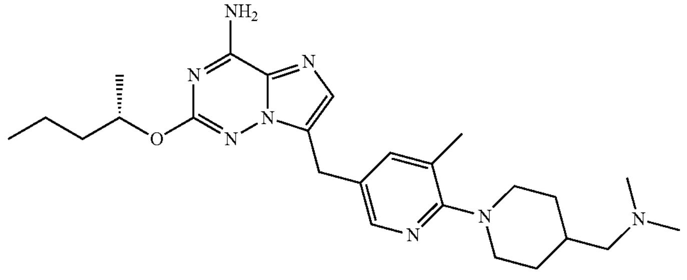
, -continued
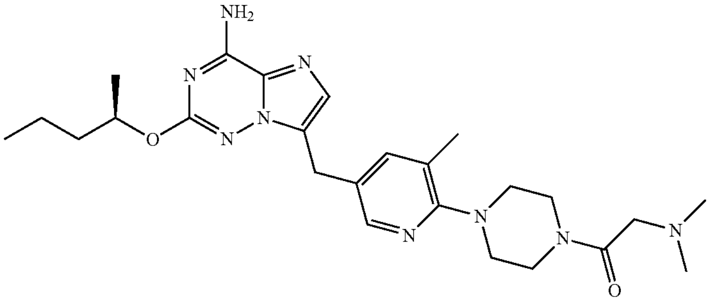
,
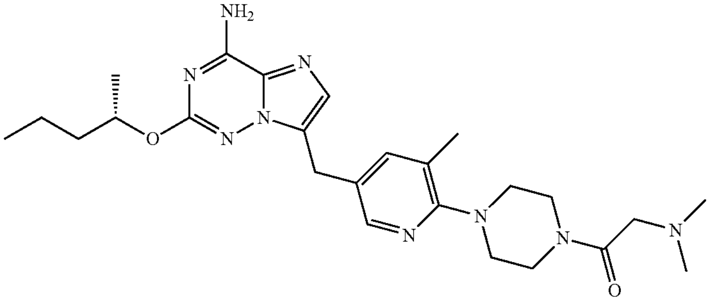
,
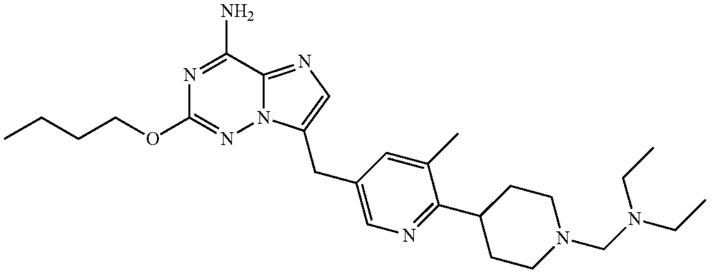
,
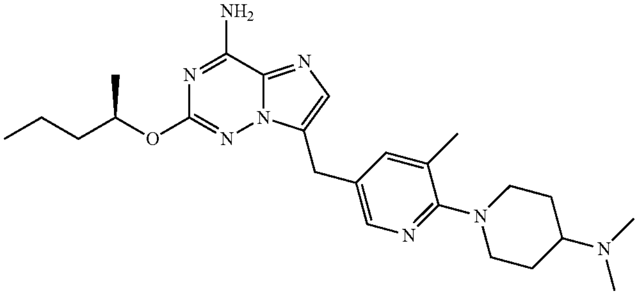
,
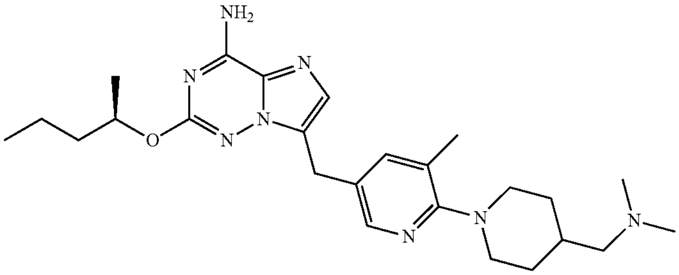
, -continued
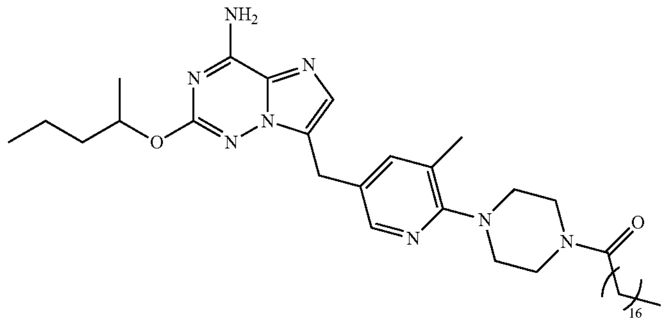
,
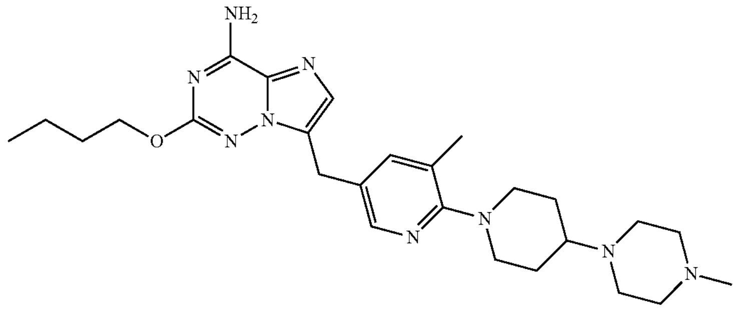
,
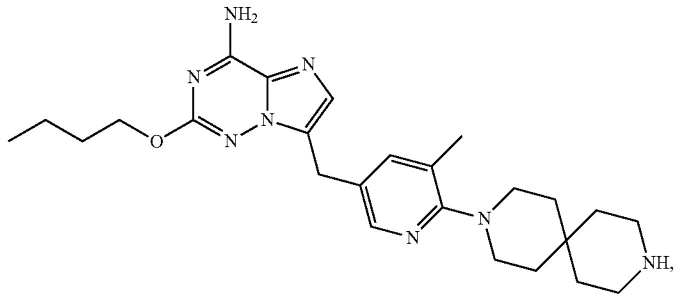
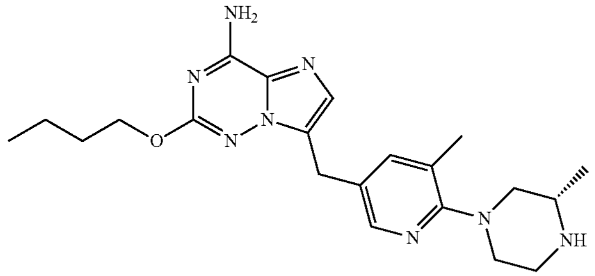
,
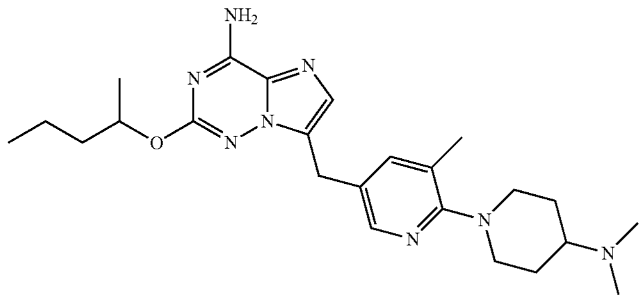
, -continued
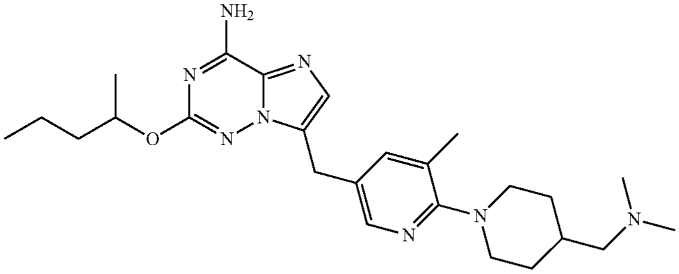
,
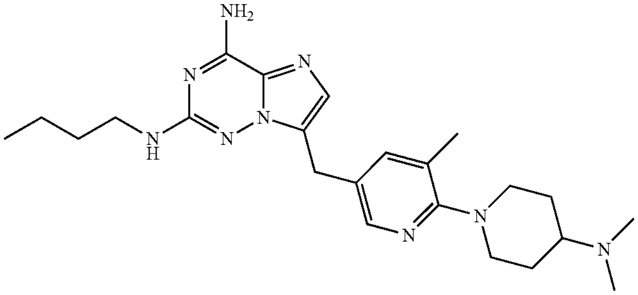
,
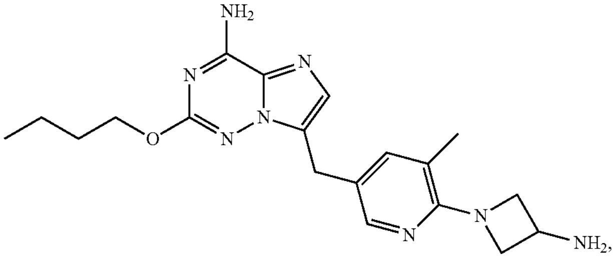
,
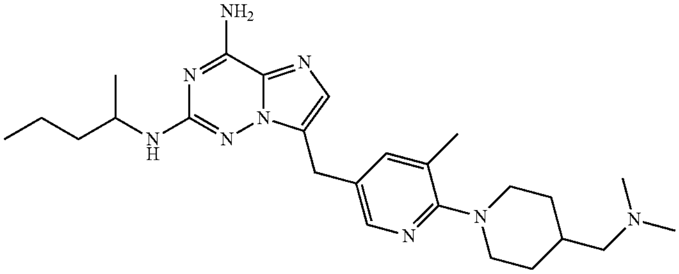
,
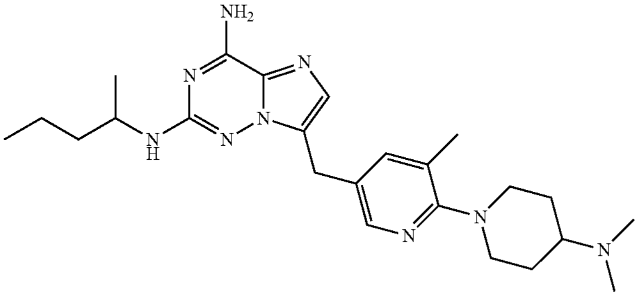
,
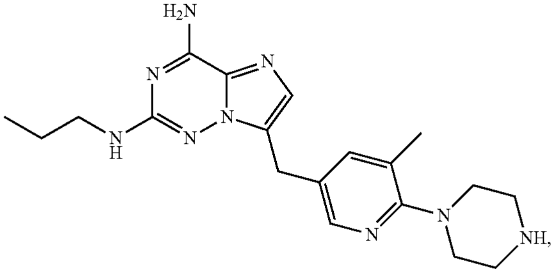
,
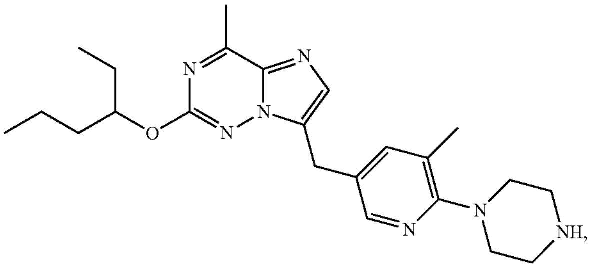
, -continued
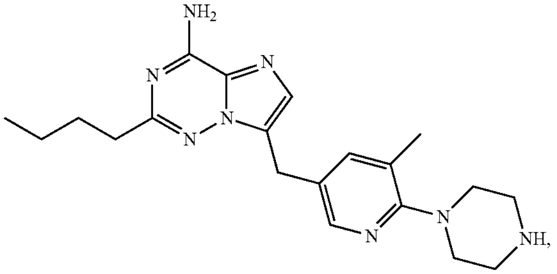
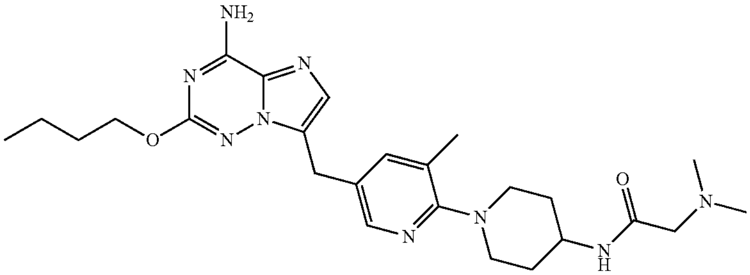
,
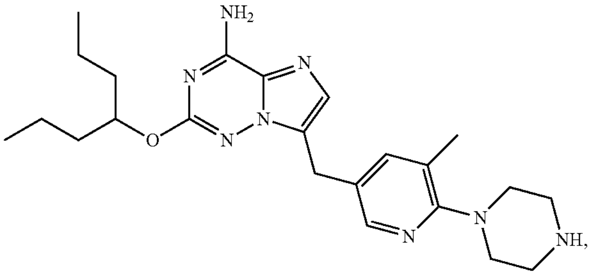
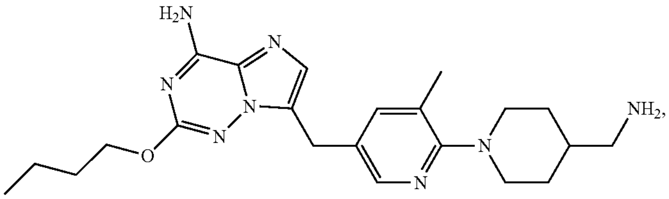
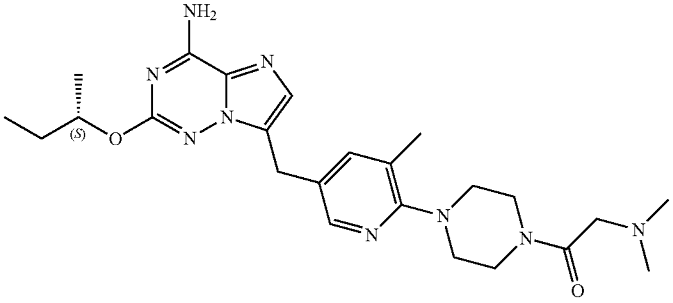
,
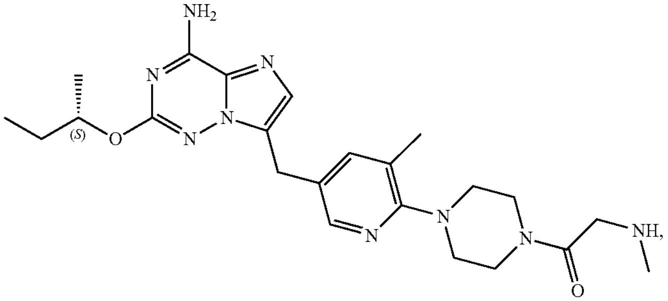

-continued
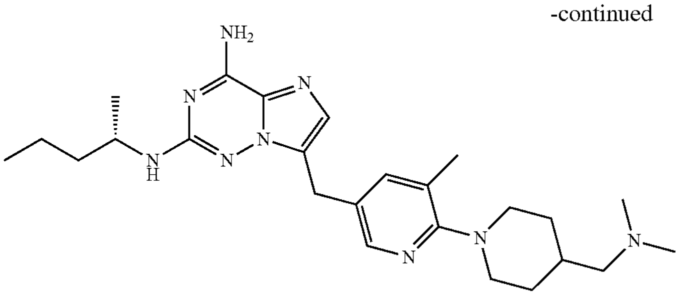
,
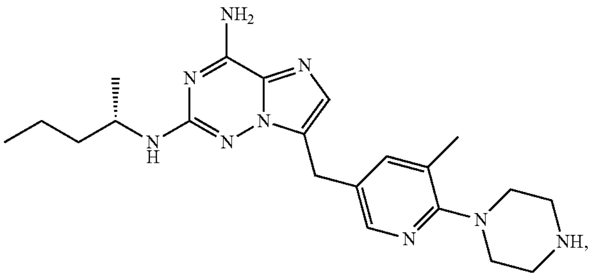
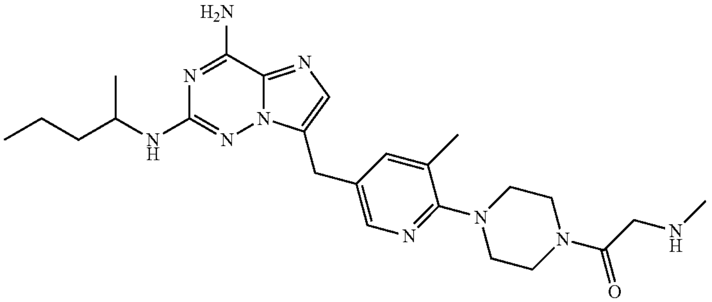
,
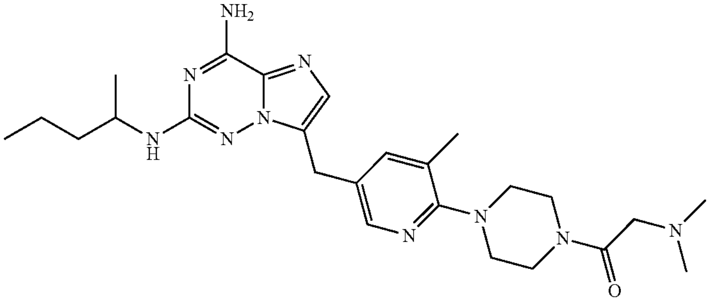
,
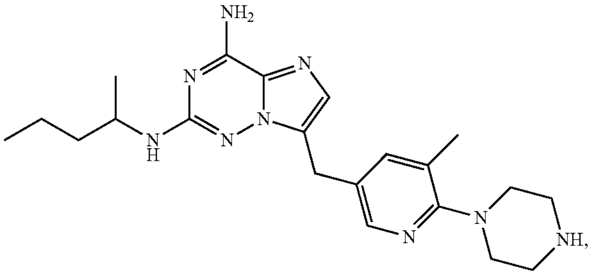
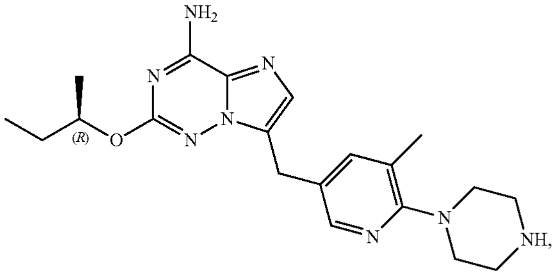
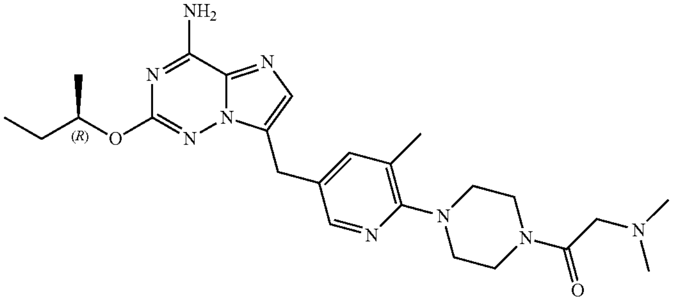
, -continued
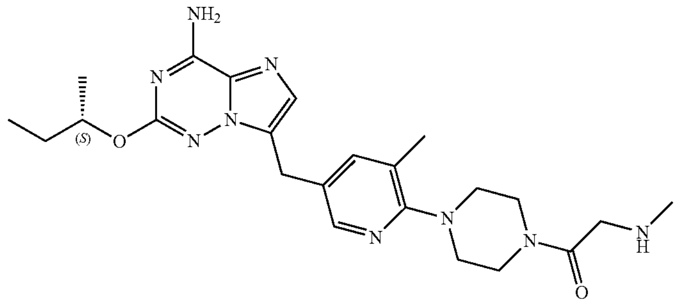
,
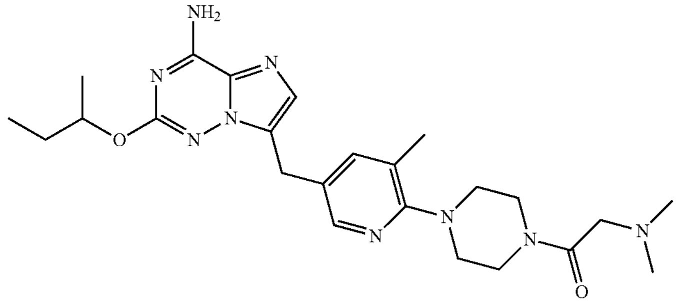
,
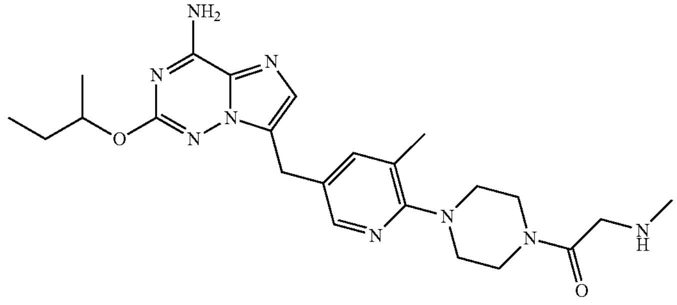
,
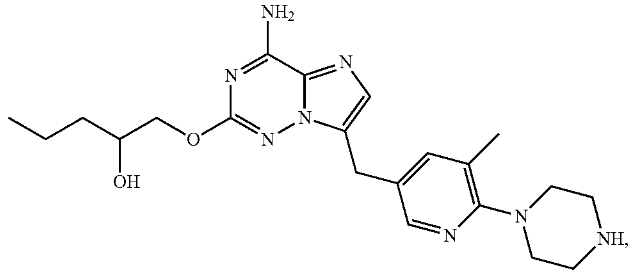
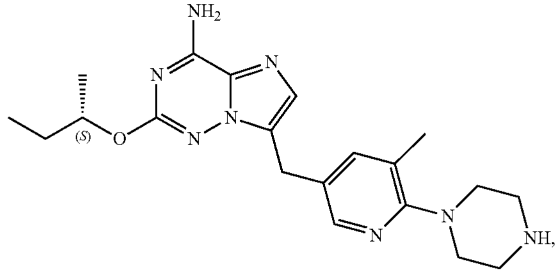

-continued
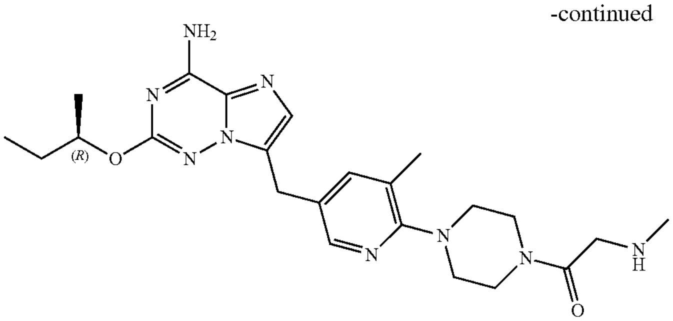
,
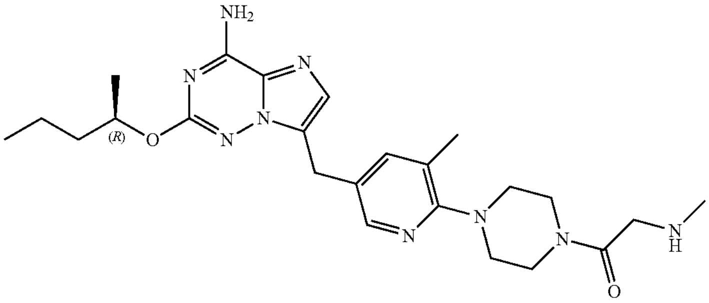
,
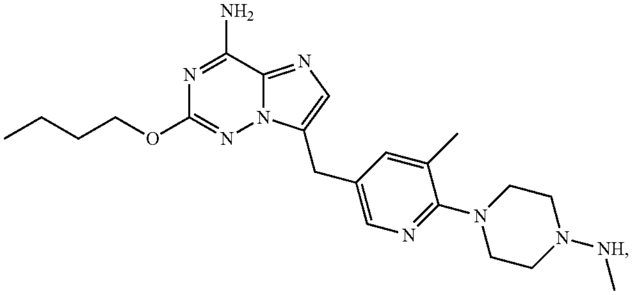
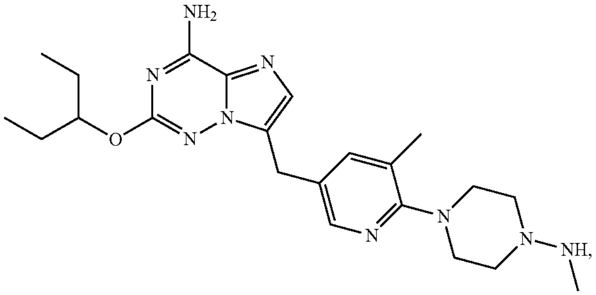
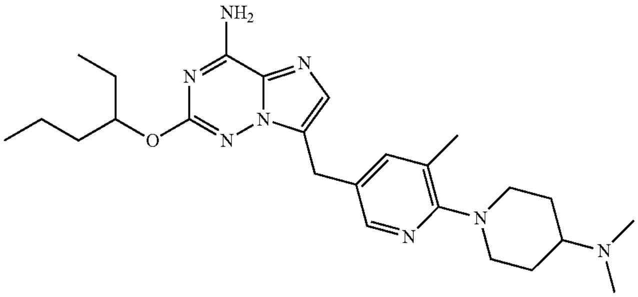
,

-continued
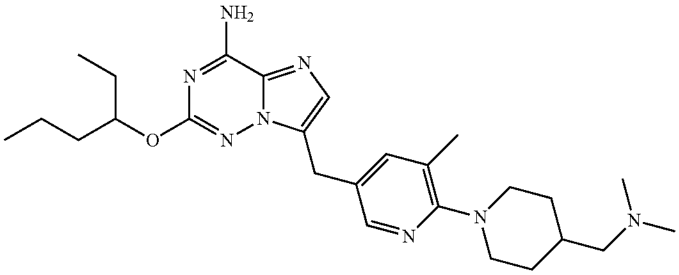
,
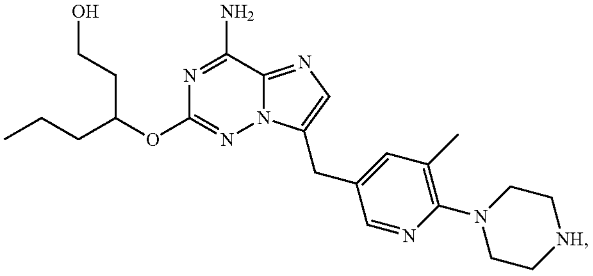
,
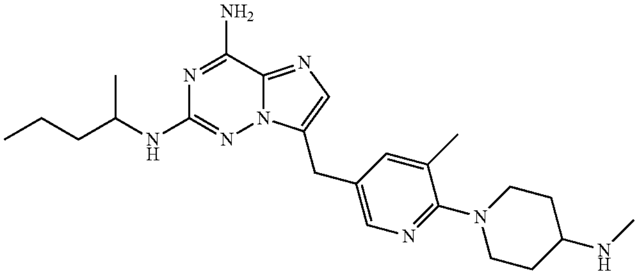
,
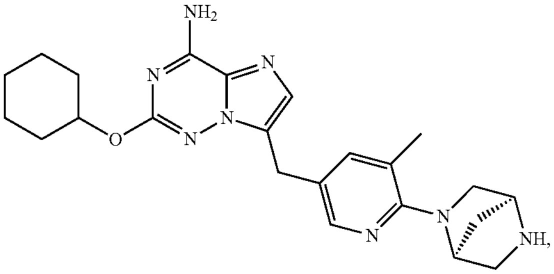
,
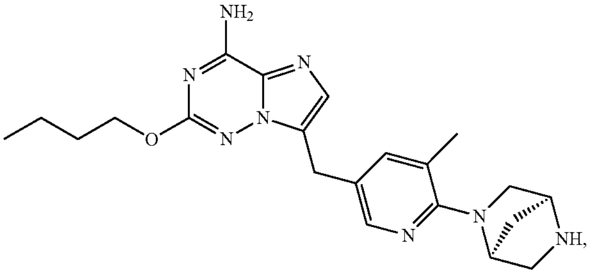
,
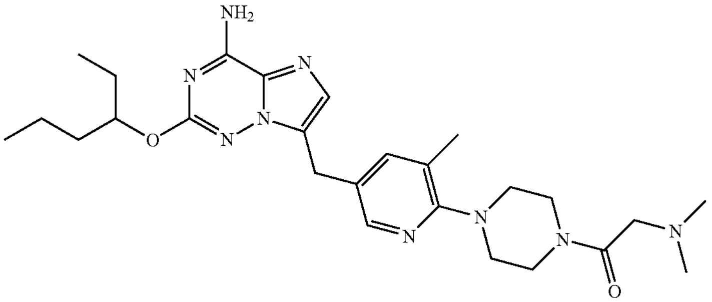
,
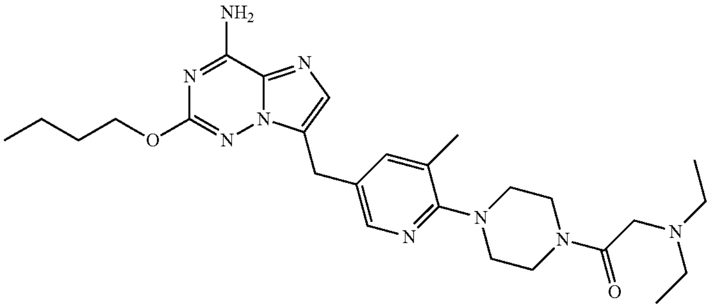
, -continued
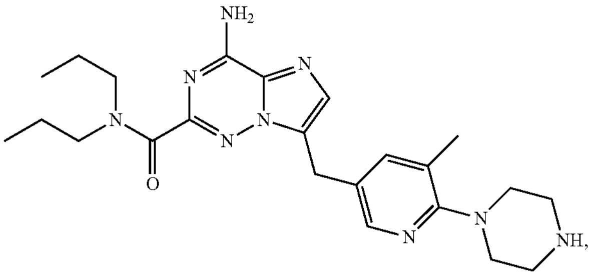
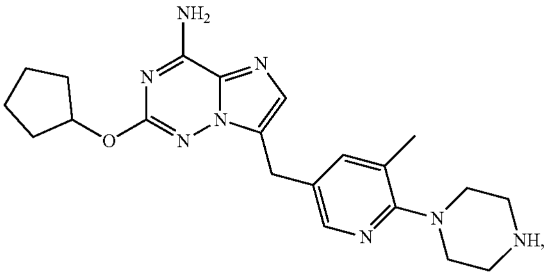
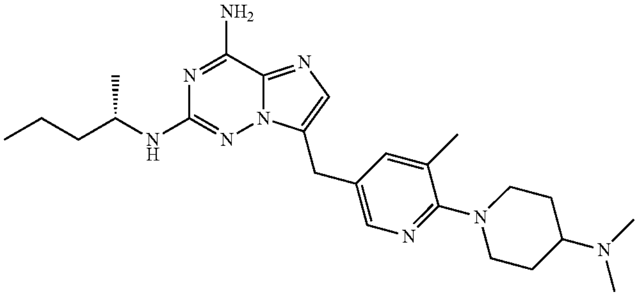
,
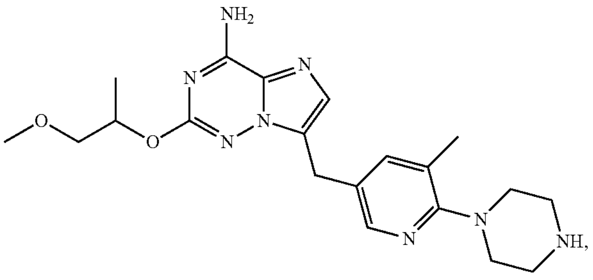
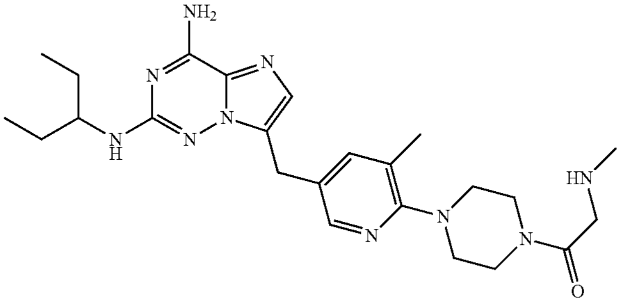
,
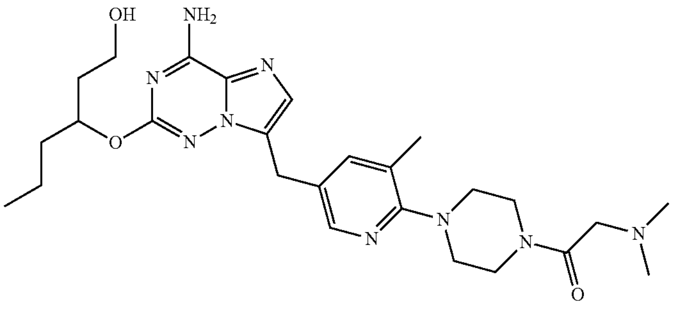
, -continued
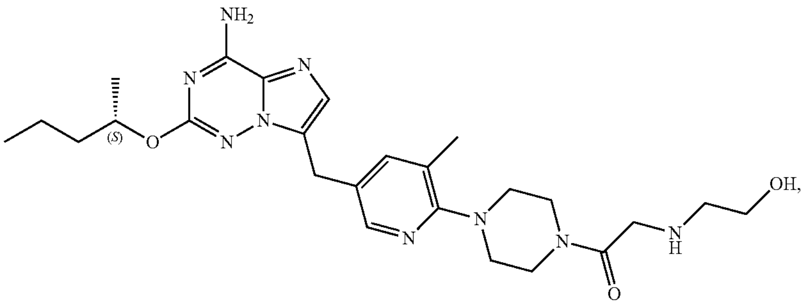
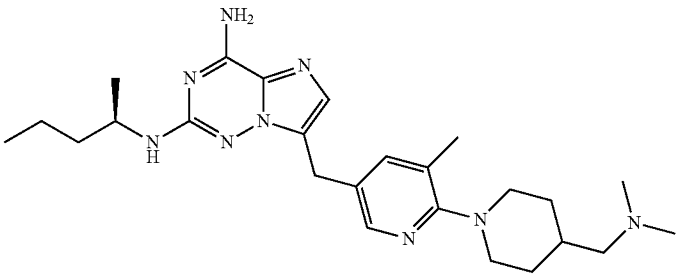
,
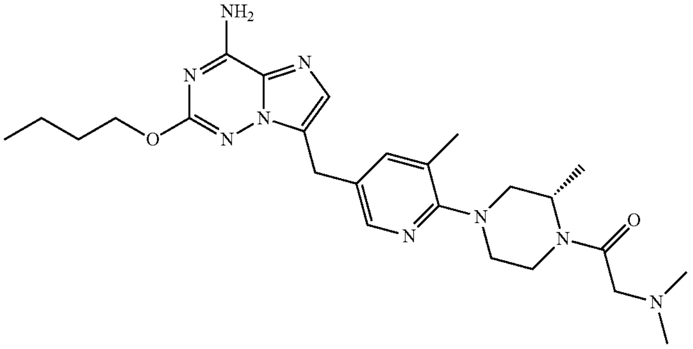
,
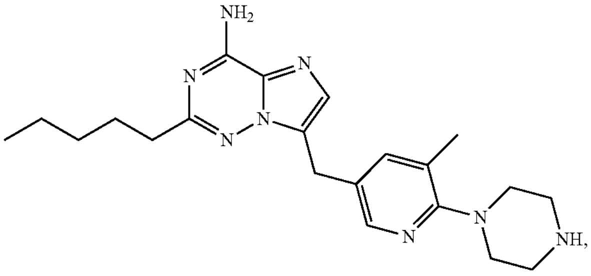
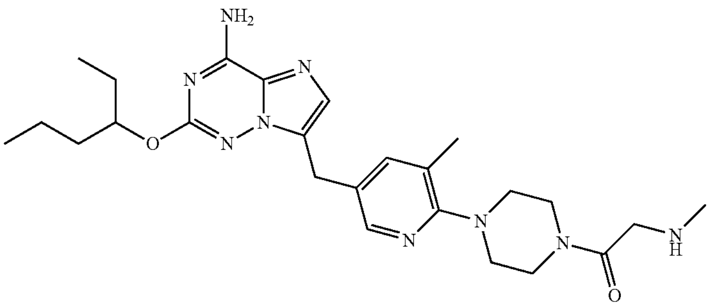
, -continued
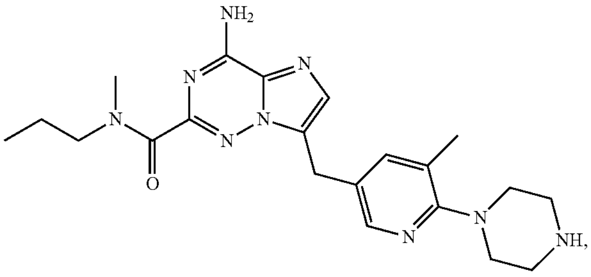
,
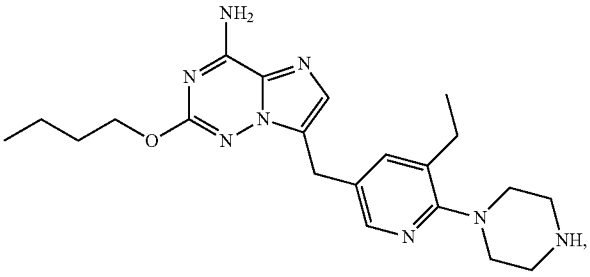
,
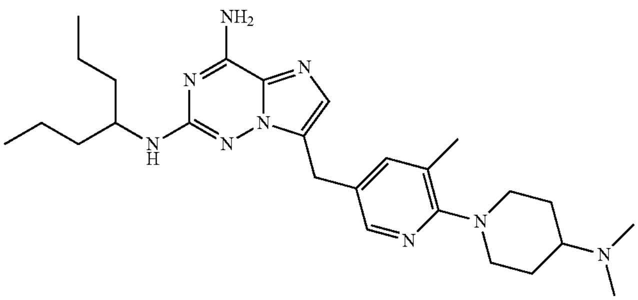
,
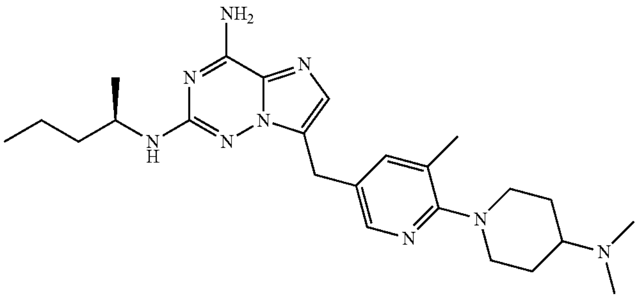
,
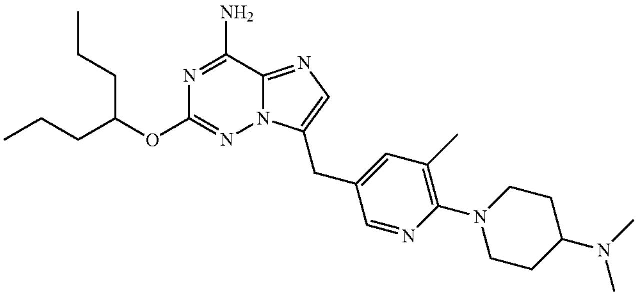
,
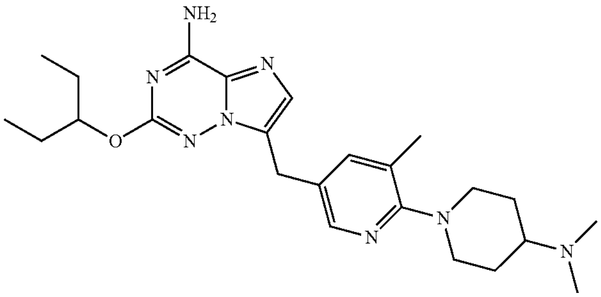
, -continued
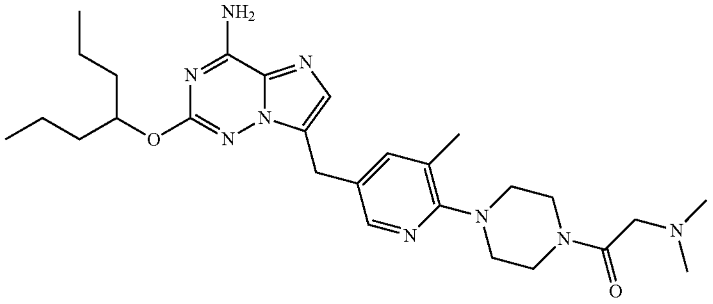
,
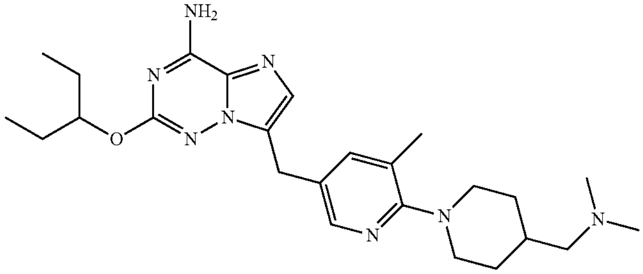
,
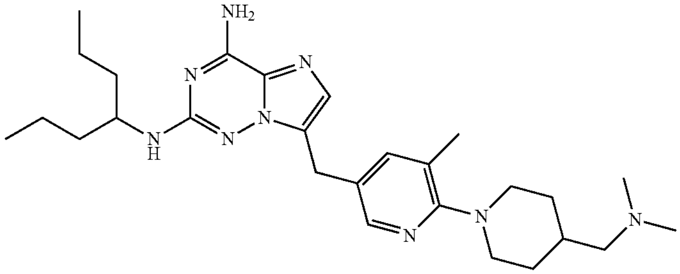
,
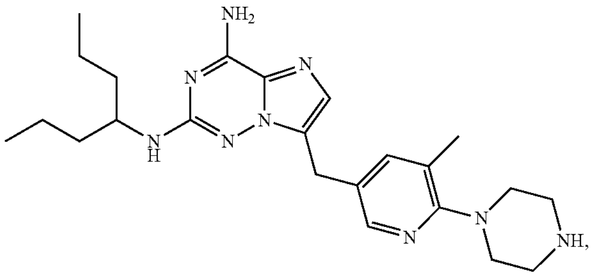
,
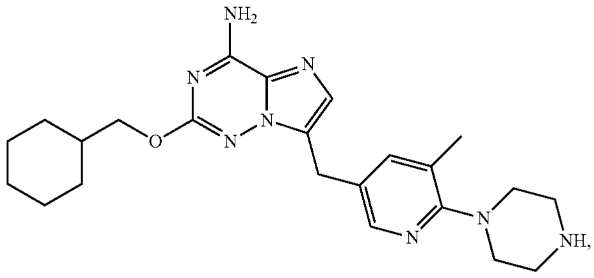
,
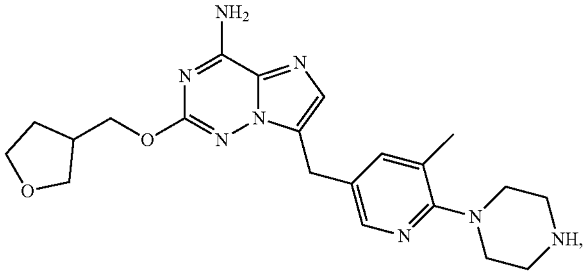
,
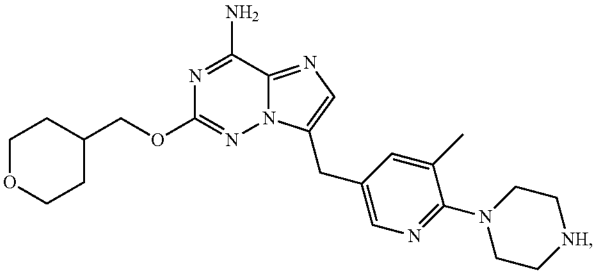
,
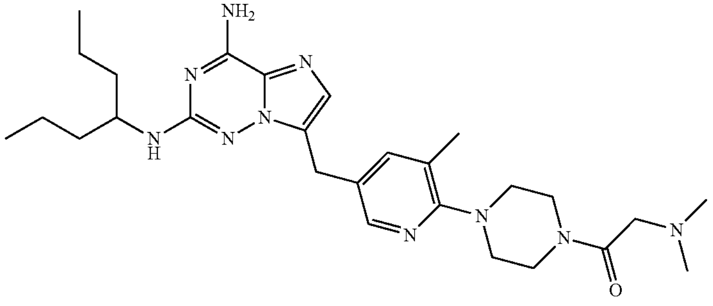
, -continued
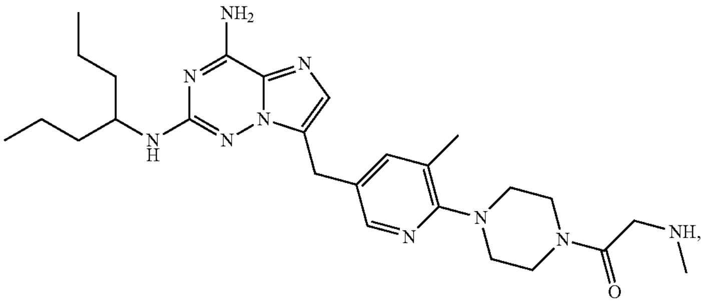
,
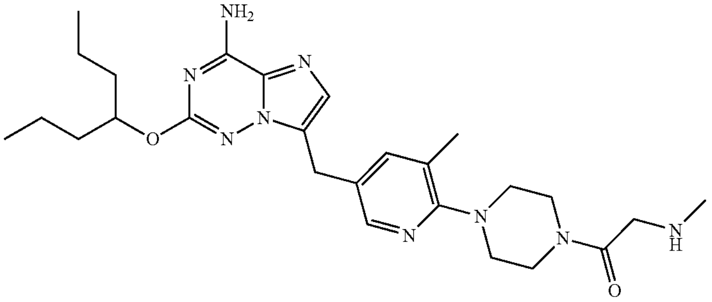
,
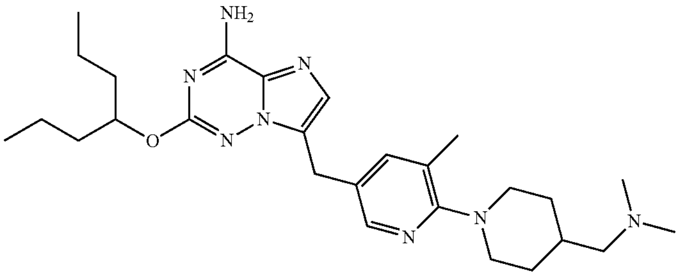
,
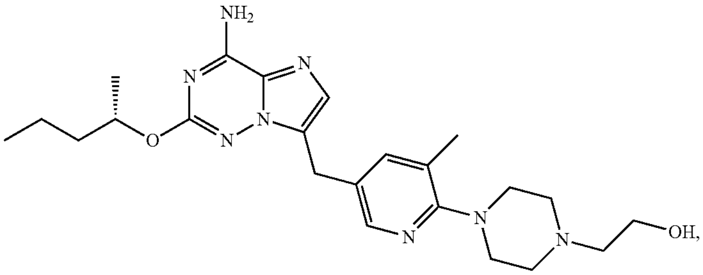
,
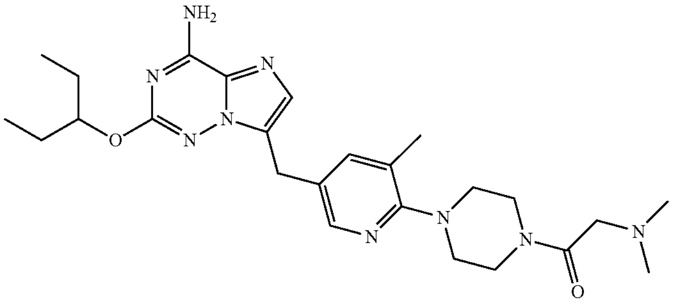
, -continued
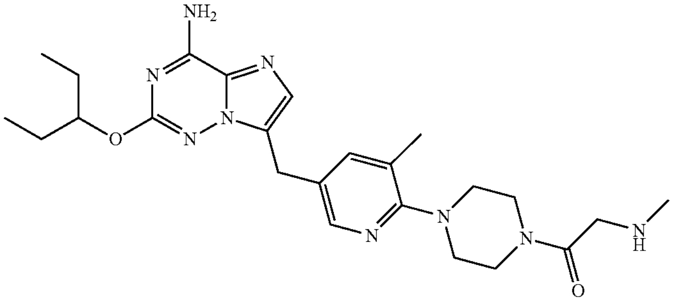
,
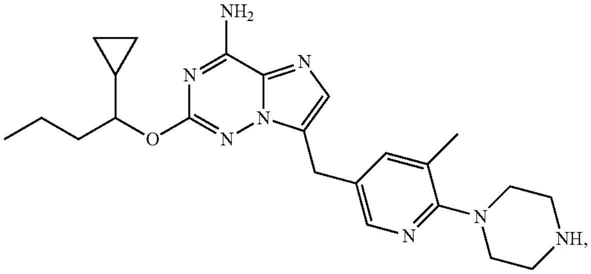
,
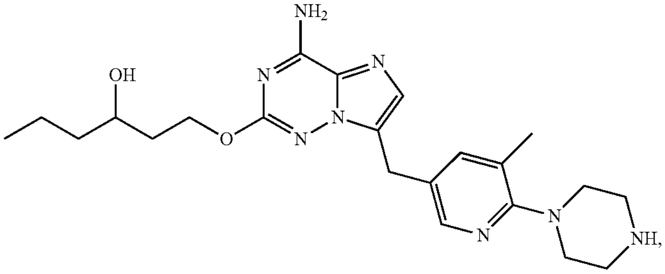
,
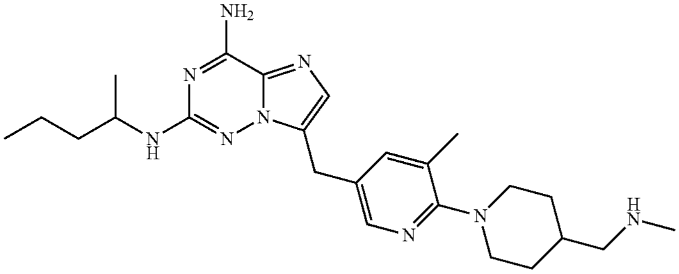
,
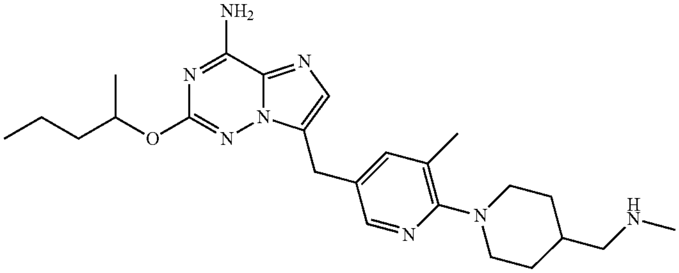
,
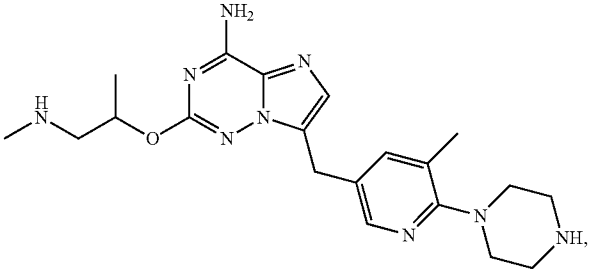
,
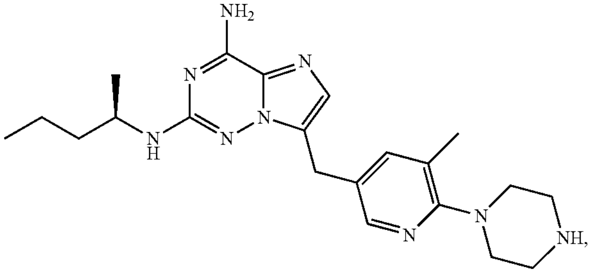
, -continued
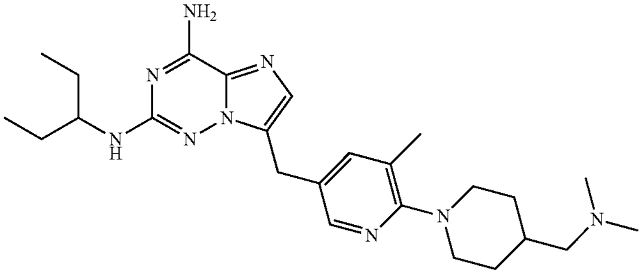
,
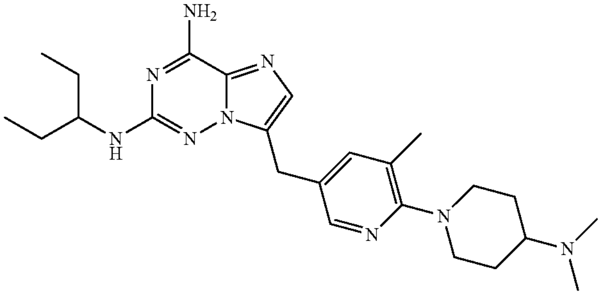
,
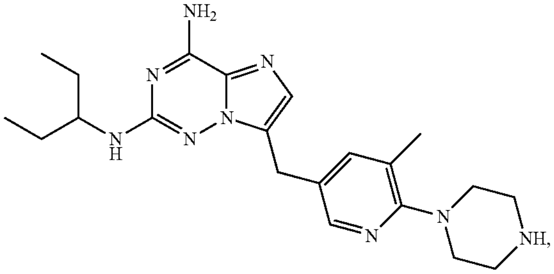
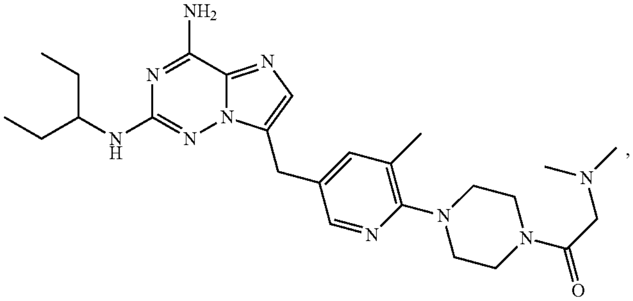
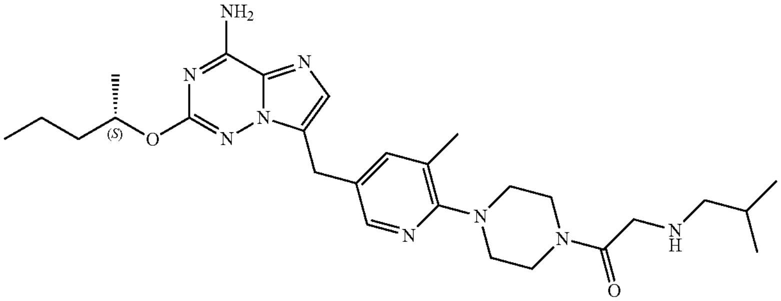
,
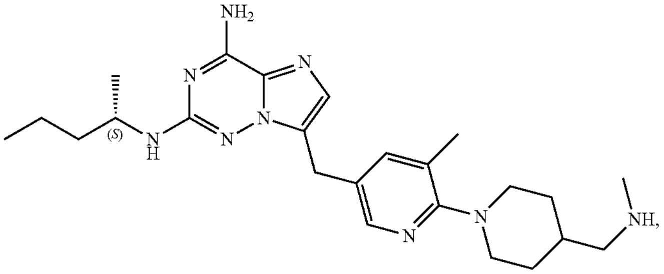

-continued
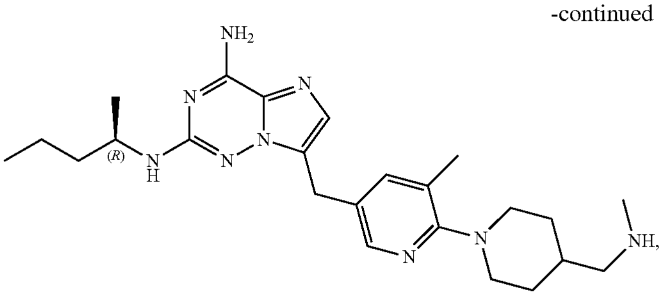
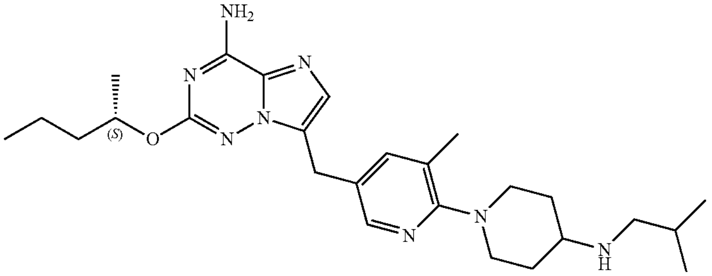
,
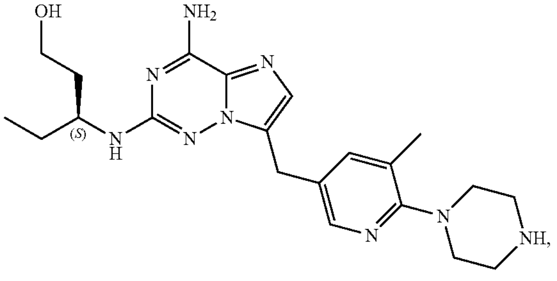
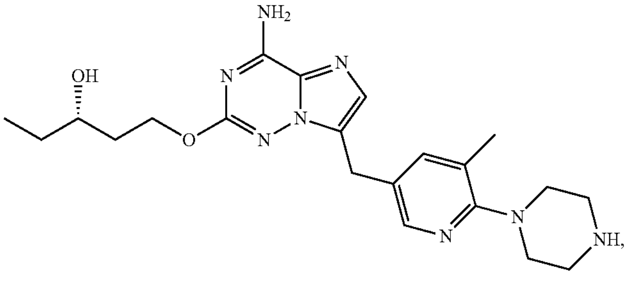
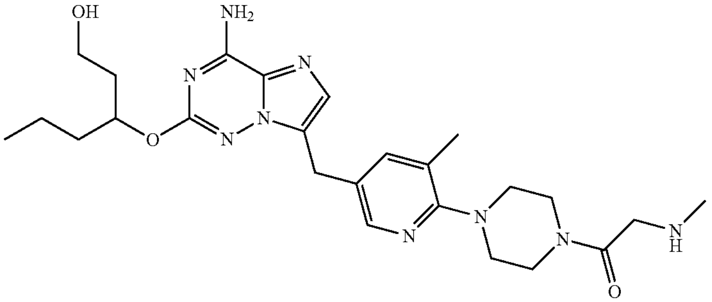
,
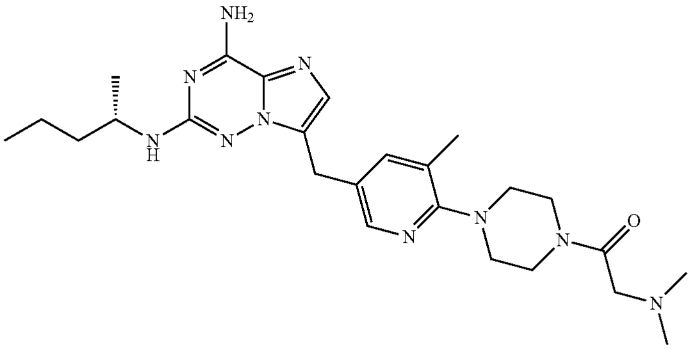
, -continued
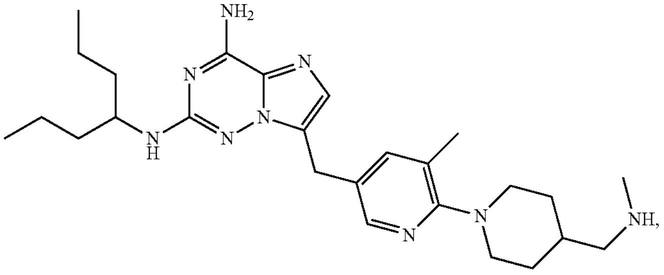
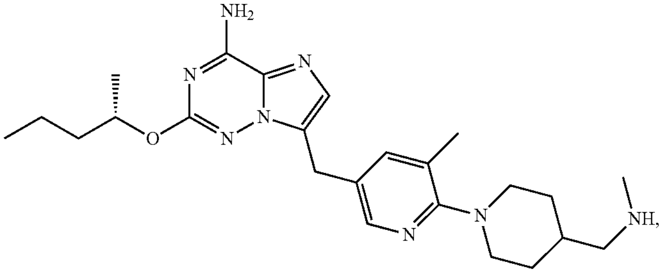
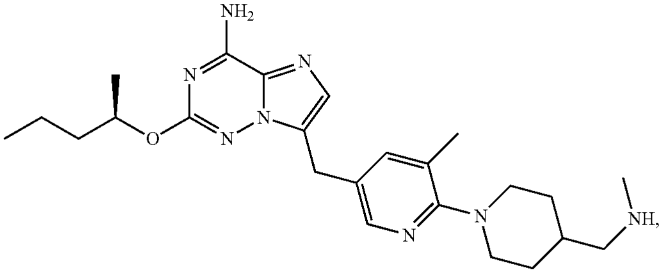
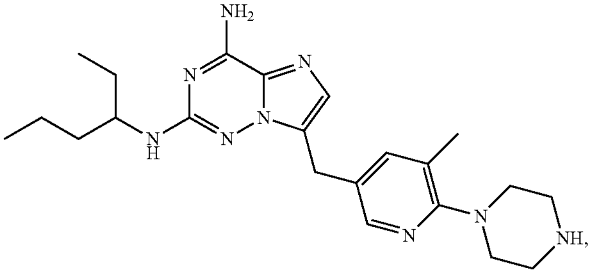
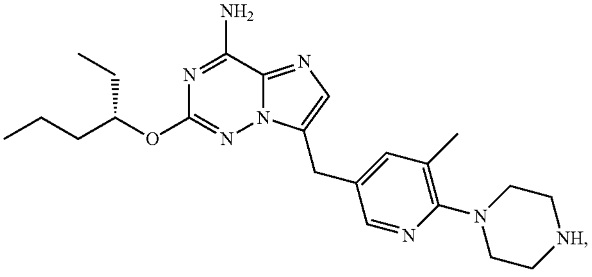
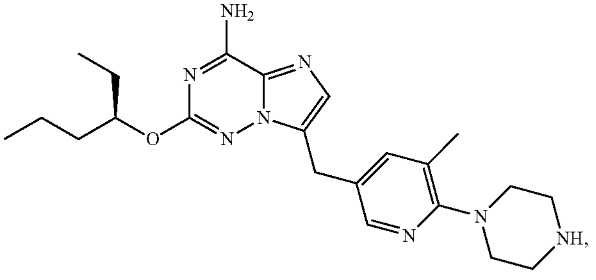
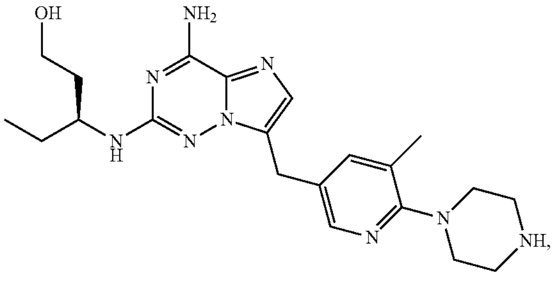
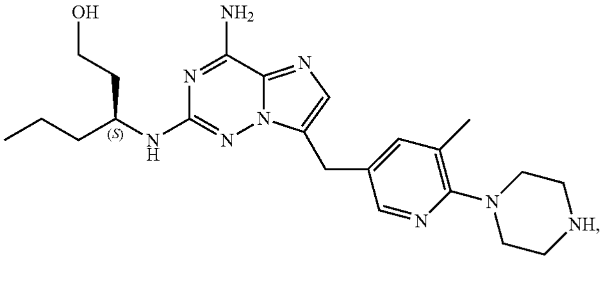
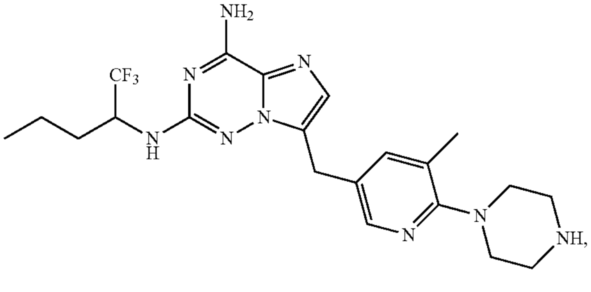

-continued
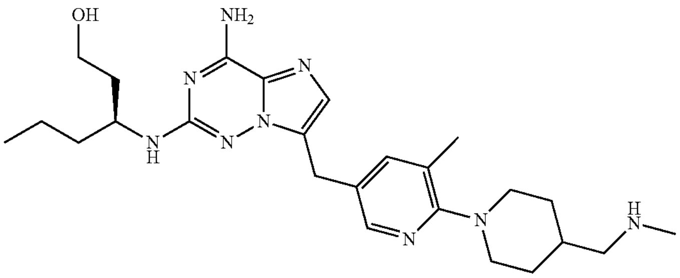
,
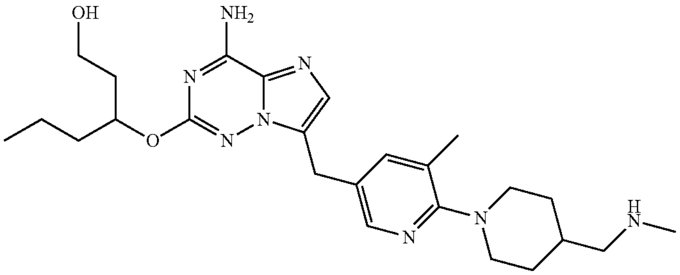
,
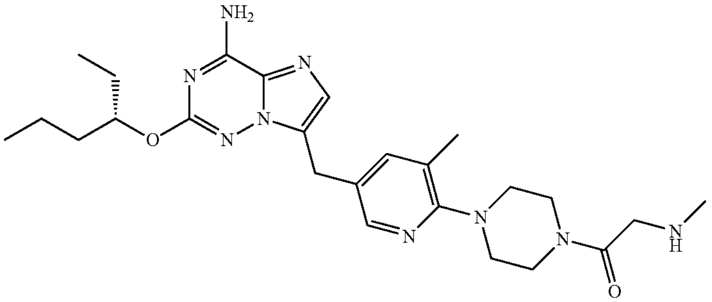
,
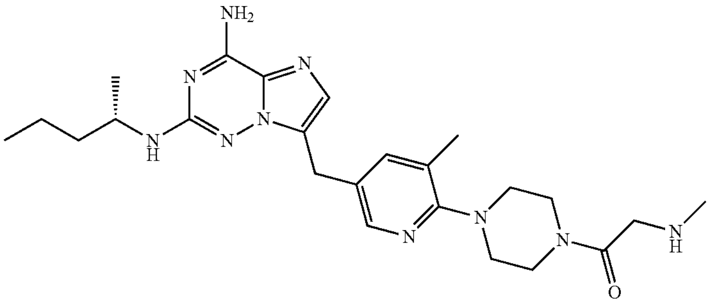
,
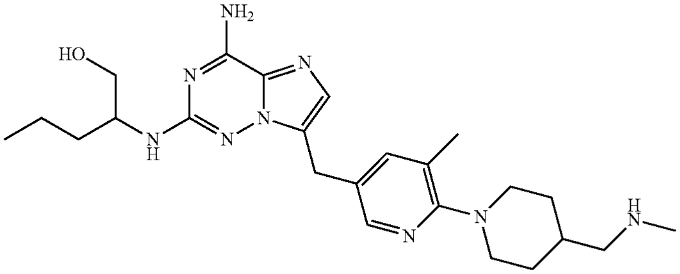
,
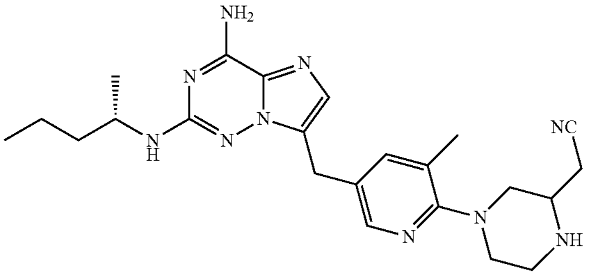
, -continued
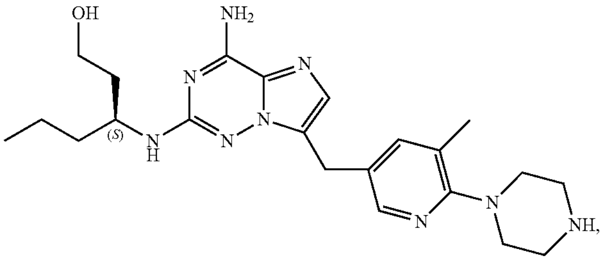
,
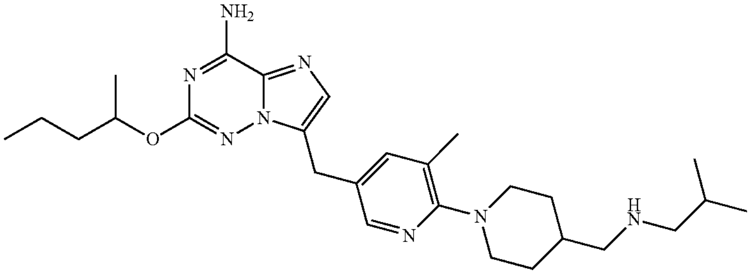
,
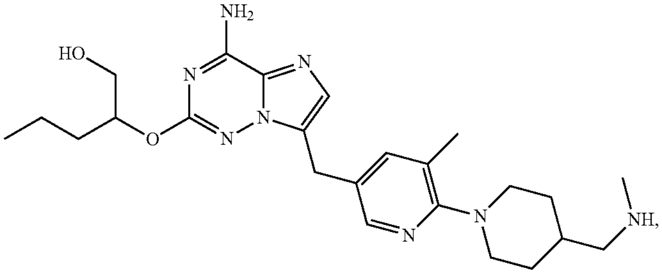
,
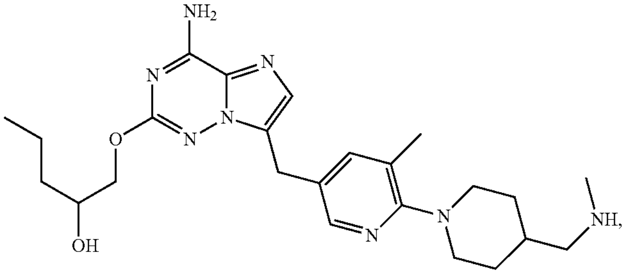
,
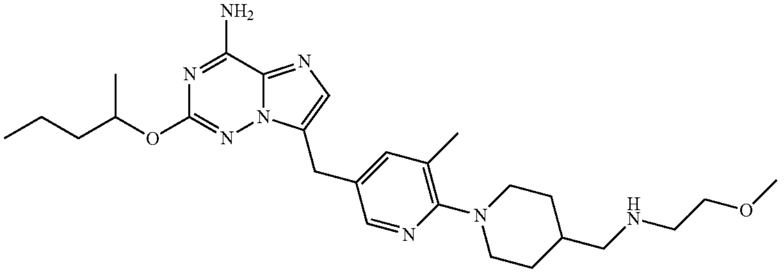
,
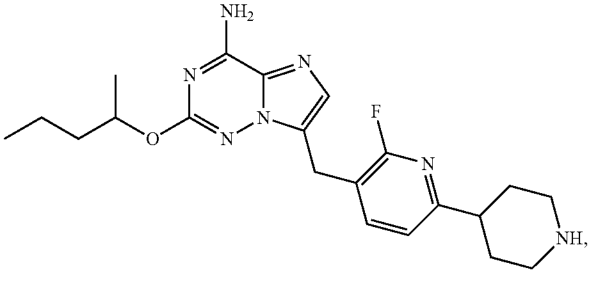
,
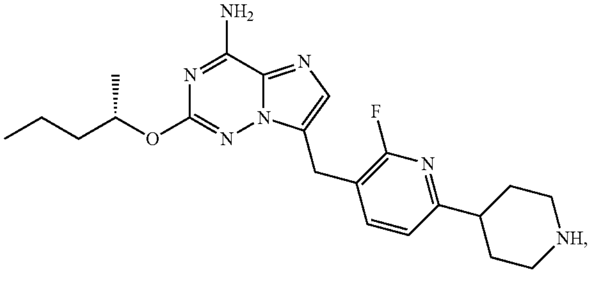
, -continued
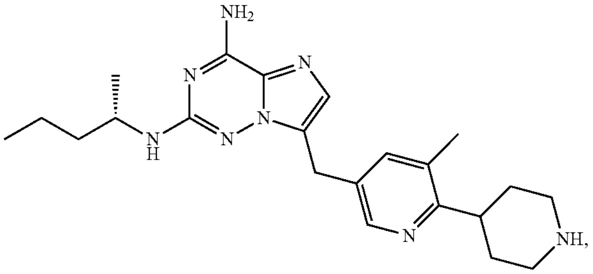
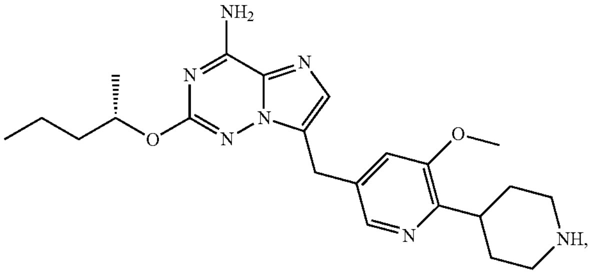
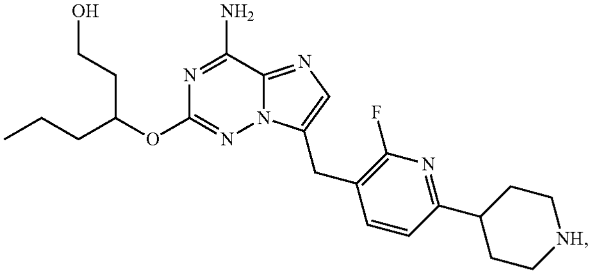
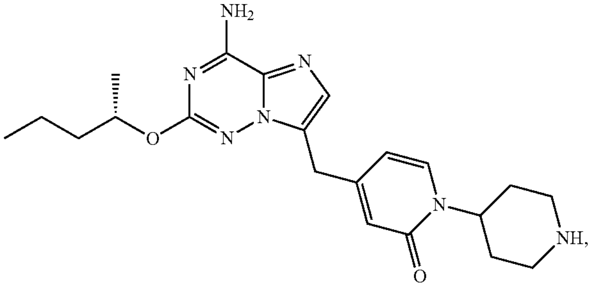
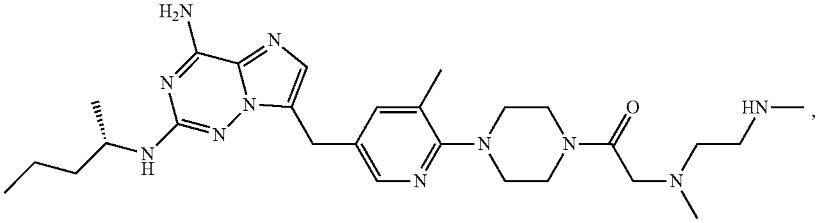
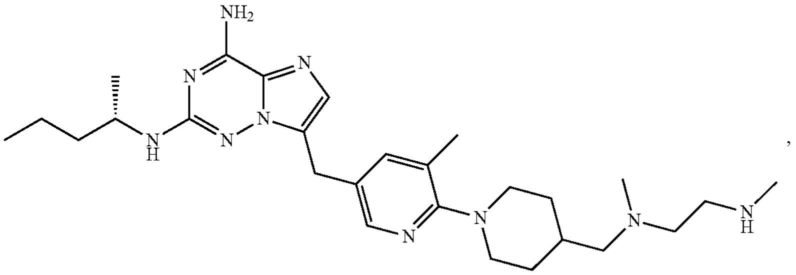
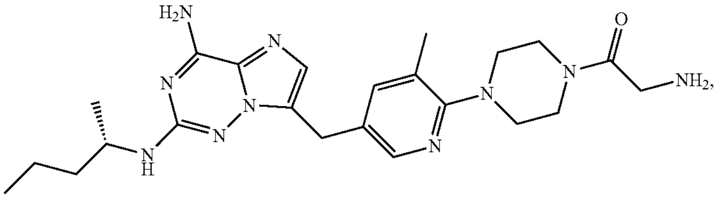
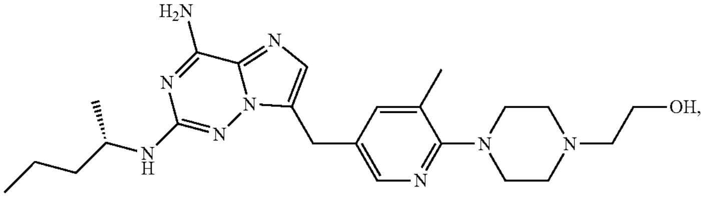

-continued
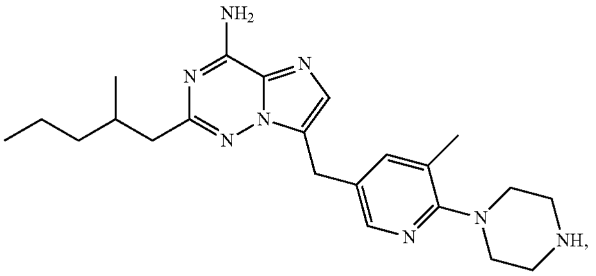
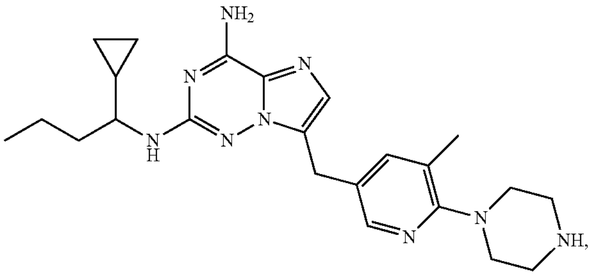
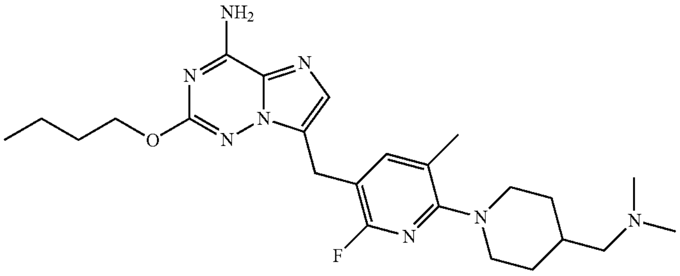
,
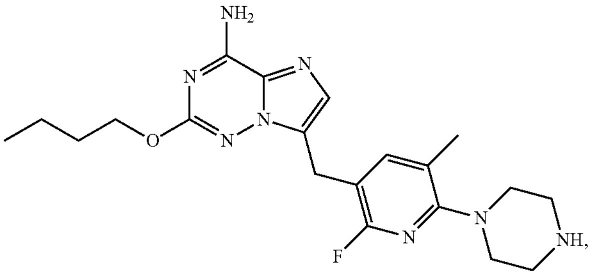
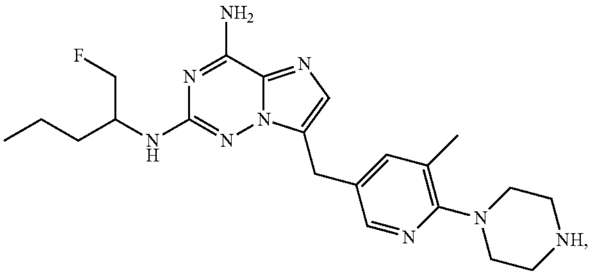
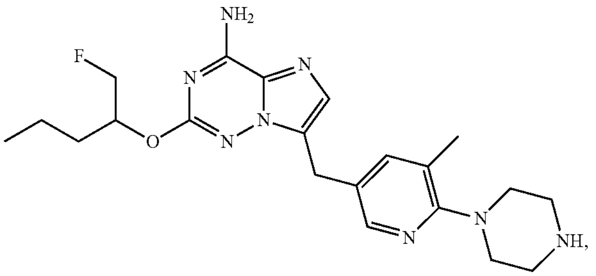
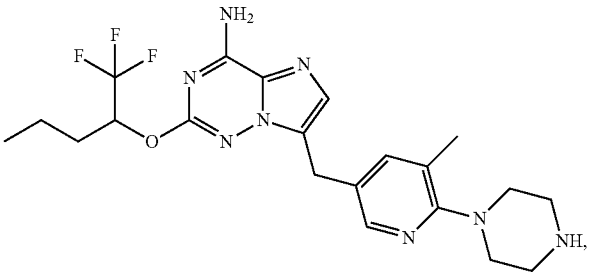
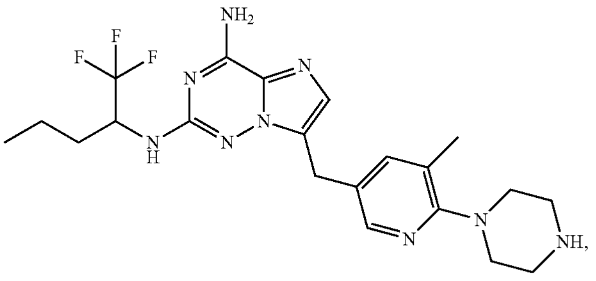
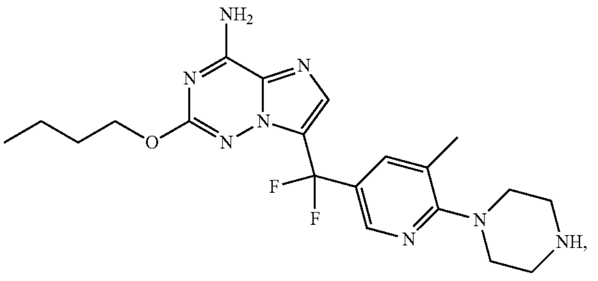
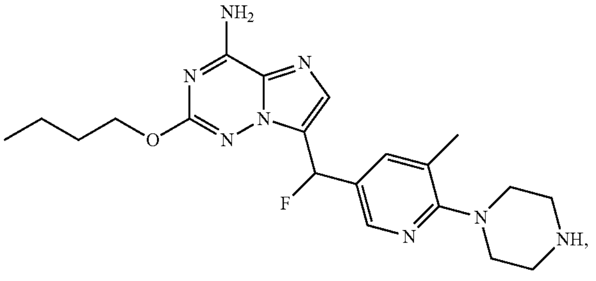
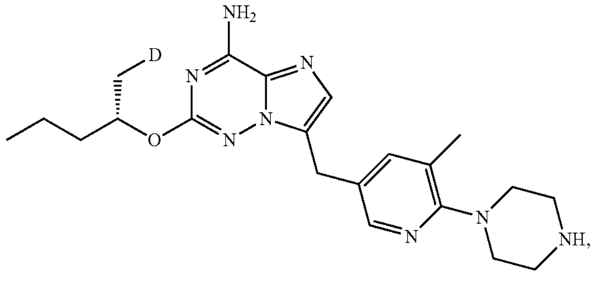

-continued
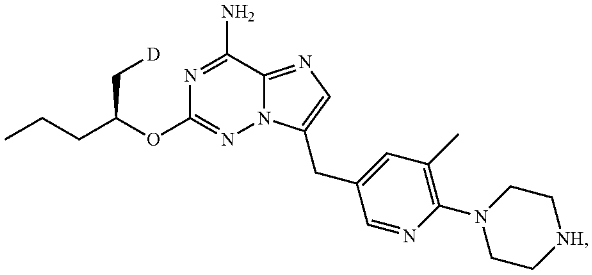,
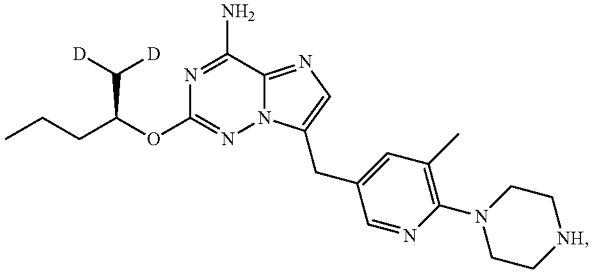,
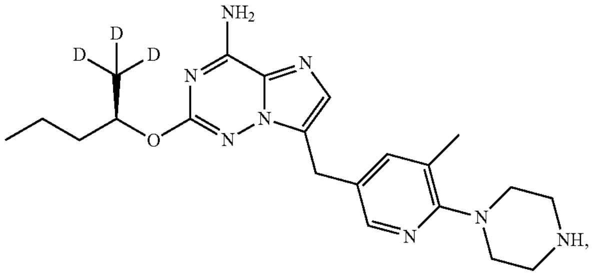,
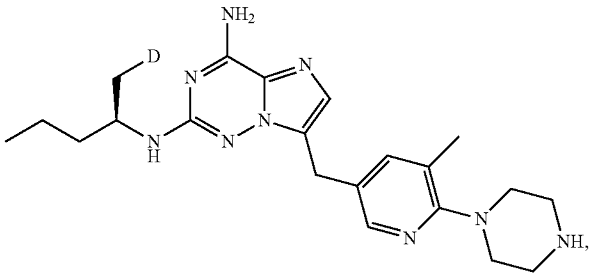,
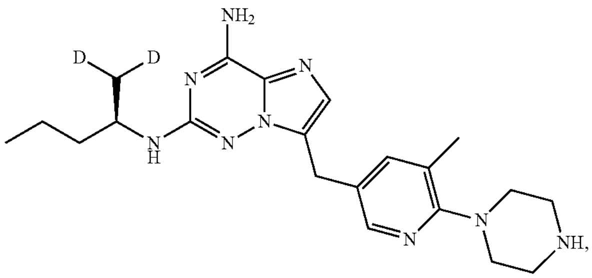,
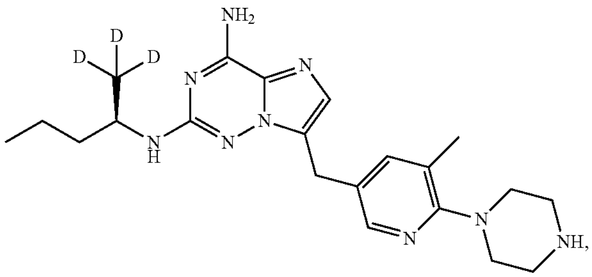,
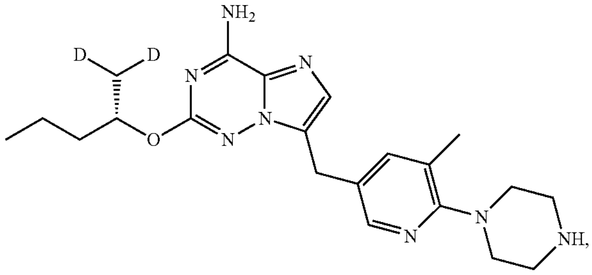,
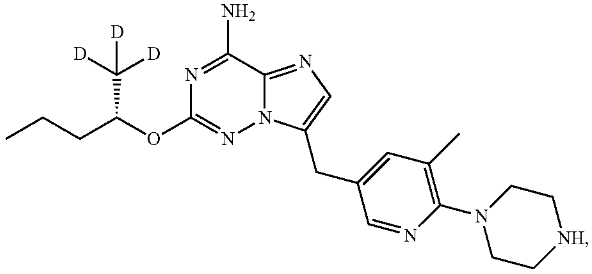,
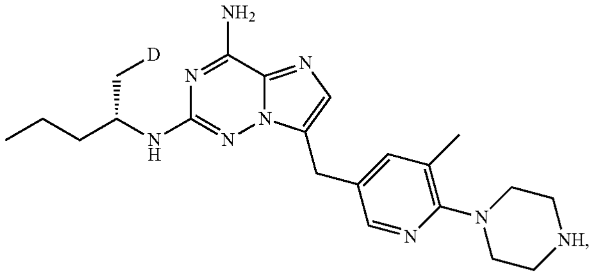,
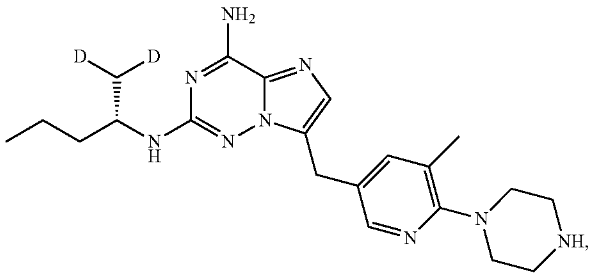,
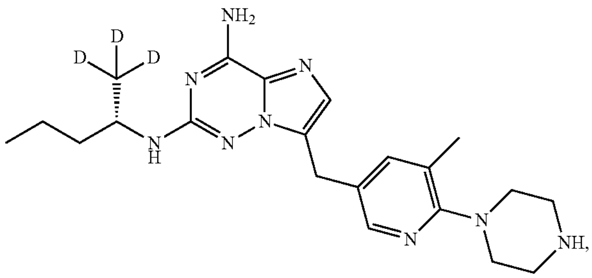, -continued
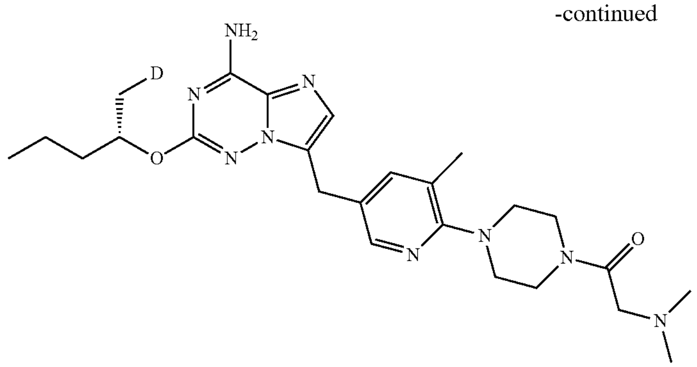
,
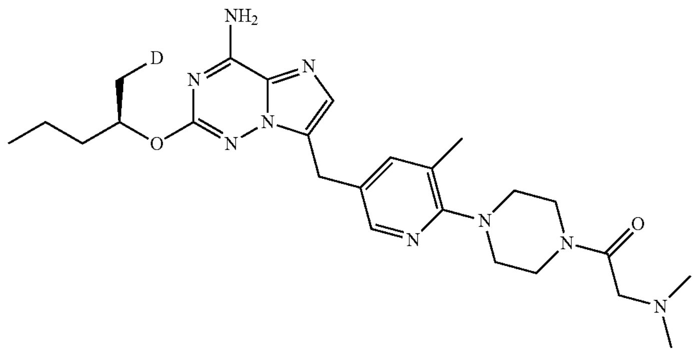
,
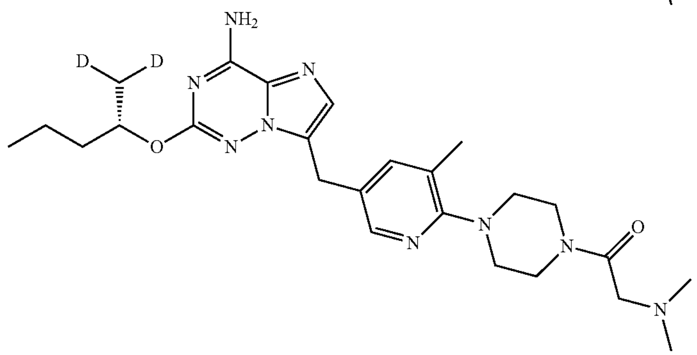
,
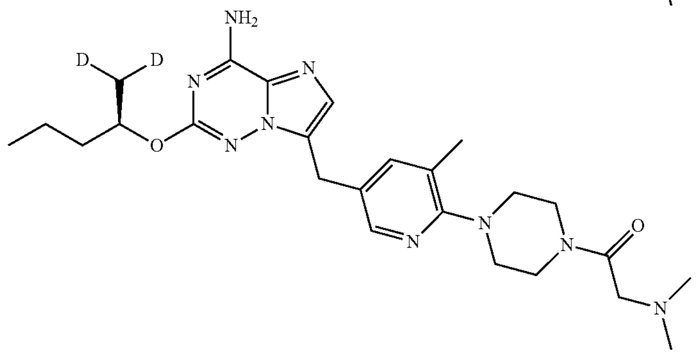
,
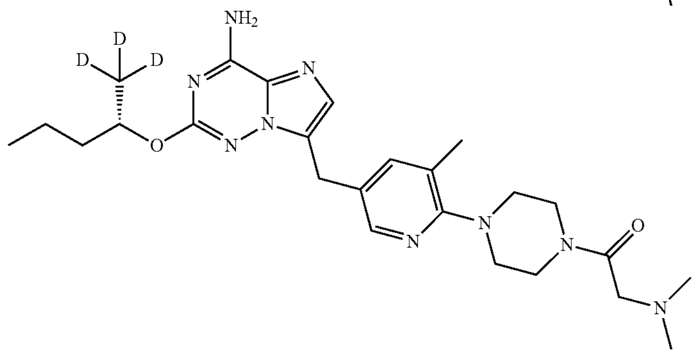
, -continued
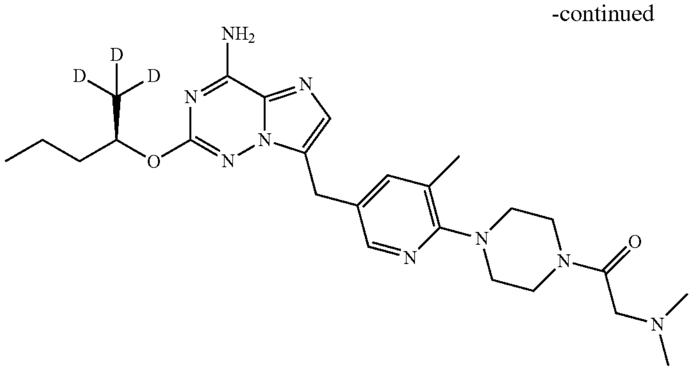
,
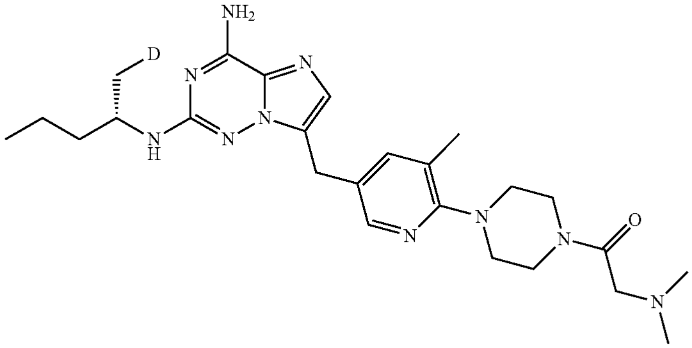
,
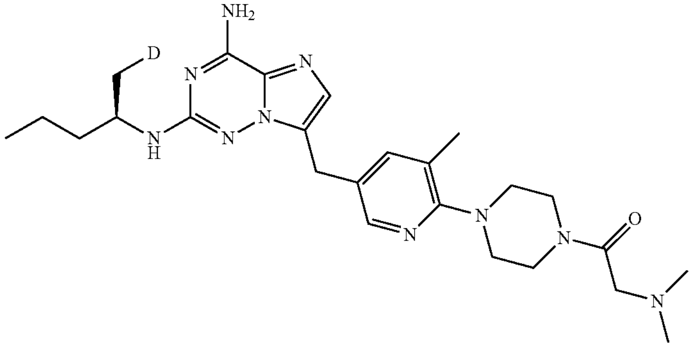
,
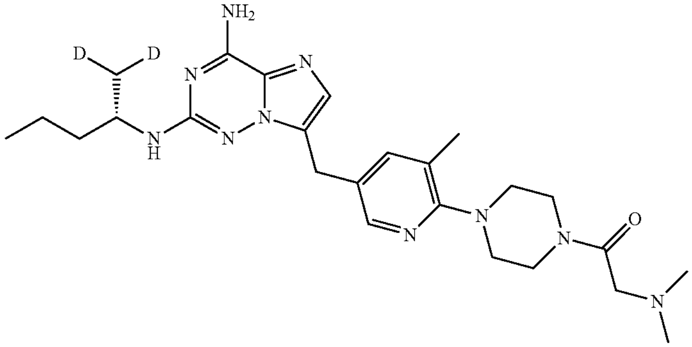
,
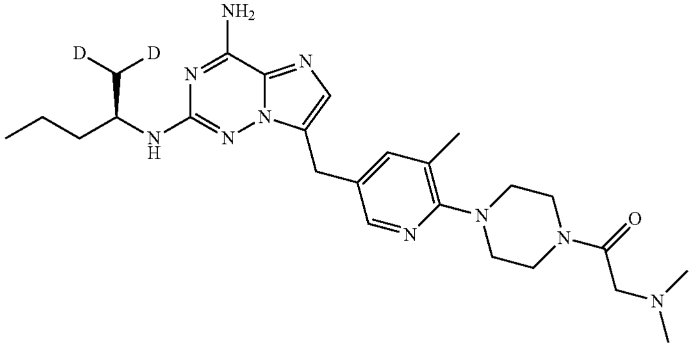
, -continued
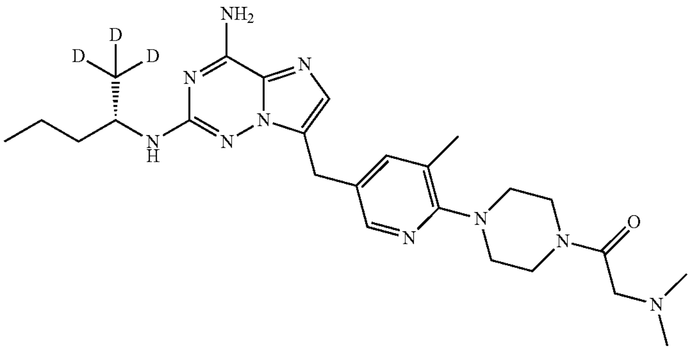
,
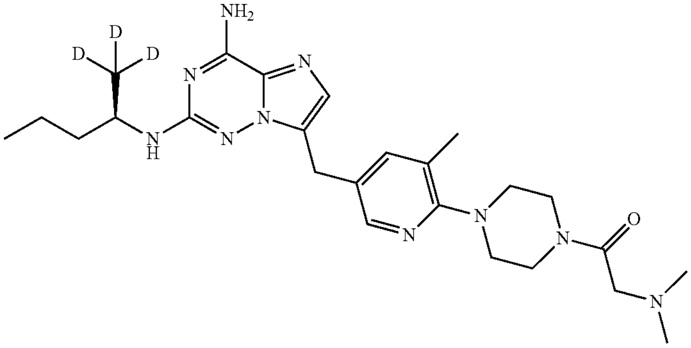
,
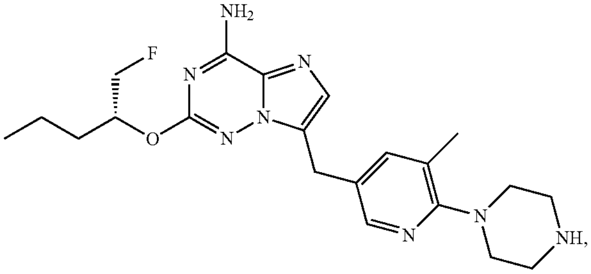
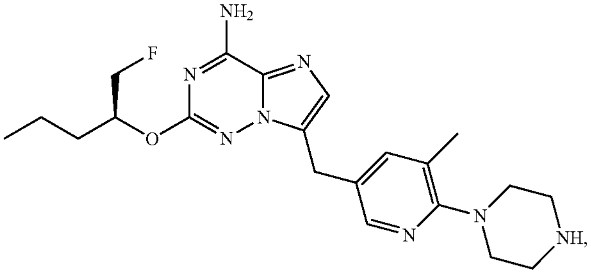
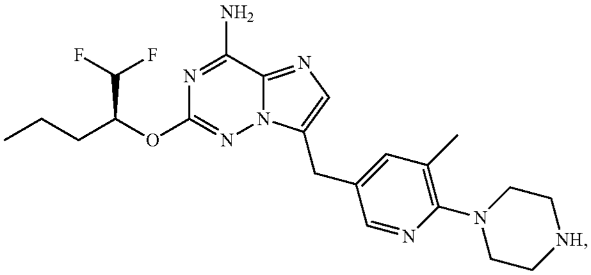
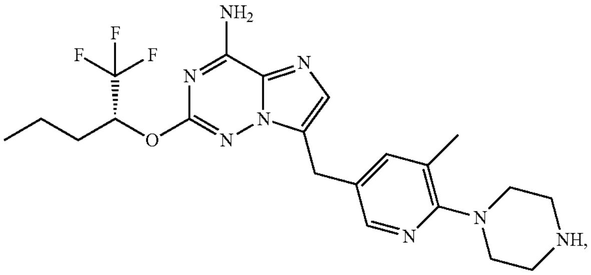
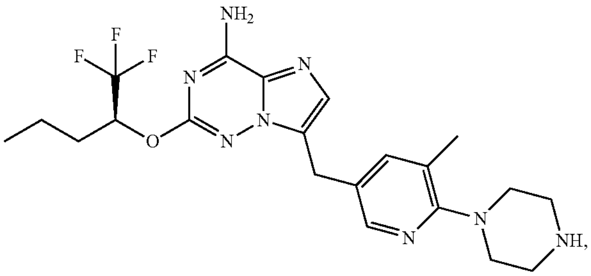
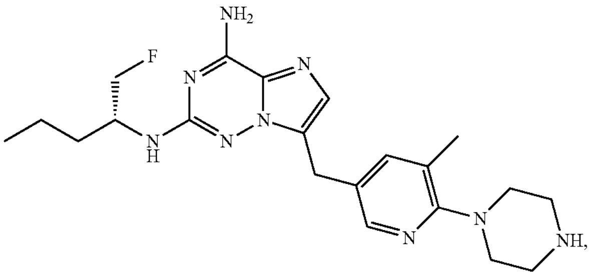

-continued
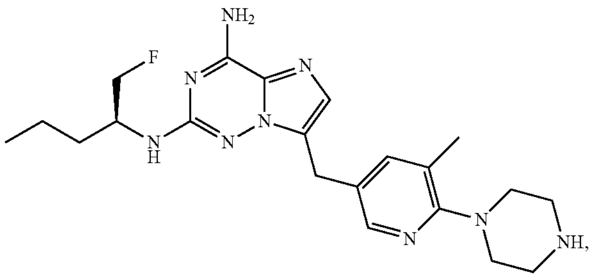,
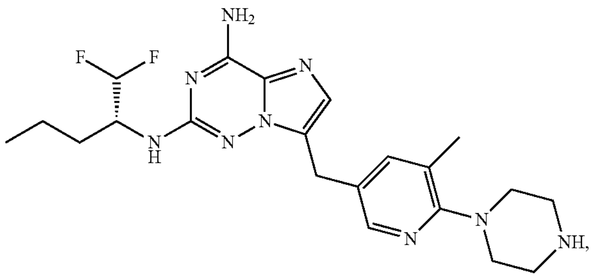,
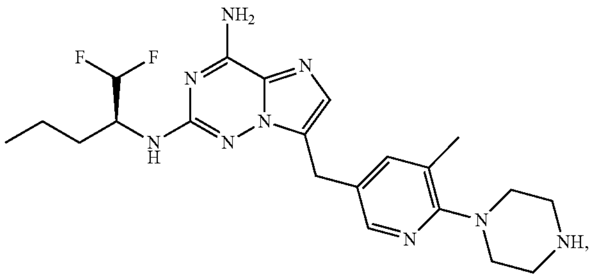,
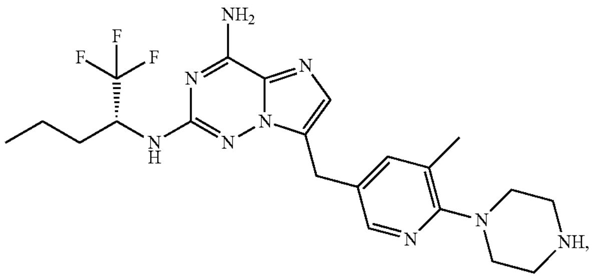,
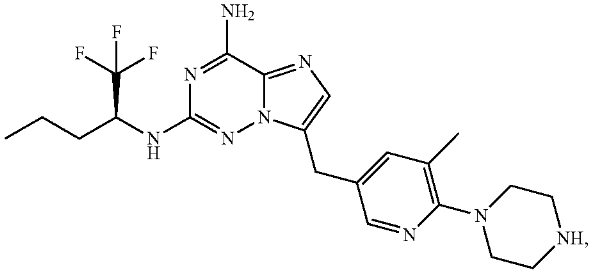,
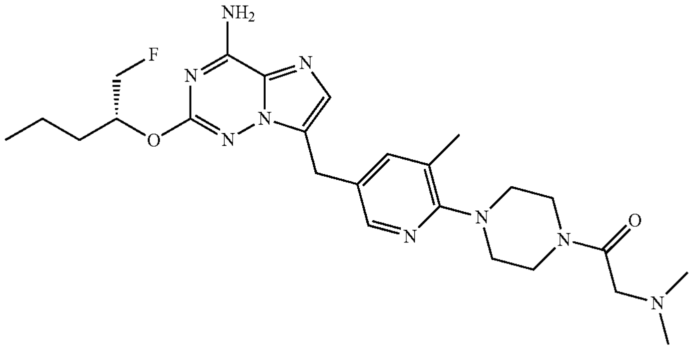,
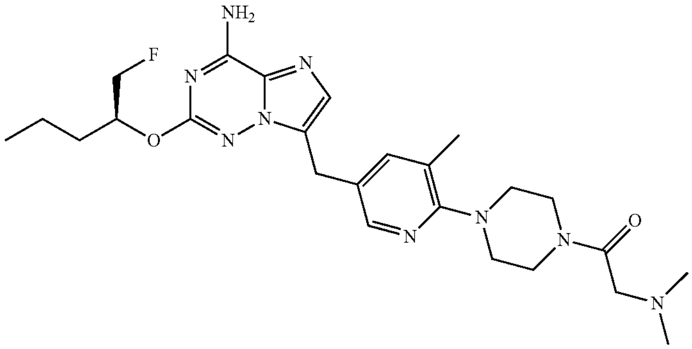, -continued
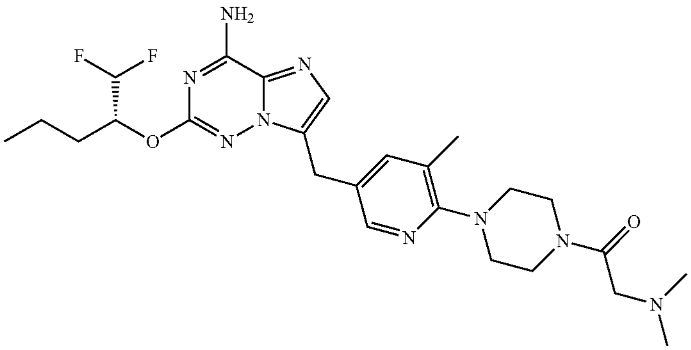
,
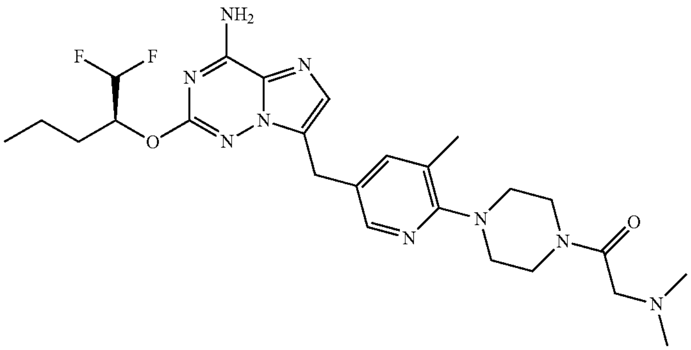
,
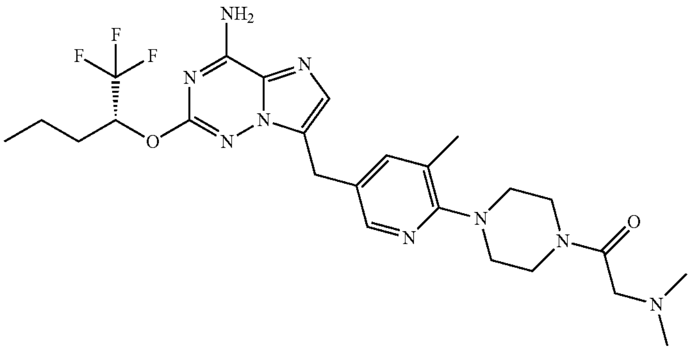
,
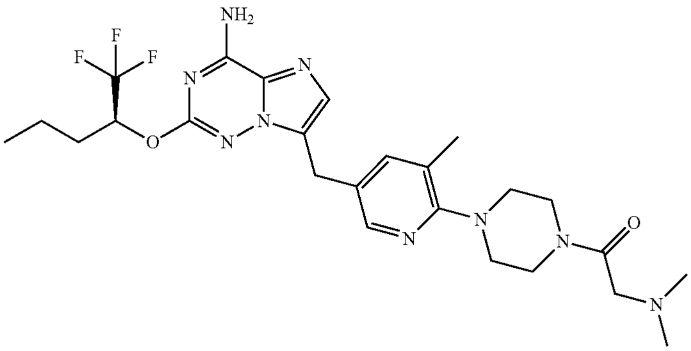
, -continued
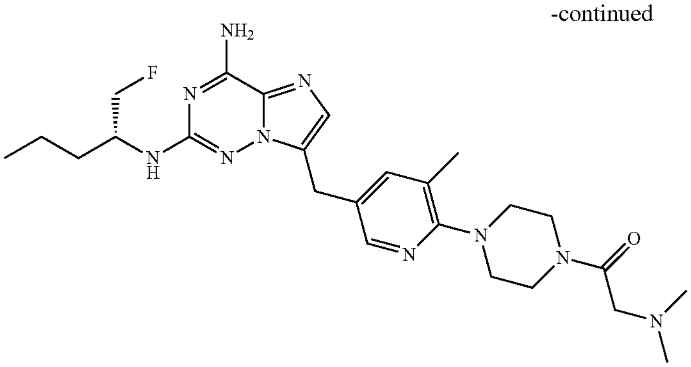
,
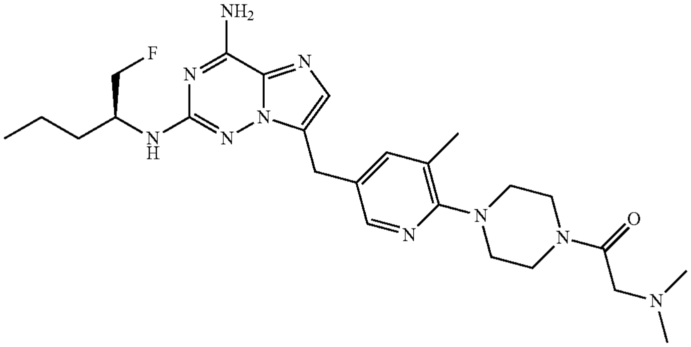
,
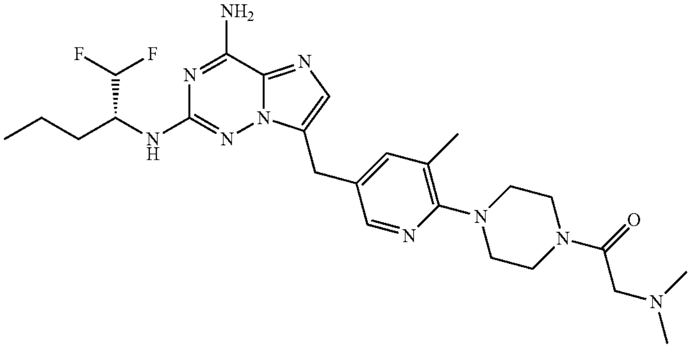
,
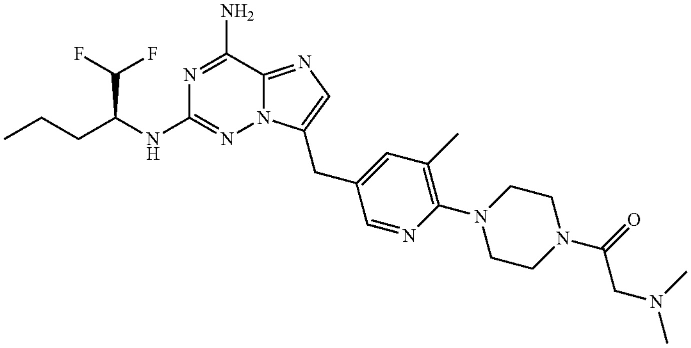
,
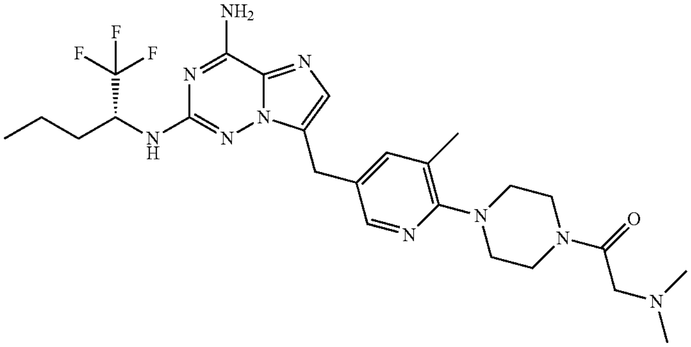
, -continued
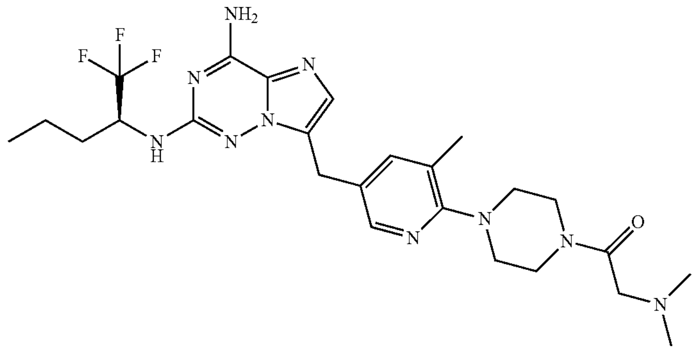
,
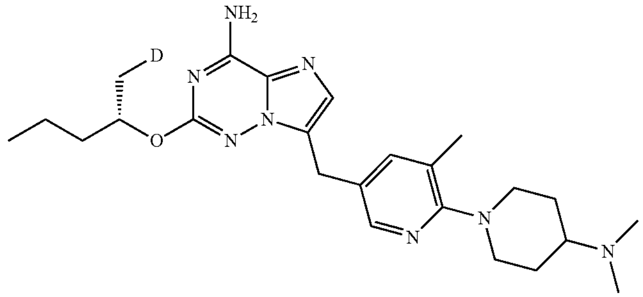
,
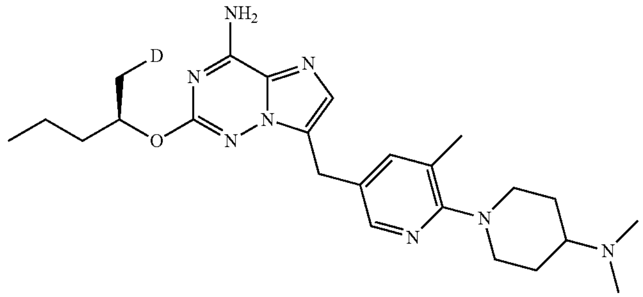
,
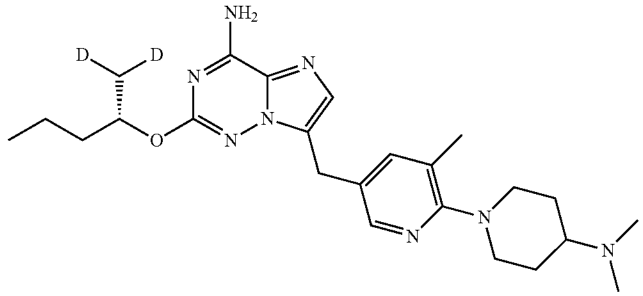
,
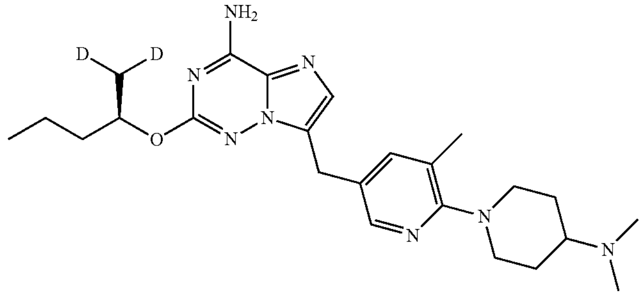
, -continued
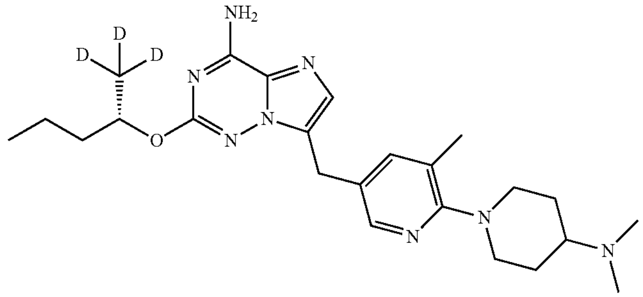
,
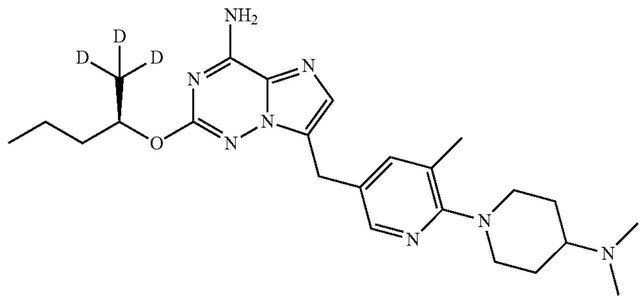
,
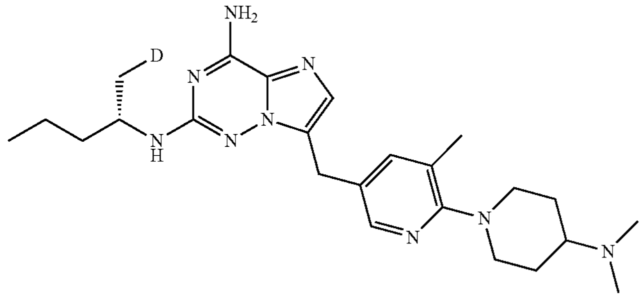
,
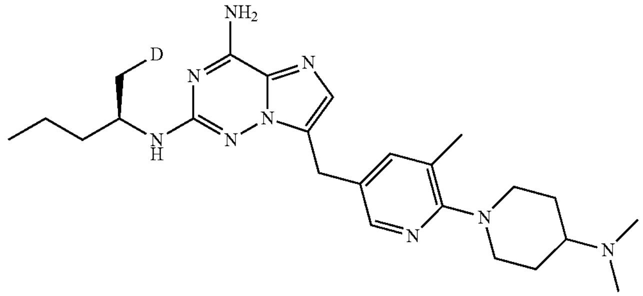
,
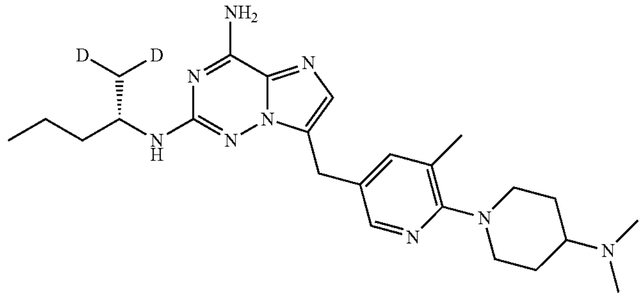
, -continued
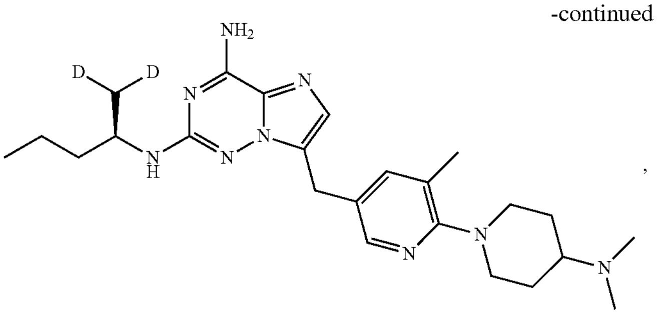
,
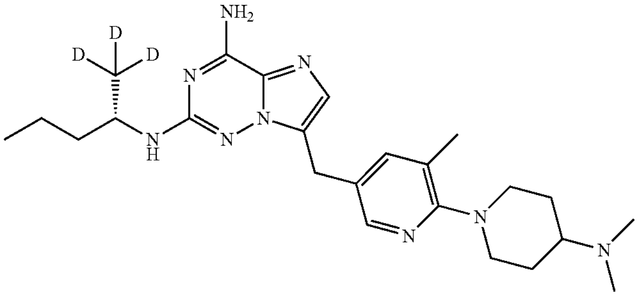
,
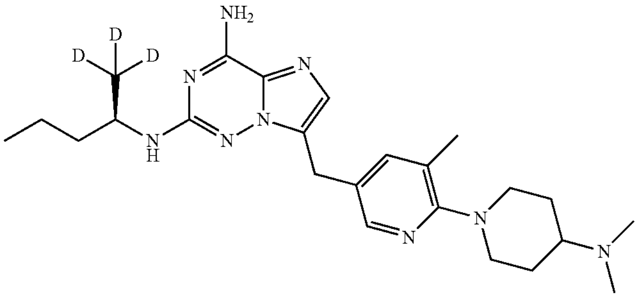
,
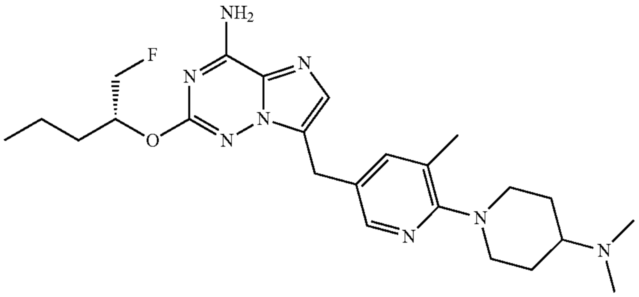
,
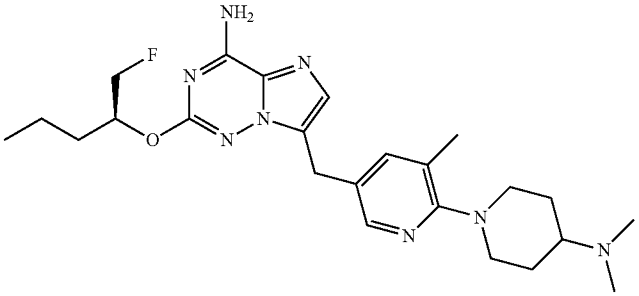
, -continued
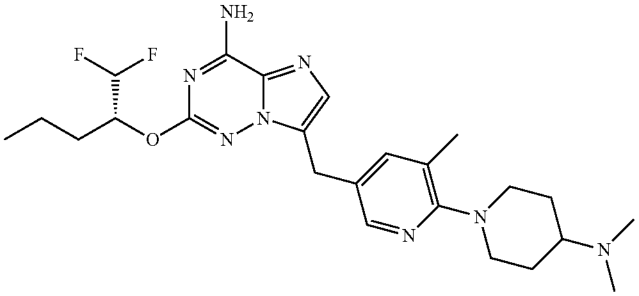
,
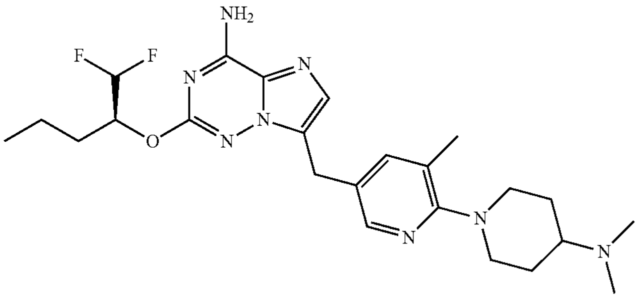
,
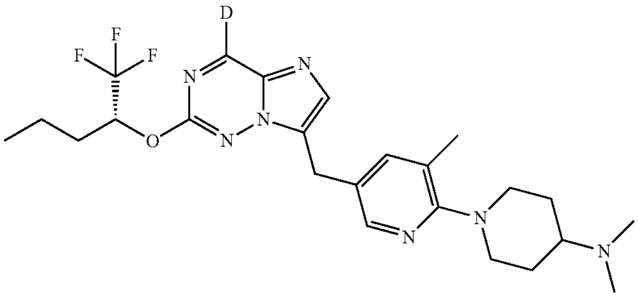
,
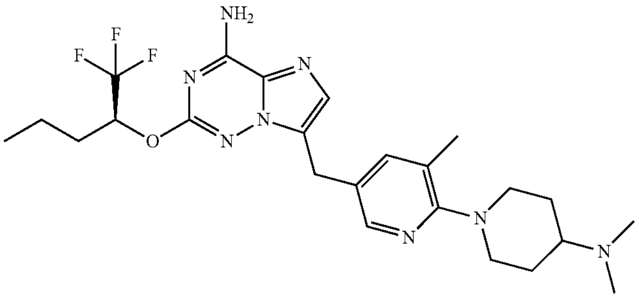
,
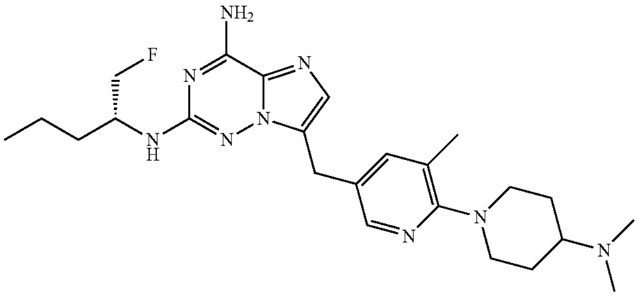
, -continued
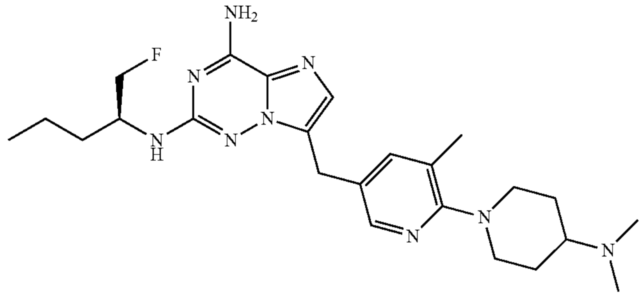
,
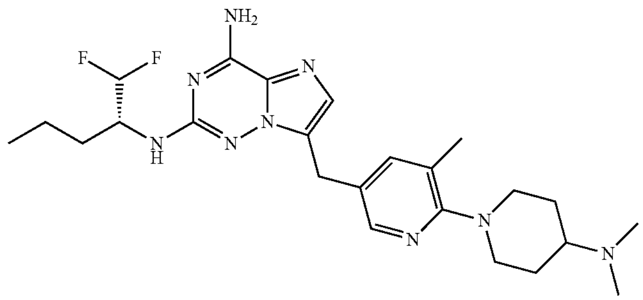
,
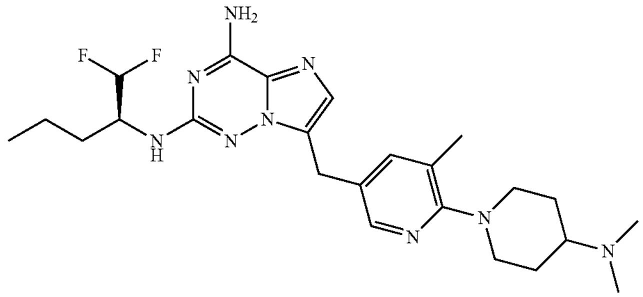
,
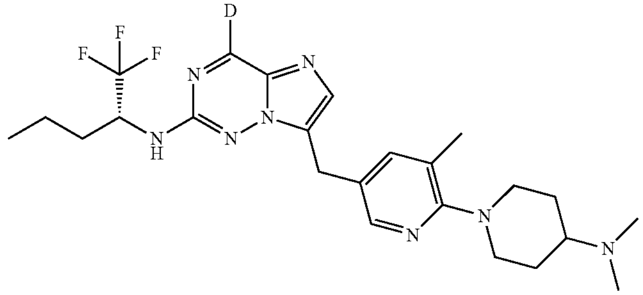
,
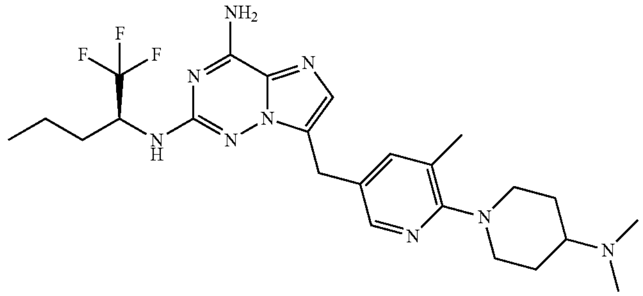
, -continued
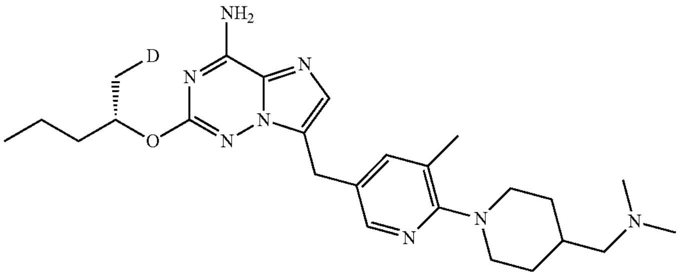
,
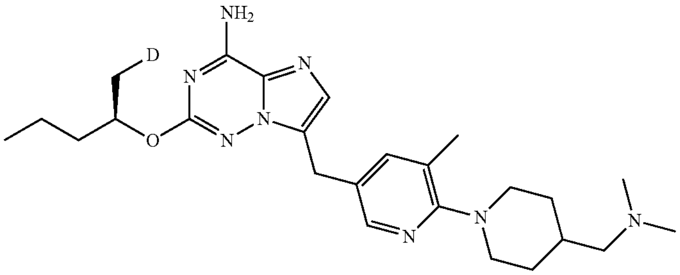
,
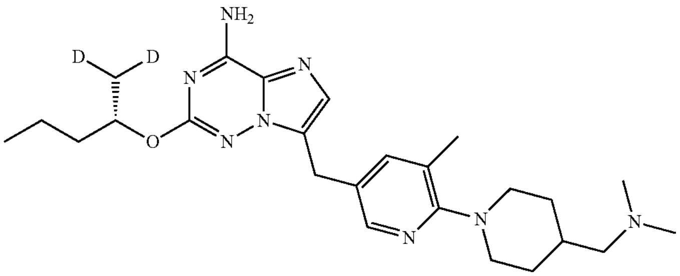
,
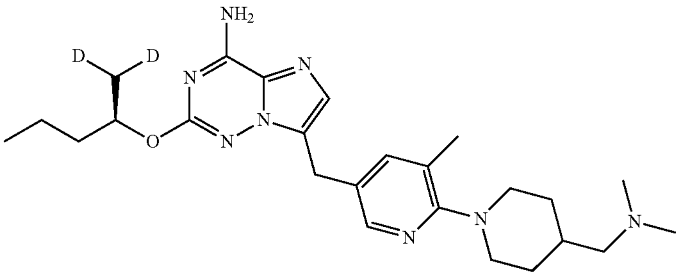
,
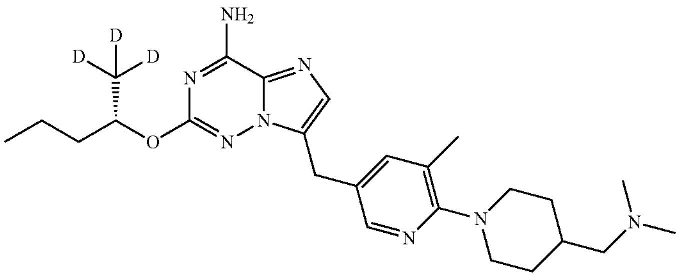
,
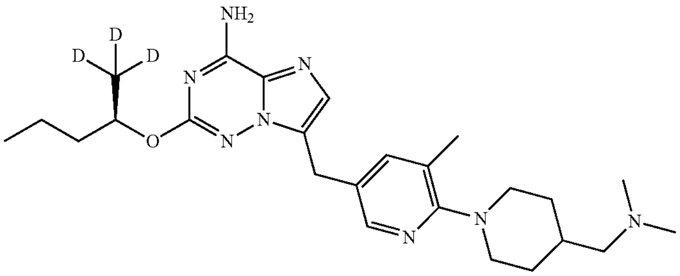
, -continued
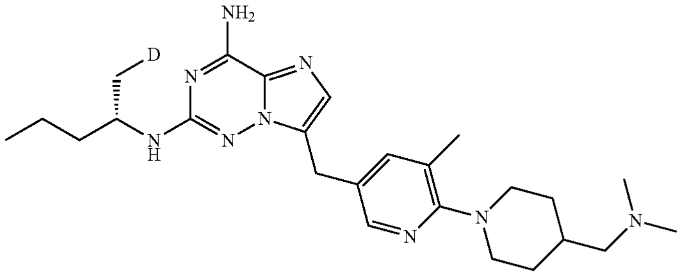
,
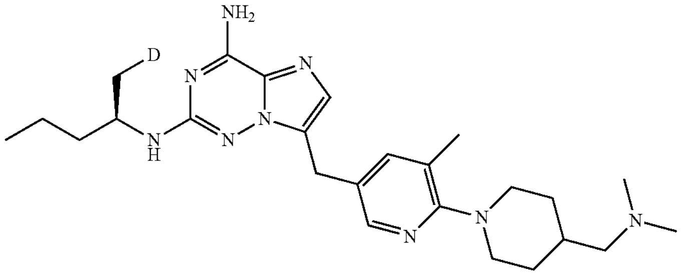
,
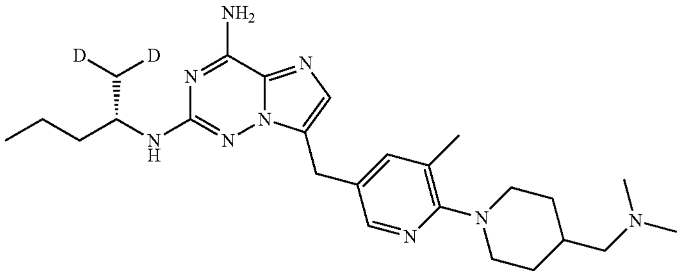
,
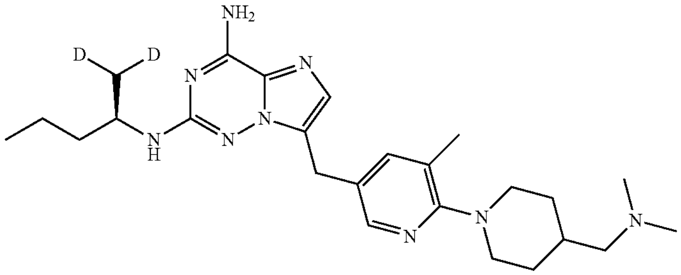
,
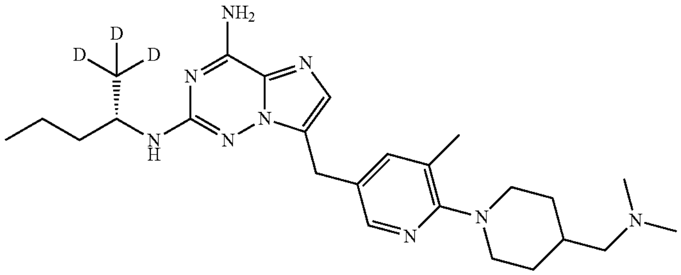
,
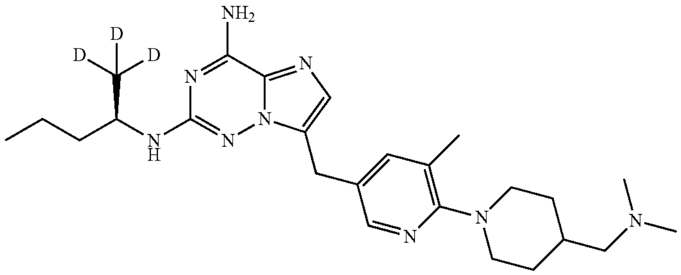
, -continued
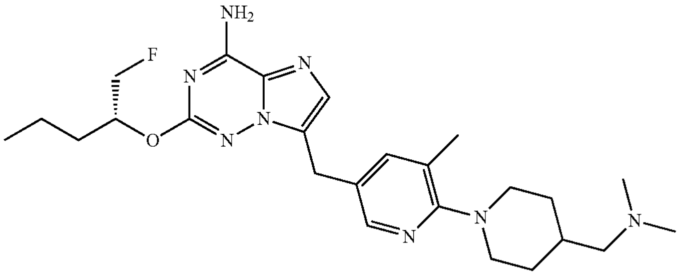
,
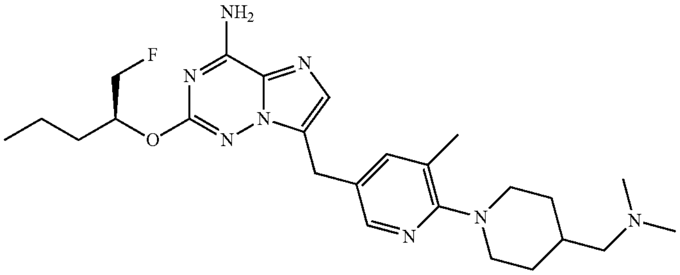
,
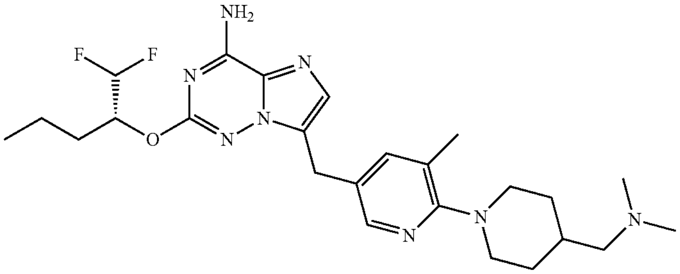
,
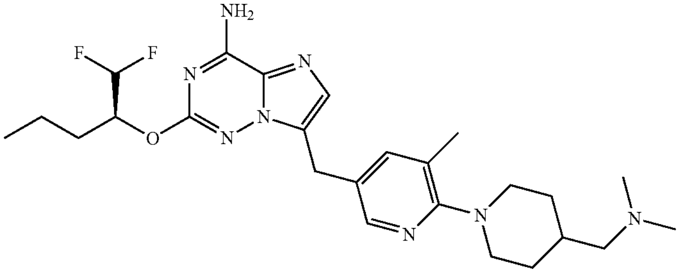
,
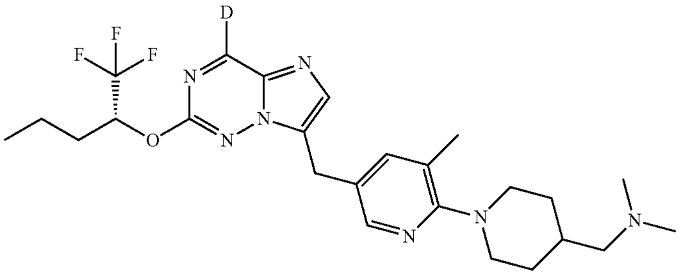
,
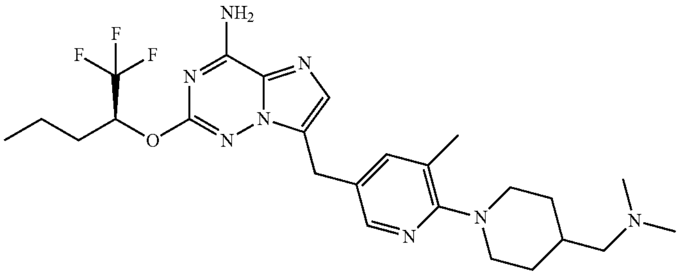
, -continued
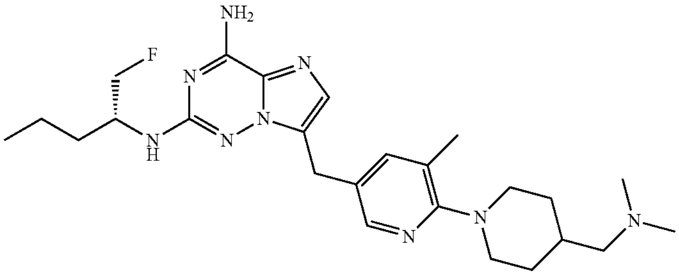
,
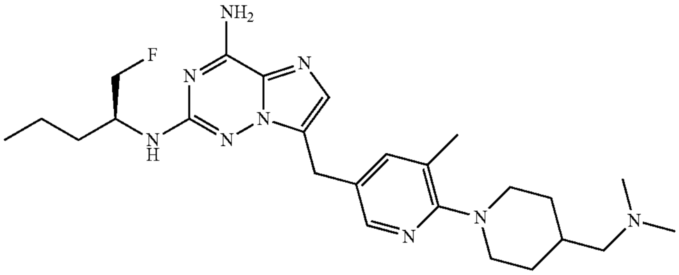
,
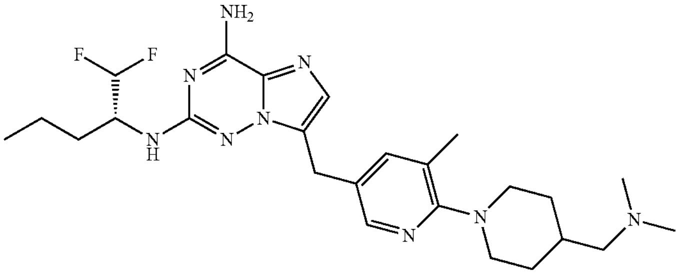
,
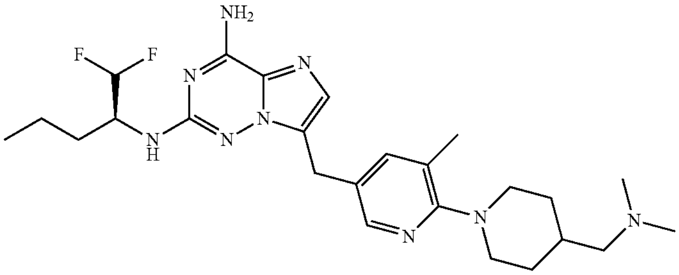
,
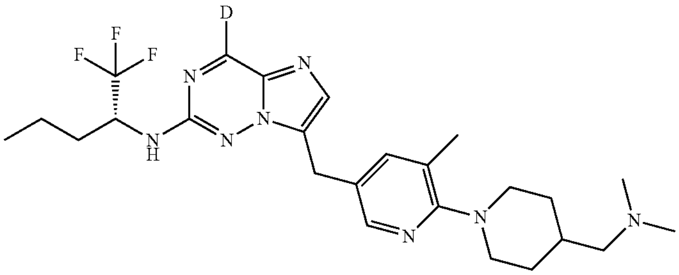
,
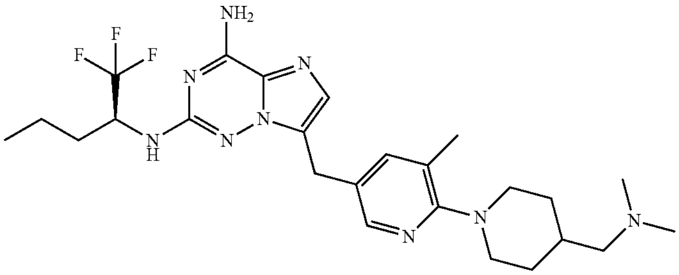
, -continued
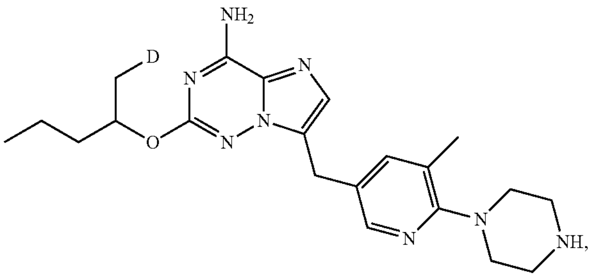
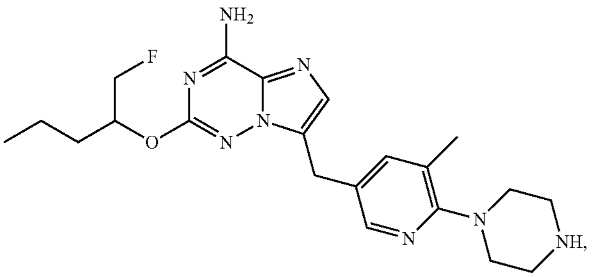
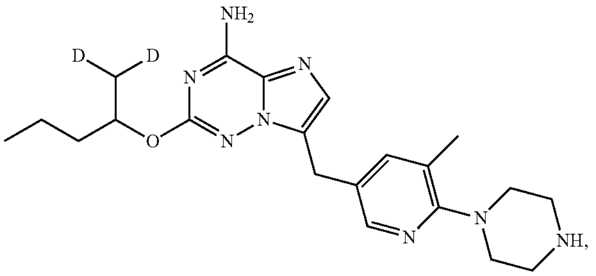
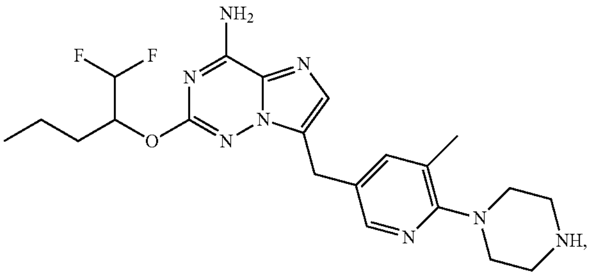
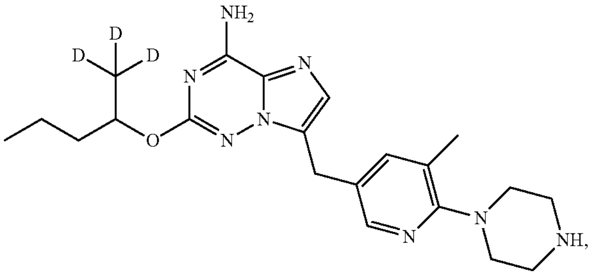
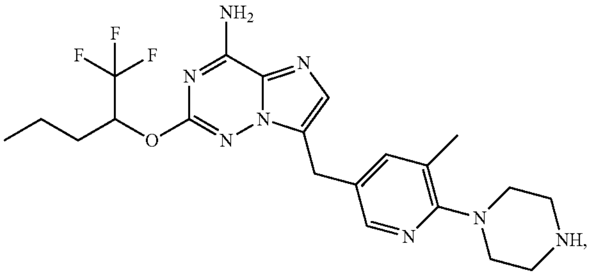
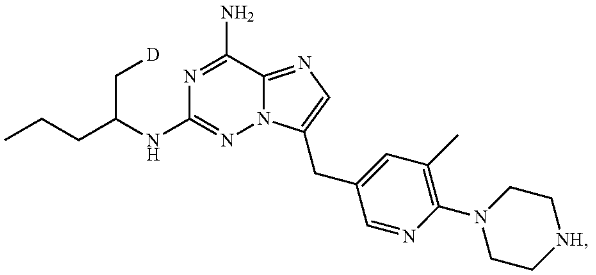
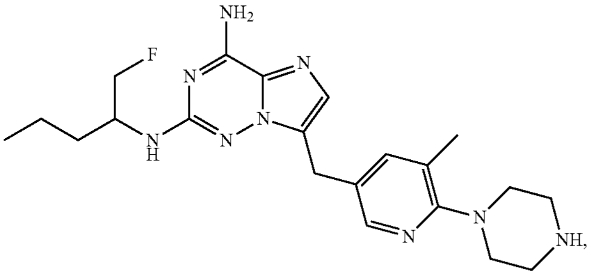
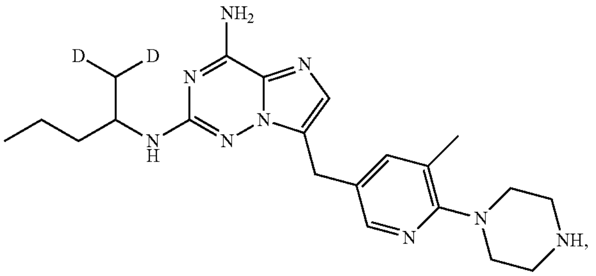
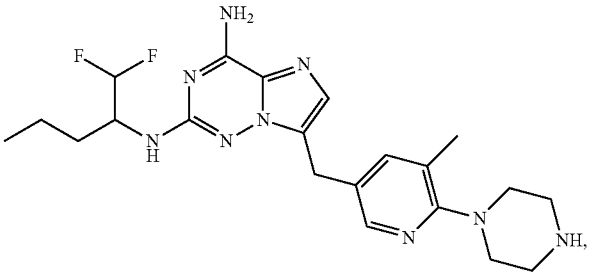
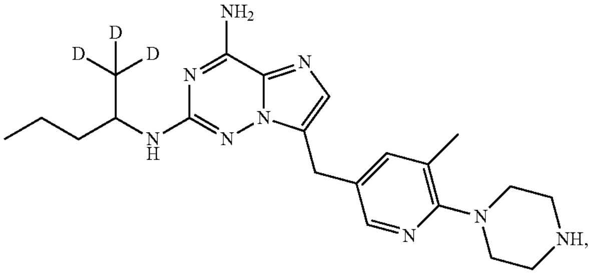

-continued
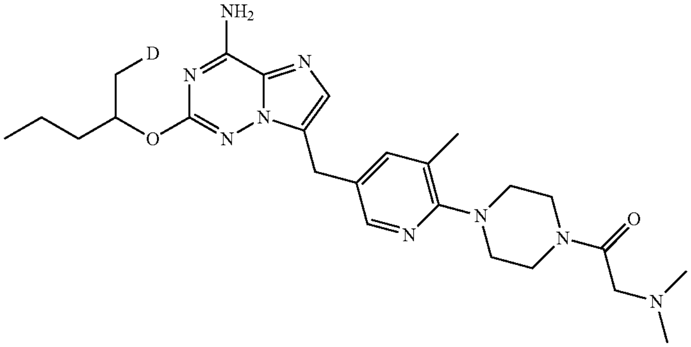
,
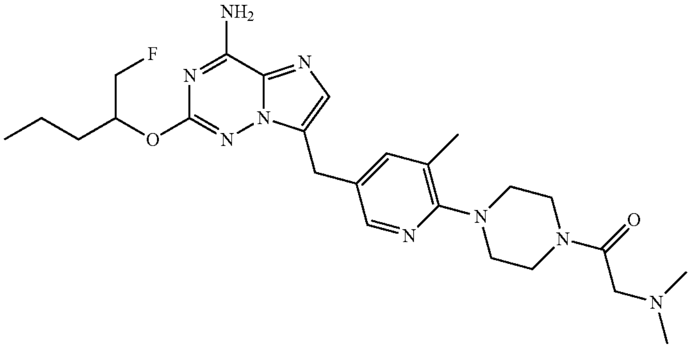
,
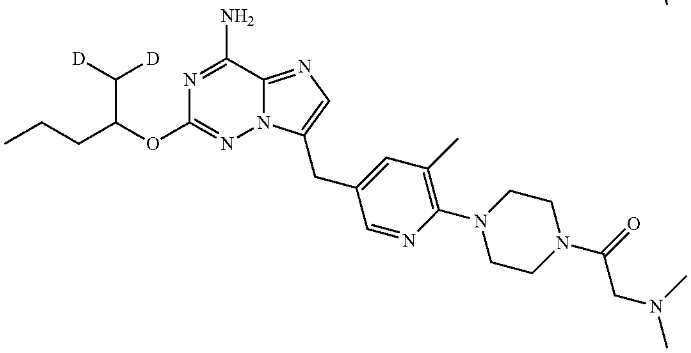
,
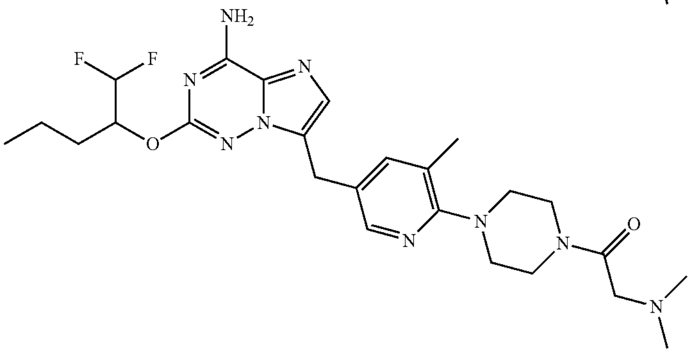
,
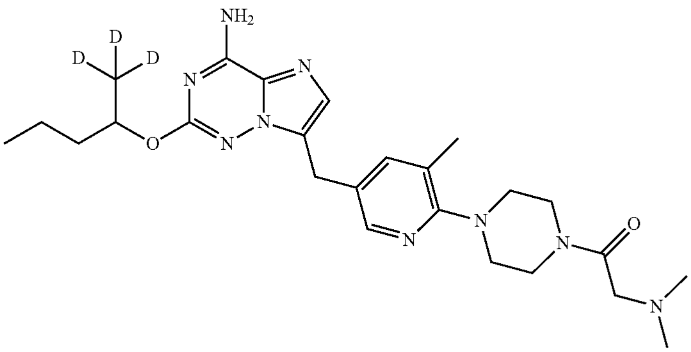
, -continued
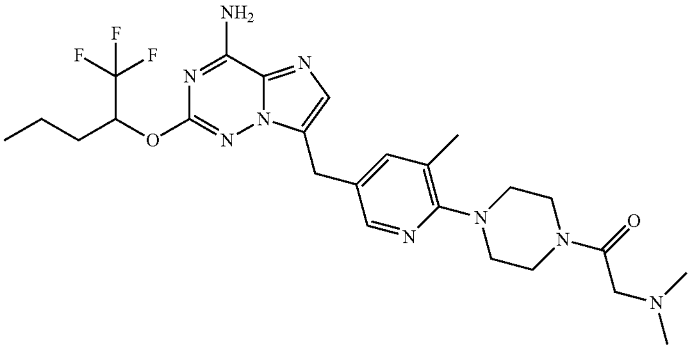
,
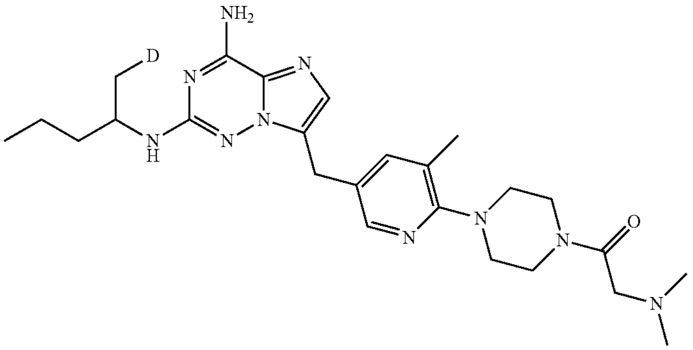
,
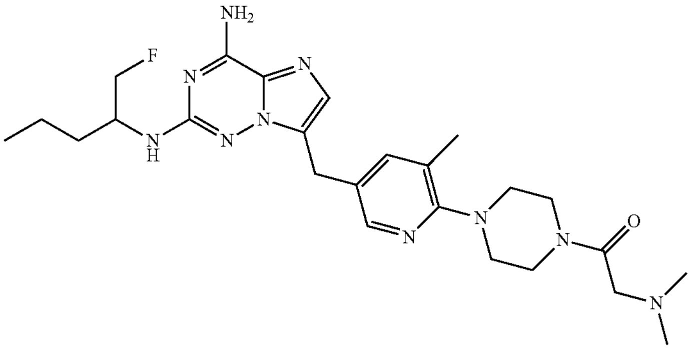
,
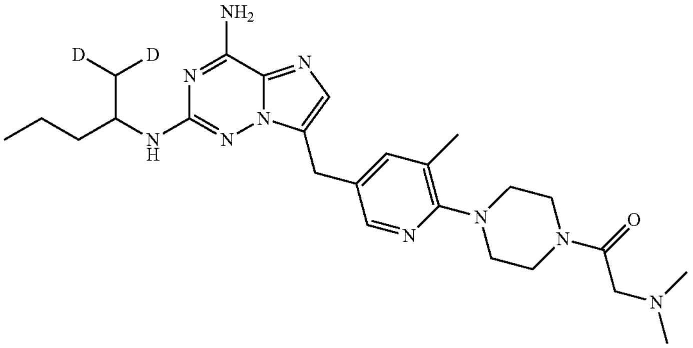
, -continued
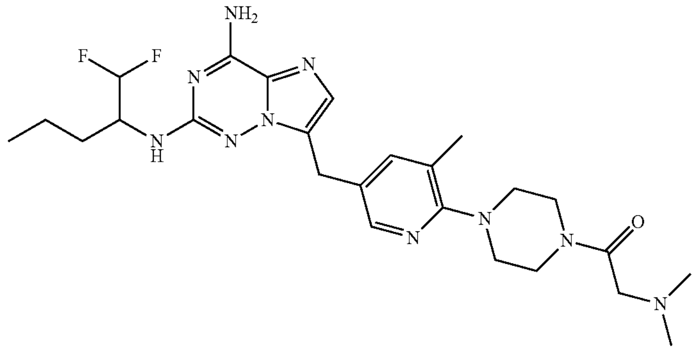
,
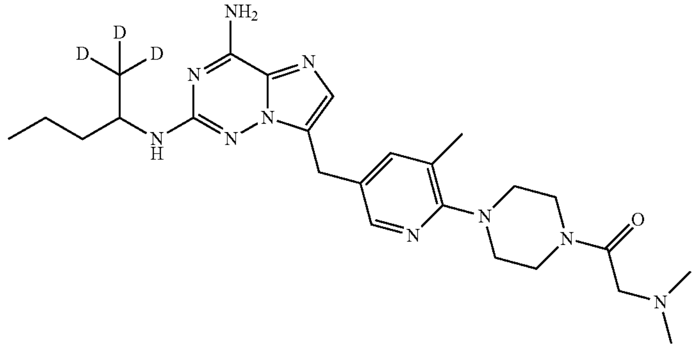
,
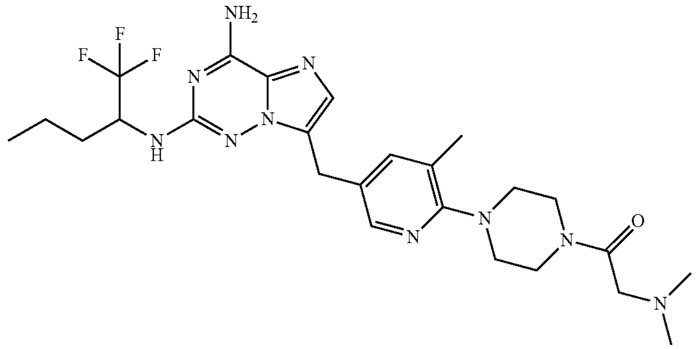
,
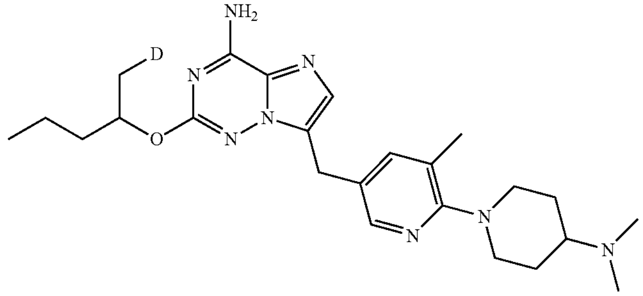
,
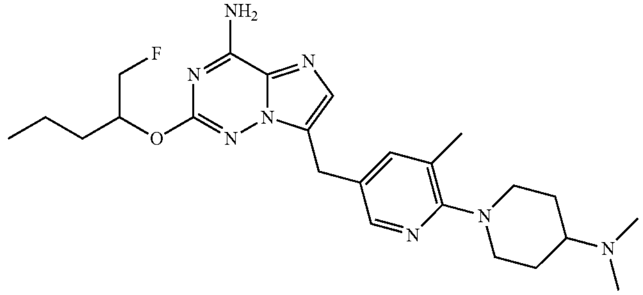
, -continued
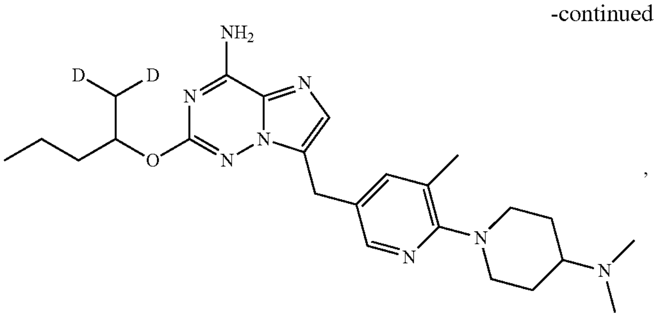
,
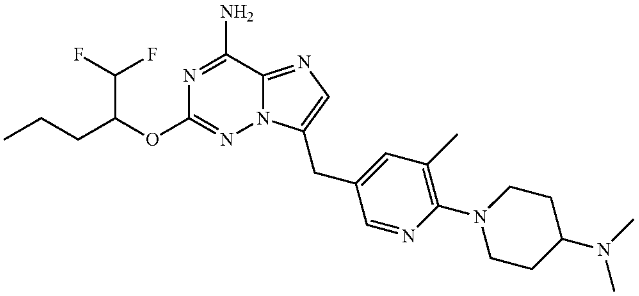
,
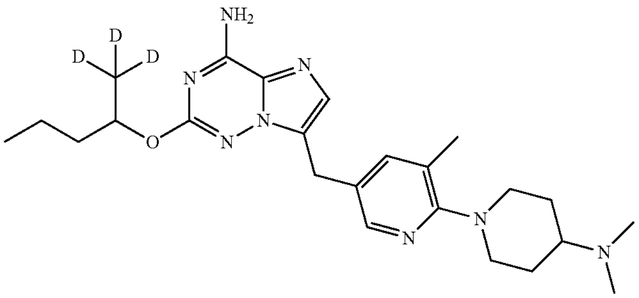
,
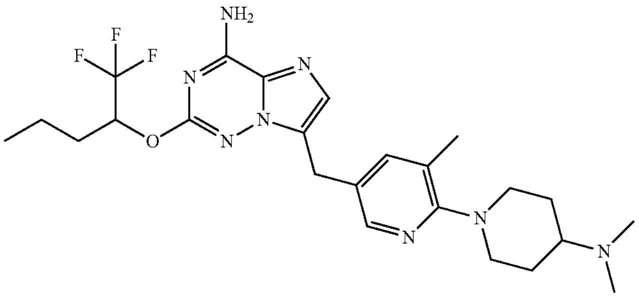
,
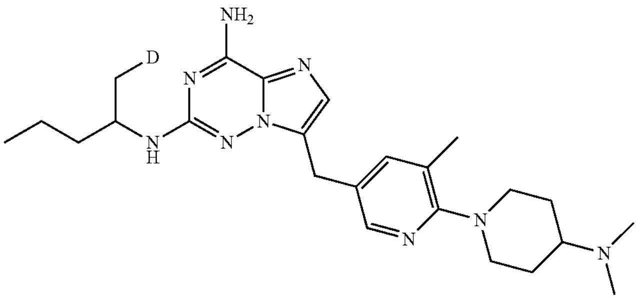
, -continued
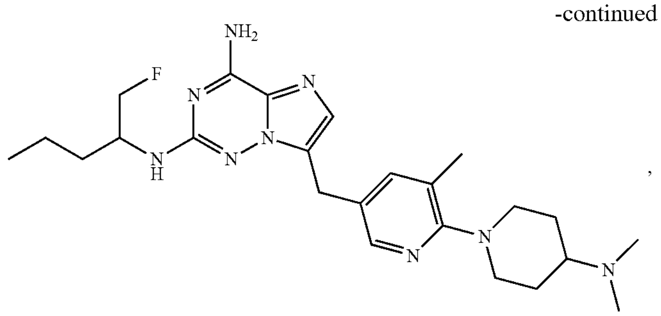
,
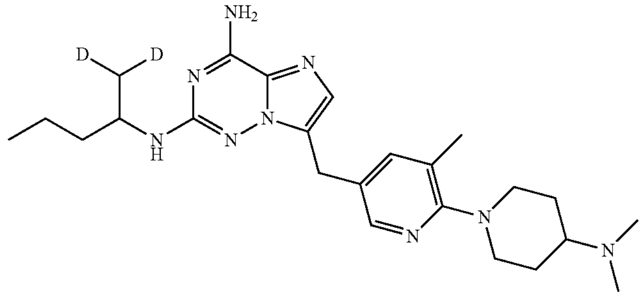
,
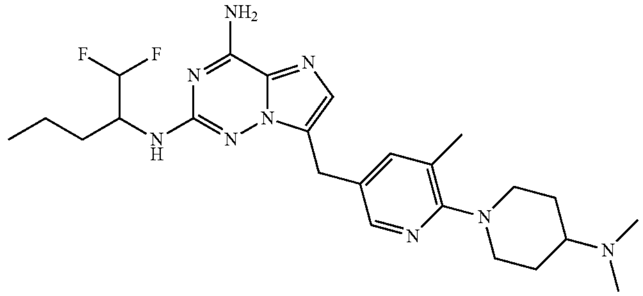
,
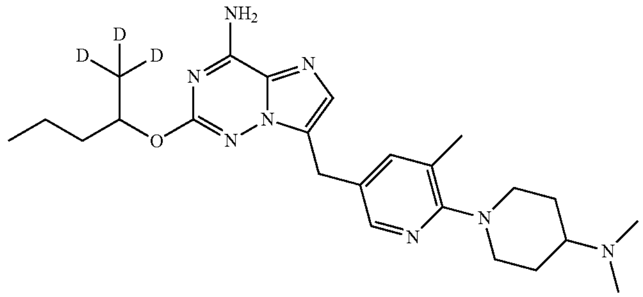
,
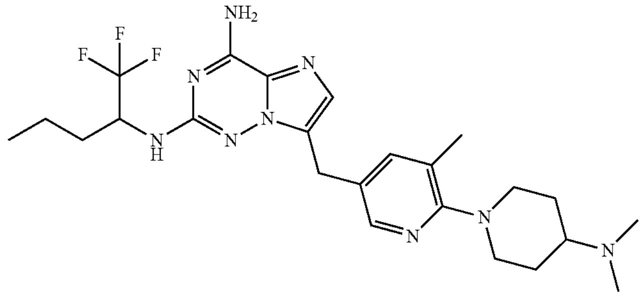
, -continued
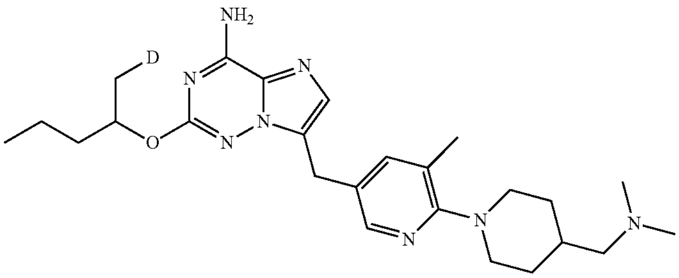
,
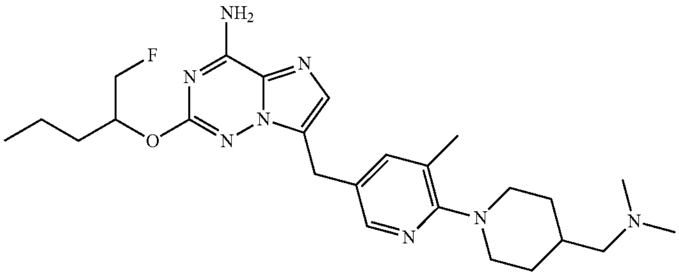
,
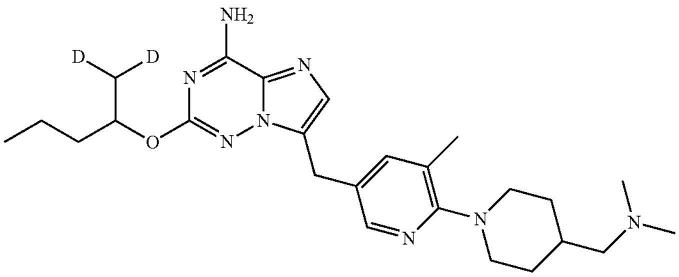
,
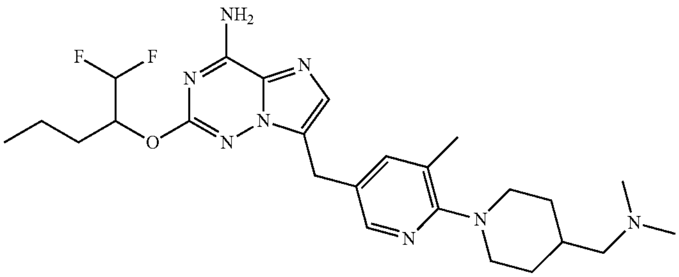
,
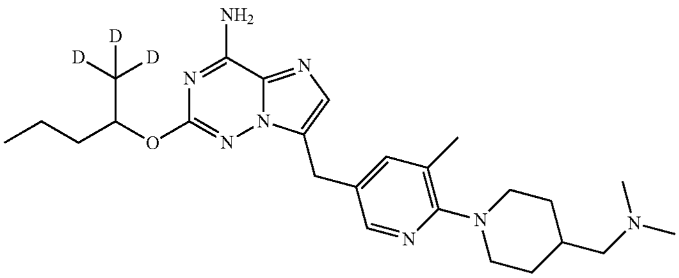
,
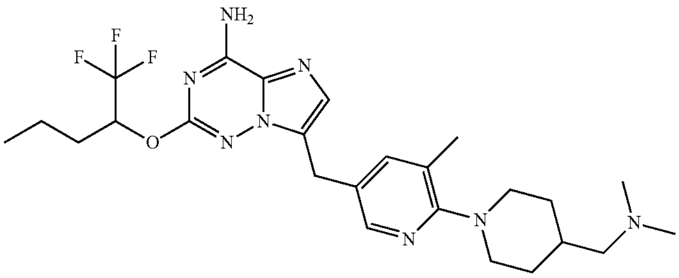
, -continued
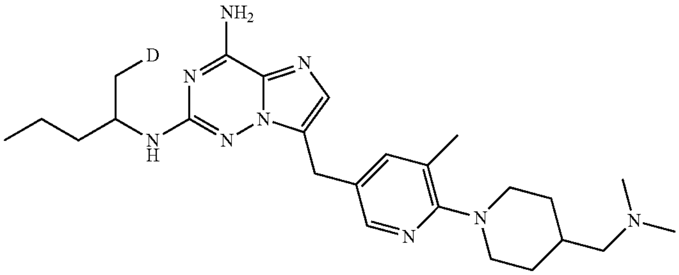
,
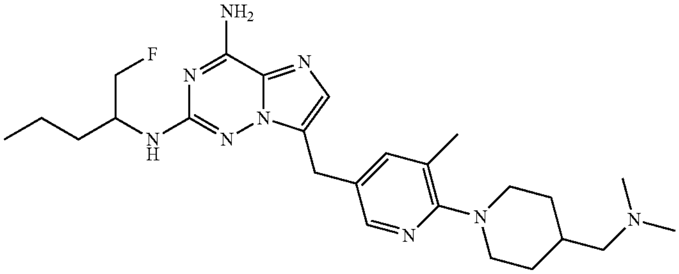
,
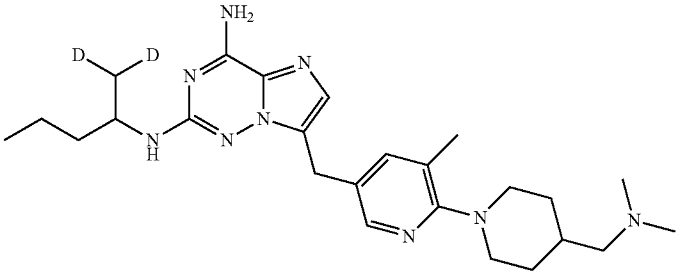
,
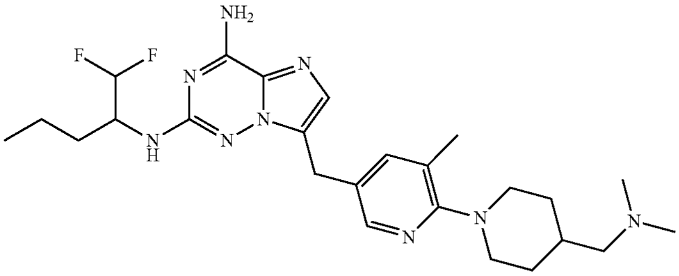
,
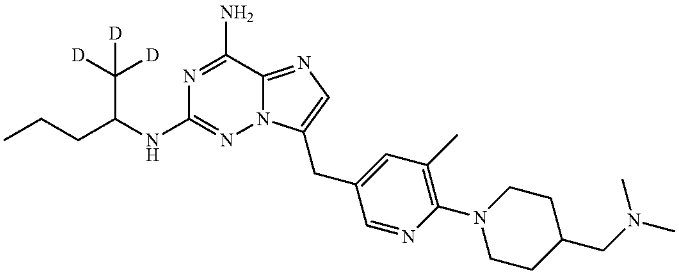
, or
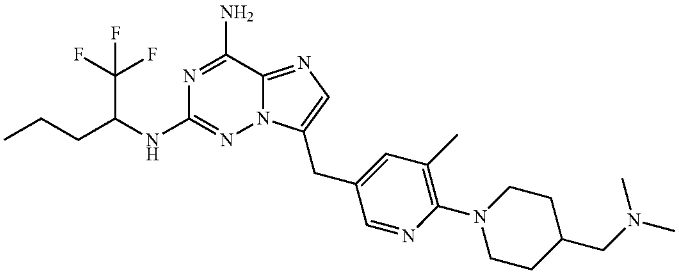
.

In the second aspect, disclosed herein is a pharmaceutical composition comprising the compound disclosed herein, including the compound of Formula (II) or the specific compounds exemplified herein, or a pharmaceutically acceptable salt thereof, and at least one pharmaceutically acceptable carrier or excipient.

In the third aspect, disclosed herein is a method of modulating TLR7, which comprise administering to an individual the compound disclosed herein, or a pharmaceutically acceptable salt thereof, including the compound of Formula (II) or the specific compounds exemplified herein.

In the fourth aspect, disclosed herein is a method of treating a disease or disorder in a patient comprising administering to the patient a therapeutically effective amount of the compound disclosed herein, or a pharmaceutically acceptable salt thereof as a TLR7 agonist, wherein the compound disclosed herein includes the compound of Formula (II) or the specific compounds exemplified herein. In some embodiments, the disease or disorder is associated with modulation of TLR, e.g., TLR-7, for example agonizing TLR-7. In some embodiments, the disease or disorder includes a viral infection caused by a virus selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C. In some embodiments, the disease or disorder includes melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, HBV, HCV, HPV, RSV, SARS, HIV, or influenza. Preferably, the disease or disorder is cancer.

DETAILED DESCRIPTION OF THE INVENTION

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The terms "alkoxy" or "alkyloxy" refers to an alkyl group, as previously defined, attached to the parent molecular moiety through an oxygen atom.

The term "amino" refers to $-NH_2$. The term "alkylamino" refers to —NH(alkyl). The term "dialkylamino" refers to $-N(alkyl)_2$. The term "halogen" herein refers to fluoro (F), chloro (Cl), bromo (Br) and iodo (I).

The term "haloalkyl" herein refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$ alkyl or halo $C_{1-4}$alkyl, but not limited to $-CF_3$, $-CH_2Cl$, $-CH_2CF_3$, $-CCl_2$, $CF_3$, and the like.

The term "alkenyl" herein refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., C2-6 alkynyl, include, but not limited to ethynyl, 1-propynyl, 2-propynyl (propargyl), 1-butynyl, 2-butynyl, and 3-butynyl groups.

The term "alkyloxy" or "alkoxy" herein refers to an alkyl group as defined above attached to the parent molecular moiety through an oxygen atom. Examples of an alkyloxy, e.g., C1-6alkyloxy or C1-4 alkyloxy includes, but not limited to, methoxy, ethoxy, isopropoxy, propoxy, n-butoxy, tert-butoxy, pentoxy and hexoxy and the like.

The term "alkoxy-alkyl-" refers to an alkyl group as defined above further substituted with an alkoxy as defined above. Examples of an alkoxy-alkyl-, e.g., C1-8alkoxy-C1-8alkyl- or C1-6alkoxy-C1-6alkyl- includes, but not limited to, methoxymethyl, ethoxymethyl, ethoxyethyl, isopropoxymethyl, or propoxymethyl and the like.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, preferably cyclohexenyl.

The term "cycloalkynyl" refers to non-aromatic cycloalkyl groups of from 5 to 10 carbon atoms having single or multiple rings and having at least one triple bond.

The term "deuterated" is used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "aryl" used alone or in combination with other terms refers to a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., C5-10 aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" herein refers to a group selected from:

- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in the aromatic ring; and
- 11- to 14-membered tricyclic rings comprising at least one heteroatom, for example, from 1 to 4, or in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The term "optionally oxidized sulfur" used herein refer to S, SO or SO2.

The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from nitrogen, oxygen or optionally oxidized sulfur. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term “spiro heterocyclyl” refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl.

The term “fused heterocyclic group” refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin.

The term “bridged heterocyclyl” refers to a 5 to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

Compounds disclosed herein may contain an asymmetric center and may thus exist as enantiomers. “Enantiomers” refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term “substantially pure” as used herein means that the target stereoisomer contains no more than 35%, such as no more than 30%, further such as no more than 25%, even further such as no more than 20%, by weight of any other stereoisomer(s). In some embodiments, the term “substantially pure” means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. Cis formation means that both substituents are found on the upper side of the 2 substituent placements on the carbon, while trans would mean that they were on opposing sides.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (“SMB”) and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (II), and salts of the stereoisomers of the compound of Formula (II), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid Formulation such as tablets, powder, granule, capsules and the like, a liquid Formulation such as water or oil suspension or other liquid Formulation such as syrup, solution, suspension or the like; for parenteral administration, the pharmaceutical composition may be solution, water solution, oil suspension concentrate, lyophilized powder or the like. Preferably, the Formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All Formulations of the pharmaceutical composition disclosed herein can be produced by the conventional methods in the pharmaceutical field. For example, the active ingredient can be mixed with one or more excipients, then to make the desired Formulation. The "pharmaceutically acceptable excipient" refers to conventional pharmaceutical carriers suitable for the desired pharmaceutical Formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term “disease” refers to any disease, discomfort, illness, symptoms or indications, and can be interchangeable with the term “disorder” or “condition”.

Throughout this specification and the claims which follow, unless the context requires otherwise, the term “comprise”, and variations such as “comprises” and “comprising” are intended to specify the presence of the features thereafter, but do not exclude the presence or addition of one or more other features. When used herein the term “comprising” can be substituted with the term “containing”, “including” or sometimes “having”.

Throughout this specification and the claims which follow, the term “Cn-m” indicates a range which includes the endpoints, wherein n and m are integers and indicate the number of carbons. Examples include C1-8, C1-6, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from room temperature to the solvent’s boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ration used.

The compounds disclosed herein can be prepared by following Scheme I.

1

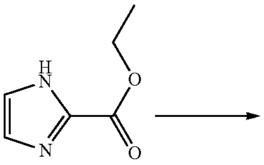

2

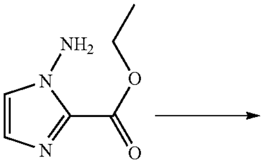

-continued

3

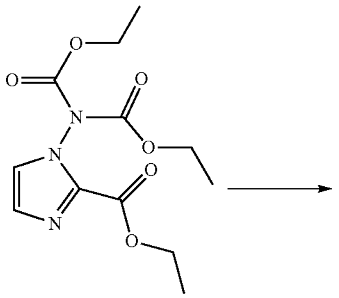

4

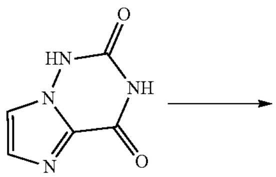

5

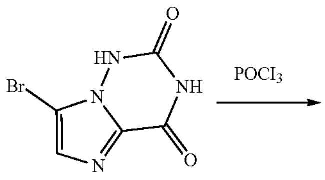

6

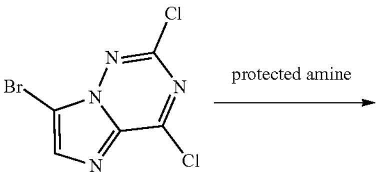

7

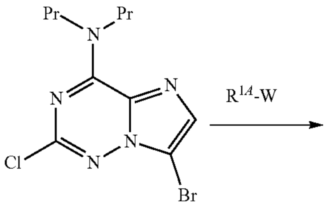

8

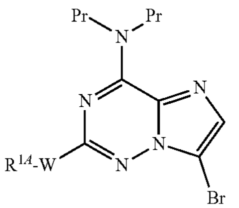

W= N or O

9

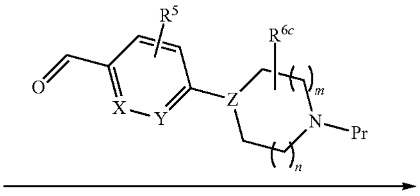

-continued

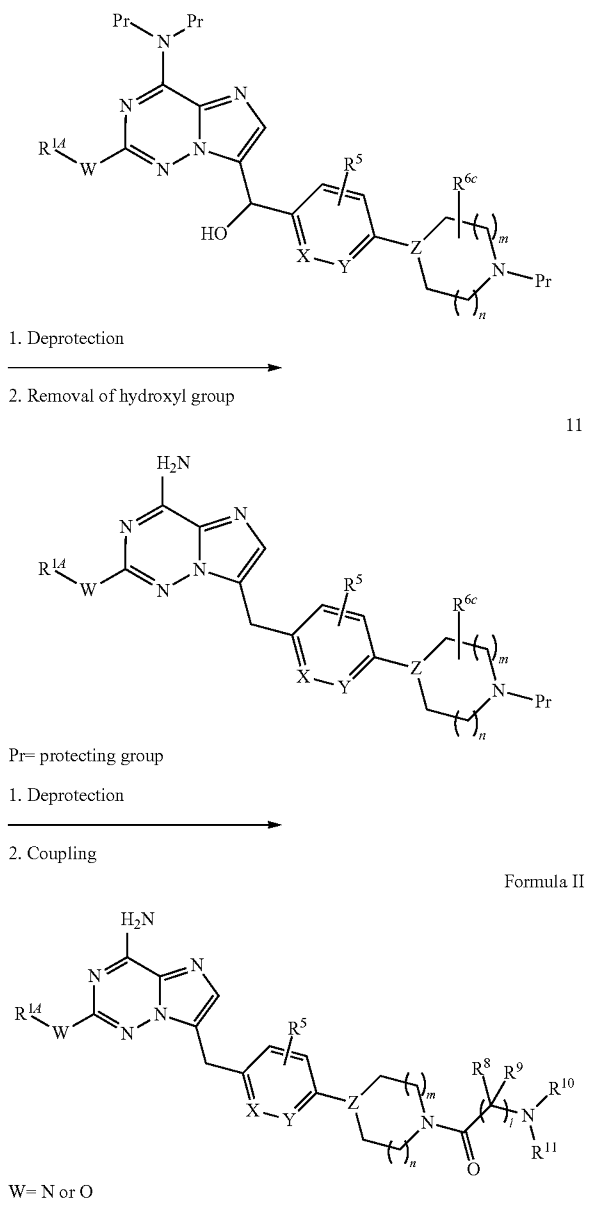

wherein —W—$R^{1A}$ is —$OR^{1a}$ or —$NR^{1a}R^{1b}$, and $R^{1a}$, $R^{1b}$, $R^5$ and $R^{6c}$ are defined as for Formula (II); $R^8$, $R^9$, $R^{10}$ and $R^{11}$ are independently $C_{1-6}$ alkyl X, Y and Z are independently CH or N, W is independently N or O, m was 0, 1, 2, or 3 and n is 1, 2, or 3.

In Scheme I, a commercially available ethyl 1H-imidazole-2-carboxylate is reacted with 2-O-(4-nitrobenzoyl)hydroxylamine to form Intermediate 2, which was reacted with ethyl carbonochloridate then the ring was closed in the presence of ammonium hydroxide to give imidazo[2,1-f][1,2,4]triazine-2,4(1H,3H)-dione. Intermediate 5 is obtained after introduction one Br atom using bromination reagent and then the dione was chloridized to form Compound 6. One chlorine atom is replaced by protected amine and another chlorine atom is reacted with RW to give Intermediate 8, which subsequently was reacted with different aldehydes under basic condition to form Intermediate 10.

The protected groups on the amine and the hydroxyl group were removed to give Intermediate 11. One compound of Formula (II) was obtained after deprotection and coupled with different acids under basic condition.

Intermediate 10 also can be prepared by following Scheme II.

Scheme II

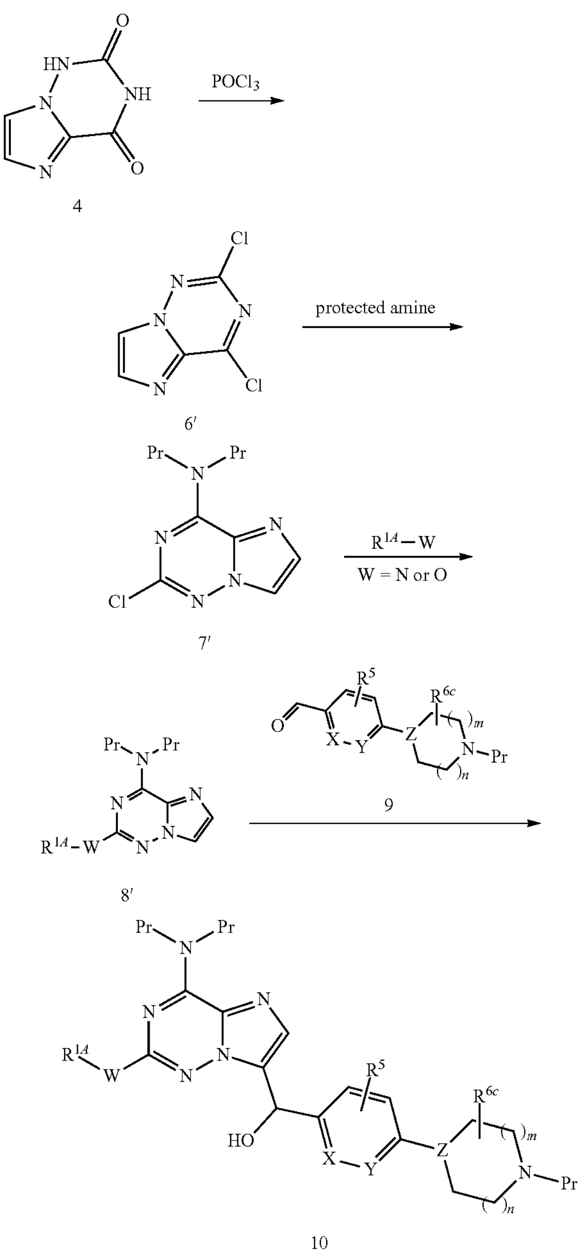

Pr = protecting group

In Scheme II, Intermediate 4 was chloridized to form Intermediate 6'. One chlorine atom was replaced by protected amine to obtain Intermediate 7', which was reacted with $R^{1A}$—W to give the key Intermediate 8', which subsequently was reacted with different aldehydes under basic condition to form Intermediate 10.

EXAMPLES

The examples below are intended to be purely exemplary and should not be considered to be limiting in any way. Unless otherwise specified, the experimental methods in the Examples described below are conventional methods. Unless otherwise specified, the reagents and materials are all commercially available. All solvents and chemicals employed are of analytical grade or chemical purity. Solvents are all redistilled before use. Anhydrous solvents are all prepared according to standard methods or reference methods. Silica gel (100-200 meshes) for column chromatography and silica gel (GF254) for thin-layer chromatography (TLC) are commercially available from Tsingdao Haiyang Chemical Co., Ltd. or Yantai Chemical Co., Ltd. of China; all are eluted with petroleum ether (60-90° C.)/ethyl acetate (v/v), and visualized by iodine or the solution of molybdphosphoric acid in ethanol unless otherwise specified. All extraction solvents, unless otherwise specified, are dried over anhydrous $Na_2SO_4$. $^1H$ NMR spectra are recorded on Bruck-400 nuclear magnetic resonance spectrometer with TMS (tetramethylsilane) as the internal standard. LC/MS data are recorded by using Agilent1100 High Performance Liquid Chromatography-Ion Trap Mass Spectrometer (LC-MSD Trap) equipped with a diode array detector (DAD) detected at 214 nm and 254 nm, and an ion trap (ESI source). All compound names except the reagents were generated by ChemDraw®.

In the following examples, the following abbreviations are used:

AcOH Acetic acid
Aq. Aqueous
BINAP 2,2'-bis(diphenylphosphino)-1,1'-binaphthalene
Brine Saturated aqueous sodium chloride solution
Bn Benzyl
BnBr Benzyl Bromide
BPO Benzoyl peroxide
BSA N,O-Bis(trimethylsilyl)acetamide
$CH_2Cl_2$ or DCM Dichloromethane
DIAD Diisopropyl azodicarboxylate
DMF N,N-Dimethylformamide
Dppf 1,1'-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc or EA Ethyl acetate
EtOH Ethanol
$Et_2O$ or ether Diethyl ether
g Grams
h or hr Hour
HATU O-(7-Azabenzotriazol-1-yl)-N,N,N',N'-tetramethyluronium hexafluorophosphate
Hex Hexane
HCl Hydrochloric acid
HMDS Hexamethyldisilazane
HPLC High-performance liquid chromatography
IBX 2-Iodoxybenzoic acid
IPA Isopropyl alcohol
i-PrOH Isopropyl alcohol
LCMS Liquid chromatography-mass spectrometry
mg Milligrams
mL Milliliters
mmol Millimole
MeCN Acetonitrile
MeOH Methanol
Min Minutes
ms or MS Mass spectrum
MTBE methyl tert-butyl ether
$Na_2SO_4$ Sodium sulfate
NBS N-Bromosuccinimide
NMP N-Methyl Pyrrolidone
PE petroleum ether
PMB (4-methoxyphenyl)methanamine
prep Preparative
Rt or rt Room temperature
sat. Saturated
TBAF Tetra-butyl ammonium fluoride
TBSCl tert-Butyldimethylsilyl chloride
t-BuOK Potassium tert-butoxide
TFA Trifluoroacetic acid
THF Tetrahydrofuran
TLC thin layer chromatography
μL Microliters

Synthesis of Intermediate-I

7-bromo-2-butoxy-N,N-bis(4-methoxybenzyl)imidazo[2,1-f][1,2,4]triazin-4-amine

Step A: ethyl 1-amino-1H-imidazole-2-carboxylate hydrochloride

To a stirred solution of ethyl 1H-imidazole-2-carboxylate (56 g, 0.4 mol) in NMP (1.2 L), t-BuOK (1M in THF, 440 ml, 0.44 mol) was added at 20-30° C. The mixture was stirred for 0.5 h. A solution of O-(4-nitrobenzoyl)hydroxylamine (80.08 g, 0.44 mol) in NMP (0.4 L) was added dropwise below 30° C. The solution was stirred at rt for 2 h. The solution was diluted with MTBE (500 ml). HCl (4M in EA, 100 ml) was added to quench the reaction. Diatomite (20 g) was added to the above mixture and then stirred for 0.5 h. The mixture was filtered. The filtrate was diluted with MTBE (2 L) and added HCl (4M in EA, 200 ml) dropwise. The suspension was stirred for 0.5 h and filtered. The filtration cake was rinsed with MTBE and dried in oven to afford the product (70 g, 91%). MS: M/e 156 $(M+1)^+$.

Step B: mixture of ethyl 1-((ethoxycarbonyl)amino)-1H-imidazole-2-carboxylate and ethyl 1-(di(ethoxycarbonyl)amino)-1H-imidazole-2-carboxylate (1:1)

To a stirred solution of ethyl 1-amino-1H-imidazole-2-carboxylate hydrochloride (80 g, 0.42 mol) in THF (900 ml) and $H_2O$ (900 ml), $NaHCO_3$ (178.9 g, 2.1 mol) was added in several portions. Ethyl chloroformate (98.55 g, 0.9 mol) was added dropwise below 30° C. The mixture was stirred at rt for 4 h. The mixture was diluted with EA (1 L) and then separated. The aqueous layer was extracted with EA (800 ml). The collected organic layer was washed with brine, dried over $Na_2SO_4$, filtered and concentrated to afford the crude product (113 g) as a yellow oil, which was used directly for the next step without further purification. MS: M/e 228 $(M+1)^+$ & M/e 300 $(M+1)^+$.

Step C: imidazo[2,1-f][1,2,4]triazine-2,4(1H,3H)-dione

Into a sealed tube, a mixture of ethyl 1-((ethoxycarbonyl)amino)-1H-imidazole-2-carboxylate and ethyl 1-(di(ethoxycarbonyl)amino)-1H-imidazole-2-carboxylate (110 g) in ammonium hydroxide (400 ml, 3.6 V) and IPA (200 ml, 1.8

V) was charged. The mixture was stirred at 120° C. overnight. After cooling, the mixture was filtered. The filtration cake was rinsed with MeOH. The filtrate was concentrated under reduced pressure. The resulting residue was slurried in MeOH, filtered and rinsed with MeOH. The resulting filtration cake and the former filtration cake were mixed and dried in oven to afford the product (56 g) as a white solid. MS: M/e 153 $(M+1)^+$.

Step D: 7-bromoimidazo[2,1-f][1,2,4]triazine-2,4(1H,3H)-dione

To a solution of imidazo[2,1-f][1,2,4]triazine-2,4(1H,3H)-dione (30 g, 0.20 mol) in $H_2O$ (1.2 L), NBS (24.6 g, 0.14 mol) was added in several portions below 25° C. The mixture was stirred at rt for 1 h. The mixture was filtered. The filtrate was concentrated to remove solvent. The resulting residue and the former filtration cake was mixed and slurried in MeOH (20 V) and then MeOH:$H_2O$ (1:1, 20 V) to afford the product (30.4 g, 94%) as a white solid. MS: M/e 231 $(M+1)^+$.

Step E: 7-bromo-2,4-dichloroimidazo[2,1-f][1,2,4]triazine

Into a 350 ml sealed tube, 7-bromoimidazo[2,1-f][1,2,4]triazine-2,4(1H,3H)-dione (10 g, 43 mmol), triethylamine hydrochloride (12 g, 88 mmol) and $POCl_3$ (100 ml) were charged. The mixture was stirred at 120° C. overnight. The mixture was concentrated to remove $POCl_3$. The residue was diluted with EA (200 ml) and sat. NaHCO3 (aq.) was added dropwise below 20° C. until pH value is higher than 7. The solution was separated. The organic layer was washed with $H_2O$, dried over $Na_2SO_4$, filtered and concentrated. The resulting residue was purified by column chromatography with 0-20% EA in PE to afford the product (8.5 g, 73%) as a white solid. MS: M/e 267 $(M+1)^+$.

Step F: 7-bromo-2-chloro-N,N-bis(4-methoxybenzyl)imidazo[2,1-f][1,2,4]triazin-4-amine To a stirred solution of 7-bromo-2,4-dichloroimidazo[2,1-f][1,2,4]triazine (30 g, 0.11 mol) in THF (500 ml), TEA (22.6 g, 0.22 mol) was added dropwise. The mixture was stirred at rt for 10 min. A solution of bis(4-methoxybenzyl)amine (31.6 g, 0.12 mol) in THF (80 ml) was added dropwise to the above solution. The mixture was stirred at rt for 2 h. The solution was quenched with $H_2O$ (300 ml) and then extracted with EA (200 ml×2). The organic layer was washed with brine, dried over $Na_2SO_4$, filtered and concentrated. The resulting residue was slurried in PE (300 ml) and filtered to afford the product (41.4 g, 76%) as a white solid. MS: M/e 488 $(M+1)^+$.

Step G: 7-bromo-2-butoxy-N,N-bis(4-methoxybenzyl)imidazo[2,1-f][1,2,4]triazin-4-amine A mixture of 7-bromo-2-chloro-N,N-bis(4-methoxybenzyl)imidazo[2,1-f][1,2,4]triazin-4-amine (35 g, 71.6 mmol) and n-BuONa/n-BuOH (20%, 200 ml) was stirred at 80° C. under $N_2$ for 1 h. The solution was quenched with $H_2O$ (200 ml). The aqueous solution was extracted with EA (150 ml×2). The collected organic layers were washed with brine, dried over $Na_2SO_4$, filtered and concentrated. The resulting residue was purified by column chromatography with 0-20% EA in PE to afford the product (33 g, 88%) as a colorless oil, which will be solidified after several hours. MS: M/e 526 $(M+1)^+$.

Compound B1: 2-butoxy-7-((5-chloro-6-(4-methylpiperazin-1-yl)pyridin-3-yl)methyl)imidazo[2,1-f][1,2,4]triazin-4-amine

Step A: methyl 5-chloro-6-(4-methylpiperazin-1-yl)nicotinate

To a solution of methyl 5,6-dichloronicotinate (2 g, 10 mmol) and DIPEA (1.93 g, 15 mmol) in DMA (20 mL), 1-methylpiperazine (1.1 g, 11 mmol) was added. Then the mixture was stirred at 100° C. for 3 h. The mixture was cooled to room temperature, diluted with water (50 mL), extracted with EtOAc (100 mL). The combined organic layers were washed with brine, dried over $Na_2SO_4$, filtered, concentrated and the residue was triturated with EA/PE=1/4 to give target compound (1.2 g, 36%). MS: M/e 270 $(M+1)^+$.

Step B: (5-chloro-6-(4-methylpiperazin-1-yl)pyridin-3-yl)methanol

To a solution of the product of Step A (0.87 g, 3.23 mmol) in EtOH (10 mL), $NaBH_4$ (370 mg, 9.7 mmol) was added. The reaction was heated at 80° C. overnight. The mixture was cooled to room temperature and concentrated, diluted with water, extracted with EtOAc (40 mL×2). The combined organic layers were washed with brine, dried over $Na_2SO_4$, filtered, and concentrated to give target compound (560 mg, crude) as oil. MS: M/e 242 $(M+1)^+$.

Step C: 5-chloro-6-(4-methylpiperazin-1-yl)nicotinaldehyde

To a solution of the product of Step B (0.56 g, 2.32 mmol) in THF (10 mL), Dess-Martin reagent (2.1 mg, 5 mmol) was added. The reaction was stirred at room temperature for 1 hour. The reaction was quenched with saturated $K_2CO_3$ solution (10 mL), diluted with EtOAc (40 mL). The mixture was filtered through a pad of Celite. The organic layer was collected, washed with brine, dried over $Na_2SO_4$, filtered, and concentrated. The residue was purified by combi flash to give target compound (250 mg, 32% for 2 steps). $^1$HNMR (400 MHz, $CDCl_3$) δ 9.88 (s, 1H), 8.54 (d, J=2.0 Hz, 1H), 8.01 (d, J=2.0 Hz, 1H), 3.79 (t, J=4.4 Hz, 4H), 2.75 (t, J=4.8 Hz, 4H), 2.46 (s, 3H) ppm. MS: M/e 240 $(M+1)^+$.

Step D: (4-(bis(4-methoxybenzyl)amino)-2-butoxyimidazo[2,1-f][1,2,4]triazin-7-yl)(5-chloro-6-(4-methylpiperazin-1-yl)pyridin-3-yl)methanol To a solution of 7-bromo-2-butoxy-N,N-bis(4-methoxybenzyl)imidazo[2,1-f][1,2,4]triazin-4-amine (150 mg, 0.285 mmol) in THF (5 mL), a solution of n-BuLi (0.44 mL, 0.71 mmol) was added dropwise maintaining the temperature between −75~−65° C. After 30 min, a mixture of the product of Step C (100 mg, 0.43 mmol) in THF (1 mL) was added dropwise. The resulting mixture was stirred at −70° C. for 1 h and then warmed to room temperature for 1 h. The reaction was quenched with saturated $NH_4Cl$ solution, extracted with EtOAc (50 mL×2), washed with brine, dried over $Na_2SO_4$, filtered, and concentrated. The residue was purified by prep-TLC (DCM/MeOH=20/1) to give target compound (60 mg, crude). MS: M/e 687 $(M+1)^+$.

Step E: 2-butoxy-7-((5-chloro-6-(4-methylpiperazin-1-yl)pyridin-3-yl)methyl)imidazo[2,1-f][1,2,4]triazin-4-amine To a mixture of the product of Step D (60 mg, 0.092 mmol) in TFA (3 mL) was added $Et_3SiH$ (1 mL). The reaction was heated at 85° C. overnight. The mixture was concentrated to dryness and the residue was purified by prep-HPLC. The collected fraction was basified with $NaHCO_3$ solution, extracted with DCM (60 mL), washed with brine, dried over $Na_2SO_4$, filtered, and concentrated to give the product (10 mg, 8% for two steps). $^1$HNMR (400 MHz, $CD_3OD$) δ 8.16 (s, 1H), 7.72 (s, 1H), 7.38 (s, 1H), 4.32-4.24 (m, 2H), 4.16 (s, 2H), 2.91-2.42 (m, 8H), 2.35 (s, 3H), 1.81-1.66 (m, 2H), 1.56-1.41 (m, 2H), 0.98 (t, J=6.8 Hz, 3H) ppm. MS: M/e 431 $(M+1)^+$.

Compound B2: 2-butoxy-7-((5-chloro-6-(piperazin-1-yl)pyridin-3-yl)methyl)imidazo[2,1-f][1,2,4]triazin-4-amine Step A: tert-butyl 4-(3-chloro-5-formylpyridin-2-yl)piperazine-1-carboxylate To a solution of 5,6-dichloronicotinaldehyde (1.76 g, 10 mmol) and DIEA (1.93 g, 15 mmol) in DMA (20 mL), tert-butyl piperazine-1-carboxylate (2 g, 11 mmol) was added. Then the mixture was stirred at 80° C. overnight. The mixture was cooled to room temperature, diluted with water (50 mL), extracted with EtOAc (50 mL×2). The combined organic layers were washed with brine, dried over $Na_2SO_4$, filtered, concentrated and the residue was purified by combi-flash to give target compound (1.9 g, 58%). $^1$HNMR (400 MHz, $CDCl_3$) δ 9.86 (s, 1H), 8.54 (d, J=2.0 Hz, 1H), 8.01 (d, J=2.0 Hz, 1H), 3.66-3.54 (m, 8H), 1.48 (s, 9H) ppm. MS: M/e 270 $(M+H-t-Bu)^+$.

Step B: tert-butyl 4-(5-((4-(bis(4-methoxybenzyl)amino)-2-butoxyimidazo[2,1-f][1,2,4]triazin-7-yl)(hydroxy)methyl)-3-chloropyridin-2-yl)piperazine-1-carboxylate To a solution of 7-bromo-2-butoxy-N,N-bis(4-methoxybenzyl)imidazo[2,1-f][1,2,4]triazin-4-amine (300 mg, 0.57 mmol) in THF (8 mL), a solution of n-BuLi (0.9 mL, 1.42 mmol) was added dropwise and maintaining the temperature between −75~−65° C. After 1 h, the product of Step A (278 mg, 0.855 mmol) in THF (4 mL) was added dropwise. The resulting mixture was stirred at −70° C. for 1 h and then warmed to room temperature overnight. The reaction was quenched with saturated $NH_4Cl$ solution, extracted with EtOAc (50 mL×2), washed with brine, dried over $Na_2SO_4$, filtered, and concentrated. The residue was purified by prep-TLC (EA/PE=1/3) to give target compound (150 mg, crude). MS: M/e 773 $(M+1)^+$.

Step C: 2-butoxy-7-((5-chloro-6-(piperazin-1-yl)pyridin-3-yl)methyl)imidazo[2,1-f][1,2,4]triazin-4-amine To a stirred solution of the product of Step B (150 mg, crude) in TFA (3 mL) was added $Et_3SiH$ (0.5 mL) and the resulting mixture was stirred at 85° C. overnight. The mixture was cooled to room temperature and concentrated to dryness. To the residue was added TFA (3 mL) and the resulting mixture was heated at 85° C. overnight. The mixture was concentrated to dryness and the residue was purified by prep-HPLC. The collected fraction was basified with $NaHCO_3$ solution, extracted with DCM (50 mL×2), washed with brine, dried over $Na_2SO_4$, filtered, and concentrated to give the target compound (46 mg, 20% for two steps). $^1$HNMR (400 MHz, DMSO-$d_6$) δ 8.18 (d, J=2.0 Hz, 1H), 8.16 (s, 1H), 8.07 (s, 1H), 7.76 (d, J=2.0 Hz, 1H), 7.35 (s, 1H), 4.20 (t, J=6.0 Hz, 2H), 4.10 (s, 2H), 3.13 (t, J=5.2 Hz, 4H), 2.85 (t, J=5.2 Hz, 4H), 1.74-1.62 (m, 2H), 1.46-1.34 (m, 2H), 0.92 (t, J=7.2 Hz, 3H) ppm. MS: M/e 417 $(M+1)^+$.

Compound B3: 2-butoxy-7-(4-(piperidin-4-yl)benzyl)imidazo[2,1-f][1,2,4]triazin-4-amine Step A: tert-butyl 4-(4-formylphenyl)piperidine-1-carboxylate To a solution of tert-butyl 4-(4-bromophenyl)piperidine-1-carboxylate (3.4 g, 10 mmol) in THF (30 mL), a solution of n-BuLi (10 mL, 16 mmol) was added dropwise maintaining the temperature between −75~−65° C. After 1 h, DMF (814 mg, 11 mmol) was added dropwise and the resulting mixture was stirred at −65° C. for 1 h. The reaction was quenched with saturated $NH_4Cl$ solution, extracted with EtOAc (60 mL×2), washed with brine, dried over $Na_2SO_4$, filtered, and concentrated. The residue was purified by column chromatography (eluting with EA/PE=1/8) to give the target compound (1.35 g, 46%) as oil. $^1$HNMR (400 MHz, $CDCl_3$) δ 9.98 (s, 1H), 7.83 (d, J=8.4 Hz, 2H), 7.37 (d, J=8.4 Hz, 2H), 4.34-4.20 (m, 2H), 2.91-2.66 (m, 3H), 1.91-1.80 (m, 2H), 1.91-1.58 (m, 2H), 1.49 (s, 9H) ppm. MS: M/e 234 $(M+H-tBu)^+$.

Step B: tert-butyl 4-(4-((4-(bis(4-methoxybenzyl)amino)-2-butoxyimidazo[2,1-f][1,2,4]triazin-7-yl)(hydroxy)methyl)phenyl)piperidine-1-carboxylate To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.6 mL, 0.95 mmol) dropwise maintaining the temperature between −75~−65° C. After 1 h, a mixture of the product of Step A (164 mg, 0.57 mmol) in THF (2 mL) was added dropwise. The resulting mixture was stirred at −70° C. for 1 h and then warmed to room temperature overnight. The reaction was quenched with saturated $NH_4Cl$ solution, extracted with EtOAc (50 mL), washed with brine, dried over $Na_2SO_4$, filtered, and concentrated. The residue was purified by prep-TLC (EA/PE=1/3) to give the target compound (63 mg, 23%). MS: M/e 737 $(M+1)^+$.

Step C: 2-butoxy-7-(4-(piperidin-4-yl)benzyl)imidazo[2,1-f][1,2,4]triazin-4-amine To a mixture of the product of Step B (63 mg, 0.086 mmol) in TFA (3 mL), $Et_3SiH$ (0.5 mL) was added. The reaction was heated at 85° C. overnight. The mixture was concentrated and the residue was purified by prep-HPLC. The collected fraction was basified with $NaHCO_3$ solution, extracted with DCM (50 mL), washed with brine, dried over $Na_2SO_4$, filtered, and concentrated to give the target compound (15 mg, 39%). $^1$HNMR (400 MHz, DMSO-$d_6$) δ 8.12 (s, 1H), 8.03 (s, 1H), 7.30 (s, 1H), 7.25 (d, J=8.4 Hz, 2H), 7.13 (d, J=8.4 Hz, 2H), 4.20 (t, J=6.4 Hz, 2H), 4.10 (s, 2H), 3.27-3.18 (m, 2H), 2.91-2.77 (m, 2H), 2.76-2.64 (m, 1H), 1.86-1.74 (m, 2H), 1.73-1.56 (m, 4H), 1.47-1.33 (m, 2H), 0.92 (t, J=7.6 Hz, 3H) ppm. MS: M/e 381 $(M+1)^+$.

Compound B4: 1-(4-(5-((4-amino-2-butoxyimidazo[2,1-f][1,2,4]triazin-7-yl)methyl)-3-chloropyridin-2-yl)piperazin-1-yl)prop-2-en-1-one To a stirred solution of 2-butoxy-7-((5-chloro-6-(piperazin-1-yl)pyridin-3-yl)methyl)imidazo[2,1-f][1,2,4]triazin-4-amine (20 mg, 0.05 mmol) in $CH_3CN$ (2 mL) at 0° C., saturated aqueous $NaHCO_3$ solution (0.5 mL) was added and followed by a solution of acryloyl chloride (4.5 mg, 0.05 mmol) in $CH_3CN$ (0.1 mL). The resulting mixture was stirred at room temperature overnight. The reaction was diluted with water, extracted with DCM (40 mL×2), washed with brine, dried over $Na_2SO_4$, filtered, and concentrated. The residue was purified by prep-TLC to give the target compound (12 mg, 51%). $^1$H NMR (400 MHz, DMSO-$d_6$) δ 8.21 (s, 1H), 8.16 (s, 1H), 8.06 (s, 1H), 7.81 (s, 1H), 7.35 (s, 1H), 6.90-6.77 (m, 1H), 6.13 (d, J=16.8 Hz, 1H), 5.70 (d, J=11.6 Hz, 1H), 4.20 (t, J=6.0 Hz, 2H), 4.11 (s, 2H), 3.80-3.61 (m, 4H), 3.26-3.14 (m, 4H), 1.75-1.60 (m, 2H), 1.46-1.33 (m, 2H), 0.92 (t, J=7.2 Hz, 3H) ppm. MS: M/e 471 $(M+1)^+$.

Compound B5: 7-((5-chloro-6-(piperazin-1-yl)pyridin-3-yl)methyl)-2-(2-methoxyethoxy)imidazo[2,1-f][1,2,4]triazin-4-amine Compound B5 was synthesized starting from the corresponding starting materials according the similar procedures described as those of Compound B2. 1H NMR (400 MHz, CD3OD) δ 8.23 (s, 1H), 7.79 (s, 1H), 7.39 (s, 1H), 4.41 (t, J=4 Hz, 2H), 4.19 (s, 2H), 3.73 (t, J=4 Hz, 2H), 3.52 (t, J=8 Hz, 4H), 3.40 (s, 3H), 3.34 (t, J=8 Hz, 4H) ppm. MS: M/e 419 $(M+1)^+$.

Compound B6: 2-butoxy-7-((6-(piperazin-1-yl)pyridin-3-yl)methyl)imidazo[2,1-f][1,2,4]triazin-4-amine Compound B6 was synthesized starting from the corresponding starting materials according the similar procedures described as those of Compound B2. $^1$HNMR (400 MHz, DMSO-$d_6$) δ 8.06 (s, 1H), 7.76 (s, 2H), 7.45-7.36 (m, 1H), 7.24 (s, 1H), 6.66 (d, J=8.8 Hz, 1H), 4.23 (t, J=6.8 Hz, 2H), 3.99 (s, 2H), 3.39-3.25 (m, 4H), 2.84-2.70 (m, 4H), 1.75-1.62 (m, 2H), 1.46-1.32 (m, 2H), 0.93 (t, J=7.2 Hz, 3H) ppm. MS: M/e 383 $(M+1)^+$.

Compound B7: 2-butoxy-7-((4-chloro-6-(piperazin-1-yl)pyridin-3-yl)methyl)imidazo[2,1-f][1,2,4]triazin-4-amine Compound B7 was synthesized starting from the corresponding starting materials according the similar procedures described as those of Compound B2. $^1$HNMR (400 MHz, DMSO-$d_6$) δ 8.14 (s, 1H), 8.12 (s, 1H), 8.04 (s, 1H), 7.21 (s, 1H), 6.87 (s, 1H), 4.21 (t, J=6.4 Hz, 2H), 4.08 (s, 2H), 3.37 (t, J=4.8 Hz, 4H), 2.73 (t, J=4.8 Hz, 4H), 1.76-1.56 (m, 2H), 1.50-1.35 (m, 2H), 0.93 (t, J=7.2 Hz, 3H) ppm. MS: M/e 417 $(M+1)^+$.

Compound B8: 2-butoxy-7-((5-methyl-6-(piperazin-1-yl)pyridin-3-yl)methyl)imidazo[2,1-f][1,2,4]triazin-4-amine Step A: tert-butyl 4-(5-formyl-3-methylpyridin-2-yl)piperazine-1-carboxylate To a solution of 6-chloro-5-methylnicotinaldehyde (0.93 g, 6 mmol) and DIEA (0.93 g, 7.2 mmol) in DMA (15 mL), tert-butyl piperazine-1-carboxylate (1.12 g, 6 mmol) was added. Then the mixture was stirred at 115° C. overnight under $N_2$. The mixture was cooled to room temperature, diluted with water (50 mL), extracted with EtOAc (60 mL), washed with brine, dried over $Na_2SO_4$, concentrated and the residue was purified by combi-flash to give the target compound (1.05 g, 58%). $^1$HNMR (400 MHz, $CDCl_3$) δ 9.91 (s, 1H), 8.53 (d, J=2.0 Hz, 1H), 7.85 (s, 1H), 3.58 (t, J=4.4 Hz, 4H), 3.37 (t, J=4.4 Hz, 4H), 2.33 (s, 3H), 1.49 (s, 9H) ppm. MS: M/e 306 $(M+1)^+$.

Step B: tert-butyl 4-(5-((4-(bis(4-methoxybenzyl)amino)-2-butoxyimidazo[2,1-f][1,2,4]triazin-7-yl)(hydroxy)methyl)-3-methylpyridin-2-yl)piperazine-1-carboxylate To a solution of 7-bromo-2-butoxy-N,N-bis(4-methoxybenzyl)imidazo[2,1-f][1,2,4]triazin-4-amine (2.62 g, 5 mmol) in THF (25 mL), a solution of n-BuLi (4.7 mL, 7.5 mmol) was added dropwise and maintaining the temperature between −75~−65° C. After 1 h, a mixture of the product of Step A (2.28 g, 7.5 mmol) in THF (7 mL) was added dropwise. The resulting mixture was stirred at −70° C. for 2 h and then warmed to room temperature overnight. The reaction was quenched with saturated $NH_4Cl$ solution, extracted with EtOAc (100 mL×2), washed with brine, dried over $Na_2SO_4$, filtered, and concentrated. The residue was purified by column chromatograph (EA/PE=1/2) to give the target compound (2.1 g, 56%). MS: M/e 753 $(M+1)^+$.

Step C: 2-butoxy-7-((5-methyl-6-(piperazin-1-yl)pyridin-3-yl)methyl)imidazo[2,1-f][1,2,4]triazin-4-amine To a mixture of the product of Step B (2.1 g, crude) in TFA (15 mL), $Et_3SiH$ (5 mL) was added and the resulting mixture was stirred at 85° C. overnight. The mixture was cooled to room temperature and concentrated to dryness. To the residue was added TFA (10 mL) and the resulting mixture was heated at 85° C. overnight. The mixture was concentrated to dryness. The crude was diluted with water, basified with $NaHCO_3$ solution, extracted with DCM (60 mL×8), washed with brine, dried over $Na_2SO_4$, filtered, and concentrated. The residue was purified by column chromatograph (eluting with DCM: (7 M $NH_3$ in MeOH)=15:1) to give the target compound (600 mg, 30% for two steps). $^1$HNMR (400 MHz, DMSO-$d_6$) δ 8.13 (s, 1H), 8.06 (s, 1H), 8.04 (s, 1H), 7.43 (s, 1H), 7.31 (s, 1H), 4.21 (t, J=6.8 Hz, 2H), 4.04 (s, 2H), 2.98-2.86 (m, 4H), 2.84-2.74 (m, 4H), 2.17 (s, 3H), 1.75-1.62 (m, 2H), 1.48-1.32 (m, 2H), 0.92 (t, J=7.6 Hz, 3H) ppm. MS: M/e 397 $(M+1)^+$.

Compound B9: 2-butoxy-7-((5-fluoro-6-(piperazin-1-yl)pyridin-3-yl)methyl)imidazo[2,1-f][1,2,4]triazin-4-amine Compound B9 was synthesized starting from the corresponding starting materials according the similar procedures described as those of Compound B2. $^1$HNMR (400 MHz, DMSO-$d_6$) δ 8.16 (s, 1H), 8.06 (s, 1H), 7.98 (s, 1H), 7.45 (d, J=9.6 Hz, 1H), 7.31 (s, 1H), 4.20 (t, J=6.4 Hz, 2H), 4.07 (s, 2H), 3.22 (t, J=4.4 Hz, 4H), 2.78 (t, J=4.4 Hz, 4H), 1.75-1.62 (m, 2H), 1.46-1.34 (m, 2H), 0.92 (t, J=7.6 Hz, 3H) ppm. MS: M/e 401 $(M+1)^+$.

Compound B10: 2-butoxy-7-((6-(piperazin-1-yl)-5-(trifluoromethyl)pyridin-3-yl)methyl)imidazo[2,1-f][1,2,4]triazin-4-amine Compound B10 was synthesized starting from the corresponding starting materials according the similar procedures described as those of Compound B2. $^1$H NMR (400 MHz, DMSO-$d_6$)) δ 8.47 (s, 1H), 8.17 (s, 1H), 8.07 (s, 1H), 8.02 (s, 1H), 7.38 (s, 1H), 4.26-4.12 (m, 4H), 3.06-3.00 (m, 4H), 2.81-2.72 (m, 4H), 1.70-1.58 (m, 2H), 1.39 (m, 2H), 0.91 (t, J=7.1 Hz, 3H) ppm. MS: M/e 451 $(M+1)^+$.

Compound B11: 2-butoxy-7-((5-methoxy-6-(piperazin-1-yl)pyridin-3-yl)methyl)imidazo[2,1-f][1,2,4]triazin-4-amine Compound B11 was synthesized starting from the corresponding starting materials according the similar procedures described as those of Compound B2. $^1$H NMR (400 MHz, DMSO-$d_6$)) δ 8.13 (s, 1H), 8.04 (s, 1H), 7.73 (s, 1H), 7.29 (s, 1H), 7.21 (s, 1H), 4.22 (t, J=6.4 Hz, 2H), 4.05 (s, 2H), 3.74 (s, 3H), 3.13 (s, 4H), 2.77 (s, 4H), 1.72-1.64 (m, 2H), 1.40 (dd, J=14.8, 7.4 Hz, 2H), 0.92 (t, J=7.3 Hz, 3H) ppm. MS: M/e 413 $(M+1)^+$.

Compound B12: 1-(4-(5-((4-amino-2-butoxyimidazo[2,1-f][1,2,4]triazin-7-yl)methyl)-3-methylpyridin-2-yl)piperazin-1-yl)-2-(dimethylamino)ethan-1-one To a mixture of 2-butoxy-7-((5-methyl-6-(piperazin-1-yl)pyridin-3-yl)methyl)imidazo[2,1-f][1,2,4]triazin-4-amine (200 mg, 0.5 mmol), dimethylglycine (52 mg, 0.5 mmol) and DIPEA (129 mg, 1 mmol) in THF (10 mL), HATU (190 mg, 0.5 mmol) was added. The reaction was stirred at room temperature overnight. The reaction was diluted with water, extracted with EA (60 mL×2), washed with brine, dried over $Na_2SO_4$, filtered, and concentrated. The residue was purified by column chromatograph (eluting with DCM: (7 M $NH_3$ in MeOH)=20:1) and further recrystallized from MeOH to give the target compound (55 mg, 22%). $^1$HNMR (400 MHz, DMSO-$d_6$) δ 8.13 (s, 1H), 8.08 (s, 1H), 8.04 (s, 1H), 7.46 (s, 1H), 7.31 (s, 1H), 4.20 (t, J=6.0 Hz, 2H), 4.05 (s, 2H), 3.70-3.49 (m, 4H), 3.09 (s, 2H), 3.05-2.90 (m, 4H), 2.21 (s, 3H), 2.18 (s, 6H), 1.75-1.62 (m, 2H), 1.50-1.34 (m, 2H), 0.92 (t, J=7.6 Hz, 3H) ppm. MS: M/e 482 $(M+1)^+$.

Compound B13: 2-butyl-7-((5-methyl-6-(piperazin-1-yl)pyridin-3-yl)methyl)imidazo[2,1-f][1,2,4]triazine-2,4-diamine Step A: 7-bromo-N2-butyl-N4,N4-bis(4-methoxybenzyl)imidazo[2,1-f][1,2,4]triazine-2,4-diamine A mixture of 7-bromo-2-chloro-N,N-bis(4-methoxybenzyl)imidazo[2,1-f][1,2,4]triazin-4-amine (244 mg, 0.5 mmol), butan-1-amine (365 mg, 5 mmol) and DIPEA (645 mg, 5 mmol) in NMP (3 mL) was stirred at 220° C. for 6 hours in a sealed tube. The mixture was poured into $H_2O$ (10 mL) and extracted with EtOAc (10 mL×3). The combined organic layers were washed with brine, dried over $Na_2SO_4$, concentrated and purified by column chromatography (petroleum ether/EtOAc=20:1~5:1) to give target compound (220 mg, 83.8%). MS: M/e 525/527 $(M+1)^+$.

Step B: tert-butyl 4-(5-((4-(bis(4-methoxybenzyl)amino)-2-(butylamino)imidazo[2,1-f][1,2,4]triazin-7-yl)(hydroxy)methyl)-3-methylpyridin-2-yl)piperazine-1-carboxylate To a stirred solution of the product of Step A (200 mg, 0.38 mmol) in dry THF (10 mL) was added dropwise n-BuLi (1.6 M, 0.59 mL, 0.95 mmol) at −78° C. After stirring for 30 min, a solution of tert-butyl 4-(5-formyl-3-methylpyridin-2-yl)piperazine-1-carboxylate (232 mg, 0.76 mmol) in THF (2 mL) was added dropwise. Then the reaction was stirred overnight. The reaction was quenched with aq.$NH_4Cl$, extracted with EtOAc (10 mL×2). The combined organic layers were washed with brine, dried over $Na_2SO_4$, concentrated and purified by Prep-TLC (petroleum ether/EtOAc=1:1) to give target compound (80 mg, 28%). MS: M/e 753 $(M+1)^+$.

Step C: N2-butyl-7-((5-methyl-6-(piperazin-1-yl)pyridin-3-yl)methyl)imidazo[2,1-f][1,2,4]triazine-2,4-diamine A mixture of the product of Step B (80 mg, 0.106 mmol) in $Et_3SiH$/TFA (0.5 mL/3 mL) was stirred at 85° C. overnight. The reaction mixture was concentrated to give the residue, which was purified by prep-HPLC to give the target compound (32 mg, 76.9%). $^1$H NMR (400 MHz, DMSO-$d_6$) δ 8.07 (s, 1H), 7.50 (br.s, 2H), 7.43 (s, 1H), 7.15 (s, 1H), 6.24 (t, J=5.6 Hz, 1H), 3.97 (s, 2H), 3.20-3.13 (m, 3H), 2.92-2.87 (m, 4H), 2.82-2.76 (m, 4H), 2.17 (s, 3H), 1.58-1.44 (m, 2H), 1.36-1.28 (m, 2H), 0.90 (t, J=7.6 Hz, 3H) ppm. MS: M/e 396 $(M+1)^+$.

Compound B14: 1-(4-(4-((4-amino-2-butoxyimidazo[2,1-f][1,2,4]triazin-7-yl)methyl)phenyl)piperidin-1-yl)-2-(dimethylamino)ethan-1-one To a mixture of 2-butoxy-7-(4-(piperidin-4-yl)benzyl)imidazo[2,1-f][1,2,4]Triazin-4-amine (20 mg, 0.052 mmol, crude), dimethylglycine (4 mg, 0.04 mmol) and DIPEA (12 mg, 0.1 mmol) in THF (3 mL), HATU (15 mg, 0.04 mmol) was added. The reaction was stirred at room temperature overnight. The reaction was diluted with water, extracted with DCM (40 mL×2), washed with brine, dried over $Na_2SO_4$, filtered, and concentrated. The residue was purified by prep-HPLC to give the target compound (5 mg, 21%). $^1$HNMR (400 MHz, DMSO-$d_6$) δ 9.47 (br.s, 1H), 8.13 (s, 1H), 8.06 (s, 1H), 7.31 (s, 1H), 7.25 (d, J=8.0 Hz, 2H), 7.15 (d, J=8.4 Hz, 2H), 4.55-4.41 (m, 1H), 4.37-4.25 (m, 2H), 4.20 (t, J=6.4 Hz, 2H), 4.10 (s, 2H), 3.25-3.08 (m, 2H), 2.86-2.70 (m, 8H), 1.86-1.73 (m, 2H), 1.73-1.56 (m, 3H), 1.50-1.29 (m, 3H), 0.92 (t, J=7.6 Hz, 3H) ppm. MS: M/e 466 $(M+1)^+$.

Compound B15: 2-butoxy-7-((5-(piperidin-4-yl)pyridin-2-yl)methyl)imidazo[2,1-f][1,2,4]triazin-4-amine Step A: (5-bromopyridin-2-yl)methanol Sodium borohydride (380 mg, 10 mmol) was added in portionwise to a solution of 5-bromopicolinaldehyde (2 g, 10 mmol) in methanol at 0° C. After stirring at rt for 1 hour, TLC showed the reaction was complete. The solution was quenched with water (5 mL), extracted with ethyl acetate (20 mL) and washed with brine (10 mL). The organic layer was dried, concentrated and purified by Combi-Flash (PE:EA=25%) to get the product (1.8 g, 90%). $^1$H NMR (400 MHz, DMSO-$d_6$) δ 8.59 (d, J=4.0 Hz, 1H), 8.04 (d, J=8.0 Hz, 1H), 7.45 (d, J=8.0 Hz, 1H), 5.52 (t, J=8.0 Hz, 1H), 4.52 (d, J=4.0 Hz, 2H) ppm. MS: M/e 188 $(M+1)^+$.

Step B: tert-butyl 6-(hydroxymethyl)-3',6'-dihydro-[3,4'-bipyridine]-1'(2'H)-carboxylate A solution of (5-bromopyridin-2-yl)methanol (300 mg, 1.6 mmol), tert-butyl 4-(4,4,5,5-tetramethyl-1,3,2-dioxaborolan-2-yl)-3,6-dihydropyridine-1(2H)-carboxylate (545 mg, 1.8 mmol), $Pd(dppf)_2Cl_2$ (147 mg, 0.18 mmol) and $Cs_2CO_3$ (1 g, 3.2 mmol) in DMF/THF (1:1, 10 mL) was heated at 90° C. under $N_2$ atmosphere overnight. The solution was cooled, diluted with water (10 mL), extracted with ethyl acetate (10 mL) and washed with brine (10 mL). The organic layer was dried over $Na_2SO_4$, filtered and concentrated to get the crude product, which was further purified by CombiFlash (PE:EA=80%) to get the pure product as a yellow oil (280 mg, 60%). MS: M/e 291 $(M+1)^+$.

Step C: tert-butyl 4-(6-(hydroxymethyl)pyridin-3-yl)piperidine-1-carboxylate

A solution of tert-butyl 6-(hydroxymethyl)-3',6'-dihydro-[3,4'-bipyridine]-1'(2'H)-carboxylate (280 mg, 1.0 mmol) and $PtO_2$ (30 mg) in methanol (10 mL) was stirred at rt under $H_2$ balloon overnight. The catalyst was filtered and the filtrate was concentrated to get the crude product, which was used directly in the next step without further purification (280 mg, crude). MS: M/e 293 $(M+1)^+$.

Step D: tert-butyl 4-(6-formylpyridin-3-yl)piperidine-1-carboxylate

Dess martin reagent (636 mg, 1.5 mmol) was added in portionwise to a solution of tert-butyl 4-(6-(hydroxymethyl)pyridin-3-yl)piperidine-1-carboxylate (280 mg, 1.0 mmol) in THF (5 mL) at 0° C. After stirring at rt for 1 hour, TLC showed the reaction was complete. The solution was quenched with water (5 mL) and extracted with ethyl acetate (10 mL). The organic layer was dried over $Na_2SO_4$, filtered and concentrated to get the crude product, which was further purified by CombiFlash (PE:EA=30%) to get the product as an oil (60 mg, 21%). MS: M/e 291 $(M+1)^+$.

Step E: tert-butyl 4-(6-((4-(bis(4-methoxybenzyl)amino)-2-butoxyimidazo[2,1-f][1,2,4]triazin-7-yl)(hydroxy)methyl)pyridin-3-yl)piperidine-1-carboxylate To a cooled solution of 7-bromo-2-butoxy-N,N-bis(4-methoxybenzyl)imidazo[2,1-f][1,2,4]triazin-4-amine (100 mg, 0.19 mmol) in THF (8 mL) at −78° C. (purged with N2), n-BuLi (1.6 M, 0.3 mL) was added dropwise. After stirring at −78° C. for 30 mins, tert-butyl 4-(6-formylpyridin-3-yl)piperidine-1-carboxylate (60 mg, 0.20 mmol) in THF (2 mL) was added. The resulting mixture was stirred at this temperature for 30 mins, and then warmed to rt overnight. The solution was quenched with $NH_4Cl$ solution (5 mL), extracted with ethyl acetate (10 mL) and washed with brine (10 mL). The organic layer was dried over $Na_2SO_4$, filtered and concentrated to get the crude product, which was further purified by Combi-Flash (PE:EA=60%) to get the pure product (40 mg, 29%). MS: M/e 738 $(M+1)^+$.

Step F: 2-butoxy-7-((5-(piperidin-4-yl)pyridin-2-yl)methyl)imidazo[2,1-f][1,2,4]triazin-4-amine A mixture of tert-butyl 4-(6-((4-(bis(4-methoxybenzyl)amino)-2-butoxyimidazo[2,1-f][1,2,4]triazin-7-yl)(hydroxy)methyl)pyridin-3-yl)piperidine-1-carboxylate (40 mg, 0.05 mmol) in triethylsilane (2 mL) and trifluoroacetic acid (2 mL) was heated at 100° C. overnight. The solvent was evaporated to get the residue, which was added with water (5 mL), extracted with ethyl acetate (5 mL), washed with $NaHCO_3$ (5 mL) and brine (5 mL). The organic layer was dried, concentrated and purified by prep-HPLC to get the product (6 mg, 30%). $^1H$ NMR (400 MHz, $CD_3OD$) δ 8.61 (s, 1H), 8.17 (d, J=8.0 Hz, 1H), 7.71 (d, J=8.0 Hz, 1H), 7.57 (s, 1H), 4.60 (s, 2H), 4.19 (t, J=8.0 Hz, 2H), 3.53 (d, J=12.0 Hz, 2H), 3.19-3.09 (m, 3H), 2.13 (d, J=12.0 Hz, 2H), 1.99-1.89 (m, 2H), 1.73-1.66 (m, 2H), 1.50-1.41 (m, 2H), 0.95 (t, J=8.0 Hz, 3H) ppm. MS: M/e 382 $(M+1)^+$.

Compound B16: 2-butoxy-7-((5-(piperazin-1-yl)pyridin-2-yl)methyl)imidazo[2,1-f][1,2,4]triazin-4-amine Step A: tert-butyl 4-(6-formylpyridin-3-yl)piperazine-1-carboxylate A solution of 5-bromopicolinaldehyde (500 mg, 2.7 mmol), tert-butyl piperazine-1-carboxylate (600 mg, 3.2 mmol), $Pd_2(dba)_3$ (80 mg, 0.16 mmol), BINAP (187 mg, 0.3 mmol) and $Cs_2CO_3$ (2.2 g, 6.8 mmol) in toluene (20 mL) was purged with $N_2$, and heated at 100° C. overnight. The solution was cooled down, concentrated, diluted with water (10 mL) and extracted with ethyl acetate (10 mL). The organic layer was dried over $Na_2SO_4$, filtered and concentrated to get the crude product, which was further purified by CombiFlash (PE:EA=40%) to get the pure product (130 mg, 17%). MS: M/e 292 $(M+1)^+$.

Step B: tert-butyl 4-(6-((4-(bis(4-methoxybenzyl)amino)-2-butoxyimidazo[2,1-f][1,2,4]triazin-7-yl)(hydroxy)methyl)pyridin-3-yl)piperazine-1-carboxylate To a cooled solution of 7-bromo-2-butoxy-N,N-bis(4-methoxybenzyl)imidazo[2,1-f][1,2,4]triazin-4-amine (150 mg, 0.28 mmol) in THF (8 mL) at −78° C. (purged with $N^2$), n-BuLi (1.6 M, 0.44 mL) was added dropwise. After stirring at −78° C. for 30 mins, tert-butyl 4-(6-formylpyridin-3-yl)piperazine-1-carboxylate (125 mg, 0.43 mmol) in THF (2 mL) was added. The resulting mixture was stirred at this temperature for 30 mins, and then warmed to rt overnight. The solution was quenched with $NH_4Cl$ solution (5 mL), extracted with ethyl acetate (10 mL) and washed with brine (10 mL). The organic layer was dried over $Na_2SO_4$, filtered and concentrated to get the crude product, which was further purified by prep-TLC (EA) to get the pure product (75 mg, 36%). MS: M/e 739 $(M+1)^+$.

Step C: 2-butoxy-7-((5-(piperazin-1-yl)pyridin-2-yl)methyl)imidazo[2,1-f][1,2,4]triazin-4-amine A solution of tert-butyl 4-(6-((4-(bis(4-methoxybenzyl)amino)-2-butoxyimidazo[2,1-f][1,2,4]triazin-7-yl)(hydroxy)methyl)pyridin-3-yl)piperazine-1-carboxylate (75 mg, 0.1 mmol) in triethylsilane (1 mL) and trifluoroacetic acid (1 mL) was heated at 80° C. overnight, and then at 100° C. for 4 hrs. The solvent was evaporated to get the residue, which was purified by prep-HPLC to get the product (15 mg, 39%). $^1H$ NMR (400 MHz, $CD_3OD$) δ 8.38 (d, J=4.0 Hz, 1H), 8.03 (dd, J=8.0 Hz, 4.0 Hz, 1H), 7.71 (d, J=12.0 Hz, 1H), 7.59 (s, 1H), 4.58 (s, 2H), 4.20 (t, J=8.0 Hz, 2H), 3.65 (t, J=4.0 Hz, 4H), 3.40 (t, J=4.0 Hz, 4H), 1.72-1.67 (m, 2H), 1.47-1.43 (m, 2H), 0.96 (t, J=8.0 Hz, 3H) ppm. MS: M/e 383 $(M+1)^+$.

Compound B17: 2-butoxy-7-((5-methoxy-6-(piperidin-4-yl)pyridin-3-yl)methyl)imidazo[2,1-f][1,2,4]triazin-4-amine Compound B17 was prepared according to the general procedure used to prepare compound B15 to give the target product (20 mg). $^1$H NMR (400 MHz, DMSO-$d_6$) δ 8.15 (s, 1H), 8.04 (br.s, 2H), 7.34 (s, 1H), 7.32 (s, 1H), 4.21 (t, J=6.4 Hz, 2H), 4.13 (s, 2H), 3.77 (s, 3H), 3.19-3.03 (m, 3H), 2.61 (t, J=11.3 Hz, 2H), 1.73-1.51 (m, 6H), 1.42-1.36 (m, 2H), 0.92 (t, J=7.3 Hz, 3H) ppm. MS: M/e 412 $(M+1)^+$.

Compound B18: N2-butyl-7-(4-(piperidin-4-yl)benzyl)imidazo[2,1-f][1,2,4]triazine-2,4-diamine Step A: tert-butyl 4-(4-((4-(bis(4-methoxybenzyl)amino)-2-(butylamino)imidazo[2,1-f][1,2,4]triazin-7-yl)(hydroxy)methyl)phenyl)piperidine-1-carboxylate To a stirred solution of 7-bromo-N2-butyl-N4,N4-bis(4-methoxybenzyl)imidazo[2,1-f][1,2,4]triazine-2,4-diamine (150 mg, 0.285 mmol) in THF (10 mL) was added dropwise n-BuLi (1.6 M, 0.35 mL, 0.428 mmol) at −78° C. After stirring for an hour under $N_2$, a solution of tert-butyl 4-(4-formylphenyl)piperidine-1-carboxylate (123 mg, 0.428 mmol) in THF (2 mL) was added dropwise at −78° C. After the addition, the reaction was stirred for 3 hours. The reaction was quenched with aq. $NH_4Cl$, extracted with EtOAc (10 mL×3). The combined organic layers were washed with brine, dried over $Na_2SO_4$, concentrated and purified by prep-TLC (petroleum ether/EtOAc=2:1) to give the target compound (98 mg, 47.8%). MS: M/e 736 $(M+1)^+$.

Step B: N2-butyl-7-(4-(piperidin-4-yl)benzyl)imidazo[2,1-f][1,2,4]triazine-2,4-diamine To a mixture of the product of Step B (98 mg, 0.102 mmol) in $Et_3SiH$/TFA (0.5 mL/3 mL) was stirred at 85° C. overnight. The reaction mixture was concentrated to give the residue, which was purified by prep-HPLC to give the target compound (45 mg, 87.2%). $^1$H NMR (400 MHz, DMSO-$d_6$) δ 8.71-8.63 (m, 1H), 8.50-8.32 (m, 1H), 7.81 (br.s, 2H), 7.42 (s, 1H), 7.29 (d, J=8.0 Hz, 2H), 7.14 (d, J=8.0 Hz, 2H), 6.58 (s, 1H), 4.09 (s, 2H), 3.36 (d, J=12.4 Hz, 2H), 3.17 (t, J=7.2 Hz, 2H), 3.05-2.92 (m, 2H), 2.82-2.72 (m, 1H), 1.89 (d, J=13.2 Hz, 2H), 1.82-1.66 (m, 2H), 1.56-1.44 (m, 2H), 1.38-1.24 (m, 2H), 0.89 (t, J=7.2 Hz, 3H) ppm. MS: M/e 380 $(M+1)^+$.

Compound B19: 2-butoxy-7-((6-(piperidin-4-yl)pyridin-3-yl)methyl)imidazo[2,1-f][1,2,4]triazin-4-amine Compound B19 was prepared according to the general procedure used to prepare compound B15 to get the product (19 mg). $^1$H NMR (400 MHz, DMSO-$d_6$ with $D_2O$) δ 8.78 (d, J=4.0 Hz, 1H), 8.30 (d, J=8.0 Hz, 1H), 7.74 (d, J=8.0 Hz, 1H), 7.66 (s, 1H), 4.44 (s, 2H), 4.28 (t, J=8.0 Hz, 2H), 3.56 (d, J=12.0 Hz, 2H), 3.35-3.32 (m, 1H), 3.30-3.14 (m, 2H), 2.19-2.11 (m, 2H), 2.08-2.04 (m, 2H), 1.75-1.71 (m, 2H), 1.50-1.46 (m, 2H), 0.97 (t, J=8.0 Hz, 3H) ppm. MS: M/e 382 $(M+1)^+$.

Compound B20: 2-butoxy-7-(4-(piperidin-3-yl)benzyl)imidazo[2,1-f][1,2,4]triazin-4-amine Compound B20 was prepared according to the general procedure used to prepare compound B15 to give the target product (37 mg). $^1$H NMR (400 MHz, DMSO-$d_6$) δ 8.76 (br.s, 1H), 8.44 (s, 1H), 8.14 (s, 1H), 8.08 (s, 1H), 7.33 (s, 1H), 7.29 (d, J=7.4 Hz, 2H), 7.20 (d, J=7.5 Hz, 2H), 4.20 (t, J=6.3 Hz, 2H), 4.12 (s, 2H), 3.33-3.23 (m, 2H), 2.98-2.88 (m, 4H), 1.86 (t, J=12.2 Hz, 2H), 1.67-1.59 (m, 4H), 1.42-1.34 (m, 2H), 0.92 (t, J=7.2 Hz, 3H). MS: M/e 381 $(M+1)^+$.

Compound B21: 2-butoxy-7-((2-fluoro-6-(piperidin-4-yl)pyridin-3-yl)methyl)imidazo[2,1-f][1,2,4]triazin-4-amine Compound B21 was prepared according to the general procedure used to prepare compound B15 to give the target product (10 mg). $^1$H NMR (400 MHz, $CD_3OD$) δ 7.76 (s, 1H), 7.42 (s, 1H) 7.16 (d, J=8 Hz, 1H), 4.28-4.21 (m, 4H), 3.35-3.27 (m, 2H), 3.14-2.99 (m, 3H), 2.10-1.87 (m, 4H), 1.78-1.69 (m, 2H), 1.52-1.41 (m, 2H), 0.98 (t, J=6.0 Hz, 3H) ppm. MS: M/e 400 $(M+1)^+$.

Compound B22: 2-(isopentyloxy)-7-((5-methyl-6-(piperazin-1-yl)pyridin-3-yl)methyl)imidazo[2,1-f][1,2,4]triazin-4-amine Compound B22 was synthesized starting from the corresponding starting materials according the similar procedures described as those of Compound B2. $^1$HNMR (400 MHz, $CD_3OD$) δ 8.15 (s, 1H), 7.61 (s, 1H), 7.43 (s, 1H), 4.38-4.28 (m, 2H), 4.19 (s, 2H), 3.42-3.33 (m, 8H), 2.29 (s, 3H), 1.92-1.76 (m, 1H), 1.72-1.63 (m, 2H) 0.97 (d, J=6.8 Hz, 6H) ppm. MS: M/e 411 $(M+1)^+$.

Compound B23: 7-((5-methyl-6-(piperazin-1-yl)pyridin-3-yl)methyl)-2-(pentyloxy)imidazo[2,1-f][1,2,4]triazin-4-amine Compound B23 was synthesized starting from the corresponding starting materials according the similar procedures described as those of Compound B2. $^1$HNMR (400 MHz, $CD_3OD$) δ 8.15 (s, 1H), 7.62 (s, 1H), 7.45 (s, 1H), 4.29 (t, J=6.4 Hz, 2H), 4.19 (s, 2H), 3.41-3.33 (m, 8H), 2.30 (s, 3H), 1.84-1.72 (m, 2H), 1.51-1.34 (m, 4H), 0.95 (t, J=6.8 Hz, 3H) ppm. MS: M/e 411 $(M+1)^+$.

Compound B24: 2-amino-1-(4-(5-((4-amino-2-butoxyimidazo[2,1-f][1,2,4]triazin-7-yl)methyl)-3-methylpyridin-2-yl)piperazin-1-yl)ethan-1-one Step A: tert-butyl (2-(4-(5-((4-amino-2-butoxyimidazo[2,1-f][1,2,4]triazin-7-yl)methyl)-3-methylpyridin-2-yl)piperazin-1-yl)-2-oxoethyl)carbamate To a mixture of 2-butoxy-7-((5-methyl-6-(piperazin-1-yl)pyridin-3-yl)methyl)imidazo[2,1-f][1,2,4]triazin-4-amine (40 mg, 0.1 mmol), (tert-butoxycarbonyl)glycine (18 mg, 0.1 mmol) and DIEA (25 mg, 0.2 mmol) in THF (5 mL) was added HATU (38 mg, 0.1 mmol). The reaction was stirred at room temperature overnight. The reaction solution was diluted with water, extracted with EA (50 mL×2), washed with brine, dried over $Na_2SO_4$, filtered, and concentrated to give the target compound (60 mg, crude). MS: M/e 554 $(M+1)^+$.

Step B: 2-amino-1-(4-(5-((4-amino-2-butoxyimidazo[2,1-f][1,2,4]triazin-7-yl)methyl)-3-methylpyridin-2-yl)piperazin-1-yl)ethan-1-one To a mixture of the product of the step A (60 mg, crude) in DCM (5 mL), a solution of 4 M HCl in EA (0.5 mL) was added. The reaction was stirred at room temperature for 5 h. The mixture was concentrated and purified by prep-HPLC to give the target compound (18 mg, 32%). $^1$H NMR (400 MHz, $CD_3OD$) δ 8.12 (s, 1H), 7.94 (s, 1H), 7.52 (s, 1H), 4.30 (t, J=6.8 Hz, 2H), 4.26 (s, 2H), 4.00 (s, 2H), 3.81 (t, J=4.8 Hz, 2H), 3.63 (t, J=4.8 Hz, 2H), 3.43-3.31 (m, 4H), 2.39 (s, 3H), 1.82-1.70 (m, 2H), 1.57-1.42 (m, 2H), 0.98 (t, J=7.6 Hz, 3H) ppm. MS: M/e 454 $(M+1)^+$.

Compound B25: 7-((5-methyl-6-(piperazin-1-yl) pyridin-3-yl)methyl)-2-(2-phenoxyethoxy)imidazo [2,1-f][1,2,4]triazin-4-amine Compound B25 was synthesized starting from the corresponding starting materials according the similar procedures described as those of Compound B2. $^1$HNMR (400 MHz, $CD_3OD$) δ 8.19 (s, 1H), 7.74 (s, 1H), 7.56 (s, 1H), 7.31-7.22 (m, 2H), 7.00-6.87 (m, 3H), 4.64 (t, J=4.0 Hz, 2H), 4.30 (t, J=4.0 Hz, 2H), 4.23 (s, 2H), 3.47-3.31 (m, 8H), 2.31 (s, 3H) ppm. MS: M/e 461 $(M+1)^+$.

Compound B26: 2-butoxy-7-(3-ethoxy-4-(piperazin-1-yl)benzyl)imidazo[2,1-f][1,2,4]triazin-4-amine Compound B26 was synthesized starting from the corresponding starting materials according the similar procedures described as those of Compound B16. $^1$H NMR (400 MHz, DMSO-d6) δ 8.11 (s, 1H), 8.02 (s, 1H), 7.27 (s, 1H), 6.91 (s, 1H), 6.80-6.74 (m, 2H), 4.22 (t, J=8.0 Hz, 2H), 4.04 (s, 2H), 3.98-3.94 (m, 2H), 2.84 (s, 8H), 1.70-1.64 (m, 2H), 1.45-1.36 (m, 2H), 1.31 (t, J=8.0 Hz, 3H), 0.93 (t, J=8.0 Hz, 3H) ppm. MS: M/e 426 $(M+1)^+$.

Compound B27: 2-butoxy-7-(4-(piperazin-1-yl)-3-(trifluoromethoxy) benzyl)imidazo[2,1-f][1,2,4]triazin-4-amine Compound B27 was synthesized starting from the corresponding starting materials according the similar procedures described as those of Compound B16. $^1$H NMR (400 MHz, DMSO-d6) δ 8.14 (s, 1H), 8.05 (s, 1H), 7.33 (s, 1H), 7.25-7.21 (m, 2H), 7.03 (d, J=12.0 Hz, 1H), 4.19 (t, J=8.0 Hz, 2H), 4.11 (s, 2H), 2.86-2.80 (m, 8H), 1.70-1.63 (m, 2H), 1.41-1.37 (m, 2H), 0.92 (t, J=8.0 Hz, 3H) ppm. MS: M/e 466 $(M+1)^+$.

Compound B28: 2-butoxy-7-((6-(piperidin-4-yl)-5-(trifluoromethyl)pyridin-3-yl)methyl)imidazo[2,1-f] [1,2,4]triazin-4-amine Compound B28 was prepared according to the general procedure used to prepare compound B15 to give the target product (10 mg). $^1$H NMR (400 MHz, DMSO-d6)) δ 8.77 (s, 1H), 8.18 (s, 1H), 8.07 (s, 2H), 7.42 (s, 1H), 4.26 (s, 2H), 4.16 (t, J=6.4 Hz, 2H), 3.12-2.92 (m, 4H), 2.65-2.58 (m, 1H), 1.84 (d, J=11.2 Hz, 2H), 1.70-1.60 (m, 2H), 1.55-1.50 (m, 2H), 1.41-1.36 (m, 2H), 0.91 (t, J=7.4 Hz, 3H). MS: M/e 412 $(M+1)^+$.

Compound B29: 4-amino-7-((5-methyl-6-(piperazin-1-yl)pyridin-3-yl)methyl)imidazo[2,1-f][1,2,4] triazin-2-ol Step A: tert-butyl (7-bromo-2-(furan-2-ylmethoxy) imidazo[2,1-f][1,2,4]triazin-4-yl)carbamate To a stirred solution of furan-2-ylmethanol (112 mg, 1.16 mmol) in THF (20 mL) was added NaH (88 mg, 2.32 mmol, 60% in oil) at 0° C. The reaction mixture was stirred at 0° C. for 0.5 h. tert-butyl (7-bromo-2-chloroimidazo[2,1-f][1,2,4]triazin-4-yl)carbamate (200 mg, 0.58 mmol) was added to the mixture and the reaction mixture was stirred at 70° C. for 6 h. The mixture was added $H_2O$ (20 mL) and extracted with EtOAc (10 ml×3). The combined organic phase was washed with brine, dried over $Na_2SO_4$ and concentrated in vacuo. The crude product was purified by column chromatography to give the product (140 mg, 59%). MS: M/e 410 $(M+1)^+$.

Step B: tert-butyl 4-(5-((4-((tert-butoxycarbonyl) amino)-2-(furan-2-ylmethoxy)imidazo[2,1-f][1,2,4] triazin-7-yl)(hydroxy)methyl)-3-methylpyridin-2-yl) piperazine-1-carboxylate To a stirred solution of tert-butyl (7-bromo-2-(furan-2-ylmethoxy)imidazo[2,1-f][1,2,4]triazin-4-yl)carbamate (210 mg, 0.51 mmol) in THF (10 mL), cooled to −78° C. and under a nitrogen atmosphere, n-BuLi (1.6 M in hexane, 1.25 mmol, 0.78 mL) was added dropwise. After stirring for 50 mins, a solution of tert-butyl 4-(5-formyl-3-methylpyridin-2-yl)piperazine-1-carboxylate (156 mg, 0.5 mmol) in THF (2 mL) was added slowly. The reaction mixture was warmed up slowly to rt and stirred for 2 h. The reaction mixture was poured into saturated ammonium chloride solution and extracted with EtOAc (15 mL×3). The combined organic phase was washed with brine, dried over $Na_2SO_4$, concentrated in vacuo. The crude product was purified by column chromatography to give the title product (70 mg, 22%). MS: M/e 637 $(M+1)^+$.

Step C: 4-amino-7-((5-methyl-6-(piperazin-1-yl) pyridin-3yl)methyl)imidazo[2,1-f][1,2,4]triazin-2-ol A solution of tert-butyl 4-(5-((4-((tert-butoxycarbonyl) amino)-2-(furan-2-ylmethoxy)imidazo[2,1-f][1,2,4]triazin-7-yl)(hydroxy)methyl)-3-methylpyridin-2-yl)piperazine-1-carboxylate (70 mg, 0.11 mmol) in TFA (3 mL) and $Et_3SiH$ (3 mL) was stirred at rt overnight. The mixture was concentrated in vacuo. The crude product was purified by prep-HPLC to give the product (15 mg, 40%). $^1$H NMR (400 MHz, DMSO-d6)) δ 8.71 (br.s, 2H), 8.08 (s, 2H), 8.00 (s, 1H), 7.48 (s, 1H), 7.28 (s, 1H), 4.05 (s, 2H), 3.21 (s, 8H), 2.21 (s, 3H) ppm. MS: M/e 341 $(M+1)^+$.

Compound B30: 7-((5-methyl-6-(piperazin-1-yl) pyridin-3-yl)methyl)-2-phenethoxyimidazo[2,1-f][1,2,4]triazin-4-amine Compound B30 was synthesized starting from the corresponding starting materials according the similar procedures described as those of Compound B8. $^1$H NMR (400 MHz, DMSO-d6) δ 8.70 (br.s, 2H), 8.19 (s, 2H), 8.10 (s, 1H), 7.52 (s, 1H), 7.43-7.26 (m, 5H), 7.26-7.18 (m, 1H), 4.40 (t, J=8 Hz, 2H), 4.09 (s, 2H), 3.26-3.16 (m, 8H), 3.02 (t, J=8 Hz, 2H), 2.17 (s, 3H) ppm. MS: M/e 445 $(M+1)^+$.

Compound B31: 7-((5-methyl-6-(piperazin-1-yl) pyridin-3-yl)methyl)-2-(3-phenylpropoxy)imidazo[2,1-f][1,2,4]triazin-4-amine Compound B31 was synthesized starting from the corresponding starting materials according the similar procedures described as those of Compound B8. $^1$H NMR (400 MHz, $CD_3OD$) δ 8.14 (s, 1H), 7.70-7.42 (m, 2H), 7.30-7.12 (m, 5H), 4.31 (t, J=8 Hz, 2H), 4.18 (t, J=8 Hz, 2H), 3.44-3.32 (m, 8H), 2.78 (t, J=8 Hz, 2H), 2.29-2.24 (m, 3H), 2.11-2.03 (m, 2H) ppm. MS: M/e 459 $(M+1)^+$.

Compound B32: 1-(4-(5-((4-amino-2-butoxyimidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-butoxyimidazo[2,1-f][1,2,4]triazin-7-yl)methyl)-3-methylpyridin-2-yl)piperazin-1-yl)-2-oxoethyl)(methyl)carbamate To a mixture of 2-butoxy-7-((5-methyl-6-(piperazin-1-yl)pyridin-3-yl)methyl)imidazo[2,1-f][1,2,4]triazin-4-amine (40 mg, 0.1 mmol), N-(tert-butoxycarbonyl)-N-methylglycine (20 mg, 0.1 mmol) and DIEA (25 mg, 0.2 mmol) in THF (5 mL) was added HATU (38 mg, 0.1 mmol). The reaction was stirred at room temperature overnight. The reaction was diluted with water, extracted with EA (40 mL×2), washed with brine, dried over $Na_2SO_4$, filtered, and concentrated to give the target compound (60 mg, crude). MS: M/e 568 $(M+1)^+$.

Step B: 1-(4-(5-((4-amino-2-butoxyimidazo[2,1-f][1,2,4]triazin-7-yl)methyl)-3-methylpyridin-2-yl)piperazin-1-yl)-2-(methylamino)ethan-1-one To a mixture of the product of the step A (60 mg, crude) in DCM (5 mL) was added a solution of 4 M HCl in EA (0.5 mL). The reaction was stirred at room temperature for 5 h. The mixture was concentrated and purified by prep-HPLC to give the title product (35 mg, 60% for two steps). $^1$HNMR (400 MHz, $CD_3OD$) δ 8.12 (s, 1H), 7.93 (s, 1H), 7.51 (s, 1H), 4.30 (t, J=6.4 Hz, 2H), 4.25 (s, 2H), 4.13 (s, 2H), 3.80 (t, J=4.8 Hz, 2H), 3.62 (t, J=4.8 Hz, 2H), 3.43-3.31 (m, 4H), 2.75 (s, 3H), 2.38 (s, 3H), 1.82-1.68 (m, 2H), 1.57-1.42 (m, 2H), 0.98 (t, J=7.6 Hz, 3H) ppm. MS: M/e 468 $(M+1)^+$.

Compound B33: 2-butoxy-7-((4-methyl-5-(piperazin-1-yl)pyridin-2-yl)methyl)imidazo[2,1-f][1,2,4]triazin-4-amine Step A: tert-butyl 4-(6-(methoxycarbonyl)-4-methylpyridin-3-yl)piperazine-1-carboxylate To a flask containing methyl 5-bromo-4-methylpicolinate (1.15 g, 5 mmol), tert-butyl piperazine-1-carboxylate (1.12 g, 6 mmol), BINAP (311 mg, 0.5 mmol), $Pd_2(dba)_3$ (575 mg, 1 mmol) and $Cs_2CO_3$ (3.26 g, 10 mmol) under nitrogen, toluene (10 mL) was added. The mixture was stirred at 100° C. overnight, after cooling to room temperature, the solvent was removed by rotary evaporation. The residue was dissolved in EA (20 mL), washed with water and brine, dried over $Na_2SO_4$, filtered, and concentrated. The residue was purified by column chromatography to give target compound (593 mg, 35%). MS: M/e 336 $(M+1)^+$.

Step B: tert-butyl 4-(6-(hydroxymethyl)-4-methylpyridin-3-yl)piperazine-1-carboxylate To a solution of the product of Step A (590 mg, 1.76 mmol) in THF (5 mL) was added $LiAlH_4$ (134 mg, 3.52 mmol). after stirring at 0° C. for 30 min, the mixture was then stirred at room temperature for another 2 hours. The reaction was quenched with saturated $NH_4Cl$ solution, extracted with EtOAc (10 mL×3), washed with brine, dried over $Na_2SO_4$, filtered, and concentrated. The residue was purified by column chromatography to give target compound (288 mg, 53%). MS: M/e 308 $(M+1)^+$.

Step C: tert-butyl 4-(6-formyl-4-methylpyridin-3-yl)piperazine-1-carboxylate

To a solution of the product of Step B (288 mg, 0.94 mmol) in DCM (5 mL) was added Dess-Martin periodinane (796 mg, 1.88 mmol). After stirring at room temperature for 1 hour, the solution was quenched with saturated $NaHCO_3$ solution (5 mL). The aqueous solution was extracted with DCM (15 ml×3). The collected organic layer was washed with brine, dried over $Na_2SO_4$, filtered and concentrated. The resulting residue was purified by column chromatography to afford the product (220 mg, 78%). MS: M/e 306 $(M+1)^+$.

Step D: tert-butyl 4-(6-((4-(bis(4-methoxybenzyl)amino)-2-butoxyimidazo[2,1-f][1,2,4]triazin-7-yl)(hydroxy)methyl)-4-methylpyridin-3-yl)piperazine-1-carboxylate To a solution of 7-bromo-2-butoxy-N,N-bis(4-methoxybenzyl)imidazo[2,1-f][1,2,4]triazin-4-amine (211 mg, 0.4 mmol) in THF (2 mL) was added dropwise a solution of n-BuLi (0.38 mL, 0.6 mmol) maintaining the temperature between −75~−65° C. After 10 min, a solution of product of Step C (183 mg, 0.6 mmol) in THF (3 mL) was added dropwise. The resulting mixture was stirred at −70° C. for 30 min. The reaction was quenched with saturated $NH_4Cl$ solution, extracted with EtOAc (10 mL×4), washed with brine, dried over $Na_2SO_4$, filtered, and concentrated. The residue was purified by column chromatography to give target compound (127 mg, 42%). MS: M/e 753 $(M+1)^+$.

Step E: 2-butoxy-7-((4-methyl-5-(piperazin-1-yl)pyridin-2-yl)methyl)imidazo[2,1-f][1,2,4]triazin-4-amine To a mixture of the product of Step D (127 mg, 0.17 mmol) in TFA (5 mL), $Et_3SiH$ (1 mL) was added. The reaction was heated at 80° C. for 2 days. The mixture was concentrated and the residue was purified by prep-HPLC. The collected fraction was basified with $NaHCO_3$ solution, extracted with DCM (30 mL), washed with brine, dried over $Na_2SO_4$, filtered, and concentrated to give the product (4 mg, 6%). 1H NMR (400 MHz, DMSO-d6) δ 9.17 (br.s, 2H), 8.17 (s, 1H), 8.06 (s, 1H), 7.33 (s, 1H), 7.21 (s, 1H), 4.24 (s, 2H), 4.15 (t, J=6.3 Hz, 2H), 3.24-3.19 (m, 4H), 3.14-3.07 (m, 4H), 2.24 (s, 3H), 1.74-1.53 (m, 3H), 1.38 (dq, J=14.6, 7.2 Hz, 3H), 0.90 (t, J=7.3 Hz, 3H). ppm. MS: M/e 398 $(M+1)^+$.

Compound B34: 2-butoxy-7-((5-methyl-6-(piperidin-1-yl)pyridin-3-yl)methyl)imidazo[2,1-f][1,2,4]triazin-4-amine Compound B34 was synthesized starting from the corresponding starting materials according the similar procedures described as those of Compound B8. $^1$H NMR (400 MHz, DMSO-d6)) δ 8.13 (s, 1H), 8.05 (s, 2H), 7.41 (d, J=2.0 Hz, 1H), 7.31 (s, 1H), 4.21 (t, J=6.5 Hz, 2H), 4.03 (s, 2H), 2.98-2.89 (m, 4H), 2.17 (s, 3H), 1.68 (dd, J=14.1, 7.4 Hz, 2H), 1.61 (t, J=7.9 Hz, 4H), 1.53 (d, J=4.6 Hz, 2H), 1.45-1.34 (m, 2H), 0.92 (t, J=7.4 Hz, 3H) ppm. MS: M/e 396 $(M+1)^+$.

Compound B35: 7-((6-(azepan-1-yl)-5-methylpyridin-3-yl)methyl)-2-butoxyimidazo[2,1-f][1,2,4]triazin-4-amine Compound B35 was synthesized starting from the corresponding starting materials according the similar procedures described as those of Compound B8. $^1$H NMR (400 MHz, DMSO-d6)) δ 8.13 (s, 1H), 8.03 (s, 1H), 7.97 (d, J=1.8 Hz, 1H), 7.33 (d, J=1.8 Hz, 1H), 7.30 (s, 1H), 4.21 (t, J=6.5 Hz, 2H), 3.99 (s, 2H), 3.37-3.28 (m, 4H), 2.18 (s, 3H), 1.75-1.63 (m, 6H), 1.59-1.51 (m, 4H), 1.46-1.35 (m, 2H), 0.92 (t, J=7.4 Hz, 3H) ppm. MS: M/e 410 $(M+1)^+$.

Compound B36: 2-butoxy-7-(3-methyl-4-(piperazin-1-yl)benzyl)imidazo[2,1-f][1,2,4]triazin-4-amine Step A: tert-butyl 4-(4-((4-(bis(4-methoxybenzyl)amino)-2-butoxyimidazo[2,1-f][1,2,4]triazin-7-yl)(hydroxy)methyl)-2-methylphenyl)piperazine-1-carboxylate To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. and stirred for 1 h. Then a solution of tert-butyl 4-(4-formyl-2-methylphenyl)piperazine-1-carboxylate (130 mg, 0.43 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (85 mg, 39.7%) as yellow oil. MS: M/e 752 $(M+1)^+$.

Step B: 2-butoxy-7-(3-methyl-4-(piperazin-1-yl)benzyl)imidazo[2,1-f][1,2,4]triazin-4-amine A mixture of tert-butyl 4-(4-((4-(bis(4-methoxybenzyl)amino)-2-butoxyimidazo[2,1-f][1,2,4]triazin-7-yl)(hydroxy)methyl)-2-methylphenyl)piperazine-1-carboxylate (85 mg, 0.11 mmol) and triethylsilane (1 mL) in TFA (2 mL) was stirred at 90° C. overnight. The mixture was concentrated and purified with prep-HPLC to give the title product (17 mg, 38%). $^1$H NMR (400 MHz, DMSO-d6) δ 8.72 (br.s, 2H), 8.14 (s, 1H), 8.08 (s, 1H), 7.32 (s, 1H), 7.16 (s, 1H), 7.11 (d, J=8.4 Hz, 1H), 6.96 (d, J=8.4 Hz, 1H), 4.22 (t, J=6.5 Hz, 2H), 4.05 (s, 2H), 3.25-3.12 (m, 4H), 3.13-2.97 (m, 4H), 2.21 (s, 3H), 1.75-1.61 (m, 2H), 1.48-1.34 (m, 2H), 0.93 (t, J=7.4 Hz, 3H) ppm. MS: M/e 396 $(M+1)^+$.

Compound B37: 1-(4-(5-((4-amino-2-butoxyimidazo[2,1-f][1,2,4]triazin-7-yl)methyl)-3-methylpyridin-2-yl)piperazin-1-yl)-3-(dimethylamino)propan-1-one A mixture of 2-butoxy-7-((5-methyl-6-(piperazin-1-yl)pyridin-3-yl)methyl)imidazo[2,1-f][1,2,4]triazin-4-amine (20 mg, 0.05 mmol), 3-(dimethylamino)propanoic acid (6 mg, 0.05 mmol), HATU (23 mg, 0.06 mmol) and DIPEA (19 mg, 0.15 mmol) in DCM (3 mL) was stirred at rt for 2 h. The mixture was extracted with DCM (10 mL) and washed with water (5 ml), dried over $Na_2SO_4$, concentrated and purified with prep-HPLC to afford the product (12 mg, 47.88%). $^1$H NMR (400 MHz, DMSO-d6) δ 9.12 (br.s, 1H), 8.16 (s, 1H), 8.10 (s, 2H), 7.54 (s, 1H), 7.35 (d, J=2.4 Hz, 1H), 4.21 (t, J=6.5 Hz, 2H), 4.08 (s, 2H), 3.64-3.56 (m, 4H), 3.35-3.01 (m, 6H), 2.87 (t, J=6.7 Hz, 2H), 2.79 (s, 3H), 2.78 (s, 3H), 2.24 (s, 3H), 1.73-1.62 (m, 2H), 1.47-1.35 (m, 2H), 0.93 (t, J=7.4 Hz, 3H) ppm. MS: M/e 496 $(M+1)^+$.

Compound B38: 2-butoxy-7-((5-methyl-6-(octahydro-2H-isoindol-2-yl) pyridin-3-yl)methyl)imidazo[2,1-f][1,2,4]triazin-4-amine Compound B38 was synthesized starting from the corresponding starting materials according the similar procedures described as those of Compound B8. $^1$H NMR (400 MHz, DMSO-$d_6$) δ 8.12 (s, 1H), 8.03 (s, 1H), 7.88 (s, 1H), 7.27 (s, 1H), 7.25 (s, 1H), 4.22 (t, J=8.0 Hz, 2H), 3.95 (s, 2H), 3.44-3.39 (m, 2H), 3.37-3.33 (m, 2H), 2.23 (s, 3H), 2.16 (s, 2H), 1.68-1.67 (m, 2H), 1.51-1.33 (m, 10H), 0.93 (t, J=8.0 Hz, 3H) ppm. MS: M/e 436 $(M+1)^+$.

Compound B39: 7-((6-(1,4-diazepan-1-yl)-5-methylpyridin-3-yl) methyl)-2-butoxyimidazo[2,1-f][1,2,4]triazin-4-amine Compound B39 was synthesized starting from the corresponding starting materials according the similar procedures described as those of Compound B8. $^1$H NMR (400 MHz, DMSO-d6) δ 8.67 (br.s, 2H), 8.16 (s, 1H), 8.10 (s, 1H), 8.04 (s, 1H), 7.51 (s, 1H), 7.34 (s, 1H), 4.22 (t, J=8.0 Hz, 2H), 4.06 (s, 2H), 3.57 (d, J=4.0 Hz, 2H), 3.37 (t, J=4.0 Hz, 2H), 3.28-3.24 (m, 4H), 2.22 (s, 2H), 2.02-2.00 (m, 2H), 1.69-1.65 (m, 2H), 1.42-1.39 (m, 2H), 0.93 (t, J=8.0 Hz, 3H) ppm. MS: M/e 411 $(M+1)^+$.

Compound B40: 1-(4-(5-((4-amino-2-butoxyimidazo[2,1-f][1,2,4]triazin-7-yl)methyl)-3-methylpyridin-2-yl)piperazin-1-yl)-2-(piperazin-1-yl)ethan-1-one Step A: tert-butyl 4-(2-(4-(5-((4-amino-2-butoxyimidazo[2,1-f][1,2,4]triazin-7-yl)methyl)-3-methylpyridin-2-yl)piperazin-1-yl)-2-oxoethyl)piperazine-1-carboxylate A mixture of 2-butoxy-7-((5-methyl-6-(piperidin-4-yl)pyridin-3-yl)methyl)imidazo[2,1-f][1,2,4]triazin-4-amine (20 mg, 0.05 mmol), 2-(4-(tert-butoxycarbonyl)piperazin-1-yl)acetic acid (15 mg, 0.06 mmol) and HATU (23 mg, 0.06 mmol), DIPEA (12.9 mg, 0.1 mmol) in THF (3 mL) was stirred overnight. The reaction mixture was poured into $H_2O$ (10 mL) and extracted with EtOAc (10 mL×3). The combined organic layers were washed with brine, dried over $Na_2SO_4$, concentrated to give the target compound (crude, 100%), which was directly used to the next step. MS: M/e 623 $(M+1)^+$.

Step B: 1-(4-(5-((4-amino-2-butoxyimidazo[2,1-f][1,2,4]triazin-7-yl)methyl)-3-methylpyridin-2-yl)piperazin-1-yl)-2-(piperazin-1-yl)ethan-1-one To a stirred solution of the product of Step A (0.05 mmol) in $CH_2Cl_2$ (5 mL), dioxane/HCl (g) (4.0 M, 2 mL) was added. After the addition, the reaction mixture was concentrated to give the residue, which was purified by prep-HPLC to give the target compound (12 mg, 45.9%). $^1$H NMR (400 MHz, DMSO-$d_6$) δ 9.20 (br.s, 2H), 8.19 (s, 1H), 8.14 (s, 1H), 8.10 (s, 1H), 7.56 (s, 1H), 7.38 (s, 1H), 4.29 (s, 2H), 4.21 (t, J=6.4 Hz, 2H), 4.09 (s, 2H), 3.66-3.62 (m, 2H), 3.49-3.45 (m, 2H), 3.43-3.30 (m, 7H), 3.12-3.09 (m, 2H), 3.07-3.01 (m, 2H), 2.24 (s, 3H), 1.76-1.63 (m, 2H), 1.49-1.34 (m, 2H), 0.90 (t, J=7.2 Hz, 3H) ppm. MS: M/e 523 $(M+1)^+$.

Compound B41: (4-(5-((4-amino-2-butoxyimidazo[2,1-f][1,2,4]triazin-7-yl)methyl)-3-methylpyridin-2-yl)piperazin-1-yl)(piperazin-2-yl)methanone Step A: di-tert-butyl 2-(4-(5-((4-amino-2-butoxyimidazo[2,1-f][1,2,4]triazin-7-yl)methyl)-3-methylpyridin-2-yl)piperazine-1-carbonyl)piperazine-1,4-dicarboxylate A mixture of 2-butoxy-7-((5-methyl-6-(piperazin-1-yl)pyridin-3-yl)methyl)imidazo[2,1-f][1,2,4]triazin-4-amine (20 mg, 0.05 mmol), 1,4-bis(tert-butoxycarbonyl)piperazine-2-carboxylic acid (20 mg, 0.06 mmol) and HATU (23 mg, 0.06 mmol), DIPEA (12.9 mg, 0.1 mmol) in THF (3 mL) was stirred overnight. The reaction mixture was poured into $H_2O$ (10 mL) and extracted with EtOAc (10 mL×3). The combined organic layers were washed with brine, dried over $Na_2SO_4$, concentrated to give the target compound (crude, 100%), which was directly used to the next step. MS: M/e 709 $(M+1)^+$.

Step B: (4-(5-((4-amino-2-butoxyimidazo[2,1-f][1,2,4]triazin-7-yl)methyl)-3-methylpyridin-2-yl)piperazin-1-yl)(piperazin-2-yl)methanone To a stirred solution of the product of Step A (0.05 mmol) in $CH_2Cl_2$ (5 mL), dioxane/HCl (g) (4.0 M, 2 mL) was added. After the addition, the reaction mixture was concentrated to give the residue, which was purified by prep-HPLC to give the target compound (10 mg, 39.3%). $^1$H NMR (400 MHz, DMSO-$d_6$) δ 8.20 (s, 1H), δ 8.16 (s, 1H), 8.11 (d, J=1.6 Hz, 1H), 7.57 (d, J=1.6 Hz, 1H), 7.39 (s, 1H), 4.80 (d, J=10.8 Hz, 1H), 4.22 (t, J=6.6 Hz, 2H), 4.09 (s, 2H), 3.780-3.72 (m, 2H), 3.65-3.50 (m, 5H), 3.29-2.95 (m, 7H), 2.24 (s, 3H), 2.08 (s, 1H), 1.74-1.62 (m, 2H), 1.48-1.35 (m, 2H), 0.93 (t, J=7.2 Hz, 3H) ppm. MS: M/e 509 $(M+1)^+$.

Compound B42: 2-(2-(1H-imidazol-1-yl)ethoxy)-7-((5-methyl-6-(piperazin-1-yl)pyridin-3-yl)methyl)imidazo[2,1-f][1,2,4]triazin-4-amine Step A: 2-(2-(1H-imidazol-1-yl)ethoxy)-7-bromo-N,N-bis(4-methoxybenzyl)imidazo[2,1-f][1,2,4]triazin-4-amine To a suspension of NaH (80 mg, 2 mmol) in THF (8 mL) was added 2-(1H-imidazol-1-yl)ethan-1-ol (224 mg, 2 mmol). After stirring at room temperature for 30 min, a solution of 7-bromo-2-chloro-N,N-bis(4-methoxybenzyl)imidazo[2,1-f][1,2,4]triazin-4-amine (240 mg, 0.5 mmol) in THF (1 mL) was added. Then the mixture was stirred at 80° C. overnight. The mixture was cooled to room temperature, diluted with water (30 mL), extracted with EtOAc (60 mL), washed with brine, dried over $Na_2SO_4$, filtered, concentrated and the residue was purified by combi-flash to give the target compound (170 mg, 60%) as solid. MS: M/e 564 $(M+1)^+$.

Compound B42 was synthesized starting from the corresponding starting materials according the similar procedures described as those of Compound B8. $^1$HNMR (400 MHz, $CD_3OD$) δ 9.06 (s, 1H), 8.17 (s, 1H), 7.76 (d, J=1.2 Hz, 1H), 7.64 (s, 1H), 7.60 (m, 1H), 7.39 (s, 1H), 4.75-4.68 (m, 4H), 4.19 (s, 2H), 3.41-3.36 (m, 8H), 2.31 (s, 3H) ppm. MS: M/e 435 $(M+1)^+$.

Compound B43: 7-((5-methyl-6-(piperazin-1-yl)pyridin-3-yl)methyl)-2-(octyloxy)imidazo[2,1-f][1,2,4]triazin-4-amine Compound B43 was synthesized starting from the corresponding starting materials according the similar procedures described as those of Compound B8. $^1$HNMR (400 MHz, DMSO-$d_6$) δ 8.67 (br.s, 2H), 8.16 (s, 1H), 8.10 (d, J=2.0 Hz, 1H), 8.09 (s, 1H), 7.52 (s, 1H), 7.34 (m, 1H), 4.20 (t, J=6.4 Hz, 2H), 4.07 (s, 2H), 3.30-3.10 (m, 8H), 2.21 (s, 3H), 1.75-1.64 (m, 2H), 1.45-1.15 (m, 10H), 0.85 (t, J=6.8 Hz, 3H) ppm. MS: M/e 453 $(M+1)^+$.

Compound B44:1-(4-(5-((4-amino-2-butoxyimidazo[2,1-f][1,2,4]triazin-7-yl)methyl)-3-methylpyridin-2-yl)piperazin-1-yl)prop-2-en-1-one To a mixture of 2-butoxy-7-((5-methyl-6-(piperazin-1-yl)pyridin-3-yl)methyl)imidazo[2,1-f][1,2,4]triazin-4-amine (40 mg, 0.1 mmol) in $CH_3CN$ (3 mL) was added saturated $NaHCO_3$ (0.5 mL) and followed by a solution of acryloyl chloride (9 mg, 0.1 mmol) in $CH_3CN$ (0.1 mL) at 0° C. The resulting mixture was stirred at room temperature overnight. The reaction was diluted with water, extracted with EA (40 mL×2), washed with brine, dried over $Na_2SO_4$, filtered, and concentrated. The residue was purified by prep-TLC to give the target compound (16 mg, 36%). $^1$HNMR (400 MHz, DMSO-$d_6$) δ 8.14 (s, 1H), 8.08 (d, J=1.6 Hz, 1H), 8.04 (s, 1H), 7.41 (d, J=1.6 Hz, 1H), 7.31 (s, 1H), 6.90-6.75 (m, 1H), 6.13 (dd, J=16.8, 2.4 Hz, 1H), 5.69 (dd, J=10.8, 2.4 Hz, 1H), 4.20 (t, J=6.4 Hz, 2H), 4.05 (s, 2H), 3.80-3.55 (m, 4H), 3.06-2.94 (m, 4H), 2.22 (s, 3H), 1.75-1.60 (m, 2H), 1.46-1.33 (m, 2H), 0.92 (t, J=7.6 Hz, 3H) ppm. MS: M/e 451 $(M+1)^+$.

Compound B45: 2-butoxy-7-(3-methoxy-4-(piperazin-1-yl)benzyl)imidazo[2,1-f][1,2,4]triazin-4-amine Compound B45 was synthesized starting from the corresponding starting materials according the similar procedures described as those of Compound B2. $^1$H NMR (400 MHz, DMSO-d6) δ 8.23-7.85 (m, 2H), 7.28 (s, 1H), 6.94 (s, 1H), 6.82-6.75 (m, 2H), 4.22 (t, J=6.4 Hz, 2H), 4.06 (s, 2H), 3.74 (s, 3H), 2.91-2.78 (m, 8H), 1.76-1.59 (m, 2H), 1.48-1.35 (m, 2H), 0.92 (t, J=7.2 Hz, 3H) ppm. MS: M/e 412 $(M+1)^+$.

Compound B46: 2-butoxy-7-(3-isopropoxy-4-(piperazin-1-yl)benzyl)imidazo[2,1-f][1,2,4]triazin-4-amine Compound B46 was synthesized starting from the corresponding starting materials according the similar procedures described as those of Compound B16. $^1$H NMR (400 MHz, DMSO-d6) δ 8.21-7.87 (m, 2H), 7.21 (s, 1H), 6.82 (s, 1H), 6.77-6.63 (m, 2H), 4.59-4.35 (m, 1H), 4.26-4.08 (m, 2H), 3.97 (s, 2H), 2.99-2.66 (m, 8H), 1.74-1.53 (m, 2H), 1.45-1.27 (m, 2H), 1.24-1.06 (m, 6H), 0.85 (t, J=7.2 Hz, 3H) ppm. MS: M/e 440 $(M+1)^+$.

Compound B47: 2-butoxy-7-((4-methyl-5-(piperidin-4-yl)pyridin-2-yl)methyl)imidazo[2,1-f][1,2,4]triazin-4-amine Step A: (5-bromo-4-methylpyridin-2-yl)methanol $BH_3$·THF (20 mL, 20 mmol) was added to a solution of 5-bromo-4-methylpicolinic acid (2.16 g, 10 mmol) in THF (10 mL). The reaction mixture was heated at 80° C. for 2 hours, was cooled to room temperature. The solution was quenched with $CH_3OH$ (10 mL) and $H_2O$ (10 ml). The aqueous solution was extracted with EA (20 ml×3). The collected organic layers were washed with brine, dried over $Na_2SO_4$, filtered and concentrated. The resulting residue was purified by column chromatography to afford the product (515 mg, 25%). MS: M/e 203 $(M+1)^+$.

Step B: tert-butyl 6-(hydroxymethyl)-4-methyl-3',6'-dihydro-[3,4'-bipyridine]-1'(2'H)-carboxylate To a flask containing (5-bromo-4-methylpyridin-2-yl) methanol (515 mg, 2.5 mmol), tert-butyl 4-(4,4,5,5-tetramethyl-1,3,2-dioxaborolan-2-yl)-3,6-dihydropyridine-1(2H)-carboxylate (1.01 g, 3.3 mmol), dppf·$PdCl_2$ (368 mg, 0.5 mmol) and $k_2CO_3$ (696 mg, 5 mmol) under nitrogen, 1,4-dioxane (10 ml) and $H_2O$ (1 mL) was added. The mixture was stirred at 80° C. overnight, after cooling to room temperature, the solvent was removed by rotary evaporation. The residue was dissolved in EA (20 mL), washed with water and brine, dried over $Na_2SO_4$, filtered, and concentrated. The residue was purified by column chromatography to give target compound (300 mg, 39%). MS: M/e 305 $(M+1)^+$.

Step C: tert-butyl 4-(6-(hydroxymethyl)-4-methylpyridin-3-yl)piperidine-1-carboxylate The product of Step B (300 mg, 0.98 mmol) was dissolved in $CH_3OH$ (5 mL), Pd/C (30 mg) was added and was evacuated saturated with hydrogen gas from a balloon and stirred at room temperature for 3 days, hydrogen was removed, the reaction mixture was filtered through a celite pad, the solid was washed with methanol and filtrate were concentrated to dryness. The residue was purified by column chromatography to give target compound (90 mg, 30%). MS: M/e 307 $(M+1)^+$.

Step D: tert-butyl 4-(6-formyl-4-methylpyridin-3-yl) piperidine-1-carboxylate

To a solution of the product of Step C (90 mg, 0.29 mmol) in DCM (2 mL), Dess-Martin periodinane (124 mg, 0.58 mmol) was added. After stirring at room temperature for 1 hour, the solution was quenched with saturated $NaHCO_3$ solution (5 mL). The aqueous solution was extracted with DCM (10 ml×4). The collected organic layers were washed with brine, dried over $Na_2SO_4$, filtered and concentrated. The resulting residue was purified by column chromatography to afford the product (75 mg, 83%).

Step E: tert-butyl 4-(6-((4-(bis(4-methoxybenzyl) amino)-2-butoxyimidazo[2,1-f][1,2,4]triazin-7-yl) (hydroxy)methyl)-4-methylpyridin-3-yl)piperidine-1-carboxylate To a solution of 7-bromo-2-butoxy-N,N-bis(4-methoxybenzyl)imidazo[2,1-f][1,2,4]triazin-4-amine (131 mg, 0.25 mmol) in THF (1 mL), a solution of n-BuLi (0.19 mL, 0.3 mmol) was added dropwise maintaining the temperature between −75∼−65° C. After 10 min, a solution of product of Step D (75 mg, 0.25 mmol) in THF (1 mL) was added dropwise. The resulting mixture was stirred at −70° C. for 30 min. The reaction was quenched with saturated $NH_4Cl$ solution, extracted with EtOAc (10 mL×4), washed with brine, dried over $Na_2SO_4$, filtered, and concentrated. The residue was purified by column chromatography to give target compound (20 mg, 11%). MS: M/e 753 $(M+1)^+$.

Step F: 2-butoxy-7-((4-methyl-5-(piperidin-4-yl) pyridin-2-yl)methyl)imidazo[2,1-f][1,2,4]triazin-4-amine To a mixture of the product of Step E (20 mg, 0.026 mmol) in TFA (2 mL), $Et_3SiH$ (0.5 mL) was added. The reaction was heated at 80° C. for 2 days. The mixture was concentrated and the residue was purified by prep-HPLC and concentrated to give the product (5 mg, 45%). $^1H$ NMR (400 MHz, $CD_3OD$) δ 8.89-8.20 (m, 1H), 7.90-7.16 (m, 2H), 4.61-4.41 (m, 2H), 4.19 (s, 2H), 3.57-3.51 (m, 2H), 3.20 (t, J=12.5 Hz, 2H), 2.78-2.65 (m, 1H), 2.63-2.36 (m, 3H), 2.21-1.93 (m, 4H), 1.80-1.63 (m, 2H), 1.51-1.41 (m, 2H), 0.96 (t, J=7.4 Hz, 3H) ppm. MS: M/e 396 $(M+1)^+$.

Compound B48: 2-butoxy-7-((4-methyl-6-(piperazin-1-yl)pyridin-3-yl)methyl)imidazo[2,1-f][1,2,4] triazin-4-amine Step A: tert-butyl 4-(5-(methoxycarbonyl)-4-methylpyridin-2-yl)piperazine-1-carboxylate DIPEA (1.7 g, 13 mmol) was added to a solution of methyl 6-chloro-4-methylnicotinate (1.85 g, 10 mmol) and tert-butyl piperazine-1-carboxylate (2.24 g, 12 mmol) in DMA (15 mL). The reaction mixture was heated at 120° C. for 3 hours, was then cooled to room temperature. The solution was quenched with $H_2O$ (10 ml). The aqueous solution was extracted with EA (20 ml×3). The collected organic layers were washed with brine, dried over $Na_2SO_4$, filtered and concentrated. The resulting residue was purified by column chromatography to afford the product (2.4 g, 72%). MS: M/e 336 $(M+1)^+$.

Step B: tert-butyl 4-(5-(hydroxymethyl)-4-methylpyridin-2-yl)piperazine-1-carboxylate To a solution of the product of Step A (670 mg, 2 mmol) in THF (5 mL), $LiAlH_4$ (112 mg, 4 mmol) was added. After stirring at 0° C. for 2 hours, the reaction was quenched with saturated $NH_4Cl$ solution, extracted with EtOAc (10 mL×5), washed with brine, dried over $Na_2SO_4$, filtered, and concentrated. The crude product was used in next step without further purification (614 mg). MS: M/e 308 $(M+1)^+$.

Step C: tert-butyl 4-(5-formyl-4-methylpyridin-2-yl) piperazine-1-carboxylate

To a solution of the product of Step A (307 mg, 1 mmol) in EA (10 mL), IBX (560 mg, 2 mmol) was added. After stirring at 80° C. for 2 hours, the reaction was cooled room temperature, the resulting mixture was filtered over celite and the solid was washed with EtOAc (10 mL×4), filtrate was concentrated in vacuo. The resulting residue was purified by column chromatography to afford the product (220 mg, 72%). MS: M/e 306 $(M+1)^+$.

Step D: tert-butyl 4-(5-((4-(bis(4-methoxybenzyl) amino)-2-butoxyimidazo[2,1-f][1,2,4]triazin-7-yl) (hydroxy)methyl)-4-methylpyridin-2-yl)piperazine-1-carboxylate To a solution of 7-bromo-2-butoxy-N,N-bis(4-methoxybenzyl)imidazo[2,1-f][1,2,4]triazin-4-amine (158 mg, 0.3 mmol) in THF (1 mL), a solution of n-BuLi (0.3 mL, 0.45 mmol) was added dropwise maintaining the temperature between −75~−65° C. After 10 min, a solution of product of Step C (138 mg, 0.45 mmol) in THF (1 mL) was added dropwise. The resulting mixture was stirred at −70° C. for 30 min. The reaction was quenched with saturated $NH_4Cl$ solution, extracted with EtOAc (10 mL×4), washed with brine, dried over $Na_2SO_4$, filtered, and concentrated. The residue was purified by column chromatography to give target compound (80 mg, 78%). MS: M/e 754 $(M+1)^+$.

Step E: 2-butoxy-7-((4-methyl-6-(piperazin-1-yl)pyridin-3-yl)methyl)imidazo[2,1-f][1,2,4]triazin-4-amine To a mixture of the product of Step D (180 mg, 0.24 mmol) in TFA (5 mL), $Et_3SiH$ (1 mL) was added. The reaction was heated at 80° C. for 2 days. The mixture was concentrated and the residue was purified by prep-HPLC. The collected fraction was basified with $NaHCO_3$ solution, extracted with DCM (30 mL), washed with brine, dried over $Na_2SO_4$, filtered, and concentrated to give the product (25 mg, 26%). $^1H$ NMR (400 MHz, $CD_3OD$) δ 8.01 (s, 1H), 7.19 (s, 1H), 6.74 (s, 1H), 4.29 (t, J=6.5 Hz, 2H), 4.11 (s, 2H), 3.68-3.51 (m, 4H), 3.20-3.04 (m, 4H), 2.30 (s, 3H), 1.92-1.68 (m, 2H), 1.59-1.39 (m, 2H), 0.98 (t, J=7.4 Hz, 3H) ppm. MS: M/e 397 $(M+1)^+$.

Compound B49: 1-(4-(5-((4-amino-2-butoxyimidazo[2,1-f][1,2,4]triazin-7-yl)methyl)-3-methylpyridin-2-yl)piperazin-1-yl)-4-(dimethylamino)butan-1-one A mixture of 2-butoxy-7-((5-methyl-6-(piperazin-1-yl)pyridin-3-yl)methyl)imidazo[2,1-f][1,2,4]triazin-4-amine (20 mg, 0.05 mmol), 4-(dimethylamino)butanoic acid (6 mg, 0.05 mmol), HATU (23 mg, 0.06 mmol) and DIPEA (19 mg, 0.15 mmol) in DCM (3 mL) was stirred at rt for 2 h. The mixture was extracted with DCM (10 mL) and washed with water (5 ml), dried over $Na_2SO_4$, concentrated and purified with prep-HPLC to give the title product (13 mg, 50.4%). $^1H$ NMR (400 MHz, DMSO-d6) δ 9.33 (br.s, 1H), 8.15 (s, 1H), 8.09 (s, 2H), 7.53 (s, 1H), 7.34 (s, 1H), 4.21 (t, J=6.6 Hz, 2H), 4.07 (s, 2H), 3.57 (d, J=14.8 Hz, 4H), 3.05 (t, J=7.6 Hz, 4H), 2.98 (s, 2H), 2.78 (s, 3H), 2.77 (s, 3H), 2.46 (t, J=7.0 Hz, 2H), 2.23 (s, 3H), 1.92-1.78 (m, 2H), 1.73-1.61 (m, 2H), 1.47-1.34 (m, 2H), 0.92 (t, J=7.4 Hz, 3H) ppm. MS: M/e 510 $(M+1)^+$.

Compound B50: 1-(4-(5-((4-amino-2-butoxyimidazo[2,1-f][1,2,4]triazin-7-yl)methyl)-3-methylpyridin-2-yl)piperazin-1-yl)-5-(dimethylamino)pentan-1-one A mixture of 2-butoxy-7-((5-methyl-6-(piperazin-1-yl)pyridin-3-yl)methyl)imidazo[2,1-f][1,2,4]triazin-4-amine (20 mg, 0.05 mmol), 5-(dimethylamino)pentanoic acid (7 mg, 0.05 mmol), HATU (23 mg, 0.06 mmol) and DIPEA (19 mg, 0.15 mmol) in DCM (3 mL) was stirred at rt for 2 h. The mixture was extracted with DCM (10 mL) and washed with water (5 ml), dried over $Na_2SO_4$, concentrated and purified with prep-HPLC to give the title product (10 mg, 37.8%). $^1H$ NMR (400 MHz, DMSO-d6) δ 9.22 (br.s, 1H), 8.15 (s, 1H), 8.08 (s, 2H), 7.52 (s, 1H), 7.33 (s, 1H), 4.21 (t, J=6.5 Hz, 2H), 4.07 (s, 2H), 3.62-3.51 (m, 4H), 3.12-2.95 (m, 6H), 2.76 (s, 3H), 2.75 (s, 3H), 2.40 (t, J=6.9 Hz, 2H), 2.22 (s, 3H), 1.74-1.58 (m, 4H), 1.58-1.49 (m, 2H), 1.46-1.34 (m, 2H), 0.92 (t, J=7.4 Hz, 3H) ppm. MS: M/e 524 $(M+1)^+$.

Compound B51: 2-butoxy-7-((5-methyl-6-(pyrrolidin-1-yl)pyridin-3-yl)methyl)imidazo[2,1-f][1,2,4]triazin-4-amine Compound B51 was synthesized starting from the corresponding starting materials according the similar procedures described as those of Compound B8. $^1H$ NMR (400 MHz, DMSO-d6))) δ 8.17 (s, 1H), 8.08 (s, 1H), 7.81 (s, 1H), 7.63 (s, 1H), 7.32 (s, 1H), 4.21 (t, J=6.4 Hz, 2H), 4.04 (s, 2H), 3.61 (s, 4H), 2.40 (s, 3H), 1.91 (s, 4H), 1.75-1.61 (m, 2H), 1.48-1.35 (m, 2H), 0.93 (t, J=7.4 Hz, 3H) ppm. MS: M/e 382 $(M+1)^+$.

Compound B52: 2-butoxy-7-((5-methyl-6-morpholinopyridin-3-yl)methyl)imidazo[2,1-f][1,2,4]triazin-4-amine Compound B52 was synthesized starting from the corresponding starting materials according the similar procedures described as those of Compound B8. $^1H$ NMR (400 MHz, DMSO-d6)) δ 8.17 (s, 1H), 8.14 (s, 1H), 8.10 (s, 1H), 7.63 (s, 1H), 7.38-7.34 (m, 1H), 4.21 (t, J=6.4 Hz, 2H), 4.10 (s, 2H), 3.76-3.67 (m, 4H), 3.10 (s, 4H), 2.23 (s, 3H), 1.76-1.61 (m, 2H), 1.48-1.31 (m, 2H), 0.93 (t, J=7.3 Hz, 3H) ppm. MS: M/e 398 $(M+1)^+$.

Compound B53: 2-butoxy-7-((2-methyl-6-(piperazin-1-yl)pyridin-3-yl) methyl)imidazo[2,1-f][1,2,4]triazin-4-amine Compound B53 was synthesized starting from the corresponding starting materials according the similar procedures described as those of Compound B8. $^1H$ NMR (400 MHz, DMSO-d6) δ 8.88 (br.s, 2H), 8.19 (s, 2H), 7.55 (d, J=8.0 Hz, 1H), 7.33 (s, 1H), 6.79 (d, J=8.0 Hz, 1H), 4.20 (t, J=8.0 Hz, 2H), 4.06 (s, 2H), 3.68 (t, J=4.0 Hz, 4H), 3.19 (s, 4H), 2.44 (s, 3H), 1.70-1.64 (m, 2H), 1.44-1.37 (m, 2H), 0.93 (t, J=8.0 Hz, 3H) ppm. MS: M/e 397 $(M+1)^+$.

Compound B54: 2-butoxy-7-((2-methyl-6-(piperidin-4-yl)pyridin-3-yl) methyl)imidazo[2,1-f][1,2,4]triazin-4-amine Step A: tert-butyl5-formyl-6-methyl-3',6'-dihydro-[2,4'-bipyridine]-1'(2'H)-carboxylate A solution of 6-chloro-2-methylnicotinaldehyde (500 mg, 3.2 mmol), tert-butyl 4-(4,4,5,5-tetramethyl-1,3,2-dioxaborolan-2-yl)-3,6-dihydropyridine-1(2H)-carboxylate (1.1 g, 3.5 mmol), $Pd(dppf)_2Cl_2$ (224 mg, 0.30 mmol) and $K_2CO_3$ (662 mg, 4.8 mmol) in dioxane/water (1:1, 10 mL) was heated at 80° C. under $N_2$ atmosphere overnight. The solution was cooled, evaporated, added with water (10 mL) and extracted with ethyl acetate (20 mL). The organic layer was dried over $Na_2SO_4$, filtered and concentrated to get the crude product, which was further purified by CombiFlash (PE:EA=25%) to get the pure product as a colorless oil (718 mg, 74%). MS: M/e 303 $(M+1)^+$.

Step B: tert-butyl 5-((4-(bis(4-methoxybenzyl)amino)-2-butoxyimidazo[2,1-f][1,2,4]triazin-7-yl)(hydroxy)methyl)-6-methyl-3',6'-dihydro-[2,4'-bipyridine]-1'(2'H)-carboxylate To a cooled solution of 7-bromo-2-butoxy-N,N-bis(4-methoxybenzyl)imidazo[2,1-f][1,2,4]triazin-4-amine (200 mg, 0.38 mmol) in THF (8 mL) at −78° C. (purged with $N^2$), n-BuLi (1.6 M, 0.60 mL) was added dropwise. After stirring at −78° C. for 30 mins, tert-butyl 5-formyl-6-methyl-3',6'-dihydro-[2,4'-bipyridine]-1'(2'H)-carboxylate (173 mg, 0.57 mmol) in THF (2 mL) was added. The resulting mixture was stirred at this temperature for 30 mins, and then warmed to rt overnight. The solution was quenched with $NH_4Cl$ solution (5 mL) and extracted with ethyl acetate (10 mL). The organic layer was dried over $Na_2SO_4$, filtered and concentrated to get the crude product, which was further purified by CombiFlash (PE:EA=35%) to get the product (123 mg, 43%). MS: M/e 750 $(M+1)^+$.

Step C: tert-butyl 4-(5-((4-(bis(4-methoxybenzyl) amino)-2-butoxyimidazo[2,1-f][1,2,4]triazin-7-yl) (hydroxy)methyl)-6-methylpyridin-2-yl)piperidine-1-carboxylate A solution of tert-butyl 5-((4-(bis(4-methoxybenzyl) amino)-2-butoxyimidazo[2,1-f][1,2,4]triazin-7-yl)(hydroxy)methyl)-6-methyl-3',6'-dihydro-[2,4'-bipyridine]-1' (2'H)-carboxylate (123 mg, 0.16 mmol) and Pd/C (27 mg) in ethyl acetate (10 mL) was stirred at rt under $H_2$ balloon for 48 hrs. The catalyst was filtered and the filtrate was concentrated to get the crude product, which was used directly in the next step (110 mg, 89%). MS: M/e 752 $(M+1)^+$.

Step D: 2-butoxy-7-((2-methyl-6-(piperidin-4-yl) pyridin-3-yl)methyl)imidazo[2,1-f][1,2,4]triazin-4-amine A solution of tert-butyl 4-(5-((4-(bis(4-methoxybenzyl) amino)-2-butoxyimidazo[2,1-f][1,2,4]triazin-7-yl)(hydroxy)methyl)-6-methylpyridin-2-yl)piperidine-1-carboxylate (110 mg, 0.15 mmol) in triethylsilane (2 mL) and trifluoroacetic acid (2 mL) was heated at 85° C. overnight, then concentrated, added with 2 mL of trifluoroacetic acid and heated at 90° C. for 6 hrs. The solvent was evaporated to get the residue, which was basified with $NaHCO_3$ (5 mL), extracted with ethyl acetate (5 mL), washed with brine. The organic layer was dried, concentrated and purified by prep-HPLC to get the product (40 mg, 69%). $^1$H NMR (400 MHz, DMSO-d6) δ 8.72 (br.s, 1H), 8.41 (br.s, 1H), 8.21 (s, 1H), 8.14 (s, 1H), 7.80 (br.s, 1H), 7.37 (s, 1H), 7.27 (br.s, 1H), 4.22 (s, 2H), 4.16 (t, J=8.0 Hz, 2H), 3.39 (d, J=12.0 Hz, 2H), 3.02-2.97 (m, 3H), 2.62 (s, 3H), 2.03-2.00 (m, 2H), 1.91-1.82 (m, 2H), 1.69-1.62 (m, 2H), 1.44-1.35 (m, 2H), 0.91 (t, J=8.0 Hz, 3H) ppm. MS: M/e 396 $(M+1)^+$.

Compound B55: 2-butoxy-7-((6-(3,5-dimethylpiperazin-1-yl)-5-methylpyridin-3-yl)methyl)imidazo[2,1-f][1,2,4]triazin-4-amine Compound B55 was synthesized starting from the corresponding starting materials according the similar procedures described as those of Compound B8. $^1$H NMR (400 MHz, DMSO-d6) δ 8.95 (br.s, 1H), 8.31 (br.s, 1H), 8.15 (s, 1H), 8.11 (s, 2H), 7.52 (s, 1H), 7.34 (s, 1H), 4.21 (t, J=8.0 Hz, 2H), 4.08 (s, 2H), 3.48-3.45 (m, 4H), 2.75-2.69 (m, 2H), 2.24 (s, 3H), 1.68-1.64 (m, 2H), 1.44-1.38 (m, 2H), 1.22 (d, J=4.0 Hz, 6H), 0.93 (t, J=8.0 Hz, 3H) ppm. MS: M/e 425 $(M+1)^+$.

Compound B56: (4-(5-((4-amino-2-butoxyimidazo [2,1-f][1,2,4]triazin-7-yl)methyl)-3-methylpyridin-2-yl)piperazin-1-yl)(piperidin-4-yl)methanone Step A: tert-butyl 4-(4-(5-((4-amino-2-butoxyimidazo[2,1-f][1,2,4]triazin-7-yl)methyl)-3-methylpyridin-2-yl)piperazine-1-carbonyl)piperidine-1-carboxylate To a mixture of 2-butoxy-7-((5-methyl-6-(piperazin-1-yl) pyridin-3-yl)methyl)imidazo[2,1-f][1,2,4]triazin-4-amine (40 mg, 0.1 mmol), 1-(tert-butoxycarbonyl)piperidine-4-carboxylic acid (23 mg, 0.1 mmol) and DIEA (25 mg, 0.2 mmol) in THF (5 mL), HATU (38 mg, 0.1 mmol) was added. The reaction was stirred at room temperature overnight. The reaction was diluted with water, extracted with EA (60 mL), washed with brine, dried over $Na_2SO_4$, filtered, and concentrated to give the target compound (60 mg, crude). MS: M/e 608 $(M+1)^+$.

Step B: (4-(5-((4-amino-2-butoxyimidazo[2,1-f][1,2,4]triazin-7-yl)methyl)-3-methylpyridin-2-yl)piperazin-1-yl)(piperidin-4-yl)methanone To a mixture of the product of the step A (60 mg, crude) in DCM (5 mL), a solution of 4 M HCl in EA (0.5 mL) was added. The reaction was stirred at room temperature for 3 h. The mixture was concentrated and purified by prep-HPLC to give the target compound (20 mg, 32%). $^1$HNMR (400 MHz, $CD_3OD$) δ 8.15 (d, J=1.6 Hz, 1H), 8.08 (s, 1H), 7.68 (d, J=2.0 Hz, 1H), 4.32 (t, J=6.8 Hz, 2H), 4.31 (s, 2H), 3.90-3.75 (m, 4H), 3.55-3.38 (m, 6H), 3.18-3.03 (m, 3H), 2.43 (s, 3H), 2.06-1.84 (m, 4H), 1.81-1.71 (m, 2H), 1.57-1.42 (m, 2H), 0.98 (t, J=7.6 Hz, 3H) ppm. MS: M/e 508 $(M+1)^+$.

Compound B57: 1-(4-(5-((4-amino-2-butoxyimidazo[2,1-f][1,2,4]triazin-7-yl)methyl)-3-methylpyridin-2-yl)piperazin-1-yl)ethan-1-one To a mixture of 2-butoxy-7-((5-methyl-6-(piperazin-1-yl) pyridin-3-yl)methyl)imidazo[2,1-f][1,2,4]triazin-4-amine (40 mg, 0.1 mmol) in THF (4 mL), DIEA (25 mg, 0.2 mmol) was added. Then a solution of acetyl chloride in DCM (0.1 mL, 1 mol/L) was added dropwise. The reaction was stirred at room temperature overnight. The reaction was diluted with water, extracted with EA (50 mL), washed with brine, dried over $Na_2SO_4$, filtered, and concentrated. The residue was purified by prep-TLC to give the target compound (20 mg, 46%). $^1$HNMR (400 MHz, DMSO-$d_6$) δ 8.14 (s, 1H), 8.08 (d, J=1.6 Hz, 1H), 8.05 (s, 1H), 7.47 (s, 1H), 7.31 (s, 1H), 4.20 (t, J=6.8 Hz, 2H), 4.05 (s, 2H), 3.61-3.50 (m, 4H), 3.01 (t, J=4.8 Hz, 2H), 2.93 (t, J=4.8 Hz, 2H), 2.21 (s, 3H), 2.03 (s, 3H), 1.74-1.60 (m, 2H), 1.51-1.34 (m, 2H), 0.92 (t, J=7.6 Hz, 3H) ppm. MS: M/e 439 $(M+1)^+$.

Compound B58: N-(2-(4-(5-((4-amino-2-butoxyimidazo[2,1-f][1,2,4]triazin-7-yl)methyl)-3-methylpyridin-2-yl)piperazin-1-yl)-2-oxoethyl)-N-methylacetamide To a mixture of 1-(4-(5-((4-amino-2-butoxyimidazo[2,1-f][1,2,4]triazin-7-yl)methyl)-3-methylpyridin-2-yl)piperazin-1-yl)-2-(methylamino)ethan-1-one hydrochloride (60 mg, crude) in THF (4 mL), DIEA (129 mg, 1 mmol) was added. Then a solution of acetyl chloride in DCM (0.1 mL, 1 mol/L) was added dropwise. The reaction was stirred at room temperature overnight. The reaction was diluted with water, extracted with EA (40 mL×2), washed with brine, dried over $Na_2SO_4$, filtered, and concentrated. The residue was purified by prep-TLC to give the title product (10 mg, 20% for three steps). $^1H$ NMR (400 MHz, $CD_3OD$) δ 8.08 (d, J=2.4 Hz, 1H), 7.55 (s, 1H), 7.34 (s, 1H), 4.40-4.31 (m, 2H), 4.28 (t, J=6.0 Hz, 2H), 4.15 (s, 2H), 3.78-3.69 (m, 2H), 3.68-3.59 (m, 2H), 3.18-3.12 (m, 2H), 3.11-3.06 (m, 2H), 3.09 (s, 2H), 2.92 (s, 1H), 2.29 (s, 3H), 2.15 (s, 2H), 2.00 (s, 1H), 1.82-1.68 (m, 2H), 1.57-1.42 (m, 2H), 0.98 (t, J=7.6 Hz, 3H) ppm. MS: M/e 510 $(M+1)^+$.

Compound B59: 2-butoxy-7-((6-(4-((dimethylamino)methyl)piperidin-1-yl)-5-methylpyridin-3-yl)methyl)imidazo[2,1-f][1,2,4]triazin-4-amine Step A: 6-(4-((dimethylamino)methyl)piperidin-1-yl)-5-methylnicotinaldehyde DIPEA (2.6 g, 20 mmol) was added to a solution of methyl 6-chloro-4-methylnicotinate (1.87 g, 12 mmol) and N,N-dimethyl-1-(piperidin-4-yl)methanamine (1.42 g, 10 mmol) in DMA (10 mL), the reaction mixture was heated at 120° C. overnight, was cooled to room temperature. The solution was quenched with $H_2O$ (10 ml). The aqueous solution was extracted with EA (25 ml×4). The collected organic layers were washed with brine, dried over $Na_2SO_4$, filtered and concentrated. The resulting residue was purified by column chromatography to afford the product (720 mg, 27%). MS: M/e 261 $(M+1)^+$.

Step B: (4-(bis(4-methoxybenzyl)amino)-2-butoxyimidazo[2,1-f][1,2,4]triazin-7-yl)(6-(4-((dimethylamino)methyl)piperidin-1-yl)-5-methylpyridin-3-yl)methanol To a solution of 7-bromo-2-butoxy-N,N-bis(4-methoxybenzyl)imidazo[2,1-f][1,2,4]triazin-4-amine (158 mg, 0.3 mmol) in THF (1 mL), a solution of n-BuLi (0.28 mL, 0.45 mmol) was added dropwise maintaining the temperature between −75~−65° C. After 10 min, a solution of product of Step A (118 mg, 0.45 mmol) in THF (1 mL) was added dropwise. The resulting mixture was stirred at −70° C. for 30 min. The reaction was quenched with saturated $NH_4Cl$ solution, extracted with EtOAc (10 mL×4), washed with brine, dried over $Na_2SO_4$, filtered, and concentrated. The residue was purified by column chromatography to give target compound (100 mg, 47%). MS: M/e 709 $(M+1)^+$.

Step C: 2-butoxy-7-((6-(4-((dimethylamino)methyl)piperidin-1-yl)-5-methylpyridin-3-yl)methyl)imidazo[2,1-f][1,2,4]triazin-4-amine To a mixture of the product of Step B (100 mg, 0.24 mmol) in TFA (4 mL), $Et_3SiH$ (1 mL) was added. The reaction was heated at 80° C. for 24 hours. The mixture was concentrated and the residue was purified by prep-HPLC. The collected fraction was basified with $NaHCO_3$ solution, extracted with DCM (30 mL), washed with brine, dried over $Na_2SO_4$, filtered, and concentrated to give the product (55 mg, 77%). $^1H$ NMR (400 MHz, $CD_3OD$) δ 8.03 (d, J=1.6 Hz, 1H), 7.47 (s, 1H), 7.32 (s, 1H), 4.27 (t, J=6.5 Hz, 2H), 4.11 (s, 2H), 3.35 (d, J=12.6 Hz, 2H), 2.74 (t, J=11.5 Hz, 2H), 2.28 (s, 2H), 2.26 (s, 6H), 2.23 (s, 3H), 1.83 (d, J=11.6 Hz, 2H), 1.77-1.61 (m, 3H), 1.49 (dt, J=15.0, 7.4 Hz, 2H), 1.33 (qd, J=12.4, 3.6 Hz, 2H), 0.97 (t, J=7.4 Hz, 3H) ppm. MS: M/e 453 $(M+1)^+$.

Compound B60: 7-((6-(4-aminopiperidin-1-yl)-5-methylpyridin-3-yl)methyl)-2-butoxyimidazo[2,1-f][1,2,4]triazin-4-amine Step A: tert-butyl (1-(5-formyl-3-methylpyridin-2-yl)piperidin-4-yl)carbamate DIPEA (2.6 g, 20 mmol) was added to a solution of methyl 6-chloro-4-methylnicotinate (1.56 g, 10 mmol) and tert-butyl piperidin-4-ylcarbamate (2.4 g, 12 mmol) in DMA (10 mL), the reaction mixture was heated at 120° C. overnight, was cooled to room temperature. The solution was quenched with $H_2O$ (10 ml). The aqueous solution was extracted with EA (25 ml×4). The collected organic layers were washed with brine, dried over $Na_2SO_4$, filtered and concentrated. The resulting residue was purified by column chromatography to afford the product (1.3 g, 41%). MS: M/e 320 $(M+1)^+$.

Step B: tert-butyl (1-(5-((4-(bis(4-methoxybenzyl)amino)-2-butoxyimidazo[2,1-f][1,2,4]triazin-7-yl)(hydroxy)methyl)-3-methylpyridin-2-yl)piperidin-4-yl)carbamate To a solution of 7-bromo-2-butoxy-N,N-bis(4-methoxybenzyl)imidazo[2,1-f][1,2,4]triazin-4-amine (158 mg, 0.3 mmol) in THF (1 mL), a solution of n-BuLi (0.28 mL, 0.45 mmol) was added dropwise maintaining the temperature between −75~−65° C. After 10 min, a solution of product of Step A (144 mg, 0.45 mmol) in THF (1 mL) was added dropwise. The resulting mixture was stirred at −70° C. for 30 min. The reaction was quenched with saturated $NH_4Cl$ solution, extracted with EtOAc (10 mL×4), washed with brine, dried over $Na_2SO_4$, filtered, and concentrated. The residue was purified by column chromatography to give target compound (140 mg, 61%). MS: M/e 767 $(M+1)^+$.

Step C: 7-((6-(4-aminopiperidin-1-yl)-5-methylpyridin-3-yl)methyl)-2-butoxyimidazo[2,1-f][1,2,4]triazin-4-amine To a mixture of the product of Step B (140 mg, 0.18 mmol) in TFA (4 mL), $Et_3SiH$ (1 mL) was added. The reaction was heated at 80° C. for 24 hours. The mixture was concentrated and the residue was purified by prep-HPLC, The collected fraction was basified with $NaHCO_3$ solution, extracted with DCM (30 mL), washed with brine, dried over $Na_2SO_4$, filtered, and concentrated to give the title product (40 mg, 54%). $^1H$ NMR (400 MHz, $CD_3OD$) δ=8.03 (s, 1H), 7.48 (s, 1H), 7.32 (s, 1H), 4.27 (t, J=6.5, 2H), 4.11 (s, 2H), 3.36 (d, J=13.0, 2H), 2.96-2.87 (m, 1H), 2.79 (t, J=11.8, 2H), 2.24 (s, 3H), 1.95 (d, J=11.1, 2H), 1.80-1.68 (m, 2H), 1.59 (qd, J=12.1, 3.8, 2H), 1.47 (dt, J=14.6, 7.4, 2H), 0.97 (t, J=7.4, 3H) ppm. MS: M/e 411 $(M+1)^+$.

Compound B61: 2-butoxy-7-(4-(3,5-dimethylpiperazin-1-yl)-3-methylbenzyl)imidazo[2,1-f][1,2,4]triazin-4-amine Compound B61 was synthesized starting from the corresponding starting materials according the similar procedures described as those of Compound B16. $^1H$ NMR (400 MHz, DMSO-d6) δ 8.10 (s, 1H), 8.01 (s, 1H), 7.28 (s, 1H), 7.10 (s, 1H), 7.05 (d, J=8.0 Hz, 1H), 6.87 (d, J=8.0 Hz, 1H), 4.21 (t, J=8.0 Hz, 2H), 4.02 (s, 2H), 2.87-2.80 (m, 4H), 2.18 (s, 3H), 2.12-2.07 (m, 2H), 1.71-1.64 (m, 2H), 1.43-1.38 (m, 2H), 0.94 (t, J=8.0 Hz, 9H) ppm. MS: M/e 424 $(M+1)^+$.

Compound B62: 2-methoxy-7-((5-methyl-6-(piperazin-1-yl)pyridin-3-yl) methyl)imidazo[2,1-f][1,2,4]triazin-4-amine Step A: tert-butyl 4-(5-((4-(bis(4-methoxybenzyl)amino)-2-chloroimidazo[2,1-f][1,2,4]triazin-7-yl)(hydroxy)methyl)-3-methylpyridin-2-yl)piperazine-1-carboxylate To a cooled solution of 7-bromo-2-chloro-N,N-bis(4-methoxybenzyl)imidazo[2,1-f][1,2,4]triazin-4-amine (1 g, 2 mmol) in THF (20 mL) at −78° C. (purged with $N^2$), n-BuLi (1.6 M, 3.2 mL) was added dropwise. After was stirred at −78° C. for 30 mins, tert-butyl 4-(5-formyl-3-methylpyridin-2-yl)piperazine-1-carboxylate (915 mg, 3.0 mmol) in THF (10 mL) was added. The resulting mixture was stirred at this temperature for 30 mins, and then warmed to rt overnight. The solution was quenched with $NH_4Cl$ solution (10 mL) and extracted with ethyl acetate (20 mL). The organic layer was dried with $Na_2SO_4$, filtered and concentrated to get the crude product, which was further purified by Combi-Flash (PE:EA=40%) to get the pure product (790 mg, 54%). MS: M/e 715 $(M+1)^+$.

Step B: tert-butyl 4-(5-((4-(bis(4-methoxybenzyl)amino)-2-methoxyimidazo[2,1-f][1,2,4]triazin-7-yl)(hydroxy)methyl)-3-methylpyridin-2-yl)piperazine-1-carboxylate Sodium methanolate (38 mg, 0.7 mmol) was added to a solution of tert-butyl 4-(5-((4-(bis(4-methoxybenzyl)amino)-2-chloroimidazo[2,1-f][1,2,4]triazin-7-yl)(hydroxy)methyl)-3-methylpyridin-2-yl)piperazine-1-carboxylate (50 mg, 0.07 mmol) in methanol (10 mL). The reaction mixture was heated at 70° C. overnight, cooled down, concentrated and further purified by Combi-Flash (PE:EA=50%) to get the pure product (40 mg, 82%). MS: M/e 711 $(M+1)^+$.

Step C: 2-methoxy-7-((5-methyl-6-(piperazin-1-yl)pyridin-3-yl)methyl)imidazo[2,1-f][1,2,4]triazin-4-amine A solution of tert-butyl 4-(5-((4-(bis(4-methoxybenzyl)amino)-2-methoxyimidazo[2,1-f][1,2,4]triazin-7-yl)(hydroxy)methyl)-3-methylpyridin-2-yl)piperazine-1-carboxylate (40 mg, 0.06 mmol) in triethylsilane (2 mL) and trifluoroacetic acid (2 mL) was heated at 85° C. overnight, then concentrated, added with 2 mL of trifluoroacetic acid and heated at 90° C. for 4 hrs. The solvent was evaporated to get the residue, which was purified by prep-HPLC to get the product (14 mg, 70%). $^1H$ NMR (400 MHz, $CD_3OD$) δ 8.08 (s, 1H), 7.57 (s, 1H), 7.35 (d, J=4.0 Hz, 1H), 4.11 (s, 2H), 3.86 (s, 3H), 3.27 (s, 8H), 2.21 (s, 3H) ppm. MS: M/e 355 $(M+1)^+$.

Compound B63: 2-ethoxy-7-((5-methyl-6-(piperazin-1-yl)pyridin-3-yl) methyl)imidazo[2,1-f][1,2,4]triazin-4-amine Compound B63 was synthesized starting from the corresponding starting materials according the similar procedures described as those of Compound B62. $^1H$ NMR (400 MHz, $CD_3OD$) δ 8.06 (s, 1H), 7.55 (s, 1H), 7.37 (s, 1H), 4.26-4.23 (m, 2H), 4.10 (s, 2H), 3.27 (s, 8H), 2.20 (s, 3H), 1.29 (t, J=8.0 Hz, 3H) ppm. MS: M/e 369 $(M+1)^+$.

Compound B64: 2-butoxy-7-(3-methyl-4-(piperidin-4-yl)benzyl)imidazo[2,1-f][1,2,4]triazin-4-amine Step A: tert-butyl4-(4-((4-(bis(4-methoxybenzyl)amino)-2-butoxyimidazo[2,1-f][1,2,4]triazin-7-yl)(hydroxy)methyl)-2-methylphenyl)-3,6-dihydropyridine-1(2H)-carboxylate To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. and stirred for 1 h. Then a solution of tert-butyl 4-(4-formyl-2-methylphenyl)-3,6-dihydropyridine-1(2H)-carboxylate (129 mg, 0.43 mmol) in THF (2 mL) was added dropwise at −78° C. After addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the product (101 mg, 47.3%) as yellow oil. MS: M/e 749 $(M+1)^+$.

Step B: tert-butyl 4-(4-((4-(bis(4-methoxybenzyl)amino)-2-butoxyimidazo[2,1-f][1,2,4]triazin-7-yl)(hydroxy)methyl)-2-methylphenyl)piperidine-1-carboxylate To a solution of tert-butyl 4-(4-((4-(bis(4-methoxybenzyl)amino)-2-butoxyimidazo[2,1-f][1,2,4]triazin-7-yl)(hydroxy)methyl)-2-methylphenyl)-3,6-dihydropyridine-1(2H)-carboxylate (101 mg, 0.135 mmol) in THF (5 mL), Pd/C (10%, 50 mg) was added and stirred under $H_2$ (1 atm) atmosphere at rt overnight. The mixture was filtered to give filterate, concentrated and purified by column chromatography (DCM/MeOH=20:1~5:1) to give the title product (97 mg, 95.8%) as yellow oil. MS: M/e 751 $(M+1)^+$.

Step C: 2-butoxy-7-(3-methyl-4-(piperidin-4-yl)benzyl)imidazo[2,1-f][1,2,4]triazin-4-amine A mixture of tert-butyl 4-(4-((4-(bis(4-methoxybenzyl)amino)-2-butoxyimidazo[2,1-f][1,2,4]triazin-7-yl)(hydroxy)methyl)-2-methylphenyl)piperidine-1-carboxylate (97 mg, 0.13 mmol) and triethylsilane (1 mL) in TFA (2 mL) was stirred at 90° C. overnight. The mixture was concentrated and purified with prep-HPLC to give the title product (38 mg, 74.5%). $^1H$ NMR (400 MHz, DMSO-d6) δ 8.68-8.65 (m, 1H), 8.40-8.38 (m, 1H), 8.13 (s, 1H), 8.05 (s, 1H), 7.32 (s, 1H), 7.12 (d, J=8.1 Hz, 2H), 7.05 (d, J=7.8 Hz, 1H), 4.21 (t, J=6.5 Hz, 2H), 4.06 (s, 2H), 3.36 (d, J=12.3 Hz, 2H), 3.05-2.94 (m, 3H), 2.27 (s, 3H), 1.85-1.70 (m, 4H), 1.70-1.65 (m, 2H), 1.47-1.35 (m, 2H), 0.92 (t, J=7.4 Hz, 3H) ppm. MS: M/e 395 $(M+1)^+$.

Compound B65: 7-((5-methyl-6-(piperazin-1-yl)pyridin-3-yl)methyl)-2-(pentan-2-yloxy)imidazo[2,1-f][1,2,4]triazin-4-amine Step A: 7-bromo-N,N-bis(4-methoxybenzyl)-2-(pentan-2-yloxy)imidazo[2,1-f][1,2,4]triazin-4-amine NaH (100 mg, 2.5 mmol) was added to a solution of pentan-2-ol (220 mg, 2.5 mmol) in THF (15 mL). After stirring at rt under $N_2$ atmosphere for 30 mins, 7-bromo-2-chloro-N,N-bis(4-methoxybenzyl)imidazo[2,1-f][1,2,4]triazin-4-amine (300 mg, 0.62 mmol) was added and the resulting mixture was heated at 60° C. overnight. The solution was cooled down, diluted with water (10 mL) and extracted with ethyl acetate (10 mL). The organic layer was dried with $Na_2SO_4$, filtered and concentrated to get the crude product, which was further purified by Combi-Flash (PE:EA=25%) to get the pure product (265 mg, 85%). MS: M/e 540 $(M+1)^+$.

Step B: tert-butyl 4-(5-((4-(bis(4-methoxybenzyl)amino)-2-(pentan-2-yloxy)imidazo[2,1-f][1,2,4]triazin-7-yl)(hydroxy)methyl)-3-methylpyridin-2-yl)piperazine-1-carboxylate To a cooled solution of 7-bromo-N,N-bis(4-methoxybenzyl)-2-(pentan-2-yloxy)imidazo[2,1-f][1,2,4]triazin-4-amine (265 mg, 0.5 mmol) in THF (8 mL) at −78° C. (purged with $N^2$), n-BuLi (1.6 M, 0.8 mL) was added dropwise. After stirring at −78° C. for 30 mins, tert-butyl 4-(5-formyl-3-methylpyridin-2-yl)piperazine-1-carboxylate (225 mg, 0.75 mmol) in THF (2 mL) was added. The resulting mixture was stirred at this temperature for 30 mins, and then warmed to rt overnight. The solution was quenched with $NH_4Cl$ solution (5 mL) and extracted with ethyl acetate (10 mL). The organic layer was dried with $Na_2SO_4$, filtered and concentrated to get the crude product, which was further purified by Combi-Flash (PE:EA=30%) to get the pure product (180 mg, 48%). MS: M/e 767 $(M+1)^+$.

Step C: 7-((5-methyl-6-(piperazin-1-yl)pyridin-3-yl)methyl)-2-(pentan-2-yloxy)imidazo[2,1-f][1,2,4]triazin-4-amine A solution of tert-butyl 4-(5-((4-(bis(4-methoxybenzyl)amino)-2-(pentan-2-yloxy)imidazo[2,1-f][1,2,4]triazin-7-yl)(hydroxy)methyl)-3-methylpyridin-2-yl)piperazine-1-carboxylate (180 mg, 0.23 mmol) in triethylsilane (2 mL) and trifluoroacetic acid (2 mL) was heated at 85° C. overnight, and then stirred at 90° C. for 4 hrs. The solvent was evaporated to get the residue, which was purified by prep-HPLC to get the product (56 mg, 58%). $^1$H NMR (400 MHz, DMSO-d6) δ 8.88 (br.s, 2H), 8.23 (br.s, 2H), 8.12 (s, 1H), 7.53 (s, 1H), 7.47 (s, 1H), 5.01-4.95 (m, 1H), 4.10 (s, 2H), 3.25-3.21 (m, 8H), 2.21 (s, 3H), 1.66-1.49 (m, 2H), 1.39-1.29 (m, 2H), 1.25 (d, J=4.0 Hz, 3H), 0.88 (t, J=8.0 Hz, 3H) ppm. MS: M/e 411 $(M+1)^+$.

Compound B66: 2-isopropoxy-7-((5-methyl-6-(piperazin-1-yl)pyridin-3-yl) methyl)imidazo[2,1-f][1,2,4]triazin-4-amine Compound B66 was synthesized starting from the corresponding starting materials according the similar procedures described as those of Compound B65. $^1$H NMR (400 MHz, DMSO-d6) δ 8.11 (s, 1H), 8.05 (d, J=4.0 Hz, 1H), 7.99 (s, 1H), 7.40 (d, J=4.0 Hz, 1H), 7.32 (s, 1H), 5.08-5.02 (m, 2H), 4.03 (s, 2H), 2.96-2.91 (m, 4H), 2.86-2.75 (m, 4H), 2.17 (s, 3H), 1.27 (d, J=8.0 Hz, 6H) ppm. MS: M/e 383 $(M+1)^+$.

Compound B67: (2S,3S)-2-amino-1-(4-(5-((4-amino-2-butoxyimidazo[2,1-f][1,2,4]triazin-7-yl)methyl)-3-methylpyridin-2-yl)piperazin-1-yl)-3-methylpentan-1-one Step A: tert-butyl ((2S,3S)-1-(4-(5-((4-amino-2-butoxyimidazo[2,1-f][1,2,4]triazin-7-yl)methyl)-3-methylpyridin-2-yl)piperazin-1-yl)-3-methyl-1-oxopentan-2-yl)carbamate To a stirred solution of (tert-butoxycarbonyl)-L-isoleucine (23.4 mg, 0.088 mmol), HATU (33.6 mg, 0.088 mmol) and DIEA (22.8 mg, 0.18 mmol) in THF (10 ml), 2-butoxy-7-((5-methyl-6-(piperazin-1-yl)pyridin-3-yl)methyl)imidazo[2,1-f][1,2,4]triazin-4-amine (35 mg, 0.088 mmol) was added. The mixture was stirred at rt for 1 h. After completing, the solution was quenched with $H_2O$ (10 ml) and then extracted with DCM (15 ml×2). The organic phase was washed with $H_2O$ (10 ml), dried and concentrated under reduced pressure to afford crude product (100 mg) as an off-white film, which was used directly for the next step without further purification. MS: M/e 610 $(M+1)^+$.

Step B: (2S,3S)-2-amino-1-(4-(5-((4-amino-2-butoxyimidazo[2,1-f][1,2,4]triazin-7-yl)methyl)-3-methylpyridin-2-yl)piperazin-1-yl)-3-methylpentan-1-one To a stirred solution of tert-butyl ((2S,3S)-1-(4-(5-((4-amino-2-butoxyimidazo[2,1-f][1,2,4]triazin-7-yl)methyl)-3-methylpyridin-2-yl)piperazin-1-yl)-3-methyl-1-oxopentan-2-yl)carbamate (100 mg, crude) in EA (10 ml), a solution of HCl in EA (4M, 5 ml) was added. The mixture was stirred at rt for 1 h. After completing, the reaction mixture was concentrated under reduced pressure. The residue was purified by prep-HPLC to afford the product (37.31 mg). $^1$H NMR (400 MHz, DMSO-d6) δ 8.24-8.01 (m, 6H), 7.64-7.51 (m, 1H), 7.42-7.33 (m, 1H), 4.41-4.30 (m, 1H), 4.21 (t, J=8 Hz, 2H), 4.09 (s, 2H), 3.85-3.53 (m, 4H), 3.15-2.96 (m, 4H), 2.24 (s, 3H), 1.87-1.75 (m, 1H), 1.73-1.62 (m, 2H), 1.52-1.35 (m, 3H), 1.22-1.07 (m, 1H), 0.97 (d, J=8 Hz, 3H), 0.92 (t, J=8 Hz, 3H), 0.87 (t, J=8 Hz, 3H) ppm. MS: M/e 510 $(M+1)^+$.

Compound B68: (S)-4-amino-2-butoxy-7-((5-methyl-6-(4-prolylpiperazin-1-yl)pyridin-3-yl)methyl)imidazo[2,1-f][1,2,4]triazine Compound B68 was synthesized starting from the corresponding starting materials according the similar procedures described as those of Compound B67. $^1$H NMR (400 MHz, DMSO-d6) δ 9.45-9.21 (m, 1H), 8.62-8.44 (m, 1H), 8.32-8.05 (m, 3H), 7.65-7.51 (m, 1H), 7.48-7.33 (m, 1H), 4.72-4.58 (m, 1H), 4.21 (t, J=8 Hz, 2H), 4.08 (s, 2H), 3.72-3.69 (m, 1H), 3.68-3.53 (m, 3H), 3.33-3.24 (m, 1H), 3.22-3.14 (m, 1H), 3.13-2.98 (m, 4H), 2.46-2.32 (m, 1H), 2.23 (s, 3H), 1.98-1.75 (m, 3H), 1.73-1.61 (m, 2H), 1.47-1.34 (m, 2H), 0.92 (t, J=8 Hz, 3H) ppm. MS: M/e 494 $(M+1)^+$.

Compound B69: (S)-2-amino-1-(4-(5-((4-amino-2-butoxyimidazo[2,1-f][1,2,4]triazin-7-yl)methyl)-3-methylpyridin-2-yl)piperazin-1-yl)-4-methylpentan-1-one Compound B69 was synthesized starting from the corresponding starting materials according the similar procedures described as those of Compound B67. $^1$H NMR (400 MHz, DMSO-d6) δ 8.22-8.03 (m, 6H), 7.61-7.49 (m, 1H), 7.43-7.32 (m, 1H), 4.49-4.37 (m, 1H), 4.21 (t, J=8 Hz, 2H), 4.08 (s, 2H), 3.84-3.74 (m, 1H), 3.69-3.59 (m, 1H), 3.58-3.46 (m, 2H), 3.20-3.12 (m, 1H), 3.11-3.03 (m, 2H), 3.01-2.95 (m, 1H), 2.23 (s, 3H), 1.78-1.55 (m, 4H), 1.52-1.35 (m, 3H), 0.98-0.87 (m, 9H) ppm. MS: M/e 510 $(M+1)^+$.

Compound B70: (S)-2-amino-1-(4-(5-((4-amino-2-butoxyimidazo[2,1-f][1,2,4]triazin-7-yl)methyl)-3-methylpyridin-2-yl)piperazin-1-yl)-3-methylbutan-1-one Compound B70 was synthesized starting from the corresponding starting materials according the similar procedures described as those of Compound B67. $^1$H NMR (400 MHz, DMSO-d6) δ 8.23-7.99 (m, 6H), 7.64-7.47 (m, 1H), 7.42-7.32 (m, 1H), 4.37-4.31 (m, 1H), 4.21 (t, J=8 Hz, 2H), 4.08 (s, 2H), 3.81-3.74 (m, 1H), 3.72-3.53 (m, 3H), 3.17-3.01 (m, 4H), 2.24 (s, 3H), 2.13-2.02 (m, 1H), 1.75-1.60 (m, 2H), 1.48-1.33 (m, 2H), 1.00 (d, J=8 Hz, 3H), 0.96-0.87 (m, 6H) ppm. MS: M/e 496 $(M+1)^+$.

Compound B71:1-(4-(5-((4-amino-2-(butylamino)imidazo[2,1-f][1,2,4]triazin-7-yl)methyl)-3-methylpyridin-2-yl)piperazin-1-yl)-2-(dimethylamino)ethan-1-one A mixture of N2-butyl-7-((5-methyl-6-(piperidin-4-yl)pyridin-3-yl)methyl)imidazo[2,1-f][1,2,4]triazine-2,4-diamine (200 mg, 0.5 mmol), dimethylglycine (62 mg, 0.6 mmol) and HATU (230 mg, 0.6 mmol), DIPEA (129 mg, 1 mmol) in THF (20 mL) was stirred overnight. The reaction mixture was poured into $H_2O$ (10 mL) and extracted with EtOAc (15 mL×3). The combined organic layers were washed with brine, dried over $Na_2SO_4$, concentrated and purified by column chromatography ($CH_2Cl_2$/MeOH=15:1~10:1, contained $NH_3$ (g)) to give crude product, which was further purified by prep-TLC ($CH_2Cl_2$/MeOH($NH_3$)=15:1) to give the target compound (100 mg, 41.5%). $^1$H NMR (400 MHz, DMSO-$d_6$) δ 8.08 (s, 1H), 7.50 (br.s, 2H), 7.47 (s, 1H), 7.15 (s, 1H), 6.24 (t, J=5.6 Hz, 1H), 3.98 (s, 2H), 3.65-3.55 (m, 4H), 3.27-3.13 (m, 4H), 3.03-2.92 (m, 4H), 2.26 (s, 6H), 2.21 (s, 3H), 1.59-1.44 (m, 2H), 1.36-1.21 (m, 2H), 0.89 (t, J=7.2 Hz, 3H) ppm. MS: M/e 481 $(M+1)^+$.

Compound B72: 2-(4-(5-((4-amino-2-butoxyimidazo[2,1-f][1,2,4]triazin-7-yl)methyl)-3-methylpyridin-2-yl)piperazin-1-yl)-N,N-dimethylacetamide A mixture of 2-butoxy-7-((5-methyl-6-(piperazin-1-yl)pyridin-3-yl)methyl)imidazo[2,1-f][1,2,4]triazin-4-amine (20 mg, 0.05 mmol) and 2-bromo-N,N-dimethylacetamide (10 mg, 0.06 mmol) and $K_2CO_3$ (14 mg, 0.1 mmol) was stirred at rt overnight, diluted with water (5 mL) and extracted with EA (5 mL×3), and dried over $N_2SO_4$, filtered and concentrated, the residue was purified by prep-HPLC to give the title product (15 mg, 63%). $^1$H NMR (400 MHz, $CD_3OD$) δ 8.16 (d, J=1.7 Hz, 1H), 7.63 (s, 1H), 7.47 (d, J=1.7 Hz, 1H), 4.39-4.26 (m, 4H), 4.19 (s, 2H), 3.68-3.37 (m, 8H), 3.00 (s, 3H), 2.99 (s, 3H), 2.29 (s, 3H), 1.87-1.68 (m, 2H), 1.59-1.41 (m, 2H), 0.98 (t, J=7.4 Hz, 3H) ppm. MS: M/e 482 $(M+1)^+$.

Compound B73: (S)-2-butoxy-7-((5-methyl-6-(2-methylpiperazin-1-yl)pyridine-3-yl)methyl)imidazo[2,1-f][1,2,4]triazin-4-amine Step A: 2,4-dichloroimidazo[2,1-f][1,2,4]triazine A mixture of imidazo[2,1-f][1,2,4]triazine-2,4(1H,3H)-dione (5.0 g, 32.9 mmol) and triethylamine hydrochloride (9.0 g, 65.7 mmol) in $POCl_3$ (50 mL) was heated in a sealed tube at 120° C. for 16 hrs. The mixture was concentrated to dryness under high vacuum and the resulting residue was diluted with 200 mL of EA, suspended and poured into 500 mL of aqueous $NaHCO_3$. The mixture was stirred at rt for 30 min. the organic layers were separated and the aqueous layer was extracted with EA (200 mL×2). The combined organics was washed with aq. $NaHCO_3$ (200 mL), brine (200 mL×3), dried over $Na_2SO_4$ and concentrated to dryness to give the title product (4.9 g, yield: 80%) as a yellow solid. MS: M/e 189 $(M+1)^+$.

Step B: 2-chloro-N,N-bis(4-methoxybenzyl)imidazo[2,1-f][1,2,4]triazin-4-amine

To a stirred solution of 2,4-dichloroimidazo[2,1-f][1,2,4]triazine (4.9 g, 25.9 mmol) in THF (30 mL), DIEA (10.0 g, 77.7 mmol) was added and followed by the solution of bis(4-methoxybenzyl)amine (7.4 g, 28.7 mmol) in THF (40 mL) at 0° C. The resulting mixture was stirred at rt for 2 hrs. The mixture was concentrated to dryness and diluted with 200 mL of EA, washed with $NaHCO_3$ (50 mL×2), brine (50 mL×2), dried, and concentrated to dryness. The resulting solid was slurried in a mixed solvent PE/EA (10:1, 200 mL) for 2 hrs. The suspension was filtered. The filter cake was dried under high vacuum to give the title product (8.7 g, yield: 82%) as a light yellow solid. MS: M/e 410 $(M+1)^+$.

Step C: 2-butoxy-N,N-bis(4-methoxybenzyl)imidazo[2,1-f][1,2,4]triazin-4-amine

A mixture of 2-chloro-N,N-bis(4-methoxybenzyl)imidazo[2,1-f][1,2,4]triazin-4-amine (8.7 g, 21.2 mmol) and a solution of sodium butanolate in n-BuOH (20%, 80 mL) was heated at 80° C. for 1 hour. The mixture was treated with 200 mL of EA and 200 mL of aq. $NaHCO_3$. The aq. layer was extracted with EA (100 mL×2). The combined organic layers were washed with brine (200 mL×3), dried over $Na_2SO_4$ and concentrated. The resulting residue was purified by column chromatography eluted with PE/EA (10:1~5:1) to give the title product (7.6 g, yield: 80%) as a light yellow solid. MS: M/e 448 $(M+1)^+$.

Step D: tert-butyl (3S)-4-(5-((4-(bis(4-methoxybenzyl)amino)-2-butoxyimidazo[2,1-f][1,2,4]triazin-7-yl)(hydroxy)methyl)-3-methylpyridin-2-yl)-3-methylpiperazine-1-carboxylate To a −78° C. solution of 2-butoxy-N,N-bis(4-methoxybenzyl)imidazo[2,1-f][1,2,4]triazin-4-amine (300 mg, 0.67 mmol) in THF (5 mL) was added n-BuLi solution (1.6 M, 0.65 mL, 1.0 mmol) in drops with a syringe under $N_2$ and the resulting mixture was stirred at −78° C. for 15 min. The solution of tert-butyl (S)-4-(5-formyl-3-methylpyridin-2-yl)-3-methylpiperazine-1-carboxylate (250 mg, 0.78 mmol) in THF (3 mL) was added with a syringe in drops at −78° C. The resulting mixture was stirred at this temperature for 1 hour and allowed warm to rt and stirred for another 1 hour. The mixture was quenched with 20 mL of aq. $NH_4Cl$ and extracted with EA (20 mL×2). The combined layers were washed with brine (20 mL×2), dried over $Na_2SO_4$ and concentrated, purified by column chromatography eluted with PE/EA (5:1~3:1) to give the title product (230 mg, crude) as a light yellow oil. MS: M/e 767 $(M+1)^+$.

Step E: (S)-2-butoxy-7-((5-methyl-6-(2-methylpiperazin-1-yl)pyridin-3-yl)methyl)imidazo[2,1-f][1,2,4]triazin-4-amine A mixture of tert-butyl (3S)-4-(5-((4-(bis(4-methoxybenzyl)amino)-2-butoxyimidazo[2,1-f][1,2,4]triazin-7-yl)(hydroxy)methyl)-3-methylpyridin-2-yl)-3-methylpiperazine-1-carboxylate (230 mg, 0.3 mmol), TFA (5 mL) and $Et_3SiH$ (3 mL) was heated at 85° C. for 16 hrs. The mixture was concentrated, and the resulting residue was treated with 10 mL of aq. $NaHCO_3$, extracted with a mixed solvent (DCM/MeOH=5:1, 10 mL×3). The combined layers were washed with brine (10 mL×2), dried over $Na_2SO_4$ and concentrated, purified by column chromatography eluted with DCM/MeOH—$NH_3$ (15:1, 5 mol/L of $NH_3$ in MeOH) to give 75 mg of crude product which was purified by prep-TLC (DCM/MeOH—$NH_3$, 10:1, 5 mol/L of $NH_3$ in MeOH) to give the title product (15 mg, yield: 5.5% for 2 steps). $^1$H NMR (400 MHz, DMSO-d6) δ 8.19-8.04 (m, 3H), 7.48 (s, 1H), 7.33 (s, 1H), 4.19 (t, J=6.4 Hz, 2H), 4.07 (s, 2H), 3.47-3.39 (m, 1H), 3.05-2.81 (m, 4H), 2.75-2.63 (m, 1H), 2.56 (dd, J=12.0, 8.0 Hz, 1H), 2.18 (s, 3H), 1.73-1.61 (m, 2H), 1.48-1.32 (m, 2H), 0.92 (t, J=7.2 Hz, 3H), 0.80 (d, J=6.4 Hz, 3H) ppm. MS: M/e 411 $(M+1)^+$.

Compound B74: (R)-2-butoxy-7-((5-methyl-6-(2-methylpiperazin-1-yl)pyridin-3-yl)methyl)imidazo[2,1-f][1,2,4]triazin-4-amine Compound B74 was synthesized starting from the corresponding starting materials according the similar procedures described as those of Compound B73. $^1$H NMR (400 MHz, DMSO-d6) δ 8.19-8.04 (m, 3H), 7.46 (s, 1H), 7.33 (s, 1H), 4.19 (t, J=6.4 Hz, 2H), 4.06 (s, 2H), 3.45-3.30 (m, 1H), 2.98-2.88 (m, 2H), 2.87-2.76 (m, 2H), 2.70-2.58 (m, 1H), 2.18 (s, 3H), 1.72-1.62 (m, 2H), 1.47-1.33 (m, 2H), 0.92 (t, J=7.6 Hz, 3H), 0.79 (d, J=6.0 Hz, 3H) ppm. MS: M/e 411 $(M+1)^+$.

Compound B75: 2-butoxy-7-((5-methyl-6-(4-(2-(methylamino)ethyl)piperazin-1-yl)pyridin-3-yl)methyl)imidazo[2,1-f][1,2,4]triazin-4-amine Step A: tert-butyl (2-(4-(5-((4-amino-2-butoxyimidazo[2,1-f][1,2,4]triazin-7-yl)methyl)-3-methylpyridin-2-yl)piperazin-1-yl)ethyl)(methyl)carbamate To a mixture of 2-butoxy-7-((5-methyl-6-(piperazin-1-yl)pyridin-3-yl)methyl)imidazo[2,1-f][1,2,4]triazin-4-amine (40 mg, 0.1 mmol), tert-butyl methyl(2-oxoethyl)carbamate (16 mg, 0.12 mmol) in DCM (4 mL) were added $NaBH(OAc)_3$ (32 mg, 0.15 mmol) and AcOH (one drop). The reaction was stirred at room temperature overnight. The reaction was diluted with water, extracted with DCM (60 mL), washed with brine, dried over $Na_2SO_4$, filtered, and concentrated. The residue was purified by prep-TLC to give the target compound (40 mg, crude). MS: M/e 554 $(M+1)^+$.

Step B: 2-butoxy-7-((5-methyl-6-(4-(2-(methylamino)ethyl)piperazin-1-yl)pyridin-3-yl)methyl)imidazo[2,1-f][1,2,4]triazin-4-amine To a mixture of the product of the step A (40 mg, crude) in DCM (5 mL), a solution of 4 M HCl in EA (0.5 mL) was added. The reaction was stirred at room temperature overnight. The mixture was concentrated and purified by prep-HPLC to give the title product (8 mg, 16% for two steps). $^1$HNMR (400 MHz, DMSO-$d_6$) δ 8.32 (s, 1H), 8.13 (s, 1H), 8.06 (s, 1H), 8.04 (s, 1H), 7.44 (s, 1H), 7.31 (s, 1H), 4.21 (t, J=6.8 Hz, 2H), 4.04 (s, 2H), 3.10-2.95 (m, 4H), 2.84 (t, J=6.0 Hz, 2H), 2.62-2.51 (m, 6H), 2.45 (s, 3H), 2.18 (s, 3H), 1.75-1.61 (m, 2H), 1.46-1.31 (m, 2H), 0.92 (t, J=7.2 Hz, 3H) ppm. MS: M/e 454 $(M+1)^+$.

Compound B76: 2-butoxy-7-((6-(4-(2-(dimethylamino)ethyl)piperazin-1-yl)-5-methylpyridin-3-yl)methyl)imidazo[2,1-f][1,2,4]triazin-4-amine Step A: 6-(4-(2-(dimethylamino)ethyl)piperazin-1-yl)-5-methylnicotinaldehyde To a solution of 6-chloro-5-methylnicotinaldehyde (0.46 g, 3 mmol) and DIEA (0.77 g, 6 mmol) in DMA (5 mL) was added N,N-dimethyl-2-(piperazin-1-yl)ethan-1-amine (0.46 g, 3 mmol). Then the mixture was stirred at 115° C. overnight under $N_2$. The mixture was cooled to room temperature, diluted with water (50 mL), extracted with EtOAc (60 mL×2), washed with brine, dried over $Na_2SO_4$, filtered, concentrated and the residue was purified by combi-flash to give the target compound (110 mg, 13%). $^1$HNMR (400 MHz, $CDCl_3$) δ 9.88 (s, 1H), 8.51 (d, J=2.0 Hz, 1H), 7.81 (d, J=2.0 Hz, 1H), 3.46 (t, J=5.2 Hz, 4H), 2.64 (t, J=4.4 Hz, 4H), 2.61-2.50 (m, 4H), 2.34 (s, 6H), 2.31 (s, 3H) ppm. MS: M/e 277 $(M+1)^+$.

Step B: (4-(bis(4-methoxybenzyl)amino)-2-butoxyimidazo[2,1-f][1,2,4]triazin-7-yl)(6-(4-(2-(dimethylamino)ethyl)piperazin-1-yl)-5-methylpyridin-3-yl)methanol To a solution of 7-bromo-2-butoxy-N,N-bis(4-methoxybenzyl)imidazo[2,1-f][1,2,4]triazin-4-amine (200 mg, 0.38 mmol) in THF (6 mL), a solution of n-BuLi (0.35 mL, 0.57 mmol) was added dropwise maintaining the temperature between −75~−65° C. After stirring 1 h, a mixture of the product of Step A (105 mg, 0.38 mmol) in THF (1 mL) was added dropwise. The resulting mixture was stirred at −70° C. for 2 h and then warmed to room temperature overnight. The reaction was quenched with saturated $NH_4Cl$ solution, extracted with EtOAc (60 mL), washed with brine, dried over $Na_2SO_4$, filtered, and concentrated to give target compound (200 mg, crude). MS: M/e 724 $(M+1)^+$.

Step C: 2-butoxy-7-((6-(4-(2-(dimethylamino)ethyl)piperazin-1-yl)-5-methylpyridin-3-yl)methyl)imidazo[2,1-f][1,2,4]triazin-4-amine To a mixture of the product of Step B (200 mg, crude) in TFA (6 mL), $Et_3SiH$ (2 mL) was added and the resulting mixture was stirred at 85° C. overnight. The mixture was cooled to room temperature and concentrated to dryness. The residue was purified by prep-HPLC to give the target compound as a FA salt (22 mg, 11% for two steps). $^1$HNMR (400 MHz, DMSO-$d_6$) δ 8.14-8.05 (m, 4H), 7.45 (s, 1H), 7.31 (s, 1H), 4.21 (t, J=6.4 Hz, 2H), 4.05 (s, 2H), 3.15-2.96 (m, 6H), 2.69 (s, 6H), 2.67-2.56 (m, 6H), 2.18 (s, 3H), 1.75-1.64 (m, 2H), 1.48-1.35 (m, 2H), 0.92 (t, J=7.6 Hz, 3H) ppm. MS: M/e 468 $(M+1)^+$.

Compound B77: 2-butoxy-7-((5-(piperidin-4-yl)pyridin-2-yl)methyl)imidazo[2,1-f][1,2,4]triazin-4-amine Compound B77 was prepared according to the general procedure used to prepare compound B15 to give the target product (15 mg). $^1$HNMR (400 MHz, DMSO-$d_6$+$D_2O$) δ 8.37 (s, 1H), 8.33 (d, J=1.6 Hz, 1H), 7.49 (d, J=1.6 Hz, 1H), 7.39 (s, 1H), 4.20 (t, J=6.4 Hz, 2H), 4.12 (s, 2H), 3.39-3.28 (m, 2H), 3.20-3.10 (m, 1H), 3.06-2.91 (m, 2H), 2.28 (s, 3H), 2.03-1.86 (m, 2H), 1.84-1.74 (m, 2H), 1.72-1.60 (m, 2H), 1.46-1.31 (m, 2H), 0.92 (t, J=7.2 Hz, 3H) ppm. MS: M/e 396 $(M+1)^+$.

Compound B78: 2-butoxy-7-((6-(4-(dimethylamino)piperidin-1-yl)-5-methylpyridin-3-yl)methyl)imidazo[2,1-f][1,2,4]triazin-4-amine Step A: 6-(4-(dimethylamino)piperidin-1-yl)-5-methylnicotinaldehyde DIPEA (1.3 g, 10 mmol) was added to a solution of methyl 6-chloro-4-methylnicotinate (778 mg, 5 mmol) and N,N-dimethylpiperidin-4-amine (1.42 g, 10 mmol) in DMA (10 mL), the reaction mixture was stirred at 120° C. for 4 hours, was cooled to room temperature. The solution was quenched with $H_2O$ (10 ml). The aqueous solution was extracted with EA (10 ml×4). The collected organic layers were washed with brine, dried over $Na_2SO_4$, filtered and concentrated. The resulting residue was purified by column chromatography to afford the product (560 mg, 47%), MS: M/e 248 $(M+1)^+$ Step B: (4-(bis(4-methoxybenzyl)amino)-2-butoxy-imidazo[2,1-f][1,2,4]triazin-7-yl)(6-(4-(dimethyl-amino)piperidin-1-yl)-5-methylpyridin-3-yl)methanol To a solution of 7-bromo-2-butoxy-N,N-bis(4-methoxy-benzyl)imidazo[2,1-f][1,2,4]triazin-4-amine (158 mg, 0.3 mmol) in THF (1 mL) was added dropwise a solution of n-BuLi (0.28 mL, 0.45 mmol) maintaining the temperature between −75~−65° C. After 10 min, a solution of product of Step A (112 mg, 0.45 mmol) in THF (1 mL) was added dropwise. The resulting mixture was stirred at −70° C. for 30 min. The reaction was quenched with saturated $NH_4Cl$ solution, extracted with EtOAc (10 mL×3), washed with brine, dried over $Na_2SO_4$, filtered, and concentrated. The residue was purified by column chromatography to give target compound (55 mg, 26%). MS: M/e 695 $(M+1)^+$.

Step C: 2-butoxy-7-((6-(4-(dimethylamino)piperidin-1-yl)-5-methylpyridin-3-yl)methyl)imidazo[2,1-f][1,2,4]triazin-4-amine To a mixture of the product of Step B (55 mg, 0.08 mmol) in TFA (5 mL) was added $Et_3SiH$ (1 mL). The reaction was heated at 80° C. for 24 hours. The mixture was concentrated and the residue was purified by prep-HPLC. The collected fraction was basified with $NaHCO_3$ solution, extracted with DCM (30 mL), washed with brine, dried over $Na_2SO_4$, filtered, and concentrated to give the title product (18 mg, 51%). $^1$H NMR (400 MHz, DMSO-d6) δ 8.13 (s, 1H), 8.05 (s, 1H), 8.04 (s, 1H), 7.42 (s, 1H), 7.30 (s, 1H), 4.20 (t, J=6.5 Hz, 2H), 4.03 (s, 2H), 3.41-3.25 (m, 3H), 2.63 (t, J=11.9 Hz, 2H), 2.19 (s, 6H), 2.17 (s, 3H), 1.80 (d, J=11.0 Hz, 2H), 1.72-1.59 (m, 2H), 1.53-1.31 (m, 4H), 0.92 (t, J=7.4 Hz, 3H) ppm. MS: M/e 439 $(M+1)^+$.

Compound B79: 7-((6-((1R,4R)-2,5-diazabicyclo[2.2.1]heptan-2-yl)-5-methylpyridin-3-yl)methyl)-2-butoxyimidazo[2,1-f][1,2,4]triazin-4-amine Compound B79 was synthesized starting from the corresponding starting materials according the similar procedures described as those of Compound B8. $^1$H NMR (400 MHz, $CD_3OD$) δ 7.90 (s, 1H), 7.33 (s, 1H), 7.21 (s, 1H), 4.26-4.11 (m, 3H), 3.99 (s, 2H), 3.74 (d, J=10.2 Hz, 1H), 3.57 (s, 1H), 3.37-3.00 (m, 3H), 2.12 (s, 3H), 2.07 (d, J=10.8 Hz, 1H), 1.84 (d, J=10.6 Hz, 1H), 1.74-1.59 (m, 2H), 1.52-1.32 (m, 2H), 0.90 (t, J=7.2 Hz, 3H) ppm. MS: M/e 409 $(M+1)^+$.

Compound B80: 2-(but-3-en-1-yloxy)-7-((5-methyl-6-(piperazin-1-yl)pyridin-3-yl)methyl)imidazo[2,1-f][1,2,4]triazin-4-amine Compound B80 was synthesized starting from the corresponding starting materials according the similar procedures described as those of Compound B8. $^1$H NMR (400 MHz, DMSO-d6) δ 8.15 (s, 1H), 8.11-8.00 (m, 2H), 7.45-7.41 (m, 1H), 7.31 (s, 1H), 5.93-5.79 (m, 1H), 5.19-5.04 (m, 2H), 4.25 (t, J=8 Hz, 2H), 4.04 (s, 2H), 2.97-2.90 (m, 4H), 2.89-2.81 (m, 4H), 2.49-2.42 (m, 2H), 2.17 (s, 3H) ppm. MS: M/e 395 $(M+1)^+$.

Compound B81: (S)-2-amino-1-(4-(5-((4-amino-2-butoxyimidazo[2,1-f][1,2,4]triazin-7-yl)methyl)-3-methylpyridin-2-yl)piperazin-1-yl)-3-phenylpropan-1-one Compound B81 was synthesized starting from the corresponding starting materials according the similar procedures described as those of Compound B67. $^1$H NMR (400 MHz, DMSO-d6) δ 8.31-8.04 (m, 6H), 7.55-7.47 (m, 1H), 7.39-7.31 (m, 3H), 7.31-7.21 (m, 3H), 4.75-4.65 (m, 1H), 4.21 (t, J=8 Hz, 2H), 4.06 (s, 2H), 3.73-3.60 (m, 1H), 3.57-3.38 (m, 2H), 3.13-2.80 (m, 7H), 2.16 (s, 3H), 1.73-1.62 (m, 2H), 1.46-1.34 (m, 2H), 0.92 (t, J=8 Hz, 3H) ppm. MS: M/e 544 $(M+1)^+$.

Compound B82: 2-butoxy-7-((5-methyl-6-(2,8-diazaspiro[4.5]decan-8-yl)pyridin-3-yl)methyl)imidazo[2,1-f][1,2,4]triazin-4-amine Compound B82 was synthesized starting from the corresponding starting materials according the similar procedures described as those of Compound B8. $^1$H NMR (400 MHz, DMSO-d6) δ 8.84 (br.s, 2H), 8.17 (s, 1H), 8.12 (s, 1H), 8.08 (s, 1H), 7.64 (d, J=14.8 Hz, 1H), 7.36 (d, J=4.8 Hz, 1H), 4.21 (t, J=6.3 Hz, 2H), 4.10 (s, 2H), 3.36-3.21 (m, 2H), 3.20-2.98 (m, 6H), 2.23 (s, 3H), 1.84 (t, J=7.2 Hz, 2H), 1.72-1.58 (m, 6H), 1.44-1.38 (m, 2H), 0.93 (t, J=7.3 Hz, 3H) ppm. MS: M/e 451 $(M+1)^+$.

Compound B83: 2-butoxy-7-((5-methyl-6-(8-azaspiro[4.5]decan-8-yl)pyridin-3-yl)methyl)imidazo[2,1-f][1,2,4]triazin-4-amine Compound B83 was synthesized starting from the corresponding starting materials according the similar procedures described as those of Compound B8. $^1$H NMR (400 MHz, DMSO-d6) δ 8.13 (s, 1H), 8.05 (s, 2H), 7.42 (s, 1H), 7.30

(s, 1H), 4.20 (t, J=6.5 Hz, 2H), 4.03 (s, 2H), 2.97-2.88 (m, 4H), 2.17 (s, 3H), 1.73-1.62 (m, 2H), 1.59-1.57 (m, 4H), 1.55-1.47 (m, 4H), 1.47-1.35 (m, 6H), 0.92 (t, J=7.4 Hz, 3H) ppm. MS: M/e 450 $(M+1)^+$.

Compound B84: N2-methyl-7-((5-methyl-6-(piperazin-1-yl)pyridin-3-yl)methyl)-N2-propylimidazo[2,1-f][1,2,4]triazine-2,4-diamine Step A: 7-bromo-N2-butyl-N4,N4-bis(4-methoxybenzyl)-N2-methyl)imidazo[2,1-f][1,2,4]triazine-2,4-diamine To a stirred solution of 7-bromo-2-chloro-N,N-bis(4-methoxybenzyl)imidazo[2,1-f][1,2,4]triazin-4-amine (300 mg, 0.62 mmol) in NMP (8 mL) was added N-methylbutan-1-amine (174 mg, 2 mmol). The reaction mixture was sealed and stirred at 200° C. for 6 h. The mixture was cooled down to rt, added $H_2O$ (20 mL) and extracted with EtOAc (10 ml×3). The combined organic phase was washed with brine, dried over $Na_2SO_4$ and concentrated in vacuo. The crude product was purified by column chromatography to give the product (250 mg, 71.4%) as white solids. MS: M/e 539 $(M+1)^+$.

Step B: tert-butyl 4-(4-((4-(bis(4-methoxybenzyl)amino)-2-(butyl(methyl)amino)imidazo[2,1-f][1,2,4]triazin-7-yl)(hydroxy)methyl)-2-methylphenyl)piperazine-1-carboxylate To a stirred solution of 7-bromo-N2-butyl-N4,N4-bis(4-methoxybenzyl)-N2-methyl)imidazo[2,1-f][1,2,4]triazine-2,4-diamine (210 mg, 0.39 mmol) in THF (10 mL), cooled to −78° C. and under a nitrogen atmosphere, n-BuLi (1.6 M in hexane, 0.9 mmol, 0.6 mL) was added dropwise. After stirring for 50 mins, a solution of tert-butyl 4-(5-formyl-3-methylpyridin-2-yl)piperazine-1-carboxylate (210 mg, 0.58 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (130 mg, 44.5%). MS: M/e 765 $(M+1)^+$.

Step C: $N^2$-butyl-$N^2$-methyl-7-((5-methyl-6-(piperazin-1-yl)pyridin-3-yl)methyl)imidazo[2,1-f][1,2,4]triazine-2,4-diamine A solution of tert-butyl 4-(4-((4-(bis(4-methoxybenzyl)amino)-2-(butyl(methyl)amino)imidazo[2,1-f][1,2,4]triazin-7-yl)(hydroxy)methyl)-2-methylphenyl)piperazine-1-carboxylate (130 mg, 0.17 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (25 mg, 35.9%). $^1H$ NMR (400 MHz, DMSO-d6) δ 8.08 (s, 1H), 7.61 (s, 2H), 7.44 (s, 1H), 7.19 (s, 1H), 3.98 (s, 2H), 3.49 (t, J=7.2 Hz, 2H), 2.99 (s, 3H), 2.99-2.81 (m, 8H), 2.17 (s, 3H), 1.56-1.45 (m, 2H), 1.3-1.24 (m, 2H), 0.90 (t, J=7.3 Hz, 3H) ppm. MS: M/e 410 $(M+1)^+$.

Compound B85: $N^2$-isopentyl-7-((5-methyl-6-(piperazin-1-yl)pyridin-3-yl)methyl)imidazo[2,1-f][1,2,4]triazine-2,4-diamine Compound B85 was synthesized starting from the corresponding starting materials according the similar procedures described as those of Compound B13. $^1H$ NMR (400 MHz, DMSO-d6) δ 8.79 (br.s, 2H), 8.12 (s, 1H), 7.93 (m, 2H), 7.51 (s, 2H), 4.05 (d, J=5.5 Hz, 2H), 3.24-3.15 (m, 6H), 2.50-2.47 (m, 4H), 2.22 (s, 3H), 1.65-1.57 (m, 1H), 1.45-1.39 (m, 2H), 0.89 (s, 3H), 0.88 (s, 3H) ppm. MS: M/e 410 $(M+1)^+$.

Compound B86: 2-butoxy-7-((5-methyl-6-(2,7-diazaspiro[3.5]nonan-7-yl)pyridin-3-yl)methyl)imidazo[2,1-f][1,2,4]triazin-4-amine Compound B86 was synthesized starting from the corresponding starting materials according the similar procedures described as those of Compound B8. $^1H$ NMR (400 MHz, DMSO-d6) δ 8.79 (br.s, 1H), 8.68 (s, 1H), 8.15 (s, 2H), 8.07 (s, 1H), 7.66-7.53 (m, 1H), 7.36 (d, J=12.8 Hz, 1H), 4.21 (t, J=6.2 Hz, 2H), 4.08 (d, J=6.6 Hz, 2H), 3.75-3.70 (m, 4H), 3.08-2.88 (m, 4H), 2.21 (d, J=5.1 Hz, 3H), 1.92-1.84 (m, 4H), 1.73-1.61 (m, 2H), 1.51-1.32 (m, 2H), 0.93 (t, J=7.2 Hz, 3H) ppm. MS: M/e 451.0 $(M+1)^+$.

Compound B87: 2-butoxy-7-((6-(3-(dimethylamino)pyrrolidin-1-yl)-5-methylpyridin-3-yl)methyl)imidazo[2,1-f][1,2,4]triazin-4-amine Compound B87 was synthesized starting from the corresponding starting materials according the similar procedures described as those of Compound B78. $^1H$ NMR (400 MHz, DMSO-d6) δ 10.32 (br.s, 1H), 8.14 (s, 2H), 7.96 (s, 1H), 7.65 (s, 1H), 7.42-7.26 (m, 1H), 4.22 (t, J=6.3 Hz, 2H), 4.07 (s, 2H), 3.95-3.71 (m, 4H), 2.86 (s, 6H), 2.36 (s, 3H), 2.35-2.28 (m, 2H), 2.23-1.14 (m, 1H), 1.77-1.62 (m, 2H), 1.43 (m, 2H), 0.93 (t, J=7.2 Hz, 3H) ppm. MS: M/e 425 $(M+1)^+$.

Compound B88: 7-((6-(4-aminopiperidin-1-yl)-5-methylpyridin-3-yl)methyl)-N2-butylimidazo[2,1-f][1,2,4]triazine-2,4-diamine Step A: tert-butyl (1-(5-((4-(bis(4-methoxybenzyl)amino)-2-(butylamino)imidazo[2,1-f][1,2,4]triazin-7-yl)(hydroxy)methyl)-3-methylpyridin-2-yl)piperidin-4-yl)carbamate To a stirred solution of 7-bromo-N2-butyl-N4,N4-bis(4-methoxybenzyl)imidazo[2,1-f][1,2,4]triazine-2,4-diamine (160 mg, 0.3 mmol) in THF (10 mL), n-BuLi (1.6 M, 0.375 mL, 0.6 mmol) was added dropwise at −78° C. After stirring for an hour under $N_2$, a solution of tert-butyl (1-(5-formyl-3-methylpyridin-2-yl)piperidin-4-yl)carbamate (144 mg, 0.45 mmol) in THF (2 mL) was added dropwise at −78° C. and the reaction was stirred for 2 hours. The reaction was quenched with aq.$NH_4Cl$, extracted with EtOAc (10 mL×3). The combined organic layers were washed with brine, dried over $Na_2SO_4$, concentrated and purified by prep-TLC (petroleum ether/EtOAc=1:1) to give the target compound (60 mg, 26.1%). MS: M/e 766 $(M+1)^+$.

Step B: 7-((6-(4-aminopiperidin-1-yl)-5-methylpyridin-3-yl)methyl)-N2-butylimidazo[2,1-f][1,2,4]triazine-2,4-diamine To a mixture of the product of Step B (60 mg, 0.078 mmol) in $Et_3SiH$/TFA (0.5 mL/3 mL) was stirred at 85° C.

overnight. The reaction mixture was concentrated to give the residue, which was purified by prep-HPLC to give the target compound (20 mg, 62.5%). $^1$H NMR (400 MHz, DMSO-$d_6$) δ 8.07 (s, 1H), 7.84 (s, 2H), 7.63 (s, 1H), 7.49 (s, 1H), 7.35-7.25 (m, 1H), 6.44 (s, 1H), 4.01 (s, 2H), 3.39 (d, J=13.2 Hz, 2H), 3.23-3.12 (m, 3H), 2.81-2.71 (m, 2H), 2.17 (s, 3H), 1.98-1.90 (m, 2H), 1.71-1.57 (m, 2H), 1.55-1.46 (m, 2H), 1.36-1.28 (m, 2H), 0.89 (t, J=7.2 Hz, 3H) ppm. MS: M/e 410 $(M+1)^+$.

Compound B89: 2-butoxy-7-((5-methyl-6-(4-(propylsulfonyl)piperazin-1-yl)pyridin-3-yl)methyl)imidazo[2,1-f][1,2,4]triazin-4-amine To a mixture of 2-butoxy-7-((5-methyl-6-(piperazin-1-yl) pyridin-3-yl)methyl)imidazo[2,1-f][1,2,4]triazin-4-amine (40 mg, 0.1 mmol) and TEA (20 mg, 0.2 mmol) in DCM (5 mL), a solution of propane-1-sulfonyl chloride (14 mg, 0.1 mmol) in DCM (0.1 mL) was added. The reaction was stirred at room temperature overnight. The reaction was diluted with water, extracted with DCM (50 mL), washed with brine, dried over $Na_2SO_4$, filtered, and concentrated. The residue was purified by prep-TLC (DCM:MeOH=10:1) to give the target compound (22 mg, 44%). $^1$HNMR (400 MHz, DMSO-$d_6$) δ 8.14 (s, 1H), 8.10 (d, J=2.0 Hz, 1H), 8.07 (s, 1H), 7.50 (s, 1H), 7.33 (s, 1H), 4.21 (t, J=6.8 Hz, 2H), 4.07 (s, 2H), 3.32-3.24 (m, 4H), 3.14-3.02 (m, 6H), 2.21 (s, 3H), 1.80-1.61 (m, 4H), 1.46-1.34 (m, 2H), 0.99 (t, J=7.6 Hz, 3H), 0.92 (t, J=7.6 Hz, 3H) ppm. MS: M/e 503 $(M+1)^+$.

Compound B90: 2-butoxy-7-(3-isopropyl-4-(piperazin-1-yl)benzyl)imidazo[2,1-f][1,2,4]triazin-4-amine Step A: tert-butyl 4-(4-((4-(bis(4-methoxybenzyl) amino)-2-butoxyimidazo[2,1-f][1,2,4]triazin-7-yl) (hydroxy)methyl)-2-(prop-1-en-2-yl)phenyl)piperazine-1-carboxylate To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.4278 mmol) was added dropwise at −78° C. and stirred for 1 h. Then a solution of tert-butyl 4-(4-formyl-2-(prop-1-en-2-yl) phenyl)piperazine-1-carboxylate (141 mg, 0.43 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (85 mg, 38.31%) as yellow oil. MS: M/e 778 $(M+1)^+$.

Step B: tert-butyl 4-(4-((4-(bis(4-methoxybenzyl) amino)-2-butoxyimidazo[2,1-f][1,2,4]triazin-7-yl) (hydroxy)methyl)-2-isopropylphenyl)piperazine-1-carboxylate To a solution of tert-butyl 4-(4-((4-(bis(4-methoxybenzyl) amino)-2-butoxyimidazo[2,1-f][1,2,4]triazin-7-yl)(hydroxy)methyl)-2-(prop-1-en-2-yl)phenyl)piperazine-1-carboxylate (85 mg, 0.11 mmol) in THF (5 mL), Pd/C (10%, 50 mg) was added and stirred under $H_2$ (1 atm) atmosphere at rt overnight. The mixture was filtered to give filtrate, concentrated and purified by column chromatography (DCM/MeOH=20:1~5:1) to give the title product (79 mg, 92.70%) as yellow oil. MS: M/e 780 $(M+1)^+$.

Step C: 2-butoxy-7-(3-isopropyl-4-(piperazin-1-yl) benzyl)imidazo[2,1-f][1,2,4]triazin-4-amine A mixture of tert-butyl 4-(4-((4-(bis(4-methoxybenzyl) amino)-2-butoxyimidazo[2,1-f][1,2,4]triazin-7-yl)(hydroxy)methyl)-2-isopropylphenyl)piperazine-1-carboxylate (79 mg, 0.10 mmol) and triethylsilane (1 mL) in TFA (2 mL) was stirred at 90° C. overnight. The mixture was concentrated and purified with prep-HPLC to give the title product. $^1$H NMR (400 MHz, DMSO-d6) δ 8.75 (s, 2H), 8.13 (s, 1H), 8.10 (s, 1H), 7.35 (d, J=4.0 Hz, 1H), 7.31 (s, 1H), 7.09 (d, J=8.0 Hz, 1H), 7.03 (d, J=8.0 Hz, 1H), 4.23 (t, J=6.0 Hz, 2H), 4.09 (s, 2H), 3.43-3.32 (m, 1H), 3.23-3.18 (m, 4H), 3.03-2.82 (m, 4H), 1.73-1.64 (m, 2H), 1.43-1.34 (m, 2H), 1.14 (d, J=6.3 Hz, 6H), 0.93 (t, J=7.0 Hz, 3H) ppm. MS: M/e 424 $(M+1)^+$.

Compound B91: 7-((6-(4-(2-aminoethyl)piperazin-1-yl)-5-methylpyridin-3-yl)methyl)-2-butoxyimidazo[2,1-f][1,2,4]triazin-4-amine Step A: tert-butyl (2-(4-(5-((4-amino-2-butoxyimidazo[2,1-f][1,2,4]triazin-7-yl)methyl)-3-methylpyridin-2-yl)piperazin-1-yl)ethyl)carbamate To a mixture of 2-butoxy-7-((5-methyl-6-(piperazin-1-yl) pyridin-3-yl)methyl)imidazo[2,1-f][1,2,4]triazin-4-amine (40 mg, 0.1 mmol), tert-butyl (2-oxoethyl)carbamate (19 mg, 0.12 mmol) in DCM (4 mL) were added $NaBH(OAc)_3$ (32 mg, 0.15 mmol) and one drop of AcOH. The reaction was stirred at room temperature overnight. The reaction was diluted with water, extracted with DCM (30 mL), washed with brine, dried over $Na_2SO_4$, filtered, and concentrated. The residue was purified by prep-TLC to give the target compound (25 mg, crude). MS: M/e 540 $(M+1)^+$.

Step B: 7-((6-(4-(2-aminoethyl)piperazin-1-yl)-5-methylpyridin-3-yl)methyl)-2-butoxyimidazo[2,1-f][1,2,4]triazin-4-amine To a mixture of the product of the step A (25 mg, crude) in DCM (5 mL), a solution of 4 M HCl in EA (0.5 mL) was added. The reaction was stirred at room temperature overnight. The mixture was concentrated and purified by prep-HPLC to give the title product (6 mg, 10% for two steps). $^1$HNMR (400 MHz, DMSO-$d_6$) δ 8.15 (s, 1H), 8.12 (s, 1H), 8.09 (s, 1H), 7.99 (br.s, 2H), 7.53 (s, 1H), 7.34 (s, 1H), 4.21 (t, J=6.4 Hz, 2H), 4.08 (s, 2H), 3.62-2.95 (m, 12H), 2.22 (s, 3H), 1.75-1.61 (m, 2H), 1.46-1.32 (m, 2H), 0.93 (t, J=7.6 Hz, 3H) ppm. MS: M/e 440 $(M+1)^+$.

Compound B92: 2-butoxy-7-(3-ethyl-4-(piperazin-1-yl)benzyl)imidazo[2,1-f][1,2,4]triazin-4-amine Compound B92 was synthesized starting from the corresponding starting materials according the similar procedures described as those of Compound B90. $^1$H NMR (400 MHz, DMSO-d6) δ 8.71 (br.s, 2H), 8.13 (s, 1H), 8.07 (s, 1H), 7.33 (d, J=3.6 Hz, 1H), 7.24 (s, 1H), 7.11 (d, J=8.1 Hz, 1H), 7.01 (d, J=8.1 Hz, 1H), 4.22 (t, J=6.4 Hz, 2H), 4.08 (s, 2H), 3.25-3.18 (m, 4H), 3.05-2.86 (m, 4H), 2.66-2.57 (m, 2H), 1.75-1.64 (m, 2H), 1.46-1.35 (m, 2H), 1.16 (t, J=7.4 Hz, 3H), 0.93 (t, J=7.3 Hz, 3H). MS: M/e 410 $(M+1)^+$.

Compound B93: 7-((5-methyl-6-(piperazin-1-yl)pyridin-3-yl)methyl)-2-propoxyimidazo[2,1-f][1,2,4]triazin-4-amine Compound B93 was synthesized starting from the corresponding starting materials according the similar procedures described as those of Compound B8. $^1$H NMR (400 MHz, DMSO-d6) δ 8.13 (s, 1H), 8.06 (s, 2H), 7.43 (s, 1H), 7.30 (s, 1H), 4.16 (d, J=8.0 Hz, 2H), 4.03 (s, 2H), 2.87-2.77 (m, 8H), 2.17 (s, 3H), 1.71-1.68 (m, 2H), 0.96 (t, J=8.0 Hz, 3H) ppm. MS: M/e 383 $(M+1)^+$.

Compound B94: 1-(4-(5-((4-amino-2-(pentan-2-yloxy)imidazo[2,1-f] [1,2,4]triazin-7-yl)methyl)-3-methylpyridin-2-yl)piperazin-1-yl)-2-(dimethylamino)ethan-1-one A solution of 7-((5-methyl-6-(piperazin-1-yl)pyridin-3-yl)methyl)-2-(pentan-2-yloxy)imidazo[2,1-f][1,2,4]triazin-4-amine (53 mg, 0.1 mmol), dimethylglycine (13 mg, 0.12 mmol), HATU (57 mg, 0.15 mmol) and DIEA (26 mg, 0.2 mmol) in THF (5 mL, with 1 mL of DMF) was stirred at rt for 2 hrs. The reaction mixture was quenched with water (5 mL), extracted with ethyl acetate (10 mL) and washed with brine (10 mL). The organic layer was dried with $Na_2SO_4$, filtered and concentrated to get the crude product, which was further purified by prep-HPLC to get the pure product (15 mg, 24%). $^1$H NMR (400 MHz, DMSO-d6) δ 9.51 (br.s, 1H), 8.14 (s, 2H), 8.09 (s, 1H), 7.55 (s, 1H), 7.41 (s, 1H), 4.99-4.95 (m, 1H), 4.30 (d, J=4.0 Hz, 2H), 4.09 (s, 2H), 3.72-3.65 (m, 2H), 3.49-3.41 (m, 2H), 3.12-3.06 (m, 4H), 2.82 (s, 3H), 2.82 (s, 3H), 2.24 (s, 3H), 1.63-1.52 (m, 2H), 1.41-1.31 (m, 2H), 1.24 (d, J=4.0 Hz, 3H), 0.88 (t, J=8.0 Hz, 3H) ppm. MS: M/e 496 $(M+1)^+$.

Compound B95: 1-(5-((4-amino-2-butoxyimidazo[2,1-f][1,2,4]triazin-7-yl)methyl)-3-methylpyridin-2-yl)-N,N-dimethylpiperidine-4-carboxamide Step A: tert-butyl 4-(dimethylcarbamoyl)piperidine-1-carboxylate To a mixture of 1-(tert-butoxycarbonyl)piperidine-4-carboxylic acid (830 mg, 3.6 mmol), dimethylamine hydrochloride (350 mg, 4.3 mmol) and DIEA (2.0 g, 15.5 mmol) in DMF (10 mL) was added HATU (1.6 g, 4.3 mmol) at rt and the mixture was stirred at rt for 16 hrs. The mixture was diluted with 30 mL of EA, washed with brine (20 mL×3), dried over $Na_2SO_4$, concentrated to give the title product (1.5 g, crude) as a light yellow oil. MS: M/e 257 $(M+1)^+$.

Step B: N,N-dimethylpiperidine-4-carboxamide hydrochloride

A suspension of tert-butyl 4-(dimethylcarbamoyl)piperidine-1-carboxylate (1.5 g, 5.85 mmol) in HCl/EA (4M, 20 mL) was stirred at rt for 3 days. The resulting suspension was filtered, and the filter cake was washed with EA (10 mL), dried under high vacuum to give the title product (380 mg, yield: 56% for 2 steps) as a white solid. MS: M/e 157 $(M+1)^+$.

Step C: 1-(5-formyl-3-methylpyridin-2-yl)-N,N-dimethylpiperidine-4-carboxamide

A mixture of 6-chloro-5-methylnicotinaldehyde (310 mg, 2 mmol), N,N-dimethylpiperidine-4-carboxamide hydrochloride (380 mg, 2 mmol) and DIEA (1.2 g, 9.3 mmol) in DMA (5 mL) was heated at 120° C. for 5 hrs. The mixture was diluted with 20 mL of aq. $NaHCO_3$, extracted with EA (20 mL×3). The combined organics was washed with brine (20 mL×3), dried, concentrated, and purified by column chromatography eluted with PE/EA/DCM (2:2:0~2:2:1) to give the title product (350 mg, yield: 64%) as brown oil. MS: M/e 276 $(M+1)^+$.

Step D: 1-(5-((4-(bis(4-methoxybenzyl)amino)-2-butoxyimidazo[2,1-f][1,2,4]triazin-7-yl)(hydroxy)methyl)-3-methylpyridin-2-yl)-N,N-dimethylpiperidine-4-carboxamide To a −78° C. solution of 2-butoxy-N,N-bis(4-methoxybenzyl)imidazo[2,1-f][1,2,4]triazin-4-amine (350 mg, 0.78 mmol) in THF (3 mL), n-BuLi solution (1.6 M, 0.6 mL, 0.96 mmol) was added dropwise with a syringe under $N_2$ and the resulting mixture was stirred at −78° C. for 15 min. A solution of 1-(5-formyl-3-methylpyridin-2-yl)-N,N-dimethylpiperidine-4-carboxamide (300 mg, 1.1 mmol) in THF (2 mL) was added with a syringe in drops at −78° C. The resulting mixture was stirred at this temperature for 0.5 hour and allowed warm to rt and stirred for 16 hrs. The mixture was quenched with 10 mL of aq. $NH_4Cl$ and extracted with EA (10 mL×3). The combined extracts was washed with brine (10 mL×3), dried over $Na_2SO_4$ and concentrated, purified by column chromatography eluted with DCM/MeOH(NH3) (50:1~30:1, 2 M of $NH_3$ in MeOH) to give the title product (290 mg, yield: 51%) as a light yellow solid. MS: M/e 723 $(M+1)^+$.

Step E: 1-(5-((4-amino-2-butoxyimidazo[2,1-f][1,2,4]triazin-7-yl)methyl)-3-methylpyridin-2-yl)-N,N-dimethylpiperidine-4-carboxamide A mixture of 1-(5-((4-(bis(4-methoxybenzyl)amino)-2-butoxyimidazo[2,1-f][1,2,4]triazin-7-yl)(hydroxy)methyl)-3-methylpyridin-2-yl)-N,N-dimethylpiperidine-4-carboxamide (290 mg, 0.4 mmol), TFA (10 mL) and $Et_3SiH$ (5 mL) was heated at 85° C. for 16 hrs. The mixture was concentrated, and the resulting residue was treated with 10 mL of aq. $NaHCO_3$, extracted with a mixed solvent (DCM/MeOH=5:1, 10 mL×2). The combined extracts was washed with brine (10 mL×2), dried over $Na_2SO_4$ and concentrated, purified by column chromatography eluted with DCM/MeOH—$NH_3$ (20:1, 2 mol/L of $NH_3$ in MeOH) to give 185 mg of crude product which was purified by prep-TLC (DCM/MeOH—$NH_3$, 15:1, 2 mol/L of $NH_3$ in MeOH) to give the title product (95 mg, yield: 51%). $^1$H NMR (400 MHz, DMSO-d6) δ 8.14 (s, 1H), 8.06 (s, 2H), 7.48 (s, 1H), 7.32 (s, 1H), 4.21 (t, J=6.4 Hz, 2H), 4.05 (s, 2H), 3.37 (d, J=12.4 Hz, 2H), 3.04 (s, 3H), 2.82 (s, 3H), 2.80-2.69 (m, 3H), 2.19 (s, 3H), 1.75-1.61 (m, 6H), 1.49-1.34 (m, 2H), 0.93 (t, J=7.6 Hz, 3H) ppm. MS: M/e 467 $(M+1)^+$.

Compound B96: N2-butyl-7-((6-(4-((dimethylamino)methyl)piperidin-1-yl)-5-methylpyridin-3-yl)methyl)imidazo[2,1-f][1,2,4]triazine-2,4-diamine Step A: (4-(bis(4-methoxybenzyl)amino)-2-(butylamino)imidazo[2,1-f][1,2,4]triazin-7-yl)(6-(4-((dimethylamino)methyl)piperidin-1-yl)-5-methylpyridin-3-yl)methanol To a stirred solution of 7-bromo-N2-butyl-N4,N4-bis(4-methoxybenzyl)imidazo[2,1-f][1,2,4]triazine-2,4-diamine (160 mg, 0.3 mmol) in THF (10 mL), n-BuLi (1.6 M, 0.375 mL, 0.6 mmol) was added dropwise at −78° C. After stirred for an hour under $N_2$, a solution of 6-(4-((dimethylamino)methyl)piperidin-1-yl)-5-methylnicotinaldehyde (120 mg, 0.45 mmol) in THF (2 mL) was added dropwise at −78° C. and the reaction was stirred for 2 hours. The reaction was quenched with aq.$NH_4Cl$, extracted with EtOAc (10 mL×3). The combined organic layers were washed with brine, dried over $Na_2SO_4$, concentrated and purified by prep-TLC ($CH_2Cl_2$/MeOH=10:1) to give the target compound (80 mg, 37.7%) as colorless oil. MS: M/e 708 $(M+1)^+$.

Step B: N2-butyl-7-((6-(4-((dimethylamino)methyl)piperidin-1-yl)-5-methylpyridin-3-yl)methyl)imidazo[2,1-f][1,2,4]triazine-2,4-diamine A mixture of the product of Step B (80 mg, 0.113 mmol) in $Et_3SiH$/TFA (0.5 mL/3 mL) was stirred at 85° C. overnight. The reaction mixture was concentrated to give the residue, which was purified by prep-HPLC to give the target compound (10 mg, 19.6%). $^1$H NMR (400 MHz, DMSO-$d_6$) δ 9.14 (br.s, 1H), 8.06 (s, 1H), 7.70 (s, 2H), 7.54 (s, 1H), 7.33 (s, 1H), 6.48 (s, 1H), 4.02 (s, 2H), 3.42-3.34 (m, 2H), 3.17 (t, J=6.4 Hz, 2H), 3.02 (t, J=6.4 Hz, 2H), 2.81 (s, 3H), 2.80 (s, 3H), 2.75-2.65 (m, 2H), 2.19 (s, 3H), 1.98-1.88 (m, 1H), 1.82-1.74 (m, 2H), 1.57-1.45 (m, 2H), 1.36-1.24 (m, 4H), 0.89 (t, J=7.2 Hz, 3H) ppm. MS: M/e 452 $(M+1)^+$.

Compound B97: (R)-2-butoxy-7-((5-methyl-6-(3-methylpiperazin-1-yl)pyridin-3-yl)methyl)imidazo[2,1-f][1,2,4]triazin-4-amine Compound B97 was synthesized starting from the corresponding starting materials according the similar procedures described as those of Compound B8. $^1$H NMR (400 MHz, DMSO-d6) δ8.13 (br.s, 1H), 8.10-7.99 (m, 2H), 7.43 (s, 1H), 7.35-7.23 (m, 1H), 4.21 (t, J=6.0 Hz, 2H), 4.04 (s, 2H), 3.19 (d, J=12.0 Hz, 2H), 3.03-2.79 (m, 3H), 2.75-2.63 (m, 1H), 2.46-2.36 (m, 1H), 2.18 (s, 3H), 1.76-1.61 (m, 2H), 1.46-1.34 (m, 2H), 1.11-0.99 (m, 3H), 0.92 (t, J=7.2 Hz, 3H) ppm. MS: M/e 411 $(M+1)^+$.

Compound B98: (R)-2-butoxy-7-(3-methyl-4-(3-methylpiperazin-1-yl)benzyl)imidazo[2,1-f][1,2,4]triazin-4-amine Compound B98 was synthesized starting from the corresponding starting materials according the similar procedures described as those of Compound B16. $^1$H NMR (400 MHz, DMSO-d6) δ 8.20-7.97 (m, 2H), 7.28 (s, 1H), 7.12 (s, 1H), 7.07 (d, J=8.0 Hz, 1H), 6.90 (d, J=8.0 Hz, 1H), 4.22 (t, J=6.4 Hz, 2H), 4.03 (s, 2H), 3.06-2.81 (m, 5H), 2.67-2.55 (m, 1H), 2.31 (t, J=10.4 Hz, 1H), 2.19 (s, 3H), 1.77-1.60 (m, 2H), 1.51-1.33 (m, 2H), 1.04 (d, J=6.0 Hz, 3H), 0.93 (t, J=7.2 Hz, 3H) ppm. MS: M/e 410 $(M+1)^+$.

Compound B99: 2-butoxy-7-(4-(piperazin-1-yl)-3-propoxybenzyl)imidazo[2,1-f][1,2,4]triazin-4-amine Compound B99 was synthesized starting from the corresponding starting materials according the similar procedures described as those of Compound B16. $^1$H NMR (400 MHz, DMSO-d6) δ8.20-7.95 (m, 2H), 7.28 (s, 1H), 6.94 (s, 1H), 6.85-6.73 (m, 2H), 4.22 (t, J=6.4 Hz, 2H), 4.05 (s, 2H), 3.88 (t, J=6.4 Hz, 2H), 3.01 (s, 8H), 1.78-1.58 (m, 4H), 1.51-1.33 (m, 2H), 0.99 (t, J=7.2 Hz, 3H), 0.93 (t, J=7.2 Hz, 3H) ppm. MS: M/e 440 $(M+1)^+$.

Compound B100: 2-((2,5,8,11-tetraoxatridecan-13-yl)oxy)-7-((5-methyl-6-(piperazin-1-yl)pyridin-3-yl)methyl)imidazo[2,1-f][1,2,4]triazin-4-amine Compound B100 was synthesized starting from the corresponding starting materials according the similar procedures described as those of Compound B8. $^1$H NMR (400 MHz, $CD_3OD$) δ 8.16 (s, 1H), 7.64 (s, 1H), 7.47 (s, 1H), 4.43 (t, J=4 Hz, 2H), 4.20 (s, 2H), 3.82 (t, J=4 Hz, 2H), 3.69-3.66 (m, 2H), 3.65-3.57 (m, 8H), 3.52-3.48 (m, 2H), 3.39-3.36 (m, 8H), 3.32 (s, 3H), 2.30 (s, 3H) ppm. MS: M/e 531 $(M+1)^+$.

Compound B101: 2-butoxy-7-((5-methyl-6-(2,8-diazaspiro[4.5]decan-2-yl)pyridin-3-yl)methyl)imidazo[2,1-f][1,2,4]triazin-4-amine Compound B101 was synthesized starting from the corresponding starting materials according the similar procedures described as those of Compound B8. $^1$H NMR (400 MHz, DMSO-d6) δ 8.58 (br.s, 2H), 8.19 (s, 1H), 8.12 (s, 1H), 7.83 (s, 1H), 7.77 (s, 1H), 7.35 (d, J=3.8 Hz, 1H), 4.22 (t, J=6.3 Hz, 2H), 4.08 (s, 2H), 3.79 (s, 2H), 3.62 (s, 2H), 3.11 (s, 4H), 2.48 (s, 3H), 1.92 (t, J=6.3 Hz, 2H), 1.83-1.62 (m, 6H), 1.42-1.33 (m, 2H), 0.93 (t, J=7.3 Hz, 3H) ppm. MS: M/e 451 $(M+1)^+$.

Compound B102: 2-butoxy-7-((5-methyl-6-(2,7-diazaspiro[3.5]nonan-2-yl)pyridin-3-yl)methyl)imidazo[2,1-f][1,2,4]triazin-4-amine Compound B102 was synthesized starting from the corresponding starting materials according the similar procedures described as those of Compound B8. $^1$H NMR (400 MHz, DMSO-d6) δ 8.63 (br.s, 1H), 8.49 (s, 1H), 8.18 (s, 1H), 8.14 (s, 1H), 7.85 (s, 1H), 7.69 (s, 1H), 7.42-7.33 (m, 1H), 4.25-4.17 (m, 6H), 4.06 (s, 2H), 3.17-2.98 (m, 4H), 2.31 (s, 3H), 2.03-1.85 (m, 4H), 1.76-1.62 (m, 2H), 1.45-1.36 (m, 2H), 0.94 (t, J=7.3 Hz, 3H) ppm. MS: M/e 437 $(M+1)^+$.

Compound B103: 2-butoxy-7-((6-(4-methoxypiperidin-1-yl)-5-methylpyridin-3-yl)methyl)imidazo[2,1-f][1,2,4]triazin-4-amine Compound B103 was synthesized starting from the corresponding starting materials according the similar procedures described as those of Compound B8. $^1$H NMR (400 MHz, DMSO-d6) δ 8.17 (br.s, 2H), 8.06 (s, 1H), 7.82 (s, 1H), 7.44-7.30 (m, 1H), 4.21 (t, J=6.4 Hz, 2H), 4.13 (s, 2H), 3.40 (s, 3H), 3.28 (s, 3H), 3.03 (s, 2H), 2.26 (s, 3H), 2.04-1.88 (m, 2H), 1.74-1.63 (m, 2H), 1.61-1.52 (m, 2H), 1.46-1.36 (m, 2H), 0.93 (t, J=7.4 Hz, 3H) ppm. MS: M/e 426 $(M+1)^+$.

Compound B104: 2-butoxy-7-((6-(4-(methoxymethyl)piperidin-1-yl)-5-methylpyridin-3-yl)methyl)imidazo[2,1-f][1,2,4]triazin-4-amine Compound B104 was synthesized starting from the corresponding starting materials according the similar procedures described as those of Compound B8. $^1$H NMR (400 MHz, DMSO-d6) δ 8.25-8.10 (m, 2H), 8.07 (s, 1H), 7.94-7.77 (m, 1H), 7.47-7.32 (m, 1H), 4.21 (t, J=6.5 Hz, 2H), 4.14 (s, 2H), 3.56 (d, J=11.9 Hz, 2H), 3.25 (s, 3H), 3.24 (d, J=6.3 Hz, 2H), 2.98-2.87 (m, 2H), 2.27 (s, 3H), 1.77 (d, J=10.5 Hz, 3H), 1.73-1.62 (m, 2H), 1.49-1.24 (m, 4H), 0.93 (t, J=7.4 Hz, 3H) ppm. MS: M/e 440 $(M+1)^+$.

Compound B105: 2-butoxy-7-((6-(3-((dimethylamino)methyl)pyrrolidin-1-yl)-5-methylpyridin-3-yl)methyl)imidazo[2,1-f][1,2,4]triazin-4-amine Compound B105 was synthesized starting from the corresponding starting materials according the similar procedures described as those of Compound B8. $^1$HNMR (400 MHz, DMSO-$d_6$) δ 9.65 (br.s, 1H), 8.18 (s, 1H), 8.11 (s, 1H), 7.86 (s, 1H), 7.74 (s, 1H), 7.34 (d, J=2.0 Hz, 1H), 4.22 (t, J=6.8 Hz, 2H), 4.07 (s, 2H), 3.96-3.80 (m, 1H), 3.75-3.59 (m, 2H), 3.56-3.42 (m, 1H), 3.21 (t, J=5.2 Hz, 2H), 2.83 (s, 3H), 2.81 (s, 3H), 2.74-2.61 (m, 1H), 2.43 (s, 3H), 2.25-2.10 (m, 1H), 1.85-1.60 (m, 3H), 1.50-1.35 (m, 2H), 0.94 (t, J=7.6 Hz, 3H) ppm. MS: M/e 439 $(M+1)^+$.

Compound B106: 2-butoxy-7-((5-methyl-6-(4-((methylamino)methyl)piperidin-1-yl)pyridine-3-yl)methyl)imidazo[2,1-f][1,2,4]triazin-4-amine Step A: tert-butyl ((1-(5-((4-(bis(4-methoxybenzyl)amino)-2-butoxyimidazo[2,1-f][1,2,4]triazin-7-yl)(hydroxy)methyl)-3-methylpyridin-2-yl)piperidin-4-yl)methyl)(methyl)carbamate To a stirred solution of 7-bromo-N2-butyl-N4,N4-bis(4-methoxybenzyl)imidazo[2,1-f][1,2,4]triazine-2,4-diamine (150 mg, 0.286 mmol) in THF (10 mL), dropwise n-BuLi (1.6 M, 0.375 mL, 0.6 mmol) was added at −78° C. After stirring for an hour under $N_2$, a solution of tert-butyl((1-(5-formyl-3-methylpyridin-2-yl)piperidin-4-yl)methyl)(methyl)carbamate (165 mg, 0.475 mmol) in THF (2 mL) was added dropwise at −78° C. and the reaction was stirred overnight. The reaction was quenched with aq.$NH_4Cl$, extracted with EtOAc (10 mL×3). The combined organic layers were washed with brine, dried over $Na_2SO_4$, concentrated and purified by combi-flash (petroleum ether/EtOAc=2:1~1:1) to give the target compound (170 mg, 74.8%) as colorless oil. MS: M/e 795 $(M+1)^+$.

Step B: 2-butoxy-7-((5-methyl-6-(4-((methylamino)methyl)piperidin-1-yl)pyridin-3-yl)methyl)imidazo[2,1-f][1,2,4]triazin-4-amine A mixture of the product of Step B (170 mg, 0.214 mmol) in $Et_3SiH$/TFA (0.5 mL/3 mL) was stirred at 85° C. overnight. The reaction mixture was concentrated to give the residue, which was purified by prep-HPLC to give the target compound (10 mg, 19.6%). $^1$H NMR (400 MHz, DMSO-$d_6$) δ 8.44 (br.s, 2H), 8.13 (br.s, 2H), 8.09 (s, 1H), 7.69 (s, 1H), 7.38-7.32 (m, 1H), 4.21 (t, J=6.4 Hz, 2H), 4.10 (s, 2H), 3.46 (s, 2H), 2.89-2.70 (m, 4H), 2.59 (t, J=5.2 Hz, 3H), 2.23 (s, 3H), 1.80 (d, J=11.6 Hz, 3H), 1.74-1.60 (m, 2H), 1.51-1.27 (m, 4H), 0.93 (t, J=7.2 Hz, 3H) ppm. MS: M/e 439 $(M+1)^+$.

Compound B107: 2-butoxy-7-((6-(4-(2-methoxyethyl)piperazin-1-yl)-5-methylpyridin-3-yl)methyl)imidazo[2,1-f][1,2,4]triazin-4-amine Compound B107 was synthesized starting from the corresponding starting materials according the similar procedures described as those of Compound B8. $^1$H NMR (400 MHz, DMSO-d6) δ 9.63 (br.s, 1H), 8.19-8.04 (m, 3H), 7.52 (s, 1H), 7.34 (s, 1H), 4.21 (t, J=6.5 Hz, 2H), 4.08 (s, 2H), 3.72-3.66 (m, 2H), 3.57-3.42 (m, 4H), 3.38 (s, 2H), 3.33 (s, 3H), 3.25-3.11 (m, 4H), 2.21 (s, 3H), 1.73-1.63 (m, 2H), 1.47-1.34 (m, 2H), 0.93 (t, J=7.4 Hz, 3H) ppm. MS: M/e 455 $(M+1)^+$.

Compound B108: 2-butoxy-7-((5-methyl-6-(4-morpholinopiperidin-1-yl)pyridine-3-yl)methyl)imidazo[2,1-f][1,2,4]triazin-4-amine Compound B108 was synthesized starting from the corresponding starting materials according the similar procedures described as those of Compound B8. $^1$H NMR (400 MHz, DMSO-$d_6$) δ 9.69 (br.s, 1H), 8.17 (s, 1H), 8.11 (s, 1H), 8.09 (s, 1H), 7.54 (s, 1H), 7.35 (s, 1H), 4.21 (t, J=6.5 Hz, 2H), 4.08 (s, 2H), 4.02 (d, J=12.1 Hz, 2H), 3.67 (t, J=11.6 Hz, 2H), 3.61-3.44 (m, 4H), 3.42-3.34 (m, 1H), 3.18-3.06 (m, 2H), 2.75 (t, J=12.4 Hz, 2H), 2.21 (s, 3H), 2.13 (d, J=10.4 Hz, 2H), 1.82-1.63 (m, 4H), 1.49-1.35 (m, 2H), 0.93 (t, J=7.2 Hz, 3H) ppm. MS: M/e 481 $(M+1)^+$.

Compound B109: 2-butoxy-7-((5-methyl-6-(4-(morpholinomethyl)piperidin-1-yl)pyridin-3-yl)methyl)imidazo[2,1-f][1,2,4]triazin-4-amine Compound B109 was synthesized starting from the corresponding starting materials according the similar procedures described as those of Compound B8. $^1$HNMR (400 MHz, DMSO-$d_6$) δ 9.48 (br.s, 1H), 8.17 (s, 1H), 8.11 (s, 1H), 8.08 (s, 1H), 7.62 (s, 1H), 7.35 (s, 1H), 4.21 (t, J=6.8 Hz, 2H), 4.09 (s, 2H), 4.02-3.92 (m, 2H), 3.72 (t, J=11.6 Hz, 2H), 3.46 (t, J=12.8 Hz, 4H), 3.15-3.00 (m, 4H), 2.79 (t, J=11.6 Hz, 2H), 2.21 (s, 3H), 2.06-1.94 (m, 1H), 1.90-1.76 (m, 2H), 1.71-1.60 (m, 2H), 1.51-1.24 (m, 4H), 0.93 (t, J=7.6 Hz, 3H) ppm. MS: M/e 495 $(M+1)^+$.

Compound B110: 2-butoxy-7-((6-(4-(2-(dimethylamino)ethyl)piperidin-1-yl)-5-methylpyridin-3-yl)methyl)imidazo[2,1-f][1,2,4]triazin-4-amine Step A: 6-(4-(2-(dimethylamino)ethyl)piperidin-1-yl)-5-methylnicotinaldehyde To a solution of 6-chloro-5-methylnicotinaldehyde (155 mg, 1 mmol) and DIEA (260 mg, 2 mmol) in DMA (5 mL), N,N-dimethyl-2-(piperidin-4-yl)ethan-1-amine (170 mg, 1.1 mmol) was added. Then the mixture was stirred at 115° C. overnight under $N_2$. The mixture was cooled to room temperature, diluted with water (50 mL), extracted with EtOAc (40 mL×2), washed with brine, dried over $Na_2SO_4$, filtered, concentrated and the residue was purified by prep-TLC to give the target compound (50 mg, 18%). MS: M/e 276 $(M+1)^+$.

Step B: (4-(bis(4-methoxybenzyl)amino)-2-butoxyimidazo[2,1-f][1,2,4]triazin-7-yl)(6-(4-(2-(dimethylamino)ethyl)piperidin-1-yl)-5-methylpyridin-3-yl)methanol To a solution of 7-bromo-2-butoxy-N,N-bis(4-methoxybenzyl)imidazo[2,1-f][1,2,4]triazin-4-amine (85 mg, 0.16 mmol) in THF (5 mL), a solution of n-BuLi (0.15 mL, 0.24 mmol) was added dropwise maintaining the temperature between −75~−65° C. After 1 h, a suspension of the product of Step A (50 mg, 0.182 mmol) in THF (2 mL) was added dropwise. The resulting mixture was stirred at −70° C. for 2 h and then warmed to room temperature overnight. The reaction was quenched with saturated $NH_4Cl$ solution, extracted with EtOAc (60 mL), washed with brine, dried over $Na_2SO_4$, filtered, and concentrated. The residue was purified by prep-TLC to give the target compound (50 mg, crude). MS: M/e 723 $(M+1)^+$.

Step C: 2-butoxy-7-((6-(4-(2-(dimethylamino)ethyl) piperidin-1-yl)-5-methylpyridin-3-yl)methyl)imidazo [2,1-f][1,2,4]triazin-4-amine To a mixture of the product of Step B (50 mg, crude) in TFA (3 mL), $Et_3SiH$ (1 mL) was added and the resulting mixture was stirred at 85° C. overnight. The mixture was cooled to room temperature and concentrated to dryness. To the residue was added TFA (3 mL) and the reaction was heated at 85° C. overnight. The mixture was concentrated and the residue was purified by prep-HPLC to give the target compound (16 mg, 17% for two steps). $^1$HNMR (400 MHz, DMSO-$d_6$) δ 9.45 (br.s, 1H), 8.19 (s, 1H), 8.13 (s, 1H), 8.08 (s, 1H), 7.72 (s, 1H), 7.37 (s, 1H), 4.21 (t, J=6.8 Hz, 2H), 4.11 (s, 2H), 3.55-3.40 (m, 2H), 3.15-3.03 (m, 2H), 2.91-2.70 (m, 8H), 2.24 (s, 3H), 1.84-1.72 (m, 2H), 1.71-1.59 (m, 4H), 1.55-1.45 (m, 1H), 1.44-1.25 (m, 4H), 0.92 (t, J=7.6 Hz, 3H) ppm. MS: M/e 467 $(M+1)^+$.

Compound B111: 1-(4-(5-((4-amino-2-(pentan-2-yloxy)imidazo[2,1-f][1,2,4]triazin-7-yl)methyl)-3-methylpyridin-2-yl)piperazin-1-yl)-2-(methylamino) ethan-1-one Step A: tert-butyl (2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl) (methyl)carbamate A solution of 7-((5-methyl-6-(piperazin-1-yl)pyridin-3-yl)methyl)-2-(pentan-2-yloxy)imidazo[2,1-f][1,2,4]triazin-4-amine (100 mg, 0.24 mmol), N-(tert-butoxy carbonyl)-N-methylglycine (55 mg, 0.29 mmol), HATU (137 mg, 0.36 mmol) and DIEA (62 mg, 0.48 mmol) in DMF (5 mL) was stirred at rt for 2 hrs. The reaction mixture was quenched with water (5 mL), extracted with ethyl acetate (10 mL) and washed with brine (10 mL). The organic layer was dried with $Na_2SO_4$, filtered and concentrated to get the crude product, which was used in the next step without further purification (140 mg, crude). MS: M/e 582 $(M+1)^+$.

Step B: 1-(4-(5-((4-amino-2-(pentan-2-yloxy)imidazo[2,1-f] [1,2,4]triazin-7-yl) methyl)-3-methylpyridin-2-yl)piperazin-1-yl)-2-(methylamino) ethan-1-one To a solution of tert-butyl (2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl)(methyl)carbamate (140 mg, crude) in EA (5 mL), HCl/EA (2M, 3 mL) was added. The solution was stirred at rt overnight. After concentration, the residue was dissolved in DCM (10 mL) and washed with $NaHCO_3$ (10 mL). The organic layer was dried with $Na_2SO_4$, filtered and concentrated to get the crude product, which was further purified by prep-HPLC to get the pure product (20 mg, 17%). $^1$H NMR (400 MHz, DMSO-d6) δ 8.09 (s, 1H), 8.07 (s, 1H), 7.98 (s, 1H), 7.44 (s, 1H), 7.32 (s, 1H), 4.98-4.94 (m, 1H), 4.05 (s, 2H), 3.58-3.51 (m, 4H), 3.39 (s, 2H), 3.00-2.95 (m, 4H), 2.30 (s, 3H), 2.20 (s, 3H), 1.62-1.51 (m, 2H), 1.41-1.33 (m, 2H), 1.23 (d, J=4.0 Hz, 3H), 0.87 (t, J=8.0 Hz, 3H) ppm. MS: M/e 482 $(M+1)^+$.

Compound 112: 2-(sec-butoxy)-7-((5-methyl-6-(piperazin-1-yl) pyridin-3-yl)methyl)imidazo[2,1-f] [1,2,4]triazin-4-amine Step A: 7-bromo-2-(sec-butoxy)-N,N-bis(4-methoxybenzyl)imidazo[2,1-f][1,2,4]triazin-4-amine NaH (96 mg, 2.4 mmol) was added to a solution of butan-2-ol (178 mg, 2.4 mmol) in THF (10 mL). After stirred at rt under $N_2$ atmosphere for 30 mins, 7-bromo-2-chloro-N,N-bis(4-methoxybenzyl)imidazo[2,1-f][1,2,4]triazin-4-amine (300 mg, 0.60 mmol) was added and the resulting mixture was heated at 65° C. overnight. The solution was cooled down, quenched with water (10 mL) and extracted with ethyl acetate (10 mL). The organic layer was dried with $Na_2SO_4$, filtered and concentrated to get the crude product, which was further purified by Combi-Flash (PE:EA=15%) to get the product (225 mg, 75%). MS: M/e 526 $(M+1)^+$.

Step B: tert-butyl 4-(5-((4-(bis(4-methoxybenzyl) amino)-2-(sec-butoxy)imidazo[2,1-f][1,2,4]triazin-7-yl)(hydroxy)methyl)-3-methylpyridin-2-yl)piperazine-1-carboxylate To a cooled solution of 7-bromo-2-(sec-butoxy)-N,N-bis (4-methoxybenzyl)imidazo[2,1-f][1,2,4]triazin-4-amine (225 mg, 0.43 mmol) in THF (8 mL) at −78° C. (purged with $N^2$), n-BuLi (1.6 M, 0.4 mL) was added dropwise. After stirred at −78° C. for 30 mins, tert-butyl 4-(5-formyl-3-methylpyridin-2-yl)piperazine-1-carboxylate (157 mg, 0.51 mmol) in THF (2 mL) was added. The resulting mixture was stirred at this temperature for 30 mins, and then warmed to rt overnight. The solution was quenched with $NH_4Cl$ solution (5 mL) and extracted with ethyl acetate (10 mL). The organic layer was dried with $Na_2SO_4$, filtered and concentrated to get the crude product, which was further purified by Combi-Flash (PE:EA=50%) to get the pure product (266 mg, 82%). MS: M/e 753 $(M+1)^+$.

Step C: 2-(sec-butoxy)-7-((5-methyl-6-(piperazin-1-yl)pyridin-3-yl)methyl)imidazo[2,1-f][1,2,4]triazin-4-amine A solution of tert-butyl 4-(5-((4-(bis(4-methoxybenzyl) amino)-2-(sec-butoxy)imidazo[2,1-f][1,2,4]triazin-7-yl) (hydroxy)methyl)-3-methylpyridin-2-yl)piperazine-1-carboxylate (266 mg, 0.35 mmol) in triethylsilane (2 mL) and trifluoroacetic acid (10 mL) was heated at 88° C. overnight. The solvent was evaporated under oil pump to get the residue, which was added with DCM (10 mL) and basified with $NaHCO_3$ solution (5 mL). The organic layer was dried, concentrated and purified by Combi-Flash (DCM: MeOH=25%, added with 40% of $NH_3$·MeOH) and prep-TLC (DCM:$NH_3$·MeOH=7:1) to get the product (15 mg, 11%). $^1$H NMR (400 MHz, DMSO-d6) δ 8.11 (s, 1H), 8.05 (s, 1H), 7.99 (s, 1H), 7.41 (s, 1H), 7.32 (s, 1H), 4.90-4.85 (m, 1H), 4.03 (s, 2H), 2.92-2.83 (m, 8H), 2.17 (s, 3H), 1.63-1.57 (m, 2H), 1.24 (d, J=8.0 Hz, 3H), 0.90 (t, J=4.0 Hz, 3H) ppm. MS: M/e 397 $(M+1)^+$.

Compound B113: 7-((5-methyl-6-(piperazin-1-yl) pyridin-3-yl)methyl)-2-(2-methylbutoxy)imidazo[2,1-f][1,2,4]triazin-4-amine Compound B113 was synthesized starting from the corresponding starting materials according the similar procedures described as those of Compound B8. $^1$H NMR (400

MHz, DMSO-d6) δ 8.14 (s, 1H), 8.06 (s, 2H), 7.43 (s, 1H), 7.30 (s, 1H), 4.10-3.99 (m, 4H), 2.91-2.82 (m, 8H), 2.17 (s, 3H), 1.81-1.78 (m, 1H), 1.47-1.42 (m, 1H), 1.21-1.15 (m, 1H), 0.95-0.88 (m, 6H) ppm. MS: M/e 411 $(M+1)^+$.

Compound B114: 2-butoxy-7-((6-(4-ethylpiperazin-1-yl)-5-methylpyridin-3-yl)methyl)imidazo[2,1-f][1,2,4]triazin-4-amine To a stirred solution of 2-butoxy-7-((5-methyl-6-(piperazin-1-yl)pyridin-3-yl)methyl)imidazo[2,1-f][1,2,4]triazin-4-amine (40 mg, 0.1 mmol) in DCM (5 mL) and MeOH (5 mL), acetaldehyde (10.8 mg, 0.1 mmol) and $NaBH_3CN$ (18 mg, 0.3 mmol) were added. The reaction mixture was stirred at Rt overnight. The mixture was poured into $H_2O$ (50 mL) and extracted with EtOAc (10 ml×3). The combined organic phases were washed with brine, dried over $Na_2SO_4$ and concentrated in vacuo. The crude product was purified by prep-HPLC to give the product (32 mg, 59.4%). $^1H$ NMR (400 MHz, DMSO-d6) δ 9.40 (br.s, 1H), 8.16-8.05 (m, 3H), 7.53 (s, 1H), 7.35 (d, J=3.5 Hz, 1H), 4.21 (t, J=6.5 Hz, 2H), 4.08 (s, 2H), 3.53-3.42 (m, 4H), 3.24-2.93 (m, 6H), 2.21 (s, 3H), 1.74-1.59 (m, 2H), 1.41 (dd, J=14.9, 7.4 Hz, 2H), 1.32-1.21 (m, 3H), 0.93 (t, J=7.4 Hz, 3H) ppm. MS: M/e 425 $(M+1)^+$.

Compound B115: 2-butoxy-7-((6-(4-ethylpiperazin-1-yl)-5-methylpyridin-3-yl)methyl)imidazo[2,1-f][1,2,4]triazin-4-amine To a stirred solution of 2-butoxy-7-((5-methyl-6-(piperazin-1-yl)pyridin-3-yl)methyl)imidazo[2,1-f][1,2,4]triazin-4-amine (40 mg, 0.1 mmol) in DCM (5 mL) and MeOH (5 mL), isobutyraldehyde (13.7 mg, 0.1 mmol) and $NaBH_3CN$ (18 mg, 0.3 mmol) were added. The reaction mixture was stirred at Rt overnight. The mixture was poured into $H_2O$ (50 mL) and extracted with EtOAc (10 ml×3). The combined layers were washed with brine, dried over $Na_2SO_4$ and concentrated in vacuo. The crude product was purified by prep-HPLC to give the product (32 mg, 35.3%). $^1H$ NMR (400 MHz, DMSO-d6) δ 9.14 (br.s, 1H), 8.20-8.03 (m, 3H), 7.52 (s, 1H), 7.35 (s, 1H), 4.22 (t, J=6.4 Hz, 2H), 4.08 (s, 2H), 3.62-3.34 (m, 4H), 3.23-3.06 (m, 4H), 3.01 (d, J=5.5 Hz, 2H), 2.21 (s, 3H), 2.11 (dt, J=13.0, 6.8 Hz, 1H), 1.74-1.63 (m, 2H), 1.48-1.33 (m, 2H), 1.04-0.86 (m, 9H) ppm. MS: M/e 453 $(M+1)^+$.

Compound B116: 2-butoxy-7-((5-methyl-6-(4-phenethylpiperazin-1-yl)pyridin-3-yl)methyl)imidazo[2,1-f][1,2,4]triazin-4-amine To a stirred solution of 2-butoxy-7-((5-methyl-6-(piperazin-1-yl)pyridin-3-yl)methyl)imidazo[2,1-f][1,2,4]triazin-4-amine (40 mg, 0.1 mmol) in DCM (5 mL) and MeOH (5 mL), 2-phenylacetaldehyde (18.5 mg, 0.1 mmol) and $NaBH_3CN$ (18 mg, 0.3 mmol) were added. The reaction mixture was stirred at Rt overnight. The mixture was poured into $H_2O$ (50 mL) and extracted with EtOAc (10 ml×3). The combined layers were washed with brine, dried over $Na_2SO_4$ and concentrated in vacuo. The crude product was purified by prep-HPLC to give the product (30 mg, 48.8%). $^1H$ NMR (400 MHz, DMSO-d6) δ 9.93 (br.s, 1H), 8.25-8.04 (m, 3H), 7.55 (s, 1H), 7.43-7.25 (m, 6H), 4.22 (t, J=6.2 Hz, 2H), 4.10 (s, 2H), 3.64-3.54 (m, 4H), 3.47-3.22 (m, 4H), 3.17-2.96 (m, 4H), 2.23 (s, 3H), 1.74-1.63 (m, 2H), 1.41-1.32 (m, 2H), 0.93 (t, J=7.3 Hz, 3H) ppm. MS: M/e 501 $(M+1)^+$.

Compound B117: (R)-7-((5-methyl-6-(piperazin-1-yl)pyridin-3-yl)methyl)-2-(pentan-2-yloxy)imidazo[2,1-f][1,2,4]triazin-4-amine Step A: (R)-7-bromo-N,N-bis(4-methoxybenzyl)-2-(pentan-2-yloxy)imidazo[2,1-f][1,2,4]triazin-4-amine NaH (984 mg, 24.6 mmol) was added to a solution of (R)-pentan-2-ol (2.2 g, 24.6 mmol) in THF (20 mL). After was stirred at rt under $N_2$ atmosphere for 30 mins, 7-bromo-2-chloro-N,N-bis(4-methoxybenzyl)imidazo[2,1-f][1,2,4]triazin-4-amine (3 g, 6.2 mmol) was added and the resulting mixture was heated at 60° C. overnight. The solution was cooled down, diluted with water (10 mL) and extracted with ethyl acetate (10 mL). The organic layer was dried with $Na_2SO_4$, filtered and concentrated to get the crude product, which was further purified by Combi-Flash (PE:EA=15%) to get the pure product (3 g, 90%). MS: M/e 540 $(M+1)^+$.

Step B: tert-butyl4-(5-((4-(bis(4-methoxybenzyl)amino)-2-(((R)-pentan-2-yl)oxy)imidazo[2,1-f][1,2,4]triazin-7-yl)(hydroxy)methyl)-3-methylpyridin-2-yl)piperazine-1-carboxylate To a cooled solution of (R)-7-bromo-N,N-bis(4-methoxybenzyl)-2-(pentan-2-yl oxy)imidazo[2,1-f][1,2,4]triazin-4-amine (1 g, 1.8 mmol) in THF (15 mL) at −78° C. (purged with $N^2$), n-BuLi (1.6 M, 1.7 mL) was added dropwise. After stirred at −78° C. for 30 mins, tert-butyl 4-(5-formyl-3-methylpyridin-2-yl)piperazine-1-carboxylate (659 mg, 2.2 mmol) in THF (5 mL) was added. The resulting mixture was stirred at this temperature for 30 mins, and then warmed to rt overnight. The solution was quenched with $NH_4Cl$ solution (10 mL) and extracted with ethyl acetate (10 mL). The organic layer was dried with $Na_2SO_4$, filtered and concentrated to get the crude product, which was further purified by Combi-Flash (PE:EA=50%) to get the pure product (800 mg, 56%). MS: M/e 767 $(M+1)^+$ Step C: (R)-7-((5-methyl-6-(piperazin-1-yl)pyridin-3-yl)methyl)-2-(pentan-2-yloxy)imidazo[2,1-f][1,2,4]triazin-4-amine A solution of tert-butyl 4-(5-((4-(bis(4-methoxybenzyl)amino)-2-(((R)-pentan-2-yl)oxy)imidazo[2,1-f][1,2,4]triazin-7-yl)(hydroxy)methyl)-3-methylpyridin-2-yl)piperazine-1-carboxylate (800 mg, 1 mmol) in triethylsilane (2 mL) and trifluoroacetic acid (8 mL) was heated at 80° C. overnight. The solvent was evaporated to get the residue, which was dissolved in EA (10 mL) and washed with $NaHCO_3$ solution (10 mL). The organic layer was dried, concentrated, purified by Combi-Flash (DCM: $NH_3$·MeOH=35%) and prep-TLC (DCM:$NH_3$·MeOH=9:1) to get the product (65 mg, 15%). $^1H$ NMR (400 MHz, DMSO-d6) δ 8.11 (s, 1H), 8.05 (s, 1H), 7.99 (s, 1H), 7.39 (s, 1H), 7.32 (s, 1H), 4.98-4.94 (m, 1H), 4.03 (s, 2H), 2.95-2.74 (m, 8H), 2.16 (s, 3H), 1.63-1.52 (m, 2H), 1.48-1.30 (m, 2H), 1.24 (d, J=4.0, 3H), 0.88 (t, J=8.0 Hz, 3H) ppm. MS: M/e 411 $(M+1)^+$.

Compound B118: (S)-7-((5-methyl-6-(piperazin-1-yl)pyridin-3-yl)methyl)-2-(pentan-2-yloxy)imidazo[2,1-f][1,2,4]triazin-4-amine Step A: tert-butyl 4-(5-((4-(bis(4-methoxybenzyl)amino)-2-(((S)-pentan-2-yl)oxy)imidazo[2,1-f][1,2,4]triazin-7-yl)(hydroxy)methyl)-3-methylpyridin-2-yl)piperazine-1-carboxylate To a cooled solution of (S)-7-bromo-N,N-bis(4-methoxybenzyl)-2-(pentan-2-yloxy)imidazo[2,1-f][1,2,4]triazin-4- amine (300 mg, 0.56 mmol) in THF (8 mL) at −78° C. (purged with $N^2$), n-BuLi (1.6 M, 0.5 mL) was added dropwise. After stirred at −78° C. for 30 mins, tert-butyl 4-(5-formyl-3-methylpyridin-2-yl) piperazine-1-carboxylate (204 mg, 0.67 mmol) in THF (2 mL) was added. The resulting mixture was stirred at this temperature for 30 mins, and then warmed to rt for 2 hrs. The solution was quenched with $NH_4Cl$ solution (10 mL) and extracted with ethyl acetate (10 mL). The organic layer was dried with $Na_2SO_4$, filtered and concentrated to get the crude product, which was further purified by Combi-Flash (PE:EA=50%) to get the pure product (300 mg, 70%). MS: M/e 767 $(M+1)^+$.

Step B: (S)-7-((5-methyl-6-(piperazin-1-yl)pyridin-3-yl)methyl)-2-(pentan-2-yloxy)imidazo[2,1-f][1,2,4]triazin-4-amine A solution of tert-butyl 4-(5-((4-(bis(4-methoxybenzyl)amino)-2-(((S)-pentan-2-yl)oxy)imidazo[2,1-f][1,2,4]triazin-7-yl)(hydroxy)methyl)-3-methylpyridin-2-yl)piperazine-1-carboxylate (300 mg, 0.39 mmol) in triethylsilane (2 mL) and trifluoroacetic acid (8 mL) was heated at 85° C. overnight. The solvent was evaporated to get the residue, which was dissolved in EA (10 mL) and washed with $NaHCO_3$ solution (10 mL). The organic layer was dried, concentrated, purified by prep-TLC (DCM:$NH_3$·MeOH=9:1) to get the product (20 mg, 13%). $^1$H NMR (400 MHz, DMSO-d6) δ 8.10 (s, 1H), 8.05 (s, 1H), 7.99 (s, 1H), 7.40 (s, 1H), 7.32 (s, 1H), 4.98-4.94 (m, 1H), 4.03 (s, 2H), 2.98-2.76 (m, 8H), 2.16 (s, 3H), 1.65-1.48 (m, 2H), 1.42-1.30 (m, 2H), 1.24 (d, J=4.0, 3H), 0.88 (t, J=8.0 Hz, 3H) ppm. MS: M/e 411 $(M+1)^+$.

Compound B119: 2-(2-(2-methoxyethoxy)ethoxy)-7-((5-methyl-6-(piperazin-1-yl)pyridin-3-yl)methyl)imidazo[2,1-f][1,2,4]triazin-4-amine Compound B119 was synthesized starting from the corresponding starting materials according the similar procedures described as those of Compound B8. $^1$H NMR (400 MHz, DMSO-d6) δ 8.68 (br.s, 2H), 8.21 (s, 1H), 8.14 (s, 1H), 8.11 (s, 1H), 7.52 (s, 1H), 7.36 (s, 1H), 4.32 (t, J=4 Hz, 2H), 4.08 (s, 2H), 3.71 (t, J=4 Hz, 2H), 3.57 (t, J=4 Hz, 2H), 3.45 (t, J=4 Hz, 2H), 3.34-3.11 (m, 11H), 2.21 (s, 3H) ppm. MS: M/e 443 $(M+1)^+$.

Compound B120: 2-((2,5,8,11,14,17-hexaoxanonadecan-19-yl)oxy)-7-((5-methyl-6-(piperazin-1-yl)pyridin-3-yl)methyl)imidazo[2,1-f][1,2,4]triazin-4-amine Compound B120 was synthesized starting from the corresponding starting materials according the similar procedures described as those of Compound B8. $^1$H NMR (400 MHz, DMSO-d6) δ 8.73 (br.s, 2H), 8.22 (s, 1H), 8.17 (s, 1H), 8.12 (s, 1H), 7.54 (s, 1H), 7.38 (s, 1H), 4.33 (t, J=4 Hz, 2H), 4.09 (s, 2H), 3.72 (t, J=4 Hz, 2H), 3.57 (t, J=4 Hz, 2H), 3.53 (t, J=4 Hz, 2H), 3.51-3.46 (m, 14H), 3.42-3.80 (m, 2H), 3.29-3.16 (m, 11H), 2.21 (s, 3H) ppm. MS: M/e 619 $(M+1)^+$.

Compound B121: 2-butoxy-7-((5-methyl-6-(4-(pyrrolidin-1-ylmethyl)piperidin-1-yl)pyridin-3-yl)methyl)imidazo[2,1-f][1,2,4]triazin-4-amine Step A: 5-methyl-6-(4-(pyrrolidin-1-ylmethyl)piperidin-1-yl)nicotinaldehyde To a solution of 6-chloro-5-methylnicotinaldehyde (155 mg, 1 mmol) and DIEA (560 mg, 4 mmol) in DMA (5 mL) was added 4-(pyrrolidin-1-ylmethyl)piperidine dihydrochloride (265 mg, 1.1 mmol). Then the mixture was stirred at 115° C. overnight under $N_2$. The mixture was cooled to room temperature, diluted with water (50 mL), extracted with EtOAc (50 mL×2), washed with brine, dried over $Na_2SO_4$, filtered, concentrated and the residue was purified by prep-TLC to give the target compound (80 mg, 28%). MS: M/e 288 $(M+1)^+$.

Step B: (4-(bis(4-methoxybenzyl)amino)-2-butoxyimidazo[2,1-f][1,2,4]triazin-7-yl)(5-methyl-6-(4-(pyrrolidin-1-ylmethyl)piperidin-1-yl)pyridin-3-yl)methanol To a solution of 7-bromo-2-butoxy-N,N-bis(4-methoxybenzyl)imidazo[2,1-f][1,2,4]triazin-4-amine (116 mg, 0.22 mmol) in THF (5 mL) was added a solution of n-BuLi (0.21 mL, 0.33 mmol) dropwise maintaining the temperature between −75∼−65° C. After 1 h, a suspension of the product of Step A (70 mg, 0.243 mmol) in THF (2 mL) was added dropwise. The resulting mixture was stirred at −70° C. for 2 h and then warmed to room temperature overnight. The reaction was quenched with saturated $NH_4Cl$ solution, extracted with EtOAc (50 mL), washed with brine, dried over $Na_2SO_4$, filtered, and concentrated. The residue was purified by prep-TLC to give the target compound (60 mg, crude). MS: M/e 735 $(M+1)^+$.

Step C: 2-butoxy-7-((5-methyl-6-(4-(pyrrolidin-1-ylmethyl)piperidin-1-yl)pyridine-3-yl)methyl)imidazo[2,1-f][1,2,4]triazin-4-amine To a mixture of the product of Step B (60 mg, crude) in TFA (2 mL) was added $Et_3SiH$ (2 mL) and the resulting mixture was stirred at 85° C. for 3 hours. The mixture was cooled to room temperature and concentrated to dryness. To the residue was added TFA (3 mL) and the reaction was heated at 85° C. overnight. The mixture was concentrated and the residue was purified by prep-HPLC to give the target compound (15 mg, 12% for two steps). $^1$HNMR (400 MHz, DMSO-d6) δ 9.24 (br.s, 1H), 8.16 (s, 1H), 8.09 (s, 1H), 8.07 (s, 1H), 7.57 (s, 1H), 7.34 (s, 1H), 4.21 (t, J=6.8 Hz, 2H), 4.07 (s, 2H), 3.66-3.52 (m, 2H), 3.46-3.31 (m, 2H), 3.31 (t, J=6.0 Hz, 2H), 3.06-2.95 (m, 2H), 2.76 (t, J=11.6 Hz, 2H), 2.20 (s, 3H), 2.10-1.95 (m, 2H), 1.94-1.75 (m, 5H), 1.72-1.60 (m, 2H), 1.50-1.24 (m, 4H), 0.93 (t, J=7.6 Hz, 3H) ppm. MS: M/e 479 $(M+1)^+$.

Compound B122: (S)-7-((6-(4-(dimethylamino)piperidin-1-yl)-5-methylpyridin-3-yl)methyl)-2-(pentan-2-yloxy)imidazo[2,1-f][1,2,4]triazin-4-amine Step A: (S)-7-bromo-N,N-bis(4-methoxybenzyl)-2-(pentan-2-yloxy)imidazo[2,1-f][1,2,4]triazin-4-amine To a solution of (S)-pentan-2-ol (5.4 g, 64.35 mmol) in THF (30 mL) was added NaH (2.4 g, 61.35 mmol) portionwise at 0° C. and stirred at rt for 1 h. Then a solution of 7-bromo-2-chloro-N,N-bis(4-methoxybenzyl)imidazo[2,1-f][1,2,4]triazin-4-amine (10 g, 20.45 mmol) in THF (20 mL) was added dropwise at 0° C., after addition, the mixture was warmed to 60° C. and stirred overnight. The mixture was quenched with saturated ammonium chloride solution (20 mL), extracted with DCM (100 mL×3). The combined organic layers were washed with brine, dried over $Na_2SO_4$, concentrated and purified by column chromatography (PE/

EA=5:1~1:1) to give the title product (10.74 g, 97.26%) as yellow oil. MS: M/e 540 (M+1)+.

Step B: (4-(bis(4-methoxybenzyl)amino)-2-(((S)-pentan-2-yl)oxy)imidazo[2,1-f][1,2,4]triazin-7-yl)(6-(4-(dimethylamino)piperidin-1-yl)-5-methylpyridin-3-yl)methanol To a solution of (S)-7-bromo-N,N-bis(4-methoxybenzyl)-2-(pentan-2-yloxy)imidazo[2,1-f][1,2,4]triazin-4-amine (200 mg, 0.37 mmol) in THF (5 mL), n-BuLi (0.35 ml, 0.56 mmol) was added dropwise at −78° C. and stirred for 1 h. Then a solution of 6-(4-(dimethylamino)piperidin-1-yl)-5-methylnicotinaldehyde (137 mg, 0.56 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (175 mg, 66.64%) as yellow oil. MS: M/e 709 (M+1)+.

Step C: (S)-7-((6-(4-(dimethylamino)piperidin-1-yl)-5-methylpyridin-3-yl)methyl)-2-(pentan-2-yloxy)imidazo[2,1-f][1,2,4]triazin-4-amine A mixture of (4-(bis(4-methoxybenzyl)amino)-2-(((S)-pentan-2-yl)oxy)imidazo[2,1-f][1,2,4]triazin-7-yl)(6-(4-(dimethylamino)piperidin-1-yl)-5-methylpyridin-3-yl)methanol (175 mg, 0.13 mmol) and triethylsilane (1 mL) in TFA (2 mL) was stirred at 90° C. overnight. The mixture was concentrated and purified with prep-HPLC to give the title product (41 mg, 36.75%). $^1$H NMR (400 MHz, DMSO-d6) δ 9.57 (s, 1H), 8.14 (s, 1H), 8.07 (s, 2H), 7.51 (s, 1H), 7.37 (s, 1H), 4.99-4.94 (m, 1H), 4.07 (s, 2H), 3.50 (d, J=12.2 Hz, 2H), 3.37-3.25 (m, 1H), 2.79 (s, 3H), 2.78 (s, 3H), 2.75-2.66 (m, 2H), 2.20 (s, 3H), 2.05 (d, J=10.9 Hz, 2H), 1.79-1.66 (m, 2H), 1.67-1.58 (m, 1H), 1.57-1.47 (m, 1H), 1.42-1.29 (m, 2H), 1.25 (d, J=6.1 Hz, 3H), 0.88 (t, J=7.3 Hz, 3H) ppm. MS: M/e 453 (M+1)+.

Compound B123: (S)-7-((6-(4-((dimethylamino)methyl)piperidin-1-yl)-5-methylpyridin-3-yl)methyl)-2-(pentan-2-yloxy)imidazo[2,1-f][1,2,4]triazin-4-amine Step A: (4-(bis(4-methoxybenzyl)amino)-2-(((S)-pentan-2-yl)oxy)imidazo[2,1-f][1,2,4]triazin-7-yl)(6-(4-((dimethylamino)methyl)piperidin-1-yl)-5-methylpyridin-3-yl)methanol To a solution of (S)-7-bromo-N,N-bis(4-methoxybenzyl)-2-(pentan-2-yloxy)imidazo[2,1-f][1,2,4]triazin-4-amine (200 mg, 0.37 mmol) in THF (5 mL), n-BuLi (0.35 ml, 0.56 mmol) was added dropwise at −78° C. and stirred for 1 h. Then a solution of 6-(4-((dimethylamino)methyl)piperidin-1-yl)-5-methylnicotinaldehyde (145 mg, 0.56 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (201 mg, 75.06%) as yellow oil. MS: M/e 723 (M+1)+.

Step B: (S)-7-((6-(4-((dimethylamino)methyl)piperidin-1-yl)-5-methylpyridin-3-yl)methyl)-2-(pentan-2-yloxy)imidazo[2,1-f][1,2,4]triazin-4-amine A mixture of product of Step A (201 mg, 0.28 mmol) and triethylsilane (1 mL) in TFA (2 mL) was stirred at 90° C. overnight. The mixture was concentrated and purified with prep-HPLC to give the title product (33 mg, 25.47%). $^1$H NMR (400 MHz, DMSO-d6) δ 9.33 (br.s, 1H), 8.17 (s, 1H), 8.11 (s, 1H), 8.07 (s, 1H), 7.64 (s, 1H), 7.39 (s, 1H), 5.03-4.89 (m, 1H), 4.10 (s, 2H), 3.46 (d, J=12.6 Hz, 2H), 3.05-3.01 (m, 2H), 2.87-2.81 (m, 8H), 2.22 (s, 3H), 1.98 (s, 1H), 1.80 (d, J=11.5 Hz, 2H), 1.69-1.59 (m, 1H), 1.58-1.46 (m, 1H), 1.42-1.28 (m, 4H), 1.25 (d, J=5.0 Hz, 3H), 0.88 (t, J=6.8 Hz, 3H). MS: M/e 467 (M+1)+.

Compound B124: (R)-1-(4-(5-((4-amino-2-(pentan-2-yloxy)imidazo[2,1-f][1,2,4]triazin-7-yl)methyl)-3-methylpyridin-2-yl)piperazin-1-yl)-2-(dimethylamino)ethan-1-one A solution of (R)-7-((5-methyl-6-(piperazin-1-yl)pyridin-3-yl)methyl)-2-(pentan-2-yloxy)imidazo[2,1-f][1,2,4]triazin-4-amine (67 mg, 0.16 mmol), dimethylglycine (21 mg, 0.2 mmol), HATU (91 mg, 0.24 mmol) and DIEA (42 mg, 0.32 mmol) in DMF (5 mL) was stirred at rt for 2 hrs. The reaction mixture was diluted with water (5 mL), extracted with ethyl acetate (10 mL) and washed with brine (10 mL). The organic layer was dried with $Na_2SO_4$, filtered and concentrated to get the crude product, which was purified by prep-TLC (DCM:$NH_3$·MeOH=10:1) to get the product (29 mg, 36%). $^1$H NMR (400 MHz, DMSO-d6) δ 8.14 (s, 1H), 8.07 (s, 1H), 7.99 (s, 1H), 7.44 (s, 1H), 7.33 (s, 1H), 4.98-4.94 (m, 1H), 4.05 (s, 2H), 3.62 (s, 2H), 3.57 (s, 2H), 3.25 (s, 2H), 3.01 (s, 2H), 2.94 (s, 2H), 2.26 (s, 6H), 2.20 (s, 3H), 1.53-1.37 (m, 2H), 1.35-1.25 (m, 2H), 1.24 (d, J=4.0 Hz, 3H), 0.88 (t, J=8.0 Hz, 3H) ppm. MS: M/e 496 (M+1)+

Compound B125: (S)-1-(4-(5-((4-amino-2-(pentan-2-yloxy)imidazo[2,1-f][1,2,4]triazin-7-yl)methyl)-3-methylpyridin-2-yl)piperazin-1-yl)-2-(dimethylamino)ethan-1-one A solution of (S)-7-((5-methyl-6-(piperazin-1-yl)pyridin-3-yl)methyl)-2-(pentan-2-yloxy)imidazo[2,1-f][1,2,4]triazin-4-amine (43 mg, 0.10 mmol), dimethylglycine (13 mg, 0.12 mmol), HATU (57 mg, 0.15 mmol) and DIEA (26 mg, 0.20 mmol) in DMF (5 mL) was stirred at rt for 2 hrs. The reaction mixture was diluted with water (5 mL), extracted with ethyl acetate (10 mL) and washed with brine (10 mL). The organic layer was dried with $Na_2SO_4$, filtered and concentrated to get the crude product, which was purified by prep-TLC (DCM:$NH_3$·MeOH=10:1) to get the product (10 mg, 20%). $^1$H NMR (400 MHz, DMSO-d6) δ 8.10 (s, 1H), 8.07 (s, 1H), 7.99 (s, 1H), 7.44 (s, 1H), 7.33 (s, 1H), 4.98-4.94 (m, 1H), 4.05 (s, 2H), 3.59 (s, 4H), 3.47 (s, 2H), 3.02 (s, 2H), 2.95 (s, 2H), 2.33 (s, 6H), 2.21 (s, 3H), 1.53-1.35 (m, 2H), 1.33-1.26 (m, 2H), 1.24 (d, J=4.0 Hz, 3H), 0.88 (t, J=8.0 Hz, 3H) ppm. MS: M/e 496 (M+1)+.

Compound B126: 2-butoxy-7-((6-(4-((diethylamino)methyl)piperidin-1-yl)-5-methylpyridin-3-yl)methyl)imidazo[2,1-f][1,2,4]triazin-4-amine Step A: 6-(4-((diethylamino)methyl)piperidin-1-yl)-5-methylnicotinaldehyde To a solution of 6-chloro-5-methylnicotinaldehyde (155 mg, 1 mmol) and DIEA (258 mg, 2 mmol) in DMA (5 mL)

was added N-ethyl-N-(piperidin-4-ylmethyl)ethanamine (190 mg, 1.1 mmol). Then the mixture was stirred at 115° C. overnight under $N_2$. The mixture was cooled to room temperature, diluted with water (50 mL), extracted with EtOAc (50 mL×2), washed with brine, dried over $Na_2SO_4$, filtered, concentrated and the residue was purified by prep-TLC to give the target compound (110 mg, 38%). MS: M/e 290 $(M+1)^+$.

Step B: (4-(bis(4-methoxybenzyl)amino)-2-butoxy-imidazo[2,1-f][1,2,4]triazin-7-yl)(6-(4-((diethyl-amino)methyl)piperidin-1-yl)-5-methylpyridin-3-yl) methanol To a solution of 7-bromo-2-butoxy-N,N-bis(4-methoxy-benzyl)imidazo[2,1-f][1,2,4]triazin-4-amine (175 mg, 0.22 mmol) in THF (8 mL) was added a solution of n-BuLi (0.31 mL, 0.5 mmol) dropwise maintaining the temperature between −75~−65° C. After 1 h, a suspension of the product of Step A (110 mg, 0.38 mmol) in THF (2 mL) was added dropwise. The resulting mixture was stirred at −70° C. for 2 h and then warmed to room temperature overnight. The reaction was quenched with saturated $NH_4Cl$ solution, extracted with EtOAc (50 mL), washed with brine, dried over $Na_2SO_4$, filtered, and concentrated. The residue was purified by prep-TLC to give the target compound (100 mg, crude). MS: M/e 737 $(M+1)^+$.

Step C: 2-butoxy-7-((6-(4-((diethylamino)methyl) piperidin-1-yl)-5-methylpyridin-3-yl)methyl)imidazo [2,1-f][1,2,4]triazin-4-amine To a mixture of the product of Step B (100 mg, crude) in TFA (4 mL) was added $Et_3SiH$ (4 mL) and the resulting mixture was stirred at 85° C. for 4 hours. The mixture was cooled to room temperature and concentrated to dryness. To the residue was added TFA (5 mL) and the reaction was heated at 85° C. overnight. The mixture was concentrated and the residue was purified by prep-HPLC to give the target compound (30 mg, 15% for two steps). $^1$HNMR (400 MHz, DMSO-$d_6$) δ 8.92 (br.s, 1H), 8.20 (s, 1H), 8.15 (s, 1H), 8.09 (s, 1H), 7.73 (s, 1H), 7.38 (d, J=4.0 Hz, 1H), 4.21 (t, J=6.4 Hz, 2H), 4.11 (s, 2H), 3.57-3.36 (m, 2H), 3.26-3.05 (m, 4H), 3.06-2.94 (m, 2H), 2.91-2.75 (m, 2H), 2.23 (s, 3H), 2.05-1.76 (m, 3H), 1.74-1.60 (m, 2H), 1.51-1.29 (m, 4H), 1.21 (t, J=7.2 Hz, 6H), 0.93 (t, J=7.6 Hz, 3H) ppm. MS: M/e 481 $(M+1)^+$.

Compound B127: (R)-7-((6-(4-(dimethylamino) piperidin-1-yl)-5-methylpyridin-3-yl)methyl)-2-(pentan-2-yloxy)imidazo[2,1-f][1,2,4]triazin-4-amine Step A: (R)-7-bromo-N,N-bis(4-methoxybenzyl)-2-(pentan-2-yloxy)imidazo[2,1-f][1,2,4]triazin-4-amine To a solution of (R)-pentan-2-ol (5.4 g, 64.35 mmol) in THF (30 mL) was added NaH (2.4 g, 61.35 mmol) portion-wise at 0° C. and stirred at rt for 1 h. Then a solution of 7-bromo-2-chloro-N,N-bis(4-methoxybenzyl)imidazo[2,1-f][1,2,4]triazin-4-amine (10 g, 20.45 mmol) in THF (20 mL) was added dropwise at 0° C., after addition, the mixture was warmed to 60° C. and stirred overnight. The mixture was quenched with saturated ammonium chloride solution (20 mL), extracted with DCM (100 mL×3). The combined organic layers were washed with brine, dried over $Na_2SO_4$, concentrated and purified by column chromatography (PE/EA=5:1~1:1) to give the title product (10.25 g, 92.63%) as yellow oil. MS: M/e 540 $(M+1)^+$.

Step B: (4-(bis(4-methoxybenzyl)amino)-2-(((R)-pentan-2-yl)oxy)imidazo[2,1-f][1,2,4]triazin-7-yl)(6-(4-(dimethylamino)piperidin-1-yl)-5-methylpyridin-3-yl)methanol To a solution of (R)-7-bromo-N,N-bis(4-methoxybenzyl)-2-(pentan-2-yloxy)imidazo[2,1-f][1,2,4]triazin-4-amine (200 mg, 0.37 mmol) in THF (5 mL), n-BuLi (0.35 ml, 0.56 mmol) was added dropwise at −78° C. and stirred for 1 h. Then a solution of 6-(4-(dimethylamino)piperidin-1-yl)-5-methylnicotinaldehyde (137 mg, 0.56 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (156 mg, 59.41%) as yellow oil. MS: M/e 709 $(M+1)^+$.

Step C: (R)-7-((6-(4-(dimethylamino)piperidin-1-yl)-5-methylpyridin-3-yl)methyl)-2-(pentan-2-yloxy) imidazo[2,1-f][1,2,4]triazin-4-amine A mixture of (4-(bis(4-methoxybenzyl)amino)-2-(((R)-pentan-2-yl)oxy)imidazo[2,1-f][1,2,4]triazin-7-yl)(6-(4-(dimethylamino)piperidin-1-yl)-5-methylpyridin-3-yl)methanol (156 mg, 0.22 mmol) and triethylsilane (1 mL) in TFA (2 mL) was stirred at 90° C. overnight. The mixture was concentrated and purified with prep-HPLC to afford the title product (54 mg, 54.30%). $^1$H NMR (400 MHz, DMSO-d6) δ 9.52 (br.s, 1H), 8.14 (s, 1H), 8.07 (s, 2H), 7.49 (s, 1H), 7.35 (s, 1H), 4.99-2.94 (m, 1H), 4.06 (s, 2H), 3.49 (d, J=11.9 Hz, 2H), 3.31 (s, 1H), 2.78 (s, 3H), 2.77 (s, 3H), 2.75-2.67 (m, 2H), 2.20 (s, 3H), 2.04 (d, J=10.4 Hz, 2H), 1.79-1.67 (m, 2H), 1.66-1.59 (m, 1H), 1.57-1.48 (m, 1H), 1.42-1.29 (m, 2H), 1.25 (d, J=6.1 Hz, 3H), 0.88 (t, J=7.3 Hz, 3H). MS: M/e 453 $(M+1)^+$.

Compound B128: (R)-7-((6-(4-((dimethylamino) methyl)piperidin-1-yl)-5-methylpyridin-3-yl) methyl)-2-(pentan-2-yloxy)imidazo[2,1-f][1,2,4] triazin-4-amine Step A: (4-(bis(4-methoxybenzyl)amino)-2-(((R)-pentan-2-yl)oxy)imidazo[2,1-f][1,2,4]triazin-7-yl)(6-(4-((dimethylamino)methyl)piperidin-1-yl)-5-methylpyridin-3-yl)methanol To a solution of (R)-7-bromo-N,N-bis(4-methoxybenzyl)-2-(pentan-2-yloxy)imidazo[2,1-f][1,2,4]triazin-4-amine (200 mg, 0.37 mmol) in THF (5 mL), n-BuLi (0.35 ml, 0.56 mmol) was added dropwise at −78° C. and stirred for 1 h. Then a solution of 6-(4-((dimethylamino)methyl)piperidin-1-yl)-5-methylnicotinaldehyde (145 mg, 0.56 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (201 mg, 75.06%) as yellow oil. MS: M/e 723 $(M+1)^+$.

Step B: (R)-7-((6-(4-((dimethylamino)methyl)piperidin-1-yl)-5-methylpyridin-3-yl)methyl)-2-(pentan-2-yloxy)imidazo[2,1-f][1,2,4]triazin-4-amine A mixture of (4-(bis(4-methoxybenzyl)amino)-2-(((R)-pentan-2-yl)oxy)imidazo[2,1-f][1,2,4]triazin-7-yl)(6-(4-((dimethylamino)methyl)piperidin-1-yl)-5-methylpyridin-3-yl)methanol (201 mg, 0.28 mmol) and triethylsilane (1 mL) in TFA (2 mL) was stirred at 90° C. overnight. The mixture was concentrated and purified with prep-HPLC to afford the title product (54 mg, 41.89%). $^1H$ NMR (400 MHz, DMSO-d6) δ 9.15 (br.s, 1H), 8.14 (s, 1H), 8.06 (s, 2H), 7.55 (s, 1H), 7.36 (s, 1H), 4.98-4.94 (m, 1H), 4.07 (s, 2H), 3.39 (s, 2H), 3.02 (t, J=5.9 Hz, 2H), 2.80 (s, 6H), 2.79 (s, 2H), 2.20 (s, 3H), 1.94 (s, 1H), 1.78 (d, J=11.9 Hz, 2H), 1.67-1.58 (m, 1H), 1.56-1.46 (m, 1H), 1.44-1.28 (m, 4H), 1.25 (d, J=6.1 Hz, 3H), 0.88 (t, J=7.3 Hz, 3H) ppm. MS: M/e 467 $(M+1)^+$.

Compound B129: 1-(4-(5-((4-amino-2-butoxyimidazo[2,1-f][1,2,4]triazin-7-yl)methyl)-3-methylpyridin-2-yl)piperazin-1-yl)octadecan-1-one To a stirred solution of 2-butoxy-7-((5-methyl-6-(piperazin-1-yl)pyridin-3-yl)methyl)imidazo[2,1-f][1,2,4]triazin-4-amine (40 mg, 0.1 mmol) in DMF (5 mL) was added stearic acid (35 mg, 0.12 mmol), HATU (116 mg, 0.3 mmol) and DIEA (25.8 mg, 0.2 mmol). The reaction mixture was stirred at Rt overnight. The mixture was poured into $H_2O$ (50 mL) and extracted with EtOAc (10 ml×3). The combined organic phases were washed with brine, dried over $Na_2SO_4$ and concentrated in vacuo. The crude product was purified by column chromatography to give the product (10 mg, 15.1%). $^1H$ NMR (400 MHz, $CDCl_3$) δ 8.14 (s, 1H), 7.37 (s, 1H), 7.28 (s, 1H), 4.29 (t, J=6.1 Hz, 2H), 4.11 (s, 2H), 3.74 (s, 2H), 3.60 (s, 2H), 3.17 (s, 2H), 3.04 (s, 2H), 2.36 (t, J=7.4 Hz, 2H), 2.26 (s, 3H), 1.82-1.73 (m, 2H), 1.63 (d, J=6.2 Hz, 2H), 1.54-1.46 (m, 2H), 1.25 (s, 28H), 0.97 (t, J=7.2 Hz, 3H), 0.87 (t, J=6.7 Hz, 3H) ppm. MS: M/e 663 $(M+1)^+$.

Compound B130: 2-butoxy-7-((5-methyl-6-(4-(4-methylpiperazin-1-yl)piperidin-1-yl)pyridin-3-yl)methyl)imidazo[2,1-f][1,2,4]triazin-4-amine Step A: 5-methyl-6-(4-(4-methylpiperazin-1-yl)piperidin-1-yl)nicotinaldehyde To a stirred solution of 6-chloro-5-methylnicotinaldehyde (310 mg, 2 mmol) in DMA (10 mL) was added 1-methyl-4-(piperidin-4-yl)piperazine (439 mg, 2.4 mmol) and DIEA (516 mg, 4 mmol). The reaction mixture was protected by $N_2$ and stirred at 120° C. for 4 hrs. The mixture was cooled down to rt, added $H_2O$ (50 mL) and extracted with DCM (10 ml×3). The combined organic phases were washed with brine, dried over $Na_2SO_4$ and concentrated in vacuo. The crude product was purified by column chromatography to give the product (130 mg, 21.5%) as yellow solids. MS: M/e 303 $(M+1)^+$.

Step B: (4-(bis(4-methoxybenzyl)amino)-2-butoxyimidazo[2,1-f][1,2,4]triazin-7-yl)(5-methyl-6-(4-(4-methylpiperazin-1-yl)piperidin-1-yl)pyridin-3-yl)methanol To a stirred solution of 7-bromo-2-butoxy-N,N-bis(4-methoxybenzyl)imidazo[2,1-f][1,2,4]triazin-4-amine (200 mg, 0.38 mmol) in THF (10 mL), cooled to −78° C. and under a nitrogen atmosphere was added n-BuLi (1.6 M in hexane, 0.95 mmol, 0.59 mL) dropwise. After stirring for 50 mins, a solution of 5-methyl-6-(4-(4-methylpiperazin-1-yl)piperidin-1-yl)nicotinaldehyde (130 mg, 0.43 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phases were washed with brine, dried over $Na_2SO_4$, concentrated in vacuo. The crude product was purified by column chromatography to give the title product (110 mg, 38.7%). MS: M/e 750 $(M+1)^+$.

Step C: 2-butoxy-7-((5-methyl-6-(4-(4-methylpiperazin-1-yl)piperidin-1-yl)pyridin-3-yl)methyl)imidazo[2,1-f][1,2,4]triazin-4-amine A solution of (4-(bis(4-methoxybenzyl)amino)-2-butoxyimidazo[2,1-f][1,2,4]triazin-7-yl)(5-methyl-6-(4-(4-methylpiperazin-1-yl)piperidin-1-yl)pyridin-3-yl)methanol (110 mg, 0.15 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 80° C. overnight. The mixture was cooled down to rt and concentrated in vacuo. The crude product was purified by prep-HPLC to give the product (15 mg, 21%). $^1H$ NMR (400 MHz, DMSO-d6) δ 8.17 (s, 1H), 8.11 (s, 1H), 8.08 (s, 1H), 7.56 (s, 1H), 7.34 (s, 1H), 4.21 (t, J=6.1 Hz, 2H), 4.08 (s, 2H), 3.52 (br.s, 6H), 3.08 (br.s, 4H), 2.83-2.75 (m, 6H), 2.21 (s, 3H), 2.04 (s, 2H), 1.75-1.61 (m, 4H), 1.43-1.35 (m, 2H), 0.93 (t, J=7.2 Hz, 3H) ppm. MS: M/e 494 $(M+1)^+$.

Compound B131: 2-butoxy-7-((5-methyl-6-(3,9-diazaspiro[5.5]undecan-3-yl)pyridin-3-yl)methyl)imidazo[2,1-f][1,2,4]triazin-4-amine Step A: tert-butyl-9-(5-formyl-3-methylpyridin-2-yl)-3,9-diazaspiro[5.5]undecane-3-carboxylate To a stirred solution of 6-chloro-5-methylnicotinaldehyde (310 mg, 2 mmol) in DMA (10 mL) was added tert-butyl 2,7-diazaspiro[3.5]nonane-7-carboxylate (500 mg, 2 mmol) and DIEA (487 mg, 3 mmol). The reaction mixture was protected by $N_2$ and stirred at 120° C. for 4 h. The mixture was cooled down to rt, added $H_2O$ (50 mL) and extracted with EtOAc (10 ml×3). The combined organic phases were washed with brine, dried over $Na_2SO_4$ and concentrated in vacuo. The crude product was purified by column chromatography to give the product (260 mg, 34.8%) as white solids. MS: M/e 374 $(M+1)^+$.

Step B: tert-butyl-9-(5-((4-(bis(4-methoxybenzyl)amino)-2-butoxyimidazo[2,1-f][1,2,4]triazin-7-yl)(hydroxy)methyl)-3-methylpyridin-2-yl)-3,9-diazaspiro[5.5]undecane-3-carboxylate To a stirred solution of 7-bromo-2-butoxy-N,N-bis(4-methoxybenzyl)imidazo[2,1-f][1,2,4]triazin-4-amine (200 mg, 0.38 mmol) in THF (10 mL), cooled to −78° C. and under a nitrogen atmosphere was added n-BuLi (1.6 M in hexane, 0.95 mmol, 0.59 mL) dropwise. After stirring for 50 mins, a solution of tert-butyl 9-(5-formyl-3-methylpyridin-2-yl)-3,9-diazaspiro[5.5]undecane-3-carboxylate (212 mg, 0.57 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phases were washed with brine, dried over $Na_2SO_4$, concentrated in vacuo. The crude product was purified by column chromatography to give the title product (120 mg, 38.6%). MS: M/e 821 (M+1)+.

Step C: 2-butoxy-7-((5-methyl-6-(3,9-diazaspiro[5.5]undecan-3-yl)pyridin-3-yl)methyl)imidazo[2,1-f][1,2,4]triazin-4-amine A solution of tert-butyl 9-(5-((4-(bis(4-methoxybenzyl)amino)-2-butoxyimidazo[2,1-f][1,2,4]triazin-7-yl)(hydroxy)methyl)-3-methylpyridin-2-yl)-3,9-diazaspiro[5.5]undecane-3-carboxylate (120 mg, 0.146 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (55 mg, 51.4%). $^1$H NMR (400 MHz, DMSO-d6) δ 8.44 (br.s, 2H), 8.20 (s, 1H), 8.15 (s, 1H), 8.08 (s, 1H), 7.73 (s, 1H), 7.36 (s, 1H), 4.21 (t, J=6.3 Hz, 2H), 4.11 (s, 2H), 3.22-3.05 (m, 8H), 2.23 (s, 3H), 1.79-1.51 (m, 10H), 1.50-1.33 (m, 2H), 0.92 (t, J=7.3 Hz, 3H) ppm. MS: M/e 465 (M+1)+.

Compound B132: (S)-2-butoxy-7-((5-methyl-6-(3-methylpiperazin-1-yl)pyridin-3-yl)methyl)imidazo[2,1-f][1,2,4]triazin-4-amine Step A: tert-butyl (S)-4-(5-formyl-3-methylpyridin-2-yl)-2-methylpiperazine-1-carboxylate The mixture of 6-chloro-5-methylnicotinaldehyde (500 mg, 3.2 mmol), tert-butyl (S)-2-methylpiperazine-1-carboxylate (645 mg, 3.2 mmol) and DIEA (832 mg, 6.4 mmol) in DMAc (10 mL) was stirred at 100° C. overnight. The reaction was diluted with water (30 mL) and extracted with EA (20 mL×3). The combined organic phase was washed with brine, dried over $Na_2SO_4$ and concentrated under reduced pressure. The residue was purified by combi-flash to obtain the title compound (350 mg, yield: 34.3%) as a yellow oil. MS: M/e 320 (M+1)+.

Step B: tert-butyl (2S)-4-(5-((4-(bis(4-methoxybenzyl)amino)-2-butoxyimidazo[2,1-f][1,2,4]triazin-7-yl)(hydroxy)methyl)-3-methylpyridin-2-yl)-2-methylpiperazine-1-carboxylate To a stirred solution of 7-bromo-2-butoxy-N,N-bis(4-methoxybenzyl)imidazo[2,1-f][1,2,4]triazin-4-amine (150 mg, 0.29 mmol) in THF (10 mL) was added n-BuLi (1.6 M, 0.36 mL) at −78° C. in $N_2$ atmosphere. The mixture was stirred at −78° C. for 1 hour. Then the product of Step A (137 mg, 0.44 mmol) in THF (0.5 mL) was added to the system at −78° C. The reaction was warmed to room temperature and stirred overnight. The reaction was quenched with saturated $NH_4Cl$ aqueous at room temperature. The mixture was extracted with EA (20 mL×3). The combined organic phases were washed with brine, dried over $Na_2SO_4$ and concentrated under reduced pressure. The residue was purified by combi-flash to afford the title compound (190 mg, yield: 85.6%) as a yellow oil. MS: M/e 767 (M+1)+.

Step C: (S)-2-butoxy-7-((5-methyl-6-(3-methylpiperazin-1-yl)pyridin-3-yl)methyl)imidazo[2,1-f][1,2,4]triazin-4-amine (TLR-281)

To a stirred solution of the product of Step B (190 mg, 0.25 mmol) in $Et_3SiH$ (4 mL) was added $CF_3COOH$ (2 mL) at room temperature. The mixture was stirred at 80° C. for 1 hour. The reaction was cooled to room temperature and concentrated under reduced pressure. The residue was dissolved into $CF_3COOH$ (4 mL). And the mixture was stirred at 80° C. overnight. The reaction was cooled to room temperature. The mixture was concentrated under reduced pressure. The residue was purified by prep-HPLC to afford the title compound (35 mg, yield: 34.1%). $^1$H NMR (400 MHz, DMSO-d6) δ 8.14 (br.s, 1H), 8.10-7.98 (m, 2H), 7.42 (s, 1H), 7.31 (s, 1H), 4.21 (t, J=6.4 Hz, 2H), 4.03 (s, 2H), 3.14 (d, J=11.6 Hz, 2H), 2.97-2.72 (m, 3H), 2.67-2.57 (m, 1H), 2.38-2.26 (m, 1H), 2.17 (s, 3H), 1.79-1.60 (m, 2H), 1.53-1.35 (m, 2H), 1.08-0.83 (m, 6H) ppm. MS: M/e 411 (M+1)+.

Compound B133: 7-((6-(4-(dimethylamino)piperidin-1-yl)-5-methylpyridin-3-yl)methyl)-2-(pentan-2-yloxy)imidazo[2,1-f][1,2,4]triazin-4-amine Step A: 7-bromo-N,N-bis(4-methoxybenzyl)-2-(pentan-2-yloxy)imidazo[2,1-f][1,2,4]triazin-4-amine To a solution of pentan-2-ol (5.4 g, 64.35 mmol) in THF (30 mL) was added NaH (2.4 g, 61.35 mmol) portion-wise at 0° C. and stirred at rt for 1 h. Then a solution of 7-bromo-2-chloro-N,N-bis(4-methoxybenzyl)imidazo[2,1-f][1,2,4]triazin-4-amine (10 g, 20.45 mmol) in THF (20 mL) was added dropwise at 0° C., after addition, the mixture was warmed to 60° C. and stirred overnight. The mixture was quenched with saturated ammonium chloride solution (20 mL), extracted with DCM (100 mL×3). The combined organic layers were washed with brine, dried over $Na_2SO_4$, concentrated and purified by column chromatography (PE/EA=5:1~1:1) to give the title product (10.54 g, 95.25%) as yellow oil. MS: M/e 540 (M+1)+.

Step B: (4-(bis(4-methoxybenzyl)amino)-2-(pentan-2-yloxy)imidazo[2,1-f][1,2,4]triazin-7-yl)(6-(4-(dimethylamino)piperidin-1-yl)-5-methylpyridin-3-yl)methanol To a solution of 7-bromo-N,N-bis(4-methoxybenzyl)-2-(pentan-2-yloxy)imidazo[2,1-f][1,2,4]triazin-4-amine (200 mg, 0.37 mmol) in THF (5 mL), n-Butyllithium (0.35 ml, 0.56 mmol) was added dropwise at −78° C. and stirred for 1 h. Then a solution of 6-(4-(dimethylamino)piperidin-1-yl)-5-methylnicotinaldehyde (137 mg, 0.56 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the title product (187 mg, 71.21%) as yellow oil. MS: M/e 709 (M+1)+.

Step C: 7-((6-(4-(dimethylamino)piperidin-1-yl)-5-methylpyridin-3-yl)methyl)-2-(pentan-2-yloxy)imidazo[2,1-f][1,2,4]triazin-4-amine A mixture of (4-(bis(4-methoxybenzyl)amino)-2-(pentan-2-yloxy)imidazo[2,1-f][1,2,4]triazin-7-yl)(6-(4-(dimethylamino)piperidin-1-yl)-5-methylpyridin-3-yl)methanol (187 mg, 0.13 mmol) and triethylsilane (1 mL) in TFA (2 mL) was stirred at 90° C. overnight. The mixture was concentrated and purified with prep-HPLC to afford the title product (68 mg, 57.04%). $^1$H NMR (400 MHz, DMSO-d6) δ 9.71 (br.s, 1H), 8.19 (s, 1H), 8.14 (s, 1H), 8.08 (s, 1H), 7.57 (s, 1H), 7.39 (d, J=4.0 Hz, 1H), 4.99-4.94 (m, 1H), 4.09 (s, 2H), 3.53 (d, J=12.1 Hz, 2H), 3.33 (s, 1H), 2.82-2.65 (m, 8H), 2.21 (s, 3H), 2.06 (d, J=11.5 Hz, 2H), 1.78-1.58 (m, 3H), 1.58-1.47 (m, 1H), 1.45-1.27 (m, 2H), 1.25 (d, J=6.1 Hz, 3H), 0.88 (t, J=7.3 Hz, 3H) ppm. MS: M/e 453 (M+1)$^+$.

Compound B134: 7-((6-(4-((dimethylamino)methyl) piperidin-1-yl)-5-methylpyridin-3-yl)methyl)-2-(pentan-2-yloxy)imidazo[2,1-f][1,2,4]triazin-4-amine Step A: (4-(bis(4-methoxybenzyl)amino)-2-(pentan-2-yloxy)imidazo[2,1-f][1,2,4]triazin-7-yl)(6-(4-((dimethylamino)methyl)piperidin-1-yl)-5-methylpyridin-3-yl)methanol To a solution of 7-bromo-N,N-bis(4-methoxybenzyl)-2-(pentan-2-yloxy)imidazo[2,1-f][1,2,4]triazin-4-amine (200 mg, 0.37 mmol) in THF (5 mL), n-BuLi (0.35 ml, 0.56 mmol) was added dropwise at −78° C. and stirred for 1 h. Then a solution of 6-(4-((dimethylamino)methyl)piperidin-1-yl)-5-methylnicotinaldehyde (145 mg, 0.56 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to afford the title product (156 mg, 58.25%) as yellow oil. MS: M/e 723 (M+1)$^+$.

Step B: 7-((6-(4-((dimethylamino)methyl)piperidin-1-yl)-5-methylpyridin-3-yl)methyl)-2-(pentan-2-yloxy)imidazo[2,1-f][1,2,4]triazin-4-amine A mixture of (4-(bis(4-methoxybenzyl)amino)-2-(pentan-2-yloxy)imidazo[2,1-f][1,2,4]triazin-7-yl)(6-(4-((dimethylamino)methyl)piperidin-1-yl)-5-methylpyridin-3-yl)methanol (156 mg, 0.21 mmol) and triethylsilane (1 mL) in TFA (2 mL) was stirred at 90° C. overnight. The mixture was concentrated and purified with prep-HPLC to afford the title product (62 mg, 61.53%). $^1$H NMR (400 MHz, DMSO-d6) δ 9.28 (br.s, 1H), 8.18 (s, 1H), 8.11 (s, 1H), 8.07 (s, 1H), 7.63 (s, 1H), 7.38 (s, 1H), 4.98-4.94 (m, 1H), 4.10 (s, 2H), 3.45 (d, J=12.5 Hz, 2H), 3.03 (t, J=6.2 Hz, 2H), 2.85 (s, 2H), 2.81 (s, 3H), 2.80 (s, 3H), 2.21 (s, 3H), 1.97 (s, 1H), 1.80 (d, J=12.4 Hz, 2H), 1.69-1.59 (m, 1H), 1.58-1.48 (m, 1H), 1.46-1.28 (m, 4H), 1.25 (d, J=6.1 Hz, 3H), 0.88 (t, J=7.3 Hz, 3H) ppm. MS: M/e 476 (M+1)$^+$.

Compound B135: N2-butyl-7-((6-(4-(dimethylamino)piperidin-1-yl)-5-methylpyridin-3-yl)methyl) imidazo[2,1-f][1,2,4]triazine-2,4-diamine Step A: (4-(bis(4-methoxybenzyl)amino)-2-(butylamino)imidazo[2,1-f][1,2,4]triazin-7-yl)(6-(4-(dimethylamino)piperidin-1-yl)-5-methylpyridin-3-yl) methanol To a stirred solution of 7-bromo-N2-butyl-N4,N4-bis(4-methoxybenzyl)imidazo[2,1-f][1,2,4]triazine-2,4-diamine (160 mg, 0.3 mmol) in THF (10 mL), n-BuLi (1.6 M, 0.47 mL, 0.76 mmol) was added dropwise at −78° C. After stirred for an hour under $N_2$, a solution of 6-(4-(dimethylamino) piperidin-1-yl)-5-methylnicotinaldehyde (111.6 mg, 0.45 mmol) in THF (2 mL) was added dropwise at −78° C. and the reaction was stirred overnight. The reaction was quenched with aq. $NH_4Cl$, extracted with EtOAc (10 mL×3). The combined organic layers were washed with brine, dried over $Na_2SO_4$, concentrated and purified by prep-TLC ($CH_2Cl_2$/MeOH=10:1) to give the target compound (102 mg, 49%) as brown oil. MS: M/e 694 (M+1)$^+$.

Step B: N2-butyl-7-((6-(4-(dimethylamino)piperidin-1-yl)-5-methylpyridin-3-yl)methyl)imidazo[2,1-f][1,2,4]triazine-2,4-diamine A mixture of the product of Step A (102 mg, 0.147 mmol) in $Et_3SiH$/TFA (2 mL/5 mL) was stirred at 85° C. overnight. The reaction mixture was concentrated to give the residue, which was purified by prep-HPLC to give the target compound (32 mg, 72.9%). $^1$H NMR (400 MHz, DMSO-$d_6$) δ 9.60 (s, 1H), 8.09 (s, 1H), 7.84 (br.s, 2H), 7.53 (s, 1H), 7.44 (s, 1H), 6.63 (s, 1H), 4.04 (s, 2H), 3.49 (d, J=12.4 Hz, 2H), 3.36-3.26 (m, 1H), 3.17 (t, J=6.8 Hz, 2H), 2.79 (s, 3H), 3.77 (s, 3H), 2.73 (t, J=12.4 Hz, 2H), 2.19 (s, 3H), 2.08-2.00 (m, 2H), 1.72-1.64 (m, 2H), 1.60-1.45 (m, 2H), 1.39-1.24 (m, 2H), 0.89 (t, J=7.3 Hz, 3H) ppm. MS: M/e 438 (M+1)$^+$.

Compound B136: 7-((6-(3-aminoazetidin-1-yl)-5-methylpyridin-3-yl)methyl)-2-butoxyimidazo[2,1-f] [1,2,4]triazin-4-amine Compound B136 was synthesized starting from the corresponding starting materials according the similar procedures described as those of Compound B8. $^1$H NMR (400 MHz, DMSO-d6) δ 8.39 (s, 1H), 8.34 (s, 2H), 8.17 (s, 1H), 8.11 (s, 1H), 7.97 (s, 1H), 7.55 (d, J=14.9 Hz, 1H), 7.32 (s, 1H), 4.44 (d, J=8.5 Hz, 2H), 4.28-3.99 (m, 7H), 2.17 (s, 3H), 1.74-1.63 (m, 2H), 1.48-1.35 (m, 2H), 0.94 (t, J=7.2 Hz, 3H) ppm. MS: M/e 383 (M+1)$^+$.

Compound B137: 7-((6-(4-((dimethylamino)methyl) piperidin-1-yl)-5-methylpyridin-3-yl)methyl)-N2-(pentan-2-yl)imidazo[2,1-f][1,2,4]triazine-2,4-diamine Step A: 7-bromo-N4,N$^4$-bis(4-methoxybenzyl)-N2-(pentan-2-yl)imidazo[2,1-f][1,2,4]triazine-2,4-diamine To a stirred solution of 7-bromo-2-chloro-N,N-bis(4-methoxybenzyl)imidazo[2,1-f][1,2,4]triazin-4-amine (1 g, 2.05 mmol) in NMP (10 mL), pentan-2-amine (1 g, 11.5 mmol) and DIEA (400 mg, 3.1 mmol) were added. The reaction mixture was sealed and stirred at 220° C. for 6 h. The mixture was cooled down to rt, added $H_2O$ (20 mL) and extracted with EtOAc (10 ml×3). The combined organic phase was washed with brine, dried over $Na_2SO_4$ and concentrated in vacuo. The crude product was purified by column chromatography to give the product (250 mg, 22.7%) as white solids. MS: M/e 539 (M+1)$^+$.

Step B: (4-(bis(4-methoxybenzyl)amino)-2-(pentan-2-ylamino)imidazo[2,1-f][1,2,4]triazin-7-yl)(4-(4-((dimethylamino)methyl)piperidin-1-yl)-3-methylphenyl)methanol To a stirred solution of 7-bromo-N$^4$,N$^4$-bis(4-methoxybenzyl)-N$^2$-(pentan-2-yl)imidazo[2,1-f][1,2,4]triazine-2,4- diamine (110 mg, 0.2 mmol) in THF (8 mL), cooled to −78° C. and under a nitrogen atmosphere, n-BuLi (1.6 M in hexane, 0.56 mmol, 0.35 mL) was added dropwise. After stirring for 50 mins, a solution of 6-(4-((dimethylamino)methyl)piperidin-1-yl)-5-methylnicotinaldehyde (90 mg, 0.34 mmol) in THF (2 mL) was slowly added. The reaction mixture was slowly warmed up to rt and stirred for 2 h. The reaction mixture was poured into saturated ammonium chloride solution and extracted by EA (15 mL×3). The combined organic layers were washed with brine, dried over $Na_2SO_4$, concentrated in vacuo. The crude product was purified by column chromatography to give the title product (80 mg, 55.6%). MS: M/e 722 $(M+1)^+$.

Step C: 7-((6-(4-((dimethylamino)methyl)piperidin-1-yl)-5-methylpyridin-3-yl)methyl)-$N^2$-(pentan-2-yl)imidazo[2,1-f][1,2,4]triazine-2,4-diamine A solution of (4-(bis(4-methoxybenzyl)amino)-2-(pentan-2-ylamino)imidazo[2,1-f][1,2,4]triazin-7-yl)(4-(4-((dimethylamino)methyl)piperidin-1-yl)-3-methylphenyl)methanol (80 mg, 0.11 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (20 mg, 38.8%). $^1$H NMR (400 MHz, DMSO-d6) δ 9.40 (br.s, 1H), 8.08 (s, 1H), 7.90 (s, 2H), 7.60 (s, 1H), 7.51 (s, 1H), 6.47 (br.s, 1H), 4.06 (s, 2H), 3.79 (s, 1H), 3.42 (d, J=11.5 Hz, 2H), 3.03 (s, 2H), 2.91-2.75 (m, 8H), 2.21 (s, 3H), 1.96 (s, 1H), 1.80 (d, J=12.1 Hz, 2H), 1.52-1.48 (m, 1H), 1.46-1.33 (m, 5H), 1.10 (d, J=6.3 Hz, 3H), 0.85 (t, J=6.8 Hz, 3H) ppm. MS: M/e 466 $(M+1)^+$.

Compound B138: 7-((6-(4-(dimethylamino)piperidin-1-yl)-5-methylpyridin-3-yl)methyl)-$N^2$-(pentan-2-yl)imidazo[2,1-f][1,2,4]triazine-2,4-diamine Step A: (4-(bis(4-methoxybenzyl)amino)-2-(pentan-2-ylamino)imidazo[2,1-f][1,2,4]triazin-7-yl)(4-(4-(dimethylamino)piperidin-1-yl)-3-methylphenyl)methanol To a stirred solution of 7-bromo-$N^4$,$N^4$-bis(4-methoxybenzyl)-$N^2$-(pentan-2-yl)imidazo[2,1-f][1,2,4]triazine-2,4-diamine (200 mg, 0.37 mmol) in THF (8 mL), cooled to −78° C. and under a nitrogen atmosphere, n-BuLi (1.6 M in hexane, 0.93 mmol, 0.58 mL) was added dropwise. After stirring for 50 mins, a solution of 6-(4-(dimethylamino)piperidin-1-yl)-5-methylnicotinaldehyde (162 mg, 0.56 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phase was washed with brine, dried over $Na_2SO_4$, concentrated in vacuo. The crude product was purified by column chromatography to give the title product (100 mg, 0.38%). MS: M/e 708 $(M+1)^+$.

Step C: 7-((6-(4-(dimethylamino)piperidin-1-yl)-5-methylpyridin-3-yl)methyl)-N2-(pentan-2-yl)imidazo[2,1-f][1,2,4]triazine-2,4-diamine A solution of (4-(bis(4-methoxybenzyl)amino)-2-(pentan-2-ylamino)imidazo[2,1-f][1,2,4]triazin-7-yl)(4-(4-(dimethylamino)piperidin-1-yl)-3-methylphenyl)methanol (100 mg, 0.14 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (70 mg, 88%). $^1$H NMR (400 MHz, DMSO-d6) δ 9.60 (br.s, 1H), 8.07 (s, 1H), 7.81 (br.s, 2H), 7.51 (s, 2H), 6.42 (s, 1H), 4.04 (s, 2H), 3.80 (s, 1H), 3.48 (d, J=10.6 Hz, 2H), 3.30 (s, 1H), 2.75 (m, 8H), 2.19 (s, 3H), 2.04 (d, J=10.3 Hz, 2H), 1.71 (d, J=10.7 Hz, 2H), 1.51 (s, 1H), 1.43-1.17 (m, 3H), 1.10 (d, J=5.5 Hz, 3H), 0.85 (s, 3H) ppm. MS: M/e 452 $(M+1)^+$.

Compound B139: 7-((5-methyl-6-(piperazin-1-yl)pyridin-3-yl)methyl)-N2-propylimidazo[2,1-f][1,2,4]triazine-2,4-diamine Step A: 7-bromo-N4,N4-bis(4-methoxybenzyl)-N2-propylimidazo[2,1-f][1,2,4]triazine-2,4-diamine To a stirred solution of 7-bromo-2-chloro-N,N-bis(4-methoxybenzyl)imidazo[2,1-f][1,2,4]triazin-4-amine (1 g, 2.05 mmol) in NMP (5 mL), propan-1-amine (1 g, 12.8 mmol) and DIEA (1 g, 7.8 mmol) were added. The reaction mixture was sealed and stirred at 230° C. for 6 h. The mixture was cooled down to rt, added $H_2O$ (20 mL) and extracted with EtOAc (10 ml×3). The combined organic phases were washed with brine, dried over $Na_2SO_4$ and concentrated in vacuo. The crude product was purified by column chromatography to give the product (700 mg, 67%) as white solids. MS: M/e 511 $(M+1)^+$.

Step B: tert-butyl 4-(5-((4-(bis(4-methoxybenzyl)amino)-2-(propylamino)imidazo[2,1-f][1,2,4]triazin-7-yl)(hydroxy)methyl)-3-methylpyridin-2-yl)piperazine-1-carboxylate To a stirred solution of 7-bromo-N4,N4-bis(4-methoxybenzyl)-N2-propylimidazo[2,1-f][1,2,4]triazine-2,4-diamine (200 mg, 0.39 mmol) in THF (8 mL), cooled to −78° C. and under a nitrogen atmosphere, n-BuLi (1.6 M in hexane, 0.59 mmol, 0.37 mL) was added dropwise. After stirring for 50 mins, a solution of product of Step A (180 mg, 0.39 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phase was washed with brine, dried over $Na_2SO_4$, concentrated in vacuo. The crude product was purified by column chromatography to give the title product (120 mg, 41.8%). MS: M/e 738 $(M+1)^+$.

Step C: 7-((5-methyl-6-(piperazin-1-yl)pyridin-3-yl)methyl)-N2-propylimidazo[2,1-f][1,2,4]triazine-2,4-diamine A solution of product of Step B (120 mg, 0.163 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (35 mg, 56.4%). $^1$H NMR (400 MHz, DMSO-d6) δ 8.70 (br.s, 2H), 8.12 (s, 1H), 7.78 (br.s, 2H), 7.53 (s, 1H), 7.44-7.41 (m, 1H), 6.59

(br.s, 1H), 4.05 (s, 2H), 3.27-3.08 (m, 8H), 3.13 (s, 2H), 2.21 (s, 3H), 1.61-1.43 (m, 2H), 0.88 (t, J=7.0 Hz, 3H) ppm. MS: M/e 382 $(M+1)^+$.

Compound B140: 2-(hexan-3-yloxy)-7-((5-methyl-6-(piperazin-1-yl)pyridin-3-yl)methyl)imidazo[2,1-f][1,2,4]triazin-4-amine Step A: 7-bromo-2-(hexan-3-yloxy)-N,N-bis(4-methoxybenzyl)imidazo[2,1-f][1,2,4]triazin-4-amine To a solution of hexan-3-ol (314 mg, 3.07 mmol) in THF (5 mL), NaH (60%, 164 mg, 4.1 mmol) was added at 0 degrees. The reaction mixture was stirred at room temperature for 20 minutes, then 7-bromo-2-chloro-N,N-bis(4-methoxybenzyl)Imidazo[2,1-f][1,2,4]triazin-4-amine (1000 mg, 2.05 mmol) was added and the resulting mixture was stirred overnight at 70° C. An aqueous ammonium chloride solution was added and the mixture was extracted with ethyl acetate. The combined organic extracts were dried over sodium sulfate, filtered and evaporated. Purification by prep-TLC (silica gel, EA:PE=1:10) afforded the title product (450 mg) as yellow oil. MS: m/e554 $(M+1)^+$.

Step B: tert-butyl 4-(5-((4-(bis(4-methoxybenzyl)amino)-2-(hexan-3-yloxy)imidazo[2,1-f][1,2,4]triazin-7-yl)(hydroxy)methyl)-3-methylpyridin-2-yl)piperazine-1-carboxylate To a solution of 7-bromo-2-(hexan-3-yloxy)-N,N-bis(4-methoxybenzyl)imidazo[2,1-f][1,2,4]triazin-4-amine (250 mg, 0.45 mmol) in THF (4 mL), a solution of n-BuLi (1.6M, 0.69 mL, 1.1 mmol) was added dropwise maintaining the temperature between −75~−65° C. After 1 h, a suspension of the tert-butyl 4-(5-formyl-3-methylpyridine-2-yl)piperazine-1-carboxylate (207 mg, 0.68 mmol) in THF (2 mL) was added dropwise. The resulting mixture was stirred at −70° C. for 2 h and then warmed to room temperature overnight. The reaction was quenched with saturated $NH_4Cl$ solution, extracted with EtOAc (20 mL×3), washed with brine, dried over $Na_2SO_4$, filtered, and concentrated. The residue was purified by prep-TLC to give the target compound (300 mg, crude yellow oil). MS: M/e 781 $(M+1)^+$.

Step C: 2-(hexan-3-yloxy)-7-((5-methyl-6-(piperazin-1-yl)pyridin-3-yl)methyl)imidazo[2,1-f][1,2,4]triazin-4-amine To a mixture of the product of Step B (250 mg, crude) in TFA (4 mL), $Et_3SiH$ (4 mL) was added and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated and the residue was purified by prep-HPLC to give the target compound (12.5 mg, 15% for two steps). TH NMR (400 MHz, DMSO-d6) δ 8.67 (br.s, 2H), 8.13-8.04 (m, 3H), 7.46 (s, 1H), 7.36 (s, 1H), 4.88 (br.s, 1H), 4.07 (s, 2H), 3.20 (br.s, 8H), 2.19 (s, 3H), 1.62-1.53 (m, 4H), 1.37-1.24 (m, 2H), 0.86 (t, J=7.0 Hz, 6H) ppm. MS: M/e 425 $(M+1)^+$.

Compound B141: 2-butyl-7-((5-methyl-6-(piperazin-1-yl)pyridin-3-yl)methyl)imidazo[2,1-f][1,2,4]triazin-4-amine Step A: 2-butyl-N,N-bis(4-methoxybenzyl)imidazo[2,1-f][1,2,4]triazin-4-amine A mixture of 2-chloro-N,N-bis(4-methoxybenzyl)imidazo[2,1-f][1,2,4]triazin-4-amine (0.5 g, 1.22 mmol), butylboronic acid (0.37 g, 3.63 mmol), sodium hydroxide (0.098 g, 2.45 mmol) and $Pd(PPh_3)_4$ (0.14 g, 0.12 mmol) in dioxane (10 ml) and $H_2O$ (2 ml) was stirred at 80° C. under $N_2$ overnight. After completion, the mixture was diluted with EA (30 ml) and then washed with brine (10 ml). The organic layer was dried over $Na_2SO_4$ and then concentrated under reduced pressure to remove solvent. The residue was purified by flash column chromatography with 0-15% EA in PE to afford the product (0.16 g, 30%) as a colorless oil. MS: M/e 432 $(M+1)^+$.

Step B: tert-butyl 4-(5-((4-(bis(4-methoxybenzyl)amino)-2-butylimidazo[2,1-f][1,2,4]triazin-7-yl)(hydroxy)methyl)-3-methylpyridin-2-yl)piperazine-1-carboxylate To a stirred solution of 2-butyl-N,N-bis(4-methoxybenzyl)imidazo[2,1-f][1,2,4]triazin-4-amine (0.22 g, 0.51 mmol) in THF (15 ml) at −78° C. under $N_2$, n-BuLi (1.6M, 0.48 ml, 0.77 mmol) was added dropwise. The solution was stirred at −78° C. for 30 min. A solution of tert-butyl 4-(5-formyl-3-methylpyridin-2-yl)piperazine-1-carboxylate (230 mg, 0.75 mmol) in THF (2 ml) was added at −78° C. dropwise. The resulting solution was warmed to rt naturally and then stirred at rt for 1 h. After completion, the solution was quenched with $H_2O$ (10 ml) and then extracted with DCM (15 ml×2). The organic phase was washed with $H_2O$ (10 ml), dried and concentrated under reduced pressure to afford crude product as a red oil, which was used directly for the next step without further purification. MS: M/e 737 $(M+1)^+$.

Step C: 2-butyl-7-((5-methyl-6-(piperazin-1-yl)pyridin-3-yl)methyl)imidazo[2,1-f][1,2,4]triazin-4-amine A mixture of product of Step B (crude), TFA (6 ml) and triethylsilane (2 ml) was stirred at 80° C. overnight. After completion, the reaction mixture was concentrated under reduced pressure to remove TFA. The residue was diluted with EA (20 ml) and then washed with aq. $NaHCO_3$ (sat., 15 ml) twice. The organic phase was dried over $Na_2SO_4$ and concentrated under reduced pressure. The residue was purified by prep-TLC and then prep-HPLC to afford the product (105 mg). $^1$H NMR (400 MHz, DMSO-d6) δ 8.76 (br.s, 2H), 8.22 (br.s, 2H), 8.11 (s, 1H), 7.53 (s, 1H), 7.45-7.32 (m, 1H), 4.13 (s, 2H), 3.22 (br.s, 8H), 2.60 (t, J=8 Hz, 2H), 2.21 (s, 3H), 1.73-1.65 (m, 2H), 1.35-1.27 (m, 2H), 0.89 (t, J=8 Hz, 3H) ppm. MS: M/e 381 $(M+1)^+$.

Compound B142: N-(1-(5-((4-amino-2-butoxyimidazo[2,1-f][1,2,4]triazin-7-yl)methyl)-3-methylpyridin-2-yl)piperidin-4-yl)-2-(dimethylamino)acetamidea A mixture of 7-((6-(4-aminopiperidin-1-yl)-5-methylpyridin-3-yl)methyl)-2-butoxyimidazo[2,1-f][1,2,4]triazin-4-amine (60 mg, 0.146 mmol), dimethylglycine (19 mg, 1.77 mmol) and DIPEA (38 mg, 0.292 mmol) in DCM (2 mL) was stirred at room temperature for 2 hours, then the reaction was quenched with $H_2O$, extracted with DCM (10 mL×3), the combined layers were washed with brine, dried over $Na_2SO_4$ and concentrated, the residue was purified by prep-HPLC to give the product (5 mg, 21%). TH NMR (400 MHz, $CD_3OD$) δ 8.10-7.89 (m, 2H), 7.46 (s, 1H), 4.29 (t, J=6.4 Hz, 2H), 4.25 (s, 2H), 4.03-3.95 (m, 1H), 3.94 (s, 2H), 3.71-3.62 (m, 2H), 3.26-3.12 (m, 2H), 2.94 (s, 6H), 2.38 (s, 3H), 2.08 (d, J=11.9 Hz, 2H), 1.83-1.60 (m, 4H), 1.55-1.47 (m, 2H), 0.98 (t, J=7.4 Hz, 3H) ppm. MS: M/e 496 $(M+1)^+$.

Compound B143: 2-(heptan-4-yloxy)-7-((5-methyl-6-(piperazin-1-yl)pyridin-3-yl)methyl)imidazo[2,1-f][1,2,4]triazin-4-amine Step A: 7-bromo-2-(heptan-4-yloxy)-N,N-bis(4-methoxybenzyl)imidazo[2,1-f][1,2,4]triazin-4-amine To a solution of heptan-4-ol (174 mg, 1.5 mmol) in THF (5 mL), NaH (60%, 80 mg, 2.0 mmol) was added at 0° C. The reaction mixture was stirred at room temperature for 20 minutes, then 7-bromo-2-chloro-N,N-bis(4-methoxybenzyl)imidazo[2,1-f][1,2,4]triazin-4-amine (487 mg, 1.0 mmol) was added and the resulting mixture was stirred overnight at 70° C. An aqueous ammonium chloride solution was added and the mixture was extracted with ethyl acetate. The combined organic extracts were dried over sodium sulfate, filtered and evaporated. Purification by prep-TLC (silica gel, EA:PE=1:10) afforded the title product (400 mg, 67%) as yellow oil. MS: m/e 568 $(M+1)^+$.

Step B: tert-butyl tert-butyl 4-(5-((4-(bis(4-methoxybenzyl)amino)-2-(heptan-4-yloxy)imidazo[2,1-f][1,2,4]triazin-7-yl)(hydroxy)methyl)-3-methylpyridin-2-yl)piperazine-1-carboxylate To a solution of 7-bromo-2-(heptan-4-yloxy)-N,N-bis(4-methoxybenzyl)imidazo[2,1-f][1,2,4]triazin-4-amine (200 mg, 0.35 mmol) in THF (4 mL) was added a solution of n-BuLi (1.6 M, 0.55 mL, 0.88 mmol) dropwise maintaining the temperature between −75~−65° C. After 1 h, a suspension of the tert-butyl 4-(5-formyl-3-methylpyridin-2-yl)piperazine-1-carboxylate (161 mg, 0.53 mmol) in THF (2 mL) was added dropwise. The resulting mixture was stirred at −70° C. for 2 h and then warmed to room temperature overnight. The reaction was quenched with saturated $NH_4Cl$ solution, extracted with EtOAc (20 mL*3), washed with brine, dried over $Na_2SO_4$, filtered, and concentrated. The residue was purified by prep-TLC to give the target compound (240 mg, crude yellow oil). MS: M/e 795 $(M+1)^+$.

Step C: 2-(heptan-4-yloxy)-7-((5-methyl-6-(piperazin-1-yl)pyridin-3-yl)methyl)imidazo[2,1-f][1,2,4]triazin-4-amine To a mixture of the product of Step B (240 mg, crude) in TFA (2 mL), $Et_3SiH$ (2 mL) was added and the resulting mixture was stirred at 85° C. for 4 hours. The mixture was cooled to room temperature and concentrated to dryness. To the residue was added TFA (4 mL) and the reaction was heated at 80° C. overnight. The mixture was concentrated and the residue was purified by prep-HPLC to give the target compound (8.2 mg, 6% for two steps). $^1$H NMR (400 MHz, DMSO-d6) δ 8.67 (br.s, 2H), 8.12 (s, 1H), 8.09 (s, 1H), 8.03 (s, 1H), 7.46 (s, 1H), 7.36 (s, 1H), 4.97 (br.s, 1H), 4.07 (s, 2H), 3.25-3.0 (m, 8H), 2.23 (s, 3H), 1.59-1.50 (m, 4H), 1.43-1.25 (m, 4H), 0.86 (t, J=8.0, 6H) ppm. MS: m/e 439 $(M+1)^+$.

Compound B144: 7-((6-(4-(aminomethyl)piperidin-1-yl)-5-methylpyridin-3-yl)methyl)-2-butoxyimidazo[2,1-f][1,2,4]triazin-4-amine Step A: tert-butyl ((1-(5-formyl-3-methylpyridin-2-yl)piperidin-4-yl)methyl)carbamate A mixture of 6-chloro-5-methylnicotinaldehyde (500 mg, 3.21 mmol), tert-butyl (piperidin-4-ylmethyl)carbamate (792 mg, 3.70 mmol) and DIEA (829 mg, 6.43 mmol) in DMA (15 ml) was stirred at 100° C. under $N_2$ overnight. After completion, the mixture was poured into water and then extracted with EA (20 ml) twice. The organic layers were washed with water, dried and concentrated under reduced pressure. The resulting residue was purified by flash column chromatography with 20%-50% EA in PE to afford product (950 mg, 89%) as a white solid. MS: M/e 334 $(M+1)^+$.

Step B: tert-butyl ((1-(5-((4-(bis(4-methoxybenzyl)amino)-2-butoxyimidazo[2,1-f][1,2,4]triazin-7-yl)(hydroxy)methyl)-3-methylpyridin-2-yl)piperidin-4-yl)methyl)carbamate To a stirred solution of 7-bromo-2-butoxy-N,N-bis(4-methoxybenzyl)imidazo[2,1-f][1,2,4]triazin-4-amine (0.2 g, 0.38 mmol) in THF (15 ml) at −78° C. under $N_2$, n-BuLi (1.6M, 0.60 ml, 0.96 mmol) was added dropwise. The solution was stirred at −78° C. for 30 min. A solution of tert-butyl ((1-(5-formyl-3-methylpyridin-2-yl)piperidin-4-yl)methyl)carbamate (190 mg, 0.57 mmol) in THF (2 ml) was added at −78° C. dropwise. The resulting solution was warmed to rt naturally and then stirred at rt for 1 h. After completion, the solution was quenched with $H_2O$ (10 ml) and then extracted with DCM (15 ml×2). The organic phase was washed with $H_2O$ (10 ml), dried and concentrated under reduced pressure to afford crude product as a yellow semi-solid, which was used directly for the next step without further purification. MS: M/e 781 $(M+1)^+$.

Step C: 7-((6-(4-(aminomethyl)piperidin-1-yl)-5-methylpyridin-3-yl)methyl)-2-butoxyimidazo[2,1-f][1,2,4]triazin-4-amine A mixture of tert-butyl ((1-(5-((4-(bis(4-methoxybenzyl)amino)-2-butoxyimidazo[2,1-f][1,2,4]triazin-7-yl)(hydroxy)methyl)-3-methylpyridin-2-yl)piperidin-4-yl)methyl)carbamate (crude), TFA (6 ml) and triethylsilane (2 ml) was stirred at 80° C. overnight. After completion, the reaction mixture was concentrated under reduced pressure to remove TFA. The residue was diluted with EA (20 ml) and then washed with aq. $NaHCO_3$ (sat., 15 ml) twice. The organic phase was dried over $Na_2SO_4$ and concentrated under reduced pressure. The residue was purified by prep-TLC and then prep-HPLC to afford the product (62.23 mg). $^1$H NMR (400 MHz, DMSO-d6) δ 8.15 (s, 1H), 8.07 (s, 2H), 7.72 (s, 3H), 7.63-7.42 (m, 1H), 7.33 (s, 1H), 4.21 (t, J=8 Hz, 2H), 4.06 (s, 2H), 3.45-3.35 (m, 2H), 2.80-2.74 (m, 2H), 2.73-2.64 (m, 2H), 2.19 (s, 3H), 1.83-1.75 (m, 2H), 1.73-1.62 (m, 3H), 1.47-1.26 (m, 4H), 0.93 (t, J=8 Hz, 3H) ppm. MS: M/e 425 $(M+1)^+$.

Compound B145: (S)-1-(4-(5-((4-amino-2-(sec-butoxy)imidazo[2,1-f] [1,2,4]triazin-7-yl)methyl)-3-methylpyridin-2-yl)piperazin-1-yl)-2-(dimethylamino)ethan-1-one A solution of (S)-2-(sec-butoxy)-7-((5-methyl-6-(piperazin-1-yl)pyridin-3-yl) methyl)imidazo[2,1-f][1,2,4]triazin-4-amine (280 mg, 0.73 mmol), dimethylglycine (91 mg, 0.88 mmol), HATU (416 mg, 1.1 mmol) and DIEA (188 mg, 0.46 mmol) in DMF (10 mL) was stirred at rt for 2 hrs. The reaction mixture was added with water (10 mL), extracted with ethyl acetate (10 mL) and washed with brine (10 mL). The organic layer was dried with $Na_2SO_4$, filtered and concentrated to get the crude product, which was purified by Combi-Flash (DCM:$NH_3$·MeOH=30%) to get the product (115 mg, 34%). $^1$H NMR (400 MHz, DMSO-d6) δ 8.12 (s, 1H), 8.08 (s, 1H), 8.00 (s, 1H), 7.45 (s, 1H), 7.33 (s, 1H), 4.90-4.87 (m, 1H), 4.05 (s, 2H), 3.59 (br.s, 4H), 3.44 (s, 2H), 3.02 (s, 2H), 2.96 (s, 2H), 2.36 (s, 6H), 2.21 (s, 3H), 1.62-1.57 (m, 2H), 1.24 (d, J=8.0 Hz, 3H), 0.90 (t, J=8.0 Hz, 3H) ppm. MS: M/e 482 $(M+1)^+$.

Compound B146: (S)-1-(4-(5-((4-amino-2-(sec-butoxy)imidazo[2,1-f][1,2,4]triazin-7-yl)methyl)-3-methylpyridin-2-yl)piperazin-1-yl)-2-(methylamino)ethan-1-one Step A: tert-butyl (S)-(2-(4-(5-((4-amino-2-(sec-butoxy)imidazo[2,1-f][1,2,4]triazin-7-yl)methyl)-3-methylpyridin-2-yl)piperazin-1-yl)-2-oxoethyl)(methyl)carbamate A solution of (S)-2-(sec-butoxy)-7-((5-methyl-6-(piperazin-1-yl)pyridin-3-yl) methyl)imidazo[2,1-f][1,2,4]triazin-4-amine (400 mg, 1.0 mmol), N-(tert-butoxy carbonyl)-N-methylglycine (227 mg, 1.2 mmol), HATU (570 mg, 1.5 mmol) and DIEA (258 mg, 2.0 mmol) in DMF (10 mL) was stirred at rt for 2 hrs. The reaction mixture was added with water (10 mL), extracted with ethyl acetate (10 mL) and washed with brine (10 mL). The organic layer was dried with $Na_2SO_4$, filtered and concentrated to get the crude product, which was used in the next step (500 mg, 87%). MS: M/e 568 $(M+1)^+$.

Step B: (S)-1-(4-(5-((4-amino-2-(sec-butoxy)imidazo[2,1-f][1,2,4]triazin-7-yl)methyl)-3-methylpyridin-2-yl)piperazin-1-yl)-2-(methylamino)ethan-1-one To a solution of tert-butyl (S)-(2-(4-(5-((4-amino-2-(sec-butoxy)imidazo[2,1-f][1,2,4]triazin-7-yl)methyl)-3-methylpyridin-2-yl)piperazin-1-yl)-2-oxoethyl)(methyl)carbamate (500 mg, 0.9 mmol) in EA (8 mL), HCl/EA (2M, 3 mL) was added. The solution was stirred at rt for 3 hrs. After concentration, the residue was dissolved in DCM (10 mL) and washed with $NaHCO_3$ (10 mL). The organic layer was dried with $Na_2SO_4$, filtered and concentrated to get the crude product, which was further purified by Combi-Flash (DCM: $NH_3$·MeOH=35%) to get the pure product (160 mg, 39%). $^1$H NMR (400 MHz, DMSO-d6) δ 8.11 (s, 1H), 8.07 (s, 1H), 8.00 (s, 1H), 7.45 (s, 1H), 7.32 (s, 1H), 4.92-4.83 (m, 1H), 4.05 (s, 2H), 3.58-3.52 (m, 4H), 3.33-3.31 (m, 2H), 3.00-2.95 (m, 4H), 2.28 (s, 3H), 2.20 (s, 3H), 1.62-1.59 (m, 2H), 1.23 (d, J=4.0 Hz, 3H), 0.89 (t, J=8.0 Hz, 3H) ppm. MS: M/e 468 $(M+1)^+$.

Compound B147: (S)-7-((6-(4-((dimethylamino)methyl)piperidin-1-yl)-5-methylpyridin-3-yl)methyl)-N2-(pentan-2-yl)imidazo[2,1-f][1,2,4]triazine-2,4-diamine Step A: (S)-7-bromo-N4,N4-bis(4-methoxybenzyl)-N2-(pentan-2-yl)imidazo[2,1-f][1,2,4]triazine-2,4-diamine To a stirred solution of 7-bromo-2-chloro-N,N-bis(4-methoxybenzyl)imidazo[2,1-f][1,2,4]triazin-4-amine (800 mg, 1.65 mmol) in NMP (5 mL), (S)-pentan-2-amine (1 g, 8.1 mmol) and DIEA (1 g, 8 mmol) were added. The reaction mixture was sealed and stirred at 230° C. for 6 h. The mixture was cooled down to rt, added $H_2O$ (20 mL) and extracted with EtOAc (10 ml×3). The combined organic phase was washed with brine, dried over $Na_2SO_4$ and concentrated in vacuo. The crude product was purified by column chromatography to give the product (485 mg, 54.6%) as white solids. MS: M/e 539 $(M+1)^+$.

Step B: (4-(bis(4-methoxybenzyl)amino)-2-(((S)-pentan-2-yl)amino)imidazo[2,1-f][1,2,4]triazin-7-yl)(6-(4-((dimethylamino)methyl)piperidin-1-yl)-5-methylpyridin-3-yl)methanol To a stirred solution of (S)-7-bromo-N4,N4-bis(4-methoxybenzyl)-N2-(pentan-2-yl)imidazo[2,1-f][1,2,4]triazine-2,4-diamine (210 mg, 0.39 mmol) in THF (8 mL), cooled to −78° C. and under a nitrogen atmosphere, n-BuLi (1.6 M in hexane, 0.56 mmol, 0.35 mL) was added dropwise. After stirring for 50 mins, a solution of 6-(4-((dimethylamino)methyl)piperidin-1-yl)-5-methylnicotinaldehyde (179 mg, 0.58 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (120 mg, 42.8%). MS: M/e 722 $(M+1)^+$.

Step C: (S)-7-((6-(4-((dimethylamino)methyl)piperidin-1-yl)-5-methylpyridin-3-yl)methyl)-N2-(pentan-2-yl)imidazo[2,1-f][1,2,4]triazine-2,4-diamine A solution of (4-(bis(4-methoxybenzyl)amino)-2-(((S)-pentan-2-yl)amino)imidazo[2,1-f][1,2,4]triazin-7-yl)(6-(4-((dimethylamino)methyl)piperidin-1-yl)-5-methylpyridin-3-yl)methanol (120 mg, 0.166 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (5 mg, 6.2%). $^1$H NMR (400 MHz, DMSO-d6) δ 8.04 (s, 1H), 7.47 (br.s, 2H), 7.41 (s, 1H), 7.14 (s, 1H), 5.98 (d, J=8.4 Hz, 1H), 3.96 (s, 2H), 3.81 (br.s, 1H), 3.28-3.23 (m, 4H), 2.64 (t, J=11.9 Hz, 2H), 2.24-2.03 (m, 8H), 1.75 (d, J=12.3 Hz, 2H), 1.61-1.48 (m, 2H), 1.43-1.19 (m, 6H), 1.10 (d, J=6.1 Hz, 3H), 0.87 (t, J=7.0 Hz, 3H) ppm. MS: M/e 486 $(M+1)^+$.

Compound B148: (S)-7-((5-methyl-6-(piperazin-1-yl)pyridin-3-yl)methyl)-N2-(pentan-2-yl)imidazo[2,1-f][1,2,4]triazine-2,4-diamine Step A: tert-butyl 4-(5-((4-(bis(4-methoxybenzyl)amino)-2-(((S)-pentan-2-yl)amino)imidazo[2,1-f][1,2,4]triazin-7-yl)(hydroxy)methyl)-3-methylpyridin-2-yl)piperazine-1-carboxylate To a stirred solution of (S)-7-bromo-N4,N4-bis(4-methoxybenzyl)-N2-(pentan-2-yl)imidazo[2,1-f][1,2,4]triazine-2,4-diamine (180 mg, 0.34 mmol) in THF (8 mL), cooled to −78° C. and under a nitrogen atmosphere, n-BuLi (1.6 M in hexane, 0.75 mmol, 0.48 mL) was added dropwise. After stirring for 50 mins, a solution of tert-butyl 4-(5-formyl-3-methylpyridin-2-yl)piperazine-1-carboxylate (153 mg, 0.5 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phase was washed with brine, dried over $Na_2SO_4$, concentrated in vacuo. The crude product was purified by column chromatography to give the title product (110 mg, 46.1%). MS: M/e 766 $(M+1)^+$.

Step B: (S)-7-((5-methyl-6-(piperazin-1-yl)pyridin-3-yl)methyl)-N2-(pentan-2-yl)imidazo[2,1-f][1,2,4]triazine-2,4-diamine A solution of tert-butyl 4-(5-((4-(bis(4-methoxybenzyl)amino)-2-(((S)-pentan-2-yl)amino)imidazo[2,1-f][1,2,4]triazin-7-yl)(hydroxy)methyl)-3-methylpyridin-2-yl)piperazine-1-carboxylate (110 mg, 0.14 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (40 mg, 67.8%). $^1$H-NMR (400 MHz, DMSO-d6) δ 8.70 (br.s, 2H), 8.11 (s, 1H), 7.64 (s, 1H), 7.50 (s, 1H), 7.26 (s, 1H), 6.19 (s, 1H), 4.02 (s, 2H), 3.80 (s, 1H), 3.19 (br.s, 8H), 2.20 (s, 3H), 1.56-1.47 (m, 1H), 1.43-1.21 (m, 3H), 1.09 (d, J=5.9 Hz, 3H), 0.86 (t, J=6.8 Hz, 3H) ppm. MS: M/e 410 $(M+1)^+$.

Compound B149: 1-(4-(5-((4-amino-2-(pentan-2-ylamino)imidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-(pentan-2-ylamino)imidazo[2,1-f][1,2,4]triazin-7-yl)methyl)-3-methylpyridin-2-yl)piperazin-1-yl)-2-oxoethyl)(methyl)carbamate To a stirred solution of 7-((5-methyl-6-(piperazin-1-yl)pyridin-3-yl)methyl)-N2-(pentan-2-yl)imidazo[2,1-f][1,2,4]triazine-2,4-diamine (80 mg, 0.2 mmol) in DMF (5 mL), N-(tert-butoxycarbonyl)-N-methylglycine (60 mg, 0.316 mmol), HATU (116 mg, 0.3 mmol) and DIEA (51 mg, 0.395 mmol) were added. The reaction mixture was stirred at Rt overnight. The mixture was poured into $H_2O$ (50 mL) and extracted with EtOAc (10 ml×3). The combined organic phase was washed with brine, dried over $Na_2SO_4$ and concentrated in vacuo. The crude product was purified by column chromatography to give the product (60 mg, 51.7%) as white solids. MS: M/e 581 $(M+1)^+$.

Step B: 1-(4-(5-((4-amino-2-(pentan-2-ylamino)imidazo[2,1-f][1,2,4]triazin-7-yl)methyl)-3-methylpyridin-2-yl)piperazin-1-yl)-2-(methylamino)ethan-1-one To a stirred solution of 4 M HCl in EA (10 ml), tert-butyl (2-(4-(5-((4-amino-2-(pentan-2-ylamino)imidazo[2,1-f][1,2,4]triazin-7-yl)methyl)-3-methylpyridin-2-yl)piperazin-1-yl)-2-oxoethyl)(methyl)carbamate (60 mg, 0.1 mmol) was added. The reaction mixture was stirred at Rt overnight. The mixture was poured into saturated $NaHCO_3$ solution (20 mL) and extracted with DCM (10 ml×3). The combined organic phase was washed with brine, dried over $Na_2SO_4$ and concentrated in vacuo. The crude product was purified by column chromatography to give the product (30 mg, 62.5%). $^1$H NMR (400 MHz, DMSO-d6) δ 8.70 (br.s, 2H), 8.09 (s, 1H), 7.78 (br.s, 1H), 7.50 (s, 1H), 7.41 (s, 1H), 6.34 (br.s, 1H), 4.09 (s, 2H), 4.03 (s, 2H), 3.80 (s, 1H), 3.64 (s, 2H), 3.48 (s, 2H), 3.06 (s, 2H), 3.00 (s, 2H), 2.57 (s, 3H), 2.22 (s, 3H), 1.51 (s, 1H), 1.47-1.21 (m, 3H), 1.10 (d, J=5.7 Hz, 3H), 0.86 (t, J=6.7 Hz, 3H) ppm. MS: M/e 481 $(M+1)^+$.

Compound B150: 7-((5-methyl-6-(piperazin-1-yl)pyridin-3-yl)methyl)-N2-(pentan-2-yl)imidazo[2,1-f][1,2,4]triazine-2,4-diamine Step A: tert-butyl 4-(5-((4-(bis(4-methoxybenzyl)amino)-2-(pentan-2-ylamino)imidazo[2,1-f][1,2,4]triazin-7-yl)(hydroxy)methyl)-3-methylpyridin-2-yl)piperazine-1-carboxylate To a stirred solution of 7-bromo-N4,N4-bis(4-methoxybenzyl)-N2-(pentan-2-yl)imidazo[2,1-f][1,2,4]triazine-2,4-diamine (1 g, 1.87 mmol) in THF (15 mL), cooled to −78° C. and under a nitrogen atmosphere, n-BuLi (1.6 M in hexane, 3.74 mmol, 2.3 mL) was added dropwise. After stirring for 50 mins, a solution of tert-butyl 4-(5-formyl-3-methylpyridin-2-yl)piperazine-1-carboxylate (854 mg, 2.8 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phase was washed with brine, dried over $Na_2SO_4$, concentrated in vacuo. The crude product was purified by column chromatography to give the title product (750 mg, 53.5%). MS: M/e 766 $(M+1)^+$.

Step B: 7-((5-methyl-6-(piperazin-1-yl)pyridin-3-yl)methyl)-N2-(pentan-2-yl)imidazo[2,1-f][1,2,4]triazine-2,4-diamine A solution of the product of Step A (750 mg, 0.98 mmol) in TFA (6 mL) and $Et_3SiH$ (6 mL) was stirred at 80° C. for 2 h. The reaction mixture was concentrated in vacuo to remove TFA and $Et_3SiH$. The residue was added TFA (10 mL) and stirred at 85° C. overnight. The mixture was cooled down to rt and concentrated in vacuo. The crude product was purified by prep-HPLC to give the product (240 mg, 60%). $^1$H NMR (400 MHz, DMSO-d6) δ 8.05 (s, 1H), 7.46 (br.s, 2H), 7.41 (s, 1H), 7.14 (s, 1H), 5.98 (d, J=8.6 Hz, 1H), 3.96 (s, 2H), 3.81 (s, 1H), 2.90 (br.s, 4H), 2.81 (br.s, 4H), 2.16 (s, 3H), 1.61-1.42 (m, 1H), 1.40-1.22 (m, 3H), 1.10 (d, J=6.3 Hz, 3H), 0.87 (t, J=7.1 Hz, 3H) ppm. MS: M/e 410 $(M+1)^+$.

Compound B151: 1-(4-(5-((4-amino-2-(pentan-2-ylamino)imidazo[2,1-f][1,2,4]triazin-7-yl)methyl)-3-methylpyridin-2-yl)piperazin-1-yl)-2-(dimethylamino)ethan-1-one To a stirred solution of 7-((5-methyl-6-(piperazin-1-yl)pyridin-3-yl)methyl)-N2-(pentan-2-yl)imidazo[2,1-f][1,2,4]triazine-2,4-diamine (60 mg, 0.147 mmol) in DMF (5 mL), dimethylglycine (30 mg, 0.291 mmol), HATU (70 mg, 0.183 mmol) and DIPEA (80 mg, 0.62 mmol) were added. The reaction mixture was stirred at Rt overnight. The mixture was poured into $H_2O$ (50 mL) and extracted with EtOAc (10 ml×3). The combined organic phase was washed with brine, dried over $Na_2SO_4$ and concentrated in vacuo. The crude product was purified by column chromatography to give the product (11 mg, 15.1%). $^1$H NMR (400 MHz, $CDCl_3$) δ 8.08 (s, 1H), 7.46 (br.s, 3H), 7.15 (s, 1H), 5.99 (d, J=8.1 Hz, 1H), 3.98 (s, 2H), 3.80 (s, 1H), 3.61 (s, 2H), 3.57 (s, 2H), 3.27 (s, 2H), 2.99 (s, 2H), 2.93 (s, 2H), 2.27 (s, 6H), 2.20 (s, 3H), 1.53-1.47 (m, 1H), 1.43-1.25 (m, 3H), 1.09 (d, J=6.4 Hz, 3H), 0.86 (t, J=7.1 Hz, 3H) ppm. MS: M/e 495 $(M+1)^+$.

Compound B152: (R)-2-(sec-butoxy)-7-((5-methyl-6-(piperazin-1-yl) pyridin-3-yl)methyl)imidazo[2,1-f][1,2,4]triazin-4-amine Step A: (R)-7-bromo-2-(sec-butoxy)-N,N-bis(4-methoxybenzyl)imidazo[2,1-f][1,2,4]triazin-4-amine NaH (656 mg, 16.4 mmol) was added to a solution of (R)-butan-2-ol (1.2 g, 16.4 mmol) in THF (20 mL). After stirred at rt under $N_2$ atmosphere for 30 mins, 7-bromo-2-chloro-N,N-bis(4-methoxybenzyl)imidazo[2,1-f][1,2,4]triazin-4-amine (2 g, 4.1 mmol) was added and the resulting mixture was heated at 60° C. overnight. The solution was cooled down, added with water (10 mL) and extracted with ethyl acetate (10 mL). The organic layer was dried with $Na_2SO_4$, filtered and concentrated to get the crude product, which was further purified by Combi-Flash (PE:EA=15%) to get the product (2 g, 95%). MS: M/e 526 $(M+1)^+$.

Step B: tert-butyl 4-(5-((4-(bis(4-methoxybenzyl) amino)-2-((R)-sec-butoxy)imidazo[2,1-f][1,2,4]triazin-7-yl)(hydroxy)methyl)-3-methylpyridin-2-yl) piperazine-1-carboxylate To a cooled solution of (R)-7-bromo-2-(sec-butoxy)-N,N-bis(4-methoxybenzyl)imidazo[2,1-f][1,2,4]triazin-4-amine (1.1 g, 2.1 mmol) in THF (35 mL) at −78° C. (purged with $N^2$), n-BuLi (1.6 M, 2 mL) was added dropwise. After stirred at −78° C. for 30 mins, tert-butyl 4-(5-formyl-3-methylpyridin-2-yl)piperazine-1-carboxylate (769 mg, 2.5 mmol) in THF (5 mL) was added. The resulting mixture was stirred at this temperature for 30 mins, and then warmed to rt overnight. The solution was quenched with $NH_4Cl$ solution (10 mL) and extracted with ethyl acetate (20 mL). The organic layer was dried with $Na_2SO_4$, filtered and concentrated to get the crude product, which was further purified by CombiFlash (PE:EA=50%) to get the pure product (430 mg, 27%). MS: M/e 753 $(M+1)^+$.

Step C: (R)-2-(sec-butoxy)-7-((5-methyl-6-(piperazin-1-yl)pyridin-3-yl)methyl)imidazo[2,1-f][1,2,4] triazin-4-amine A solution of tert-butyl 4-(5-((4-(bis(4-methoxybenzyl) amino)-2-((R)-sec-butoxy)imidazo[2,1-f][1,2,4]triazin-7-yl)(hydroxy)methyl)-3-methylpyridin-2-yl)piperazine-1-carboxylate (430 mg, 0.57 mmol) in triethylsilane (1 mL) and trifluoroacetic acid (4 mL) was heated at 80° C. overnight. The solvent was evaporated under oil pump to get the residue, which was dissolved in EA (10 mL) and washed with $NaHCO_3$ solution (10 mL). The organic layer was dried, concentrated and purified by prep-TLC (DCM:$NH_3$·MeOH=7:1) to get the product (100 mg, 44%). $^1H$ NMR (400 MHz, DMSO-d6) δ 8.11 (s, 1H), 8.05 (s, 1H), 7.99 (s, 1H), 7.41 (s, 1H), 7.32 (s, 1H), 4.92-4.83 (m, 1H), 4.03 (s, 2H), 2.95-2.74 (m, 8H), 2.17 (s, 3H), 1.65-1.59 (m, 2H), 1.24 (d, J=8.0 Hz, 3H), 0.90 (t, J=8.0 Hz, 3H) ppm. MS: M/e 397 $(M+1)^+$.

Compound B153: (R)-1-(4-(5-((4-amino-2-(sec-butoxy)imidazo[2,1-f][1,2,4]triazin-7-yl)methyl)-3-methylpyridin-2-yl)piperazin-1-yl)-2-(dimethylamino)ethan-1-one A solution of (R)-2-(sec-butoxy)-7-((5-methyl-6-(piperazin-1-yl)pyridin-3-yl) methyl)imidazo[2,1-f][1,2,4]triazin-4-amine (40 mg, 0.10 mmol), dimethylglycine (12 mg, 0.12 mmol), HATU (57 mg, 0.15 mmol) and DIEA (26 mg, 0.20 mmol) in DMF (5 mL) was stirred at rt for 2 hrs. The reaction mixture was added with water (5 mL), extracted with ethyl acetate (10 mL) and washed with brine (10 mL). The organic layer was dried with $Na_2SO_4$, filtered and concentrated to get the crude product, which was purified by prep-TLC (DCM:$NH_3$·MeOH=7:1) to get the product (12 mg, 25%). $^1H$ NMR (400 MHz, DMSO-d6) δ 8.12 (s, 1H), 8.08 (s, 1H), 8.00 (s, 1H), 7.45 (s, 1H), 7.33 (s, 1H), 4.92-4.83 (m, 1H), 4.05 (s, 2H), 3.58 (br.s, 6H), 3.06-2.92 (m, 4H), 2.42 (s, 6H), 2.21 (s, 3H), 1.65-1.59 (m, 2H), 1.24 (d, J=4.0 Hz, 3H), 0.90 (t, J=8.0 Hz, 3H) ppm. MS: M/e 482 $(M+1)^+$.

Compound B154: (S)-1-(4-(5-((4-amino-2-(pentan-2-yloxy)imidazo[2,1-f][1,2,4]triazin-7-yl)methyl)-3-methylpyridin-2-yl)piperazin-1-yl)-2-(methylamino) ethan-1-one Step A: tert-butyl (S)-(2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl) (methyl)carbamate A solution of (S)-7-((5-methyl-6-(piperazin-1-yl)pyridin-3-yl)methyl)-2-(pentan-2-yloxy)imidazo[2,1-f][1,2,4]triazin-4-amine (375 mg, 0.90 mmol), N-(tert-butoxycarbonyl)-N-methylglycine (207 mg, 1.1 mmol), HATU (513 mg, 1.4 mmol) and DIEA (232 mg, 1.8 mmol) in DMF (10 mL) was stirred at rt for 2 hrs. The reaction mixture was added with water (10 mL), extracted with ethyl acetate (10 mL) and washed with brine (10 mL). The organic layer was dried with $Na_2SO_4$, filtered and concentrated to get the crude product, which was used in the next step (120 mg, 23%). MS: M/e 582 $(M+1)^+$.

Step B: (S)-1-(4-(5-((4-amino-2-(pentan-2-yloxy) imidazo[2,1-f][1,2,4]triazin-7-yl)methyl)-3-methylpyridin-2-yl)piperazin-1-yl)-2-(methylamino) ethan-1-one A solution of tert-butyl (S)-(2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl)(methyl)carbamate (120 mg, 0.2 mmol) in EA (5 mL) was added with HCl/EA (2M, 2 mL). The solution was stirred at rt for 3 hrs. After concentration, the residue was dissolved in DCM (10 mL) and washed with $NaHCO_3$ (5 mL). The organic layer was dried with $Na_2SO_4$, filtered and concentrated to get the crude product, which was further purified by prep-TLC (DCM:$NH_3$·MeOH=7:1) to get the pure product (25 mg, 25%). $^1H$ NMR (400 MHz, DMSO-d6) δ 8.11 (s, 1H), 8.07 (s, 1H), 7.99 (s, 1H), 7.44 (s, 1H), 7.33 (s, 1H), 5.01-4.87 (m, 1H), 4.05 (s, 2H), 3.58-3.52 (m, 4H), 3.32 (s, 2H), 2.99-2.94 (m, 4H), 2.27 (s, 3H), 2.20 (s, 3H), 1.65-1.50 (m, 2H), 1.38-1.33 (m, 2H), 1.24 (d, J=4.0 Hz, 3H), 0.87 (t, J=8.0 Hz, 3H) ppm. MS: M/e 482 $(M+1)^+$.

Compound B155: 1-(4-(5-((4-amino-2-(sec-butoxy) imidazo[2,1-f][1,2,4]triazin-7-yl)methyl)-3-methylpyridin-2-yl)piperazin-1-yl)-2-(dimethylamino) ethan-1-one A solution of 2-(sec-butoxy)-7-((5-methyl-6-(piperazin-1-yl)pyridin-3-yl) methyl)imidazo[2,1-f][1,2,4]triazin-4-amine (30 mg, 0.08 mmol), dimethylglycine (10 mg, 0.09 mmol), HATU (46 mg, 0.12 mmol) and DIEA (21 mg, 0.16 mmol) in DMF (5 mL) was stirred at rt for 2 hrs. The reaction mixture was added with water (5 mL), extracted with ethyl acetate (10 mL) and washed with brine (5 mL). The organic layer was dried with $Na_2SO_4$, filtered and concentrated to get the crude product, which was purified by prep-TLC (DCM:$NH_3$·MeOH=8:1) to get the product (16 mg, 44%). $^1$H NMR (400 MHz, DMSO-d6) δ 8.11 (s, 1H), 8.07 (s, 1H), 8.00 (s, 1H), 7.44 (s, 1H), 7.32 (s, 1H), 4.92-4.83 (m, 1H), 4.05 (s, 2H), 3.63-3.57 (m, 4H), 3.21-3.14 (m, 2H), 3.02-2.92 (m, 4H), 2.23 (s, 6H), 2.20 (s, 3H), 1.65-1.58 (m, 2H), 1.24 (d, J=4.0 Hz, 3H), 0.89 (t, J=8.0 Hz, 3H) ppm. MS: M/e 482 $(M+1)^+$.

Compound B156: 1-(4-(5-((4-amino-2-(sec-butoxy)imidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-(sec-butoxy)imidazo[2,1-f][1,2,4]triazin-7-yl)methyl)-3-methylpyridin-2-yl)piperazin-1-yl)-2-oxoethyl)(methyl)carbamate A solution of 2-(sec-butoxy)-7-((5-methyl-6-(piperazin-1-yl)pyridin-3-yl)methyl)imidazo[2,1-f][1,2,4]triazin-4-amine (30 mg, 0.08 mmol), N-(tert-butoxy carbonyl)-N-methylglycine (17 mg, 0.09 mmol), HATU (46 mg, 0.12 mmol) and DIEA (21 mg, 0.16 mmol) in DMF (5 mL) was stirred at rt for 2 hrs. The reaction mixture was added with water (5 mL), extracted with ethyl acetate (10 mL) and washed with brine (5 mL). The organic layer was dried with $Na_2SO_4$, filtered and concentrated to get the crude product, which was used in the next step (40 mg, crude). MS: M/e 568 $(M+1)^+$.

Step B: 1-(4-(5-((4-amino-2-(sec-butoxy)imidazo[2,1-f] [1,2,4]triazin-7-yl) methyl)-3-methylpyridin-2-yl)piperazin-1-yl)-2-(methylamino)ethan-1-one A solution of tert-butyl (2-(4-(5-((4-amino-2-(sec-butoxy)imidazo[2,1-f][1,2,4]triazin-7-yl)methyl)-3-methylpyridin-2-yl)piperazin-1-yl)-2-oxoethyl)(methyl)carbamate (40 mg, crude) in EA (2 mL) was added with HCl/EA (2M, 1 mL). The solution was stirred at rt for 2 hrs. After concentration, the residue was dissolved in DCM (10 mL) and washed with $NaHCO_3$ (5 mL). The organic layer was dried with $Na_2SO_4$, filtered and concentrated to get the crude product, which was further purified by prep-TLC (DCM:$NH_3$·MeOH=8:1) to get the pure product (15 mg, 47%). $^1$H NMR (400 MHz, DMSO-d6) δ 8.73 (br.s, 2H), 8.12 (s, 1H), 8.08 (s, 1H), 8.01 (s, 1H), 7.47 (s, 1H), 7.27 (s, 1H), 7.14-7.02 (m, 1H), 4.92-4.83 (m, 1H), 4.09-4.06 (m, 2H), 3.63 (s, 2H), 3.47 (s, 2H), 3.05-2.99 (m, 4H), 2.57 (s, 2H), 2.22 (s, 3H), 1.62-1.59 (m, 2H), 1.24 (d, J=4.0 Hz, 3H), 0.90 (t, J=8.0 Hz, 3H) ppm. MS: M/e 468 $(M+1)^+$.

Compound B157: 1-((4-amino-7-((5-methyl-6-(piperazin-1-yl)pyridin-3-yl)methyl)imidazo[2,1-f][1,2,4]triazin-2-yl)oxy)hexan-3-ol Step A: tert-butyl 4-(5-((4-(bis(4-methoxybenzyl)amino)-2-chloroimidazo[2,1-f][1,2,4]triazin-7-yl)(hydroxy)methyl)-3-methylpyridin-2-yl)piperazine-1-carboxylate To a solution of 7-bromo-2-chloro-N,N-bis(4-methoxybenzyl)imidazo[2,1-f][1,2,4]triazin-4-amine (2000 mg, 4.1 mmol) in THF (20 mL) was added a solution of n-BuLi (1.6M, 3.84 mL, 6.15 mmol) dropwise maintaining the temperature between −75~−65° C. After 1 h, a suspension of the tert-butyl 4-(5-formyl-3-methylpyridin-2-yl)piperazine-1-carboxylate (1500 mg, 4.9 mmol) in THF (15 mL) was added dropwise. The resulting mixture was stirred at −70° C. for 2 h and then warmed to room temperature for 4 h. The reaction was quenched with saturated $NH_4Cl$ solution, extracted with EtOAc (50 mL×3), washed with brine, dried over $Na_2SO_4$, filtered, and concentrated. The residue was purified by prep-TLC to give the target compound (1.9 g, yellow oil). MS: m/e 715 $(M+1)^+$.

Step B: 2-chloro-7-((5-methyl-6-(piperazin-1-yl)pyridin-3-yl)methyl)imidazo[2,1-f][1,2,4]triazin-4-amine To a mixture of the product of Step A (1500 mg, 2.1 mmol) in TFA (5 mL) was added $Et_3SiH$ (5 mL) and the resulting mixture was stirred at 85° C. for 4 hours. The mixture was cooled to room temperature and concentrated to dryness. To the residue was added TFA (10 mL) and the reaction was heated at 80° C. overnight. The mixture was concentrated and the residue was purified by prep-HPLC to give the target compound as a TFA salt (700 mg, crude).

Step C: tert-butyl 4-(5-((4-((tert-butoxycarbonyl)amino)-2-chloroimidazo[2,1-f][1,2,4]triazin-7-yl)methyl)-3-methylpyridin-2-yl)piperazine-1-carboxylate Di-tert-butyl dicarbonate (510 mg, 1.42 mmol) was added in small portions over 15 min to a mixture of 2-chloro-7-((5-methyl-6-(piperazin-1-yl)pyridin-3-yl)methyl)imidazo[2,1-f][1,2,4]triazin-4-amine (993 mg, 4.97 mmol), triethylamine (573 mg, 5.68 mmol), and 4-dimethylaminopyridine (DMAP; 17 mg) in anhydrous $CH_2Cl_2$ (50 mL) at 0° C. 20 minutes after the addition was complete, the mixture was warmed to room temperature. After 2 h, the reaction mixture was diluted in water and extracted with $CH_2Cl_2$. The combined organic extracts were washed with saturated aqueous NaCl, dried over $MgSO_4$, and concentrated to afford the product (540 mg, 68%).

Step D: tert-butyl 4-(5-((4-((tert-butoxycarbonyl)amino)-2-((3-((tert-butyldimethylsilyl)oxy)hexyl)oxy)imidazo[2,1-f][1,2,4]triazin-7-yl)methyl)-3-methylpyridin-2-yl)piperazine-1-carboxylate To a solution of 1-((tert-butyldimethylsilyl)oxy)pentan-2-ol (50 mg, 0.23 mmol) in THF (2 mL), NaH (60%, 20 mg, 0.35 mmol) was added at 0 degrees. The reaction mixture was stirred at room temperature for 20 minutes, then tert-butyl 4-(5-((4-((tert-butoxycarbonyl)amino)-2-chloroimidazo[2,1-f][1,2,4]triazin-7-yl)methyl)-3-methylpyridin-2-yl)piperazine-1-carboxylate (120 mg, 0.23 mmol) was added and the resulting mixture was stirred overnight at 70° C. An aqueous ammonium chloride solution was added and the mixture was extracted with ethyl acetate. The combined organic extracts were dried over sodium sulfate, filtered and evaporated. Purification by prep-TLC (silica gel, EA:PE=1:10) afforded the product (35 mg, 22%). MS: m/e 741 $(M+1)^+$.

Step E: 1-((4-amino-7-((5-methyl-6-(piperazin-1-yl)pyridin-3-yl)methyl)imidazo[2,1-f][1,2,4]triazin-2-yl)oxy)hexan-3-ol TFA (0.5 ml) was added to the mixture of the product of step D in DCM (3 ml). The reaction mixture was stirred at room temperature for 3 h. The mixture was concentrated and the residue was purified by prep-HPLC to give the target compound (5.2 mg, 26%). $^1$H NMR (400 MHz, DMSO-d6) δ 8.68 (br.s, 2H), 8.17 (s, 2H), 8.10 (s, 1H), 7.52 (s, 1H), 7.33 (s, 1H), 4.07 (br.s, 4H), 3.78 (s, 1H), 3.21 (br.s, 8H), 2.21 (s, 3H), 1.47-1.26 (m, 4H), 0.89 (br.s, 3H) ppm. MS: m/e 427 $(M+1)^+$.

Compound B158: (S)-2-(sec-butoxy)-7-((5-methyl-6-(piperazin-1-yl) pyridin-3-yl)methyl)imidazo[2,1-f][1,2,4]triazin-4-amine Step A: (S)-7-bromo-2-(sec-butoxy)-N,N-bis(4-methoxybenzyl)imidazo[2,1-f][1,2,4]triazin-4-amine NaH (984 mg, 24.6 mmol) was added to a solution of (S)-butan-2-ol (1.8 g, 24.6 mmol) in THF (30 mL). After stirred at rt under $N_2$ atmosphere for 30 mins, 7-bromo-2-chloro-N,N-bis(4-methoxybenzyl)imidazo[2,1-f][1,2,4]triazin-4-amine (3 g, 6.2 mmol) was added and the resulting mixture was heated at 60° C. for 2 hrs. The solution was cooled down, added with water (10 mL) and extracted with ethyl acetate (10 mL). The organic layer was dried with $Na_2SO_4$, filtered and concentrated to get the crude product, which was further purified by CombiFlash (PE:EA=15%) to get the product (3.1 g, 96%). MS: M/e 526 $(M+1)^+$.

Step B: tert-butyl 4-(5-((4-(bis(4-methoxybenzyl) amino)-2-((S)-sec-butoxy)imidazo[2,1-f][1,2,4]triazin-7-yl)(hydroxy)methyl)-3-methylpyridin-2-yl) piperazine-1-carboxylate To a cooled solution of (S)-7-bromo-2-(sec-butoxy)-N,N-bis(4-methoxybenzyl)imidazo[2,1-f][1,2,4]triazin-4-amine (3 g, 5.7 mmol) in THF (35 mL) at −78° C. (purged with $N^2$), n-BuLi (1.6 M, 5.3 mL) was added dropwise. After stirred at −78° C. for 30 mins, tert-butyl 4-(5-formyl-3-methylpyridin-2-yl)piperazine-1-carboxylate (2.1 g, 6.8 mmol) in THF (5 mL) was added. The resulting mixture was stirred at this temperature for 30 mins, and then warmed to rt overnight. The solution was quenched with $NH_4Cl$ solution (10 mL) and extracted with ethyl acetate (20 mL). The organic layer was dried with $Na_2SO_4$, filtered and concentrated to get the crude product, which was further purified by CombiFlash (PE:EA=40%) to get the pure product (2.7 g, 63%). MS: M/e 753 $(M+1)^+$.

Step C: (S)-2-(sec-butoxy)-7-((5-methyl-6-(piperazin-1-yl)pyridin-3-yl)methyl)imidazo[2,1-f][1,2,4] triazin-4-amine A solution of tert-butyl 4-(5-((4-(bis(4-methoxybenzyl) amino)-2-((S)-sec-butoxy)imidazo[2,1-f][1,2,4]triazin-7-yl) (hydroxy)methyl)-3-methylpyridin-2-yl)piperazine-1-carboxylate (2.7 g, 3.6 mmol) in triethylsilane (3 mL) and trifluoroacetic acid (3 mL) was heated at 80° C. for 4 hrs. The solvent was evaporated, 5 mL of TFA was added and the solution was heated at 80° C. for 9 hrs. The solvent was evaporated under oil pump to get the residue, which was added with EA (10 mL) and basified with $NaHCO_3$ solution (10 mL). The aqueous layer was extracted with DCM (with 10% of MeOH) for three times. The combined organic layers were dried, concentrated, slurried in DCM (20 mL), was filtered and dried to get the product (700 mg, 50%). $^1$H NMR (400 MHz, DMSO-d6) δ 8.11 (s, 1H), 8.07 (s, 1H), 8.00 (s, 1H), 7.43 (s, 1H), 7.32 (s, 1H), 4.92-4.83 (m, 1H), 4.04 (s, 2H), 3.02-2.98 (m, 8H), 2.18 (s, 3H), 1.63-1.57 (m, 2H), 1.24 (d, J=8.0 Hz, 3H), 0.90 (d, J=8.0 Hz, 3H) ppm. MS: M/e 397 $(M+1)^+$.

Compound B159: (R)-1-(4-(5-((4-amino-2-(sec-butoxy)imidazo[2,1-f] [1,2,4]triazin-7-yl)methyl)-3-methylpyridin-2-yl)piperazin-1-yl)-2-(methylamino) ethan-1-one Step A: tert-butyl (R)-(2-(4-(5-((4-amino-2-(sec-butoxy)imidazo[2,1-f][1,2,4]triazin-7-yl)methyl)-3-methylpyridin-2-yl)piperazin-1-yl)-2-oxoethyl) (methyl)carbamate A solution of (R)-2-(sec-butoxy)-7-((5-methyl-6-(piperazin-1-yl)pyridin-3-yl) methyl)imidazo[2,1-f][1,2,4]triazin-4-amine (40 mg, 0.1 mmol), N-(tert-butoxycarbonyl)-N-methylglycine (23 mg, 0.12 mmol), HATU (57 mg, 0.15 mmol) and DIEA (26 mg, 0.2 mmol) in DMF (5 mL) was stirred at rt for 2 hrs. The reaction mixture was added with water (5 mL), extracted with ethyl acetate (10 mL) and washed with brine (10 mL). The organic layer was dried with $Na_2SO_4$, filtered and concentrated to get the crude product, which was used in the next step (140 mg, crude). MS: M/e 568 $(M+1)^+$ Step B: (R)-1-(4-(5-((4-amino-2-(sec-butoxy)imidazo[2,1-f][1,2,4]triazin-7-yl) methyl)-3-methylpyridin-2-yl)piperazin-1-yl)-2-(methylamino)ethan-1-one A solution of tert-butyl (R)-(2-(4-(5-((4-amino-2-(sec-butoxy)imidazo[2,1-f][1,2,4]triazin-7-yl)methyl)-3-methylpyridin-2-yl)piperazin-1-yl)-2-oxoethyl)(methyl)carbamate (50 mg, crude) in EA (5 mL) was added with HCl/EA (2M, 1 mL). The solution was stirred at rt for 2 hrs. After concentration, the residue was dissolved in EA (10 mL) and washed with $NaHCO_3$ (10 mL). The organic layer was dried with $Na_2SO_4$, filtered and concentrated to get the crude product, which was further purified by prep-TLC (DCM: $NH_3$·MeOH=7:1) to get the pure product (18 mg, 44%). $^1$H NMR (400 MHz, DMSO-d6) δ 8.74 (br.s, 2H), 8.16 (br.s, 1H), 8.09 (s, 1H), 7.50 (s, 1H), 7.39 (s, 1H), 4.93-4.72 (m, 1H), 4.08 (br.s, 4H), 3.64 (s, 2H), 3.48 (s, 2H), 3.07-3.01 (m, 4H), 2.57 (s, 3H), 2.22 (s, 3H), 1.62-1.57 (m, 2H), 1.24 (d, J=8.0 Hz, 3H), 0.90 (t, J=8.0 Hz, 3H) ppm. MS: M/e 468 $(M+1)^+$ Compound B160: (R)-1-(4-(5-((4-amino-2-(pentan-2-yloxy)imidazo[2,1-f][1,2,4]triazin-7-yl)methyl)-3-methylpyridin-2-yl)piperazin-1-yl)-2-(methylamino) ethan-1-one Step A: tert-butyl (R)-(2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl) (methyl)carbamate A solution of (R)-7-((5-methyl-6-(piperazin-1-yl)pyridin-3-yl)methyl)-2-(pentan-2-yloxy)imidazo[2,1-f][1,2,4]triazin-4-amine (70 mg, 0.17 mmol), N-(tert-butoxycarbonyl)-N-methylglycine (39 mg, 0.20 mmol), HATU (97 mg, 0.26 mmol) and DIEA (44 mg, 0.34 mmol) in DMF (5 mL) was stirred at rt for 2 hrs. The reaction mixture was added with water (5 mL), extracted with ethyl acetate (10 mL) and washed with brine (5 mL). The organic layer was dried with $Na_2SO_4$, filtered and concentrated to get the crude product, which was used in the next step (70 mg, 70%). MS: M/e 582 $(M+1)^+$ Step B: (R)-1-(4-(5-((4-amino-2-(pentan-2-yloxy)imidazo[2,1-f][1,2,4]triazin-7-yl)methyl)-3-methylpyridin-2-yl)piperazin-1-yl)-2-(methylamino)ethan-1-one A solution of tert-butyl (R)-(2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl)(methyl)carbamate (70 mg, 0.14 mmol) in EA (3 mL) was added with HCl/EA (2M, 1 mL). The solution was stirred at rt for 3 hrs. After concentration, the residue was dissolved in DCM (10 mL) and washed with $NaHCO_3$ (5 mL). The organic layer was dried with $Na_2SO_4$, filtered and concentrated to get the crude product, which was further purified by prep-TLC ($DCM:NH_3{\cdot}MeOH=7:1$) to get the pure product (28 mg, 48%). $^1H$ NMR (400 MHz, DMSO-d6) δ 8.11 (s, 1H), 8.07 (s, 1H), 7.99 (s, 1H), 7.44 (s, 1H), 7.33 (s, 1H), 5.02-4.83 (m, 1H), 4.05 (s, 2H), 3.58-3.52 (m, 4H), 3.39 (s, 2H), 2.99-2.95 (m, 4H), 2.27 (s, 3H), 2.20 (s, 3H), 1.64-1.50 (m, 2H), 1.37-1.32 (m, 2H), 1.24 (d, J=4.0 Hz, 3H), 0.87 (t, J=8.0 Hz, 3H) ppm. MS: M/e 482 $(M+1)^+$.

Compound B161: 2-butoxy-7-((5-methyl-6-(4-(methylamino)piperidin-1-yl)pyridin-3-yl)methyl)imidazo[2,1-f][1,2,4]triazin-4-amine Step A: tert-butyl (1-(5-((4-(bis(4-methoxybenzyl)amino)-2-butoxyimidazo[2,1-f][1,2,4]triazin-7-yl)(hydroxy)methyl)-3-methylpyridin-2-yl)piperidin-4-yl)(methyl)carbamate To a stirred solution of 7-bromo-2-butoxy-N,N-bis(4-methoxybenzyl)imidazo[2,1-f][1,2,4]triazin-4-amine (200 mg, 0.38 mmol) in THF (10 mL), cooled to −78° C. and under a nitrogen atmosphere, n-BuLi (1.6 M in hexane, 0.95 mmol, 0.59 mL) was added dropwise. After stirring for 50 mins, a solution of tert-butyl (1-(5-formyl-3-methylpyridin-2-yl)piperidin-4-yl)(methyl)carbamate (214 mg, 0.57 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (130 mg, 43.9%). MS: M/e 781 $(M+1)^+$.

Step B: 2-butoxy-7-((5-methyl-6-(4-(methylamino)piperidin-1-yl)pyridin-3-yl)methyl)imidazo[2,1-f][1,2,4]triazin-4-amine A solution of tert-butyl (1-(5-((4-(bis(4-methoxybenzyl)amino)-2-butoxyimidazo[2,1-f][1,2,4]triazin-7-yl)(hydroxy)methyl)-3-methylpyridin-2-yl)piperidin-4-yl)(methyl)carbamate (130 mg, 0.167 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 80° C. overnight. The mixture was cooled down to rt and concentrated in vacuo. The crude product was purified by prep-HPLC to give the product (30 mg, 42.9%). $^1H$ NMR (400 MHz, DMSO-d6) δ 8.13 (s, 1H), 8.04 (s, 2H), 7.42 (s, 1H), 7.30 (s, 1H), 4.20 (t, J=6.4 Hz, 2H), 4.03 (s, 2H), 3.28 (s, 2H), 2.67 (t, J=11.5 Hz, 2H), 2.45-2.98 (m, 1H), 2.30 (s, 3H), 2.16 (s, 3H), 1.87 (d, J=11.6 Hz, 2H), 1.74-1.61 (m, 2H), 1.44-1.31 (m, 4H), 0.92 (t, J=7.3 Hz, 3H) ppm. MS: M/e 425 $(M+1)^+$.

Compound B162: 7-((5-methyl-6-(piperazin-1-yl)pyridin-3-yl)methyl)-2-(pentan-3-yloxy)imidazo[2,1-f][1,2,4]triazin-4-amine Step A: N,N-bis(4-methoxybenzyl)-2-(pentan-3-yloxy)imidazo[2,1-f][1,2,4]triazin-4-amine To a solution of pentan-3-ol (500 mg, 5.68 mmol) in THF (5 mL), NaH (230 mg, 5.70 mmol) was added at 0° C. The resulting mixture was stirred at rt for 30 min. A solution of 2-chloro-N,N-bis(4-methoxybenzyl)imidazo[2,1-f][1,2,4]triazin-4-amine (410 mg, 1.0 mmol) in THF was added in drops. After the addition was finished, the resulting mixture was heated at 60° C. for 16 hrs. The mixture was quenched with 10 mL of aq. $NH_4Cl$ and extracted with EA (10 mL×3). The combined extracts was washed with brine (10 mL×3), dried over $Na_2SO_4$ and concentrated, purified by column chromatography eluted with PE/EA (10:1~5:1) to give the title product (360 mg, yield: 78%) as a light yellow oil. MS: M/e 462 $(M+1)^+$.

Step B: tert-butyl 4-(5-((4-(bis(4-methoxybenzyl)amino)-2-(pentan-3-yloxy)imidazo[2,1-f][1,2,4]triazin-7-yl)(hydroxy)methyl)-3-methylpyridin-2-yl)piperazine-1-carboxylate To a −78° C. solution of N,N-bis(4-methoxybenzyl)-2-(pentan-3-yloxy)imidazo[2,1-f][1,2,4]triazin-4-amine (350 mg, 0.83 mmol) in THF (4 mL), n-BuLi solution (1.6 M, 0.83 mL, 1.33 mmol) was added dropwise with a syringe under $N_2$ and the resulting mixture was stirred at −78° C. for 20 min. A solution of tert-butyl 4-(5-formyl-3-methylpyridin-2-yl)piperazine-1-carboxylate (280 mg, 0.92 mmol) in THF (3 mL) was added with a syringe in drops at −78° C. The resulting mixture was stirred at this temperature for 0.5 hour and allowed warm to rt and stirred for 2 hrs. The mixture was quenched with 10 mL of aq. $NH_4Cl$ and extracted with EA (10 mL×3). The combined extracts was washed with brine (10 mL×3), dried over $Na_2SO_4$ and concentrated, purified by column chromatography eluted with PE/EA (3:1) to give the title product (360 mg, yield: 57%) as a light brown oil. MS: M/e 767 $(M+1)^+$.

Step C: 7-((5-methyl-6-(piperazin-1-yl)pyridin-3-yl)methyl)-2-(pentan-3-yloxy)imidazo[2,1-f][1,2,4]triazin-4-amine A mixture of tert-butyl 4-(5-((4-(bis(4-methoxybenzyl)amino)-2-(pentan-3-yloxy)imidazo[2,1-f][1,2,4]triazin-7-yl)(hydroxy)methyl)-3-methylpyridin-2-yl)piperazine-1-carboxylate (360 mg, 0.47 mmol), TFA (10 mL) and $Et_3SiH$ (5 mL) was heated at 80° C. for 5 hrs and the mixture was concentrated under high vacuum. The resulting residue was added 20 mL of TFA and heated at 80° C. for 16 hrs. The mixture was concentrated, and the resulting residue was treated with 10 mL of aq. $NaHCO_3$, extracted with a mixed solvent (DCM/MeOH=3:1, 10 mL×3). The combined extracts was washed with brine (10 mL×2), dried over $Na_2SO_4$ and concentrated, purified by column chromatography eluted with DCM/MeOH—$NH_3$ (20:1, 2 mol/L of $NH_3$ in MeOH) to give 185 mg of crude product which was purified by column chromatography (DCM/MeOH—$NH_3$, 20:1~10:1, 7 mol/L of $NH_3$ in MeOH), the resulting crude product was purified by prep-HPLC to give the title product (25 mg, yield: 13%). $^1$H NMR (400 MHz, $CD_3OD$) δ 8.03 (s, 1H), 7.45 (s, 1H), 7.35 (s, 1H), 4.86-4.78 (m, 1H), 4.12 (s, 2H), 3.14-3.04 (m, 4H), 3.04-2.96 (m, 4H), 2.24 (s, 3H), 1.75-1.60 (m, 4H), 0.92 (t, J=7.2 Hz, 6H). MS: M/e 411 $(M+1)^+$.

Compound B163: 7-((6-(4-(dimethylamino)piperidin-1-yl)-5-methyl pyridin-3-yl)methyl)-2-(hexan-3-yloxy)imidazo[2,1-f][1,2,4]triazin-4-amine Step A: 7-bromo-2-(hexan-3-yloxy)-N,N-bis(4-methoxybenzyl)imidazo[2,1-f][1,2,4]triazin-4-amine NaH (320 mg, 8 mmol) was added to a solution of hexan-3-ol (816 mg, 8 mmol) in THF (10 mL). After stirred at r.t under $N_2$ atmosphere for 30 mins, 7-bromo-2-chloro-N,N-bis(4-methoxybenzyl)imidazo[2,1-f][1,2,4]triazin-4-amine (1 g, 2 mmol) was added and the resulting mixture was heated at 60° C. overnight. The solution was cooled down, diluted with water (10 mL) and extracted with ethyl acetate (10 mL). The organic layer was dried with $Na_2SO_4$, filtered and concentrated to get the crude product, which was further purified by CombiFlash (PE:EA=20%) to get the product (810 mg, 74%). MS: M/e 554 $(M+1)^+$.

Step B: (4-(bis(4-methoxybenzyl)amino)-2-(hexan-3-yloxy)imidazo[2,1-f][1,2,4] triazin-7-yl)(6-(4-(dimethylamino)piperidin-1-yl)-5-methylpyridin-3-yl)methanol To a cooled solution of 7-bromo-2-(hexan-3-yloxy)-N,N-bis(4-methoxybenzyl) imidazo[2,1-f][1,2,4]triazin-4-amine (400 mg, 0.72 mmol) in THF (10 mL) at −78° C., purged with $N_2$ was added with n-BuLi (1.6 M, 0.6 mL) dropwise. After stirred at −78° C. for 30 mins, 6-(4-(dimethylamino) piperidin-1-yl)-5-methylnicotinaldehyde (197 mg, 0.8 mmol) in THF (2 mL) was added. The resulting mixture was stirred at this temperature for 30 mins, and then warmed to r.t overnight. The solution was quenched with $NH_4Cl$ solution (10 mL) and extracted with ethyl acetate (10 mL). The organic layer was dried with $Na_2SO_4$, filtered and concentrated to get the crude product, which was further purified by CombiFlash (PE:EA=40%) to get the pure product (240 mg, 46%). MS: M/e 723 $(M+1)^+$.

Step C: 7-((6-(4-(dimethylamino)piperidin-1-yl)-5-methyl pyridin-3-yl)methyl)-2-(hexan-3-yloxy)imidazo[2,1-f][1,2,4]triazin-4-amine A solution of (4-(bis(4-methoxybenzyl)amino)-2-(hexan-3-yloxy)imidazo[2,1-f][1,2,4]triazin-7-yl)(6-(4-(dimethylamino)piperidin-1-yl)-5-methylpyridin-3-yl)methanol (240 mg, 0.33 mmol) in triethylsilane (1 mL) and trifluoroacetic acid (3 mL) was heated at 80° C. overnight. The solvent was evaporated under oil pump to get the residue, which was added with EA (10 mL) and basified with $NaHCO_3$ solution (10 mL). The aqueous layer was extracted with DCM (with 10% of MeOH) for three times. The combined organic layers were dried, concentrated and purified by prep-TLC (DCM:MeOH=10:1, 2M $NH_3$·MeOH) get the product (48 mg, 31%). $^1$H NMR (400 MHz, $CD_3OD$) δ 8.01 (s, 1H), 7.45 (s, 1H), 7.36 (s, 1H), 4.99-4.94 (m, 1H), 4.13 (s, 2H), 3.48 (d, J=12.0 Hz, 2H), 2.82-2.76 (m, 3H), 2.57 (s, 6H), 2.25 (s, 3H), 2.04 (d, J=12.0 Hz, 2H), 1.70-1.62 (m, 6H), 1.40-1.30 (m, 2H), 0.94-0.89 (m, 6H) ppm. MS: M/e 466 $(M+1)^+$.

Compound B164: 7-((6-(4-((dimethylamino)methyl) piperidin-1-yl)-5-methylpyridin-3-yl)methyl)-2-(hexan-3-yloxy)imidazo[2,1-f][1,2,4]triazin-4-amine Step A: 7-bromo-2-(hexan-3-yloxy)-N,N-bis(4-methoxybenzyl)imidazo[2,1-f][1,2,4]triazin-4-amine NaH (320 mg, 8 mmol) was added to a solution of hexan-3-ol (816 mg, 8 mmol) in THF (10 mL). After stirred at r.t under $N_2$ atmosphere for 30 mins, 7-bromo-2-chloro-N,N-bis(4-methoxybenzyl)imidazo[2,1-f][1,2,4]triazin-4-amine (1 g, 2 mmol) was added and the resulting mixture was heated at 60° C. overnight. The solution was cooled down, diluted with water (10 mL) and extracted with ethyl acetate (10 mL). The organic layer was dried with $Na_2SO_4$, filtered and concentrated to get the crude product, which was further purified by CombiFlash (PE:EA=20%) to get the product (810 mg, 74%). MS: M/e 554 $(M+1)^+$.

Step B: (4-(bis(4-methoxybenzyl)amino)-2-(hexan-3-yloxy)imidazo[2,1-f][1,2,4]triaz in-7-yl)(6-(4-((dimethylamino)methyl)piperidin-1-yl)-5-methylpyridin-3-yl)methanol To a cooled solution of 7-bromo-2-(hexan-3-yloxy)-N,N-bis(4-methoxybenzyl) imidazo[2,1-f][1,2,4]triazin-4-amine (400 mg, 0.72 mmol) in THF (8 mL) at −78° C., purged with $N_2$ was added with n-BuLi (1.6 M, 0.6 mL) dropwise. After stirred at −78° C. for 30 mins, 6-(4-((dimethylamino) methyl)piperidin-1-yl)-5-methylnicotine aldehyde (208 mg, 0.8 mmol) in THF (2 mL) was added. The resulting mixture was stirred at this temperature for 30 mins, and then warmed to r.t overnight. The solution was quenched with $NH_4Cl$ solution (10 mL) and extracted with ethyl acetate (10 mL). The organic layer was dried with $Na_2SO_4$, filtered and concentrated to get the crude product, which was further purified by CombiFlash (PE:EA=40%) to get the pure product (320 mg, 60%). MS: M/e 737 $(M+1)^+$.

Step C: 7-((6-(4-((dimethylamino)methyl)piperidin-1-yl)-5-methylpyridin-3-yl) methyl)-2-(hexan-3-yloxy)imidazo[2,1-f][1,2,4]triazin-4-amine A solution of (4-(bis(4-methoxybenzyl)amino)-2-(hexan-3-yloxy)imidazo [2,1-f][1,2,4]triazin-7-yl)(6-(4-((dimethylamino)methyl)piperidin-1-yl)-5-methylpyridin-3-yl)methanol (320 mg, 0.43 mmol) in triethylsilane (1 mL) and trifluoroacetic acid (3 mL) was heated at 80° C. overnight. The solvent was evaporated under oil pump to get the residue, which was added with EA (10 mL) and basified with $NaHCO_3$ solution (10 mL). The aqueous layer was extracted with DCM (with 10% of MeOH) for three times. The combined organic layers were dried, concentrated and purified by prep-TLC (DCM:MeOH=10:1, 2M $NH_3$·MeOH) get the product (55 mg, 26%). $^1$H NMR (400 MHz, $CD_3OD$) δ 7.99 (s, 1H), 7.43 (s, 1H), 7.35 (s, 1H), 4.99-4.93 (m, 1H), 4.12 (s, 2H), 3.36 (d, J=12.0 Hz, 2H), 2.75 (t, J=12.0 Hz, 2H), 2.43 (s, 2H), 2.39 (s, 6H), 2.23 (s, 3H), 1.80 (d, J=12.0 Hz, 2H), 1.68-1.61 (m, 5H), 1.37-1.28 (m, 4H), 0.93-0.87 (m, 6H) ppm. MS: M/e 466 $(M+1)^+$.

Compound B165: 3-((4-amino-7-((5-methyl-6-(piperazin-1-yl)pyridin-3-yl)methyl)imidazo[2,1-f][1,2,4]triazin-2-yl)oxy)hexan-1-ol Step A: hexane-1,3-diol To a stirred suspension of LAH (0.76 g, 20 mmol) in THF (10 mL) was added dropwise a solution of methyl 3-hydroxyhexanoate (1.46 g, 10 mmol) in THF (5 mL) at 0° C. After the addition, the reaction was stirred for 2 hours. The reaction was quenched with $H_2O$ (0.76 mL), aq.NaOH (15%, 0.76 mL), followed by $H_2O$ (2.28 mL), then filtered. The filtrate was concentrated and purified by column chromatography (petroleum ether/EtOAc=2:1~1:1) to give the target compound (634 mg, 53.7%) as colorless oil.

Step B: 1-((tert-butyldimethylsilyl)oxy)hexan-3-ol

To a stirred solution of the product of step A (634 mg, 5.37 mmol) in $CH_2Cl_2$ (15 mL) was added Imidazole (730 mg, 10.74 mmol), then a solution of TBS-Cl (730 mg, 4.83 mmol) in $CH_2Cl_2$ (3 mL) was added dropwise at 0° C. After the addition, the reaction mixture was stirred for 2 hours. The reaction mixture was concentrated to give the residue, which was purified by column chromatography (petroleum ether/EtOAc=1:1) to give the target compound (1.1 g, 88.2%) as colorless oil.

Step C: 7-bromo-2-((1-((tert-butyldimethylsilyl)oxy) hexan-3-yl)oxy)-N,N-bis(4-methoxybenzyl)imidazo [2,1-f][1,2,4]triazin-4-amine To a stirred solution of the product of step B (464 mg, 2 mmol) in THF (10 mL) was added NaH (60%, 80 mg). After stirred for 30 min, 7-bromo-2-chloro-N,N-bis(4-methoxybenzyl)imidazo[2,1-f][1,2,4]triazin-4-amine (488 mg, 1 mmol) was added. After the addition, the reaction was stirred at 60° C. overnight. The reaction mixture was treated with $H_2O$ (20 mL), extracted with EtOAc (15 mL×2). The combined organic layers were washed with brine, dried over $Na_2SO_4$, concentrated and purified by column chromatography (petroleum ether/EtOAc=10:1) to give the target compound (530 mg, 77.5%) as colorless oil. MS: M/e 684 $(M+1)^+$.

Step D: tert-butyl 4-(5-((4-(bis(4-methoxybenzyl) amino)-2-((1-((tert-butyldimethylsilyl)oxy)hexan-3-yl)oxy)imidazo[2,1-f][1,2,4]triazin-7-yl)(hydroxy) methyl)-3-methylpyridin-2-yl)piperazine-1-carboxylate To a stirred solution of product of step C (530 mg, 0.78 mmol) in THF (10 mL) was added dropwise n-BuLi (1.6 M, 0.97 mL) at −78° C. After stirred for half an hour, a solution of tert-butyl 4-(5-formyl-3-methylpyridin-2-yl)piperazine-1-carboxylate (283 mg, 0.93 mmol) in THF (5 mL) was added dropwise at −78° C. Then the mixture was stirred for 2 hours. The reaction was quenched with aq.$NH_4Cl$, extracted with EtOAc (15 mL×3). The combined organic layers were washed with brine, dried over $Na_2SO_4$, concentrated and purified by column chromography (petroleum ether/EtOAc=10:1~2:1) to give the target compound (420 mg, 59.3%) as colorless oil. MS: M/e 911 $(M+1)^+$.

Step E: 3-((4-amino-7-((5-methyl-6-(piperazin-1-yl) pyridin-3-yl)methyl)imidazo[2,1-f][1,2,4]triazin-2-yl)oxy)hexan-1-ol A mixture of the product of step D (420 mg, 0.46 mmol) in TFA/$Et_3SiH$ (5 mL/3 mL) was stirred at 80° C. for 3 days. The reaction mixture was concentrated to give the residue, which was purified by prep-HPLC to give the target compound. $^1$H NMR (400 MHz, DMSO-d6) δ 8.10 (s, 1H), 8.06 (s, 1H), 7.99 (s, 1H), 7.41 (s, 1H), 7.32 (s, 1H), 5.12-4.99 (m, 1H), 4.48-4.42 (m, 1H), 4.03 (s, 2H), 3.49 (s, 2H), 2.94-2.76 (m, 8H), 2.17 (s, 3H), 1.82-1.72 (m, 2H), 1.65-1.55 (m, 2H), 1.41-1.20 (m, 2H), 0.86 (t, J=7.2 Hz, 3H) ppm. MS: M/e 441 $(M+1)^+$.

Compound B166: 7-((5-methyl-6-(4-(methylamino) piperidin-1-yl)pyridin-3-yl)methyl)-N2-(pentan-2-yl) imidazo[2,1-f][1,2,4]triazine-2,4-diamine Step A: tert-butyl (1-(4-((4-(bis(4-methoxybenzyl) amino)-2-(pentan-2-ylamino)imidazo[2,1-f][1,2,4] triazin-7-yl)(hydroxy)methyl)-2-methylphenyl)piperidin-4-yl)(methyl)carbamate To a stirred solution of 7-bromo-N4,N4-bis(4-methoxybenzyl)-N2-(pentan-2-yl)imidazo[2,1-f][1,2,4]triazine-2,4-diamine (200 mg, 0.37 mmol) in THF (8 mL), cooled to −78° C. and under a nitrogen atmosphere was added n-BuLi (1.6 M in hexane, 0.95 mmol, 0.59 mL) by dropwise. After stirring for 50 mins, a solution of tert-butyl (1-(5-formyl-3-methylpyridin-2-yl)piperidin-4-yl)(methyl)carbamate (211 mg, 0.55 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (130 mg, 44.3%). MS: M/e 794 $(M+1)^+$.

Step B: 7-((5-methyl-6-(4-(methylamino)piperidin-1-yl)pyridin-3-yl)methyl)-N2-(pentan-2-yl)imidazo [2,1-f][1,2,4]triazine-2,4-diamine A solution of the product of step A (130 mg, 0.163 mmol) in TFA (5 mL) and $Et_3SiH$ (5 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (60 mg, 84.5%). $^1$H NMR (400 MHz, DMSO-d6) δ 8.04 (s, 1H), 7.48 (s, 2H), 7.41 (s, 1H), 7.14 (s, 1H), 5.98 (d, J=8.4 Hz, 1H), 3.96 (s, 2H), 3.81-3.77 (m, 1H), 3.27 (s, 2H), 2.66 (t, J=11.7 Hz, 2H), 2.46 (s, 1H), 2.32 (s, 3H), 2.16 (s, 3H), 1.88 (d, J=11.2 Hz, 2H), 1.55-1.47 (m, 1H), 1.40-1.25 (m, 5H), 1.10 (d, J=6.3 Hz, 3H), 0.86 (t, J=6.8 Hz, 3H) ppm. MS: M/e 438 $(M+1)^+$.

Compound B167: 2-(cyclohexyloxy)-7-((5-methyl-6-(piperazin-1-yl)pyridin-3-yl)methyl)imidazo[2,1-f] [1,2,4]triazin-4-amine Compound B167 was synthesized starting from the corresponding starting materials according the similar procedures described as those of Compound B8. $^1$H NMR (400 MHz, DMSO-d6) δ 8.11-8.00 (m, 3H), 7.38 (s, 1H), 7.34 (s, 1H), 4.77 (s, 1H), 4.03 (s, 2H), 2.90 (s, 4H), 2.81 (s, 4H), 2.16 (s, 3H), 1.91 (s, 2H), 1.71 (s, 2H), 1.53 (s, 1H), 1.51-1.13 (m, 6H) ppm. MS: M/e 423 $(M+1)^+$.

Compound B168: 7-((6-((1S,4S)-2,5-diazabicyclo [2.2.1]heptan-2-yl)-5-methylpyridin-3-yl)methyl)-2-butoxyimidazo[2,1-f][1,2,4]triazin-4-amine Compound B168 was synthesized starting from the corresponding starting materials according the similar procedures described as those of Compound B8. $^1$H NMR (400

MHz, DMSO-d6) δ 8.11 (s, 1H), 8.02 (s, 1H), 7.90 (s, 1H), 7.28 (s, 2H), 4.45 (s, 1H), 4.22 (t, J=6.3 Hz, 2H), 3.96 (s, 2H), 3.61 (d, J=8.1 Hz, 1H), 3.52 (s, 1H), 3.06 (t, J=10.1 Hz, 2H), 2.82 (d, J=9.6 Hz, 1H), 2.13 (s, 3H), 1.72-1.63 (m, 3H), 1.58-1.52 (m, 1H), 1.45-1.37 (m, 2H), 1.23 (s, 1H), 0.93 (t, J=7.3 Hz, 3H) ppm. MS: M/e 409 $(M+1)^+$.

Compound B169: 1-(4-(5-((4-amino-2-(hexan-3-yloxy)imidazo[2,1-f][1,2,4]triazin-7-yl)methyl)-3-methylpyridin-2-yl)piperazin-1-yl)-2-(dimethylamino)ethan-1-one Dimethylglycine (21 mg, 0.21 mmol) was dissolved in 3 ml DMF followed by addition of HATU (143 mg, 0.38 mmol) and DIEA (53 mg, 0.42 mmol). The mixture was stirred for 1 h and then 2-(hexan-3-yloxy)-7-((5-methyl-6-(piperazin-1-yl)pyridin-3-yl)methyl)imidazo[2,1-f][1,2,4]triazin-4-amine (80 mg, 0.19 mmol) was added. The reaction was stirred and monitored by TLC. After 4 h, the reaction was quenched with water, extracted with EtOAc (10 mL×3), washed with brine, dried over $Na_2SO_4$, filtered, and concentrated. The residue was purified by prep-HPLC to give the target compound (15 mg). $^1$H NMR (400 MHz, DMSO-d6) δ 8.11 (s, 1H), 8.07 (s, 1H), 7.99 (s, 1H), 7.42 (s, 1H), 7.33 (s, 1H), 4.92-4.80 (m, 1H), 4.04 (s, 2H), 3.65-3.56 (m, 4H), 3.08 (s, 2H), 2.99-2.82 (m, 4H), 2.20 (s, 3H), 2.17 (s, 6H), 1.69-1.49 (m, 4H), 1.41-1.19 (m, 2H), 0.86 (t, J=6.7 Hz, 6H) ppm. MS: m/e 510 $(M+1)^+$.

Compound B170: 1-(4-(5-((4-amino-2-butoxyimidazo[2,1-f][1,2,4]triazin-7-yl)methyl)-3-methylpyridin-2-yl)piperazin-1-yl)-2-(diethylamino)ethan-1-one To a mixture of 2-butoxy-7-((5-methyl-6-(piperazin-1-yl)pyridin-3-yl)methyl)imidazo[2,1-f][1,2,4]triazin-4-amine (80 mg, 0.2 mmol), diethylglycine hydrochloride (33 mg, 0.2 mmol) and DIEA (52 mg, 0.4 mmol) in THF (5 mL) was added HATU (76 mg, 0.2 mmol). The reaction was stirred at room temperature overnight. The reaction was diluted with water, extracted with EA (60 mL), washed with brine, dried over $Na_2SO_4$, filtered, and concentrated. The residue was purified by prep-TLC (DCM: (7 M $NH_3$ in MeOH)=15:1) to give the target compound (22 mg, 21%). $^1$HNMR (400 MHz, $CD_3OD$) δ 8.09 (s, 1H), 7.53 (s, 1H), 7.34 (s, 1H), 4.28 (t, J=6.0 Hz, 2H), 4.15 (s, 2H), 3.91 (s, 2H), 3.82-3.60 (m, 4H), 3.17-2.90 (m, 8H), 2.29 (s, 3H), 1.80-1.69 (m, 2H), 1.58-1.42 (m, 2H), 1.30-1.16 (m, 6H), 0.98 (t, J=7.6 Hz, 3H) ppm. MS: M/e 510 $(M+1)^+$.

Compound B171: 4-amino-7-((5-methyl-6-(piperazin-1-yl)pyridin-3-yl)methyl)-N,N-dipropylimidazo[2,1-f][1,2,4]triazine-2-carboxamide Step A: methyl 4-(bis(4-methoxybenzyl)amino)imidazo[2,1-f][1,2,4]triazine-2-carboxylate To a solution of 2-chloro-N,N-bis(4-methoxybenzyl)imidazo[2,1-f][1,2,4]triazin-4-amine (2.23 g, 5 mmol) and TEA (1.01 g, 10 mmol) in MeOH (20 mL) was added Pd(dppf)$Cl_2$ (365 mg, 0.5 mmol). Then the mixture was stirred at 100° C. under CO (10 bar) overnight. The mixture was cooled to room temperature, concentrated to dryness, diluted with water (50 mL), extracted with EtOAc (60 mL×4). The combined organic layers were washed with brine, dried over $Na_2SO_4$, filtered, concentrated and the residue was purified by combi flash to give target compound (1.2 g, 55%). $^1$HNMR (400 MHz, $CDCl_3$) δ 7.93 (s, 1H), 7.64 (s, 1H), 7.35 (d, J=7.6 Hz, 2H), 7.22 (d, J=6.4 Hz, 2H), 6.87 (d, J=8.0 Hz, 4H), 5.71 (s, 2H), 4.94 (s, 2H), 4.03 (d, J=1.6 Hz, 3H), 3.80 (s, 6H) ppm. MS: M/e 434 $(M+H)^+$.

Step B: 4-(bis(4-methoxybenzyl)amino)imidazo[2,1-f][1,2,4]triazine-2-carboxylic acid To a solution of the product of step A (1.2 g, 2.77 mmol) in MeOH (12 mL) was added a solution of 2N NaOH solution (8.3 mL, 11.08 mmol). The reaction was stirred at room temperature overnight. MeOH was removed under reduced pressure. The residue was diluted with water, acidified with 2N HCl to pH 4. The suspension was filtered, washed with water, dried to give target compound (1.1 g, 95%). MS: M/e 420 $(M+1)^+$.

Step C: 4-(bis(4-methoxybenzyl)amino)-N,N-dipropylimidazo[2,1-f][1,2,4]triazine-2-carboxamide To a mixture of the product of step B (418 mg, 1 mmol), dipropylamine (101 mg, 1 mmol) and DIEA (258 mg, 2 mmol) in DMF (10 mL) was added HATU (380 mg, 1 mmol). The resulting mixture was stirred at room temperature overnight. The mixture was diluted with water, extracted with EtOAc (60 mL), washed with brine, dried over $Na_2SO_4$, filtered, concentrated and the residue was purified by combi flash to give target compound (400 mg, 80%). MS: M/e 503 $(M+1)^+$.

Step D: tert-butyl 4-(5-((4-(bis(4-methoxybenzyl)amino)-2-(dipropylcarbamoyl)imidazo[2,1-f][1,2,4]triazin-7-yl)(hydroxy)methyl)-3-methylpyridin-2-yl)piperazine-1-carboxylate To a solution of the product of step C (200 mg, 0.39 mmol) in THF (5 mL) was added a solution of n-BuLi (0.36 mL, 0.59 mmol) drop wise maintaining the temperature between −75~−65° C. After 1 h, a mixture of tert-butyl 4-(5-formyl-3-methylpyridin-2-yl)piperazine-1-carboxylate (131 mg, 0.43 mmol) in THF (1 mL) was added drop wise. The resulted mixture was stirred at −70° C. for 1 h and then warmed to room temperature overnight. The reaction was quenched with saturated $NH_4Cl$ solution, extracted with EtOAc (60 mL×2), washed with brine, dried over $Na_2SO_4$, filtered, and concentrated. The residue was purified by prep-TLC (EA/PE=1/1) to give target compound (130 mg, crude). MS: M/e 808 $(M+1)^+$.

Step E: 4-amino-7-((5-methyl-6-(piperazin-1-yl)pyridin-3-yl)methyl)-N,N-dipropylimidazo[2,1-f][1,2,4]triazine-2-carboxamide To a mixture of the product of step D (130 mg, crude) in TFA (3 mL) was added $Et_3SiH$ (3 mL) and the resulting mixture was stirred at 85° C. for 4 h. The mixture was cooled to room temperature and concentrated to dryness. To the residue was added TFA (5 mL) and the resulting mixture was heated at 85° C. for 2 days. The mixture was concentrated to dryness and the residue was purified by prep-HPLC to give target compound (40 mg, 19% for two steps). $^1$HNMR (400 MHz, DMSO-$d_6$) δ 8.74 (s, 2H), 8.43 (s, 1H), 8.40 (s, 1H), 8.06 (s, 1H), 7.50 (s, 1H), 7.47 (s, 1H), 4.14 (s, 2H), 3.32 (t, J=6.8 Hz, 2H), 3.27-3.15 (m, 8H), 3.05 (t, J=6.8 Hz, 2H), 2.20 (s, 3H), 1.66-1.52 (m, 2H), 1.50-1.35 (m, 2H), 0.90 (t, J=7.6 Hz, 3H), 0.61 (t, J=7.2 Hz, 3H) ppm. MS: M/e 452 $(M+1)^+$.

Compound B172: 2-(cyclopentyloxy)-7-((5-methyl-6-(piperazin-1-yl)pyridin-3-yl)methyl)imidazo[2,1-f][1,2,4]triazin-4-amine Compound B172 was synthesized starting from the corresponding starting materials according the similar procedures described as those of Compound B8. $^1H$ NMR (400 MHz, DMSO-d6) δ 8.10 (s, 1H), 8.06 (s, 1H), 7.98 (s, 1H), 7.42 (s, 1H), 7.32 (s, 1H), 5.19 (s, 1H), 4.04 (s, 2H), 2.93 (s, 4H), 2.85 (s, 4H), 2.17 (s, 3H), 1.90 (s, 2H), 1.69 (s, 4H), 1.58 (s, 2H) ppm. MS: M/e 409.0 $(M+1)^+$.

Compound B173: (S)-7-((6-(4-(dimethylamino)piperidin-1-yl)-5-methylpyridin-3-yl)methyl)-N2-(pentan-2-yl)imidazo[2,1-f][1,2,4]triazine-2,4-diamine Step A: (4-(bis(4-methoxybenzyl)amino)-2-(((S)-pentan-2-yl)amino)imidazo[2,1-f][1,2,4]triazin-7-yl)(6-(4-(dimethylamino)piperidin-1-yl)-5-methylpyridin-3-yl)methanol To a stirred solution of (S)-7-bromo-N4,N4-bis(4-methoxybenzyl)-N2-(pentan-2-yl)imidazo[2,1-f][1,2,4]triazine-2,4-diamine (200 mg, 0.37 mmol) in THF (10 mL), cooled to −78° C. and under a nitrogen atmosphere was added n-BuLi (1.6 M in hexane, 0.96 mmol, 0.58 mL) by dropwise. After stirring for 50 mins, a solution of 6-(4-(dimethylamino)piperidin-1-yl)-5-methylnicotinaldehyde (162 mg, 0.56 mmol) in THF (2 mL) was slowly added. The reaction mixture was slowly warmed up to rt and stirred for 2 h. The reaction mixture was poured to Saturated ammonium chloride solution and extracted by EtOAc (15 mL×3). The combined organic phase was washed with brine, dried over $Na_2SO_4$, concentrated in vacuo. The crude product was purified by column chromatography to give the title product (150 mg, 57.3%). MS: M/e 708.0 $(M+1)^+$.

Step B: (S)-7-((6-(4-(dimethylamino)piperidin-1-yl)-5-methylpyridin-3-yl)methyl)-N2-(pentan-2-yl)imidazo[2,1-f][1,2,4]triazine-2,4-diamine A solution of (4-(bis(4-methoxybenzyl)amino)-2-(((S)-pentan-2-yl)amino)imidazo[2,1-f][1,2,4]triazin-7-yl)(6-(4-(dimethylamino)piperidin-1-yl)-5-methylpyridin-3-yl)methanol (150 mg, 0.21 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 80° C. overnight. The mixture was cooled down to rt and concentrated in vacuo. The crude product was purified by prep-HPLC to give the product (12 mg, 12.5%). $^1H$ NMR (400 MHz, DMSO-d6) δ 8.04 (s, 1H), 7.47 (br.s, 2H), 7.41 (s, 1H), 7.14 (s, 1H), 5.98 (d, J=8.4 Hz, 1H), 3.96 (s, 2H), 3.87-3.80 (m, 1H), 3.34 (s, 2H), 2.62 (t, J=12.0 Hz, 2H), 2.21 (s, 7H), 2.16 (s, 3H), 1.81 (d, J=12.0 Hz, 2H), 1.52-1.21 (m, 6H), 1.10 (d, J=5.7 Hz, 3H), 0.87 (t, J=6.4 Hz, 3H) ppm. MS: M/e 453.0 $(M+1)^+$.

Compound B174: 2-((1-methoxypropan-2-yl)oxy)-7-((5-methyl-6-(piperazin-1-yl)pyridin-3-yl)methyl)imidazo[2,1-f][1,2,4]triazin-4-amine Step A: 7-bromo-N,N-bis(4-methoxybenzyl)-2-((1-methoxypropan-2-yl)oxy)imidazo[2,1-f][1,2,4]triazin-4-amine To a stirred solution of 1-methoxypropan-2-ol (135 mg, 1.5 mmol) in THF was added sodium hydride (115 mg, 3 mmol). The reaction was stirred at rt for 30 mins. 7-bromo-2-chloro-N,N-bis(4-methoxybenzyl)imidazo[2,1-f][1,2,4]triazin-4-amine (486 mg, 1 mmol) was added to the mixture. The reaction was stirred at 60° C. overnight. The reaction mixture was cooled down to rt and poured into $H_2O$. The mixture was extracted by EtOAc (15 mL×3). The combined organic phases were washed with brine, dried over $Na_2SO_4$, concentrated in vacuo. The crude product was purified by column chromatography to give the title product (260 mg, 48%). MS: M/e 544 $(M+1)^+$.

Step B: tert-butyl 4-(5-((4-(bis(4-methoxybenzyl)amino)-2-((1-methoxypropan-2-yl)oxy)imidazo[2,1-f][1,2,4]triazin-7-yl)(hydroxy)methyl)-3-methylpyridin-2-yl)piperazine-1-carboxylate To a stirred solution of the product of step A (150 mg, 0.27 mmol) in THF (10 mL), cooled to −78° C. and under a nitrogen atmosphere was added n-BuLi (1.6 M in hexane, 0.67 mmol, 0.42 mL) by dropwise. After stirring for 50 mins, a solution of tert-butyl 4-(5-formyl-3-methylpyridin-2-yl)piperazine-1-carboxylate (126 mg, 0.41 mmol) in THF (2 mL) was slowly added. The reaction mixture was slowly warmed up to rt and stirred overnight. The reaction mixture was poured into saturated ammonium chloride solution and extracted by EtOAc (15 mL×3). The combined organic phases were washed with brine, dried over $Na_2SO_4$, concentrated in vacuo. The crude product was purified by column chromatography to give the title product (130 mg, 62.8%). MS: M/e 769 $(M+1)^+$.

Step C: 2-((1-methoxypropan-2-yl)oxy)-7-((5-methyl-6-(piperazin-1-yl)pyridin-3-yl)methyl)imidazo[2,1-f][1,2,4]triazin-4-amine A solution of the product of step B (130 mg, 0.169 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 80° C. overnight. The mixture was cooled down to rt and concentrated in vacuo. The crude product was purified by prep-HPLC to give the product (2.6 mg, 3.6%). $^1H$ NMR (400 MHz, DMSO-d6) δ 8.15 (s, 1H), 8.05 (s, 2H), 7.40 (s, 1H), 7.33 (s, 1H), 5.10 (d, J=4.0 Hz, 1H), 4.04 (s, 2H), 3.54-3.40 (m, 3H), 3.27 (s, 3H), 2.93 (s, 4H), 2.85 (s, 4H), 2.17 (s, 3H), 1.23 (d, J=5.9 Hz, 3H) ppm. MS: M/e 413 $(M+1)^+$.

Compound B175: 1-(4-(5-((4-amino-2-(pentan-3-ylamino)imidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-(pentan-3-ylamino)imidazo[2,1-f][1,2,4]triazin-7-yl)methyl)-3-methylpyridin-2-yl)piperazin-1-yl)-2-oxoethyl)(methyl)carbamate To a stirred solution of 7-((5-methyl-6-(piperazin-1-yl)pyridin-3-yl)methyl)-N2-(pentan-3-yl)imidazo[2,1-f][1,2,4]triazine-2,4-diamine (100 mg, 0.24 mmol) in DMF (5 mL) was added N-(tert-butoxycarbonyl)-N-methylglycine (25 mg, 0.243 mmol), HATU (141 mg, 0.36 mmol) and DIEA (96 mg, 0.69 mmol). The reaction mixture was stirred at r.t. for overnight. The mixture was poured into $H_2O$ (50 mL) and extracted with EtOAc (10 ml×3). The combined organic phase was washed with brine, dried over $Na_2SO_4$ and concentrated in vacuo. The crude product was purified by column chromatography to give the product (86 mg, 63.5%). MS: M/e 581.0 (M+1)$^+$.

Step B: 1-(4-(5-((4-amino-2-(pentan-3-ylamino) imidazo[2,1-f][1,2,4]triazin-7-yl)methyl)-3-methylpyridin-2-yl)piperazin-1-yl)-2-(methylamino) ethan-1-one To a stirred solution of the product step A (84 mg, 0.144 mmol) in HCl (4 M in EA, 10 ml). The reaction mixture was stirred at rt for overnight. The mixture was poured into Saturated $NaHCO_3$ solution (20 mL) and extracted with DCM (10 ml×3). The combined organic phase was washed with brine, dried over $Na_2SO_4$ and concentrated in vacuo. The crude product was purified by column chromatography to give the product (15 mg, 21.5%). $^1$H NMR (400 MHz, $CDCl_3$-d6) δ 8.08 (s, 1H), 7.47 (s, 3H), 7.15 (s, 1H), 5.96 (d, J=8.7 Hz, 1H), 3.98 (s, 2H), 3.59 (s, 3H), 3.55 (s, 2H), 3.51 (s, 2H), 3.00 (s, 2H), 2.95 (s, 2H), 2.36 (s, 3H), 2.20 (s, 3H), 1.52-1.39 (m, 4H), 0.84 (t, J=7.3 Hz, 6H) ppm. MS: M/e 481.0 (M+1)$^+$.

Compound B176: 1-(4-(5-((4-amino-2-((1-hydroxyhexan-3-yl)oxy)imidazo[2,1-f][1,2,4]triazin-7-yl) methyl)-3-methylpyridin-2-yl)piperazin-1-yl)-2-(dimethylamino)ethan-1-one A mixture of 3-((4-amino-7-((5-methyl-6-(piperazin-1-yl) pyridin-3-yl)methyl)imidazo[2,1-f][1,2,4]triazin-2-yl)oxy) hexan-1-ol (20 mg, 0.045 mmol), dimethylglycine (4.7 mg, 0.045 mmol), HATU (20 mg, 0.054 mmol) and DIPEA (12 mg, 0.09 mmol) in DMF (3 mL) was stirred at room temperature overnight. The reaction mixture was poured into $H_2O$ (10 mL) and extracted with EtOAc (10 mL). The organic layer was separated, washed with brine, dried over $Na_2SO_4$, concentrated and purified by prep-HPLC to give target compound (12 mg). $^1$H NMR (400 MHz, DMSO-$d_6$) δ 9.51 (br.s, 1H), 8.17-8.00 (m, 3H), 7.50 (s, 1H), 7.35 (s, 1H), 5.11-5.00 (m, 1H), 4.31 (d, J=4.8 Hz, 2H), 4.07 (s, 2H), 3.65-3.60 (m, 2H), 3.51-3.42 (m, 4H), 3.10-3.00 (m, 4H), 3.05 (s, 3H), 3.04 (s, 3H), 2.22 (s, 3H), 1.88-1.69 (m, 2H), 1.65-1.56 (m, 2H), 1.43-1.21 (m, 2H), 0.86 (t, J=7.2 Hz, 3H) ppm. MS: M/e 526 (M+1)$^+$.

Compound B177: (S)-1-(4-(5-((4-amino-2-(pentan-2-yloxy)imidazo[2,1-f][1,2,4]triazin-7-yl)methyl)-3-methylpyridin-2-yl)piperazin-1-yl)-2-((2-hydroxyethyl)amino)ethan-1-one Step A: N-(tert-butoxycarbonyl)-N-(2-hydroxyethyl)glycine NaOH solution (1N, 0.84 mL) was added to a solution of (2-hydroxyethyl) glycine (100 mg, 0.84 mmol) and $Boc_2O$ (201 mg, 0.92 mmol) in dioxane (2 mL) and water (1 mL). After stirred at r.t overnight, the solution was acidified with citric acid solution pH=3 and extracted with ethyl acetate (10 mL) for twice. The combined organic layers were dried with $Na_2SO_4$, filtered and concentrated to get the crude product, which was used directly in next step without further purification (220 mg, crude). MS: M/e 164 (M−56)$^+$.

Step B: tert-butyl (S)-(2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl)(2-hydroxyethyl)carbamate A solution of (S)-7-((5-methyl-6-(piperazin-1-yl)pyridin-3-yl)methyl)-2-(pentan-2-yloxy)imidazo[2,1-f][1,2,4]triazin-4-amine (80 mg, 0.20 mmol), N-(tert-butoxycarbonyl)-N-(2-hydroxyethyl)glycine (100 mg, 0.24 mmol), HATU (114 mg, 0.3 mmol) and DIEA (52 mg, 0.4 mmol) in DMF (5 mL) was stirred at r.t for 2 hrs. The reaction mixture was added with water (5 mL), extracted with ethyl acetate (10 mL) and washed with brine (10 mL). The organic layer was dried with $Na_2SO_4$, filtered and concentrated to get the crude product, which was purified by prep-TLC (DCM:7M $NH_3$·MeOH=11:1) to get the product (30 mg, 25%). MS: M/e 612 (M+1)$^+$.

Step C: (S)-1-(4-(5-((4-amino-2-(pentan-2-yloxy) imidazo[2,1-f][1,2,4]triazin-7-yl)methyl)-3-methylpyridin-2-yl)piperazin-1-yl)-2-((2-hydroxyethyl) amino)ethan-1-one HCl/dioxane (4M, 2 mL) was added to a solution of the product of step B (30 mg, 0.05 mmol) in EA (2 mL). The reaction mixture was stirred at r.t for 2 hrs. After concentration, the residue was dissolved in EA (5 mL) and washed with $NaHCO_3$ (5 mL). The organic layer was dried with $Na_2SO_4$, filtered and concentrated to get the crude product, which was further purified by prep-HPLC to get the pure product (10 mg, 40%). $^1$H NMR (400 MHz, $CD_3OD$) δ 8.10 (s, 1H), 7.82 (s, 1H), 7.50 (s, 1H), 5.10-5.03 (m, 1H), 4.24 (s, 2H), 4.17 (s, 2H), 3.84-3.78 (m, 4H), 3.61 (s, 2H), 3.33 (s, 2H), 3.27 (s, 2H), 3.19 (t, J=8.0 Hz, 2H), 2.37 (s, 3H), 1.72-1.56 (m, 2H), 1.46-1.40 (m, 2H), 1.30 (s, 3H), 0.94 (t, J=8.0 Hz, 3H) ppm. MS: M/e 512 (M+1)$^+$.

Compound B178: (R)-7-((6-(4-((dimethylamino)methyl) piperidin-1-yl)-5-methylpyridin-3-yl)methyl)-N2-(pentan-2-yl)imidazo[2,1-f][1,2,4]triazine-2,4-diamine Compound B137 was separated into two enantiomeric stereoisomers, Compound B147 (first peak) and Compound B178 (second peak) by chiral prep-HPLC. The chiral separation conditions are shown below.

| Column | CHIRALPAK AD-H |
|---|---|
| Column size | 2 cm × 25 cm, 5 um |
| Injection | 0.4 ML |
| Mobile phase | Hex(2 mMNH3—MeOH):EtOH = 93:7 |
| Flow rate | 20 ml/min |
| Wavelength | UV 220 nm |
| Temperature | 25° C. |
| Sample solution | 38.6 mg/ml in EtOH |
| Prep-HPLC equipment | Prep-Gilson-HPLC |

Compound B178: $^1$H NMR (400 MHz, DMSO-d6) δ 8.04 (s, 1H), 7.47 (s, 2H), 7.40 (s, 1H), 7.14 (s, 1H), 5.98 (d, J=8.3 Hz, 1H), 3.96 (s, 2H), 3.80 (s, 1H), 3.28 (s, 4H), 2.63 (t, J=11.9 Hz, 2H), 2.15 (s, 9H), 1.74 (d, J=11.6 Hz, 2H), 1.53 (s, 1H), 1.44-1.16 (m, 6H), 1.10 (d, J=5.7 Hz, 3H), 0.86 (d, J=6.5 Hz, 3H) ppm. MS: M/e 466 (M+1)$^+$.

Compound B179: (S)-1-(4-(5-((4-amino-2-butoxy-imidazo[2,1-f][1,2,4]triazin-7-yl)methyl)-3-methylpyridin-2-yl)-2-methylpiperazin-1-yl)-2-(dimethylamino)ethan-1-one To a stirred solution of (S)-2-butoxy-7-((5-methyl-6-(3-methylpiperazin-1-yl)pyridin-3-yl)methyl)imidazo[2,1-f][1,2,4]triazin-4-amine (40 mg, 0.01 mmol), dimethylglycine (10 mg, 0.01 mmol) and HATU (38 mg, 0.01 mmol) in DMF (2 mL) was added DIEA (0.1 mL) at room temperature. The mixture was stirred at room temperature for 12 hours. The reaction was diluted with water (4 mL) and extracted with EA (5 mL×3). The combined organic phase were washed with brine, dried over $Na_2SO_4$ and concentrated under reduced pressure. The residue was purified by prep-HPLC to afford the title compound (35 mg, yield: 57.5%), $^1$H NMR (400 MHz, DMSO-d6) δ 8.21 (s, 1H), 8.18 (s, 1H), 8.11 (s, 1H), 7.55 (s, 1H), 7.40 (s, 1H), 4.49-4.27 (m, 2H), 4.26-4.16 (m, 2H), 4.09 (s, 2H), 3.56-3.34 (m, 2H), 3.33-3.07 (m, 2H), 2.95-2.63 (m, 8H), 2.27 (s, 3H), 2.08 (s, 1H), 1.76-1.61 (m, 2H), 1.50-1.36 (m, 3H), 1.34-1.20 (m, 2H), 0.93 (t, J=7.2 Hz, 3H) ppm. MS: M/e 496 $(M+1)^+$.

Compound B180: 7-((5-methyl-6-(piperazin-1-yl)pyridin-3-yl)methyl)-2-pentylimidazo[2,1-f][1,2,4]triazin-4-amine Step A: (E)-N,N-bis(4-methoxybenzyl)-2-(pent-1-en-1-yl)imidazo[2,1-f][1,2,4]triazin-4-amine A mixture of 2-chloro-N,N-bis(4-methoxybenzyl)imidazo[2,1-f][1,2,4]triazin-4-amine (0.5 g, 1.22 mmol), (E)-pent-1-en-1-ylboronic acid (0.21 g, 1.84 mmol), $Pd(dppf)_2Cl_2$ (45 mg, 0.062 mmol), $Na_2CO_3$ (0.26 g, 2.45 mmol) in dioxane (15 ml) and $H_2O$ (4 ml) was stirred at 90° C. under $N_2$ atmosphere for 7 h. The mixture was diluted with EA (20 ml) and then washed with brine (10 ml×2). The organic layer was dried and concentrated under reduced pressure. The residue was purified by flash column chromatography with 0-20% EA in PE to afford product (0.5 g, 92%) as a colorless oil. MS: M/e 444 $(M+1)^+$.

Step B: tert-butyl (E)-4-(5-((4-(bis(4-methoxybenzyl)amino)-2-(pent-1-en-1-yl)imidazo[2,1-f][1,2,4]triazin-7-yl)(hydroxy)methyl)-3-methylpyridin-2-yl)piperazine-1-carboxylate To a stirred solution of (E)-N,N-bis(4-methoxybenzyl)-2-(pent-1-en-1-yl)imidazo[2,1-f][1,2,4]triazin-4-amine (300 mg, 0.68 mmol) in THF (15 ml), was added n-BuLi (1.6 M, 1.1 ml, 1.76 mmol) under $N_2$ at −78° C. and then stirred for 0.5 h. A solution of tert-butyl 4-(5-formyl-3-methylpyridin-2-yl)piperazine-1-carboxylate (338 mg, 1.01 mmol) in THF (2 ml) was added at −78° C. and then warmed to r.t naturally. The solution was stirred at r.t for 1 h. After completed, the solution was quenched with $H_2O$ (2 ml) and then concentrated. The residue was diluted with EA (30 ml) and then washed with brine (10 ml×2). The organic layer was dried and concentrated. The residue was purified by flash column chromatography with 0-10% MeOH in DCM to afford product (0.5 g, crude) as a light yellow gum, which was used directly for the next step without further purification. MS: M/e 749 $(M+1)^+$.

Step C: tert-butyl 4-(5-((4-(bis(4-methoxybenzyl)amino)-2-pentylimidazo[2,1-f][1,2,4]triazin-7-yl)(hydroxy)methyl)-3-methylpyridin-2-yl)piperazine-1-carboxylate A mixture of the product of step B (0.5 g, crude) and Pd/C (0.05 g) in MeOH was stirred at r.t under $H_2$ for 7 h. After completed, the mixture was filtered through diatomite. The filtrate was concentrated under reduced pressure to afford product (crude) as an off-white oil, which was used directly for the next step without further purification. MS: M/e 751 $(M+1)^+$.

Step D: 7-((5-methyl-6-(piperazin-1-yl)pyridin-3-yl)methyl)-2-pentylimidazo[2,1-f][1,2,4]triazin-4-amine A mixture of the product of step C (crude) in TFA (6 ml) and triethylsilane (2 ml) was stirred at 95° C. overnight. After completed, the mixture was concentrated under reduced pressure. The residue was purified by prep-TLC and then prep-HPLC to afford product (7.68 mg). $^1$H NMR (400 MHz, DMSO-d6) δ 8.62 (s, 2H), 8.11 (s, 1H), 7.98 (s, 2H), 7.51 (s, 1H), 7.32 (s, 1H), 4.11 (s, 2H), 3.25-3.16 (m, 8H), 2.58 (t, J=8 Hz, 2H), 2.20 (s, 3H), 1.85-1.60 (m, 2H), 1.35-1.23 (m, 4H), 0.93-0.79 (m, 3H) ppm. MS: M/e 395 $(M+1)^+$.

Compound B181: 1-(4-(5-((4-amino-2-(hexan-3-yloxy)imidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-(hexan-3-yloxy)imidazo[2,1-f][1,2,4]triazin-7-yl)methyl)-3-methylpyridin-2-yl)piperazin-1-yl)-2-oxoethyl)(methyl)carbamate N-(tert-butoxycarbonyl)-N-methylglycine (39 mg, 0.21 mmol) were dissolved in DMF (3 mL) followed by addition of HATU (143 mg, 0.38 mmol) and DIEA (53 mg, 0.42 mmol). The mixture was stirred for 1 h and then 2-(hexan-3-yloxy)-7-((5-methyl-6-(piperazin-1-yl)pyridin-3-yl)methyl)imidazo[2,1-f][1,2,4]triazin-4-amine (80 mg, 0.19 mmol) was added. The reaction was stirred and monitored by TLC. After 4 h, the reaction was quenched with water, extracted with EtOAc (10 mL×3), washed with brine, dried over $Na_2SO_4$, filtered, and concentrated. The residue was purified by prep-TLC (DCM:MeOH=10: 1) to give the target compound (60 mg, 47%). MS: m/e 596 $(M+1)^+$.

Step B: 1-(4-(5-((4-amino-2-(hexan-3-yloxy)imidazo[2,1-f][1,2,4]triazin-7-yl)methyl)-3-methylpyridin-2-yl)piperazin-1-yl)-2-(methylamino)ethan-1-one Tert-butyl (2-(4-(5-((4-amino-2-(hexan-3-yloxy)imidazo[2,1-f][1,2,4]triazin-7-yl)methyl)-3-methylpyridin-2-yl)piperazin-1-yl)-2-oxoethyl)(methyl)carbamate (60 mg, 0.10 mmol) was dissolved in DCM (3 ml) followed by addition TFA (0.5 ml). After 4 h, the organic phase was concentrated under reduced pressure and the crude product was purified by prep-HPLC to give the desired product (13 mg, 26%). $^1$H NMR (400 MHz, DMSO-d6) δ 8.68 (s, 2H), 8.11 (s, 1H), 8.07 (s, 2H), 7.49 (s, 1H), 7.38 (s, 1H), 4.92-4.88 (m, 1H), 4.08 (s, 4H), 3.81 (s, 2H), 3.48 (s, 2H), 3.09 (s, 2H), 3.07 (s, 2H), 2.56 (s, 3H), 2.22 (s, 3H), 1.72-1.48 (m, 4H), 1.32-1.21 (m, 2H), 0.87 (t, J=6.3 Hz, 6H) ppm. MS: m/e 496 $(M+1)^+$.

Compound B182: 4-amino-N-butyl-N-methyl-7-((5-methyl-6-(piperazin-1-yl)pyridin-3-yl)methyl)imidazo[2,1-f][1,2,4]triazine-2-carboxamide Step A: 4-(bis(4-methoxybenzyl)amino)-N-butyl-N-methyl)imidazo[2,1-f][1,2,4]triazine-2-carboxamide To a mixture of 4-(bis(4-methoxybenzyl)amino)imidazo[2,1-f][1,2,4]triazine-2-carboxylic acid (418 mg, 1 mmol), N-methylbutan-1-amine (87 mg, 1 mmol) and DIEA (258 mg, 2 mmol) in DMF (10 mL) was added HATU (380 mg, 1 mmol). The resulting mixture was stirred at room temperature overnight. The mixture was diluted with water, extracted with EtOAc (60 mL), washed with brine, dried over $Na_2SO_4$, filtered, concentrated and the residue was purified by combi flash to give target compound (410 mg, 84%). MS: M/e 489 $(M+1)^+$.

Step B: tert-butyl 4-(5-((4-(bis(4-methoxybenzyl)amino)-2-(butyl(methyl)carbamoyl)imidazo[2,1-f][1,2,4]triazin-7-yl)(hydroxy)methyl)-3-methylpyridin-2-yl)piperazine-1-carboxylate To a solution of the product of step A (41 mg, 0.85 mmol) in THF (10 mL) was added a solution of n-BuLi (0.79 mL, 1.27 mmol) drop wise maintaining the temperature between −75~−65° C. After 1 h, a mixture of tert-butyl 4-(5-formyl-3-methylpyridin-2-yl)piperazine-1-carboxylate (285 mg, 0.93 mmol) in THF (2 mL) was added drop wise. The resulted mixture was stirred at −70° C. for 1 h and then warmed to room temperature overnight. The reaction was quenched with saturated $NH_4Cl$ solution, extracted with EtOAc (60 mL×2), washed with brine, dried over $Na_2SO_4$, filtered, and concentrated. The residue was purified by prep-TLC (EA/PE=1/1) to give target compound (150 mg, crude). MS: M/e 794 $(M+1)^+$.

Step C: 4-amino-N-butyl-N-methyl-7-((5-methyl-6-(piperazin-1-yl)pyridin-3-yl)methyl)imidazo[2,1-f][1,2,4]triazine-2-carboxamide To a mixture of the product of step B (130 mg, crude) in TFA (3 mL) was added $Et_3SiH$ (3 mL) and the resulting mixture was stirred at 85° C. for 4 h. The mixture was cooled to room temperature and concentrated to dryness. To the residue was added TFA (5 mL) and the resulting mixture was heated at 85° C. for 2 days. The mixture was concentrated to dryness and the residue was purified by prep-HPLC to give target compound (50 mg, 17% for two steps). $^1H$ NMR (400 MHz, DMSO-$d_6$) δ 8.74 (s, 2H), 8.44 (s, 1H), 8.38 (d, J=12.8 Hz, 1H), 8.07 (d, J=12.0 Hz, 1H), 7.75-7.41 (m, 2H), 4.14 (s, 2H), 3.41 (t, J=6.8 Hz, 1H), 3.28-3.16 (m, 8H), 3.13 (t, J=6.8 Hz, 1H), 2.94 (s, 1.6H), 2.82 (s, 1.4H), 2.20 (s, 3H), 1.60-1.41 (m, 2H), 1.36-1.25 (m, 1H), 1.15-1.02 (m, 1H), 0.94 (t, J=7.2 Hz, 1.4H), 0.94 (t, J=6.4 Hz, 1.6H) ppm. MS: M/e 438 $(M+1)^+$.

Compound B183: 2-butoxy-7-((5-ethyl-6-(piperazin-1-yl)pyridin-3-yl)methyl)imidazo[2,1-f][1,2,4]triazin-4-amine Step A: tert-butyl 4-(3-bromo-5-(methoxycarbonyl)pyridin-2-yl)piperazine-1-carboxylate A mixture of methyl 5-bromo-6-chloronicotinate (5 g, 20 mmol), tert-butyl piperazine-1-carboxylate (5.58 g, 30 mmol) and DIPEA (7.74 g, 60 mmol) in DMSO (50 mL) was stirred at 120° C. overnight. The mixture was extracted with DCM (100 mL×3). The combined organic layers were washed with water and brine, dried over $Na_2SO_4$, concentrated and purified by column chromatography (DCM/MeOH=40:1~5:1) to give the desired product (7.32 g, 91.50%) as yellow solid. MS: M/e 400 $(M+1)^+$.

Step B: tert-butyl 4-(5-(methoxycarbonyl)-3-vinylpyridin-2-yl)piperazine-1-carboxylate 4-(3-bromo-5-(methoxycarbonyl)pyridin-2-yl)piperazine-1-carboxylate (7.32 g, 18.35 mmol), 4,4,5,5-tetramethyl-2-vinyl-1,3,2-dioxaborolane (3.39 g, 22.02 mmol), Pd(dppf)$Cl_2$ (2.68 g, 3.669 mmol) and $Cs_2CO_3$ (11.96 g, 36.69 mmol) in dioxane (80 mL) and water (10 mL) was stirred at 100° C. overnight. To cool down r.t and the mixture was extracted with DCM (100 mL×3). The combined organic layers were washed with water and brine, dried over $Na_2SO_4$, concentrated and purified by column chromatography (DCM/MeOH=40:1~5:1) to give the target compound (5.46 g, 85.8%) as yellow solid. MS: M/e 348 $(M+1)^+$.

Step C: 6-(4-(tert-butoxycarbonyl)piperazin-1-yl)-5-vinylnicotinic acid

A mixture of the product of step B (5.46 g, 15.73 mmol) and NaOH (3.15 g, 78.67 mmol) in MeOH (2 mL) and water (10 mL) was stirred at 50° C. for 3 h. The mixture was quenched with HCl solution, extracted with DCM (100 mL×3). The combined organic layers were washed with water and brine, dried over $Na_2SO_4$, concentrated and purified by column chromatography (DCM/MeOH=20:1~5:1) to give the target compound (4.98 g, 95.04%) as yellow solid. MS: M/e 334 $(M+1)^+$.

Step D: 6-(4-(tert-butoxycarbonyl)piperazin-1-yl)-5-ethylnicotinic acid

A mixture of the product of step C (4.98 g, 14.9 mmol) and Pd/C (500 mg, 10%) in MeOH (2 mL) was stirred at r.t. for 5 h. The mixture was filtered, concentrated and purified by column chromatography (DCM/MeOH=20:1~5:1) to give the target compound (4.68 g, 93.41%) as yellow solid. MS: M/e 336 $(M+1)^+$.

Step E: tert-butyl 4-(3-ethyl-5-(hydroxymethyl)pyridin-2-yl)piperazine-1-carboxylate To a mixture of the product of step D (4.68 g, 13.97 mmol) in THF (20 mL) was added LAH (1.06 g, 27.94 mmol) and stirred at r.t. for 3 h. The mixture was quenched with NaOH solution, extracted with DCM (100 mL×3). The combined organic layers were washed with water and brine, dried over $Na_2SO_4$, concentrated and purified by column chromatography (DCM/MeOH=20:1~5:1) to give the target compound (3.88 g, 86.5%) as yellow solid. MS: M/e 322 $(M+1)^+$.

Step F: tert-butyl 4-(3-ethyl-5-formylpyridin-2-yl)piperazine-1-carboxylate

A mixture of the product of step E (3.88 g, 12.08 mmol) and Dess-Martin periodinane (7.68 g, 18.13 mmol) in DCM (20 mL) was stirred at r.t. for 3 h. The mixture was quenched with saturated $NaHCO_3$ solution, extracted with DCM (100 mL×3). The combined organic layers were washed with water and brine, dried over $Na_2SO_4$, concentrated and purified by column chromatography (DCM/MeOH=20:1~5:1) to give the target compound (3.54 g, 91.8%) as yellow solid. MS: M/e 320 $(M+1)^+$.

Step G: tert-butyl 4-(5-((4-(bis(4-methoxybenzyl)amino)-2-butoxyimidazo[2,1-f][1,2,4]triazin-7-yl)(hydroxy)methyl)-3-ethylpyridin-2-yl)piperazine-1-carboxylate To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol)

was added dropwise at −78° C. and stirred for 1 h. Then a solution of the product of step F (136 mg, 0.43 mmol) in THF (2 mL) was added dropwise at −78° C., after addition, the mixture was warmed to r.t. and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the target compound (134 mg, 60.5%) as yellow oil. MS: M/e 778 $(M+1)^+$.

Step H: 2-butoxy-7-((5-ethyl-6-(piperazin-1-yl)pyridin-3-yl)methyl)imidazo[2,1-f][1,2,4]triazin-4-amine A mixture of the product of step G (134 mg, 0.17 mmol) and triethylsilane (1 mL) in TFA (2 mL) was stirred at 90° C. overnight. The mixture was concentrated and purified with prep-HPLC to give the title product (32 mg, 45.25%). $^1H$ NMR (400 MHz, DMSO-d6) δ 8.99 (br.s, 2H), 8.15 (s, 1H), 8.12 (s, 1H), 8.07 (s, 1H), 7.61 (s, 1H), 7.33 (s, 1H), 4.21 (s, 2H), 4.10 (s, 2H), 3.22-3.15 (m, 8H), 2.58 (d, J=7.2 Hz, 2H), 1.74-1.62 (m, 2H), 1.41 (dd, J=14.1, 7.0 Hz, 2H), 1.16 (t, J=7.0 Hz, 3H), 0.93 (t, J=7.0 Hz, 3H) ppm. MS: M/e 411 $(M+1)^+$.

Compound B184: 7-((6-(4-(dimethylamino)piperidin-1-yl)-5-methyl pyridin-3-yl)methyl)-N2-(heptan-4-yl)imidazo[2,1-f][1,2,4]triazine-2,4-diamine Step A: N2-(heptan-4-yl)-N4,N4-bis(4-methoxybenzyl)imidazo[2,1-f][1,2,4]triazine-2,4-diamine A solution of 2-chloro-N,N-bis(4-methoxybenzyl)imidazo[2,1-f][1,2,4]triazin-4-amine (3 g, 7.3 mmol), heptan-4-amine (2.5 g, 22 mmol) and DIEA (2.8 g, 22 mmol) in NMP (9 mL) was heated in a sealed tube at 230° C. for 5 hrs. The reaction mixture was cooled, diluted with water (10 mL) and extracted with ethyl acetate (20 mL). The organic layer was washed with brine (20 mL), dried with $Na_2SO_4$, filtered and concentrated to get the crude product, which was further purified by CombiFlash (PE:EA=15%) to get the product (1.9 g, 53%) as a colorless oil. MS: M/e 249 $(M+1)^+$.

Step B: (4-(bis(4-methoxybenzyl)amino)-2-(heptan-4-ylamino)imidazo[2,1-f][1,2,4]triazin-7-yl)(6-(4-(dimethylamino)piperidin-1-yl)-5-methylpyridin-3-yl)methanol To a cooled solution of N2-(heptan-4-yl)-N4,N4-bis(4-methoxybenzyl)imidazo [2,1-f][1,2,4]triazine-2,4-diamine (200 mg, 0.41 mmol) in THF (8 mL) at −78° C., purged with $N_2$ was added with n-BuLi (1.6 M, 0.65 mL) dropwise. After stirred at −78° C. for 30 mins, 6-(4-(dimethylamino)piperidin-1-yl)-5-methylnicotinaldehyde (152 mg, 0.6 mmol) in THF (2 mL) was added. The resulting mixture was stirred at this temperature for 30 mins, and then warmed to r.t overnight. The solution was quenched with $NH_4Cl$ solution (10 mL) and extracted with ethyl acetate (10 mL). The organic layer was dried with $Na_2SO_4$, filtered and concentrated to get the crude product, which was further purified by CombiFlash (DCM:MeOH=15%, 4M $NH_3$·MeOH) to get the pure product (170 mg, 57%) as a yellow oil. MS: M/e 736 $(M+1)^+$.

Step C: 7-((6-(4-(dimethylamino)piperidin-1-yl)-5-methyl pyridin-3-yl)methyl)-N2-(heptan-4-yl)imidazo[2,1-f][1,2,4]triazine-2,4-diamine A solution of (4-(bis(4-methoxybenzyl)amino)-2-(heptan-4-ylamino)imidazo [2,1-f][1,2,4]triazin-7-yl)(6-(4-(dimethylamino)piperidin-1-yl)-5-methylpyridin-3-yl)methanol (170 mg, 0.23 mmol) in triethylsilane (2 mL) and trifluoroacetic acid (2 mL) was heated at 80° C. overnight. The solvent was evaporated under oil pump to get the residue, which was added with EA (10 mL) and basified with $NaHCO_3$ solution (10 mL). The aqueous layer was extracted with DCM (with 10% of MeOH) for three times. The combined organic layers were dried, concentrated and purified by prep-TLC (DCM:MeOH=10:1, 7M $NH_3$·MeOH) get the product (35 mg, 32%). $^1H$ NMR (400 MHz, DMSO-d6) δ 8.05 (s, 1H), 7.43 (br.s, 2H), 7.40 (s, 1H), 7.15 (s, 1H), 5.93 (d, J=8.0 Hz, 1H), 3.95 (s, 2H), 3.79 (s, 1H), 3.39 (s, 2H), 2.64 (t, J=12.0 Hz, 2H), 2.38 (s, 6H), 2.16 (s, 3H), 1.88 (d, J=8.0 Hz, 2H), 1.57-1.54 (m, 2H), 1.42-1.29 (m, 8H), 0.85 (d, J=4.0 Hz, 6H) ppm. MS: M/e 480 $(M+1)^+$.

Compound B185: (R)-7-((6-(4-(dimethylamino)piperidin-1-yl)-5-methylpyridin-3-yl)methyl)-N2-(pentan-2-yl)imidazo[2,1-f][1,2,4]triazine-2,4-diamine Compound B138 was separated into two enantiomeric stereoisomers, Compound B173 (first peak) and Compound B185 (second peak) by chiral prep-HPLC. The chiral separation conditions are shown below.

| Column | CHIRALPAK AD-H |
|---|---|
| Column size | 2 cm × 25 cm, 5 um |
| Injection | 0.4 ML |
| Mobile phase | Hex(2 mMNH3—MeOH):EtOH = 93:7 |
| Flow rate | 20 ml/min |
| Wavelength | UV 220 nm |
| Temperature | 25° C. |
| Sample solution | 38.6 mg/ml in EtOH |
| Prep-HPLC equipment | Prep-Gilson-HPLC |

Compound B185: $^1H$ NMR (400 MHz, DMSO-d6) δ 8.04 (s, 1H), 7.47 (br.s, 2H), 7.41 (s, 1H), 7.14 (s, 1H), 5.98 (d, J=8.3 Hz, 1H), 3.96 (s, 2H), 3.88-3.77 (m, 1H), 3.36 (s, 2H), 2.62 (t, J=11.9 Hz, 2H), 2.21 (s, 7H), 2.16 (s, 3H), 1.81 (d, J=11.8 Hz, 2H), 1.53-1.21 (m, 3H), 1.10 (d, J=6.2 Hz, 3H), 0.87 (t, J=7.1 Hz, 3H) ppm. MS: M/e 452.0 $(M+1)^+$.

Compound B186: 7-((6-(4-(dimethylamino)piperidin-1-yl)-5-methylpyridin-3-yl)methyl)-2-(heptan-4-yloxy)imidazo[2,1-f][1,2,4]triazin-4-amine Step A: (4-(bis(4-methoxybenzyl)amino)-2-(heptan-4-yloxy)imidazo[2,1-f][1,2,4]triazin-7-yl)(6-(4-(dimethylamino)piperidin-1-yl)-5-methylpyridin-3-yl)methanol Under argon, n-BuLi (1.6M, 0.44 ml, 0.7 mmol) was added to a solution of 7-bromo-2-(heptan-4-yloxy)-N,N-bis(4-methoxybenzyl)imidazo[2,1-f][1,2,4]triazin-4-amine (200 mg, 0.35 mmol) in anhydrous THF (3 mL). The reaction mixture was stirred at −78° C. for 20 minutes, then 6-(4-(dimethylamino)piperidin-1-yl)-5-methylnicotinaldehyde (104 mg, 0.42 mmol) was added and the resulting mixture was stirred 4 h at rt. An aqueous ammonium chloride solution was added and the mixture was extracted with diethyl ether and ethyl acetate. The combined organic extracts were dried over sodium sulfate, filtered and evaporated. Purification by prep-TLC (silica gel, EA:PE=1:1) afforded desired product (140 mg, 52%). MS: m/e 737 $(M+1)^+$.

Step B: 7-((6-(4-(dimethylamino)piperidin-1-yl)-5-methylpyridin-3-yl)methyl)-2-(heptan-4-yloxy)imidazo[2,1-f][1,2,4]triazin-4-amine (4-(bis(4-methoxybenzyl)amino)-2-(heptan-4-yloxy)imidazo[2,1-f][1,2,4]triazin-7-yl)(6-(4-(dimethylamino)piperidin-1-yl)-5-methylpyridin-3-yl)methanol (140 mg, 0.19 mmol) was dissolved in TFA (3 ml) followed by addition $Et_3SiH$ (3 ml). The mixture was stirred at 80° C. for 3 h. The mixture was cooled to room temperature, and concentrated under reduced pressure. another TFA (3 ml) was added and the mixture was stirred at 80° C. for 3 h. The mixture was cooled to room temperature, and concentrated under reduced pressure. The crude product was purified by prep-HPLC to give the desired product (27 mg, 30%). $^1$H NMR (400 MHz, DMSO-d6) δ 9.55 (s, 1H), 8.13 (s, 2H), 8.10 (s, 1H), 7.47 (s, 1H), 7.37 (s, 1H), 4.97 (t, J=5.8 Hz, 1H), 4.06 (s, 2H), 3.49 (d, J=12.3 Hz, 2H), 3.31 (s, 1H), 2.83-2.65 (m, 8H), 2.19 (s, 3H), 2.05 (d, J=11.2 Hz, 2H), 1.72 (q, J=12.4 Hz, 2H), 1.65-1.46 (m, 4H), 1.43-1.19 (m, 4H), 0.86 (t, J=7.3 Hz, 6H) ppm. MS: m/e 481 $(M+1)^+$.

Compound B187: 7-((6-(4-(dimethylamino)piperidin-1-yl)-5-methylpyridin-3-yl)methyl)-2-(pentan-3-yloxy)imidazo[2,1-f][1,2,4]triazin-4-amine Step A: N,N-bis(4-methoxybenzyl)-2-(pentan-3-yloxy)imidazo[2,1-f][1,2,4]triazin-4-amine To a solution of pentan-3-ol (4.3 g, 48.90 mmol) in THF (30 mL) was added NaH (3.9 g, 97.80 mmol) portion-wise at 0° C. and stirred at r.t. for 1 h. Then a solution of 2-chloro-N,N-bis(4-methoxybenzyl)imidazo[2,1-f][1,2,4]triazin-4-amine (10 g, 24.45 mmol) in THF (20 mL) was added dropwise at 0° C., after addition, the mixture was warmed slowly to 70° C. and stirred for overnight. The mixture was quenched with saturated ammonium chloride solution (20 mL), extracted with DCM (100 mL×3). The combined organic layers were washed with brine, dried over $Na_2SO_4$, concentrated and purified by column chromatography (PE/EA=5:1~1:1) to the target product (10.70 g, 94.9%) as yellow oil. MS: M/e 462 $(M+1)^+$.

Step B: (4-(bis(4-methoxybenzyl)amino)-2-(pentan-3-yloxy)imidazo[2,1-f][1,2,4]triazin-7-yl)(6-(4-(dimethylamino)piperidin-1-yl)-5-methylpyridin-3-yl)methanol To a solution of the product of step A (200 mg, 0.43 mmol) in THF (5 mL), n-Butyllithium (0.41 ml, 0.65 mmol) was added dropwise at −78° C. and stirred for 1 h. Then a solution of 6-(4-(dimethylamino)piperidin-1-yl)-5-methylnicotinaldehyde (129 mg, 0.52 mmol) in THF (2 mL) was added dropwise at −78° C., after addition, the mixture was warmed to r.t. and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the target product (178 mg, 57.9%) as yellow oil. MS: M/e 709 $(M+1)^+$.

Step C: 7-((6-(4-(dimethylamino)piperidin-1-yl)-5-methylpyridin-3-yl)methyl)-2-(pentan-3-yloxy)imidazo[2,1-f][1,2,4]triazin-4-amine A mixture of the product of step B (178 mg, 0.25 mmol) and triethylsilane (1 mL) in TFA (2 mL) was stirred at 90° C. overnight. The mixture was concentrated and purified with prep-HPLC to give the target product (34 mg, 30%). $^1$H NMR (400 MHz, DMSO-d6) δ 9.53 (s, 1H), 8.14 (s, 1H), 8.07 (s, 2H), 7.51 (s, 1H), 7.37 (s, 1H), 4.82-4.74 (m, 1H), 4.07 (s, 2H), 3.50 (d, J=13.0 Hz, 2H), 3.36-3.25 (m, 1H), 2.78 (s, 3H), 2.74 (s, 3H), 2.72-2.70 (m, 2H), 2.20 (s, 3H), 2.07 (s, 1H), 2.03 (s, 1H), 1.78-1.68 (m, 2H), 1.66-1.57 (m, 4H), 0.87 (t, J=7.4 Hz, 6H) ppm. MS: M/e 453 $(M+1)^+$.

Compound B188: 1-(4-(5-((4-amino-2-(heptan-4-yloxy)imidazo[2,1-f][1,2,4]triazin-7-yl)methyl)-3-methylpyridin-2-yl)piperazin-1-yl)-2-(dimethylamino)ethan-1-one dimethylglycine (18 mg, 0.18 mmol) were dissolved in DMF (3 mL) followed by addition of HATU (122 mg, 0.32 mmol) and DIEA (45 mg, 0.38 mmol). The mixture was stirred for 1 h and then 2-(hexan-3-yloxy)-7-((5-methyl-6-(piperazin-1-yl)pyridin-3-yl)methyl)imidazo[2,1-f][1,2,4]triazin-4-amine (70 mg, 0.16 mmol) was added. The reaction was stirred and monitored by TLC. After 4 h, the reaction was quenched with water, extracted with EtOAc (10 mL*3), washed with brine, dried over $Na_2SO_4$, filtered, and concentrated. The residue was purified by prep-HPLC to give the target compound (2 mg, 2.3%). TH NMR (400 MHz, $CDCl_3$) δ 8.12 (s, 1H), 7.34 (d, J=1.5 Hz, 1H), 7.27 (s, 1H), 5.07-4.98 (m, 1H), 4.09 (s, 2H), 3.78-3.71 (m, 2H), 3.63 (s, 4H), 3.18-3.04 (m, 4H), 2.73 (s, 6H), 2.24 (s, 3H), 1.63-1.50 (m, 2H), 1.44-1.39 (m, 2H), 1.39-1.25 (m, 4H), 0.90 (t, J=7.3 Hz, 6H) ppm. MS: m/e 524 $(M+1)^+$.

Compound B189: 7-((6-(4-((dimethylamino)methyl)piperidin-1-yl)-5-methylpyridin-3-yl)methyl)-2-(pentan-3-yloxy)imidazo[2,1-f][1,2,4]triazin-4-amine Step A: N,N-bis(4-methoxybenzyl)-2-(pentan-3-yloxy)imidazo[2,1-f][1,2,4]triazin-4-amine To a solution of pentan-3-ol (4.3 g, 48.90 mmol) in THF (30 mL) was added NaH (3.9 g, 97.80 mmol) portion-wise at 0° C. and stirred at r.t. for 1 h. Then a solution of 2-chloro-N,N-bis(4-methoxybenzyl)imidazo[2,1-f][1,2,4]triazin-4-amine (10 g, 24.45 mmol) in THF (20 mL) was added dropwise at 0° C., after addition, the mixture was warmed slowly to 70° C. and stirred for overnight. The mixture was quenched with saturated ammonium chloride solution (20 mL), extracted with DCM (100 mL×3). The combined organic layers were washed with brine, dried over $Na_2SO_4$, concentrated and purified by column chromatography (PE/EA=5:1~1:1) to the target product (10.70 g, 94.9%) as yellow oil. MS: M/e 462 $(M+1)^+$.

Step B: (4-(bis(4-methoxybenzyl)amino)-2-(pentan-3-yloxy)imidazo[2,1-f][1,2,4]triazin-7-yl)(6-(4-((dimethylamino)methyl)piperidin-1-yl)-5-methylpyridin-3-yl)methanol To a solution product of step A (200 mg, 0.43 mmol) in THF (5 mL), n-Butyllithium (0.41 ml, 0.65 mmol) was added dropwise at −78° C. and stirred for 1 h. Then a solution of 6-(4-((dimethylamino)methyl)piperidin-1-yl)-5-methylnicotinaldehyde (136 mg, 0.52 mmol) in THF (2 mL) was added dropwise at −78° C., after addition, the mixture was warmed to r.t. and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to afford the target product (153 mg, 48.85%) as yellow oil. MS: M/e 723 $(M+1)^+$.

Step C: 7-((6-(4-((dimethylamino)methyl)piperidin-1-yl)-5-methylpyridin-3-yl)methyl)-2-(pentan-3-yloxy)imidazo[2,1-f][1,2,4]triazin-4-amine A mixture of the product of step B (153 mg, 0.21 mmol) and triethylsilane (1 mL) in TFA (2 mL) was stirred at 90° C. overnight. The mixture was concentrated and purified with prep-HPLC to give the target product (53 mg, 53.7%). $^1$H NMR (400 MHz, DMSO-d6) δ 9.16 (s, 1H), 8.14 (s, 1H), 8.06 (s, 2H), 7.56 (s, 1H), 7.36 (s, 1H), 4.82-4.73 (m, 1H), 4.08 (s, 2H), 3.41 (d, J=12.5 Hz, 2H), 3.02 (t, J=6.3 Hz, 2H), 2.81 (s, 3H), 2.80 (s, 3H), 2.76 (s, 2H), 2.20 (s, 3H), 1.95 (s, 1H), 1.79 (d, J=12.1 Hz, 2H), 1.70-1.54 (m, 4H), 1.38-1.27 (m, 2H), 0.87 (t, J=7.4 Hz, 6H) ppm. MS: M/e 467 $(M+1)^+$.

Compound B190: 7-((6-(4-((dimethylamino)methyl)piperidin-1-yl)-5-methylpyridin-3-yl)methyl)-N2-(heptan-4-yl)imidazo[2,1-f][1,2,4]triazine-2,4-diamine Step A: N2-(heptan-4-yl)-N4,N4-bis(4-methoxybenzyl)imidazo[2,1-f][1,2,4]triazine-2,4-diamine A solution of 2-chloro-N,N-bis(4-methoxybenzyl)imidazo[2,1-f][1,2,4]triazin-4-amine (3 g, 7.3 mmol), heptan-4-amine (2.5 g, 22 mmol) and DIEA (2.8 g, 22 mmol) in NMP (9 mL) was heated in a sealed tube at 230° C. for 5 hrs. The reaction mixture was cooled, added with water (10 mL) and extracted with ethyl acetate (20 mL). The organic layer was washed with brine (20 mL), dried with $Na_2SO_4$, filtered and concentrated to get the crude product, which was further purified by CombiFlash (PE:EA=15%) to get the product (1.9 g, 53%) as a colorless oil. MS: M/e 249 $(M+1)^+$.

Step B: (4-(bis(4-methoxybenzyl)amino)-2-(heptan-4-ylamino)imidazo[2,1-f][1,2,4]triazin-7-yl)(6-(4-((dimethylamino)methyl)piperidin-1-yl)-5-methylpyridin-3-yl)methanol To a cooled solution of N2-(heptan-4-yl)-N4,N4-bis(4-methoxybenzyl)imidazo [2,1-f][1,2,4]triazine-2,4-diamine (300 mg, 0.6 mmol) in THF (10 mL) at −78° C., purged with N2 was added with n-BuLi (1.6 M, 1 mL) dropwise. After stirred at −78° C. for 30 mins, 6-(4-((dimethylamino)methyl)piperidin-1-yl)-5-methylnicotinaldehyde (240 mg, 0.92 mmol) in THF (3 mL) was added. The resulting mixture was stirred gradually to r.t overnight. The solution was quenched with $NH_4Cl$ solution (10 mL) and extracted with ethyl acetate (10 mL). The organic layer was dried with $Na_2SO_4$, filtered and concentrated to get the crude product, which was further purified by CombiFlash (DCM:MeOH=10%, 4M $NH_3$·MeOH) to get the pure product (168 mg, 37%) as a yellow oil. MS: M/e 750 $(M+1)^+$.

Step C: 7-((6-(4-((dimethylamino)methyl)piperidin-1-yl)-5-methylpyridin-3-yl) methyl)-N2-(heptan-4-yl)imidazo[2,1-f][1,2,4]triazine-2,4-diamine A solution of (4-(bis(4-methoxybenzyl)amino)-2-(heptan-4-ylamino)imidazo [2,1-f][1,2,4]triazin-7-yl)(6-(4-((dimethylamino)methyl)piperidin-1-yl)-5-methylpyridin-3-yl) methanol (168 mg, 0.23 mmol) in triethylsilane (2 mL) and trifluoroacetic acid (2 mL) was heated at 80° C. overnight. The solvent was evaporated under oil pump to get the residue, which was added with EA (10 mL) and basified with $NaHCO_3$ solution (10 mL). The aqueous layer was extracted with DCM (with 10% of MeOH) for three times. The combined organic layers were dried, concentrated and purified by prep-TLC (DCM:MeOH=10:1, 7M $NH_3$·MeOH) get the product (30 mg, 27%). $^1$H NMR (400 MHz, $CD_3OD$) δ 7.88 (s, 1H), 7.34 (s, 1H), 7.10 (s, 1H), 3.97 (s, 2H), 3.75-3.72 (m, 1H), 3.27 (d, J=12.0 Hz, 2H), 2.67 (t, J=12.0 Hz, 2H), 2.53 (s, 2H), 2.45 (s, 6H), 2.13 (s, 3H), 1.75 (d, J=12.0 Hz, 3H), 1.37-1.17 (m, 10H), 0.79 (t, J=8.0 Hz, 6H) ppm. MS: M/e 494 $(M+1)^+$.

Compound B191: N2-(heptan-4-yl)-7-((5-methyl-6-(piperazin-1-yl)pyridin-3-yl)methyl)imidazo[2,1-f][1,2,4]triazine-2,4-diamine Step A: tert-butyl 4-(5-((4-(bis(4-methoxybenzyl)amino)-2-(heptan-4-ylamino) imidazo[2,1-f][1,2,4]triazin-7-yl)(hydroxy)methyl)-3-methylpyridin-2-yl)piperazine-1-carboxylate To a cooled solution of N2-(heptan-4-yl)-N4,N4-bis(4-methoxybenzyl)imidazo [2,1-f][1,2,4]triazine-2,4-diamine (1.1 g, 2.3 mmol) in THF (20 mL) at −78° C., purged with $N_2$ was added with n-BuLi (1.6 M, 4.3 mL) dropwise. After stirred at −78° C. for 30 mins, tert-butyl 4-(5-formyl-3-methylpyridin-2-yl)piperazine-1-carboxylate (1 g, 3.4 mmol) in THF (5 mL) was added.

The resulting mixture was stirred gradually to r.t overnight. The solution was quenched with $NH_4Cl$ solution (10 mL) and extracted with ethyl acetate (20 mL). The organic layer was dried with $Na_2SO_4$, filtered and concentrated to get the crude product, which was further purified by CombiFlash (DCM:MeOH=10%, 4M $NH_3$·MeOH) to get the pure product (1.1 g, 62%) as a yellow oil. MS: M/e 794 $(M+1)^+$.

Step B: N2-(heptan-4-yl)-7-((5-methyl-6-(piperazin-1-yl)pyridin-3-yl)methyl) imidazo[2,1-f][1,2,4]triazine-2,4-diamine A solution of tert-butyl 4-(5-((4-(bis(4-methoxybenzyl)amino)-2-(heptan-4-ylamino)imidazo[2,1-f][1,2,4]triazin-7-yl)(hydroxy)methyl)-3-methylpyridin-2-yl)piperazine-1-carboxylate (1.1 g, 1.4 mmol) in triethylsilane (3 mL) and trifluoroacetic acid (3 mL) was heated at 80° C. overnight. The solvent was evaporated under oil pump to get the residue, which was added with EA (10 mL) and basified with $NaHCO_3$ solution (10 mL). The aqueous layer was extracted with DCM (with 10% of MeOH) for three times. The combined organic layers were dried, concentrated and purified by CombiFlash (DCM:MeOH=25%, 4M $NH_3$·MeOH) get the product (340 mg, 56%). $^1$H NMR (400 MHz, DMSO-d6) δ 8.06 (d, J=4.0 Hz, 1H), 7.42 (br.s, 2H), 7.39 (s, 1H), 7.15 (s, 1H), 5.92 (d, J=8.0 Hz, 1H), 3.95 (s, 2H), 3.79 (s, 1H), 2.89 (d, J=8.0 Hz, 4H), 2.81 (d, J=8.0 Hz, 4H), 2.16 (s, 3H), 1.43-1.35 (m, 4H), 1.31-1.23 (m, 4H), 0.85 (t, J=8.0 Hz, 6H) ppm. MS: M/e 438 $(M+1)^+$.

Compound B192: 2-(cyclohexylmethoxy)-7-((5-methyl-6-(piperazin-1-yl)pyridin-3-yl)methyl)imidazo[2,1-f][1,2,4]triazin-4-amine Compound B192 was synthesized starting from the corresponding starting materials according the similar procedures described as those of Compound B8. $^1$H NMR (400 MHz, DMSO-d6) δ 8.14 (s, 1H), 8.09 (s, 1H), 8.06 (s, 1H), 7.49 (s, 1H), 7.32 (s, 1H), 4.06 (s, 2H), 4.02 (d, J=5.9 Hz, 2H), 3.16 (s, 8H), 2.20 (s, 3H), 1.71-1.68 (m, 5H), 1.26-1.14 (m, 4H), 1.06-0.99 (m, 2H) ppm. MS: M/e 437.0 $(M+1)^+$.

Compound B193: 7-((5-methyl-6-(piperazin-1-yl)pyridin-3-yl)methyl)-2-((tetrahydrofuran-3-yl)methoxy)imidazo[2,1-f][1,2,4]triazin-4-amine Compound B193 was synthesized starting from the corresponding starting materials according the similar procedures described as those of Compound B8. $^1$H NMR (400 MHz, DMSO-d6) δ 8.18 (s, 1H), 8.07 (s, 2H), 7.43 (s, 1H), 7.31 (s, 1H), 4.23-4.16 (m, 1H), 4.10 (t, J=9.1 Hz, 1H), 4.04 (s, 2H), 3.77 (t, J=7.3 Hz, 2H), 3.67-3.60 (m, 1H), 3.53-3.48 (m, 1H), 2.93 (s, 4H), 2.85 (s, 4H), 2.64 (m, 1H), 2.18 (s, 3H), 2.06-1.96 (m, 1H), 1.65 (m, 1H) ppm. MS: M/e 424.9 $(M+1)^+$.

Compound B194: 7-((5-methyl-6-(piperazin-1-yl)pyridin-3-yl)methyl)-2-((tetrahydro-2H-pyran-4-yl)methoxy)imidazo[2,1-f][1,2,4]triazin-4-amine Compound B194 was synthesized starting from the corresponding starting materials according the similar procedures described as those of Compound B8. $^1$H NMR (400 MHz, DMSO-d6) δ 8.16 (s, 1H), 8.06 (s, 2H), 7.43 (s, 1H), 7.31 (s, 1H), 4.07 (d, J=6.6 Hz, 2H), 4.04 (s, 2H), 3.90-3.82 (m, 2H), 3.33 (s, 2H), 2.92 (d, J=4.7 Hz, 4H), 2.83 (d, J=4.6 Hz, 4H), 2.18 (s, 3H), 1.99 (s, 1H), 1.63 (d, J=12.4 Hz, 2H), 1.35-1.24 (m, 2H) ppm. MS: M/e 439.0 $(M+1)^+$.

Compound B195: 1-(4-(5-((4-amino-2-(heptan-4-ylamino)imidazo[2,1-f] [1,2,4]triazin-7-yl)methyl)-3-methylpyridin-2-yl)piperazin-1-yl)-2-(dimethylamino)ethan-1-one A solution of N2-(heptan-4-yl)-7-((5-methyl-6-(piperazin-1-yl)pyridine-3-yl) methyl)imidazo[2,1-f][1,2,4]triazine-2,4-diamine (100 mg, 0.2 mmol), dimethylglycine (23 mg, 0.2 mmol), HATU (114 mg, 0.3 mmol) and DIEA (52 mg, 0.4 mmol) in DMF (5 mL) was stirred at r.t for 2 hrs. The reaction mixture was added with water (5 mL), extracted with ethyl acetate (10 mL) and washed with brine (5 mL). The organic layer was dried with $Na_2SO_4$, filtered and concentrated to get the crude product, which was purified by prep-TLC (DCM:7M $NH_3$·MeOH=9:1) to get the product (35 mg, 30%). $^1$H NMR (400 MHz, DMSO-d6) δ 8.08 (s, 1H), 7.45 (br.s, 2H), 7.44 (s, 1H), 7.16 (s, 1H), 5.93 (d, J=8.0 Hz, 1H), 3.97 (s, 2H), 3.75-3.67 (m, 3H), 3.60-3.55 (m, 4H), 3.02-3.96 (m, 4H), 2.48 (s, 6H), 2.20 (s, 3H), 1.42-1.23 (m, 8H), 0.84 (t, J=8.0 Hz, 6H) ppm. MS: M/e 523 $(M+1)^+$.

Compound B196: 1-(4-(5-((4-amino-2-(heptan-4-ylamino)imidazo[2,1-f] [1,2,4]triazin-7-yl)methyl)-3-methylpyridin-2-yl)piperazin-1-yl)-2-(methylamino)ethan-1-one Step A: tert-butyl (2-(4-(5-((4-amino-2-(heptan-4-ylamino)imidazo[2,1-f][1,2,4] triazin-7-yl)methyl)-3-methylpyridin-2-yl)piperazin-1-yl)-2-oxoethyl)(methyl)carbamate A solution of N2-(heptan-4-yl)-7-((5-methyl-6-(piperazin-1-yl)pyridin-3-yl) methyl)imidazo[2,1-f][1,2,4]triazine-2,4-diamine (170 mg, 0.39 mmol), N-(tert-butoxycarbonyl)-N-methylglycine (73 mg, 0.39 mmol), HATU (222 mg, 0.6 mmol) and DIEA (100 mg, 0.78 mmol) in DMF (5 mL) was stirred at r.t for 2 hrs. The reaction mixture was added with water (10 mL), extracted with ethyl acetate (10 mL) and washed with brine (10 mL). The organic layer was dried with $Na_2SO_4$, filtered and concentrated to get the crude product, which was purified by CombiFlash (PE:EA=40%) to get the product (220 mg, 92%). MS: M/e 609 $(M+1)^+$.

Step B: 1-(4-(5-((4-amino-2-(heptan-4-ylamino)imidazo[2,1-f] [1,2,4]triazin-7-yl) methyl)-3-methylpyridin-2-yl)piperazin-1-yl)-2-(methylamino)ethan-1-one A solution of tert-butyl (2-(4-(5-((4-amino-2-(heptan-4-ylamino)imidazo[2,1-f][1,2,4]triazin-7-yl)methyl)-3-methylpyridin-2-yl)piperazin-1-yl)-2-oxoethyl)(methyl)carbamate (220 mg, 0.36 mmol) in DCM (3 mL) was added with HCl/dioxane (4M, 1 mL). The solution was stirred at r.t for 2 hrs. After concentration, the residue was dissolved in DCM (10 mL) and washed with $NaHCO_3$ (5 mL). The organic layer was dried with $Na_2SO_4$, filtered and concentrated to get the crude product, which was further purified by prep-TLC (DCM:$NH_3$·MeOH=9:1) to get the pure product (80 mg, 44%). $^1$H NMR (400 MHz, DMSO-d6) δ 8.06 (br.s, 2H), 7.45 (br.s, 3H), 7.16 (s, 1H), 5.93 (d, J=8.0 Hz, 1H), 3.98 (s, 2H), 3.95 (s, 2H), 3.78 (s, 1H), 3.61 (s, 2H), 3.47 (s, 2H), 3.03-2.97 (m, 4H), 2.50 (s, 3H), 2.21 (s, 3H), 1.41-1.22 (m, 8H), 0.84 (t, J=8.0 Hz, 6H) ppm. MS: M/e 509 $(M+1)^+$.

Compound B197: 1-(4-(5-((4-amino-2-(heptan-4-yloxy)imidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-(heptan-4-yloxy)imidazo[2,1-f][1,2,4]triazin-7-yl)methyl)-3-methylpyridin-2-yl)piperazin-1-yl)-2-oxoethyl)(methyl)carbamate dimethylglycine (47 mg, 0.23 mmol) were dissolved in DMF (3 mL) followed by addition of HATU (173 mg, 0.46 mmol) and DIEA (65 mg, 0.51 mmol). The mixture was stirred for 1 h and then 2-(heptan-4-yloxy)-7-((5-methyl-6-(piperazin-1-yl)pyridin-3-yl)methyl)imidazo[2,1-f][1,2,4]triazin-4-amine (100 mg, 0.23 mmol) was added. The reaction was stirred and monitored by TLC. After 4 h, the reaction was quenched with water, extracted with EtOAc (10 mL×3), washed with brine, dried over $Na_2SO_4$, filtered, and concentrated. The residue was purified by prep-TLC (DCM:MeOH=10:1) to give the target compound (100 mg, 71%). MS: m/e 610 $(M+1)^+$.

Step B: 1-(4-(5-((4-amino-2-(heptan-4-yloxy)imidazo[2,1-f][1,2,4]triazin-7-yl)methyl)-3-methylpyridin-2-yl)piperazin-1-yl)-2-(methylamino)ethan-1-one Tert-butyl (2-(4-(5-((4-amino-2-(heptan-4-yloxy)imidazo[2,1-f][1,2,4]triazin-7-yl)methyl)-3-methylpyridin-2-yl)piperazin-1-yl)-2-oxoethyl)(methyl)carbamate (100 mg, 0.16 mmol) was dissolved in DCM (3 ml) followed by addition TFA (0.5 ml). After 4 h, the organic phase was concentrated under reduced pressure and the crude product was purified by prep-HPLC to give the desired products (3 mg, 3.6%). $^1$H NMR (400 MHz, $CD_3OD$) δ 7.95 (d, J=1.8 Hz, 1H), 7.37 (s, 1H), 7.27 (s, 1H), 4.99-4.89 (m, 1H), 4.04 (s, 2H), 3.68-3.60 (m, 2H), 3.54-3.48 (m, 2H), 3.42 (d, J=6.9 Hz, 2H), 3.03-2.92 (m, 4H), 2.33 (s, 3H), 2.18 (s, 3H), 1.64-1.44 (m, 4H), 1.39-1.15 (m, 4H), 0.81 (t, J=7.4 Hz, 6H) ppm. MS: m/e 510 $(M+1)^+$.

Compound B198: 7-((6-(4-((dimethylamino)methyl)piperidin-1-yl)-5-methylpyridin-3-yl)methyl)-2-(heptan-4-yloxy)imidazo[2,1-f][1,2,4]triazin-4-amine Step A: (4-(bis(4-methoxybenzyl)amino)-2-(heptan-4-yloxy)imidazo[2,1-f][1,2,4]triazin-7-yl)(6-(4-((dimethylamino)methyl)piperidin-1-yl)-5-methylpyridin-3-yl)methanol Under argon, n-BuLi (1.6M, 0.44 ml, 0.7 mmol) was added to a solution of 7-bromo-2-(heptan-4-yloxy)-N,N-bis(4-methoxybenzyl)imidazo[2,1-f][1,2,4]triazin-4-amine (200 mg, 0.35 mmol) in anhydrous THF (3 mL). The reaction mixture was stirred at −78° C. for 20 minutes, then 6-(4-((dimethylamino)methyl)piperidin-1-yl)-5-methylnicotinaldehyde (109 mg, 0.42 mmol) was added and the resulting mixture was stirred 4 h at rt. An aqueous ammonium chloride solution was added and the mixture was extracted with diethyl ether and ethyl acetate. The combined organic extracts were dried over sodium sulfate, filtered and evaporated. Purification by prep-TLC (silica gel, EA:PE=1:1) afforded desired products (150 mg, 57%). MS: m/e 751 $(M+1)^+$.

Step B: 7-((6-(4-((dimethylamino)methyl)piperidin-1-yl)-5-methylpyridin-3-yl)methyl)-2-(heptan-4-yloxy)imidazo[2,1-f][1,2,4]triazin-4-amine (4-(bis(4-methoxybenzyl)amino)-2-(heptan-4-yloxy)imidazo[2,1-f][1,2,4]triazin-7-yl)(6-(4-((dimethylamino)methyl)piperidin-1-yl)-5-methylpyridin-3-yl)methanol (150 mg, 0.20 mmol) was dissolved in TFA (3 ml) followed by addition $Et_3SiH$ (3 ml). The mixture was stirred at 80° C. for 3 h. The mixture was cooled to room temperature, and concentrated under reduced pressure. another TFA (3 ml) was added and the mixture was stirred at 80° C. for 3 h. The mixture was cooled to room temperature, and concentrated under reduced pressure. The crude product was purified by prep-HPLC to give the desired products (7 mg, 7%). TH NMR (400 MHz, $CD_3OD$) δ 7.89 (d, J=1.9 Hz, 1H), 7.32 (d, J=1.7 Hz, 1H), 7.27 (s, 1H), 4.98-4.88 (m, 1H), 4.03 (s, 2H), 3.32-3.23 (m, 2H), 2.65 (dd, J=12.2, 10.5 Hz, 2H), 2.23-2.11 (m, 11H), 1.75 (d, J=12.7 Hz, 2H), 1.65-1.42 (m, 5H), 1.38-1.15 (m, 6H), 0.85-0.75 (m, 6H) ppm. MS: m/e 495 $(M+1)^+$.

Compound B199: (S)-2-(4-(5-((4-amino-2-(pentan-2-yloxy)imidazo[2,1-f][1,2,4]triazin-7-yl)methyl)-3-methylpyridin-2-yl)piperazin-1-yl)ethan-1-ol To a mixture of (S)-7-((5-methyl-6-(piperazin-1-yl)pyridin-3-yl)methyl)-2-(pentan-2-yloxy)imidazo[2,1-f][1,2,4]triazin-4-amine (41 mg, 0.1 mmol) and TEA (20 mg, 0.2 mmol) in DMF (2 mL) was added 2-bromoethan-1-ol (13 mg, 0.11 mmol). The reaction was stirred at room temperature overnight. The reaction was diluted with water, extracted with EA (50 mL), washed with brine, dried over $Na_2SO_4$, filtered, and concentrated. The residue was purified by prep-TLC (DCM: (7 M $NH_3$ in MeOH)=15:1) to give the target compound (5 mg, 11%). $^1$HNMR (400 MHz, $CD_3OD$) δ 8.03 (d, J=2.0 Hz, 1H), 7.45 (d, J=1.6 Hz, 1H), 7.35 (s, 1H), 5.08-4.97 (m, 1H), 4.13 (s, 2H), 3.73 (t, J=6.0 Hz, 2H), 3.16-3.08 (m, 4H), 2.80-2.67 (m, 4H), 2.63 (t, J=6.0 Hz, 2H), 2.24 (s, 3H), 1.82-1.65 (m, 1H), 1.61-1.50 (m, 1H), 1.47-1.35 (m, 2H), 1.29 (d, J=6.0 Hz, 3H), 0.92 (t, J=7.6 Hz, 3H) ppm. MS: M/e 455 $(M+1)^+$.

Compound B200: 1-(4-(5-((4-amino-2-(pentan-3-yloxy)imidazo[2,1-f][1,2,4]triazin-7-yl)methyl)-3-methylpyridin-2-yl)piperazin-1-yl)-2-(dimethylamino)ethan-1-one A mixture of 7-((5-methyl-6-(piperazin-1-yl)pyridin-3-yl)methyl)-2-(pentan-3-yloxy)imidazo[2,1-f][1,2,4]triazin-4-amine (20 mg, 0.05 mmol), dimethylglycine (5 mg, 0.05 mmol), HATU (22 mg, 0.06 mmol) and DIPEA (19 mg, 0.15 mmol) in DCM (3 mL) was stirred at r.t. for 2 h. The mixture was extracted with DCM (10 mL) and washed with water (5 ml), dried over $Na_2SO_4$, concentrated and purified with prep-HPLC to give the target product (20 mg, 82.8%). $^1$H NMR (400 MHz, DMSO-d6) δ 8.11 (s, 1H), 8.07 (s, 1H), 7.99 (s, 1H), 7.43 (s, 1H), 7.33 (s, 1H), 4.83-4.73 (m, 1H), 4.05 (s, 2H), 3.62 (s, 2H), 3.57 (s, 2H), 3.25 (s, 2H), 3.00 (s, 2H), 2.94 (s, 2H), 2.26 (s, 6H), 2.20 (s, 3H), 1.70-1.52 (m, 4H), 0.87 (t, J=7.4 Hz, 6H) ppm. MS: M/e 496 $(M+1)^+$.

Compound B201: 1-(4-(5-((4-amino-2-(pentan-3-yloxy)imidazo[2,1-f][1,2,4]triazin-7-yl)methyl)-3-methylpyridin-2-yl)piperazin-1-yl)-2-(methylamino)ethan-1-one Step A: tert-butyl (2-(4-(5-((4-amino-2-(pentan-3-yloxy)imidazo[2,1-f][1,2,4]triazin-7-yl)methyl)-3-methylpyridin-2-yl)piperazin-1-yl)-2-oxoethyl)(methyl)carbamate A mixture of 7-((5-methyl-6-(piperazin-1-yl)pyridin-3-yl)methyl)-2-(pentan-3-yloxy)imidazo[2,1-f][1,2,4]triazin-4-amine (20 mg, 0.05 mmol), N-(tert-butoxycarbonyl)-N-methylglycine (9 mg, 0.05 mmol), HATU (22 mg, 0.06 mmol) and DIPEA (19 mg, 0.15 mmol) in DCM (3 mL) was stirred at r.t. for 2 h. The mixture was extracted with DCM (10 mL) and washed with water (5 ml), dried over $Na_2SO_4$, concentrated and purified with prep-HPLC to give the target product (24 mg, 84.7%). MS: M/e 582 $(M+1)^+$.

Step B: 1-(4-(5-((4-amino-2-(pentan-3-yloxy)imidazo[2,1-f][1,2,4]triazin-7-yl)methyl)-3-methylpyridin-2-yl)piperazin-1-yl)-2-(methylamino)ethan-1-one A mixture of the product of step A (24 mg, 0.041 mmol) in hydrochloric acid 1,4-dioxane (2 mL) was stirred at r.t. overnight. The mixture was concentrated and purified by prep-HPLC to give the target product (17 mg, 85.6%). $^1$H NMR (400 MHz, DMSO-d6) δ 8.11 (s, 1H), 8.07 (s, 1H), 7.99 (s, 1H), 7.43 (s, 1H), 7.33 (s, 1H), 4.82-4.74 (m, 1H), 4.05 (s, 2H), 3.58 (s, 2H), 3.52 (s, 2H), 3.32 (s, 3H), 3.00 (s, 2H), 2.95 (s, 2H), 2.29 (s, 2H), 2.20 (s, 3H), 1.67-1.57 (m, 4H), 0.87 (t, J=7.4 Hz, 6H) ppm. MS: M/e 482 $(M+1)^+$.

Compound B202: 2-(1-cyclopropylbutoxy)-7-((5-methyl-6-(piperazin-1-yl)pyridin-3-yl)methyl)imidazo[2,1-f][1,2,4]triazin-4-amine Step A: tert-butyl 4-(5-((4-((tert-butoxycarbonyl)amino)-2-(1-cyclopropylbutoxy)imidazo[2,1-f][1,2,4]triazin-7-yl)methyl)-3-methylpyridin-2-yl)piperazine-1-carboxylate To a stirred solution of 1-cyclopropylbutan-1-ol (64 mg, 0.56 mmol) in THF was added sodium hydride (45 mg, 1.12 mmol). The reaction was stirred at rt for 30 mins. tert-butyl 4-(5-((4-((tert-butoxycarbonyl)amino)-2-chloroimidazo[2,1-f][1,2,4]triazin-7-yl)methyl)-3-methylpyridin-2-yl)piperazine-1-carboxylate (100 mg, 0.28 mmol) was added to the mixture. The reaction was stirred at 60° C. overnight. The reaction mixture was cooled down to rt and poured into $H_2O$. The mixture was extracted with EtOAc (15 mL×3). The combined organic phase was washed with brine, dried over $Na_2SO_4$, concentrated in vacuo. The crude product was purified by column chromatography to give the title product (30 mg, 25.8%). MS: M/e 636.9 $(M+1)^+$.

Step B: 2-(1-cyclopropylbutoxy)-7-((5-methyl-6-(piperazin-1-yl)pyridin-3-yl)methyl)imidazo[2,1-f][1,2,4]triazin-4-amine To a stirred solution of the product of Step A (30 mg, 0.045 mmol) in HCl/EA (4 M, 20 ml) was stirred at rt for 2 h. The reaction mixture was concentrated in vacuo. The residue was added to $NaHCO_3$ (1M, 20 ml) and extracted by EtOAc (15 mL×3). The combined organic phase was washed with brine, dried over $Na_2SO_4$, concentrated in vacuo. The crude product was purified by column chromatography to give the title product (10 mg, 50.7%). $^1H$ NMR (400 MHz, DMSO-d6) δ 8.14 (s, 1H), 8.05 (s, 1H), 8.01 (s, 1H), 7.40 (s, 1H), 7.34 (s, 1H), 4.41 (d, J=5.8 Hz, 1H), 4.03 (s, 2H), 3.07 (s, 8H), 2.18 (s, 3H), 1.76-1.59 (m, 2H), 1.44-1.31 (m, 2H), 1.24 (s, 1H), 1.04 (d, J=4.4 Hz, 1H), 0.86 (t, J=7.0 Hz, 3H), 0.52 (s, 1H), 0.43-0.23 (m, 3H) ppm. MS: M/e 437.0 $(M+1)^+$.

Compound B203: 1-((4-amino-7-((5-methyl-6-(piperazin-1-yl)pyridin-3-yl)methyl)imidazo[2,1-f][1,2,4]triazin-2-yl)oxy)hexan-3-ol Step A: 7-bromo-2-((3-((tert-butyldimethylsilyl)oxy)hexyl)oxy)-N,N-bis(4-methoxybenzyl)imidazo[2,1-f][1,2,4]triazin-4-amine To a stirred solution of the product of 1-((tert-butyldimethylsilyl)oxy)hexan-3-ol (3.1 g, 15.1 mmol) in THF (50 mL) was added NaH (60%, 0.536 g, 13.4 mmol). After stirred for 30 min, 7-bromo-2-chloro-N,N-bis(4-methoxybenzyl)imidazo[2,1-f][1,2,4]triazin-4-amine (3.26 g, 6.68 mmol) was added. After the addition, the reaction was stirred at 60° C. for 2 days. The reaction mixture was treated with $H_2O$ (20 mL), extracted with EtOAc (30 mL×2). The combined organic layers were washed with brine, dried over $Na_2SO_4$, concentrated and purified by column chromatography (petroleum ether/EtOAc=20:1) to give the product (4.2 g, is mixture of 7-bromo-2-((3-((tert-butyldimethylsilyl)oxy)hexyl)oxy)-N,N-bis(4-methoxybenzyl)imidazo[2,1-f][1,2,4]triazin-4-amine and 7-bromo-2-((1-((tert-butyldimethylsilyl)oxy)hexan-3-yl)oxy)-N,N-bis(4-methoxybenzyl)imidazo[2,1-f][1,2,4]triazin-4-amine). MS: M/e 684 $(M+1)^+$.

Step B: tert-butyl 4-(5-((4-(bis(4-methoxybenzyl)amino)-2-((3-((tert-butyldimethylsilyl)oxy)hexyl)oxy)imidazo[2,1-f][1,2,4]triazin-7-yl)(hydroxy)methyl)-3-methylpyridin-2-yl)piperazine-1-carboxylate To a stirred solution of product of step A (4.2 g, 6.15 mmol) in THF (50 mL) was added dropwise n-BuLi (1.6 M, 7.7 mL, 12.3 mmol) at −78° C. After stirred for half an hour, a solution of tert-butyl 4-(5-formyl-3-methylpyridin-2-yl)piperazine-1-carboxylate (2.24 g, 7.38 mmol) in THF (10 mL) was added dropwise at −78° C. Then the mixture was stirred for 2 hours. The reaction was quenched with aq.$NH_4Cl$, extracted with EtOAc (40 mL×2). The combined organic layers were washed with brine, dried over $Na_2SO_4$, concentrated and purified by column chromography (petroleum ether/EtOAc=10:1~2:1) to give the target compound (3.08 g, 55%, is a mixture of tert-butyl 4-(5-((4-(bis(4-methoxybenzyl)amino)-2-((3-((tert-butyldimethylsilyl)oxy)hexyl)oxy)imidazo[2,1-f][1,2,4]triazin-7-yl)(hydroxy)methyl)-3-methylpyridin-2-yl)piperazine-1-carboxylate and tert-butyl 4-(5-((4-(bis(4-methoxybenzyl)amino)-2-((1-((tert-butyldimethylsilyl)oxy)hexan-3-yl)oxy)imidazo[2,1-f][1,2,4]triazin-7-yl)(hydroxy)methyl)-3-methylpyridin-2-yl)piperazine-1-carboxylate). MS: M/e 911 $(M+1)^+$.

Step C: 1-((4-amino-7-((5-methyl-6-(piperazin-1-yl)pyridin-3-yl)methyl)imidazo[2,1-f][1,2,4]triazin-2-yl)oxy)hexan-3-ol A mixture of the product of step B (4.5 g, 4.95 mmol) in TFA/$Et_3SiH$ (20 mL/10 mL) was stirred at 80° C. for 2 days. The reaction mixture was concentrated to give the residue, which was dissolved in MeOH (20 mL), aq.NaOH (2.0 M, 5 mL) was added and stirred for a weekend. There were 2 peaks showed on HPLC with the same MS. After purified by prep-HPLC to give the target product (60 mg). $^1H$ NMR (400 MHz, DMSO-d6) δ 8.17-8.02 (m, 3H), 7.44 (d, J=1.6 Hz, 1H), 7.31 (s, 1H), 4.51 (d, J=5.6 Hz, 1H), 4.30 (t, J=6.4 Hz, 2H), 4.04 (s, 2H), 3.65-3.61 (m, 1H), 2.93-2.87 (m, 4H), 2.82-2.76 (m, 4H), 1.86-1.58 (m, 2H), 1.46-1.21 (m, 4H), 0.87 (t, J=7.2 Hz, 3H) ppm. MS: M/e 441 $(M+1)^+$.

Compound B204: 7-((5-methyl-6-(4-((methylamino)methyl)piperidin-1-yl) pyridin-3-yl)methyl)-N2-(pentan-2-yl)imidazo[2,1-f][1,2,4]triazine-2,4-diamine Step A: tert-butyl ((1-(5-formyl-3-methylpyridin-2-yl)piperidin-4-yl)methyl)(methyl) carbamate A solution of 6-chloro-5-methylnicotinaldehyde (1.6 g, 10.5 mmol), tert-butyl methyl(piperidin-4-ylmethyl)carbamate (2.4 g, 10.5 mmol) and DIEA (2.7 g, 21 mmol) in DMSO (20 mL) was heated at 80° C. overnight. The solution was cooled down, added with water (10 mL), extracted with ethyl acetate (20 mL) and washed with brine (20 mL). The organic layer was dried with $Na_2SO_4$, filtered and concentrated to get the crude product, which was purified by CombiFlash (PE:EA=30%) to get the product (2.7 g, 75%). MS: M/e 348 $(M+1)^+$.

Step B: tert-butyl ((1-(5-((4-(bis(4-methoxybenzyl)amino)-2-(pentan-2-ylamino) imidazo[2,1-f][1,2,4]triazin-7-yl)(hydroxy)methyl)-3-methylpyridin-2-yl)piperidin-4-yl)methyl)(methyl)carbamate To a cooled solution of N4,N4-bis(4-methoxybenzyl)-N2-(pentan-2-yl)imidazo [2,1-f][1,2,4]triazine-2,4-diamine (1.8 g, 3.9 mmol) in THF (20 mL) at −78° C., purged with N2 was added n-BuLi (1.6 M, 7.3 mL) dropwise. After stirred at −78° C. for 30 mins, tert-butyl ((1-(5-formyl-3-methylpyridin-2-yl)piperidin-4-yl)methyl)(methyl) carbamate (1.6 g, 4.7 mmol) in THF (10 mL) was added. The resulting mixture was stirred at this temperature for 30 mins, and then warmed to r.t overnight. The solution was quenched with $NH_4Cl$ solution (10 mL) and extracted with ethyl acetate (30 mL). The organic layer was dried with $Na_2SO_4$, filtered and concentrated to get the crude product, which was further purified by Combi-Flash (PE:EA=50%) to get the pure product (1.7 g, 54%). MS: M/e 808 $(M+1)^+$.

Step C: 7-((5-methyl-6-(4-((methylamino)methyl) piperidin-1-yl)pyridin-3-yl)methyl)-N2-(pentan-2-yl) imidazo[2,1-f][1,2,4]triazine-2,4-diamine A solution of the product of step B (2.3 g, 2.9 mmol) in triethylsilane (5 mL) and trifluoroacetic acid (5 mL) was heated at 80° C. overnight. The solvent was evaporated under oil pump to get the residue, which was added with EA (30 mL) and basified with $NaHCO_3$ solution (20 mL). The organic layer was dried, concentrated and purified by CombiFlash (DCM:MeOH=25%, 4M $NH_3$·MeOH) and prep-TLC (DCM:7M·$NH_3$·MeOH=10:1) to get the product (750 mg, 59%). $^1H$ NMR (400 MHz, DMSO-d6) δ 8.05 (s, 1H), 7.47 (br.s, 2H), 7.42 (s, 1H), 7.14 (s, 1H), 5.99 (d, J=8.0 Hz, 1H), 3.96 (s, 2H), 3.82-3.79 (m, 1H), 3.30 (s, 3H), 2.72 (d, J=4.0 Hz, 2H), 2.63 (t, J=12.0 Hz, 2H), 2.51 (s, 3H), 2.16 (s, 3H), 1.79-1.76 (m, 3H), 1.53-1.50 (m, 1H), 1.39-1.29 (m, 5H), 1.10 (d, J=8.0 Hz, 3H), 0.86 (t, J=8.0 Hz, 3H) ppm. MS: M/e 452 $(M+1)^+$.

Compound B205: 7-((5-methyl-6-(4-((methylamino) methyl)piperidin-1-yl)pyridin-3-yl)methyl)-2-(pentan-2-yloxy)imidazo[2,1-f][1,2,4]triazin-4-amine Step A: tert-butyl ((1-(5-((4-(bis(4-methoxybenzyl) amino)-2-(pentan-2-yloxy)imidazo[2,1-f][1,2,4]triazin-7-yl)(hydroxy)methyl)-3-methylpyridin-2-yl) piperidin-4-yl)methyl)(methyl)carbamate To a solution of N,N-bis(4-methoxybenzyl)-2-(pentan-2-yloxy)imidazo[2,1-f][1,2,4]triazin-4-amine (200 mg, 0.43 mmol) in THF (5 mL), n-BuLi (0.41 ml, 0.65 mmol) was added dropwise at −78° C. and stirred for 1 h. Then a solution of tert-butyl ((1-(5-formyl-3-methylpyridin-2-yl) piperidin-4-yl)methyl)(methyl)carbamate (181 mg, 0.52 mmol) in THF (2 mL) was added dropwise at −78° C., after addition, the mixture was warmed to r.t. and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the target product (241 mg, 68.67%). MS: M/e 810 $(M+1)^+$.

Step B: 7-((5-methyl-6-(4-((methylamino)methyl) piperidin-1-yl)pyridin-3-yl)methyl)-2-(pentan-2-yloxy)imidazo[2,1-f][1,2,4]triazin-4-amine A mixture of the product of step A (241 mg, 0.30 mmol) and triethylsilane (1 mL) in TFA (2 mL) was stirred at 90° C. overnight. The mixture was concentrated and purified with prep-HPLC to give the title product (78 mg, 58%). $^1H$ NMR (400 MHz, DMSO-d6) δ 8.11 (s, 1H), 8.04 (d, J=1.9 Hz, 1H), 7.99 (s, 1H), 7.38 (d, J=1.9 Hz, 1H), 7.32 (s, 1H), 5.01-4.91 (m, 1H), 4.02 (s, 2H), 3.30 (d, J=12.5 Hz, 4H), 2.61 (t, J=11.8 Hz, 2H), 2.40 (d, J=6.6 Hz, 2H), 2.29 (s, 3H), 2.15 (s, 2H), 1.75 (d, J=10.9 Hz, 2H), 1.68-1.60 (m, 1H), 1.56-1.47 (m, 2H), 1.42-1.29 (m, 2H), 1.28-1.21 (m, 5H), 0.88 (t, J=7.3 Hz, 3H) ppm. MS: M/e 453 $(M+1)^+$.

Compound B206: 7-((5-methyl-6-(piperazin-1-yl) pyridin-3-yl)methyl)-2-((1-(methylamino)propan-2-yl)oxy)imidazo[2,1-f][1,2,4]triazin-4-amine Step A: N,N-bis(4-methoxybenzyl)-2-((1-(methylamino)propan-2-yl)oxy)imidazo[2,1-f][1,2,4]triazin-4-amine To a stirred solution of tert-butyl (2-hydroxypropyl) (methyl)carbamate (350 mg, 2 mmol) in THF was added sodium hydride (160 mg, 4 mmol). The reaction was stirred at rt for 30 mins. 2-chloro-N,N-bis(4-methoxybenzyl)imidazo[2,1-f][1,2,4]triazin-4-amine (405 mg, 1 mmol) was added to the mixture. The reaction was stirred at 60° C. overnight. The reaction mixture was cooled down to rt and poured into $H_2O$. The mixture was extracted by EtOAc (15 mL×3). The combined organic phase was washed with brine, dried over $Na_2SO_4$, concentrated in vacuo. The crude product was purified by column chromatography to give the title product (120 mg, 26%). MS: M/e 463.0 $(M+1)^+$.

Step B: tert-butyl (2-((4-(bis(4-methoxybenzyl) amino)imidazo[2,1-f][1,2,4]triazin-2-yl)oxy)propyl) (methyl)carbamate To a stirred solution of the product of step A (120 mg, 0.26 mmol) in DCM (20 mL) was added di-tert-butyl dicarbonate (110 mg, 0.52 mmol) and 4-DMAP (60 mg, 0.52 mmol). The reaction was stirred at rt overnight. The mixture was quenched with $H_2O$ (20 ml) and extracted by EtOAc (15 mL×3). The combined organic phase was washed with brine, dried over $Na_2SO_4$, concentrated in vacuo. The crude product was purified by column chromatography to give the title product (190 mg, 100%). MS: M/e 563.0 $(M+1)^+$.

Step C: tert-butyl 4-(5-((4-(bis(4-methoxybenzyl) amino)-2-((1-((tert-butoxycarbonyl)(methyl)amino) propan-2-yl)oxy)imidazo[2,1-f][1,2,4]triazin-7-yl) (hydroxy)methyl)-3-methylpyridin-2-yl)piperazine-1-carboxylate To a stirred solution of the product of step B (190 mg, 0.34 mmol) in THF (10 mL), cooled to −78° C. and under a nitrogen atmosphere was added n-BuLi (1.6 M in hexane, 0.68 mmol, 0.43 mL) by dropwise. After stirring for 50 mins, a solution of tert-butyl 4-(5-formyl-3-methylpyridin-2-yl)piperazine-1-carboxylate (154 mg, 0.5 mmol) in THF (2 mL) was slowly added. The reaction mixture was slowly warmed up to rt and stirred overnight. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (130 mg, 44%). MS: M/e 867.9 $(M+1)^+$.

Step D: 7-((5-methyl-6-(piperazin-1-yl)pyridin-3-yl) methyl)-2-((1-(methylamino)propan-2-yl)oxy)imidazo[2,1-f][1,2,4]triazin-4-amine A solution of the product of step C (130 mg, 0.149 mmol) in TFA (5 mL) and $Et_3SiH$ (5 mL) was stirred at 80° C. for 2 h. The reaction mixture was concentrated in vacuo to remove TFA and $Et_3SiH$. The residue was added TFA (5 mL) and stirred at 80° C. for overnight. The mixture was cooled down to rt and concentrated in vacuo. The crude product was purified by prep-HPLC to give the product (1.4 mg, 2.2%).

$^1H$ NMR (400 MHz, DMSO-d6) δ 8.11 (s, 1H), 7.52 (s, 1H), 7.38 (s, 1H), 5.34-5.27 (m, 1H), 4.17 (s, 2H), 3.42-3.32 (m, 10H), 2.75 (s, 3H), 2.28 (s, 3H), 2.04 (s, 1H), 1.40 (d, J=6.2 Hz, 3H), 1.29 (s, 2H) ppm. MS: M/e 411.9 $(M+1)^+$.

Compound B207: (R)-7-((5-methyl-6-(piperazin-1-yl)pyridin-3-yl)methyl)-N2-(pentan-2-yl)imidazo[2,1-f][1,2,4]triazine-2,4-diamine Compound B151 was separated into two enantiomeric stereoisomers, Compound B207 (first peak) and Compound B148 (second peak), by chiral prep-HPLC. The chiral separation conditions are shown below.

| Column | CHIRALPAK IF |
|---|---|
| Column size | 3 cm × 25 cm, 5 um |
| Injection | 1.0 mL |
| Mobile phase | HeX(2 mM NH3—MeOH):(EtOH:MeOH = 3:2) = 75:25 |
| Flow rate | 30 mL/min |
| Wavelength | UV 220 nm |
| Temperature | 25° C. |
| Sample solution | 50.6 mg/ml in MeOH:DCM = 3:1 |
| Prep-SFC equipment | Prep-HPLC-Gilson |

Compound B207: $^1H$ NMR δ 8.06 (d, J=1.5 Hz, 1H), 7.48 (s, 1H), 7.42 (s, 2H), 7.14 (s, 1H), 5.99 (d, J=8.5 Hz, 1H), 3.96 (s, 2H), 3.80 (dd, J=13.4, 6.9 Hz, 1H), 2.89 (d, J=4.9 Hz, 4H), 2.81 (d, J=4.7 Hz, 4H), 2.16 (s, 3H), 1.52 (d, J=7.6 Hz, 1H), 1.41-1.28 (m, 3H), 1.10 (d, J=6.5 Hz, 3H), 0.86 (t, J=7.1 Hz, 3H) ppm. MS: M/e 410.0 $(M+1)^+$.

Compound B208: 7-((6-(4-((dimethylamino)methyl)piperidin-1-yl)-5-methylpyridin-3-yl)methyl)-N2-(pentan-3-yl)imidazo[2,1-f][1,2,4]triazine-2,4-diamine Step A: N4,N4-bis(4-methoxybenzyl)-N2-(pentan-3-yl)imidazo[2,1-f][1,2,4]triazine-2,4-diamine To a stirred solution of 2-chloro-N,N-bis(4-methoxybenzyl)imidazo[2,1-f][1,2,4]triazin-4-amine (2 g, 5 mmol) in Dioxane (20 mL) and $H_2O$ (0.5 mL) was added pentan-3-amine (870 mg, 10 mmol), $Pd_2(dba)_3$ (475 mg, 0.5 mmol), X-Phos (476 mg, 0.1 mmol) and t-BuONa (1.45 g, 15 mmol). The reaction mixture was protected by N. and stirred at 120° C. overnight. The mixture was cooled down to rt, added $H_2O$ (20 mL) and extracted with EtOAc (10 mL×3). The combined organic phase was washed with brine, dried over $Na_2SO_4$ and concentrated in vacuo. The crude product was purified by column chromatography to give the product (1.5 g, 65.2%) as yellow oil. MS: M/e 460.9 $(M+1)^+$.

Step B: (4-(bis(4-methoxybenzyl)amino)-2-(pentan-3-ylamino)imidazo[2,1-f][1,2,4]triazin-7-yl)(6-(4-((dimethylamino)methyl)piperidin-1-yl)-5-methylpyridin-3-yl)methanol To a stirred solution of N4,N4-bis(4-methoxybenzyl)-N2-(pentan-3-yl)imidazo[2,1-f][1,2,4]triazine-2,4-diamine (200 mg, 0.43 mmol) in THF (8 mL), cooled to −78° C. and under a nitrogen atmosphere was added n-BuLi (1.6 M in hexane, 1.08 mmol, 0.67 mL) by dropwise. After stirring for 50 mins, a solution of 6-(4-((dimethylamino)methyl)piperidin-1-yl)-5-methylnicotinaldehyde (142 mg, 0.65 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (140 mg, 45.1%). MS: M/e 722.0 $(M+1)^+$.

Step C: 7-((6-(4-((dimethylamino)methyl)piperidin-1-yl)-5-methylpyridin-3-yl)methyl)-N2-(pentan-3-yl)imidazo[2,1-f][1,2,4]triazine-2,4-diamine A solution of (4-(bis(4-methoxybenzyl)amino)-2-(pentan-3-ylamino)imidazo[2,1-f][1,2,4]triazin-7-yl)(6-(4-((dimethylamino)methyl)piperidin-1-yl)-5-methylpyridin-3-yl)methanol (140 mg, 0.193 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (9 mg, 9.5%). $^1H$ NMR (400 MHz, DMSO-d6) δ 8.04 (s, 1H), 7.42 (br.s, 2H), 7.41 (s, 1H), 7.14 (s, 1H), 5.95 (d, J=8.8 Hz, 1H), 3.95 (s, 2H), 3.59-3.57 (m, 1H), 3.29 (d, J=12.6 Hz, 2H), 2.63 (t, J=11.4 Hz, 2H), 2.15 (s, 3H), 2.11 (s, 6H), 2.08 (d, J=6.8 Hz, 2H), 1.74 (d, J=11.8 Hz, 2H), 1.53-1.41 (m, 4H), 1.26-1.11 (m, 3H), 0.84 (t, J=7.4 Hz, 6H) ppm. MS: M/e 466.0 $(M+1)^+$.

Compound B209: 7-((6-(4-(dimethylamino)piperidin-1-yl)-5-methylpyridin-3-yl)methyl)-N2-(pentan-3-yl)imidazo[2,1-f][1,2,4]triazine-2,4-diamine Step A: (4-(bis(4-methoxybenzyl)amino)-2-(pentan-3-ylamino)imidazo[2,1-f][1,2,4]triazin-7-yl)(6-(4-(dimethylamino)piperidin-1-yl)-5-methylpyridin-3-yl)methanol To a stirred solution of N4,N4-bis(4-methoxybenzyl)-N2-(pentan-3-yl)imidazo[2,1-f][1,2,4]triazine-2,4-diamine (200 mg, 0.43 mmol) in THF (8 mL), cooled to −78° C. and under a nitrogen atmosphere was added n-BuLi (1.6 M in hexane, 1.08 mmol, 0.67 mL) by dropwise. After stirring for 50 mins, a solution of 6-(4-(dimethylamino)piperidin-1-yl)-5-methylnicotinaldehyde (160 mg, 0.65 mmol) in THF (2 mL) was slowly added. The reaction mixture was slowly warmed up to rt and stirred for 2 h. The reaction mixture was poured into Saturated ammonium chloride solution and extracted by EtOAc (15 mL×3). The combined organic phase was washed with brine, dried over $Na_2SO_4$, concentrated in vacuo. The crude product was purified by column chromatography to give the title product (140 mg, 45.1%). MS: M/e 708.0 $(M+1)^+$.

Step B: 7-((6-(4-(dimethylamino)piperidin-1-yl)-5-methylpyridin-3-yl)methyl)-N2-(pentan-3-yl)imidazo[2,1-f][1,2,4]triazine-2,4-diamine A solution of (4-(bis(4-methoxybenzyl)amino)-2-(pentan-3-ylamino)imidazo[2,1-f][1,2,4]triazin-7-yl)(6-(4-(dimethylamino)piperidin-1-yl)-5-methylpyridin-3-yl)methanol (140 mg, 0.197 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (10 mg, 11.2%). $^1H$ NMR (400

MHz, DMSO-d6) δ 8.04 (s, 1H), 7.42 (br.s, 2H), 7.41 (s, 2H), 7.14 (s, 1H), 5.65 (d, J=8 Hz, 1H), 3.95 (s, 2H), 3.62-3.58 (m, 1H), 3.36 (s, 2H), 2.62 (t, J=12 Hz, 2H), 2.20 (s, 6H), 2.16 (s, 3H), 1.80 (d, J=12 Hz, 2H), 1.51-1.43 (m, 6H), 0.83 (t, J=7.4 Hz, 6H) ppm. MS: M/e 452.0 $(M+1)^+$.

Compound B210: 7-((5-methyl-6-(piperazin-1-yl)pyridin-3-yl)methyl)-N2-(pentan-3-yl)imidazo[2,1-f][1,2,4]triazine-2,4-diamine Step A: (tert-butyl 4-(5-((4-(bis(4-methoxybenzyl)amino)-2-(pentan-3-ylamino)imidazo[2,1-f][1,2,4]triazin-7-yl)(hydroxy)methyl)-3-methylpyridin-2-yl)piperazine-1-carboxylate To a stirred solution of N4,N4-bis(4-methoxybenzyl)-N2-(pentan-3-yl)imidazo[2,1-f][1,2,4]triazine-2,4-diamine (1 g, 2.2 mmol) in THF (50 mL), cooled to −78° C. and under a nitrogen atmosphere was added n-BuLi (1.6 M in hexane, 6.6 mmol, 4.1 mL) by dropwise. After stirring for 50 mins, a solution of tert-butyl 4-(5-formyl-3-methylpyridin-2-yl)piperazine-1-carboxylate (1 g, 3.3 mmol) in THF (10 mL) was slowly added. The reaction mixture was slowly warmed up to rt and stirred for 2 h. The reaction mixture was poured to Saturated ammonium chloride solution and extracted by EtOAc (15 mL×3). The combined organic phase was washed with brine, dried over $Na_2SO_4$, concentrated in vacuo. The crude product was purified by column chromatography to give the title product (950 mg, 56.5%). MS: M/e 765.9 $(M+1)^+$.

Step B: 7-((5-methyl-6-(piperazin-1-yl)pyridin-3-yl)methyl)-N2-(pentan-3-yl)imidazo[2,1-f][1,2,4]triazine-2,4-diamine A solution of tert-butyl 4-(5-((4-(bis(4-methoxybenzyl)amino)-2-(pentan-3-ylamino)imidazo[2,1-f][1,2,4]triazin-7-yl)(hydroxy)methyl)-3-methylpyridin-2-yl)piperazine-1-carboxylate (900 mg, 1.17 mmol) in TFA (10 mL) and $Et_3SiH$ (10 mL) was stirred at 80° C. for 2 h. The reaction mixture was concentrated in vacuo to remove TFA and $Et_3SiH$. The residue was added TFA (20 mL) and stirred at 85° C. overnight. The mixture was cooled down to rt and concentrated in vacuo. The crude product was purified by prep-HPLC to give the product (300 mg, 62.3%). $^1H$ NMR (400 MHz, DMSO-d6) δ 8.06 (d, J=1.9 Hz, 1H), 7.42 (br.s, 2H), 7.41 (s, 1H), 7.14 (s, 1H), 5.95 (d, J=8.7 Hz, 1H), 3.96 (s, 2H), 3.59-3.57 (m, 1H), 2.94-2.86 (m, 4H), 2.85-2.76 (m, 4H), 2.16 (s, 3H), 1.55-1.39 (m, 4H), 0.84 (t, J=7.4 Hz, 6H) ppm. MS: M/e 411.0 $(M+1)^+$.

Compound B211: 1-(4-(5-((4-amino-2-(pentan-3-ylamino)imidazo[2,1-f][1,2,4]triazin-7-yl)methyl)-3-methylpyridin-2-yl)piperazin-1-yl)-2-(dimethylamino)ethan-1-one To a stirred solution of 7-((5-methyl-6-(piperazin-1-yl)pyridin-3-yl)methyl)-N2-(pentan-3-yl)imidazo[2,1-f][1,2,4]triazine-2,4-diamine (60 mg, 0.147 mmol) in DMF (5 mL) was added dimethylglycine (15 mg, 0.146 mmol), HATU (92 mg, 0.24 mmol) and DIEA (56 mg, 0.43 mmol). The reaction mixture was stirred at Rt for overnight. The mixture was poured into $H_2O$ (50 mL) and extracted with EtOAc (10 ml×3). The combined organic phase was washed with brine, dried over $Na_2SO_4$ and concentrated in vacuo. The crude product was purified by column chromatography to give the product (25 mg, 34.7%). $^1H$ NMR (400 MHz, $CDCl_3$-d6) δ 8.08 (s, 1H), 7.47 (br.s, 3H), 7.15 (s, 1H), 5.96 (d, J=8.8 Hz, 1H), 3.98 (s, 2H), 3.59 (s, 6H), 3.05-2.91 (m, 4H), 2.39 (s, 6H), 2.15 (s, 3H), 2.11 (s, 6H), 2.08 (d, J=6.8 Hz, 2H), 1.74 (d, J=11.8 Hz, 2H), 1.53-1.42 (m, 4H), 0.84 (t, J=7.4 Hz, 6H) ppm. MS: M/e 495.0 $(M+1)^+$.

Compound B212: (S)-1-(4-(5-((4-amino-2-(pentan-2-yloxy)imidazo[2,1-f][1,2,4]triazin-7-yl)methyl)-3-methylpyridin-2-yl)piperazin-1-yl)-2-(isobutylamino)ethan-1-one Step A: N-(tert-butoxycarbonyl)-N-isobutylglycine NaOH solution (1N, 1.2 mL) was added to a solution of isobutylglycine (100 mg, 0.60 mmol) and $Boc_2O$ (261 mg, 1.2 mmol) in dioxane (3 mL) and water (1 mL). After stirred at r.t overnight, the solution was acidified with citric acid solution pH=3 and extracted with ethyl acetate (10 mL) for twice. The combined organic layers were dried with $Na_2SO_4$, filtered and concentrated to get the crude product, which was used directly (160 mg, crude). MS: M/e 175 $(M-56)^+$.

Step B: tert-butyl (S)-(2-(4-(5-((4-amino-2-(pentan-2-yloxy)imidazo[2,1-f][1,2,4] triazin-7-yl)methyl)-3-methylpyridin-2-yl)piperazin-1-yl)-2-oxoethyl)(isobutyl)carbamate A solution of (S)-7-((5-methyl-6-(piperazin-1-yl)pyridin-3-yl)methyl)-2-(pentan-2-yloxy)imidazo[2,1-f][1,2,4]triazin-4-amine (100 mg, 0.24 mmol), N-(tert-butoxycarbonyl)-N-isobutylglycine (67 mg, 0.29 mmol), HATU (137 mg, 0.36 mmol) and DIEA (62 mg, 0.48 mmol) in DMF (5 mL) was stirred at r.t for 2 hrs. The reaction mixture was quenched with water (5 mL), extracted with ethyl acetate (10 mL) and washed with brine (10 mL). The organic layer was dried over $Na_2SO_4$, filtered and concentrated to get the crude product, which was purified by CombiFlash (DCM: $4MNH_3{\cdot}MeOH$=20%) to get the product (100 mg, 66%). MS: M/e 624 $(M+1)^+$.

Step C: (S)-1-(4-(5-((4-amino-2-(pentan-2-yloxy)imidazo[2,1-f][1,2,4]triazin-7-yl) methyl)-3-methylpyridin-2-yl)piperazin-1-yl)-2-(isobutylamino)ethan-1-one HCl/dioxane (4M, 2 mL) was added to a solution of tert-butyl (S)-(2-(4-(5-((4-amino-2-(pentan-2-yloxy)imidazo[2,1-f][1,2,4]triazin-7-yl)methyl)-3-methylpyridin-2-yl)piperazin-1-yl)-2-oxoethyl)(isobutyl)carbamate (100 mg, 0.16 mmol) in EA (2 mL). The reaction mixture was stirred at r.t for 2 hrs. After concentration, the residue was dissolved in EA (10 mL) and washed with $NaHCO_3$ (5 mL). The organic layer was dried over $Na_2SO_4$, filtered and concentrated to get the crude product, which was further purified by prep-TLC (DCM:4M $NH_3{\cdot}MeOH$=10:1) to get the pure product (30 mg, 36%). $^1H$ NMR (400 MHz, DMSO-d6) δ 8.11 (s, 1H), 8.07 (s, 1H), 8.00 (s, 1H), 7.44 (s, 1H), 7.33 (s, 1H), 4.98-4.93 (m, 1H), 4.05 (s, 2H), 3.58 (s, 2H), 3.52 (s, 2H), 3.43 (s, 2H), 3.00 (s, 2H), 2.95 (s, 2H), 2.34 (d, J=8.0 Hz, 2H), 2.20 (s, 3H), 1.62-1.54 (m, 4H), 1.53-1.47 (m, 1H), 1.37-1.32 (m, 2H), 1.23 (s, 3H), 0.87 (t, J=8.0 Hz, 9H) ppm. MS: M/e 524 $(M+1)^+$.

Compound B213: (S)-7-((5-methyl-6-(4-((methylamino)methyl)piperidin-1-yl)pyridin-3-yl)methyl)-N2-(pentan-2-yl)imidazo[2,1-f][1,2,4]triazine-2,4-diamine Step A: tert-butyl ((1-(5-((4-(bis(4-methoxybenzyl)amino)-2-(((S)-pentan-2-yl)amino)imidazo[2,1-f][1,2,4]triazin-7-yl)(hydroxy)methyl)-3-methylpyridin-2-yl)piperidin-4-yl)methyl)(methyl)carbamate To a solution of (S)—N4,N4-bis(4-methoxybenzyl)-N2-(pentan-2-yl)imidazo[2,1-f][1,2,4]triazine-2,4-diamine (6.27 g, 13.63 mmol) in THF (60 mL) was added a solution of n-BuLi (25 mL, 40 mmol) dropwise maintaining the temperature between −75~−65° C. After 0.5 h, a mixture of tert-butyl ((1-(5-formyl-3-methylpyridin-2-yl)piperidin-4-yl)methyl)(methyl)carbamate (5.67 g, 16.35 mmol) in THF (30 mL) was added dropwise. The resulted mixture was stirred at −70° C. for 2 h and then warmed to room temperature and stirred overnight. The reaction was quenched with saturated $NH_4Cl$ solution, extracted with EtOAc (100 mL×2), washed with brine, dried over $Na_2SO_4$, filtered, and concentrated. The residue was purified by combi-flash to give the target compound (8.3 g, crude). MS: M/e 808 $(M+1)^+$.

Step B: (S)-7-((5-methyl-6-(4-((methylamino)methyl)piperidin-1-yl)pyridin-3-yl)methyl)-N2-(pentan-2-yl)imidazo[2,1-f][1,2,4]triazine-2,4-diamine To a mixture of the product of step A (8.3 g, crude) in TFA (20 mL) was added $Et_3SiH$ (20 mL) and the resulting mixture was stirred at 85° C. overnight. The mixture was concentrated and the residue was diluted with EA/$H_2O$, basified with $Na_2CO_3$ solution to pH=9, extracted with EA (100 mL×2). The combined organic layers were washed with brine, dried over $Na_2SO_4$, filtered, and concentrated. The residue was purified by combi-flash (eluting with DCM: (7 M $NH_3$ in MeOH)=20:1) to give the target compound (1.06 g, 17% for two steps). $^1$H NMR (400 MHz, DMSO-$d_6$) δ 8.05 (d, J=1.6 Hz, 1H), 7.48 (br.s, 2H), 7.41 (s, 1H), 7.14 (s, 1H), 5.98 (d, J=8.4, 1H), 3.96 (s, 2H), 3.87-3.72 (m, 1H), 3.35-3.23 (m, 2H), 2.71-2.52 (m, 4H), 2.45 (s, 3H), 2.16 (s, 3H), 1.84-1.70 (m, 2H), 1.68-1.45 (m, 2H), 1.41-1.19 (m, 5H), 1.10 (d, J=6.0 Hz, 3H), 0.86 (t, J=7.2 Hz, 3H) ppm. MS: M/e 452 $(M+1)^+$.

Compound B214: (R)-7-((5-methyl-6-(4-((methylamino)methyl)piperidin-1-yl)pyridin-3-yl)methyl)-N2-(pentan-2-yl)imidazo[2,1-f][1,2,4]triazine-2,4-diamine Compound B204 (700 mg) was separated by chiral prep-HPLC (column: CHIRALPAK AD, mobile phase: Hex (2 Mm NH3-MeOH):(EtOH:MeOH=1:1)=90:10) to obtain two enantiomeric stereoisomers: Compound B213 (230 mg, first peak) and Compound B214 (210 mg second peak) The condition of prep-SFC was below

| Column | CHIRALPAK AD |
|---|---|
| Column size | 2 cm × 25 cm, 5 μm |
| Injection | 0.5 mL |
| Mobile phase | Hex(2 mM NH3—MeOH):(EtOH:MeOH = 1:1) = 90:10 |

-continued

| Column | CHIRALPAK AD |
|---|---|
| Flow rate | 20 mL/min |
| Wave length | UV 220 nm |
| Temperature | 25° C. |
| Sample solution | 4.88 mg/ml in MeOH:EtOH = 1:1 |
| Prep-SFC equipment | Prep-HPLC-Gilson |

Compound B214: $^1$H NMR (400 MHz, DMSO-d6) δ 8.04 (s, 1H), 7.47 (br.s, 2H), 7.40 (s, 1H), 7.14 (s, 1H), 5.98 (d, J=8.0 Hz, 1H), 3.96 (s, 2H), 3.82-3.79 (m, 1H), 3.29 (d, J=12.0 Hz, 2H), 2.61 (t, J=12.0 Hz, 2H), 2.47 (d, J=8.0 Hz, 2H), 2.33 (s, 3H), 2.15 (s, 3H), 1.76 (d, J=12.0 Hz, 2H), 1.57-1.49 (m, 2H), 1.35-1.23 (m, 5H), 1.10 (d, J=8.0 Hz, 3H), 0.86 (t, J=8.0 Hz, 3H) ppm. MS: M/e 452 $(M+1)^+$.

Compound B215: (S)-7-((6-(4-(isobutylamino)piperidin-1-yl)-5-methylpyridin-3-yl)methyl)-2-(pentan-2-yloxy)imidazo[2,1-f][1,2,4]triazin-4-amine Step A: tert-butyl (1-(5-((4-(bis(4-methoxybenzyl)amino)-2-(((S)-pentan-2-yl)oxy) imidazo[2,1-f][1,2,4]triazin-7-yl)(hydroxy)methyl)-3-methylpyridin-2-yl)piperidin-4-yl)carbamate Under argon, n-BuLi (1.6M, 0.35 ml, 0.55 mmol) was added to a solution of (S)-7-bromo-N,N-bis(4-methoxybenzyl)-2-(pentan-2-yloxy)imidazo[2,1-f][1,2,4]triazin-4-amine (250 mg, 0.46 mmol) in anhydrous THF (3 mL). The reaction mixture was stirred at −78° C. for 20 minutes, then tert-butyl (1-(5-formyl-3-methylpyridin-2-yl)piperidin-4-yl)carbamate (162 mg, 0.51 mmol) was added in THF dropwise and the resulting mixture was stirred 4 h at rt. An aqueous ammonium chloride solution was added and the mixture was extracted with diethyl ether and ethyl acetate. The combined organic extracts were dried over sodium sulfate, filtered and evaporated. Purification by prep-TLC (silica gel, EA:PE=1:1) afforded desired products (150 mg, 41%), MS: m/e 781 $(M+1)^+$.

Step B: (S)-7-((6-(4-aminopiperidin-1-yl)-5-methylpyridin-3-yl)methyl)-2-(pentan-2-yloxy)imidazo[2,1-f][1,2,4]triazin-4-amine The product of step A (150 mg, 0.19 mmol) was dissolved in TFA (3 ml) followed by addition $Et_3SiH$ (3 ml). The mixture was stirred at 80° C. for 3 h. cooled to room temperature, and concentrated under reduced pressure. Another TFA (3 mL) was added and the mixture was stirred at 80° C. for 3 h. The mixture was cooled to room temperature, and concentrated under reduced pressure. The resulting crude oil was dissolved in water and extracted with EA, the aqueous layer was adjusted pH to 12 with aqueous $K_2CO_3$ and extracted with EtOAc (3×20 mL).). The combined organic layers were dried $Na_2SO_4$ and evaporated in vacuo to give the crude product (60 mg, 49%). MS: m/e 425 $(M+1)^+$.

Step C: (S)-7-((6-(4-(isobutylamino)piperidin-1-yl)-5-methylpyridin-3-yl)methyl)-2-(pentan-2-yloxy) imidazo[2,1-f][1,2,4]triazin-4-amine The product of step B (40 mg, 0.09 mmol) was dissolved in MeOH (1 ml) followed by addition of isobutyraldehyde (6.8 mg, 0.09 mmol) and acetic acid (1 drop). The mixture was stirred for 30 minutes and then $NaBH_4$ (4 mg, 0.09 mmol) was added. The reaction was stirred and monitored by TLC. After 2 h the mixture was diluted with EA and washed with water and brine. The organic layer was dried over magnesium sulfate and the solvent was removed under reduced pressure. The crude product was purified by prep-HPLC to give the product (8 mg, 18%). $^1$H NMR (400 MHz, DMSO-d6) δ 8.10 (s, 1H), 8.06-7.91 (m, 2H), 7.38 (s, 1H), 7.31 (s, 1H), 4.99-4.94 (m, 1H), 4.02 (s, 2H), 3.28 (d, J=12.4 Hz, 2H), 3.09-2.87 (m, 1H), 2.66 (t, J=11.5 Hz, 2H), 2.49-2.42 (m, 1H), 2.36 (d, J=6.3 Hz, 2H), 2.16 (s, 3H), 1.86 (d, J=10.8 Hz, 2H), 1.70-1.46 (m, 3H), 1.42-1.27 (m, 5H), 1.25 (d, J=6.2 Hz, 3H), 0.88 (t, J=7.2 Hz, 9H) ppm. MS: m/e 481 $(M+1)^+$.

Compound B216 and compound B217: (S)-3-((4-amino-7-((5-methyl-6-(piperazin-1-yl)pyridin-3-yl)methyl)imidazo[2,1-f][1,2,4]triazin-2-yl)oxy)pentan-1-ol and (S)-1-((4-amino-7-((5-methyl-6-(piperazin-1-yl)pyridin-3-yl)methyl)imidazo[2,1-f][1,2,4]triazin-2-yl)oxy)pentan-3-ol Step A: (S)-pentane-1,3-diol To a stirred suspension of LAH (0.286 g, 7.58 mmol) in THF (10 mL) was added dropwise a solution of methyl (S)-3-hydroxypentanoate (0.5 g, 3.79 mmol) in THF (5 mL) at 0° C. After the addition, the reaction was stirred for 2 hours. The reaction was quenched with $H_2O$ (0.286 mL), aq.NaOH (15%, 0.286 mL), followed by $H_2O$ (0.858 mL), EtOAc (20 mL) was added and filtered. The filtrate was concentrated and purified by column chromatography (petroleum ether/EtOAc=2:1~1:1) to give the target compound (300 mg, 76.1%).

Step B: (S)-1-((tert-butyldimethylsilyl)oxy)pentan-3-ol

To a stirred solution of the product of step A (300 mg, 2.88 mmol) in $CH_2Cl_2$ (20 mL) was added Imidazole (39 mg, 5.76 mmol), then a solution of TBS-Cl (391 mg, 2.6 mmol) in $CH_2Cl_2$ (5 mL) was added dropwise at 0° C. After the addition, the reaction mixture was stirred overnight. The reaction mixture was concentrated to give the residue, which was purified by column chromatography (petroleum ether/EtOAc=1:1) to give the target compound (460 mg, 73.3%).

Step C: (S)-7-bromo-2-((1-((tert-butyldimethylsilyl)oxy)pentan-3-yl)oxy)-N,N-bis(4-methoxybenzyl)imidazo[2,1-f][1,2,4]triazin-4-amine and (S)-7-bromo-2-((3-((tert-butyldimethylsilyl)oxy)pentyl)oxy)imidazo[2,1-f][1,2,4]triazin-4-amine To a stirred solution of the product of step B (460 mg, 2.11 mmol) in THF (20 mL) was added NaH (0.168 g, 4.2 mmol, 60%). After stirred for 30 min, 7-bromo-2-chloro-N,N-bis(4-methoxybenzyl)imidazo[2,1-f][1,2,4]triazin-4-amine (686 mg, 1.4 mmol) was added. After the addition, the reaction was stirred at 60° C. overnight. The reaction mixture was treated with $H_2O$ (20 mL), extracted with EtOAc (30 mL×2). The combined organic layers were washed with brine, dried over $Na_2SO_4$, concentrated and purified by column chromatography (petroleum ether/EtOAc=20:1) to give the target compound (650 mg, 69.3%) as a mixture. MS: M/e 670 $(M+1)^+$.

Step D: tert-butyl 4-(5-((4-(bis(4-methoxybenzyl)amino)-2-(((S)-1-((tert-butyldimethylsilyl)oxy)pentan-3-yl)oxy)imidazo[2,1-f][1,2,4]triazin-7-yl)(hydroxy)methyl)-3-methylpyridin-2-yl)piperazine-1-carboxylate and tert-butyl 4-(5-((4-(bis(4-methoxybenzyl)amino)-2-(((S)-3-((tert-butyldimethylsilyl)oxy)pentyl)oxy)imidazo[2,1-f][1,2,4]triazin-7-yl)(hydroxy)methyl)-3-methylpyridin-2-yl)piperazine-1-carboxylate To a stirred solution of product of step C (650 mg, 0.97 mmol) in dry THF (20 mL) was added dropwise n-BuLi (1.6 M, 1.2 mL, 1.94 mmol) at −78° C. After stirred for 30 mins, a solution of tert-butyl 4-(5-formyl-3-methylpyridin-2-yl)piperazine-1-carboxylate (353 mg, 1.16 mmol) in THF (10 mL) was added dropwise at −78° C. Then the mixture was stirred for 2 hours. The reaction was quenched with aq.$NH_4Cl$, extracted with EtOAc (40 mL×2). The combined organic layers were washed with brine, dried over $Na_2SO_4$, concentrated and purified by column chromatography (petroleum ether/EtOAc=5:1~1:1) to give the target compound (619 g, 71.2%) as a mixture. MS: M/e 897 $(M+1)^+$.

Step E: (S)-3-((4-amino-7-((5-methyl-6-(piperazin-1-yl)pyridin-3-yl)methyl)imidazo[2,1-f][1,2,4]triazin-2-yl)oxy)pentan-1-ol and (S)-1-((4-amino-7-((5-methyl-6-(piperazin-1-yl)pyridin-3-yl)methyl)imidazo[2,1-f][1,2,4]triazin-2-yl)oxy)pentan-3-ol A mixture of the product of step D (619 mg, 0.69 mmol) in TFA/$Et_3SiH$ (5 mL/5 mL) was stirred at 80° C. for 2 days. The reaction mixture was concentrated to give the residue, which was dissolved in MeOH (20 mL), aq.NaOH (2.0 M, 5 mL) was added and stirred overnight. Most MeOH was removed and the aqueous layer was extracted with EtOAc (20 mL×2). The combined organic layers were washed with brine, dried over $Na_2SO_4$, concentrated to give the residue and purified by prep-TLC ($CH_2Cl_2$/MeOH($NH_3$)=10:1) to give crude product. There were 2 peaks showed on HPLC with the same MS. After purified by prep-HPLC, two compounds were obtained, Compound B216 (120 mg) and Compound B217 (40 mg).

Compound B216: 3-((4-amino-7-((5-methyl-6-(piperazin-1-yl)pyridin-3-yl)methyl)imidazo[2,1-f][1,2,4]triazin-2-yl)oxy)hexan-1-ol; $^1$H NMR (400 MHz, DMSO-d6) δ 8.17-7.94 (m, 3H), 7.42 (s, 1H), 7.31 (s, 1H), 5.05-4.88 (m, 1H), 4.48-4.43 (m, 1H), 4.03 (s, 2H), 3.57-3.42 (m, 2H), 2.92-2.86 (m, 4H), 2.82-2.76 (m, 4H), 2.17 (s, 3H), 1.85-1.71 (m, 2H), 1.71-1.56 (m, 2H), 0.87 (t, J=7.4 Hz, 3H) ppm. MS: M/e 427 $(M+1)^+$.

Compound B217: 1-((4-amino-7-((5-methyl-6-(piperazin-1-yl)pyridin-3-yl)methyl)imidazo[2,1-f][1,2,4]triazin-2-yl)oxy)hexan-3-ol; $^1$H NMR (400 MHz, DMSO-d6) δ 8.19-8.00 (m, 3H), 7.44 (s, 1H), 7.30 (s, 1H), 4.52 (d, J=5.6 Hz, 1H), 4.30 (t, J=6.4 Hz, 2H), 4.03 (s, 2H), 3.52 (s, 1H), 2.97-2.86 (m, 4H), 2.84-2.74 (m, 4H), 2.17 (s, 3H), 1.86-1.76 (m, 1H), 1.71-1.61 (m, 1H), 1.47-1.30 (m, 2H), 0.87 (t, J=7.2 Hz, 3H) ppm. MS: M/e 427 $(M+1)^+$.

Compound B218: 1-(4-(5-((4-amino-2-((1-hydroxyhexan-3-yl)oxy)imidazo[2,1-f][1,2,4]triazin-7-yl)methyl)-3-methylpyridin-2-yl)piperazin-1-yl)-2-(methylamino)ethan-1-one A mixture of 3-((4-amino-7-((5-methyl-6-(piperazin-1-yl)pyridin-3-yl)methyl)imidazo[2,1-f][1,2,4]triazin-2-yl)oxy)hexan-1-ol (20 mg, 0.045 mmol), N-(tert-butoxycarbonyl)-

N-methylglycine (8.5 mg, 0.045 mmol), HATU (20 mg, 0.054 mmol) and DIPEA (12 mg, 0.09 mmol) in DMF (3 mL) was stirred at room temperature overnight. The reaction mixture was poured into $H_2O$ (10 mL) and extracted with EtOAc (10 mL). The organic layer was separated, washed with brine, dried over $Na_2SO_4$, concentrated to give the residue, which was dissolved in $CH_2Cl_2$ (5 mL) and dioxane/HCl (2 mL, 4.0 M) was added. The reaction was stirred overnight. The reaction mixture was concentrated and purified by prep-HPLC to give the target compound (12 mg). $^1H$ NMR (400 MHz, DMSO-$d_6$+$D_2O$) δ 8.07 (s, 1H), 7.62 (s, 1H), 7.46 (s, 1H), 5.16-5.00 (m, 1H), 4.12 (s, 2H), 4.07 (s, 2H), 3.65 (s, 2H), 3.53-3.43 (m, 4H), 3.15-3.06 (m, 4H), 2.59 (s, 3H), 2.25 (s, 3H), 1.85-1.72 (m, 2H), 1.65-1.55 (m, 2H), 1.40-1.20 (m, 2H), 0.85 (t, J=7.2 Hz, 3H) ppm. MS: M/e 512 $(M+1)^+$.

Compound B219: (S)-1-(4-(5-((4-amino-2-(pentan-2-ylamino)imidazo[2,1-f][1,2,4]triazin-7-yl)methyl)-3-methylpyridin-2-yl)piperazin-1-yl)-2-(dimethylamino)ethan-1-one To a mixture of (S)-7-((5-methyl-6-(piperazin-1-yl)pyridin-3-yl)methyl)-N2-(pentan-2-yl)imidazo[2,1-f][1,2,4]triazine-2,4-diamine (1.6 g, 3.91 mmol), dimethylglycine (362 mg, 3.52 mmol) and DIEA (1 g, 7.82 mmol) in DMF (10 mL) was added HATU (1.48 g, 3.91 mmol). The reaction was stirred at room temperature overnight. The reaction was diluted with water, extracted with EA (80 mL×2), washed with brine, dried over $Na_2SO_4$, filtered, and concentrated. The residue was purified by column chromatograph (eluting with DCM: (7 M $NH_3$ in MeOH)=20:1) and further purified by prep-HPLC to give the target compound (575 mg, 30%). $^1H$ NMR (400 MHz, DMSO-$d_6$) δ 8.07 (d, J=1.6 Hz, 1H), 7.46 (br.s, 2H), 7.45 (d, J=2.0 Hz, 1H), 7.15 (s, 1H), 5.98 (d, J=8.4 Hz, 1H), 3.98 (s, 2H), 3.88-3.74 (m, 1H), 3.72-3.60 (m, 2H), 3.59-3.50 (m, 2H), 3.11 (s, 2H), 3.05-2.87 (m, 4H), 2.20 (s, 3H), 2.19 (s, 6H), 1.59-1.45 (m, 1H), 1.43-1.22 (m, 3H), 1.09 (d, J=6.0 Hz, 3H), 0.85 (t, J=7.2 Hz, 3H) ppm. MS: M/e 495 $(M+1)^+$.

Compound B220: N2-(heptan-4-yl)-7-((5-methyl-6-(4-((methylamino) methyl)piperidin-1-yl)pyridin-3-yl)methyl)imidazo[2,1-f][1,2,4]triazine-2,4-diamine Step A: tert-butyl ((1-(5-((4-(bis(4-methoxybenzyl) amino)-2-(heptan-4-ylamino) imidazo[2,1-f][1,2,4] triazin-7-yl)(hydroxy)methyl)-3-methylpyridin-2-yl) piperidin-4-yl)methyl)(methyl)carbamate To a cooled solution of N2-(heptan-4-yl)-N4,N4-bis(4-methoxybenzyl)imidazo [2,1-f][1,2,4]triazine-2,4-diamine (1 g, 2 mmol) in THF (20 mL) at −78° C., purged with $N_2$ was added with n-BuLi (1.6 M, 3.8 mL) dropwise. After stirred at −78° C. for 30 mins, tert-butyl ((1-(5-formyl-3-methylpyridin-2-yl)piperidin-4-yl)methyl)(methyl) carbamate (0.83 g, 2.4 mmol) in THF (5 mL) was added. The resulting mixture was stirred gradually to r.t overnight. The solution was quenched with $NH_4Cl$ solution (10 mL) and extracted with ethyl acetate (10 mL). The organic layer was dried with $Na_2SO_4$, filtered and concentrated to get the crude product, which was further purified by CombiFlash (PE: EA=40%) to get the product (1 g, 58%). MS: M/e 836 $(M+1)^+$.

Step B: N2-(heptan-4-yl)-7-((5-methyl-6-(4-((methylamino)methyl)piperidin-1-yl) pyridin-3-yl)methyl) imidazo[2,1-f][1,2,4]triazine-2,4-diamine A solution of tert-butyl ((1-(5-((4-(bis(4-methoxybenzyl) amino)-2-(heptan-4-ylamino)imidazo[2,1-f][1,2,4]triazin-7-yl)(hydroxy)methyl)-3-methylpyridin-2-yl)piperidin-4-yl) methyl)(methyl)carbamate (1 g, 1.2 mmol) in triethylsilane (1 mL) and trifluoroacetic acid (1 mL) was heated at 40° C. overnight. After concentrated, the residue was added with 2 mL of TFA and heated at 80° C. for 2 hrs. The solvent was evaporated to get the crude product, which was added with EA (10 mL) and basified with $NaHCO_3$ solution (10 mL). The aqueous layer was dried, concentrated and purified by prep-TLC (DCM:MeOH=10:1, 7M $NH_3$·MeOH) get the product (120 mg, 21%). $^1H$ NMR (400 MHz, DMSO-d6) δ 8.05 (s, 1H), 7.45 (br.s, 2H), 7.39 (s, 1H), 7.15 (s, 1H), 5.92 (d, J=8.0 Hz, 1H), 3.95 (s, 2H), 3.81-3.75 (m, 1H), 3.30 (d, J=12.0 Hz, 3H), 2.65-2.58 (m, 4H), 2.41 (s, 3H), 2.15 (s, 3H), 1.77 (d, J=12.0 Hz, 2H), 1.69-1.63 (m, 1H), 1.46-1.36 (m, 4H), 1.33-1.23 (m, 6H), 0.85 (t, J=8.0 Hz, 6H) ppm. MS: M/e 480 $(M+1)^+$.

Compound B221 and Compound B222: (S)-7-((5-methyl-6-(4-((methylamino)methyl)piperidin-1-yl) pyridin-3-yl)methyl)-2-(pentan-2-yloxy)imidazo[2,1-f][1,2,4]triazin-4-amine, and (R)-7-((5-methyl-6-(4-((methylamino)methyl)piperidin-1-yl)pyridin-3-yl)methyl)-2-(pentan-2-yloxy)imidazo[2,1-f][1,2,4] triazin-4-amine Compound B205 (370 mg) was separated by chiral prep-HPLC to obtain two enantiomeric stereoisomers: the first peak Compound B221 (Peak-1, 135 mg) and the second peak Compound B222 (Peak-2, 151 mg). The chiral separation conditions are shown below.

| Column | CHIRALPAK ID |
|---|---|
| Column size | 2 cm × 25 cm, 5 μm |
| Injection | 0.3 mL |
| Mobile phase | (HeX:DCM = 3:1)(0.2% IPA):EtOH = 90:10 |
| Flow rate | 20 mL/min |
| Wavelength | UV 220 nm |
| Temperature | 25° C. |
| Sample solution | 29.15 mg/ml in DCM:EtOH = 1:1 |
| Prep-SFC equipment | Prep-HPLC-Gilson |

Compound B221: $^1H$ NMR (400 MHz, DMSO-d6) δ 8.10 (s, 1H), 8.03 (d, J=1.9 Hz, 1H), 7.99 (s, 1H), 7.38 (d, J=1.8 Hz, 1H), 7.32 (s, 1H), 5.00-4.94 (m, 1H), 4.02 (s, 2H), 3.27 (s, 2H), 2.61 (t, J=11.9 Hz, 2H), 2.39 (d, J=6.6 Hz, 2H), 2.28 (s, 3H), 2.15 (s, 3H), 1.75 (d, J=10.9 Hz, 2H), 1.66-1.59 (m, 1H), 1.56-1.46 (m, 2H), 1.41-1.29 (m, 2H), 1.28-1.20 (m, 5H), 0.88 (t, J=7.3 Hz, 3H) ppm. MS: M/e 453 $(M+1)^+$.

Compound B222: $^1H$ NMR (400 MHz, DMSO-d6) δ 8.11 (s, 1H), 8.04 (d, J=2.0 Hz, 1H), 7.99 (s, 1H), 7.38 (d, J=1.8 Hz, 1H), 7.32 (s, 1H), 4.98-4.94 (m, 1H), 4.02 (s, 2H), 3.30 (s, 2H), 2.61 (t, J=11.9 Hz, 2H), 2.39 (d, J=6.6 Hz, 2H), 2.28 (s, 3H), 2.15 (s, 3H), 1.75 (d, J=11.1 Hz, 2H), 1.67-1.59 (m, 1H), 1.56-1.47 (m, 2H), 1.41-1.30 (m, 2H), 1.27-1.20 (m, 5H), 0.88 (t, J=7.3 Hz, 3H) ppm. MS: M/e 453 $(M+1)^+$.

Compound B223: N2-(hexan-3-yl)-7-((5-methyl-6-(piperazin-1-yl)pyridin-3-yl)methyl)imidazo[2,1-f] [1,2,4]triazine-2,4-diamine Step A: N2-(hexan-3-yl)-N4,N4-bis(4-methoxybenzyl)imidazo[2,1-f][1,2,4]triazine-2,4-diamine To a sealed tube charged with 2-chloro-N,N-bis(4-methoxybenzyl)imidazo[2,1-f][1,2,4]triazin-4-amine (900 mg, 2.2 mmol), DIEA (1.7 g, 13.2 mmol) and hexan-3- amine hydrochloride (904 mg, 6.6 mmol), was added NMP (5 mL) under nitrogen atmosphere. The suspension was stirred for 6 h at 220° C., and cooled to rt, The reaction mixture was diluted with water and extracted with $CH_2Cl_2$. The combined organic extracts were washed with Brine, dried over $Na_2SO_4$, and concentrated. The crude product was purified by column chromatography on silica gel (DCM) and (EA:PE=1:1) to give the product (400 mg. 38%). MS: m/e 475 $(M+1)^+$.

Step B: tert-butyl 4-(5-((4-(bis(4-methoxybenzyl)amino)-2-(hexan-3-ylamino)imidazo[2,1-f][1,2,4]triazin-7-yl)(hydroxy)methyl)-3-methylpyridin-2-yl)piperazine-1-carboxylate Under argon, n-BuLi (1.31 mL, 2.1 mmol, 1.6M) was added to a solution of the product of step A (400 mg, 0.84 mmol) in anhydrous THF (5 mL). The reaction mixture was stirred at −78° C. for 20 minutes, then tert-butyl 4-(5-formyl-3-methylpyridin-2-yl)piperazine-1-carboxylate (308 mg, 1.02 mmol) was added and the resulting mixture was stirred 4 h at rt. An aqueous ammonium chloride solution was added and the mixture was extracted with diethyl ether and ethyl acetate. The combined organic layers were dried over sodium sulfate, filtered and evaporated. Purification by prep-TLC (silica gel, EA:PE=1:1) afforded desired products (280 mg, yield 42%). MS: m/e 780 $(M+1)^+$.

Step C: N2-(hexan-3-yl)-7-((5-methyl-6-(piperazin-1-yl)pyridin-3-yl)methyl)imidazo[2,1-f][1,2,4]triazine-2,4-diamine The product of step B was dissolved in TFA (3 ml) followed by addition $Et_3SiH$ (3 ml). The mixture was stirred at 80° C. for 3 h. cooled to room temperature, and concentrated under reduced pressure. Another TFA (3 ml) was added and the mixture was stirred at 80° C. for 3 h. The mixture was cooled to room temperature, and concentrated under reduced pressure. The crude product was purified by prep-HPLC to give the desired products (90 mg, Yield 59%). $^1$H NMR (400 MHz, DMSO-d6) δ 8.06 (d, J=2.0 Hz, 1H), 7.44 (br.s, 2H), 7.40 (s, 1H), 7.14 (s, 1H), 5.93 (d, J=8.9 Hz, 1H), 3.95 (s, 2H), 3.68 (d, J=7.6 Hz, 1H), 2.95-2.84 (m, 4H), 2.83-2.74 (m, 4H), 2.33 (s, 1H), 2.16 (s, 3H), 1.50-1.36 (m, 4H), 1.34-1.25 (m, 2H), 0.87-0.82 (m, 6H) ppm. MS: m/e 424 $(M+1)^+$.

Compound B224 and compound B225: (S)-2-(hexan-3-yloxy)-7-((5-methyl-6-(piperazin-1-yl)pyridin-3-yl)methyl)imidazo [2,1-f][1,2,4]triazin-4-amine, and (R)-2-(hexan-3-yloxy)-7-((5-methyl-6-(piperazin-1-yl)pyridin-3-yl)methyl)imidazo [2,1-f][1,2,4]triazin-4-amine Compound B140 (1.5 g) was separated by chiral prep-HPLC to obtain two enantiomeric stereoisomers: the first peak Compound B224 (Peak-1) and the second peak Compound B225 (Peak-2). The condition of rep-SFC was below.

| Column | CHIRALPAK ID |
|---|---|
| Column size | 2 cm × 25 cm, 5 um |
| Injection | 0.5 mL |
| Mobile phase | (HeX:DCM = 3:1)(2 mM NH3—MeOH):IPA = 90:10 |
| Flow rate | 20 mL/min |
| Wave length | UV 220 nm |
| Temperature | 25° C. |
| Sample solution | 10 mg/ml in DCM:EtOH = 1:1 |

Compound B224: $^1$H NMR (400 MHz, DMSO-d6) δ 8.11 (s, 1H) 8.05 (s, 1H), 7.99 (s, 1H), 7.39 (d, J=1.7 Hz, 1H), 7.33 (s, 1H), 4.90-4.84 (m, 1H), 4.03 (s, 2H), 2.95-2.88 (m, 4H), 2.85-2.78 (m, 4H), 2.16 (s, 3H), 1.70-1.49 (m, 4H), 1.41-1.19 (m, 3H), 0.92-0.71 (m, 6H) ppm. MS: m/e 425 $(M+1)^+$.

Compound B225: $^1$H NMR (400 MHz, DMSO-d6) δ 8.10 (s, 1H), 8.06 (s, 1H), 7.99 (s, 1H), 7.39 (d, J=1.7 Hz, 1H), 7.33 (s, 1H), 4.90-4.84 (m, 1H), 4.03 (s, 2H), 2.95-2.88 (m, 4H), 2.85-2.78 (m, 4H), 2.16 (s, 3H), 1.70-1.49 (m, 4H), 1.41-1.19 (m, 3H), 0.89-0.71 (m, 6H) ppm. MS: m/e 425 $(M+1)^+$.

Compound B226: (S)-3-((4-amino-7-((5-methyl-6-(piperazin-1-yl)pyridin-3-yl)methyl)imidazo[2,1-f][1,2,4]triazin-2-yl)amino)hexan-1-ol Step A: (S)-3-((4-(bis(4-methoxybenzyl)amino)imidazo[2,1-f][1,2,4]triazin-2-yl)amino)hexan-1-ol A mixture of 2-chloro-N,N-bis(4-methoxybenzyl)imidazo[2,1-f][1,2,4]triazin-4-amine (1.64 g, 4 mmol), (S)-3-aminohexan-1-ol hydrochloride (2.4 g, 16 mmol) and DIPEA (4.1 g, 32 mmol) in NMP (10 mL) was stirred at 240° C. in a sealed tube for 7 hours. The reaction mixture was cooled to rt and poured into $H_2O$ (50 mL), extracted with EtOAc (50 mL×3). The combined organic layers were washed with aq.HCl, brine, dried over $Na_2SO_4$, concentrated and purified by column chromatography (petroleum ether/EtOAc=5:1~1:1) to give the target compound (1.1 g, 56.1%). MS: M/e 491 $(M+1)^+$.

Step B: (S)—N2-(1-((tert-butyldimethylsilyl)oxy)hexan-3-yl)-N4,N4-bis(4-methoxybenzyl)imidazo[2,1-f][1,2,4]triazine-2,4-diamine To a stirred solution of product of step A (1.1 g, 2.24 mmol) in $CH_2Cl_2$ (20 mL) was added Imidazole (0.3 g, 4.48 mmol), then the mixture was cooled to 0° C. and a solution of TBSCl (0.4 g, 2.7 mmol) in $CH_2Cl_2$ (5 mL) was added dropwise. After the addition, the reaction was stirred overnight. The reaction mixture was concentrated to give the residue, which was purified by column chromatography (petroleum ether/EtOAc=20:1) to give the target compound (1.0 g, 73.9%). MS: M/e 605 $(M+1)^+$.

Step C: tert-butyl 4-(5-((4-(bis(4-methoxybenzyl)amino)-2-(((S)-1-((tert-butyldimethylsilyl)oxy)hexan-3-yl)amino)imidazo[2,1-f][1,2,4]triazin-7-yl)(hydroxy)methyl)-3-methylpyridin-2-yl)piperazine-1-carboxylate To a stirred solution of the product of step B (500 mg, 0.83 mmol) in THF (20 mL) was added dropwise n-BuLi (1.6 M, 1.03 mL, 1.66 mL) at −78° C. After stirred for 30 min, a solution of tert-butyl 4-(5-formyl-3-methylpyridin-2-yl)piperazine-1-carboxylate (300 mg, 0.99 mmol) in THF (5 mL) was added dropwise at −78° C. After the addition, the reaction was stirred overnight. The reaction was quenched with aq.$NH_4Cl$, extracted with EtOAc (20 mL×3). The combined organic layers were washed with brine, dried over $Na_2SO_4$, concentrated and purified by column chromatography (petroleum ether/EtOAc=5:1–2:1) to give the target compound (300 mg, 39.7%). MS: M/e 910 $(M+1)^+$.

Step D: (S)-3-((4-amino-7-((5-methyl-6-(piperazin-1-yl)pyridin-3-yl)methyl)imidazo[2,1-f][1,2,4]triazin-2-yl)amino)hexan-1-ol A mixture of the product of step C (300 mg, 0.33 mmol) in TFA/$Et_3SiH$ (5 mL/3 mL) was stirred at 85° C. for 2 days. The reaction mixture was concentrated to give the residue, which was dissolved in MeOH (5 mL), aq.NaOH (2.0 M, 2 mL) was added and stirred for two days. Most MeOH was removed to give the aqueous layer and extracted with EtOAc (10 mL×3). The combined organic layers were washed with brine, dried over $Na_2SO_4$, concentrated to give the residue, which was purified by prep-HPLC to give the target compound (15 mg). $^1H$ NMR (400 MHz, DMSO-d6) δ 8.09 (d, J=2.0 Hz, 1H), 7.62-7.38 (m, 3H), 7.14 (s, 1H), 6.01 (d, J=8.8 Hz, 1H), 4.38 (s, 1H), 3.97 (s, 2H), 3.90-3.80 (m, 1H), 3.52-3.45 (m, 3H), 3.12-3.01 (m, 7H), 2.18 (s, 3H), 1.67-1.60 (m, 2H), 1.55-1.38 (m, 2H), 1.38-1.24 (m, 2H), 0.84 (t, J=7.3 Hz, 3H) ppm. MS: M/e 440 $(M+1)^+$.

Compound B227: 7-((5-methyl-6-(piperazin-1-yl)pyridin-3-yl)methyl)-N2-(1,1,1-trifluoropentan-2-yl)imidazo[2,1-f][1,2,4]triazine-2,4-diamine Step A: 2,2,2-trifluoro-N-methoxy-N-methylacetamide 2,2,2-trifluoroacetic anhydride (10.5 g, 50 mmol) was added dropwise to a suspension of N,O-dimethylhydroxylamine hydrochloride (5.36 g, 55 mmol) in $CH_2Cl_2$ (100 mL) at 0° C. After stirred for 15 min, pyridine (6.8 g, 100 mmol) was added dropwise at 0° C. over 15 min. After the addition, the reaction was stirred overnight. The reaction mixture was treated with $H_2O$ (30 mL), the organic layer was separated, dried over $Na_2SO_4$, concentrated under reduce pressure to give the target compound (6.6 g, 84%).

Step B: 1,1,1-trifluoropentan-2-one

To a stirred solution of the product of step A (6.6 g, 42 mmol) in THF (100 mL) was added dropwise propylmagnesium bromide (23 mL, 46.2 mmol) at 0° C. After the addition, the reaction was stirred overnight. The reaction was quenched with aq.$NH_4Cl$, extracted with EtOAc (50 mL). The organic layer was separated, which was directly used to the next step.

Step C: 1,1,1-trifluoropentan-2-one oxime

Hydroxylamine hydrochloride (23 g, 0.336 mol) and AcONa (27 g, 0.336 mol) were dissolved in $H_2O$ (200 mL) and a solution of the product of step B (42 mmol) in THF (50 mL) was added dropwise. After the addition, the reaction was stirred overnight. The mixture was extracted with EtOAc (30 mL×3), the combined organic layers were washed with brine, dried over $Na_2SO_4$, concentrated to give the target compound (3.4 g, 52.2%) as colorless oil. MS: M/e 156 $(M+1)^+$.

Step D: 1,1,1-trifluoropentan-2-amine hydrochloride

To a stirred suspension of LAH (1.25 g, 32.9 mmol) in THF (50 mL) was added dropwise a solution of the product of step C (3.4 g, 21.9 mmol) in THF (20 mL) at 0° C. After the addition, the reaction was stirred overnight. The reaction was quenched with $H_2O$ (1.25 mL), aq.NaOH (15%, 1.25 mL), followed by $H_2O$ (3.75 mL) and filtered. Dioxane/HCl (4.0 M, 10 mL) was added to the filtrate and stirred overnight, then concentrated to give the residue, which was treated with Petroleum ether (50 mL) and filtered. The cake was collected, dried to give the target compound (1.1 g, 28.1%) as a white solid. MS: M/e 142 $(M+1)^+$.

Step E: N4,N4-bis(4-methoxybenzyl)-N2-(1,1,1-trifluoropentan-2-yl)imidazo[2,1-f][1,2,4]triazine-2,4-diamine A mixture of 2-chloro-N,N-bis(4-methoxybenzyl)imidazo[2,1-f][1,2,4]triazin-4-amine (409 mg, 1 mmol), the product of step D (357 mg, 2 mmol), $Pd_2(dba)_3$ (91.6 mg, 0.1 mmol), X-phos (95.2 mg, 0.2 mmol) and $Cs_2CO_3$ (652 mg, 2 mmol) in dioxane (15 mL) was stirred for 2 days under $N_2$. The reaction mixture was filtered and the filtrate was treated with EtOAc/$H_2O$ (100 mL/50 mL). The combined organic layers were washed with brine, dried over $Na_2SO_4$, concentrated and purified by column chromatography ($CH_2Cl_2$/MeOH=50:1) to give the target compound (50 mg, 9.7%). MS: M/e 515 $(M+1)^+$.

Step F: tert-butyl 4-(5-((4-(bis(4-methoxybenzyl)amino)-2-((1,1,1-trifluoropentan-2-yl)amino)imidazo[2,1-f][1,2,4]triazin-7-yl)(hydroxy)methyl)-3-methylpyridin-2-yl)piperazine-1-carboxylate To a stirred solution of the product of step E (50 mg, 0.097 mmol) in THF (5 mL) was added dropwise n-BuLi (1.6 M, 0.12 mL, 0.19 mmol) at −78° C. After stirred for 30 min, a solution of tert-butyl 4-(5-formyl-3-methylpyridin-2-yl)piperazine-1-carboxylate (35.4 mg, 0.11 mmol) in THF (2 mL) was added dropwise. After the addition, the reaction was stirred overnight. And was quenched with aq.$NH_4Cl$, extracted with brine, dried over $Na_2SO_4$, concentrated and purified by prep-TLC (petroleum ether/EtOAc=2:1) to give the residue, which was further purified by prep-TLC ($CH_2Cl_2$/MeOH=20:1) to give the target compound (16 mg, 20.2%).

Step G: 7-((5-methyl-6-(piperazin-1-yl)pyridin-3-yl)methyl)-N2-(1,1,1-trifluoropentan-2-yl)imidazo[2,1-f][1,2,4]triazine-2,4-diamine A mixture of the product of step F (16 mg, 0.02 mmol) in TFA/$Et_3SiH$ (2 mL/2 mL) was stirred at 85° C. overnight. The reaction mixture was concentrated to give the residue, which was purified by prep-HPLC to give the target compound (5 mg). $^1H$ NMR (400 MHz, DMSO-d6) δ 8.70 (br.s, 2H), 8.10 (d, J=1.7 Hz, 1H), 7.85 (br.s, 2H), 7.50 (s, 1H), 7.31 (s, 1H), 7.00-6.92 (m, 1H), 4.66-4.55 (m, 1H), 4.03 (s, 2H), 3.26-3.15 (m, 8H), 2.19 (s, 3H), 1.83-1.54 (m, 2H), 1.49-1.26 (m, 2H), 0.85 (t, J=7.2 Hz, 3H) ppm. MS: M/e 464 $(M+1)^+$.

Compound B228: (S)-3-((4-amino-7-((5-methyl-6-(4-((methylamino)methyl)piperidin-1-yl)pyridin-3-yl)methyl)imidazo[2,1-f][1,2,4]triazin-2-yl)amino)hexan-1-ol Step A: tert-butyl ((1-(5-((4-(bis(4-methoxybenzyl)amino)-2-((1-((tert-butyldimethylsilyl)oxy)hexan-3-yl)oxy)imidazo[2,1-f][1,2,4]triazin-7-yl)methyl)-3-methylpyridin-2-yl)piperidin-4-yl)methyl)(methyl)carbamate To a stirred solution of (S)—N2-(1-((tert-butyldimethylsilyl)oxy)hexan-3-yl)-N4,N4-bis(4-methoxybenzyl)imidazo

[2,1-f][1,2,4]triazine-2,4-diamine (342 mg, 0.5 mmol) in THF (10 mL) was added dropwise n-BuLi (1.6 M, 0.63 mL, 1 mL) at −78° C. After stirred for 30 min, a solution of tert-butyl ((1-(5-formyl-3-methylpyridin-2-yl)piperidin-4-yl)methyl)(methyl)carbamate (208 mg, 0.6 mmol) in THF (3 mL) was added dropwise at −78° C. After the addition, the reaction was stirred overnight. The reaction was quenched with aq.$NH_4Cl$, extracted with EtOAc (10 mL×2). The combined organic layers were washed with brine, dried over $Na_2SO_4$, concentrated and purified by column chromatography (petroleum ether/EtOAc=5:1~2:1) to give the target compound (180 mg, 37.8%). MS: M/e 952 $(M+1)^+$.

Step B: (S)-3-((4-amino-7-((5-methyl-6-(4-((methylamino)methyl)piperidin-1-yl)pyridin-3-yl)methyl)imidazo[2,1-f][1,2,4]triazin-2-yl)amino)hexan-1-ol A mixture of the product of step A (180 mg, 0.189 mmol) in TFA/$Et_3SiH$ (3 mL/3 mL) was stirred at 90° C. overnight. The reaction mixture was concentrated to give the residue, which was dissolved in MeOH (5 mL), aq.NaOH (2.0 M, 2 mL) was added and stirred overnight. Most MeOH was removed to give the aqueous layer and extracted with EtOAc (10 mL×3). The combined organic layers were washed with brine, dried over $Na_2SO_4$, concentrated to give the residue, which was purified by prep-TLC ($CH_2Cl_2$/MeOH (contained $NH_3$)=10:1) to give the target compound (15 mg). $^1H$ NMR (400 MHz, $CD_3OD$) δ 8.03 (d, J=2.0 Hz, 1H), 7.50 (s, 1H), 7.20 (s, 1H), 4.07 (s, 2H), 3.98-3.90 (m, 1H), 3.69-3.59 (m, 2H), 3.44-3.38 (m, 2H), 2.97 (d, J=6.4 Hz, 2H), 2.79 (t, J=11.6 Hz, 2H), 2.73 (s, 3H), 2.25 (s, 3H), 1.89-1.82 (m, 3H), 1.82-1.63 (m, 2H), 1.55-1.45 (m, 3H), 1.44-1.31 (m, 2H), 0.88 (t, J=7.3 Hz, 3H) ppm. MS: M/e 482 $(M+1)^+$.

Compound B229: 3-((4-amino-7-((5-methyl-6-(4-((methylamino)methyl)piperidin-1-yl)pyridin-3-yl)methyl)imidazo[2,1-f][1,2,4]triazin-2-yl)oxy)hexan-1-ol Step A: tert-butyl ((1-(5-((4-(bis(4-methoxybenzyl)amino)-2-(((S)-1-((tert-butyldimethylsilyl)oxy)hexan-3-yl)amino)imidazo[2,1-f][1,2,4]triazin-7-yl)(hydroxy)methyl)-3-methylpyridin-2-yl)piperidin-4-yl)methyl)(methyl)carbamate To a stirred solution of 7-bromo-2-((1-((tert-butyldimethylsilyl)oxy)hexan-3-yl)oxy)-N,N-bis(4-methoxybenzyl)imidazo[2,1-f][1,2,4]triazin-4-amine (342 mg, 0.5 mmol) in dry THF (10 mL) was added dropwise n-BuLi (0.63 mL, 1 mmol) at −78° C. After stirred for 30 mins, a solution of tert-butyl ((1-(5-formyl-3-methylpyridin-2-yl)piperidin-4-yl)methyl)(methyl)carbamate (208 mg, 0.6 mmol) in THF (3 mL) was added dropwise. After the addition, the reaction was stirred for 2 hours. The reaction was quenched with aq.$NH_4Cl$, extracted with EtOAc (10 mL×2). The combined organic layers were washed with brine, dried over $Na_2SO_4$, concentrated and purified by column chromatography (petroleum ether/EtOAc=2:1) to give the target compound (180 mg, 37.8%). MS: M/e 953 $(M+1)^+$.

Step B: 3-((4-amino-7-((5-methyl-6-(4-((methylamino)methyl)piperidin-1-yl)pyridin-3-yl)methyl)imidazo[2,1-f][1,2,4]triazin-2-yl)oxy)hexan-1-ol A mixture of the product of step A (180 mg, 0.189 mmol) in TFA/$Et_3SiH$ (3 mL/3 mL) was stirred at 90° C. overnight. The reaction mixture was concentrated to give the residue, which was dissolved in MeOH (5 mL) and aq.NaOH (2.0 M, 2 mL) was added. Then the reaction mixture was stirred overnight. Most of MeOH was removed and the aqueous layer was extracted with EtOAc (20 mL×3). The combined organic layers were washed with brine, dried over $Na_2SO_4$, concentrated and purified by prep-TLC ($CH_2Cl_2$/MeOH ($NH_3$, 7.0 M)=10:1) to give crude product, which was further purified by prep-HPLC to give the target compound (15 mg). $^1H$ NMR (400 MHz, DMSO-d6) δ 8.34 (s, 2H), 8.16-8.02 (m, 3H), 7.58 (s, 1H), 7.36 (s, 1H), 5.12-4.98 (m, 1H), 4.08 (s, 2H), 3.57-3.33 (m, 4H), 2.87 (s, 2H), 2.75 (t, J=11.6 Hz, 2H), 2.62-2.56 (m, 3H), 2.20 (s, 3H), 1.86-1.72 (m, 5H), 1.65-1.56 (m, 2H), 1.43-1.27 (m, 4H), 0.86 (t, J=7.2 Hz, 3H) ppm. MS: M/e 483 $(M+1)^+$.

Compound B230: (S)-1-(4-(5-((4-amino-2-(hexan-3-yloxy)imidazo[2,1-f][1,2,4]triazin-7-yl)methyl)-3-methylpyridin-2-yl)piperazin-1-yl)-2-(methylamino)ethan-1-one Step A: tert-butyl (S)-(2-(4-(5-((4-amino-2-(hexan-3-yloxy)imidazo[2,1-f][1,2,4]triazin-7-yl)methyl)-3-methylpyridin-2-yl)piperazin-1-yl)-2-oxoethyl)(methyl)carbamate N-(tert-butoxycarbonyl)-N-methylglycine (25 mg, 0.13 mmol) were dissolved in DMF (1 ml) followed by addition of HATU (54 mg, 0.14 mmol) and DIPEA (23 mg, 0.18 mmol). The mixture was stirred for 1 h and then (S)-2-(hexan-3-yloxy)-7-((5-methyl-6-(piperazin-1-yl)pyridin-3-yl)methyl)imidazo[2,1-f][1,2,4]triazin-4-amine (50 mg, 0.12 mmol) was added. The reaction was stirred and monitored by TLC. After 16 h the mixture was diluted with EA and washed with water and brine. The organic layer was dried over magnesium sulfate and the solvent was removed under reduced pressure to give the crude product (70 mg, Yield 75%). MS: m/e 596 $(M+1)^+$.

Step B: (S)-1-(4-(5-((4-amino-2-(hexan-3-yloxy)imidazo[2,1-f][1,2,4]triazin-7-yl)methyl)-3-methylpyridin-2-yl)piperazin-1-yl)-2-(methylamino)ethan-1-one TFA (1 ml) was added to a solution of tert-butyl (S)-(2-(4-(5-((4-amino-2-(hexan-3-yloxy)imidazo[2,1-f][1,2,4]triazin-7-yl)methyl)-3-methylpyridin-2-yl)piperazin-1-yl)-2-oxoethyl)(methyl)carbamate (70 mg, crude) in DCM (3 mL). The mixture was stirred at rt for 2 h. then concentrated under reduced pressure. The crude product was purified by prep-HPLC to give the desired products (26 mg, Yield 44%). $^1H$ NMR (400 MHz, DMSO-d6) δ 8.11 (s, 1H), 8.07 (s, 1H), 7.99 (s, 1H), 7.43 (d, J=1.7 Hz, 1H), 7.33 (s, 1H), 4.90-4.84 (m, 1H), 4.05 (s, 2H), 3.58-3.52 (m, 4H), 2.99-2.94 (m, 4H), 2.27 (s, 3H), 2.20 (s, 3H), 1.71-1.49 (m, 4H), 1.41-1.17 (m, 2H), 0.87-0.71 (m, 6H) ppm. MS: m/e 496 $(M+1)^+$.

Compound B231: (S)-1-(4-(5-((4-amino-2-(pentan-2-ylamino)imidazo[2,1-f][1,2,4]triazin-7-yl)methyl)-3-methylpyridin-2-yl)piperazin-1-yl)-2-(methylamino)ethan-1-one Step A: tert-butyl (S)-(2-(4-(5-((4-amino-2-(pentan-2-ylamino)imidazo[2,1-f][1,2,4]triazin-7-yl)methyl)-3-methylpyridin-2-yl)piperazin-1-yl)-2-oxoethyl)(methyl)carbamate To a mixture of N-(tert-butoxycarbonyl)-N-methylglycine (945 mg, 5 mmol) and DIEA (1.54 g, 6 mmol) in DMF (10 mL) was added HATU (1.9 g, 5 mmol). After 30 min, a solution of (S)-7-((5-methyl-6-(piperazin-1-yl)pyridin-3-yl)methyl)-N2-(pentan-2-yl)imidazo[2,1-f][1,2,4]triazine-2,4-diamine (2.04 g, 5 mmol) in DMF (5 mL) was added. The reaction was stirred at room temperature overnight. The reaction was diluted with water, extracted with EA (100 mL×2), washed with brine, dried over $Na_2SO_4$, filtered, and concentrated. The residue was purified by combi flash to give the target compound (2.3 g, 80%). MS: M/e 581 $(M+1)^+$.

Step B: (S)-1-(4-(5-((4-amino-2-(pentan-2-ylamino)imidazo[2,1-f][1,2,4]triazin-7-yl)methyl)-3-methylpyridin-2-yl)piperazin-1-yl)-2-(methylamino)ethan-1-one To a mixture of the product of the step A (2.23 g, 3.84 mmol) in DCM/MeOH (20 mL/5 mL) was added a solution of 4 M HCl in dioxane (10 mL). The reaction was stirred at room temperature overnight. The mixture was concentrated. The residue was diluted with water, basified with saturated $NaHCO_3$ solution to pH=8, extracted with DCM (60 mL×3), washed with brine, dried over $Na_2SO_4$, filtered, and concentrated. The residue was purified by combi-flash to give the target compound (1.3 g, 70%). $^1H$ NMR (400 MHz, DMSO-$d_6$) δ 8.07 (d, J=2.0 Hz, 1H), 7.49 (br.s, 2H), 7.45 (d, J=2.0 Hz, 1H), 7.15 (s, 1H), 6.00 (d, J=8.4 Hz, 1H), 3.98 (s, 2H), 3.89-3.75 (m, 1H), 3.65-3.46 (m, 4H), 3.33 (s, 2H), 3.03-2.90 (m, 4H), 2.27 (s, 3H), 2.20 (s, 3H), 1.64-1.45 (m, 1H), 1.42-1.24 (m, 3H), 1.09 (d, J=6.4 Hz, 3H), 0.85 (t, J=7.2 Hz, 3H) ppm. MS: M/e 481 $(M+1)^+$.

Compound B232: 2-((4-amino-7-((5-methyl-6-(4-((methylamino)methyl)piperidin-1-yl)pyridin-3-yl)methyl)imidazo[2,1-f][1,2,4]triazin-2-yl)amino)pentan-1-ol Step A: N2-(1-((tert-butyldimethylsilyl)oxy)pentan-2-yl)-N4,N4-bis(4-methoxybenzyl) imidazo [2,1-f][1,2,4]triazine-2,4-diamine TBS-Cl (132 mg, 0.88 mmol) was added to a mixture of 2-((4-(bis(4-methoxybenzyl)amino)imidazo[2,1-f][1,2,4]triazin-2-yl)amino)pentan-1-ol (350 mg, 0.73 mmol), DMAP (9 mg, 0.073 mmol), and imidazole (100 mg, 1.47 mmol) in anhydrous $CH_2Cl_2$ (10 mL) at rt and stirred overnight. The reaction mixture was diluted with water and extracted with $CH_2Cl_2$. The combined organic layers were washed with saturated aqueous NaCl, dried over $Na_2SO_4$, and concentrated. The crude material was purified by column chromatography on silica gel (EA/PE, 1:2) to give the product as yellow oil (220 mg, Yield 43%). MS: m/e 591 $(M+1)^+$.

Step B: tert-butyl ((1-(5-((4-(bis(4-methoxybenzyl)amino)-2-((1-((tert-butyldimethylsilyl) oxy)pentan-2-yl)amino)imidazo[2,1-f][1,2,4]triazin-7-yl)(hydroxy)methyl)-3-methylpyridin-2-yl)piperidin-4-yl)methyl)(methyl)carbamate Under argon, n-BuLi (0.44 ml, 0.7 mmol, 1.6M) was added to a solution of N2-(1-((tert-butyldimethylsilyl)oxy)pentan-2-yl)-N4,N4-bis(4-methoxybenzyl)imidazo [2,1-f][1,2,4]triazine-2,4-diamine (220 mg, 0.38 mmol) in anhydrous THF (3 mL). The reaction mixture was stirred at −78° C. for 20 minutes, then tert-butyl ((1-(5-formyl-3-methylpyridin-2-yl)piperidin-4-yl)methyl)(methyl)carbamate (197 mg, 0.57 mmol) was added and the resulting mixture was stirred 4 h at rt. An aqueous ammonium chloride solution was added and the mixture was extracted with diethyl ether and ethyl acetate. The combined organic layers were dried over sodium sulfate, filtered and evaporated. Purification by prep-TLC (silica gel, EA:PE=1:1) afforded desired products (170 mg, Yield 48%). MS: m/e 938 $(M+1)^+$.

Step C: 2-((4-amino-7-((5-methyl-6-(4-((methylamino)methyl)piperidin-1-yl)pyridin-3-yl)methyl)imidazo[2,1-f][1,2,4]triazin-2-yl)amino)pentan-1-ol The product of step B (180 mg, 0.19 mmol) was dissolved in TFA (2 ml) followed by addition $Et_3SiH$ (2 ml). The mixture was stirred at 80° C. for 3 h. and cooled to room temperature, concentrated under reduced pressure. Another TFA (3 ml) was added and the mixture was stirred at 80° C. for 3 h. The mixture was cooled to room temperature, and concentrated under reduced pressure. The crude product was purified by prep-HPLC to give the desired products (9 mg, Yield 10%). $^1H$ NMR (400 MHz, DMSO-d6) δ 8.05 (d, J=2.0 Hz, 1H), 7.50 (br.s, 2H), 7.41 (d, J=1.8 Hz, 1H), 7.14 (s, 1H), 5.77 (d, J=8.7 Hz, 1H), 4.58 (br.s, 1H), 3.96 (s, 2H), 3.81-3.75 (m, 1H), 3.48-3.42 (m, 1H), 3.36-3.24 (m, 3H), 2.61 (t, J=11.4 Hz, 2H), 2.37 (d, J=6.6 Hz, 2H), 2.27 (s, 3H), 2.16 (s, 3H), 1.75 (d, J=10.7 Hz, 2H), 1.65-1.15 (m, 7H), 0.86 (t, J=7.3 Hz, 3H) ppm. MS: m/e 468 $(M+1)^+$.

Compound B233: 2-((S)-4-(5-((4-amino-2-(((S)-pentan-2-yl)amino)imidazo[2,1-f][1,2,4]triazin-7-yl)methyl)-3-methylpyridin-2-yl)piperazin-2-yl)acetonitrile Step A: benzyl (S)-2-(cyanomethyl)-4-(5-formyl-3-methylpyridin-2-yl)piperazine-1-carboxylate A mixture of 6-chloro-5-methylnicotinaldehyde (400 mg, 2.57 mmol), benzyl (S)-2-(cyanomethyl)piperazine-1-carboxylate hydrochloride (760 mg, 2.57 mmol) and DIEA (1000 mg, 7.75 mmol) in DMSO (10 ml) and $H_2O$ (one drop) was stirred at 110° C. under $N_2$ for 4 hr. After completed, the mixture was poured into water and then extracted with EA (30 ml) twice. The organic layer was washed with water, dried and concentrated under reduced pressure. The resulting residue was purified by flash column chromatography with 10%~60% EA in PE to afford product (800 mg, 82%) as a yellow oil. MS: M/e 379 $(M+1)^+$.

Step B: benzyl (2S)-4-(5-((4-(bis(4-methoxybenzyl)amino)-2-(((S)-pentan-2-yl)amino)imidazo[2,1-f][1,2,4]triazin-7-yl)(hydroxy)methyl)-3-methylpyridin-2-yl)-2-(cyanomethyl)piperazine-1-carboxylate To a stirred solution of (S)—N4,N4-bis(4-methoxybenzyl)-N2-(pentan-2-yl)imidazo[2,1-f][1,2,4]triazine-2,4-diamine (0.32 g, 0.70 mmol) in THF (15 ml) at −78° C. under $N_2$, was added n-BuLi (1.6M, 1.1 ml, 1.76 mmol) dropwise. The solution was stirred at −78° C. for 30 min. A solution of benzyl (S)-2-(cyanomethyl)-4-(5-formyl-3-methylpyridin-2-yl)piperazine-1-carboxylate (400 mg, 1.06 mmol) in THF (2 ml) was added at −78° C. dropwise. The resulting solution was warmed to r.t naturally and then stirred at r.t for 1 h. After completed, the solution was quenched with $H_2O$ (20 ml) and then extracted with DCM (25 ml×2). The organic phase was washed with $H_2O$ (10 ml), dried and concentrated under reduced pressure. The resulting residue was purified by flash column chromatography with 0~10% MeOH in DCM to afford product (500 mg, crude). MS: M/e 839 $(M+1)^+$.

Step C: 2-((S)-4-(5-((4-amino-2-(((S)-pentan-2-yl) amino)imidazo[2,1-f][1,2,4]triazin-7-yl)methyl)-3-methylpyridin-2-yl)piperazin-2-yl)acetonitrile A mixture of benzyl (2S)-4-(5-((4-(bis(4-methoxybenzyl) amino)-2-(((S)-pentan-2-yl)amino)imidazo[2,1-f][1,2,4]triazin-7-yl)(hydroxy)methyl)-3-methylpyridin-2-yl)-2-(cyanomethyl)piperazine-1-carboxylate (500 mg, crude), TFA (10 ml) and triethylsilane (2 ml) was stirred at 80° C. overnight. After completed, the reaction mixture was concentrated under reduced pressure to remove TFA. The residue was diluted with EA (30 ml) and then washed with aq.$NaHCO_3$ (sat., 15 ml) twice. The organic phase was dried over $Na_2SO_4$ and concentrated under reduced pressure. The residue was purified by prep-TLC and then prep-HPLC to afford product (5.65 mg); $^1H$ NMR (400 MHz, $CD_3OD$) δ 8.18 (s, 1H), 7.71-7.55 (m, 2H), 4.19 (s, 2H), 3.90 (d, J=8 Hz, 2H), 3.71-3.33 (m, 7H), 3.22-2.63 (m, 6H), 2.30 (s, 3H), 1.50-1.33 (m, 3H), 1.18-1.14 (m, 4H), 0.91 (t, J=8.0 Hz, 3H) ppm. MS: M/e 449 $(M+1)^+$.

Compound B234: 7-((6-(4-((isobutylamino)methyl) piperidin-1-yl)-5-methylpyridin-3-yl)methyl)-2-(pentan-2-yloxy)imidazo[2,1-f][1,2,4]triazin-4-amine Step A: benzyl 4-((isobutylamino)methyl)piperidine-1-carboxylate A mixture of benzyl 4-formylpiperidine-1-carboxylate (1 g, 4.05 mmol), 2-methylpropan-1-amine (443 g, 6.07 mmol) and sodium triacetoxyborohydride (1.72 g, 8.09 mmol) in DCM (10 mL) was stirred at r.t. for 2 h. The mixture was quenched with saturated sodium bicarbonate solution (10 mL), extracted with DCM (30 mL×3). The combined organic layers were washed with brine, dried over $Na_2SO_4$, concentrated to give benzyl 4-((isobutylamino)methyl)piperidine-1-carboxylate (1.13 g, 91.81%) as colorless oil. MS: M/e 305 $(M+1)^+$.

Step B: benzyl 4-(((tert-butoxycarbonyl)(isobutyl) amino)methyl)piperidine-1-carboxylate A mixture of benzyl 4-((isobutylamino)methyl)piperidine-1-carboxylate (1 g, 3.29 mmol), di-tert-butyl dicarbonate (1.08 g, 4.93 mmol) and DIPEA (848 mg, 6.58 mmol) in DCM (10 mL) was stirred at r.t. for 2 h. The mixture was quenched with water (10 mL), extracted with DCM (30 mL×3). The combined organic layers were washed with water and brine, dried over $Na_2SO_4$, concentrated to give the title product (1.25 g, 94.06%) as yellow oil. MS: M/e 405 $(M+1)^+$.

Step C: tert-butyl isobutyl(piperidin-4-ylmethyl)carbamate

A mixture of benzyl 4-(((tert-butoxycarbonyl)(isobutyl) amino)methyl)piperidine-1-carboxylate (1.25 g, 3.09 mmol) and palladium on active carbon (300 mg, 10%) in MeOH (10 mL) was stirred under $H_2$ atmosphere (1 atm) at r.t. for 2 h. The mixture was filtered and concentrated to give tert-butyl isobutyl(piperidin-4-ylmethyl)carbamate (0.79 g, 94.80%) as yellow oil. MS: M/e 271 $(M+1)^+$.

Step D: tert-butyl ((1-(5-formyl-3-methylpyridin-2-yl)piperidin-4-yl)methyl)(isobutyl)carbamate A mixture of 6-chloro-5-methylnicotinaldehyde (400 mg, 2.56 mmol), tert-butyl isobutyl(piperidin-4-ylmethyl)carbamate (692 mg, 2.56 mmol) and DIPEA (0.99 g, 7.69 mmol) in DMSO (10 mL) was stirred at 100° C. overnight. The mixture was diluted with water and extracted with DCM (30 mL×3). The combined organic layers were washed with brine, dried over $Na_2SO_4$, concentrated and purified by column chromatography (DCM/MeOH=20:1~5:1) to give the title product (0.82 g, 82.21%) as yellow oil. MS: M/e 390 $(M+1)^+$.

Step E: tert-butyl ((1-(5-((4-(bis(4-methoxybenzyl) amino)-2-(pentan-2-yloxy)imidazo[2,1-f][1,2,4]triazin-7-yl)(hydroxy)methyl)-3-methylpyridin-2-yl) piperidin-4-yl)methyl)(isobutyl)carbamate To a solution of N,N-bis(4-methoxybenzyl)-2-(pentan-2-yloxy)imidazo[2,1-f][1,2,4]triazin-4-amine (200 mg, 0.43 mmol) in THF (5 mL), n-Butyllithium (0.41 ml, 0.65 mmol) was added dropwise at −78° C. and stirred for 1 h. Then a solution of tert-butyl ((1-(5-formyl-3-methylpyridin-2-yl) piperidin-4-yl)methyl)(isobutyl)carbamate (202 mg, 0.52 mmol) in THF (2 mL) was added dropwise at −78° C., after addition, the mixture was warmed to r.t. and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give the product (240 mg, 65.01%) as yellow oil. MS: M/e 852 $(M+1)^+$.

Step F: 7-((6-(4-((isobutylamino)methyl)piperidin-1-yl)-5-methylpyridin-3-yl)methyl)-2-(pentan-2-yloxy)imidazo[2,1-f][1,2,4]triazin-4-amine A mixture of tert-butyl ((1-(5-((4-(bis(4-methoxybenzyl) amino)-2-(pentan-2-yloxy)imidazo[2,1-f][1,2,4]triazin-7-yl)(hydroxy)methyl)-3-methylpyridin-2-yl)piperidin-4-yl) methyl)(isobutyl)carbamate (240 mg, 0.28 mmol) and triethylsilane (1 mL) in TFA (2 mL) was stirred at 90° C. overnight. The mixture was concentrated and purified with prep-HPLC to give the title product (89 mg, 63.8%). $^1H$ NMR (400 MHz, DMSO-d6) δ 8.11 (br.s, 3H), 8.05 (s, 1H), 8.00 (s, 1H), 7.42 (s, 1H), 7.32 (s, 1H), 4.96 (dd, J=12.2, 6.2 Hz, 1H), 4.04 (s, 2H), 3.35 (d, J=12.5 Hz, 3H), 2.90-2.85 (m, 2H), 2.81-2.74 (m, 2H), 2.69-2.64 (m, 2H), 2.17 (s, 3H), 1.97 (dt, J=13.5, 6.8 Hz, 1H), 1.82 (d, J=10.4 Hz, 3H), 1.66-1.59 (m, 1H), 1.55-1.48 (m, 1H), 1.40-1.28 (m, 4H), 1.25 (d, J=6.1 Hz, 3H), 0.96 (s, 3H), 0.94 (s, 3H), 0.88 (t, J=7.3 Hz, 3H) ppm. MS: M/e 495 $(M+1)^+$.

Compound B235: 2-((4-amino-7-((5-methyl-6-(4-((methylamino)methyl)piperidin-1-yl)pyridin-3-yl) methyl)imidazo[2,1-f][1,2,4]triazin-2-yl)oxy)pentan-1-ol Step A: 7-bromo-2-((1-((tert-butyldimethylsilyl)oxy) pentan-2-yl)oxy)-N,N-bis(4-methoxybenzyl)imidazo [2,1-f][1,2,4]triazin-4-amine and 7-bromo-2-((2-((tert-butyldimethylsilyl)oxy)pentyl)oxy)-N,N-bis(4-methoxybenzyl)imidazo[2,1-f][1,2,4]triazin-4-amine To a solution of 1-((tert-butyldimethylsilyl)oxy)pentan-2-ol (336 mg, 1.5 mmol) in THF (5 mL) was added NaH (60%, 82 mg, 2 mmol) at 0 degrees. The reaction mixture was stirred at room temperature for 20 minutes, then 7-bromo-2-chloro-N,N-bis(4-methoxybenzyl)imidazo[2,1-f][1,2,4]triazin-4-amine (500 mg, 1.02 mmol) was added and the resulting mixture was stirred overnight at 70° C. An aqueous ammonium chloride solution was added and the mixture was extracted with ethyl acetate. The combined organic extracts were dried over sodium sulfate, filtered and evaporated. Purification by prep-TLC (silica gel, EA:PE=1:10-1:1) afforded 260 mg (38%) 7-bromo-2-((1-((tert-butyldimethylsilyl)oxy)pentan-2-yl)oxy)-N,N-bis(4-methoxybenzyl)imidazo[2,1-f][1,2,4]triazin-4-amine and 7-bromo-2-((2-((tert-butyldimethylsilyl)oxy)pentyl)oxy)-N,N-bis(4-methoxybenzyl)imidazo[2,1-f][1,2,4]triazin-4-amine. MS: m/e 670 $(M+1)^+$.

Step B: tert-butyl ((1-(5-((4-(bis(4-methoxybenzyl)amino)-2-((1-((tert-butyldimethylsilyl)oxy)pentan-2-yl)oxy)imidazo[2,1-f][1,2,4]triazin-7-yl)(hydroxy)methyl)-3-methylpyridin-2-yl)piperidin-4-yl)methyl)(methyl)carbamate and tert-butyl ((1-(5-((4-(bis(4-methoxybenzyl)amino)-2-((2-((tert-butyldimethylsilyl)oxy)pentyl)oxy)imidazo[2,1-f][1,2,4]triazin-7-yl)(hydroxy)methyl)-3-methylpyridin-2-yl)piperidin-4-yl)methyl)(methyl)carbamate Under argon, n-BuLi (1.6M, 0.51 ml, 0.81 mmol) was added to a solution of the mixture of 2-((1-((tert-butyldimethylsilyl)oxy)pentan-2-yl)oxy)-N,N-bis(4-methoxybenzyl)imidazo[2,1-f][1,2,4]triazin-4-amine and (160 mg, 0.27 mmol) in anhydrous THF (3 mL). The reaction mixture was stirred at −78° C. for 20 minutes, then tert-butyl ((1-(5-formyl-3-methylpyridin-2-yl)piperidin-4-yl)methyl)(methyl)carbamate (141 mg, 0.40 mmol) was added at −78° C. and the resulting mixture was stirred 2 h at rt. An aqueous ammonium chloride solution was added and the mixture was extracted with diethyl ether and ethyl acetate. The combined organic extracts were dried over sodium sulfate, filtered and evaporated. Purification by prep-TLC (silica gel, EA:PE=1:1) afforded desired products (80 mg). Yield 31%. MS: m/e 939 $(M+1)^+$.

Step C: 2-((4-amino-7-((5-methyl-6-(4-((methylamino)methyl)piperidin-1-yl)pyridin-3-yl)methyl)imidazo[2,1-f][1,2,4]triazin-2-yl)oxy)pentan-1-ol and 1-((4-amino-7-((5-methyl-6-(4-((methylamino)methyl)piperidin-1-yl)pyridin-3-yl)methyl)imidazo[2,1-f][1,2,4]triazin-2-yl)oxy)pentan-2-ol The product of step B (80 mg) was dissolved in TFA (1 ml) followed by addition $Et_3SiH$ (1 ml). The mixture was stirred at 80° C. for 2 h. The mixture was cooled to room temperature, and concentrated under reduced pressure. Another TFA (1 ml) was added and the mixture was stirred at 80° C. for 3 h. The mixture was cooled to room temperature, and concentrated under reduced pressure. The crude product was purified by prep-HPLC to give the desired products Compound B235 (3 mg) and Compound B236 (3 mg). MS: m/e 469 $(M+1)^+$. Yield 7.5%. TH NMR (400 MHz, $CD_3OD$) δ 8.01 (s, 1H), 7.96 (s, 1H), 7.47 (s, 1H), 5.04 (d, J=5.5 Hz, 1H), 4.25 (s, 2H), 3.69 (dd, J=14.4, 9.0 Hz, 4H), 3.16-3.07 (m, 2H), 3.01 (t, J=7.0 Hz, 2H), 2.75 (d, J=4.4 Hz, 3H), 2.37 (s, 3H), 2.01 (dd, J=8.0, 4.7 Hz, 1H), 1.95 (d, J=12.7 Hz, 2H), 1.73-1.63 (m, 2H), 1.53 (dt, J=17.4, 5.8 Hz, 2H), 1.45-1.31 (m, 2H), 0.98-0.87 (m, 3H) ppm; MS: m/e 469 $(M+1)^+$.

Compound B236: 1-((4-amino-7-((5-methyl-6-(4-((methylamino)methyl)piperidin-1-yl)pyridin-3-yl)methyl)imidazo[2,1-f][1,2,4]triazin-2-yl)oxy)pentan-2-ol The target product Compound 236 and Compound B235 can be obtained by pre-HLPC. $^1$H NMR (400 MHz, DMSO-d6) δ 8.33 (s, 2H), 8.17 (s, 1H), 8.11-8.03 (m, 2H), 7.53 (s, 1H), 7.33 (s, 1H), 4.07 (d, J=5.3 Hz, 4H), 3.77 (s, 1H), 3.39 (d, J=12.0 Hz, 2H), 2.87 (d, J=5.9 Hz, 2H), 2.71 (t, J=12.4 Hz, 2H), 2.58 (t, J=5.3 Hz, 3H), 2.20 (s, 3H), 1.78 (d, J=9.7 Hz, 3H), 1.53-1.23 (m, 6H), 0.89 (t, J=6.4 Hz, 3H) ppm. MS: m/e 469 $(M+1)^+$.

Compound B237: 7-((6-(4-(((2-methoxyethyl)amino)methyl)piperidin-1-yl)-5-methylpyridin-3-yl)methyl)-2-(pentan-2-yloxy)imidazo[2,1-f][1,2,4]triazin-4-amine Step A: benzyl 4-(((2-methoxyethyl)amino)methyl)piperidine-1-carboxylate A mixture of benzyl 4-formylpiperidine-1-carboxylate (1 g, 4.05 mmol), 2-methoxyethan-1-amine (455 g, 6.07 mmol) and sodium triacetoxyborohydride (1.72 g, 8.09 mmol) in DCM (10 mL) was stirred at r.t. for 2 h. The mixture was quenched with saturated sodium bicarbonate solution (10 mL), extracted with DCM (30 mL×3). The combined organic layers were washed with brine, dried over $Na_2SO_4$, concentrated to give desired product (1.15 g, 92.83%). MS: M/e 307 $(M+1)^+$.

Step B: benzyl 4-(((tert-butoxycarbonyl)(2-methoxyethyl)amino)methyl)piperidine-1-carboxylate A mixture of benzyl 4-(((2-methoxyethyl)amino)methyl)piperidine-1-carboxylate (1 g, 3.29 mmol), di-tert-butyl dicarbonate (1.07 g, 4.90 mmol) and DIPEA (843 mg, 6.53 mmol) in DCM (10 mL) was stirred at r.t. for 2 h. The mixture was quenched with water (10 mL), extracted with DCM (30 mL×3). The combined organic layers were washed with water and brine, dried over $Na_2SO_4$, concentrated to give the product (1.22 g, 91.95%). MS: M/e 407 $(M+1)^+$.

Step C: tert-butyl (2-methoxyethyl)(piperidin-4-ylmethyl)carbamate

A mixture of benzyl 4-(((tert-butoxycarbonyl)(2-methoxyethyl)amino)methyl)piperidine-1-carboxylate (1.22 g, 3.00 mmol) and palladium on active carbon (300 mg, 10%) in MeOH (10 mL) was stirred under $H_2$ atmosphere (1 atm) at r.t. for 2 h. The mixture was filtered and concentrated to give tert-butyl (2-methoxyethyl)(piperidin-4-ylmethyl)carbamate (0.68 g, 83.20%) as yellow oil. MS: M/e 273 $(M+1)^+$.

Step D: tert-butyl ((1-(5-formyl-3-methylpyridin-2-yl)piperidin-4-yl)methyl)(2-methoxyethyl)carbamate A mixture of 6-chloro-5-methylnicotinaldehyde (400 mg, 2.56 mmol), tert-butyl isobutyl(piperidin-4-ylmethyl)carbamate (697 mg, 2.56 mmol) and DIPEA (0.99 g, 7.69 mmol) in DMSO (10 mL) was stirred at 100° C. overnight. The mixture was diluted with water and extracted with DCM (30 mL×3). The combined organic layers were washed with brine, dried over $Na_2SO_4$, concentrated and purified by column chromatography (DCM/MeOH=20:1~5:1) to give the product (0.79 g, 78.80%). MS: M/e 392 $(M+1)^+$.

Step E: tert-butyl ((1-(5-((4-(bis(4-methoxybenzyl)amino)-2-(pentan-2-yloxy)imidazo[2,1-f][1,2,4]triazin-7-yl)(hydroxy)methyl)-3-methylpyridin-2-yl)piperidin-4-yl)methyl)(2-methoxyethyl)carbamate To a solution of N,N-bis(4-methoxybenzyl)-2-(pentan-2-yloxy)imidazo[2,1-f][1,2,4]triazin-4-amine (200 mg, 0.43 mmol) in THF (5 mL), n-Butyllithium (0.41 ml, 0.65 mmol) was added dropwise at −78° C. and stirred for 1 h. Then a solution of tert-butyl ((1-(5-formyl-3-methylpyridin-2-yl)piperidin-4-yl)methyl)(2-methoxyethyl)carbamate (204 mg, 0.52 mmol) in THF (2 mL) was added dropwise at −78° C., after addition, the mixture was warmed to r.t. and stirred for 3 h. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1~5:1) to give tert-butyl ((1-(5-((4-(bis(4-methoxybenzyl)amino)-2-(pentan-2-yloxy)imidazo[2,1-f][1,2,4]triazin-7-yl)(hydroxy)methyl)-3-methylpyridin-2-yl)piperidin-4-yl)methyl)(2-methoxyethyl)carbamate (230 mg, 62.15%). MS: M/e 854 $(M+1)^+$.

Step F: 7-((6-(4-(((2-methoxyethyl)amino)methyl)piperidin-1-yl)-5-methylpyridin-3-yl)methyl)-2-(pentan-2-yloxy)imidazo[2,1-f][1,2,4]triazin-4-amine A mixture of tert-butyl ((1-(5-((4-(bis(4-methoxybenzyl)amino)-2-(pentan-2-yloxy)imidazo[2,1-f][1,2,4]triazin-7-yl)(hydroxy)methyl)-3-methylpyridin-2-yl)piperidin-4-yl)methyl)(2-methoxyethyl)carbamate (230 mg, 0.27 mmol) and triethylsilane (1 mL) in TFA (2 mL) was stirred at 90° C. overnight. The mixture was concentrated and purified with prep-HPLC to give the product (75 mg, 55.97%). $^1H$ NMR (400 MHz, DMSO-d6) δ 8.44 (br.s, 2H), 8.14 (s, 1H), 8.06 (s, 2H), 7.56 (s, 1H), 7.36 (s, 1H), 5.02-4.92 (m, 1H), 4.08 (s, 2H), 3.63-3.55 (m, 2H), 3.43 (s, 1H), 3.40 (s, 1H), 3.32 (s, 3H), 3.19-3.09 (m, 2H), 2.94-2.85 (m, 2H), 2.74 (t, J=11.9 Hz, 2H), 2.20 (s, 3H), 1.87-1.78 (m, 3H), 1.66-1.60 (m, 1H), 1.56-1.48 (m, 1H), 1.41-1.30 (m, 4H), 1.25 (d, J=6.1 Hz, 3H), 0.88 (t, J=7.3 Hz, 3H) ppm. MS: M/e 497 $(M+1)^+$.

Compound B238: 7-((2-fluoro-6-(piperidin-4-yl)pyridin-3-yl)methyl)-2-(pentan-2-yloxy)imidazo[2,1-f][1,2,4]triazin-4-amine Step A: tert-butyl 5-((4-(bis(4-methoxybenzyl)amino)-2-(pentan-2-yloxy)imidazo[2,1-f][1,2,4]triazin-7-yl)(hydroxy)methyl)-6-fluoro-3',6'-dihydro-[2,4'-bipyridine]-1'(2'H)-carboxylate To a stirred solution of N,N-bis(4-methoxybenzyl)-2-(pentan-2-yloxy)imidazo[2,1-f][1,2,4]triazin-4-amine (461 mg, 1 mmol) in dry THF (10 mL) was added dropwise n-BuLi (1.25 mL, 2 mmol) at −78° C. After stirred for half an hour, a solution of tert-butyl 6-fluoro-5-formyl-3',6'-dihydro-[2,4'-bipyridine]-1'(2'H)-carboxylate (367 mg, 1.2 mmol) in THF (3 mL) was added dropwise. After the addition, the reaction was stirred for 2 hours. The reaction was quenched with aq.$NH_4Cl$, extracted with EtOAc (10 mL×2). The combined organic layers were washed with brine, dried over $Na_2SO_4$, concentrated and purified by column chromatography (petroleum ether/EtOAc=10:1~3:1) to give the target compound (340 mg, 44.3%) as a light brown solid. MS: M/e 768 $(M+1)^+$.

Step B: tert-butyl 4-(5-((4-(bis(4-methoxybenzyl)amino)-2-(pentan-2-yloxy)imidazo[2,1-f][1,2,4]triazin-7-yl)(hydroxy)methyl)-6-fluoropyridin-2-yl)piperidine-1-carboxylate Pd/C (200 mg) was added to a stirred solution of the product of step A (340 mg, 0.443 mmol) in EtOAc (30 mL), and the mixture was stirred overnight under $H_2$ (1 atm). The reaction mixture was filtered and the filtrate was concentrated to give the target compound (342 mg, 100%) as a white solid. MS: M/e 770 $(M+1)^+$.

Step C: 7-((2-fluoro-6-(piperidin-4-yl)pyridin-3-yl)methyl)-2-(pentan-2-yloxy)imidazo[2,1-f][1,2,4]triazin-4-amine A mixture of the product of step A (342 mg, 0.442 mmol) in TFA/$Et_3SiH$ (3 mL/3 mL) was stirred at 85° C. overnight. The reaction mixture was concentrated to give the residue, which was purified by prep-HPLC to give the target compound as TFA salt, which was dissolved in $H_2O$ (10 mL) and basified to pH=10-12 with aq.$Na_2CO_3$, extracted with $CH_2Cl_2$ (20 mL), dried over $Na_2SO_4$, concentrated to give the target compound (30 mg). $^1H$ NMR (400 MHz, DMSO-$d_6$) δ 8.14 (s, 1H), 8.08 (s, 1H), 7.69-7.62 (m, 1H), 7.35 (s, 1H), 7.11 (d, J=7.6 Hz, 1H), 4.97-4.80 (m, 1H), 4.13 (s, 2H), 3.02 (d, J=12.0 Hz, 2H), 2.73-2.62 (m, 1H), 2.58 (t, J=12.4 Hz, 2H), 1.76-1.68 (m, 2H), 1.66-1.43 (m, 4H), 1.41-1.23 (m, 2H), 1.18 (d, J=6.0 Hz, 3H), 0.85 (t, J=7.2 Hz, 3H) ppm. MS: M/e 414 $(M+1)^+$.

Compound B239: (S)-7-((2-fluoro-6-(piperidin-4-yl)pyridin-3-yl)methyl)-2-(pentan-2-yloxy)imidazo[2,1-f][1,2,4]triazin-4-amine Step A: tert-butyl 5-((4-(bis(2,4-dimethoxybenzyl)amino)-2-(((S)-pentan-2-yl)oxy)imidazo[2,1-f][1,2,4]triazin-7-yl)(hydroxy)methyl)-6-fluoro-3',6'-dihydro-[2,4'-bipyridine]-1'(2'H)-carboxylate To a stirred solution of (S)—N-(2,4-dimethoxybenzyl)-N-(3,4-dimethoxybenzyl)-2-(pentan-2-yloxy)imidazo[2,1-f][1,2,4]triazin-4-amine (1.042 g, 2 mmol) in dry THF (20 mL) was added dropwise n-BuLi (2.5 mL, 4 mmol) at −78° C. After stirred for half an hour, a solution of tert-butyl 6-fluoro-5-formyl-3',6'-dihydro-[2,4'-bipyridine]-1'(2'H)-carboxylate (0.734 g, 2.4 mmol) in THF (5 mL) was added dropwise. After the addition, the reaction was stirred for 2 hours. The reaction was quenched with aq.$NH_4Cl$, extracted with EtOAc (20 mL×3). The combined organic layers were washed with brine, dried over $Na_2SO_4$, concentrated and purified by column chromatography (petroleum ether/EtOAc=5:1~2:1) to give the target compound (1.01 g, 61%) as a light yellow solid. MS: M/e 828 $(M+1)^+$.

Step B: tert-butyl 4-(5-((4-(bis(2,4-dimethoxybenzyl)amino)-2-(((S)-pentan-2-yl)oxy)imidazo[2,1-f][1,2,4]triazin-7-yl)(hydroxy)methyl)-6-fluoropyridin-2-yl)piperidine-1-carboxylate Pd/C (200 mg) was added to a stirred solution of the product of step A (1.01 g mg, 1.22 mmol) in EtOAc (20 mL), and the mixture was stirred overnight under $H_2$ (1 atm). The reaction mixture was filtered and the filtrate was concentrated to give the target compound (1.01 g, 100%) as a white solid. MS: M/e 830 $(M+1)^+$.

Step C: (4-amino-2-(((S)-pentan-2-yl)oxy)imidazo[2,1-f][1,2,4]triazin-7-yl)(2-fluoro-6-(piperidin-4-yl)pyridin-3-yl)methanol A mixture of the product of step B (1.01 g, 1.22 mmol) in TFA/$H_2O$ (9 mL/1 mL) was stirred at 40° C. overnight. The reaction mixture was concentrated to give the residue, which was treated with $H_2O$ (20 mL) and extracted with EtOAc (20 mL). The organic layer was discarded and the aqueous layer was basified to pH=13-14 with NaOH and extracted with $CH_2Cl_2$/IPA (3:1, 30 mL×3). The organic layers were washed with brine, dried over $Na_2SO_4$, concentrated to give the target compound (218 mg, 41.6%) as colorless syrup. MS: M/e 430 $(M+1)^+$.

Step D: (S)-7-((2-fluoro-6-(piperidin-4-yl)pyridin-3-yl)methyl)-2-(pentan-2-yloxy)imidazo[2,1-f][1,2,4]triazin-4-amine A mixture of the product of step C (218 mg, 0.51 mmol) in TFA/$Et_3SiH$ (3 mL/3 mL) was stirred at 70° C. overnight. The reaction mixture was concentrated to give the residue, which was purified by prep-HPLC to give the target compound (116 mg). $^1H$ NMR (400 MHz, DMSO-$d_6$) δ 8.58 (s, 1H), 8.27 (s, 1H), 8.15 (s, 1H), 8.05 (s, 1H), 7.77-7.67 (m, 1H), 7.39 (s, 1H), 7.16 (d, J=7.2 Hz, 1H), 4.96-4.85 (m, 1H), 4.15 (s, 2H), 3.36 (d, J=12.8 Hz, 2H), 3.08-2.90 (m, 4H), 2.05-1.74 (m, 4H), 1.69-1.43 (m, 2H), 1.43-1.25 (m, 2H), 1.18 (d, J=6.0 Hz, 3H), 0.85 (t, J=7.2 Hz, 3H) ppm. MS: M/e 414 $(M+1)^+$.

Compound B240: (S)-7-((5-methyl-6-(piperidin-4-yl)pyridin-3-yl)methyl)-N2-(pentan-2-yl)imidazo[2,1-f][1,2,4]triazine-2,4-diamine Step A: tert-butyl 5-formyl-3-methyl-3',6'-dihydro-[2,4'-bipyridine]-1'(2'H)-carboxylate A mixture of 6-chloro-5-methylnicotinaldehyde (750 mg, 5.0 mmol), tert-butyl 4-(4,4,5,5-tetramethyl-1,3,2-dioxaborolan-2-yl)-3,6-dihydropyridine-1(2H)-carboxylate (1.8 g, 6.0 mmol), $Pd(PPh_3)_4$ (300 mg, 0.25 mmol), and $K_2CO_3$ (1.4 g, 10 mmol) in Dioxane/$H_2O$ (12 mL/3 mL) was stirred at 100° C. under $N_2$ for 16 hrs. The mixture was diluted with 20 mL of EA, washed with brine (10 mL×3), dried over $Na_2SO_4$ and concentrated under reduced pressure. The residue was purified by column chromatography (PE/EA=3:1~1:1) to obtain the title compound (1.3 g, yield: 89%). MS: M/e 303 $(M+1)^+$.

Step B: tert-butyl 5-((4-(bis(2,4-dimethoxybenzyl)amino)-2-(((S)-pentan-2-yl)amino)imidazo[2,1-f][1,2,4]triazin-7-yl)(hydroxy)methyl)-3-methyl-3',6'-dihydro-[2,4'-bipyridine]-1'(2'H)-carboxylate To a solution of (S)—N4,N4-bis(2,4-dimethoxybenzyl)-N2-(pentan-2-yl)imidazo[2,1-f][1,2,4]triazine-2,4-diamine (260 mg, 0.5 mmol) in THF (2 mL) was added n-BuLi (1.6 M, 1.0 mL, 1.6 mmol) at −78° C. in $N_2$ atmosphere. The mixture was stirred at −78° C. for 30 min. Then the solution of the product of step A (450 mg, 1.5 mmol) in THF (4 mL) was added to the system at −78° C. The reaction was stirred for 30 min, and then warmed to room temperature and stirred for 16 hrs. The reaction was quenched with saturated $NH_4Cl$ (10 mL) at room temperature and extracted with EA (10 mL×3). The combined organic phase was washed with brine (10 mL×3), dried over $Na_2SO_4$ and concentrated under reduced pressure. The residue was purified by column chromatography to obtain the title compound (200 mg, yield: 49%). MS: M/e 823 $(M+1)^+$.

Step C: tert-butyl 4-(5-((4-(bis(2,4-dimethoxybenzyl)amino)-2-(((S)-pentan-2-yl)amino)imidazo[2,1-f][1,2,4]triazin-7-yl)(hydroxy)methyl)-3-methylpyridin-2-yl)piperidine-1-carboxylate A mixture of the product of step B (200 mg, 0.24 mmol) and Pd/C (wet, 170 mg) in MeOH (7 mL) was stirred under $H_2$ at rt for 7 hrs. The mixture was filtered and the filtrate was concentrated to obtain the title product (200 mg) as a white solid. MS: M/e 825 $(M+1)^+$.

Step D: (4-amino-2-(((S)-pentan-2-yl)amino)imidazo[2,1-f][1,2,4]triazin-7-yl)(5-methyl-6-(piperidin-4-yl)pyridin-3-yl)methanol tert-butyl 4-(5-((4-(bis(2,4-dimethoxybenzyl)amino)-2-(((S)-pentan-2-yl)amino)imidazo[2,1-f][1,2,4]triazin-7-yl)(hydroxy)methyl)-3-methylpyridin-2-yl)piperidine-1-carboxylate (180 mg, 0.21 mmol) in TFA/$H_2O$ (9:1, 10 mL) was stirred at rt for 16 hrs. The reaction was concentrated under reduced pressure. 10 mL $H_2O$ was added. The mixture was stirred at RT for 10 min then was filtered. The filtrate was extracted with DCM (10 mL×2) to remove the impurities. The aqueous layer was basified by aq.NaOH (4M) to pH>10, extracted with DCM/IPA (5:1, 10 mL×3). The combined extracts were washed with brine (20 mL×3), dried over $Na_2SO_4$ and concentrated to give the title product (45 mg, yield: 51%). MS: M/e 425 $(M+1)^+$.

Step E: (S)-7-((5-methyl-6-(piperidin-4-yl)pyridin-3-yl)methyl)-N2-(pentan-2-yl)imidazo[2,1-f][1,2,4]triazine-2,4-diamine A mixture of (4-amino-2-(((S)-pentan-2-yl)amino)imidazo[2,1-f][1,2,4]triazin-7-yl)(5-methyl-6-(piperidin-4-yl)pyridin-3-yl)methanol (45 mg, 0.11 mmol), TFA (3 mL) and $Et_3SiH$ (3 mL) was stirred at 70° C. for 16 hrs. Another TFA (3 mL) and $Et_3SiH$ (3 mL) were added and the resulted mixture was stirred at 70° C. for another 20 hrs. The reaction mixture was concentrated under reduced pressure. The residue was dissolved into $H_2O$ (10 mL) and extracted with DCM (5 mL×2). The organic phase was discarded. The inorganic phase was basified by aq.NaOH (4 M) to pH>10. The mixture was extracted with DCM/iPrOH (5:1, 5 mL×5). The combined organic phase was washed with brine (10 mL×2), dried over $Na_2SO_4$ and concentrated. The residue was purified by prep-TLC (DCM/MeOH($NH_3$)=8:1) to obtain the title compound (12 mg, yield: 28%). $^1H$ NMR (400 MHz, $CD_3OD$) δ 8.33 (s, 1H), 7.54 (s, 1H), 7.27 (s, 1H), 4.25-4.06 (m, 2H), 3.93-3.77 (m, 1H), 3.49 (d, J=12.8 Hz, 2H), 3.29-3.23 (m, 1H), 3.21-3.09 (m, 2H), 2.35 (s, 3H), 2.15-2.00 (m, 2H), 1.99-1.88 (m, 2H), 1.65-1.49 (m, 1H), 1.49-1.30 (m, 3H), 1.14 (d, J=6.4 Hz, 3H), 0.91 (t, J=7.2 Hz, 3H) ppm. MS: M/e 409 $(M+1)^+$.

Compound B241: (S)-7-((5-methoxy-6-(piperazin-1-yl)pyridin-3-yl)methyl)-2-(pentan-2-yloxy)imidazo[2,1-f][1,2,4]triazin-4-amine Step A: 6-chloro-5-methoxynicotinaldehyde To a solution of 5-bromo-2-chloro-3-methoxypyridine (3 g, 13.51 mmol) in THF (100 mL) was added n-BuLi (9.3 mL, 14.88 mmol) under $N_2$ at −78° C. After stirring for 0.5 h at −78° C., morpholine-4-carbaldehyde (1.7 g, 14.78 mmol) was added. The reaction mixture was warmed to 25° C. and stirred for 2.5 h. After completed, the reaction mixture was quenched with aq $NH_4Cl$ (50 mL) and extracted with DCM (3×50 mL). The combined organic layers was dried over $Na_2SO_4$ and concentrated under vacuum to get a residue. The residue was purified by column chromatography on silica gel eluting with ethyl acetate in petroleum ether (40%) to afford the title compound (500 mg, 22%). $^1H$ NMR (400 MHz, $CDCl_3$) δ 10.08 (s, 1H), 8.45 (s, 1H), 7.63 (s, 1H), 4.00 (s, 3H) ppm.

Step B: tert-butyl 4-(5-formyl-3-methoxypyridin-2-yl)piperazine-1-carboxylate

To a solution of 6-chloro-5-methoxynicotinaldehyde (1.2 g, 6.98 mmol) in DMF (20 mL) was added tert-butyl piperazine-1-carboxylate (1.94 g, 10.45 mmol) and $K_2CO_3$ (1.92 g, 13.91 mmol) under $N_2$. The reaction mixture was stirred for 12 h at 80° C. and. After completed, the reaction mixture was quenched with water (50 mL) and extracted with EtOAc (3×50 mL). The combined organic layers was dried over $Na_2SO_4$ and concentrated under vacuum to get a residue. The residue was purified by column chromatography on silica gel eluting with ethyl acetate in petroleum ether (40%) to afford the title compound (1.6 g, 71%). $^1H$ NMR (400 MHz, $CDCl_3$) δ 9.85 (s, 1H), 8.23 (s, 1H), 7.42 (s, 1H), 3.89 (s, 3H), 3.75-3.67 (m, 4H), 3.58-3.51 (m, 4H), 1.49 (s, 9H) ppm. MS: M/e 322 $(M+1)^+$.

Step C: tert-butyl 4-(5-((4-(bis(2,4-dimethoxybenzyl)amino)-2-(((S)-pentan-2-yl)oxy)imidazo[2,1-f][1,2,4]triazin-7-yl)(hydroxy)methyl)-3-methoxypyridin-2-yl)piperazine-1-carboxylate To a solution of (R)-7-bromo-N,N-bis(2,4-dimethoxybenzyl)-2-(pentan-2-yloxy)imidazo[2,1-f][1,2,4]triazin-4-amine (500 mg, 0.832 mmol) in THF (10 mL) was added n-BuLi (1.6 mL, 2.56 mmol) under $N_2$ at −78° C. After stirring for 0.5 h at −78° C., tert-butyl 4-(5-formyl-3-methoxypyridin-2-yl)piperazine-1-carboxylate (400 mg, 1.25 mmol) was added. The reaction mixture was stirred for 2.5 h at −78° C. After completed, the reaction mixture was quenched with aq $NH_4Cl$ (30 mL) and extracted with DCM (3×30 mL). The combined organic layers was dried over $Na_2SO_4$ and concentrated under vacuum to get a residue. The residue was purified by column chromatography on silica gel eluting with ethyl acetate in petroleum ether (60%) to afford the title compound (620 mg, 88%). MS: M/e 843 $(M+1)^+$.

Step D: (4-amino-2-(((S)-pentan-2-yl)oxy)imidazo[2,1-f][1,2,4]triazin-7-yl)(5-methoxy-6-(piperazin-1-yl)pyridin-3-yl)methanol tert-butyl-4-(5-((4-(bis(2,4-dimethoxybenzyl)amino)-2-(((R)-pentan-2-yl)oxy) imidazo[2,1-f][1,2,4]triazin-7-yl)(hydroxy)methyl)-3-methoxypyridin-2yl)piperazine-1-carboxylate (500 mg, 0.593 mmol) was dissolved in TFA (8 mL) and $H_2O$ (0.8 mL) under $N_2$. The reaction mixture was stirred for 12 h at 40° C. After completed, the solvent was removed by in vacuo. The residue was diluted with water (20 mL) and DCM (30 mL) and the aqueous phase was acid with 1 N HCl to adjust PH=2-3. The aqueous phase was washed with DCM (3×20 mL) and based with 2 N NaOH to adjust PH=13-14 and extracted with DCM/i-PrOH (5/1, 3×120 mL). The combined organic layers was dried over $Na_2SO_4$ and concentrated under vacuum to afford the title compound (350 mg, crude). MS: M/e 443 $(M+1)^+$.

Step E: (S)-7-((5-methoxy-6-(piperazin-1-yl)pyridin-3-yl)methyl)-2-(pentan-2-yloxy)imidazo[2,1-f][1,2,4]triazin-4-amine (4-amino-2-(((S)-pentan-2-yl)oxy)imidazo[2,1-f][1,2,4]triazin-7-yl)(5-methoxy-6-(piperazin-1-yl)pyridin-3-yl)methanol (350 mg, crude) was dissolved in TFA (5 mL) and $Et_3SiH$ (5 mL) under $N_2$. The reaction mixture was stirred for 12 h at 90° C. After completed, the solvent was removed by in vacuo. The residue was diluted with water (20 mL) and DCM (20 mL) and the aqueous phase was acid with 1 N HCl to adjust PH=2-3. The aqueous phase was washed with DCM (3×20 mL) and based with 2 N NaOH to adjust PH=13-14 and extracted with DCM/i-PrOH (5/1, 3×100 mL). The combined organic layers was dried over $Na_2SO_4$ and concentrated under vacuum to get a residue. The residue was purified by Prep-TLC (DCM/$CH_3OH$ ($NH_3$)=10/1) to afford the title compound (3 mg). $^1H$ NMR (400 MHz, $CD_3OD$) δ 7.79 (s, 1H), 7.52 (s, 1H), 7.35 (s, 1H), 5.12-5.03 (m, 1H), 4.21 (s, 2H), 3.86 (s, 3H), 3.59 (d, J=4.8 Hz, 5H), 1.79-1.67 (m, 1H), 1.63-1.51 (m, 1H), 1.52-1.35 (m, 3H), 1.33-1.26 (m, 5H), 0.93 (t, J=7.2 Hz, 3H) ppm. MS: M/e 427 $(M+1)^+$.

Compound B242: 3-((4-amino-7-((2-fluoro-6-(piperidin-4-yl)pyridin-3 yl) methyl)imidazo[2,1-f][1,2,4]triazin-2-yl)oxy)hexan-1-ol Step A: 3-(benzyloxy)propanal To a solution of 3-(benzyloxy)propan-1-ol (5 g, 30.12 mmol) in DCM (100 mL) was added DMP (19 g, 44.81 mmol) under $N_2$ at 0° C. The reaction mixture was stirred for 5 h at 25° C. After completed, the reaction mixture was filtered and the filter was concentrated under vacuum to get a residue. The residue was purified by column chromatography on silica gel eluting with ethyl acetate in petroleum ether (20%) to afford the title compound (4.2 g, 85%). $^1H$ NMR (400 MHz, $CDCl_3$) δ 9.80 (d, J=1.6 Hz, 1H), 7.40-7.26 (m, 5H), 4.53 (s, 2H), 3.87-3.72 (m, 2H), 2.73-2.65 (m, 2H) ppm.

Step B: 1-(benzyloxy)hexan-3-ol

To a solution of 3-(benzyloxy)propanal (4.2 g, 25.61 mmol) in THF (100 mL) was added propylmagnesium bromide (18 mL, 36.00 mmol) under $N_2$ at 0° C. The reaction mixture was stirred for 1 h at 25° C. After completed, the reaction mixture was quenched with aq $NH_4Cl$ (50 mL) and extracted with EtOAc (3×50 mL). The combined organic layers were dried over $Na_2SO_4$ and concentrated under vacuum to get a residue. The residue was purified by column chromatography on silica gel eluting with ethyl acetate in petroleum ether (30%) to afford the title compound (3.4 g, 64%). $^1H$ NMR (400 MHz, DMSO-$d_6$) δ 7.40-7.19 (m, 5H), 4.44 (s, 2H), 4.32 (d, J=4.8 Hz, 1H), 3.59-3.43 (m, 3H), 1.71-0.45 (m, 2H), 1.44-1.20 (m, 4H), 0.85 (t, J=6.4 Hz, 3H) ppm. MS: M/e 209 $(M+1)^+$.

Step C: 2-((1-(benzyloxy)hexan-3-yl)oxy)-7-bromo-N,N-bis(2,4-dimethoxybenzyl)imidazo[2,1-f][1,2,4]triazin-4-amine To a solution of 1-(benzyloxy)hexan-3-ol (3 g, 14.42 mmol) in DMF (50 mL) was added NaH (1.3 g, 32.50 mmol)

under $N_2$ at 0° C. After stirring for 0.5 h at 25° C., 7-bromo-2-chloro-N,N-bis(2,4-dimethoxybenzyl)imidazo[2,1-f][1,2,4]triazin-4-amine (4.4 g, 8.01 mmol) was added. The reaction mixture was stirred for 1 h at 80° C. After completed, the reaction mixture was quenched with water (50 mL) and extracted with EtOAc (3×50 mL). The combined organic layers was dried over $Na_2SO_4$ and concentrated under vacuum to get a residue. The residue was purified by column chromatography on silica gel eluting with ethyl acetate in petroleum ether (40%) to afford the title compound (3 g, crude). MS: M/e 720, 722 $(M+1)^+$.

Step D: tert-butyl 5-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)-6-fluoro-3',6'-dihydro-[2,4'-bipyridine]-1'(2'H)-carboxylate To a solution of 2-((1-(benzyloxy)hexan-3-yl)oxy)-7-bromo-N,N-bis(2,4-dimethoxybenzyl)imidazo[2,1-f][1,2,4]triazin-4-amine (600 mg, 0.83 mmol) in THF (12 mL) was added n-BuLi (1.8 mL, 2.88 mmol) under $N_2$ at −78° C. After stirring for 0.5 h at −78° C., tert-butyl 6-fluoro-5-formyl-3',6'-dihydro-[2,4'-bipyridine]-1'(2'H)-carboxylate (430 mg, 1.405 mmol) was added. The reaction mixture was stirred for 2.5 h at −78° C. After completed, the reaction mixture was quenched with aq $NH_4Cl$ (30 mL) and extracted with DCM (3×30 mL). The combined organic layers was dried over $Na_2SO_4$ and concentrated under vacuum to get a residue. The residue was purified by column chromatography on silica gel eluting with ethyl acetate in petroleum ether (60%) to afford the title compound (400 mg, 45%). MS: M/e 948 $(M+1)^+$.

Step E: tert-butyl 4-(5-((4-(bis(2,4-dimethoxybenzyl)amino)-2-((1-hydroxyhexan-3-yl)oxy)imidazo[2,1-f][1,2,4]triazin-7-yl)(hydroxy)methyl)-6-fluoropyridin-2-yl) piperidine-1-carboxylate To a solution of tert-butyl 5-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)-6-fluoro-3',6'-dihydro-[2,4'-bipyridine]-1'(2'H)-carboxylate (390 mg, 0.411 mmol) in EtOAc (15 mL) was added Pd/C (200 mg). The reaction mixture was stirred for 16 h at 25° C. under $H_2$. After completed, the reaction mixture was filtered and the filter was concentrated under vacuum to afford the title compound (300 mg, crude). MS: M/e 860 $(M+1)^+$.

Step F: 3-((4-amino-7-((2-fluoro-6-(piperidin-4-yl)pyridin-3-yl)(hydroxy)methyl) imidazo[2,1-f][1,2,4]triazin-2-yl)oxy)hexan-1-ol tert-butyl 4-(5-((4-(bis(2,4-dimethoxybenzyl)amino)-2-((1-hydroxyhexan-3-yl)oxy)imidazo[2,1-f][1,2,4]triazin-7-yl)(hydroxy)methyl)-6-fluoropyridin-2-yl) pip-eridine-1-carboxylate (300 mg, crude) was dissolved in TFA (8 mL) and $H_2O$ (0.8 mL) under $N_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust pH=2-3. The aqueous phase was washed with DCM (3×20 mL) and based with 2 N NaOH to adjust pH=13-14 and extracted with DCM/i-PrOH (5/1, 3×100 mL). The combined organic layers were dried over $Na_2SO_4$ and concentrated under vacuum to afford the title compound (80 mg, crude), MS: M/e 460 $(M+1)^+$.

Step G: 3-((4-amino-7-((2-fluoro-6-(piperidin-4-yl)pyridin-3-yl)methyl)imidazo[2,1-f][1,2,4]triazin-2-yl)oxy)hexan-1-ol 3-((4-amino-7-((2-fluoro-6-(piperidin-4-yl)pyridin-3-yl)(hydroxy)methyl) imid-azo[2,1-f][1,2,4]triazin-2-yl)oxy)hexan-1-ol (80 mg, crude) was dissolved in TFA (5 mL) and $Et_3SiH$ (5 mL) under $N_2$. The reaction mixture was stirred for 12 h at 90° C. After completed, the solvent was removed by in vacuo. The residue was diluted with water (20 mL) and DCM (20 mL) and the aqueous phase was acid with 1 N HCl to adjust PH=2-3. The aqueous phase was washed with DCM (3×20 mL) and based with 2 N NaOH to adjust pH=13-14 and extracted with DCM/i-PrOH (5/1, 3×100 mL). The combined organic layers were dried over $Na_2SO_4$ and concentrated under vacuum to get a residue. The residue was purified by prep-HPLC with the following conditions: Column: XBridge Prep C18 OBD Column 19×150 mm 5 um; Mobile Phase A: Water (0.1% TFA), Mobile Phase B: MeOH; Flow rate: 17 mL/min; 214/254 nm to afford the title compound (11 mg). $^1H$ NMR (400 MHz, $CD_3OD$) δ 7.80-7.71 (m, 1H), 7.47 (s, 1H), 7.16 (d, J=7.2 Hz, 1H), 5.21-5.10 (m, 1H), 4.24 (s, 2H), 3.67-3.57 (m, 2H), 3.48 (d, J=12.4 Hz, 2H), 3.12 (t, J=12.4 Hz, 2H), 3.01 (t, J=11.2 Hz, 1H), 2.16-2.05 (m, 2H), 2.05-1.79 (m, 4H), 1.78-1.57 (m, 2H), 1.49-1.31 (m, 2H), 0.90 (t, J=7.2 Hz, 3H) ppm. MS: M/e 444 $(M+1)^+$.

Compound B243: (S)-4-((4-amino-2-(pentan-2-yloxy)imidazo[2,1-f][1,2,4]triazin-7-yl)methyl)-1-(piperidin-4-yl)pyridin-2(1H)-one Step A: tert-butyl 4-(4-bromo-2-oxopyridin-1(2H)-yl)piperidine-1-carboxylate To a solution of 4-bromopyridin-2(1H)-one (1.74 g, 10 mmol) and tert-butyl 4-((methylsulfonyl)oxy)piperidine-1-carboxylate (3.06 g, 11 mmol) in dioxane (40 mL) was added $Cs_2CO_3$ (6.5 g, 20 mmol). The reaction was heated at 100° C. for five days. The reaction was cooled to room temperature, diluted with water (100 mL), extracted with ethyl acetate (150 mL), washed with brine (80 mL). The organic layer was dried, concentrated and purified by Combi Flash to get the product (3.2 g, 89%). $^1$HNMR (400 MHz, $CDCl_3$) δ 7.18-7.10 (m, 1H), 6.86-6.81 (m, 1H), 6.42-6.34 (m, 1H), 5.06-4.94 (m, 1H), 4.40-4.20 (m, 2H), 2.89 (t, J=11.6 Hz, 2H), 1.94-1.86 (m, 2H), 1.72-1.55 (m, 2H), 1.48 (s, 9H) ppm. MS: M/e 357 $(M+1)^+$ Step B: tert-butyl 4-(4-formyl-2-oxopyridin-1(2H)-yl)piperidine-1-carboxylate To a solution of the product of step A (356 mg, 1 mmol), $Na_2CO_3$ (106 mg, 1 mmol) in DMF (10 mL) were added $Pd(dppf)_2Cl_2$ (73 mg, 0.1 mmol) and $Et_3SiH$ (232 g, 2 mmol), followed by mesitylene (60 mg, 0.5 mmol). The mixture was heated at 95° C. under CO (3 bar) for 5 hours. The solution was cooled, added with water (30 mL), extracted with ethyl acetate (50 mL×3) and washed with brine, dried on $Na_2SO_4$, filtered and concentrated to get the crude product, which was further purified by Combi Flash to get the pure product (123 mg, 40%). $^1$HNMR (400 MHz, $CDCl_3$) δ 9.88 (s, 1H), 7.41 (d, J=6.8 Hz, 1H), 7.01 (s, 1H), 6.62 (d, J=7.2 Hz, 1H), 5.15-4.96 (m, 1H), 4.45-4.20 (m, 2H), 3.00-2.82 (m, 2H), 1.98-1.86 (m, 2H), 1.76-1.60 (m, 2H), 1.48 (s, 9H) ppm. MS: M/e 307 $(M+1)^+$ Step C: tert-butyl 4-(4-((4-(bis(2,4-dimethoxybenzyl)amino)-2-(((S)-pentan-2-yl)oxy)imidazo[2,1-f][1,2,4]triazin-7-yl)(hydroxy)methyl)-2-oxopyridin-1(2H)-yl)piperidine-1-carboxylate To a cooled solution of (S)-7-bromo-N,N-bis(2,4-dimethoxybenzyl)-2-(pentan-2-yloxy)imidazo[2,1-f][1,2,4]triazin-4-amine (213 mg, 0.356 mmol) in THF (8 mL) at −78° C., purged with $N_2$ was added with n-BuLi (1.6 M, 0.35 mL) dropwise. After stirred at −78° C. for 30 mins, a solution of the product of step B (120 mg, 0.39 mmol) in THF (2 mL) was added. The resulting mixture was stirred at this temperature for 30 mins, and then warmed to r.t overnight. The solution was quenched with $NH_4Cl$ solution (5 mL), extracted with ethyl acetate (6 mL) and washed with brine (30 mL). The organic layer was dried with $Na_2SO_4$, filtered and concentrated to get the crude product, which was further purified by combi flash to get the desired product (120 mg, crude, 41%). MS: M/e 828 $(M+1)^+$.

Step D: 4-((4-amino-2-(((S)-pentan-2-yl)oxy)imidazo[2,1-f][1,2,4]triazin-7-yl)(hydroxy)methyl)-1-(piperidin-4-yl)pyridin-2(1H)-one A solution of the product of step C (120 mg, 0.145 mmol) in TFA/$Et_3SiH$ (4 mL/0.5 mL) was heated at 35° C. overnight. The mixture was concentrated to dryness, water (30 mL) was added and the resulting mixture was stirred at rt for 30 min. A precipitate was formed, filtered, washed with water (5 mL). The filtrate was collected, extracted with DCM (50 mL×2). The water phase was collected, treated with 2N NaOH to pH-14, extracted with DCM/IPA (3/1, 60 mL×3). The organic layer was washed with brine, dried with $Na_2SO_4$, filtered and concentrated to get the crude product (30 mg, 50%). MS: M/e 428 $(M+1)^+$ Step E: (S)-4-((4-amino-2-(pentan-2-yloxy)imidazo[2,1-f][1,2,4]triazin-7-yl)methyl)-1-(piperidin-4-yl)pyridin-2(1H)-one A mixture of the product of the step D (30 mg, crude) in triethylsilane (2 mL) and trifluoroacetic acid (2 mL) was heated at 85° C. for 10 h. The solvent was cooled and evaporated to get the residue, which was purified by prep-HPLC to get the product (10 mg, 27%). $^1$HNMR (400 MHz, $CD_3OD$) δ 7.55-7.48 (m, 2H), 6.42 (s, 1H), 6.39 (d, J=7.2 Hz, 1H), 5.10-4.98 (m, 1H), 4.96-4.89 (m, 1H), 4.13 (s, 2H), 3.60-3.50 (m, 2H), 3.26-3.12 (m, 2H), 2.25-2.04 (m, 4H), 1.80-1.64 (m, 1H), 1.62-1.51 (m, 1H), 1.50-1.34 (m, 2H), 1.28 (d, J=6.0 Hz, 3H), 0.92 (t, J=7.2 Hz, 3H) ppm. MS: M/e 412 $(M+1)^+$ Compound B244: (S)-1-(4-(5-((4-amino-2-(pentan-2-ylamino)imidazo[2,1-f][1,2,4]triazin-7-yl)methyl)-3-methylpyridin-2-yl)piperazin-1-yl)-2-(methyl(2-(methylamino)ethyl)amino)ethan-1-one Step A: tert-butyl (S)-(2-((2-(4-(5-((4-amino-2-(pentan-2-ylamino)imidazo[2,1-f][1,2,4]triazin-7-yl)methyl)-3-methylpyridin-2-yl)piperazin-1-yl)-2-oxoethyl)(methyl)amino)ethyl)(methyl)carbamate To a mixture of (S)-1-(4-(5-((4-amino-2-(pentan-2-ylamino)imidazo[2,1-f][1,2,4]triazin-7-yl)methyl)-3-methylpyridin-2-yl)piperazin-1-yl)-2-(methylamino)ethan-1-one (48 mg, 0.1 mmol) and tert-butyl methyl(2-oxoethyl)carbamate (26 mg, 0.15 mmol) in THF (5 mL) was added AcOH (2 drop) and sodium triacetoxyborohydride (63 mg, 0.3 mmol). The reaction was stirred at room temperature overnight. The reaction solution was diluted with water, extracted with EA (60 mL×3), washed with brine, dried over $Na_2SO_4$, filtered, and concentrated. The residue was purified by prep-TLC to give target compound (30 mg, 46%). MS: M/e 638 $(M+1)^+$.

Step B: (S)-1-(4-(5-((4-amino-2-(pentan-2-ylamino)imidazo[2,1-f][1,2,4]triazin-7-yl)methyl)-3-methylpyridin-2-yl)piperazin-1-yl)-2-(methyl(2-(methylamino)ethyl)amino)ethan-1-one To a mixture of the product of the step A (30 mg, 0.046 mmol) in DCM (4 mL) was added a solution of 4M HCl in dioxane (0.5 mL). The reaction was stirred at room temperature overnight. The mixture was concentrated to dryness and the residue was purified by prep-HPLC to give target compound (20 mg, 55%). $^1$H NMR (400 MHz, $CD_3OD$) δ 8.12 (s, 1H), 7.80 (s, 1H), 7.68 (s, 1H), 4.23 (s, 2H), 4.18 (s, 2H), 3.94-3.85 (m, 1H), 3.83-3.77 (m, 2H), 3.65-3.57 (m, 2H), 3.44-3.34 (m, 4H), 3.28-3.22 (m, 4H), 2.87 (s, 3H), 2.79 (s, 3H), 2.36 (s, 3H), 1.65-1.25 (m, 4H), 1.16 (d, J=6.8 Hz, 3H), 0.91 (t, J=6.8 Hz, 3H) ppm. MS: M/e 538 $(M+1)^+$.

Compound B245: (S)-7-((5-methyl-6-(4-((methyl(2-(methylamino)ethyl)amino)methyl)piperidin-1-yl)pyridin-3-yl)methyl)-N2-(pentan-2-yl)imidazo[2,1-f][1,2,4]triazine-2,4-diamine Step A: tert-butyl (S)-(2-(((1-(5-((4-amino-2-(pentan-2-ylamino)imidazo[2,1-f][1,2,4]triazin-7-yl)methyl)-3-methylpyridin-2-yl)piperidin-4-yl)methyl)(methyl)amino)ethyl)(methyl)carbamate To a mixture of (S)-7-((5-methyl-6-(4-((methylamino)methyl)piperidin-1-yl)pyridin-3-yl)methyl)-N2-(pentan-2-yl)imidazo[2,1-f][1,2,4]triazine-2,4-diamine (45 mg, 0.1 mmol) and tert-butyl methyl(2-oxoethyl)carbamate (26 mg, 0.15 mmol) in THF (5 mL) was added AcOH (2 drop) and sodium triacetoxyborohydride (63 mg, 0.3 mmol). The reaction was stirred at room temperature overnight. The reaction solution was diluted with water, extracted with EA (50 mL×2), washed with brine, dried over $Na_2SO_4$, filtered, and concentrated to give a residue (80 mg, crude) which used directly for next step. MS: M/e 609 $(M+1)^+$.

Step B: (S)-7-((5-methyl-6-(4-((methyl(2-(methylamino)ethyl)amino)methyl)piperidin-1-yl)pyridin-3-yl)methyl)-N2-(pentan-2-yl)imidazo[2,1-f][1,2,4]triazine-2,4-diamine To a mixture of the product of the step A (80 mg, crude) in DCM (10 mL) was added a solution of 4M HCl in dioxane (0.5 mL). The reaction was stirred at room temperature overnight. The mixture was concentrated to dryness and the residue was purified by prep-HPLC to give target compound (57 mg, 75% for two steps). $^1$H NMR (400 MHz, $CD_3OD$) δ 8.05 (s, 2H), 7.73 (s, 1H), 4.27 (s, 2H), 3.96-3.82 (m, 1H), 3.74 (d, J=11.6 Hz, 2H), 3.62-3.46 (m, 4H), 3.26-3.10 (m, 4H), 2.97 (s, 3H), 2.79 (s, 3H), 2.39 (s, 3H), 2.30-2.15 (m, 1H), 2.01 (d, J=11.6 Hz, 2H), 1.66-1.25 (m, 6H), 1.15 (d, J=6.4 Hz, 3H), 0.89 (t, J=6.8 Hz, 3H) ppm. MS: M/e 509 $(M+1)^+$.

Compound B246: (S)-2-amino-1-(4-(5-((4-amino-2-(pentan-2-ylamino)imidazo[2,1-f][1,2,4]triazin-7-yl)methyl)-3-methylpyridin-2-yl)piperazin-1-yl)ethan-1-one Step A: tert-butyl (S)-(2-(4-(5-((4-amino-2-(pentan-2-ylamino)imidazo[2,1-f][1,2,4]triazin-7-yl)methyl)-3-methylpyridin-2-yl)piperazin-1-yl)-2-oxoethyl) carbamate To a mixture of (S)-7-((5-methyl-6-(piperazin-1-yl)pyridin-3-yl)methyl)-N2-(pentan-2-yl)imidazo[2,1-f][1,2,4]triazine-2,4-diamine (480 mg, 1.17 mmol), (tert-butoxycarbonyl)glycine (205 mg, 1.17 mmol) and DIEA (302 mg, 2.3 mmol) in DMF (10 mL) was added HATU (445 mg, 1.17 mmol). The reaction was stirred at room temperature overnight. The reaction was diluted with water, extracted with EA (60 mL×2), washed with brine, dried over $Na_2SO_4$, filtered, and concentrated. The residue was purified by combi flash to give the target compound (520 mg, 78%). MS: M/e 567 $(M+1)^+$.

Step B: (S)-2-amino-1-(4-(5-((4-amino-2-(pentan-2-ylamino)imidazo[2,1-f][1,2,4]triazin-7-yl)methyl)-3-methylpyridin-2-yl)piperazin-1-yl)ethan-1-one To a mixture of the product of the step A (520 mg, 0.92 mmol) in DCM/MeOH (10 mL/2 mL) was added a solution of 4 M HCl in EtOAc (2 mL). The reaction was stirred at room temperature overnight. The mixture was concentrated. The residue was diluted with water, basified with saturated $NaHCO_3$ solution to pH~8, extracted with DCM/IPA (20/1, 60 mL×3), washed with brine, dried over $Na_2SO_4$, filtered, and concentrated to give the free base (410 mg). The residue (40 mg) was further purified by prep-TLC to give the target compound (13 mg). $^1$HNMR (400 MHz, DMSO-$d_6$) δ 8.08 (s, 1H), 7.47 (br.s, 2H), 7.46 (s, 1H), 7.16 (s, 1H), 5.99 (d, J=8.4 Hz, 1H), 3.98 (s, 2H), 3.89-3.76 (m, 1H), 3.66-3.54 (m, 2H), 3.52-3.40 (m, 2H), 3.38 (s, 2H), 3.25-3.10 (s, 2H), 3.03-2.90 (m, 4H), 2.20 (s, 3H), 1.61-1.45 (m, 1H), 1.42-1.20 (m, 3H), 1.10 (d, J=6.0 Hz, 3H), 0.85 (t, J=7.2 Hz, 3H) ppm. MS: M/e 467 $(M+1)^+$.

Compound B247: (S)-2-(4-(5-((4-amino-2-(pentan-2-ylamino)imidazo[2,1-f][1,2,4]triazin-7-yl)methyl)-3-methylpyridin-2-yl)piperazin-1-yl)ethan-1-ol To a mixture of (S)-7-((5-methyl-6-(piperazin-1-yl)pyridin-3-yl)methyl)-N2-(pentan-2-yl)imidazo[2,1-f][1,2,4]triazine-2,4-diamine (410 mg, 1 mmol) and 2-bromoethan-1-ol (150 mg, 1.2 mmol) in DMF (6 mL) was added TEA (202 mg, 2 mmol). The reaction was stirred at room temperature for 2 days. The reaction was diluted with water, extracted with EA (60 mL×3), washed with brine, dried over $Na_2SO_4$, filtered, and concentrated. The residue was purified by combi flash to give the target compound (185 mg, 41%). $^1$HNMR (400 MHz, $CD_3OD$) δ 8.01 (s, 1H), 7.46 (d, 1H), 7.19 (s, 1H), 4.07 (s, 2H), 3.98-3.78 (m, 1H), 3.72 (t, J=6.0 Hz, 2H), 3.18-3.08 (m, 4H), 2.80-2.67 (m, 4H), 2.63 (t, J=5.6 Hz, 2H), 2.23 (s, 3H), 1.71-1.21 (m, 4H), 1.14 (d, J=6.4 Hz, 3H), 0.89 (t, J=7.2 Hz, 3H) ppm. MS: M/e 454 $(M+1)^+$.

Compound C1: 2-butoxy-8-(3-(pyrrolidin-1-ylmethyl)benzyl)pyrazolo[1,5-a][1,3,5]triazin-4-amine Step A: tert-butyl (2-butoxypyrazolo[1,5-a][1,3,5]triazin-4-yl)carbamate To a stirred solution of 2-butoxypyrazolo[1,5-a][1,3,5]triazin-4-amine (50 mg, 0.24 mmol) in THF (15 mL), Di-tert-butyl dicarbonate (130 mg, 0.6 mmol) and DMAP (10 mg, 0.08 mmol) was added. The reaction mixture was stirred at rt overnight. The mixture was diluted $H_2O$ (20 mL) and extracted with EtOAc (10 ml×3). The combined organic layers were washed with brine, dried over $Na_2SO_4$ and concentrated in vacuo. The crude product was purified by column chromatography to give the product (100 mg, 100%) as white solids. MS: M/e 308 $(M+1)^+$.

Step B: tert-butyl (8-bromo-2-butoxypyrazolo[1,5-a][1,3,5]triazin-4-yl)carbamate To a stirred solution of tert-butyl (2-butoxypyrazolo[1,5-a][1,3,5]triazin-4-yl)carbamate (100 mg, 0.3 mmol) in MeCN (10 mL), NBS (115 mg, 0.6 mmol) was added. The reaction mixture was stirred at rt for 2 h. The mixture was concentrated in vacuo. The crude product was purified by column chromatography to give the product (150 mg, 100%) as white solids. MS: M/e 386 $(M+1)^+$.

Step C: tert-butyl (2-butoxy-8-(hydroxy(3-(pyrrolidin-1-ylmethyl)phenyl)methyl)pyrazolo[1,5-a][1,3,5]triazin-4-yl)carbamate To a stirred solution of tert-butyl (8-bromo-2-butoxypyrazolo[1,5-a][1,3,5]triazin-4-yl)carbamate (150 mg, 0.3 mmol) in THF (10 mL), cooled to −78° C. and under a nitrogen atmosphere, n-BuLi (1.6 M in hexane, 0.75 mmol, 0.47 mL) was added dropwise. After stirring for 20 mins, a solution of 3-(pyrrolidin-1-ylmethyl)benzaldehyde (85 mg, 0.45 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo. The crude product was purified by column chromatography to give the title product (100 mg, 67%). MS: M/e 498 $(M+1)^+$.

Step D: 2-butoxy-8-(3-(pyrrolidin-1-ylmethyl)benzyl)pyrazolo[1,5-a][1,3,5]triazin-4-amine A solution of tert-butyl (2-butoxy-8-(hydroxy(3-(pyrrolidin-1-ylmethyl)phenyl)methyl)pyrazolo[1,5-a][1,3,5]triazin-4-yl)carbamate (100 mg, 0.2 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (10 mg, 13.1%). $^1$H NMR (400 MHz, DMSO-d6)) δ 8.45 (s, 1H), 8.16 (s, 1H), 7.80 (s, 1H), 7.35-7.02 (m, 4H), 4.27 (s, 2H), 3.95 (s, 2H), 3.67 (s, 2H), 2.38-2.32 (m, 4H), 1.68-1.62 (m, 4H), 1.40 (s, 2H), 1.19-1.15 (m, 2H), 0.90-0.85 (m, 3H) ppm. MS: M/e 381 $(M+1)^+$.

Compound C2: 2-butoxy-8-(4-(pyrrolidin-1-ylmethyl)benzyl)pyrazolo[1,5-a][1,3,5]triazin-4-amine Step A: tert-butyl (2-butoxy-8-(hydroxy(4-(pyrrolidin-lylmethyl)phenyl)methyl)pyrazolo[1,5-a][1,3,5]triazin-4-yl)carbamate To a stirred solution of tert-butyl (8-bromo-2-butoxypyrazolo[1,5-a][1,3,5]triazin-4-yl)carbamate (100 mg, 0.26 mmol) in THF (10 mL), cooled to −78° C. and under a nitrogen atmosphere, n-BuLi (1.6 M in hexane, 0.75 mmol, 0.47 mL) was added dropwise. After stirring for 20 mins, a solution of 4-(pyrrolidin-1-ylmethyl)benzaldehyde (100 mg, 0.52 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo to give the crude product (220 mg, 100%) which was used directly in next step. MS: M/e 497 $(M+1)^+$.

Step B: 2-butoxy-8-(4-(pyrrolidin-1-ylmethyl)benzyl)pyrazolo[1,5-a][1,3,5]triazin-4-amine A solution of tert-butyl (2-butoxy-8-(hydroxy(4-(pyrrolidin-1-ylmethyl)phenyl)methyl)pyrazolo[1,5-a][1,3,5]triazin-4-yl)carbamate (220 mg, 0.26 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (10 mg, 10.1%). $^1H$ NMR (400 MHz, DMSO-d6)) δ 8.47 (s, 1H), 8.17 (s, 1H), 7.87 (s, 1H), 7.19 (s, 4H), 4.26 (t, J=6.4 Hz, 2H), 3.82 (s, 2H), 3.50 (s, 2H), 2.39-2.31 (m, 4H), 1.72-1.61 (m, 6H), 1.40 (dq, J=14.3, 7.2 Hz, 2H), 0.98-0.87 (m, 3H) ppm. MS: M/e 381 $(M+1)^+$.

Compound C3: 5-butoxy-3-((5-chloro-6-(piperazin-1-yl)pyridin-3-yl)methyl)pyrazolo[1,5-c]pyrimidin-7-amine Step A: methyl 7-amino-5-hydroxypyrazolo[1,5-c]pyrimidine-3-carboxylate To a solution of dimethyl 3-oxopentanedioate (50 g, 0.29 mol) in ethanol (500 mL), DMF-DMA (34.5 g, 0.29 mol) was added and the mixture was stirred at rt for 2 hrs. Then hydrazinecarboximidamide hydrochloride (35.4 g, 0.32 mol) was added and the solution was heated at 80° C. for 3 hrs. After was cooled down to rt, the precipitated solid was filtered and dried to get the product as a yellow solid (24 g, 40%). $^1H$ NMR (400 MHz, DMSO-d6) δ 10.99 (br.s, 1H), 8.24 (s, 1H), 7.82 (br.s, 2H), 6.27 (s, 1H), 3.76 (s, 3H) ppm. MS: M/e 209 $(M+1)^+$ Step B: methyl 7-amino-5-butoxypyrazolo[1,5-c]pyrimidine-3-carboxylate 1-iodobutane (6.6 g, 36 mmol) was added to a solution of methyl 7-amino-5-hydroxypyrazolo[1,5-c]pyrimidine-3-carboxylate (5 g, 24 mmol) in DMF (100 mL). The solution was stirred at rt overnight. Water (50 mL) was added and the precipitated solid was filtered and dried to get the desired product as a yellow solid (6.1 g, 96%). $^1H$ NMR (400 MHz, DMSO-d6) δ 8.30 (s, 1H), 8.01 (br.s, 1H), 6.35 (s, 1H), 4.20 (t, J=8.0 Hz, 2H), 3.77 (s, 3H), 1.71-1.66 (m, 2H), 1.45-1.38 (m, 2H), 0.89 (t, J=8.0 Hz, 3H) ppm. MS: M/e 265 $(M+1)^+$.

Step C: methyl 7-(bis(tert-butoxycarbonyl)amino)-5-butoxypyrazolo[1,5-c] pyrimidine-3-carboxylate $(Boc)_2O$ (7.7 g, 35.2 mmol) was added dropwise to a solution of methyl 7-amino-5-butoxypyrazolo[1,5-c]pyrimidine-3-carboxylate (3.1 g, 11.7 mmol) and DMAP (714 mg, 5.9 mmol) in THF (250 mL). After additional, the suspension became clear. It was continued to stir at rt for 2 hrs, then concentrated and purified by CombiFlash (PE:EA=25%) to get the product (4.2 g, 78%). $^1H$ NMR (400 MHz, DMSO-d6) δ 8.37 (s, 1H), 7.27 (s, 1H), 7.23 (s, 1H), 4.30 (t, J=8.0 Hz, 2H), 3.91 (s, 3H), 1.80-1.76 (m, 2H), 1.54-1.45 (m, 2H), 1.29 (s, 9H), 0.97 (t, J=8.0 Hz, 3H) ppm. MS: M/e 465 $(M+1)^+$.

Step D: tert-butyl (5-butoxy-3-(hydroxymethyl)pyrazolo[1,5-c]pyrimidin-7-yl) carbamate To a solution of Lithium aluminium hydride (782 mg, 20.6 mmol) in THF (60 mL) at 0° C., methyl 7-(bis(tert-butoxycarbonyl)amino)-5-butoxypyrazolo[1,5-c]pyrimidine-3-carboxylate (4.2 g, 10.3 mmol) in THF (20 mL) was added dropwise. The resulting mixture was stirred gradually to rt over 2 hrs. Then it was quenched with 0.8 mL of water, followed with 0.8 mL of NaOH solution (15%) and 2.4 mL of water. The solid was filtered and the cake was slurried with 100 mL of methanol for 1 hour. After filtration, the filtered cake was once again slurried with 100 mL of methanol. After filtration, the combined filtrate was evaporated to get the desired product (1.9 g, 50%). $^1H$ NMR (400 MHz, $CD_3OD$) δ 7.76 (s, 1H), 6.14 (s, 1H), 4.64 (s, 1H), 4.04 (t, J=8.0 Hz, 2H), 1.79-1.75 (m, 2H), 1.54-1.44 (m, 12H), 0.97 (t, J=8.0 Hz, 3H) ppm. MS: M/e 337 $(M+1)^+$.

Step E: tert-butyl (5-butoxy-3-formylpyrazolo[1,5-c]pyrimidin-7-yl)carbamate

To a cooled solution of tert-butyl (5-butoxy-3-(hydroxymethyl)pyrazolo[1,5-c]pyrimidin-7-yl)carbamate (1.2 g, 3.6 mmol) in THF (110 mL) at 0° C., Dess-Martin reagent (3.1 g, 7.2 mmol) was added. It was stirred at 0° C. for 30 mins, and then gradually to rt for 30 mins. The solution was quenched with water at 0° C. to a clear solution and extracted with ethyl acetate (80 mL). The organic layer was concentrated and purified by CombiFlash (PE:EA=25%) to get the product as a colorless oil (270 mg, 23%). $^1H$ NMR (400 MHz, DMSO-d6) δ 10.19 (s, 1H), 9.91 (s, 1H), 8.60 (s, 1H), 7.01 (s, 1H), 4.31 (t, J=8.0 Hz, 2H), 1.76-1.70 (m, 2H), 1.52-1.40 (m, 12H), 0.95 (t, J=8.0 Hz, 3H) ppm. MS: M/e 335 $(M+1)^+$.

Step F: tert-butyl 4-(5-((5-butoxy-7-((tert-butoxycarbonyl)amino)pyrazolo[1,5-c]pyrimidin-3-yl)(hydroxy)methyl)-3-chloropyridin-2-yl)piperazine-1-carboxylate To a cooled solution of tert-butyl 4-(5-bromo-3-chloropyridin-2-yl)piperazine-1-carboxylate (289 mg, 0.8 mmol) in THF (15 mL) at −78° C. (purged with $N^2$), n-BuLi (1.6 M, 1.2 mL) was added dropwise. After was stirred at −78° C. for 30 mins, tert-butyl (5-butoxy-3-formylpyrazolo[1,5-c]pyrimidin-7-yl)carbamate (270 mg, 0.8 mmol) in THF (5 mL) was added. The resulting mixture was stirred at this temperature for 30 mins, and then warmed to rt for 2 hrs. The solution was quenched with $NH_4Cl$ solution (10 mL) and extracted with ethyl acetate (10 mL). The organic layer was dried with $Na_2SO_4$, filtered and concentrated to get the crude product, which was further purified by CombiFlash (PE:

EA=50%) and prep-TLC (PE:EA=1:1) to get the pure product (80 mg, 16%). MS: M/e 632 $(M+1)^+$.

Step G: 5-butoxy-3-((5-chloro-6-(piperazin-1-yl)pyridin-3-yl)methyl)pyrazolo[1,5-c]pyrimidin-7-amine A mixture of tert-butyl 4-(5-((5-butoxy-7-((tert-butoxycarbonyl)amino) pyrazolo[1,5-c]pyrimidin-3-yl)(hydroxy)methyl)-3-chloropyridin-2-yl)piperazine-1-carboxylate (20 mg, 0.03 mmol) in triethylsilane (0.5 mL) and trifluoroacetic acid (0.5 mL) was heated at 30° C. for 2 hrs. Then it was concentrated under oil pump at 60° C. to get the crude product, which was purified by prep-TLC (DCM:MeOH=7:1) to get the product (5 mg, 38%). $^1H$ NMR (400 MHz, $CD_3OD$) δ 8.12 (t, J=8.0 Hz, 1H), 7.75 (d, J=4.0 Hz, 1H), 7.64 (s, 1H), 6.97 (d, J=4.0 Hz, 1H), 5.97 (d, J=8.0 Hz, 1H), 4.12-4.09 (m, 3H), 3.51-3.38 (m, 4H), 2.91-2.65 (m, 4H), 1.76-1.72 (m, 2H), 1.49-1.45 (m, 2H), 0.98 (t, J=8.0 Hz, 3H) ppm. MS: M/e 416 $(M+1)^+$.

Compound C4: 6-propoxy-3-(4-(pyrrolidin-1-ylmethyl)benzyl)imidazo[1,2-b]pyridazin-8-amine Step A: 6-chloro-N,N-bis(4-methoxybenzyl)imidazo[1,2-b]pyridazin-8-amine To a stirred solution of 8-bromo-6-chloroimidazo[1,2-b]pyridazine (2 g, 8.7 mmol) in DMF (20 mL), bis(4-methoxybenzyl)amine (2.7 g, 10.44 mmol) and DIEA (2.3 g, 17.4 mmol) were added. The reaction mixture was stirred at 90° C. overnight. The mixture was diluted with $H_2O$ (50 mL) and extracted with EtOAc (20 ml×3). The combined organic phase was washed with brine, dried over $Na_2SO_4$ and concentrated in vacuo. The crude product was purified by column chromatography to give the product (2.8 mg, 80%) as white solids. MS: M/e 308 $(M+1)^+$.

Step B: N,N-bis(4-methoxybenzyl)-6-propoxyimidazo[1,2-b]pyridazin-8-amine

To a stirred solution of 6-chloro-N,N-bis(4-methoxybenzyl)imidazo[1,2-b]pyridazin-8-amine (2.2 g, 5.4 mmol) in butyl alcohol (10 mL), sodium butanolate (50 ml, 4M in butyl alcohol) was added. The reaction mixture was stirred at 95° C. overnight. The mixture was concentrated in vacuo. The residue was added $H_2O$ (50 mL) and extracted with EtOAc (20 ml×3). The combined organic phase was washed with brine, dried over $Na_2SO_4$ and concentrated in vacuo. The crude product was purified by column chromatography to give the product (2 g, 85.8%) as white solids. MS: M/e 437 $(M+1)^+$.

Step C: 8-(bis(4-methoxybenzyl)amino)-6-propoxyimidazo[1,2-b]pyridazine-3-carbaldehyde In a 100 ml round bottom flask was added DMF (5 ml), $POCl_3$ (900 mg, 5.88 mmol) was added to DMF at 0° C. The reaction was stirred at 0° C. for 30 mins. To this solution, N,N-bis(4-methoxybenzyl)-6-propoxyimidazo[1,2-b]pyridazin-8-amine (300 mg, 0.69 mmol) was added. The reaction was stirred at rt overnight. The mixture was added $H_2O$ (50 mL) and extracted with EtOAc (20 ml×3). The combined organic phase was washed with brine, dried over $Na_2SO_4$ and concentrated in vacuo. The crude product was purified by column chromatography to give the product (300 mg, 94%) as yellow solids. MS: M/e 475 $(M+1)^+$.

Step D: (8-(bis(4-methoxybenzyl)amino)-6-propoxyimidazo[1,2-b]pyridazin-3-yl)(4-(pyrrolidin-1-ylmethyl)phenyl)methanol To a stirred solution of 1-(4-bromobenzyl)pyrrolidine (140 mg, 0.55 mmol) in THF (10 mL), cooled to −78° C. and under a nitrogen atmosphere, n-BuLi (1.6 M in hexane, 0.93 mmol, 0.58 mL) was added dropwise. After stirring for 50 mins, a solution of 8-(bis(4-methoxybenzyl)amino)-6-propoxyimidazo[1,2-b]pyridazine-3-carbaldehyde (150 mg, 0.37 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phase was washed with brine, dried over $Na_2SO_4$, concentrated in vacuo to give the product (60 mg, 25.6%). MS: M/e: 636 $(M+1)^+$.

Step E: 6-butoxy-3-(4-(pyrrolidin-1-ylmethyl)benzyl)imidazo[1,2-b]pyridazin-8-amine A solution of (8-(bis(4-methoxybenzyl)amino)-6-propoxyimidazo[1,2-b]pyridazin-3-yl)(4-(pyrrolidin-1-ylmethyl)phenyl)methanol (60 mg, 0.09 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (5 mg, 14.2%). $^1H$ NMR (400 MHz, DMSO-d6) δ 9.83 (s, 1H), 8.04 (s, 1H), 7.74 (s, 1H), 7.39 (d, J=7.5 Hz, 2H), 7.30 (d, J=7.7 Hz, 2H), 7.04 (s, 2H), 4.29 (d, J=5.4 Hz, 2H), 4.20 (t, J=6.1 Hz, 2H), 3.95 (s, 2H), 3.30 (s, 2H), 3.06 (s, 2H), 2.01 (s, 2H), 1.91-1.77 (m, 2H), 1.69-1.56 (m, 2H), 1.35-1.19 (m, 2H), 0.85 (t, J=7.3 Hz, 3H) ppm. MS: M/e 380 $(M+1)^+$.

Compound C5: 6-butoxy-3-((5-methyl-6-(piperazin-1-yl)pyridin-3-yl)methyl)imidazo[1,2-b]pyridazin-8-amine Step A: tert-butyl 4-(5-((8-(bis(4-methoxybenzyl)amino)-6-butoxyimidazo[1,2-b]pyridazin-3-yl)(hydroxy)methyl)-3-methylpyridin-2-yl)piperazine-1-carboxylate To a stirred solution of tert-butyl 4-(5-bromo-3-methylpyridin-2-yl)piperazine-1-carboxylate (180 mg, 0.44 mmol) in THF (10 mL), cooled to −78° C. and under a nitrogen atmosphere, n-BuLi (1.6 M in hexane, 0.99 mmol, 0.618 mL) was added dropwise. After stirring for 50 mins, a solution of 8-(bis(4-methoxybenzyl)amino)-6-propoxyimidazo[1,2-b]pyridazine-3-carbaldehyde (201 mg, 0.66 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo to give the product (120 mg, 24.2%). MS: M/e: 752 $(M+1)^+$.

Step B: 6-butoxy-3-((5-methyl-6-(piperazin-1-yl)pyridin-3-yl)methyl)imidazo[1,2-b]pyridazin-8-amine A solution of tert-butyl 4-(5-((8-(bis(4-methoxybenzyl)amino)-6-butoxyimidazo[1,2-b]pyridazine-3-yl)(hydroxy)

methyl)-3-methylpyridin-2-yl)piperazine-1-carboxylate (120 mg, 0.16 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (10 mg, 15.8%). $^1H$ NMR (400 MHz, DMSO-d6) δ 8.68 (br.s, 2H), 8.14-8.10 (m, 1H), 8.05 (s, 1H), 7.89-7.83 (m, 1H), 7.39 (s, 1H), 7.16-7.11 (m, 2H), 4.24 (br.s, 2H), 3.84 (s, 2H), 3.26-3.14 (m, 8H), 2.18 (s, 3H), 1.72-1.59 (m, 2H), 1.33-1.27 (m, 2H), 0.86 (t, J=7.6, 3H) ppm. MS: M/e 396 $(M+1)^+$.

Compound C6: 2-butoxy-7-((5-methyl-6-(piperazin-1-yl)pyridin-3-yl)methyl)-5H-pyrrolo [3,2-d]pyrimidin-4-amine Step A: 2,4-dichloro-5-((2-(trimethylsilyl)ethoxy)methyl)-5H-pyrrolo[3,2-d]pyrimidine To a solution of 2,4-dichloro-5H-pyrrolo[3,2-d]pyrimidine (3.76 g, 20 mmol) in DMF (40 mL), DIPEA (4.2 mL, 24 mmol) and (2-(chloromethoxy)ethyl)trimethylsilane (4.3 mL, 24 mmol) were added. Then the mixture was stirred at room temperature overnight. The reaction was concentrated, diluted with water (5 mL), extracted with EtOAc (30 mL×5). The combined organic layers were washed with brine, dried over $Na_2SO_4$, concentrated and the residue was purified by flash chromatography to give target compound (3 g, 47%) as a white solid. MS: M/e 318 $(M+1)^+$.

Step B: 2-chloro-5-((2-(trimethylsilyl)ethoxy)methyl)-5H-pyrrolo[3,2-d]pyrimidin-4-amine Aqueous ammonia (20 mL) was added to a solution of 2,4-dichloro-5-((2-(trimethylsilyl)ethoxy)methyl)-5H-pyrrolo[3,2-d]pyrimidine (5 g, 15.8 mmol) in propan-2-ol (20 mL), the reaction mixture was stirred in autoclave at 95° C. for 7 hours, extracted with EtOAc (25 mL×4). The combined organic layers were washed with brine, dried over $Na_2SO_4$, concentrated and the residue was purified by flash chromatography to give target compound (3.2 g, 68%) as a white solid. MS: M/e 299 $(M+1)^+$.

Step C: 2-butoxy-5-((2-(trimethylsilyl)ethoxy)methyl)-5H-pyrrolo[3,2-d]pyrimidin-4-amine A mixture of 2-chloro-5-((2-(trimethylsilyl)ethoxy)methyl)-5H-pyrrolo[3,2-d]pyrimidin-4-amine (3 g, 10 mmol) and n-BuONa/n-BuOH (20%, 9.6 ml) was stirred at 80° C. for 5 hours. The solution was quenched with $H_2O$ (10 ml). The aqueous solution was extracted with EA (20 ml×4). The collected organic layers were washed with brine, dried over $Na_2SO_4$, filtered and concentrated. The resulting residue was purified by column chromatography to afford product (3.3 g, 95%). MS: M/e 337 $(M+1)^+$.

Step D: 2-butoxy-5H-pyrrolo[3,2-d]pyrimidin-4-amine

A mixture of 2-butoxy-5-((2-(trimethylsilyl)ethoxy)methyl)-5H-pyrrolo[3,2-d]pyrimidin-4-amine (3.3 g, 10 mmol) and $CF_3COOH$ was stirred at room temperature overnight. The reaction was quenched with saturated $NaHCO_3$ solution. The aqueous solution was extracted with EA (20 ml×3). The collected organic layer was washed with brine, dried over $Na_2SO_4$, filtered and concentrated. The resulting residue was purified by column chromatography to afford the product (1.53 g, 74%). MS: M/e 207 $(M+1)^+$.

Step E: tert-butyl 4-(5-((4-amino-2-butoxy-5H-pyrrolo[3,2-d]pyrimidin-7-yl)(hydroxy)methyl)-3-methylpyridin-2-yl)piperazine-1-carboxylate A mixture of 2-butoxy-5H-pyrrolo[3,2-d]pyrimidin-4-amine (206 mg, 1 mmol), tert-butyl 4-(5-formyl-3-methylpyridin-2-yl)piperazine-1-carboxylate (458 mg, 1.5 mmol) and $K_2CO_3$ (166 mg, 1.5 mmol) in $CH_3OH$ (1 mL) and $H_2O$ (1 mL) was stirred at room temperature for two days. The reaction was quenched with saturated $NaHCO_3$ solution. The aqueous solution was extracted with EA (25 ml×4). The collected organic layers were washed with brine, dried over $Na_2SO_4$, filtered and concentrated. The resulting residue was purified by column chromatography to afford the product (203 mg, 40%) MS: M/e 512 $(M+1)^+$.

Step F: 2-butoxy-7-((5-methyl-6-(piperazin-1-yl)pyridin-3-yl)methyl)-5H-pyrrolo[3,2-d]pyrimidin-4-amine To a stirred solution of product step A (206 mg, 0.5 mmol) in DCM (5 mL) at −15° C., $Et_3SiH$ (0.5 mL) and TFA (0.5 mL) were added. The reaction mixture was stirred at 0° C. overnight. The solution was quenched with saturated $NaHCO_3$ solution (5 mL). The aqueous solution was extracted with EA (10 ml×4). The collected organic layers were washed with brine, dried over $Na_2SO_4$, filtered and concentrated. The resulting residue was purified by column chromatography to afford the product (82 mg, 41%). $^1H$ NMR (400 MHz, $CDCl_3$) δ 10.45 (s, 1H), 8.04 (d, J=4 Hz, 1H), 7.46 (s, 1H), 7.16 (d, J=4 Hz, 1H), 6.65 (s, 2H), 4.19 (t, J=4 Hz, 2H), 3.77 (s, 2H), 2.91-2.75 (m, 8H), 1.68-1.61 (m, 2H), 1.42-1.35 (m, 2H), 0.93 (t, J=8.0 Hz, 3H) ppm. MS: M/e 396 $(M+1)^+$.

HEK293-Blue hTLR7 Reporter Assay:

HEK-Blue-hTLR7 cell line (Invivogen, Cat. No. hkb-htlr7) was designed so that the expression of the secreted embryonic alkaline phosphatase (SEAP) was induced by activating NF-κ and AP-1 via stimulating human TLR7 with TLR7 agonists.

HEK-Blue-hTLR7 cells were seeded at a density of $4\times10^4$ cells/well in a volume of 180 μL in a 96-well plate in DMEM (Cat. No. 11965-092) supplemented with 10% (v/v) heat-inactivated fetal bovine serum (FBS) (Gibco, 10099-1441), 100 U/ml penicillin and 100 μg/ml streptomycin (Gibco, 15140122) containing 50 U/mL penicillin, 50 mg/mL streptomycin and 10% (v/v) heat-inactivated fetal bovine serum. The cells were settled for 5 hrs, then treated with increasing amounts of tested compounds at 37° C. for 24 hrs. Then 20 μL of the supernatant from each well was incubated with 180 μL Quanti-blue substrate solution at 37° C. for 10-30 mins before the activity of the SEAP was determined at 620-655 nm using a spectrophotometer. The EC50 value for each compound was calculated with GraphPad Prism software using the sigmoidal dose-response function.

TLR7 Stimulation Determined Using HEK-Blue Detection

This assay was designed for studying the stimulation of human TLR7 protein in HEK-Blue hTLR7 tool cell line by monitoring the activation of NF-κB. HEK-Blue hTLR7 cells were obtained by co-transfection of the hTLR7 gene and an optimized secreted embryonic alkaline phosphatase (SEAP) reporter gene into HEK293 cells. The SEAP reporter gene was placed under the control of the IFN-β minimal promoter fused to five NF-κB and AP-1-binding sites. Stimulation with a TLR7 ligand activates NF-κB and AP-1 which induce the expression of SEAP. Levels of SEAP can be easily determined with HEK-Blue Detection, a cell culture medium that allows for real-time detection of SEAP. HEK-Blue Detection contains all the nutrients necessary for cell growth and a specific SEAP color substrate. The hydrolysis of the substrate by SEAP produces a purple/blue color that can be measured with a spectrophotometer.

When growing to 50-80% confluency, HEK-Blue hTLR7 cells were plated into 96-well plate (costar 3599) at a density of 40000 cells/well. Then compounds were added with serial dilutions over 10 points with a 0.04 nM-10 μM final concentration range in 0.1% DMSO/HEK-Blue Detection. The plates were then incubated for 16 hr at 37° C. in 5% $CO_2$ and vortex for 30 s before measurement. The optical density at 620-655 nm was read on BMG PHERAstar FSX instrument. The EC50 for each compound was determined by calculating the percentages of the maximum activation identified with Resiquimod.

TABLE 1

Compounds B series ("D" refers to EC50 > 10 μmol; B1-B232 was tested by QUANTI-BLUE assay; B233-B247 was tested by HEK-Blue Detection)

| Compound number | EC50(nmol) | Compound number | EC50 (nmol) |
|---|---|---|---|
| B1 | 501 | B2 | 434 |
| B3 | 327 | B4 | D |
| B5 | 1225 | B6 | 421 |
| B7 | 2384 | B8 | 136 |
| B9 | 345 | B10 | 417 |
| B11 | 247 | B12 | 44 |
| B13 | 48 | B14 | 96 |
| B15 | 509 | B16 | 1441 |
| B17 | 149 | B18 | 171 |
| B19 | 227 | B20 | 7991 |
| B21 | 115 | B22 | 496 |
| B23 | 487 | B24 | 210 |
| B25 | D | B26 | 295 |
| B27 | 971 | B28 | 302 |
| B29 | D | B30 | D |
| B31 | D | B32 | 66 |
| B33 | 218 | B34 | D |
| B35 | D | B36 | 182 |
| B37 | 148 | B38 | D |
| B39 | 465 | B40 | 908 |
| B41 | 600 | B42 | D |
| B43 | D | B44 | 6657 |
| B45 | 418 | B46 | 960 |
| B47 | 462 | B48 | 4770 |
| B49 | 124 | B50 | 151 |
| B51 | D | B52 | D |
| B53 | 803 | B54 | 158 |
| B55 | 196 | B56 | 422 |
| B57 | 3801 | B58 | 3248 |
| B59 | 20 | B60 | 50 |
| B61 | 660 | B62 | D |
| B63 | 900 | B64 | 448 |
| B65 | 26 | B66 | 146 |
| B67 | 336 | B68 | 106 |
| B69 | 313 | B70 | 212 |
| B71 | 31 | B72 | 493 |
| B73 | 532 | B74 | 73 |
| B75 | 121 | B76 | 94 |
| B77 | 311 | B78 | 47 |
| B79 | 505 | B80 | 242 |
| B81 | 4438 | B82 | 431 |
| B83 | D | B84 | 1001 |
| B85 | 1363 | B86 | 202 |
| B87 | 435 | B88 | 61 |
| B89 | D | B90 | 2361 |
| B91 | 150 | B92 | 464 |
| B93 | 641 | B94 | 13 |

TABLE 1-continued

Compounds B series ("D" refers to EC50 > 10 μmol; B1-B232 was tested by QUANTI-BLUE assay; B233-B247 was tested by HEK-Blue Detection)

| Compound number | EC50(nmol) | Compound number | EC50 (nmol) |
|---|---|---|---|
| B95 | 4381 | B96 | 17 |
| B97 | 163 | B98 | 1127 |
| B99 | 926 | B100 | D |
| B101 | 425 | B102 | 464 |
| B103 | 7958 | B104 | D |
| B105 | 177 | B106 | 71 |
| B107 | 185 | B108 | 159 |
| B109 | 161 | B110 | 43 |
| B111 | 9.8 | B112 | 37 |
| B113 | 447 | B114 | 168 |
| B115 | 190 | B116 | 1191 |
| B117 | 62 | B118 | 3.7 |
| B119 | D | B120 | D |
| B121 | 31 | B122 | 2.6 |
| B123 | 1.9 | B124 | 51 |
| B125 | 2.5 | B126 | 22 |
| B127 | 56 | B128 | 41 |
| B129 | D | B130 | 38 |
| B131 | 98 | B132 | 48 |
| B133 | 5.6 | B134 | 6 |
| B135 | 22 | B136 | 4979 |
| B137 | 4.1 | B138 | 5.5 |
| B139 | 88 | B140 | 8.7 |
| B141 | 154 | B142 | 45 |
| B143 | 7.8 | B144 | D |
| B145 | 8 | B146 | 10 |
| B147 | 2.2 | B148 | 6.5 |
| B149 | 6.3 | B150 | 2.5 |
| B151 | 3 | B152 | 56 |
| B153 | 49 | B154 | 1.6 |
| B155 | 8.3 | B156 | 9.7 |
| B157 | 667 | B158 | 6.5 |
| B159 | 48 | B160 | 25 |
| B161 | 11 | B162 | 8 |
| B163 | 2.5 | B164 | 4.1 |
| B165 | 7 | B166 | 2.6 |
| B167 | 497 | B168 | 124 |
| B169 | 2.9 | B170 | 29 |
| B171 | NA | B172 | 260 |
| B173 | 2.3 | B174 | 48 |
| B175 | 3.3 | B176 | 8.6 |
| B177 | N.D. | B178 | 17 |
| B179 | 38 | B180 | 270 |
| B181 | 7.8 | B182 | NA |
| B183 | 93 | B184 | 3.6 |
| B185 | 25 | B186 | 4.9 |
| B187 | 29 | B188 | 3.6 |
| B189 | 19 | B190 | 4.4 |
| B191 | 7.9 | B192 | 2680 |
| B193 | 902 | B194 | 80 |
| B195 | 2.8 | B196 | 5.7 |
| B197 | 3.9 | B198 | 4.1 |
| B199 | 8.1 | B200 | 25 |
| B201 | 28 | B202 | 15 |
| B203 | NA | B204 | 7.3 |
| B205 | 6.5 | B206 | 5610 |
| B207 | 56 | B208 | 7.4 |
| B209 | 9.2 | B210 | 12 |
| B211 | 7.7 | B212 | 6.2 |
| B213 | 2.6 | B214 | 23 |
| B215 | 4.2 | B216 | 1080 |
| B217 | 2440 | B218 | 46 |
| B219 | 2.4 | B220 | 3.6 |
| B221 | 3.9 | B222 | 60 |
| B223 | 6 | B224 | 5.1 |
| B225 | 26 | B226 | 46 |
| B227 | 25 | B228 | 37 |
| B229 | 14 | B230 | 4.8 |
| B231 | 4.1 | B232 | 31 |
| B233 | 18.4 | B234 | 5.3 |
| B235 | 63 | B236 | 648 |
| B237 | 8.5 | B238 | 6.7 |
| B239 | 3.3 | B240 | 1 |

TABLE 1-continued

| Compounds B series ("D" refers to EC50 > 10 µmol; B1-B232 was tested by QUANTI-BLUE assay; B233-B247 was tested by HEK-Blue Detection) | | | |
|---|---|---|---|
| Compound number | EC50(nmol) | Compound number | EC50 (nmol) |
| B241 | 5.5 | B242 | 9.8 |
| B243 | 35 | B244 | 12 |
| B245 | 2.5 | B246 | 10.9 |
| B247 | 0.6 | | |

TLR8 Stimulation determined using HEK-Blue Detection

TABLE 2

| Compounds C series ("D" refers to EC50 > 10 µmol; C1-C6 was tested by QUANTI-BLUE assay) | | | |
|---|---|---|---|
| Compound number | EC50 (nmol) | Compound number | EC50 (nmol) |
| C1 | D | C2 | D |
| C3 | D | C4 | D |
| C5 | D | C6 | 1075 |

This assay was designed for studying the stimulation of human TLR 8 protein in HEK-Blue hTLR8 tool cell line by monitoring the activation of NF-κB. HEK-Blue hTLR8 cells were obtained by co-transfection of the hTLR8 gene and an optimized secreted embryonic alkaline phosphatase (SEAP) reporter gene into HEK293 cells. The SEAP reporter gene was placed under the control of the IFN-β minimal promoter fused to five NF-κB and AP-1-binding sites. Stimulation with a TLR 8 ligand activates NF-κB and AP-1 which induce the expression of SEAP. Levels of SEAP can be easily determined with HEK-Blue Detection, a cell culture medium that allows for real-time detection of SEAP. HEK-Blue Detection contains all the nutrients necessary for cell growth and a specific SEAP color substrate. The hydrolysis of the substrate by SEAP produces a purple/blue color that can be measured with a spectrophotometer.

When growing to 50-80% confluency, HEK-Blue hTLR7/8 cells were plated into 96-well plate (costar 3599) at a density of 40000 cells/well. Then compounds were added with serial dilutions over 10 points with a 1 nM-10 uM final concentration range in 0.1% DMSO/HEK-Blue Detection. The plates were then incubated for 16 hr at 37° C. in 5% $CO_2$. The optical density at 620-655 nm was read on BMG PHERAstar FSX instrument. The EC50 for each compound was determined by calculating the percentages of the maximum activation identified with Resiquimod or Motolimod.

TABLE 3

| Compounds for HEK-Blue hTLR8 Cells ("D" refers to EC50 > 10 umol) | | | |
|---|---|---|---|
| Compound number | EC50 (nmol) | Compound number | EC50 (nmol) |
| B21 | 250 | B118 | 197 |
| B122 | 262 | B123 | 310 |
| B140 | 530 | B147 | D |
| B165 | 150 | B190 | D |
| B195 | D | B213 | D |
| B219 | D | B233 | D |
| B234 | 451 | B235 | 3632 |
| B236 | D | B238 | 169 |

TABLE 3-continued

| Compounds for HEK-Blue hTLR8 Cells ("D" refers to EC50 > 10 umol) | | | |
|---|---|---|---|
| Compound number | EC50 (nmol) | Compound number | EC50 (nmol) |
| B239 | 122 | B240 | 1510 |
| B241 | 445 | B242 | 74 |
| B243 | 365 | B244 | D |
| B245 | 485 | B246 | D |
| B247 | D | | |

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

What is claimed is:

1. A compound of Formula (II), (II)

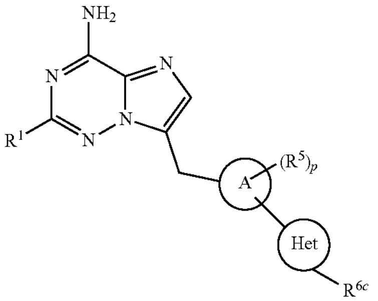

or a pharmaceutically acceptable salt thereof, or a stereoisomer thereof, wherein $R^1$ is —$OR^{1a}$ or —$NHR^{1a}$, wherein $R^{1a}$ is a branched —$C_{4-8}$alkyl, wherein the branched substituent is at the alpha position with respect to the oxygen or nitrogen atom;

Ring A is pyridyl;

Het is piperidinyl or piperazinyl;

$R^5$ is $C_{1-8}$ alkyl;

p is 0 or 1;

$R^{6c}$ is hydrogen, —$COR^{6d}$, or $C_{1-8}$ alkyl, wherein the $C_{1-8}$ alkyl is optionally substituted with one, two or three substituents $R^{6g}$;

$R^{6d}$ is $C_{1-8}$ alkyl, wherein the $C_{1-8}$ alkyl is optionally substituted with one or two or three substituents $R^{6g}$;

$R^{6g}$, at each occurrence, is independently —$OR^{6h}$, —$SR^{6h}$, or —$NR^{6h}R^{6i}$, $R^{6h}$ and $R^{6i}$ are independently hydrogen or $C_{1-8}$ alkyl, wherein the $C_{1-8}$ alkyl is optionally substituted with a substituent selected from hydroxyl or $C_{1-8}$ alkylamino.

2. The compound according to claim 1, wherein $R^1$ is —$OR^{1a}$ or —$NHR^{1a}$, wherein $R^{1a}$ is butan-2-yl, pentan-2-yl, pentan-3-yl, heptan-2-yl, heptan-3-yl, heptan-4-yl, octan-2-yl, octan-3-yl, octan-4-yl, or octan-5-yl.

3. The compound according to claim 1, wherein $R^5$ is —$C_{1-6}$alkyl; and p is 1.

4. The compound according to claim 1, wherein $R^5$ and Het-$R^6$ are at ortho positions on ring A.

5. The compound according to claim 1, wherein Het is piperidinyl, and the piperidinyl is piperidin-1-yl, piperidin- 2-yl, piperidin-3-yl, piperidin-4-yl, or piperidin-5-yl, or piperazinyl is piperazin-1-yl, piperazin-2-yl, or piperazin-3-yl.

6. The compound according to claim 1, wherein $R^{6c}$ is —$COR^{6d}$, wherein $R^{6d}$ is —$C_{1-8}$alkyl optionally substituted with one or two substituents $R^{6g}$, wherein $R^{6g}$ is —$NR^{6h}R^{6i}$, wherein $R^{6h}$ and $R^{6i}$ are each independently hydrogen or —$C_{1-8}$alkyl.

7. The compound according to claim 1, wherein $R^{6c}$ is —$COR^{6d}$, wherein $R^{6d}$ is $C_{1-6}$alkyl or $C_{1-4}$alkyl optionally substituted with one or two substituents Rog, wherein $R^{6g}$ is —$NR^{6h}R^{6i}$, wherein $R^{6h}$ and $R^{6i}$ are each independently hydrogen, $C_{1-6}$alkyl, or $C_{1-4}$alkyl.

8. The compound according to claim 1, wherein $R^{6c}$ is:

acetyl, 2-(dimethylamino)acetyl, aminoacetyl, 2-(methylamino)acetyl, 3-(dimethylamino)propanoyl, 4-(dimethylamino)butanoyl, 5-(dimethylamino)pentanoyl, (2S, 3S)-2-amino-3-methylpentanoyl, 2-(methylamino) acetyl, 2-amino-4-methylpentanoyl, 2-amino-3-methylbutanoyl, 2-(dimethylamino)acetyl;

methyl, ethyl, isobutyl, (methylamino)methyl, 2-(dimethylamino)ethyl, (dimethylamino)methyl, 2-aminoethyl, or 2-(methylamino)ethyl; or dimethylamino or amino.

9. The compound according to claim 1, wherein ring A is pyridyl, and the methylene group and Het on the pyridyl are in para positions of the pyridyl, and said pyridyl is further optionally substituted with one $R^5$, wherein $R^5$ is $C_{1-8}$ alkyl.

10. A compound, or a pharmaceutically acceptable salt thereof, or a stereoisomer thereof, selected from:

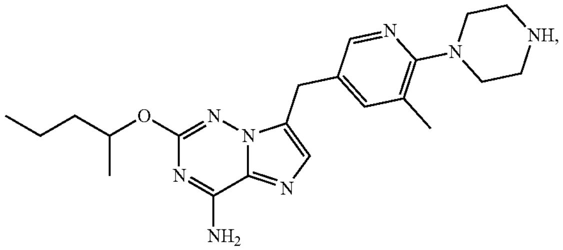

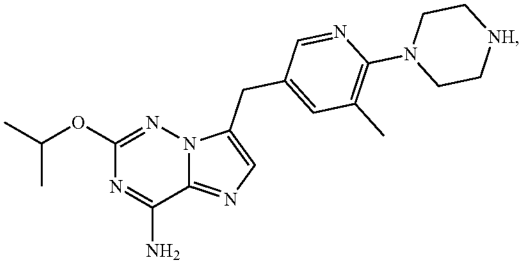

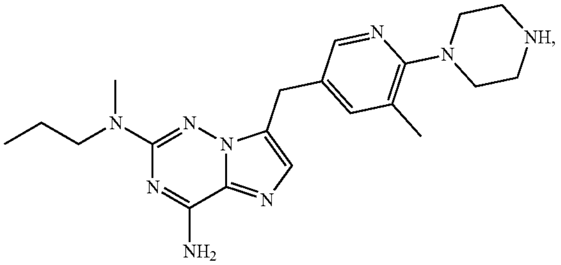

-continued

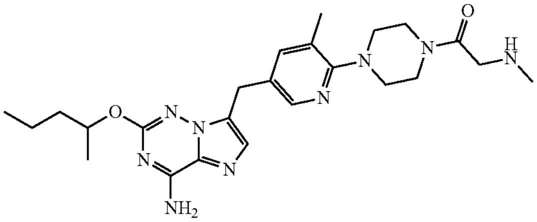

,

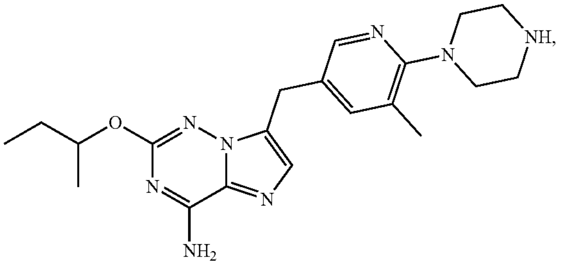

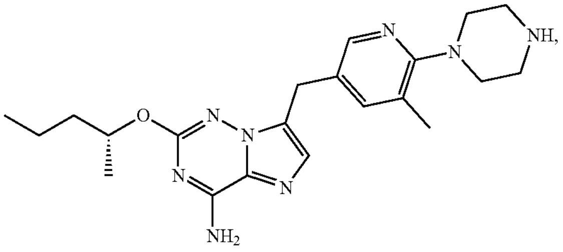

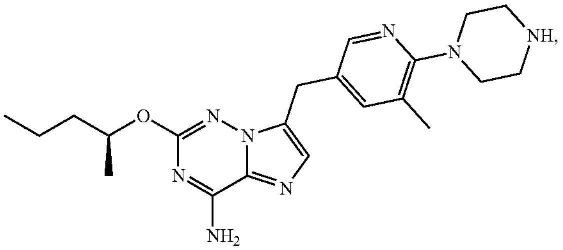

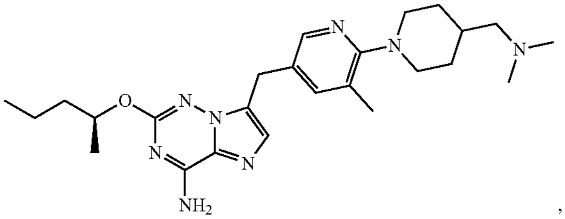

,

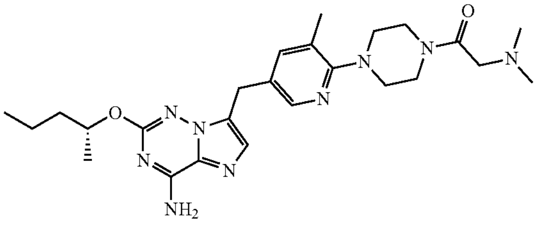

,

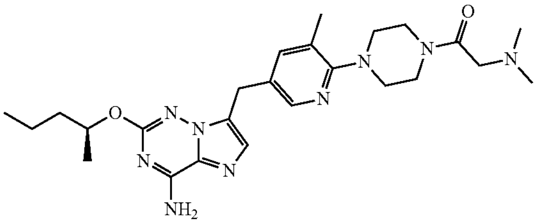

,

-continued
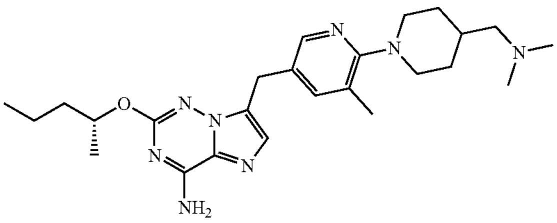
,
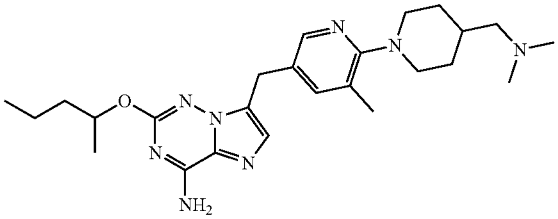
,
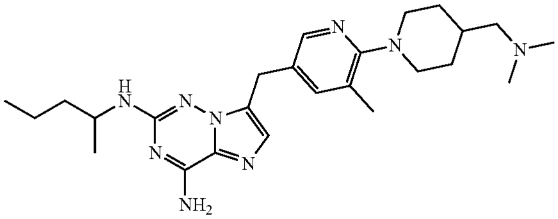
,
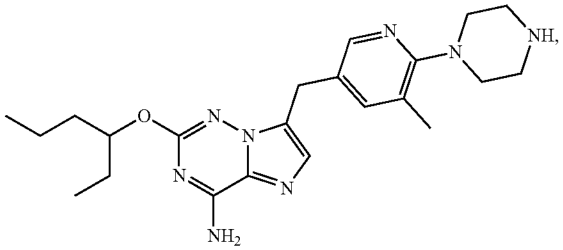
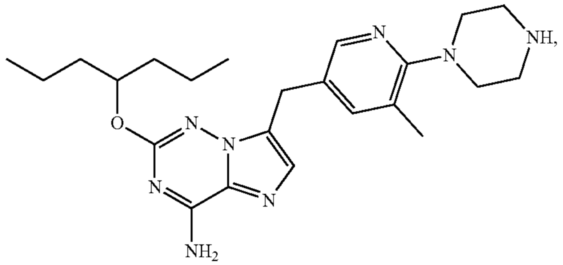
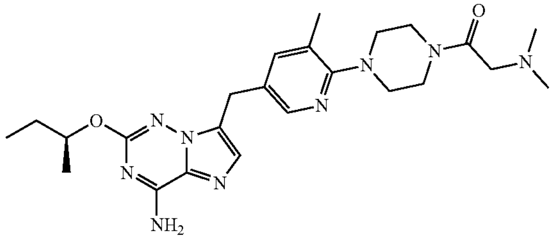
,
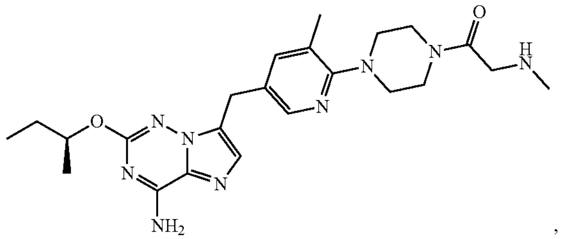
,
-continued
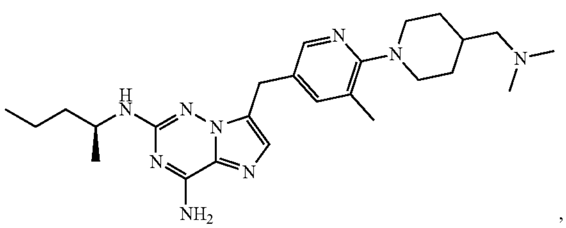
,
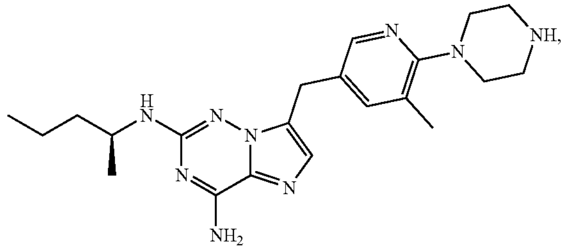
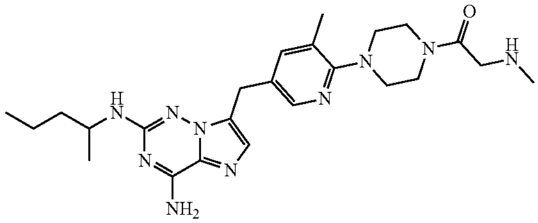
,
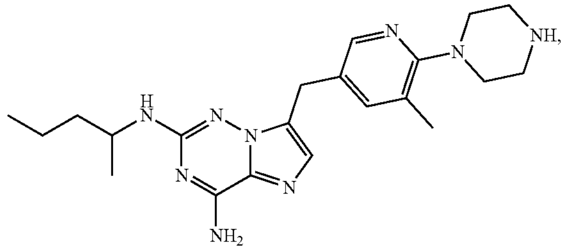
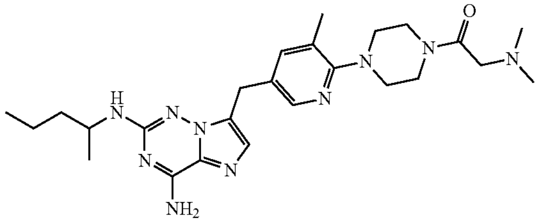
,
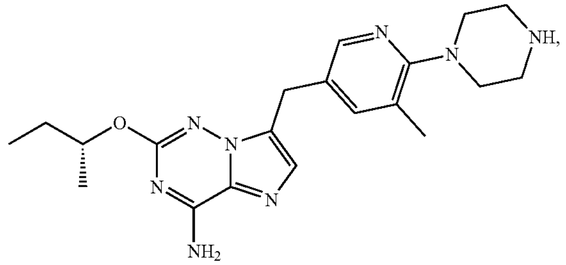
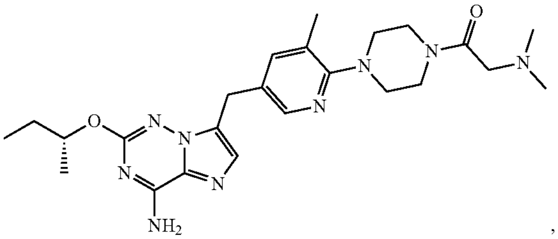
, -continued
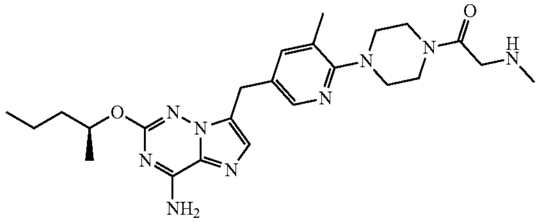
,
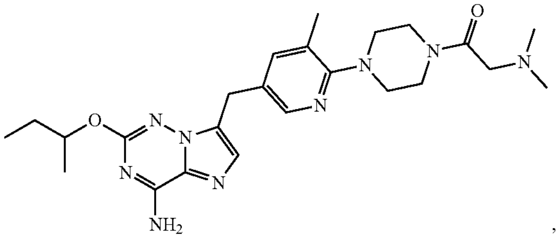
,
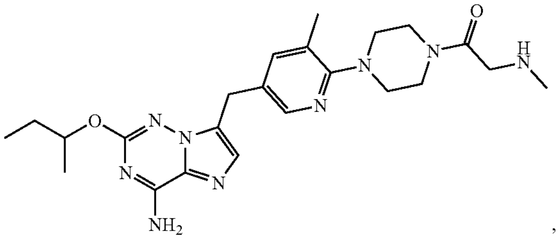
,
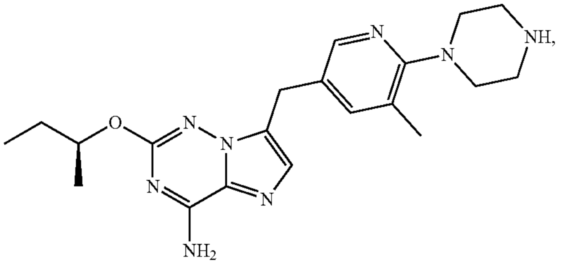
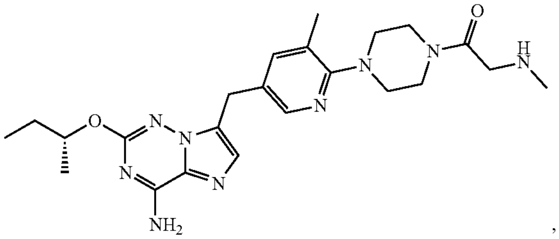
,
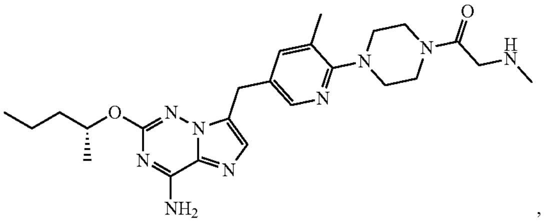
,
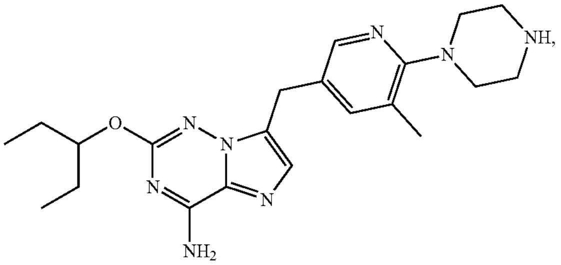
-continued
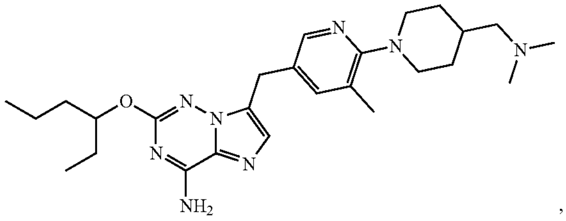
,
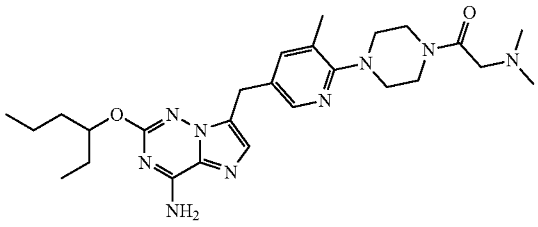
,
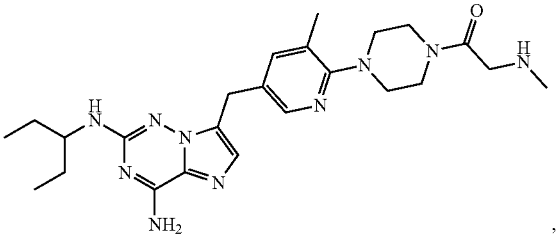
,
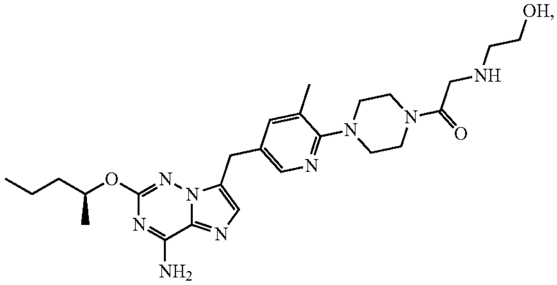
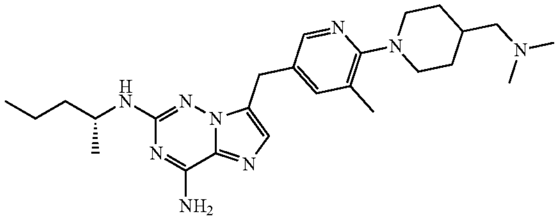
,
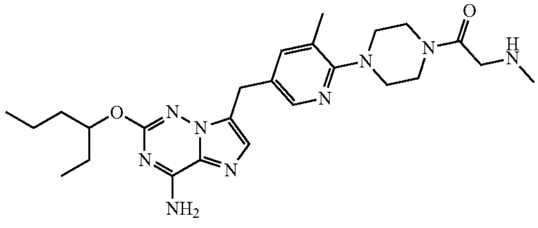
,
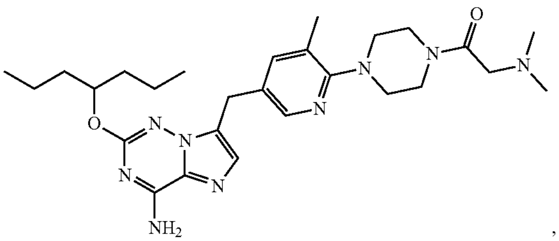
, -continued
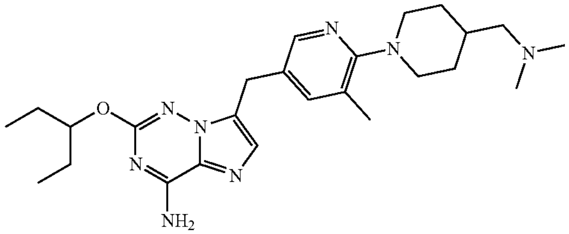
,
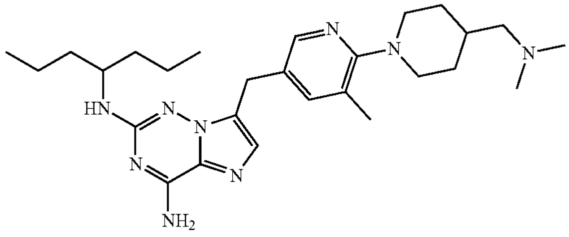
,
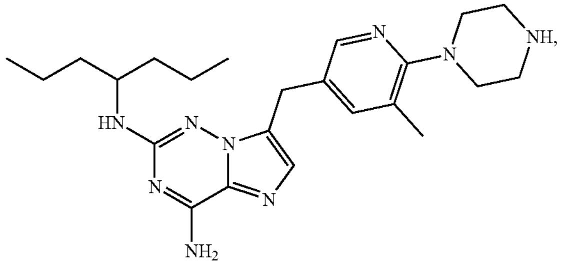
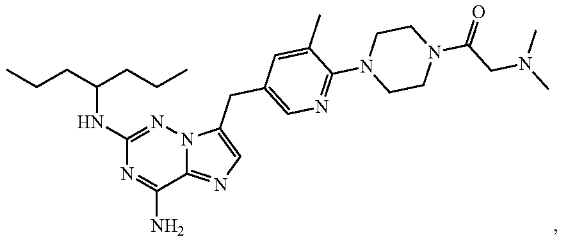
,
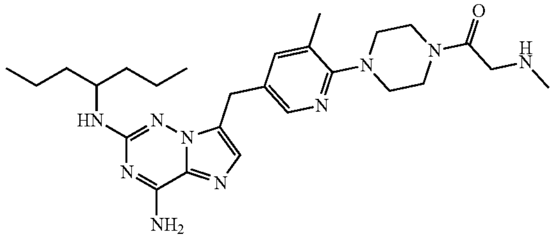
,
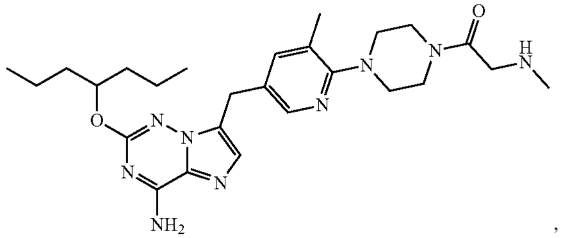
,
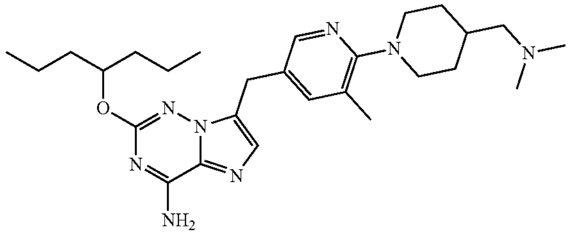
,
-continued
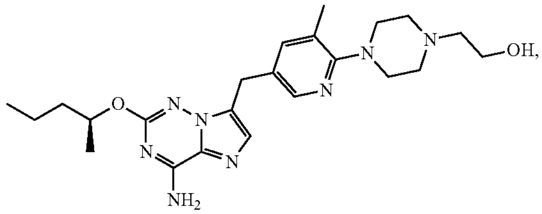
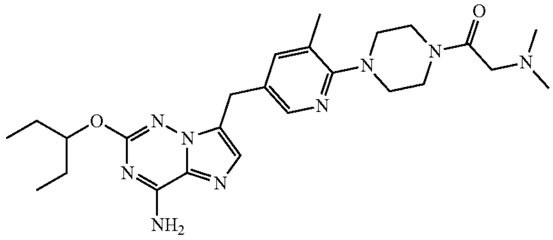
,
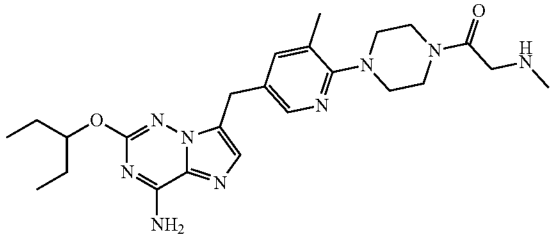
,
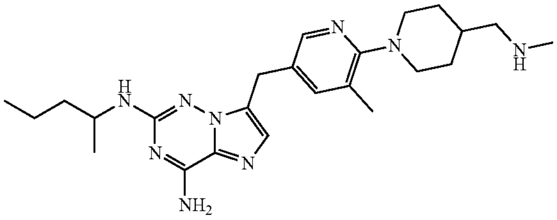
,
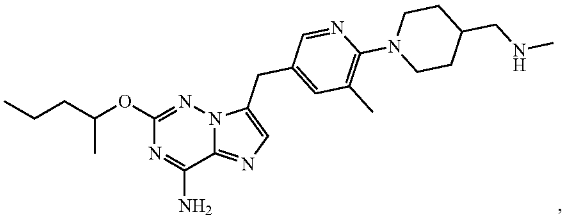
,
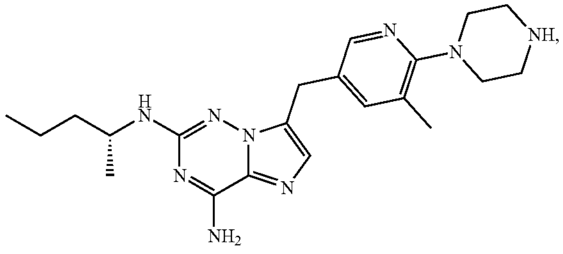
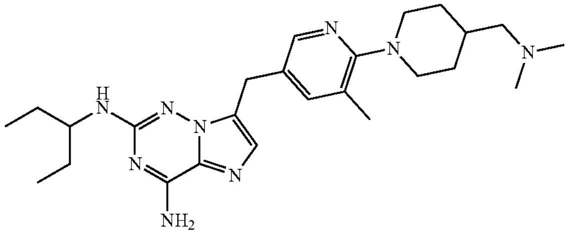
, -continued
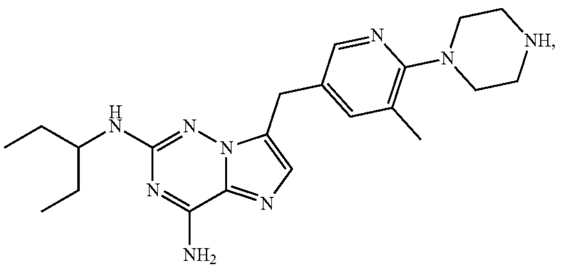
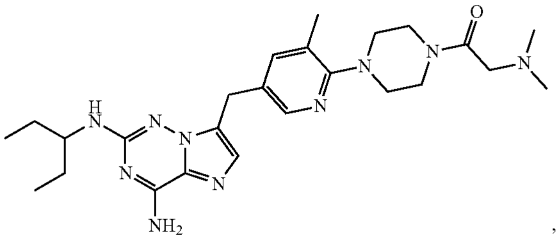
,
-continued
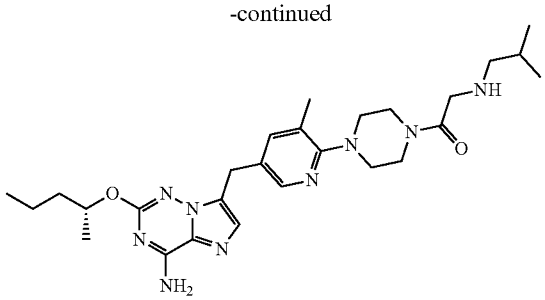
,
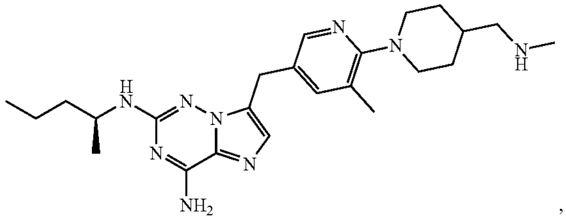
,
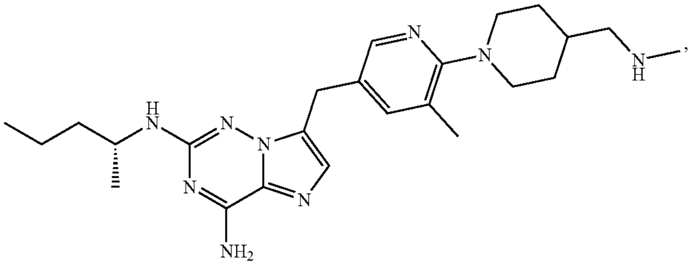
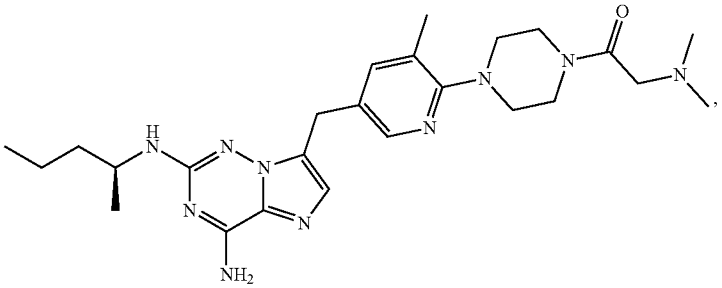
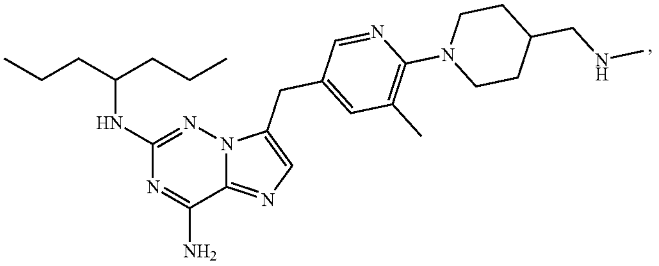
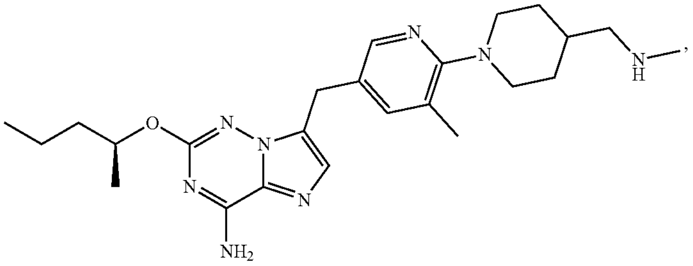

-continued
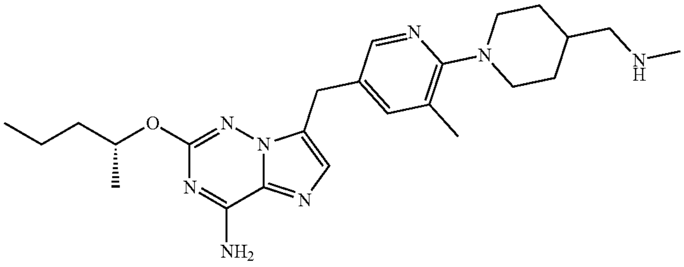
,
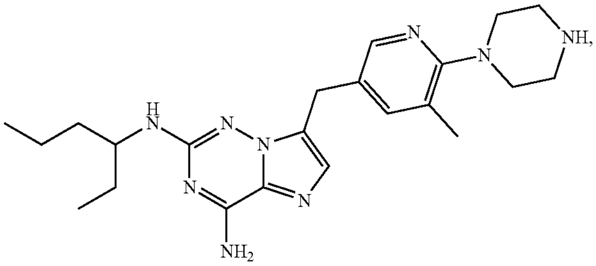
,
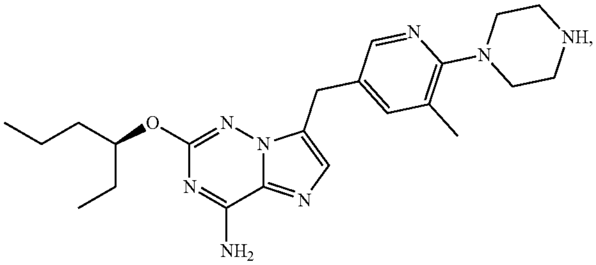
,
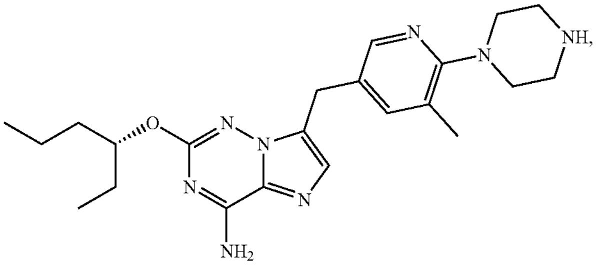
,
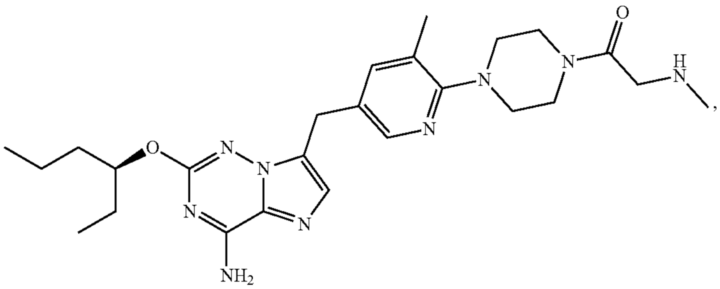
,
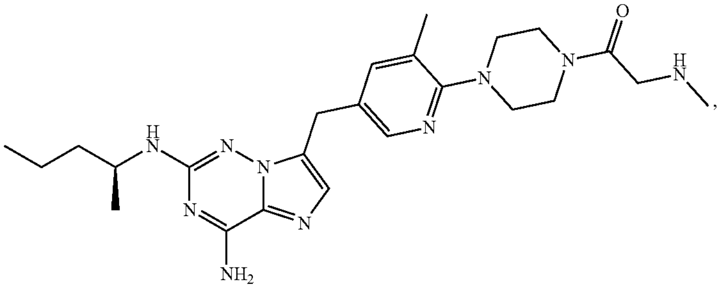
, -continued
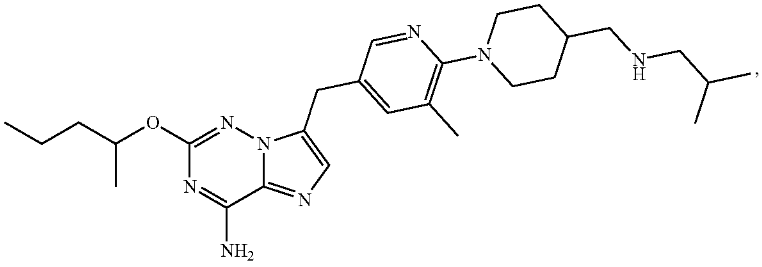
,
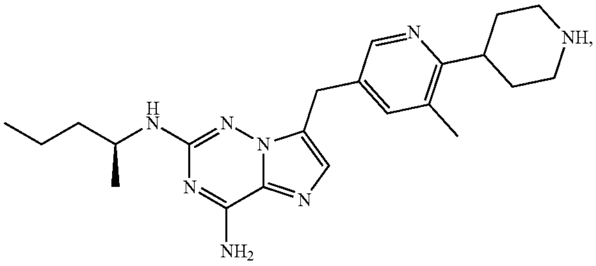
,
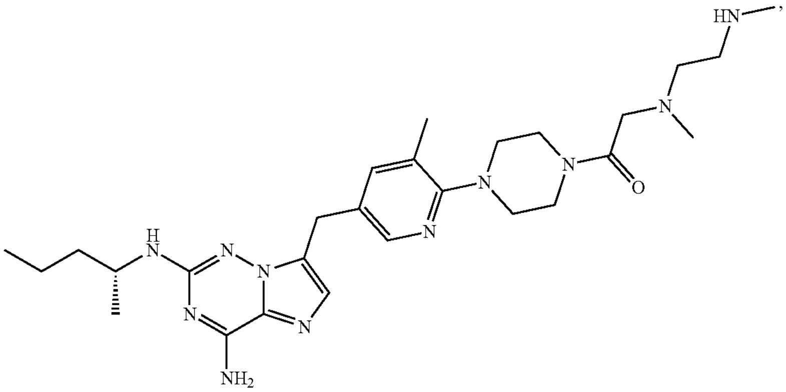
,
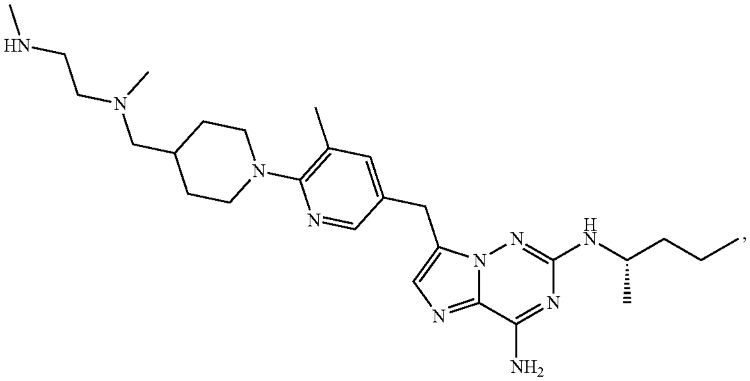
,
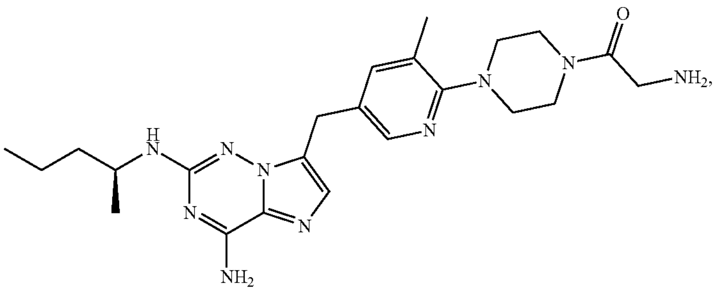
, or -continued

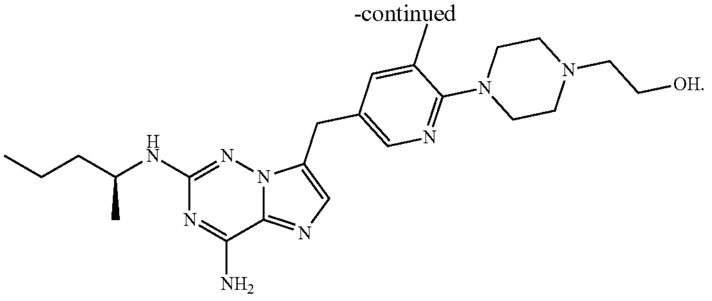

11. A pharmaceutical composition comprising the compound according to claim 1, or a pharmaceutically acceptable salt thereof, and at least one pharmaceutically acceptable carrier or excipient.

12. A method of modulating TLR7, which comprises administering to an individual the compound according to claim 1, or a pharmaceutically acceptable salt thereof.

13. A method of treating a disease or disorder in a patient comprising administering to the patient a therapeutically effective amount of the compound according to claim 1, or a pharmaceutically acceptable salt thereof as a TLR7 agonist.

14. The method according to claim 13, wherein the disease or disorder is cancer.

* * * * *